(12) United States Patent
Kwok et al.

(10) Patent No.: US 8,148,367 B2
(45) Date of Patent: Apr. 3, 2012

(54) RENIN INHIBITORS

(75) Inventors: Lily Kwok, San Diego, CA (US); Betty Lam, Spring Valley, CA (US); Zhe Li, San Diego, CA (US); Zhiyuan Zhang, San Diego, CA (US)

(73) Assignee: Takeda Pharmaceutical Company Limited, Osaka (JP)

(*) Notice: Subject to any disclaimer, the term of this patent is extended or adjusted under 35 U.S.C. 154(b) by 250 days.

(21) Appl. No.: 12/522,888

(22) PCT Filed: Jan. 9, 2008

(86) PCT No.: PCT/US2008/050632
§ 371 (c)(1),
(2), (4) Date: Jul. 23, 2009

(87) PCT Pub. No.: WO2008/089005
PCT Pub. Date: Jul. 24, 2008

(65) Prior Publication Data
US 2010/0105665 A1   Apr. 29, 2010

(51) Int. Cl.
| | |
|---|---|
| *A61K 31/5355* | (2006.01) |
| *A61K 31/536* | (2006.01) |
| *A61K 31/496* | (2006.01) |
| *A61K 31/4178* | (2006.01) |
| *C07D 233/90* | (2006.01) |
| *C07D 401/04* | (2006.01) |
| *C07D 401/06* | (2006.01) |
| *C07D 401/12* | (2006.01) |
| *C07D 401/14* | (2006.01) |
| *C07D 403/06* | (2006.01) |
| *C07D 403/14* | (2006.01) |
| *C07D 413/10* | (2006.01) |
| *C07D 413/12* | (2006.01) |
| *C07D 417/06* | (2006.01) |
| *C07D 417/14* | (2006.01) |

(52) U.S. Cl. ............... 514/230.5; 514/232.2; 514/235.8; 514/253.06; 514/253.09; 514/254.05; 514/254.07; 514/254.03; 514/254.02; 544/105; 544/121; 544/363; 544/364; 544/367; 544/369; 544/370

(58) Field of Classification Search .................. None
See application file for complete search history.

(56) References Cited

U.S. PATENT DOCUMENTS

| | | | |
|---|---|---|---|
| 2,717,908 A | 9/1955 | Snyder | |
| 3,303,199 A | 2/1967 | Doebel et al. | |
| 2005/0014765 A1* | 1/2005 | Mailliet et al. | 514/254.02 |

FOREIGN PATENT DOCUMENTS

| | | |
|---|---|---|
| EP | 1253469 EP | 10/2002 |
| JP | 2005091951 | 4/2005 |
| WO | WO/2004/089915 | 10/2004 |
| WO | WO/2007/094513 | 8/2007 |

OTHER PUBLICATIONS

Holsworth et al. Bioorganic & Medicinal Chemistry Letters vol. 16, pp. 2500-2504 (2006).*
Schmieder, Current Hypertension Reports, vol. 9, pp. 415-421 (2007).*
Database Beilstein Beilstein Institute for Organic Chemistry J. of Organic Chemistry, vol. 27, 1962, p. 2500-4 Database accession No. 804092 XP002484556.
Database CA Chemical Abstract Services, Columbus, Ohio, US. Yasuda et al. "Imidazoledicarboxylic acid derivatives", STN Database accession No. 1979:137809 XP002484557, (1979).
Database CA Chemical Abstract Services, Columbus, Ohio, US. Yasuda et al. "Imidazoledicarboxylic acid derivatives", STN Database accession No. 1981:30771 XP002484558, (1981).
Erhard et al. "Cardiotonic Agents. 5. Fragments from heterocycle-phenyl-imidazole pharmacophore" J. of Med. Chem., vol. 32, 1989, p. 1173-6, XP00990528.
Maibaum et al. "Renin inhibitors as novel treatments for cardiovascular disease" Expert Opinions, vol. 13, No. 5, 2003, p. 589-603. XP002327881.
Yokokawa et al. "Recent advances in the discovery of non-peptidic direct renin inhibitors . . . " Expert Opinions Therapeurtic Patents, 2008, vol. 18 No. 6, p. 581-602. XP002484555.
Database Beilstein Beilstein Institute for Organic Chemistry, Bio Org Med Chem, vol. 11, No. 8, 2003, p. 1621-30 Database accession No. 804092 XP002484559.
Database Beilstein Beilstein Institute for Organic Chemistry, Neunhoeffer, Tetrahedron, vol. 48, No. 4, 1992, p. 651-62, Database accession No. 1777376, 4861213, XP002484786.
Lee et al. "Rhodium carbenoid . . . " Org. Ltrs., vol. 5, No. 4, 2003, p. 511-4 XP002484785.

* cited by examiner

*Primary Examiner* — Emily Bernhardt
(74) *Attorney, Agent, or Firm* — Matthew J. Russo; C. Amy Smith

(57) ABSTRACT

Disclosed are compounds, pharmaceutical compositions, kits, articles of manufacture, methods of using, and methods of preparing compounds having the formula:

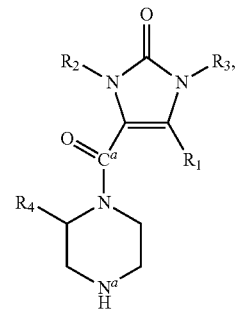

wherein the variables are as defined herein. The disclosed compounds are inhibitors of Renin.

13 Claims, 1 Drawing Sheet

FIGURE 1

DNA Sequence Encoding First PCR Primer [SEQ ID NO: 1]

1 AAGCTTATGG ATGGATGGAG A

DNA Sequence Encoding Second PCR Primer [SEQ ID NO: 2]

1 GGATCCTCAG CGGGCCAAGG C

# RENIN INHIBITORS

FIELD OF THE INVENTION

The present invention relates to compounds that may be used to inhibit Renin, as well as compositions of matter and kits comprising these compounds. The invention also relates to methods for inhibiting renin and treatment methods using compounds according to the present invention.

BACKGROUND OF THE INVENTION

The renin-angiotensin-aldosterone system ("RAAS") is one of the hormonal mechanisms involved in regulating pressure/volume homeostasis and also in the development of hypertension, a condition that can progress to more serious cardiovascular diseases such as congestive heart failure. Activation of RAAS begins with secretion of the enzyme renin from juxtaglomerular cells in the kidney.

Renin, a member of the aspartyl protease family, passes from the kidneys into the blood where it cleaves angiotensinogen to generate the decapeptide angiotensin I. Angiotensin I is then cleaved in the lungs, the kidneys and other organs by the angiotensin-converting enzyme (ACE) to form the octapeptide angiotensin II. Angiotensin II, which is known to work on at least two receptor subtypes ($AT_1$ and $AT_2$), increases blood pressure both directly by arterial vasoconstriction and indirectly by liberating from the adrenal glands the sodium-ion-retaining hormone aldosterone. Angiotensin II also produces other physiological effects such as promoting sodium and fluid retention, inhibiting renin secretion, increasing sympathetic nervous system activity, stimulating vasopressin secretion, causing a positive cardiac inotropic effect and modulating other hormonal systems.

Modulation of the RAAS represents a major advance in the treatment of cardiovascular diseases. In particular, the rationale to develop renin inhibitors lies in its specificity (Kleinert H. D., *Cardiovasc. Drugs*, 1995, 9, 645). The only substrate known for renin is angiotensinogen, which can only be processed (under physiological conditions) by Renin. Inhibitors of the enzymatic activity of renin are therefore expected to bring about a reduction in the formation of angiotensin I and angiotensin II.

In view of the foregoing, renin is an especially attractive target for the discovery of new therapeutics for cardiovascular disease, hypertension, congestive heart failure, myocardial infarction, renal protection, inflammation, neurological diseases, cancer and other diseases. Accordingly, there is a need to find new renin inhibitors for use as therapeutic agents to treat human diseases. In particular, there is a continued need for metabolically stable, orally bioavailable renin inhibitors that can be prepared on a large scale.

SUMMARY OF THE INVENTION

The present invention relates to compounds that have activity for inhibiting renin and to methods of making these compounds. The present invention also provides compositions, articles of manufacture and kits comprising these compounds.

In one aspect, the invention is directed to a pharmaceutical composition that comprises a renin inhibitor according to the present invention as an active ingredient. Pharmaceutical compositions according to the invention may optionally comprise 0.001%-100% of one or more inhibitors of this invention. These pharmaceutical compositions may be administered or coadministered by a wide variety of routes, including for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compositions may also be administered or coadministered in slow release dosage forms.

In another aspect, the invention is also directed to kits for treating disease states associated with Renin. In one embodiment, the kit comprises a composition comprising at least one renin inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another aspect, the invention is related to an article of manufacture that comprises a composition comprising at least one renin inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

In still another aspect, the invention is related to methods for using compounds, compositions, kits and articles of manufacture.

In one embodiment, the compounds, compositions, kits and articles of manufacture are used to inhibit Renin.

In another embodiment, the compounds, compositions, kits and articles of manufacture are used to treat a disease state for which renin possess activity that contributes to the pathology and/or symptomology of the disease state.

In another embodiment, a compound is administered to a subject wherein renin activity within the subject is altered, preferably reduced.

In another embodiment, a prodrug of a compound is administered to a subject that is converted to the compound in vivo where it inhibits Renin.

In another embodiment, a method of inhibiting renin is provided that comprises contacting a renin with a compound according to the present invention.

In another embodiment, a method of inhibiting renin is provided that comprises causing a compound according to the present invention to be present in a subject in order to inhibit renin in vivo.

In another embodiment, a method of inhibiting a renin is provided that comprises administering a first compound to a subject that is converted in vivo to a second compound wherein the second compound inhibits renin in vivo. It is noted that the compounds of the present invention may be the first or second compounds.

In another embodiment, a therapeutic method is provided that comprises administering a compound according to the present invention.

In another embodiment, a method of treating a condition in a patient that is known to be mediated by Renin, or which is known to be treated by renin inhibitors, comprising administering to the patient a therapeutically effective amount of a compound according to the present invention.

In another embodiment, a method is provided for treating a disease state for which renin possess activity that contributes to the pathology and/or symptomology of the disease state, the method comprising: causing a compound according to the present invention to be present in a subject in a therapeutically effective amount for the disease state.

In another embodiment, a method is provided for treating a disease state for which renin possess activity that contributes to the pathology and/or symptomology of the disease state, the method comprising: administering a first compound to a subject that is converted in vivo to a second compound such that the second compound is present in the subject in a therapeutically effective amount for the disease state. It is noted that the compounds of the present invention may be the first or second compounds.

In another embodiment, a method is provided for treating a disease state for which renin possess activity that contributes to the pathology and/or symptomology of the disease state, the method comprising: administering a compound according to the present invention to a subject such that the compound is present in the subject in a therapeutically effective amount for the disease state.

In another embodiment, a method is provided for using a compound according to the present invention in order to manufacture a medicament for use in the treatment of a disease state that is known to be mediated by Renin, or that is known to be treated by renin inhibitors.

In a further aspect, the invention is related to methods for preparing compounds, compositions and kits according to the present invention. For example, several synthetic schemes are provided herein for synthesizing compounds according to the present invention. The invention further provides reagents that are useful in the preparation of the compounds.

It is noted in regard to all of the above embodiments that the present invention is intended to encompass all pharmaceutically acceptable ionized forms (e.g., salts) and solvates (e.g., hydrates) of the compounds, regardless of whether such ionized forms and solvates are specified since it is well know in the art to administer pharmaceutical agents in an ionized or solvated form. It is also noted that unless a particular stereochemistry is specified, recitation of a compound is intended to encompass all possible stereoisomers (e.g., enantiomers or diastereomers depending on the number of chiral centers), independent of whether the compound is present as an individual isomer or a mixture of isomers. Further, unless otherwise specified, recitation of a compound is intended to encompass all possible resonance forms and tautomers. With regard to the claims, the language "compound having the formula" and "compound of the formula" is intended to encompass the compound and all pharmaceutically acceptable ionized forms and solvates, all possible stereoisomers, and all possible resonance forms and tautomers unless otherwise specifically specified in the particular claim.

It is further noted that prodrugs may also be administered which are altered in vivo and become a compound according to the present invention. The various methods of using the compounds of the present invention are intended, regardless of whether prodrug delivery is specified, to encompass the administration of a prodrug that is converted in vivo to a compound according to the present invention. It is also noted that certain compounds of the present invention may be altered in vivo prior to inhibit renin and thus may themselves be prodrugs for another compound. Such prodrugs of another compound may or may not themselves independently have renin inhibitory activity.

BRIEF DESCRIPTION OF THE FIGURES

FIG. 1 illustrates SEQ ID NO: 1 and 2 referred to in this application.

DEFINITIONS

Unless otherwise stated, the following terms used in the specification and claims shall have the following meanings for the purposes of this Application.

"Alicyclic" means a moiety comprising a non-aromatic ring structure. Alicyclic moieties may be saturated or partially unsaturated with one, two or more double or triple bonds. Alicyclic moieties may also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with $C_{3-8}$ rings such as cyclopropane, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

"Aliphatic" means a moiety characterized by a straight or branched chain arrangement of constituent carbon atoms and may be saturated or partially unsaturated with one, two or more double or triple bonds.

"Alkoxy" means an oxygen moiety having a further alkyl substituent. The alkoxy groups of the present invention can be optionally substituted.

"Alkyl" represented by itself means a straight or branched, saturated or unsaturated, aliphatic radical having a chain of carbon atoms, optionally with oxygen (See "oxaalkyl") or nitrogen atoms (See "azaalkyl") between the carbon atoms. $C_X$ alkyl and $C_{X-Y}$ alkyl are typically used where X and Y indicate the number of carbon atoms in the chain. For example, $C_{1-6}$ alkyl includes alkyls that have a chain of between 1 and 6 carbons (e.g., methyl, ethyl, propyl, isopropyl, butyl, sec-butyl, isobutyl, tert-butyl, pentyl, hexyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl, heteroarylalkyl) means a straight or branched, saturated or unsaturated aliphatic divalent radical having the number of atoms indicated or when no atoms are indicated means a bond (e.g., $(C_{6-10})$aryl$(C_{1-3})$alkyl includes, benzyl, phenethyl, 1-phenylethyl, 3-phenylpropyl, 2-thienylmethyl, 2-pyridinylmethyl and the like).

"Alkenyl" means a straight or branched, carbon chain that contains at least one carbon-carbon double bond. Examples of alkenyl include vinyl, allyl, isopropenyl, pentenyl, hexenyl, heptenyl, 1-propenyl, 2-butenyl, 2-methyl-2-butenyl, and the like.

"Alkynyl" means a straight or branched, carbon chain that contains at least one carbon-carbon triple bond. Examples of alkynyl include ethynyl, propargyl, 3-methyl-1-pentynyl, 2-heptynyl and the like.

"Alkylene", unless indicated otherwise, means a straight or branched, saturated or unsaturated, aliphatic, divalent radical. $C_X$alkylene and $C_{X-Y}$alkylene are typically used where X and Y indicate the number of carbon atoms in the chain. For example, $C_{1-6}$ alkylene includes methylene (—$CH_2$—), ethylene (—$CH_2CH_2$—), trimethylene (—$CH_2CH_2CH_2$—), tetramethylene (—$CH_2CH_2CH_2CH_2$—) 2-butenylene (—$CH_2CH=CHCH_2$—), 2-methyltetramethylene (—$CH_2CH(CH_3)CH_2CH_2$—), pentamethylene (—$CH_2CH_2CH_2CH_2CH_2$—) and the like.

"Alkenylene" means a straight or branched, divalent carbon chain having one or more carbon-carbon double bonds. Examples of alkenylene include ethene-1,2-diyl, propene-1,3-diyl, methylene-1,1-diyl, and the like.

"Alkynylene" means a straight or branched, divalent carbon chain having one or more carbon-carbon triple bonds. Examples of alkynylene include ethyne-1,2-diyl, propyne-1,3-diyl, and the like.

"Alkylidene" means a straight or branched saturated or unsaturated, aliphatic radical connected to the parent molecule by a double bond. $C_X$ alkylidene and $C_{X-Y}$ alkylidene are typically used where X and Y indicate the number of carbon atoms in the chain. For example, $C_{1-6}$ alkylidene includes methylene ($=CH_2$), ethylidene ($=CHCH_3$), isopropylidene ($=C(CH_3)_2$), propylidene ($=CHCH_2CH_3$), allylidene ($=CH-CH=CH_2$), and the like).

"Amino" means the radical —$NR_aR_b$, where $R_a$ and $R_b$ are each independently hydrogen or a non-hydrogen substituent. Representative amino groups include, without limits, —$NH_2$, —$NHCH_3$, —$N(CH_3)_2$, —$NHC_{1-10}$-alkyl, —$N(C_{1-10}$-alkyl)$_2$, —NHaryl, —NHheteroaryl, —N(aryl)$_2$, —N(heteroaryl)$_2$, and the like. Optionally, $R_a$ and $R_b$ together with the nitrogen may also form a ring. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are sp$^2$ hybridized and the total number of pi electrons is equal to 4n+2. An aromatic ring may be such that the ring atoms are only carbon atoms or may include carbon and non-carbon atoms (see Heteroaryl).

"Aryl" means a monocyclic or polycyclic ring assembly where all the ring atoms are carbon atoms, and at least one of the rings comprising the ring assembly is an aromatic ring. If one or more ring atoms is not carbon (e.g., N, S), the aryl is a heteroaryl. $C_X$ aryl and $C_{X-Y}$ aryl are typically used where X and Y indicate the number of carbon atoms in the ring.

"Azaalkyl" means an alkyl, as defined above, except where one or more substituted or unsubstituted nitrogen atoms (—N—) are positioned between carbon atoms of the alkyl. For example, an ($C_{2-6}$) azaalkyl refers to a chain comprising between 2 and 6 carbons and one or more nitrogen atoms positioned between the carbon atoms.

"Bicyclic" means a two-ringed ring assembly where the two rings are fused together, linked by a single bond or linked by two bridging atoms.

"Bicycloalkyl" means a saturated or partially unsaturated fused bicyclic or bridged polycyclic ring assembly.

"Bicycloaryl" means a ring assembly of two rings, wherein the rings are linked by a single bond or fused and at least one of the rings comprising the ring assembly is an aromatic ring. $C_X$ bicycloaryl and $C_{X-Y}$ bicycloaryl are typically used where X and Y indicate the number of carbon atoms in the bicyclic ring assembly and directly attached to the ring.

"Bridging ring" as used herein refers to a ring that is bonded to another ring to form a compound having a bicyclic structure where two ring atoms that are common to both rings are not directly bound to each other. Non-exclusive examples of common compounds having a bridging ring include borneol, norbornane, 7-oxabicyclo[2.2.1]heptane, and the like. One or both rings of the bicyclic system may also comprise heteroatoms.

"Carbamoyl" means the radical —OC(O)$NR_aR_b$ where $R_a$ and $R_b$ are each independently two further substituents where a hydrogen or carbon atom is attached to the nitrogen.

"Carbocycle" refers to a ring where all the ring atoms are carbon atoms.

"Carbocyclic ketone derivative" means a carbocyclic derivative wherein the ring contains a —C(=O)— moiety.

"Carbonyl" typically means a divalent radical —C(=O)—. It is noted that the term "carbonyl" when referring to a monovalent substituent can alternatively refer to a substituted carbonyl or acyl group, —C(=O)$R_a$, where $R_a$ is hydrogen or a non-hydrogen substituent on the carbonyl carbon, forming different carbonyl-containing groups including acids, acid halides, aldehydes, amides, esters, and ketones.

"Carboxy" typically means a divalent radical —C(O)O—. It is noted that the term "carboxy" when referring to a monovalent substituent means a substituted carboxy, —C(O)O$R_a$, where $R_a$ is hydrogen or a non-hydrogen substituent on the carboxyl group forming different carboxy containing groups including acids and esters. It is further noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Cycloalkyl" means a radical comprising a non-aromatic, saturated or partially unsaturated, monocyclic, fused or bridged polycyclic ring assembly. $C_X$ cycloalkyl and $C_{X-Y}$ cycloalkyl are typically used where X and Y indicate the number of carbon atoms in the ring assembly. For example, $C_{3-10}$ cycloalkyl includes cyclopropyl, cyclobutyl, cyclopentyl, cyclohexyl, cyclohexenyl, 2,5-cyclohexadienyl, bicyclo [2.2.2]octyl, adamantan-1-yl, decahydronaphthyl, oxocyclohexyl, dioxocyclohexyl, thiocyclohexyl, 2-oxobicyclo[2.2.1]hept-1-yl, and the like.

"Cycloalkylene" means a divalent radical comprising a saturated or partially unsaturated, monocyclic or polycyclic ring assembly. $C_X$ cycloalkylene and $C_{X-Y}$ cycloalkylene are typically used where X and Y indicate the number of carbon atoms in the ring assembly.

"Disease" specifically includes any unhealthy condition of an animal or part thereof and includes an unhealthy condition that may be caused by, or incident to, medical or veterinary therapy applied to that animal, i.e., the "side effects" of such therapy.

"Fused ring" as used herein refers to a multi-ring assembly wherein the rings comprising the ring assembly are so linked that the ring atoms that are common to two rings are directly bound to each other. The fused ring assemblies may be saturated, partially saturated, carbocyclics, heterocyclics, aromatics, heteroaromatics, and the like. Non-exclusive examples of common fused rings include decalin, naphthalene, anthracene, phenanthrene, indole, benzofuran, purine, quinoline, and the like.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like (e.g., halo-substituted ($C_{1-3}$)alkyl includes chloromethyl, dichloromethyl, difluoromethyl, trifluoromethyl, 2,2,2-trifluoroethyl, perfluoroethyl, 2,2,2-trifluoro-1,1-dichloroethyl, and the like).

"Heteroalkyl" means alkyl, as defined in this Application, provided that one or more of the atoms within the alkyl chain is a heteroatom.

"Heteroaryl" means a monocyclic or polycyclic ring assembly wherein at least one ring atom is a heteroatom and the remaining ring atoms are carbon, and at least one of the rings comprising the ring assembly is an aromatic ring. Monocyclic heteroaryl groups include, but are not limited to, cyclic aromatic groups having five or six ring atoms, wherein at least one ring atom is a heteroatom and the remaining ring atoms are carbon. The nitrogen atoms of such heteroaryl rings can be optionally quaternerized and the sulfur atoms of such heteroaryl rings can be optionally oxidized. Heteroaryl groups of this invention include, but are not limited to, those derived from furan, imidazole, isothiazole, isoxazole, oxadiazole, oxazole, 1,2,3-oxadiazole, pyrazine, pyrazole, pyridazine, pyridine, pyrimidine, pyrroline, thiazole, 1,3,4-thiadiazole, triazole and tetrazole. "Heteroaryl" also includes polycyclic ring assemblies, wherein a heteroaromatic ring is fused or linked by a bond to one or more rings independently selected from the group consisting of an aromatic ring, a cycloalkyl ring, a cycloalkenyl ring, a heterocycloalkyl ring and another heteroaromatic ring. Bicyclic or tricyclic heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole and 2(1H)-pyridinone. The polycyclic heteroaryl ring assembly can be attached to the parent molecule through either the heteroaryl group itself or the aryl, cycloalkyl, cycloalkenyl or heterocycloalkyl group to which it is fused. The heteroaryl groups of this invention can be substituted or unsubstituted.

"Heterobicycloaryl" means bicycloaryl, as defined in this Application, provided that one or more of the atoms within the ring assembly is a heteroatom. For example, hetero($C_{4-12}$)bicycloaryl as used in this Application includes, but is not limited to, indoline, 2-amino-4-oxo-3,4-dihydropteridin-6-yl, tetrahydroisoquinolinyl, and the like.

"Heterocycloalkyl" means cycloalkyl, as defined in this Application, provided that one or more of the atoms forming the ring is a heteroatom. Non-exclusive examples of heterocycloalkyl include piperidyl, 4-morpholyl, 4-piperazinyl, pyrrolidinyl, perhydropyrrolizinyl, 1,3-dioxanyl, 1,4-dioxanyl and the like.

"Heteroatom" refers to an atom that is not a carbon atom. Particular examples of heteroatoms include, but are not limited to nitrogen, oxygen, and sulfur.

"Heteroatom moiety" includes a moiety where the atom by which the moiety is attached is not a carbon. Examples of heteroatom moieties include —N=, —$NR_c$—, —$N^+(O^-)$=, —O—, —S— or —$S(O)_2$—, wherein $R_c$ is a further substituent.

"Heterobicycloalkyl" means bicycloalkyl, as defined in this Application, provided that one or more of the atoms within the ring is a heteroatom. For example hetero($C_{9-12}$) bicycloalkyl as used in this application includes, but is not limited to, 3-aza-bicyclo[4.1.0]hept-3-yl, 2-aza-bicyclo[3.1.0]hex-2-yl, 3-aza-bicyclo[3.1.0]hex-3-yl, and the like.

"Heterocycle" refers to a ring moiety, saturated, unsaturated or aromatic, where at least one ring atom is a heteroatom and the remaining ring atoms are carbon.

"Heterocycloalkylene" means cycloalkylene, as defined in this Application, provided that one or more of the ring member carbon atoms is replaced by a heteroatom.

"Hydroxy" means the radical —OH.

"$IC_{50}$" refers to the molar concentration of an inhibitor that produces 50% inhibition of the target enzyme.

"Iminoketone derivative" means a derivative comprising the moiety —C(NR)—, wherein R comprises a hydrogen or carbon atom attached to the nitrogen.

"Isomers" mean any compounds having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four different substituents (where no two are the same) is termed a "chiral center." A compound with one chiral center has two enantiomeric forms of opposite chirality. A mixture of equal amounts of the two enantiomeric forms is termed a "racemic mixture." A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

"Linker" means a series of atoms sequentially connected by chemical bonds and in a continuous linking relation which extends between two attachment points. A linker may be linear, cyclic or a combination of linear portions and cyclic portions.

The length of the linker or "the number of atoms as measured between the two defined attachment points" refers only to the atoms that are in the sequential linking relation; atoms that are attached to one linker atom, but are not in this continuous linking relationship with another linker atoms (e.g., a substituent on one of the linker atom) are not counted towards the length of the linker.

The method of counting atoms is the same for linker groups that comprise only a linear portion and for linker groups that comprise substituents extending from a chain of atoms to form cyclic groups: only the atoms sequentially linking the attachment points defined for L are counted toward the atom number, not the substituents. Further, only ring atoms on the shorter side of the ring that are in continuous sequential linking relationship with the rest of the linker group are counted. For example, in the following example of a Linker L

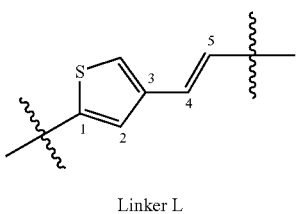

Linker L where a substituent from each of linker atoms 1 and 3 are taken together to form the five-membered ring, the number of atoms constituting the length of this Linker L is 5, which includes the three ring atoms (atoms 1, 2, and 3) on the shorter side of the 5-membered heterocyclic ring and the two atoms (atoms 4 and 5) on the linear portion of the linker.

"Moiety" means an interconnected group of atoms, generally referred to by its most characteristic structural component. For example, a "carbonyl moiety" refers to groups that contain a carbonyl group.

"Nitro" means the radical —$NO_2$.

"Oxaalkyl" means an alkyl, as defined above, except where one or more oxygen atoms (—O—) are positioned between carbon atoms of the alkyl. For example, an $(C_{2-6})$oxaalkyl refers to a chain comprising between 2 and 6 carbons wherein one or more oxygen atoms is positioned between two carbon atoms.

"Oxy" typically means the radical —O—. It is noted that the term "oxy" when referring to a monovalent radical can alternatively refer to a substituents oxy group, —OR—, where R is hydrogen or a non-hydrogen substituent on the oxy radical forming oxy-containing groups including hydroxy, alkoxy, aryloxy, heteroaryloxy and carbonyloxy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo [2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Prodrug" means a compound that is convertible in vivo metabolically into an inhibitor according to the present invention. The prodrug itself may or may not also have renin inhibitory activity. For example, an inhibitor comprising a hydroxy group may be administered as an ester that is converted by hydrolysis in vivo to the hydroxy compound. Suitable esters that may be converted in vivo into hydroxy compounds include acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, an inhibitor comprising an amine group may be administered as an amide or as an N-alkyl (particularly N-methyl or N-ethyl) that is converted by hydrolysis or oxidation in vivo to the amine compound.

"Protected derivatives" means derivatives of inhibitors in which a reactive site or sites are blocked with protecting groups. Protected derivatives are useful in the preparation of inhibitors or in themselves may be active as inhibitors. Examples of protected group includes, but are not limited to, acetyl, tetrahydropyran, methoxymethyl ether, β-methoxyethoxymethyl ether, p-methoxybenzyl, methylthiomethyl ether, pivaloyl, silyl ether, carbobenzyloxy, benzyl, tert-butoxycarbonyl, p-methoxyphenyl, 9-fluorenylmethyloxycarbonyl, acetals, ketals, acylals, dithianes, methylesters, benzyl esters, tert-butyl esters, and silyl esters. A comprehensive list of suitable protecting groups can be found in T. W. Greene, *Protecting Groups in Organic Synthesis,* 3rd edition, John Wiley & Sons, Inc. 1999.

"Ring" means a carbocyclic or a heterocyclic system.

"Substituent convertible to hydrogen in vivo" means any group that is convertible to a hydrogen atom by enzymological or chemical means including, but not limited to, hydrolysis, reduction and oxidation. Examples include hydrolyzable groups, such as acyl groups, groups having an oxycarbonyl group, amino acid residues, peptide residues, o-nitrophenylsulfenyl, trimethylsilyl, tetrahydro-pyranyl, diphenylphosphinyl, and the like. Examples of acyl groups include formyl, acetyl, trifluoroacetyl, and the like. Examples of groups having an oxycarbonyl group include ethoxycarbonyl, t-butoxycarbonyl [(—O)CO—C(CH$_3$)$_3$], benzyloxycarbonyl, p-methoxybenzyloxycarbonyl, vinyloxycarbonyl, β-(p-toluenesulfonyl)ethoxycarbonyl, and the like. Examples of suitable amino acid residues include amino acid residues per se and amino acid residues that are protected with a protecting group. Suitable amino acid residues include, but are not limited to, residues of Gly (glycine), Ala (alanine; —C(O)CH (NH2)CH$_3$), Arg (arginine), Asn (asparagine), Asp (aspartic acid), Cys (cysteine), Glu (glutamic acid), His (histidine), Ile (isoleucine), Leu (leucine; —C(O)CH(NH$_2$)CH$_2$CH(CH$_3$)$_2$ Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable protecting groups include those typically employed in peptide synthesis, including acyl groups (such as formyl and acetyl), arylmethyloxycarbonyl groups (such as benzyloxycarbonyl and p-nitrobenzyloxycarbonyl), t-butoxycarbonyl groups [—(O) CO—C(CH$_3$)$_3$], and the like. Suitable peptide residues include peptide residues comprising two to five, and optionally two to three, of the aforesaid amino acid residues.

Examples of such peptide residues include, but are not limited to, residues of such peptides as Ala-Ala [—C(O)CH(NH)CH$_3$—C(O)CH(NH$_2$)CH$_3$)], Gly-Phe, Nva-Nva, Ala-Phe, Gly-Gly, Gly-Gly-Gly, Ala-Met, Met-Met, Leu-Met and Ala-Leu. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethyloxycarbonyl groups (such as benzyloxycarbonyl and p-nitrobenzyloxycarbonyl), t-butoxycarbonyl groups [—(O)CO—C(CH$_3$)$_3$], and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and halogenoethoxycarbonyl groups (such as β,β,β-trichloroethoxycarbonyl and β-iodoethoxycarbonyl). Further examples of substituents "convertible to hydrogen in vivo" include enzymatic oxidizable groups such as N-alkyls, particularly N-methyl and N-ethyl.

"Substituted or unsubstituted" or "optionally substituted" means that a given moiety may consist of only hydrogen atoms bound at available valences (unsubstituted) or may further comprise one or more non-hydrogen atoms bound through available valencies (substituted). The substituents of an "optionally substituted" group may include, without limitation one or more substituents independently selected from the group or designated subsets thereof, aldehyde, (C$_{1-10}$)alkyl, alkylene, alkylidene, amide, amino, aminoalkyl, aryl, bicycloalkyl, bicycloaryl, carbamoyl, carbocyclyl, carboxyl, carbonyl group, cycloalkyl, cycloalkylene, ester, halo, heterobicycloalkyl, heterocycloalkylene, heteroaryl, heterobicycloaryl, heterocycloalkyl, oxo, hydroxy, iminoketone, ketone, nitro, oxaalkyl, and oxoalkyl moieties, each of which may optionally also be substituted or unsubstituted.

In one particular embodiment, examples of substituents include, but are not limited to, hydrogen, halo, nitro, cyano, thio, oxy, hydroxy, carbonyloxy, (C$_{1-10}$)alkoxy, (C$_{4-14}$)aryloxy, hetero(C$_{1-13}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, (C$_{1-10}$)azaalkyl, imino(C$_{1-10}$)alkyl, (C$_{3-12}$)cycloalkyl(C$_{1-5}$)alkyl, hetero(C$_{3-12}$) cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl. In addition, the substituent is itself optionally substituted by a further substituent. In one particular embodiment, examples of the further substituent include, but are not limited to, hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$) alkyl, sulfinyl(C$_{1-10}$)alkyl, (C$_{1-10}$)azaalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl.

"Sulfinyl" means the radical —S(O)—. It is noted that the term "sulfinyl" when referring to a monovalent substituent can alternatively refer to a substituted sulfinyl group, —S(=O)R, where R is hydrogen or a non-hydrogen substituent on the sulfur atom forming different sulfinyl groups including sulfinic acids, sulfinamides, sulfinyl esters, and sulfoxides.

"Sulfonyl" means the radical —S(O)$_2$—. It is noted that the term "sulfonyl" when referring to a monovalent substituent can alternatively refer to a substituted sulfonyl group, —S(=O)$_2$R, where R is hydrogen or a non-hydrogen substituent on the sulfur atom forming different sulfonyl groups including sulfonic acids, sulfonamides, sulfonate esters, and sulfones.

"Therapeutically effective amount" means that amount which, when administered to an animal for treating a disease, is sufficient to effect such treatment for the disease.

"Thiocarbonyl" means the radical —C(S)—. It is noted that the term "thiocarbonyl" when referring to a monovalent substituent can alternatively refer to a substituted thiocarbonyl group, —C(=S)$_2$R, where R is hydrogen or a non-hydrogen substituent on the carbon atom forming different thiocarbonyl groups including thioacids, thioamides, thioesters, and thioketones.

"Treatment" or "treating" means any administration of a compound of the present invention and includes:
(1) preventing the disease from occurring in an animal which may be predisposed to the disease but does not yet experience or display the pathology or symptomatology of the disease,
(2) inhibiting the disease in an animal that is experiencing or displaying the pathology or symptomatology of the diseased (i.e., arresting further development of the pathology and/or symptomatology), or
(3) ameliorating the disease in an animal that is experiencing or displaying the pathology or symptomatology of the diseased (i.e., reversing the pathology and/or symptomatology).

DETAILED DESCRIPTION OF THE INVENTION

The present invention relates to compounds, compositions, kits and articles of manufacture that may be used to inhibit Renin. The present invention also relates to methods for inhibiting renin and treatment methods using compounds according to the present invention. The present invention further relates to method of making the inhibitors of the invention and compounds that are useful in the preparation of the inhibitors of the invention.

It is noted that the compounds of the present invention may also possess inhibitory activity for other aspartyl proteases (e.g., pepsin, gastricsin, napsin, BACE 1 & 2 and cathepsin D and E) and thus may be used to address disease states associated with these other family members. In addition, the compounds of the present invention may be useful as inhibitors of plasmepsins to treat malaria and as inhibitors of *Candida albicans* secreted aspartyl proteases to treat fungal infections.

In the first aspect, the invention relates to renin inhibiting compounds and their polymorphs, solvates, esters, tautomers, enantiomers, pharmaceutical acceptable salts, and prodrugs.

In one embodiment, compounds of the present invention is of the formula:

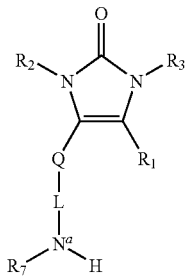

wherein
$N^a$ denotes a nitrogen atom;
L is a linker moiety between 1-5 atoms in length as measured between Q and $N^a$;
Q is selected from the group consisting of —C(=O)—, —C(=S)—, and —C(=NR$_{12}$)—;
$R_1$ is selected from the group consisting of hydrogen, carbonyl, oxycarbonyl, aminocarbonyl, $(C_{1-10})$alkylamino, sulfonamido, sulfonyl, sulfinyl, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicyoloaryl $(C_{1-5})$alkyl, $(C_{3-12})$cycloalkyl, hetero$(C_{2-12})$cycloalkyl, $(C_{9-12})$bicycloalkyl, hetero$(C_{2-12})$bicycloalkyl, $(C_{5-12})$ aryl, hetero$(C_{2-10})$aryl, $(C_{9-12})$bicycloaryl and hetero $(C_{4-12})$bicycloaryl, each substituted or unsubstituted;
$R_2$ is selected from the group consisting of hydrogen, alkoxy, aryloxy, heteroaryloxy, $(C_{1-10})$alkyl, halo$(C_{1-10})$ alkyl, alkoxy$(C_{1-10})$alkyl, carbonyl$(C_{1-3})$alkyl, thiocarbonyl$(C_{1-3})$alkyl, carboxamido$(C_{1-3})$alkyl, amido$(C_{1-3})$ alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$ alkyl, hetero$(C_{2-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{4-12})$bicyoloaryl$(C_{1-5})$alkyl, $(C_{3-12})$ cycloalkyl, hetero$(C_{2-12})$cycloalkyl, $(C_{9-12})$ bicycloalkyl, hetero$(C_{3-12})$bicycloalkyl, $(C_{5-12})$aryl, hetero$(C_{2-10})$aryl, $(C_{9-12})$bicycloaryl and hetero$(C_{4-12})$ bicycloaryl, each substituted or unsubstituted;
$R_3$ is selected from the group consisting of hydrogen, alkoxy, aryloxy, heteroaryloxy, $(C_{1-10})$alkyl, halo$(C_{1-10})$ alkyl, alkoxy$(C_{1-10})$alkyl, carbonyl$(C_{1-3})$alkyl, thiocarbonyl$(C_{1-3})$alkyl, carboxamido$(C_{1-3})$alkyl, sulfonyl $(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero $(C_{2-12})$cycloalkyl$(C_{1-5})$alkyl, aryl$(C_{1-10})$alkyl, heteroaryl$(C_{1-5})$alkyl, $(C_{9-12})$bicyclo aryl$(C_{1-5})$alkyl, hetero$(C_{4-12})$bicyoloaryl$(C_{1-5})$alkyl, $(C_{3-12})$cycloalkyl, hetero$(C_{2-12})$cycloalkyl, $(C_{9-12})$bicycloalkyl, hetero $(C_{3-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted;
$R_7$ is selected from the group consisting of hydrogen, $(C_{1-10})$alkyl, halo$(C_{1-10})$alkyl, carbonyl$(C_{1-3})$alkyl, carboxamidoalkyl, amidoalkyl, thiocarbonyl$(C_{1-3})$alkyl, sulfonyl$(C_{1-3})$alkyl, sulfinyl$(C_{1-3})$alkyl, amino$(C_{1-10})$ alkyl, imino$(C_{1-3})$alkyl, alkoxy$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero $(C_{2-10})$aryl, $(C_{9-12})$bicycloaryl and hetero$(C_{4-12})$bicycloaryl, each substituted or unsubstituted, or $R_7$ and a substituent of L are taken together to form a ring; and
$R_{12}$ is selected from the group consisting of hydrogen, hydroxyl, alkoxy, aryloxy, heteroaryloxy, $(C_{1-10})$alkyl, halo$(C_{1-10})$alkyl, $(C_{3-12})$cycloalkyl$(C_{1-5})$alkyl, hetero $(C_{2-12})$cycloalkyl$(C_{1-5})$alkyl, aryl$(C_{1-10})$alkyl, heteroaryl$(C_{1-5})$alkyl, $(C_{3-12})$cycloalkyl, hetero$(C_{2-12})$cycloalkyl, $(C_{5-12})$aryl, hetero$(C_{2-10})$aryl, each substituted or unsubstituted;
provided that $R_1$ and $R_3$ are not both hydrogen;
wherein
the compound includes any hydrate, solvate, ester, tautomer, enantiomer, and pharmaceutically acceptable salt form of the compound.

In another embodiment, compounds of the present invention is of the formula:

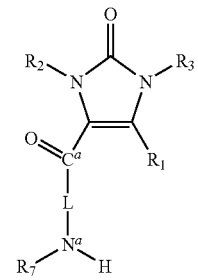

wherein
$C^a$ denotes a carbon atom;
$N^a$ denotes a nitrogen atom;
L is a linker moiety between 1-5 atoms in length as measured between $C^a$ and $N^a$;
$R_1$ is selected from the group consisting of hydrogen, carbonyl, oxycarbonyl, aminocarbonyl, $(C_{1-10})$alkylamino, sulfonamido, sulfonyl, sulfinyl, $(C_{1-10})$alkyl, halo $(C_{1-10})$alkyl, alkoxy$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicyclo aryl $(C_{1-5})$alkyl, $(C_{3-12})$cycloalkyl, hetero$(C_{2-12})$cycloalkyl, $(C_{9-12})$bicycloalkyl, hetero$(C_{2-12})$bicycloalkyl, $(C_{5-12})$ aryl, hetero$(C_{2-10})$aryl, $(C_{9-12})$bicycloaryl and hetero $(C_{4-12})$bicycloaryl, each substituted or unsubstituted;
$R_2$ is selected from the group consisting of hydrogen, alkoxy, aryloxy, heteroaryloxy, $(C_{1-10})$alkyl, halo$(C_{1-10})$ alkyl, alkoxy$(C_{1-10})$alkyl, carbonyl$(C_{1-3})$alkyl, thiocarbonyl$(C_{1-3})$alkyl, carboxamido$(C_{1-3})$alkyl, amido$(C_{1-3})$ alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$ alkyl, hetero$(C_{2-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{4-12})$bicycloaryl$(C_{1-5})$alkyl, $(C_{3-12})$ cycloalkyl, hetero$(C_{2-12})$cycloalkyl, $(C_{9-12})$ bicycloalkyl, hetero$(C_{3-12})$bicycloalkyl, $(C_{5-12})$aryl, hetero($C_{2-10}$)aryl, ($C_{9-12}$)bicycloaryl and hetero($C_{4-12}$)bicycloaryl, each substituted or unsubstituted;

$R_3$ is selected from the group consisting of hydrogen, alkoxy, aryloxy, heteroaryloxy, ($C_{1-10}$)alkyl, halo($C_{1-10}$) alkyl, alkoxy($C_{1-10}$)alkyl, carbonyl($C_{1-3}$)alkyl, thiocarbonyl($C_{1-3}$)alkyl, carboxamido($C_{1-3}$)alkyl, sulfonyl ($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero ($C_{2-12}$)cycloalkyl($C_{1-5}$)alkyl, aryl($C_{1-10}$)alkyl, heteroaryl($C_{1-5}$)alkyl, ($C_{9-12}$)bicyclo aryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero ($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted; and $R_7$ is selected from the group consisting of hydrogen, ($C_{1-10}$)alkyl, halo($C_{1-10}$)alkyl, carbonyl($C_{1-3}$)alkyl, carboxamido alkyl, amido alkyl, thiocarbonyl($C_{1-3}$)alkyl, sulfonyl($C_{1-3}$)alkyl, sulfinyl($C_{1-3}$)alkyl, amino($C_{1-10}$) alkyl, imino($C_{1-3}$)alkyl, alkoxy($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicyclo aryl($C_{1-5}$)alkyl, hetero($C_{4-12}$)bicyclo aryl($C_{1-5}$)alkyl, ($C_{3-12}$)cyclo alkyl, hetero ($C_{2-12}$)cyclo alkyl, ($C_{9-12}$)bicyclo alkyl, hetero ($C_{3-12}$)bicyclo alkyl, ($C_{5-12}$)aryl, hetero($C_{2-10}$)aryl, ($C_{9-12}$)bicycloaryl and hetero($C_{4-12}$)bicycloaryl, each substituted or unsubstituted, or $R_7$ and a substituent of L are taken together to form a ring;

provided that $R_1$ and $R_3$ are not both hydrogen;

wherein the compound includes any hydrate, solvate, ester, tautomer, enantiomer, and pharmaceutically acceptable salt form of the compound.

In another embodiment, compounds of the present invention is of the formula:

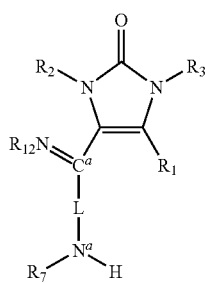

wherein $C^a$ denotes a carbon atom;

$N^a$ denotes a nitrogen atom;

L is a linker moiety between 1-5 atoms in length as measured between $C^a$ and $N^a$, wherein the first atom of L attaching to $C^a$ is a nitrogen atom;

$R_1$ is selected from the group consisting of hydrogen, carbonyl, oxycarbonyl, aminocarbonyl, ($C_{1-10}$)alkylamino, sulfonamido, sulfonyl, sulfinyl, ($C_{1-10}$)alkyl, halo ($C_{1-10}$)alkyl, alkoxy($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl ($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicyclo aryl ($C_{1-5}$)alkyl, ($C_{3-12}$)cycloalkyl, hetero($C_{2-12}$)cycloalkyl, ($C_{9-12}$)bicycloalkyl, hetero($C_{2-12}$)bicycloalkyl, ($C_{5-12}$) aryl, hetero($C_{2-10}$)aryl, ($C_{9-12}$)bicycloaryl and hetero ($C_{4-12}$)bicycloaryl, each substituted or unsubstituted;

$R_2$ is selected from the group consisting of hydrogen, alkoxy, aryloxy, heteroaryloxy, ($C_{1-10}$)alkyl, halo($C_{1-10}$) alkyl, alkoxy($C_{1-10}$)alkyl, carbonyl($C_{1-3}$)alkyl, thiocarbonyl($C_{1-3}$)alkyl, carboxamido($C_{1-3}$)alkyl, amido($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$) alkyl, hetero($C_{2-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{4-12}$)bicycloaryl($C_{1-5}$)alkyl, ($C_{3-12}$) cycloalkyl, hetero($C_{2-12}$)cycloalkyl, ($C_{9-12}$) bicycloalkyl, hetero($C_{3-12}$)bicycloalkyl, ($C_{5-12}$)aryl, hetero($C_{2-10}$)aryl, ($C_{9-12}$)bicycloaryl and hetero($C_{4-12}$) bicycloaryl, each substituted or unsubstituted;

$R_3$ is selected from the group consisting of hydrogen, alkoxy, aryloxy, heteroaryloxy, ($C_{1-10}$)alkyl, halo($C_{1-10}$) alkyl, alkoxy($C_{1-10}$)alkyl, carbonyl($C_{1-3}$)alkyl, thiocarbonyl($C_{1-3}$)alkyl, carboxamido($C_{1-3}$)alkyl, sulfonyl ($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero ($C_{2-12}$)cycloalkyl($C_{1-5}$)alkyl, aryl($C_{1-10}$)alkyl, heteroaryl($C_{1-5}$)alkyl, ($C_{9-12}$)bicyclo aryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero ($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted;

$R_7$ is selected from the group consisting of hydrogen, ($C_{1-10}$)alkyl, halo($C_{1-10}$)alkyl, carbonyl($C_{1-3}$)alkyl, carboxamidoalkyl, amidoalkyl, thiocarbonyl($C_{1-3}$)alkyl, sulfonyl($C_{1-3}$)alkyl, sulfinyl($C_{1-3}$)alkyl, amino($C_{1-10}$) alkyl, imino($C_{1-3}$)alkyl, alkoxy($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero ($C_{2-10}$)aryl, ($C_{9-12}$)bicycloaryl and hetero($C_{4-12}$)bicycloaryl, each substituted or unsubstituted, or $R_7$ and a substituent of L are taken together to form a ring; and $R_{12}$ is selected from the group consisting of hydrogen, hydroxyl, alkoxy, aryloxy, heteroaryloxy, ($C_{1-10}$)alkyl, halo($C_{1-10}$)alkyl, ($C_{3-12}$)cycloalkyl($C_{1-5}$)alkyl, hetero ($C_{2-12}$)cycloalkyl($C_{1-5}$)alkyl, aryl($C_{1-10}$)alkyl, heteroaryl($C_{1-5}$)alkyl, ($C_{3-12}$)cycloalkyl, hetero($C_{2-12}$)cycloalkyl, ($C_{5-12}$)aryl, hetero($C_{2-10}$)aryl, each substituted or unsubstituted;

provided that $R_1$ and $R_3$ are not both hydrogen;

wherein the compound includes any hydrate, solvate, ester, tautomer, enantiomer, and pharmaceutically acceptable salt form of the compound.

In another embodiment, compounds of the present invention is of the formula

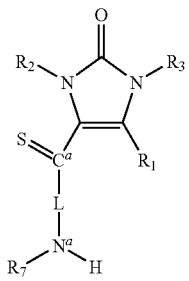

wherein
$C^a$ denotes a carbon atom;
$N^a$ denotes a nitrogen atom;
L is a linker moiety between 1-5 atoms in length as measured between $C^a$ and $N^a$, wherein the first atom of L attaching to $C^a$ is a nitrogen atom;
$R_1$ is selected from the group consisting of hydrogen, carbonyl, oxycarbonyl, aminocarbonyl, $(C_{1-10})$alkylamino, sulfonamido, sulfonyl, sulfinyl, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{2-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted;
$R_2$ is selected from the group consisting of hydrogen, alkoxy, aryloxy, heteroaryloxy, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, carboxamido$(C_{1-3})$alkyl, amido$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted;
$R_3$ is selected from the group consisting of hydrogen, alkoxy, aryloxy, heteroaryloxy, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, carboxamido$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicyclo aryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted; and
$R_7$ is selected from the group consisting of hydrogen, $(C_{1-10})$alkyl, halo$(C_{1-10})$alkyl, carbonyl$(C_{1-3})$alkyl, carboxamidoalkyl, amidoalkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, alkoxy$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted, or $R_7$ and a substituent of L are taken together to form a ring;
provided that $R_1$ and $R_3$ are not both hydrogen;
wherein
the compound includes any hydrate, solvate, ester, tautomer, enantiomer, and pharmaceutically acceptable salt form of the compound.

In one variation of any one of the preceding embodiments, L is a linker moiety between 1-4 atoms in length as measured between Q and $N^a$ or between $C^a$ and $N^a$.

In another variation, L is a linker moiety between 2-4 atoms in length as measured between Q and $N^a$ or between $C^a$ and $N^a$.

In another variation, L is a linker moiety between 3-4 atoms in length as measured between Q and $N^a$ or between $C^a$ and $N^a$.

In another variation, one or more of the atoms of L that provide the 1-5 atom length as measured between Q and $N^a$ or between $C^a$ and $N^a$ form a portion of a substituted or unsubstituted three, four, five, six, or seven membered ring.

In another variation, one or more of the atoms of L that provide the 1-5 atom length as measured between Q and $N^a$ or between $C^a$ and $N^a$ form a portion of a substituted or unsubstituted three, four, five, six, or seven membered cycloalkyl and heterocycloalkyl ring.

In another variation, one or more of the atoms of L that provide the 1-5 atom length as measured between Q and $N^a$ or between $C^a$ and $N^a$ form a portion of a substituted or unsubstituted three, four, five, six, seven, eight or nine membered alicyclic and heteroalicyclic ring.

In another variation, one or more of the atoms of L that provide the 1-5 atom length as measured between Q and $N^a$ or between $C^a$ and $N^a$ form a portion of a substituted or unsubstituted three, four, five, six, seven, eight or nine membered aromatic ring.

In another variation, one or more of the atoms of L that provide the 1-5 atom length as measured between Q and $N^a$ or between $C^a$ and $N^a$ form a portion of a ring selected from the group consisting of cyclopropane, cyclobutane, cyclopentane, cyclopentene, cyclopentadiene, cyclohexane, cyclohexene, cyclohexadiene, benzene, cycloheptane, cycloheptene, and cycloheptadiene, cyclooctane, cyclooctene, and cyclooctadiene, each substituted or unsubstituted.

In another variation, one or more of the atoms of L that provide the 1-5 atom length as measured between Q and $N^a$ or between $C^a$ and $N^a$ form a portion of a ring selected from the group consisting of benzene, biphenyl, pyran, pyridine, piperidine, dioxane, morpholine, dithiane, thiomorpholine, pyridazine, pyrimidine, pyrazine, piperazine, and triazine, each substituted or unsubstituted.

In another variation, one or more of the atoms of L that provide the 1-5 atom length as measured between Q and $N^a$ or between $C^a$ and $N^a$ form a portion of a moiety selected from the group consisting of furan, thiofuran, pyrrole, isopyrrole, pyrazole, isoimidazole, triazole, isoxazole, oxazole, thiazole, isothiazole, oxadiazole, oxatriazole, pyridine, pyridazine, pyrimidine, pyrazine, triazine, benzofuran, isobenzofuran, benzothiofuran, isobenzothiofuran, indole, isobenzazole, quinoline, isoquinoline, cinnoline, quinazoline, naphthyridine, and pyridopyridine, each substituted or unsubstituted.

In another variation, the atoms of L in a direct chain between Q and $N^a$ or between $C^a$ and $N^a$ are selected from the group consisting of carbon, oxygen, nitrogen, and sulfur atoms.

In another variation, the atoms of L in a direct chain between Q and $N^a$ or between $C^a$ and $N^a$ are selected from the group consisting of carbon and nitrogen atoms.

In another variation, when Q is —C(O)—, the atoms of L in a direct chain between Q and $N^a$ or between $C^a$ and $N^a$ are all carbon atoms.

In another variation, one or more of the atoms of L that provide the 1-5 atom length as measured between Q and $N^a$ or between $C^a$ and $N^a$ form a portion of a substituted or unsubstituted piperazine ring.

In another variation, L is -$(A)_k$;
wherein
k is selected from the group consisting of 1, 2, 3, 4 and 5;
each A is independently selected from the group consisting of —$NR_9$—, —O—, —S—, and —$CR_5R_6$—,
where
$R_5$ and $R_6$ are each independently selected from the group consisting of hydrogen, oxycarbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicyclo aryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl, and hetero($C_{4-12}$)bicycloaryl, each substituted or unsubstituted, and $R_6$ may be absent when the carbon to which it is bound forms part of a double bond, and $R_5$ and $R_6$ on a given carbon may be taken together to form =O, =S, or =$NR_{10}$, wherein $R_{10}$ is selected from the group consisting of hydrogen, hydroxyl, alkoxy, aryloxy, heteroaryloxy, ($C_{1-10}$)alkyl, halo($C_{1-10}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-4}$)alkyl, ($C_{3-12}$)cycloalkyl, hetero($C_{2-12}$)cycloalkyl, ($C_{5-12}$)aryl, and hetero($C_{2-10}$)aryl, each substituted or unsubstituted;

$R_9$ is selected from the group consisting of hydrogen, alkoxy, aryloxy, heteroaryloxy, ($C_{1-10}$)alkyl, halo($C_{1-10}$)alkyl, carbonyl($C_{1-3}$)alkyl, aminocarbonylalkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, alkoxy($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicyclo aryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{4-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted, and $R_9$ may be absent when the nitrogen to which it is attached forms part of a double bond; and any two adjacent $R_5$, $R_6$, $R_7$ and $R_9$ may be taken together to form a substituted or unsubstituted five, six, seven or eight membered ring.

In another variation, L is *—$NR_9$-$(A)_{k'}$-,
wherein
* indicates the point of attachment of —$NR_9$-$(A)_{k'}$- to either Q or $C^a$;
k' is selected from the group consisting of 1, 2, 3 and 4;
each A is independently selected from the group consisting of —$NR_9$—, —O—, —S—, and —$CR_5R_6$—
where
$R_5$ and $R_6$ are each independently selected from the group consisting of hydrogen, oxycarbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero ($C_{4-12}$)bicyclo aryl($C_{1-5}$)alkyl, ($C_{3-12}$)cyclo alkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl, and hetero($C_{4-12}$)bicycloaryl, each substituted or unsubstituted, and $R_5$ and $R_6$ on a given carbon may be taken together to form =O, =S, or =$NR_{10}$, where $R_{10}$ is selected from the group consisting of hydrogen, hydroxyl, alkoxy, aryloxy, heteroaryloxy, ($C_{1-10}$)alkyl, halo($C_{1-10}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{3-12}$)cycloalkyl, hetero($C_{2-12}$)cycloalkyl, ($C_{5-12}$)aryl, and hetero($C_{2-10}$)aryl, each substituted or unsubstituted, and $R_6$ is absent when the carbon to which it is bound forms part of a double bond;

$R_9$ is selected from the group consisting of hydrogen, alkoxy, aryloxy, heteroaryloxy, ($C_{1-10}$)alkyl, halo($C_{1-10}$)alkyl, carbonyl($C_{1-3}$)alkyl, aminocarbonylalkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, alkoxy($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicyclo aryl($C_{1-5}$)alkyl, hetero($C_{4-12}$)bicyclo aryl($C_{1-5}$)alkyl, ($C_{3-12}$)cycloalkyl, hetero($C_{2-12}$)cycloalkyl, ($C_{9-12}$)bicycloalkyl, hetero($C_{4-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted, $R_9$ is absent when the nitrogen to which it is bound forms part of a double bond; and any two adjacent $R_5$ and $R_6$ may be taken together to form a five, six, seven, or eight membered ring, each substituted or unsubstituted, $R_9$ and one of $R_5$ and $R_6$ may be taken together to form a five, six, seven, or eight membered ring, each substituted or unsubstituted, $R_7$ and one of $R_5$ and $R_6$ may be taken together to form a five, six, seven, or eight membered ring, each substituted or unsubstituted, and $R_7$ and $R_9$ may be taken together to form a five, six, seven, or eight membered ring, each substituted or unsubstituted.

In another variation, -L-N$^a$R$_7$H is selected from the group consisting of

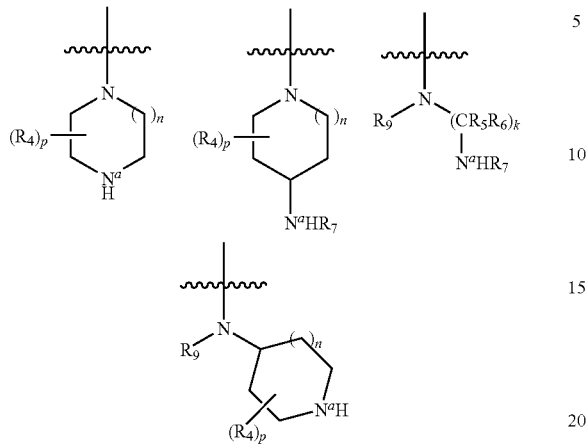

where
k is 0, 1, 2, 3, 4 or 5;
n is 0, 1 or 2;
p is 0, 1, 2, 3 or 4;
each R$_4$ is independently selected from the group consisting of hydrogen, oxo, oxyalkyl, alkoxycarbonyl, carbonyl, thioalkyl, alkoxy, oxycarbonyl, aminocarbonyl, amino, amido, carboxamido, sulfonyl, sulfinyl, (C$_{1-10}$)alkyl, halo(C$_{1-10}$)alkyl, oxyalkyl, alkoxyalkyl, alkylthioalkyl, carbonyl(C$_{1-3}$)alkyl, thiocarbonyl (C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, carboxamido (C$_{1-10}$)alkyl, amido(C$_{1-10}$)alkyl, (C$_{3-12}$)cycloalkyl (C$_{1-5}$)alkyl, hetero(C$_{2-12}$)cycloalkyl(C$_{1-5}$)alkyl, aryl (C$_{1-10}$)alkyl, heteroaryl(C$_{1-5}$)alkyl, aryloxyalkyl, heteroarylalkyl, (C$_{9-12}$)bicycloaryl(C$_{1-5}$)alkyl, hetero (C$_{4-12}$)bicycloaryl(C$_{1-5}$)alkyl, (C$_{3-12}$)cycloalkyl, hetero(C$_{2-12}$)cycloalkyl, (C$_{9-12}$)bicycloalkyl, hetero (C$_{3-12}$)bicycloalkyl, (C$_{5-12}$)aryl, hetero(C$_{2-10}$)aryl, (C$_{9-12}$)bicycloaryl, and hetero(C$_{4-12}$)bicycloaryl, each substituted or unsubstituted;
R$_5$ and R$_6$ are each independently selected from the group consisting of hydrogen, oxycarbonyl, sulfonyl, sulfinyl, (C$_{1-10}$)alkyl, halo(C$_{1-10}$)alkyl, carbonyl (C$_{1-3}$)alkyl, thiocarbonyl(C$_{1-3}$)alkyl, sulfonyl(C$_{1-3}$) alkyl, sulfinyl(C$_{1-3}$)alkyl, amino(C$_{1-10}$)alkyl, imino (C$_{1-3}$)alkyl, (C$_{3-12}$)cycloalkyl(C$_{1-5}$)alkyl, hetero (C$_{2-12}$)cycloalkyl(C$_{1-5}$)alkyl, aryl(C$_{1-10}$)alkyl, heteroaryl(C$_{1-5}$)alkyl, (C$_{9-12}$)bicyclo aryl(C$_{1-5}$)alkyl, hetero(C$_{4-12}$)bicycloaryl(C$_{1-5}$)alkyl, (C$_{3-12}$)cycloalkyl, hetero(C$_{2-12}$)cycloalkyl, (C$_{9-12}$)bicycloalkyl, hetero(C$_{3-12}$)bicycloalkyl, (C$_{5-12}$)aryl, hetero(C$_{2-10}$)aryl, (C$_{9-12}$)bicycloaryl, and hetero(C$_{4-12}$) bicycloaryl, each substituted or unsubstituted, and R$_5$ and R$_6$ on a given carbon may be taken together to form =O, =S, or =NR$_{10}$, where R$_{10}$ is selected from the group consisting of hydrogen, hydroxyl, alkoxy, aryloxy, heteroaryloxy, (C$_{1-10}$)alkyl, halo (C$_{1-10}$)alkyl, (C$_{3-12}$)cycloalkyl(C$_{1-5}$)alkyl, hetero (C$_{2-12}$)cycloalkyl(C$_{1-5}$)alkyl, aryl(C$_{1-10}$)alkyl, heteroaryl(C$_{1-5}$)alkyl, (C$_{3-12}$)cycloalkyl, hetero(C$_{2-12}$) cycloalkyl, (C$_{5-12}$)aryl, and hetero(C$_{2-10}$)aryl, each substituted or unsubstituted, and R$_6$ is absent when the carbon to which it is bound forms part of a double bond;

R$_7$ is selected from the group consisting of hydrogen, (C$_{1-10}$)alkyl, halo(C$_{1-10}$)alkyl, carbonyl(C$_{1-3}$)alkyl, carboxamidoalkyl, amidoalkyl, thiocarbonyl(C$_{1-3}$) alkyl, sulfonyl(C$_{1-3}$)alkyl, sulfinyl(C$_{1-3}$)alkyl, amino (C$_{1-10}$)alkyl, imino(C$_{1-3}$)alkyl, alkoxy(C$_{1-3}$)alkyl, (C$_{3-12}$)cycloalkyl(C$_{1-5}$)alkyl, hetero(C$_{2-12}$)cycloalkyl(C$_{1-5}$)alkyl, aryl(C$_{1-10}$)alkyl, heteroaryl (C$_{1-5}$)alkyl, (C$_{9-12}$)bicycloaryl(C$_{1-5}$)alkyl, hetero (C$_{4-12}$)bicycloaryl(C$_{1-5}$)alkyl, (C$_{3-12}$)cycloalkyl, hetero(C$_{2-12}$)cycloalkyl, (C$_{9-12}$)bicycloalkyl, hetero (C$_{3-12}$)bicycloalkyl, (C$_{5-12}$)aryl, hetero(C$_{2-10}$)aryl, (C$_{9-12}$)bicycloaryl and hetero(C$_{4-12}$)bicycloaryl, each substituted or unsubstituted, and R$_9$ is selected from the group consisting of hydrogen, alkoxy, aryloxy, heteroaryloxy, (C$_{1-10}$)alkyl, halo (C$_{1-10}$)alkyl, carbonyl(C$_{1-3}$)alkyl, aminocarbonylalkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$) alkyl, alkoxy(C$_{1-3}$)alkyl, (C$_{3-12}$)cycloalkyl(C$_{1-5}$) alkyl, hetero(C$_{2-12}$)cycloalkyl(C$_{1-5}$)alkyl, aryl(C$_{1-10}$) alkyl, heteroaryl(C$_{1-5}$)alkyl, (C$_{9-12}$)bicyclo aryl(C$_{1-5}$) alkyl, hetero(C$_{4-12}$)bicycloaryl(C$_{1-5}$)alkyl, (C$_{3-12}$) cycloalkyl, hetero(C$_{2-12}$)cycloalkyl, (C$_{9-12}$) bicycloalkyl, hetero(C$_{4-12}$)bicycloalkyl, (C$_{5-12}$)aryl, hetero(C$_{2-10}$)aryl, (C$_{9-12}$)bicycloaryl, and hetero (C$_{4-12}$)bicycloaryl, each substituted or unsubstituted.

In another embodiment, the compound has the formula

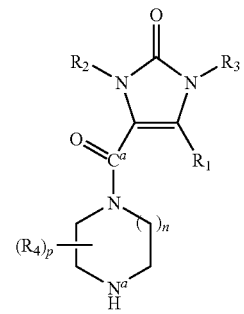

wherein
C$_a$ denotes a carbon atom;
N$_a$ denotes a nitrogen atom;
n is 0, 1, or 2;
p is 0, 1, 2, 3, or 4; and
R$_1$ is selected from the group consisting of hydrogen, carbonyl, oxycarbonyl, aminocarbonyl, (C$_{1-10}$)alkylamino, sulfonamido, sulfonyl, sulfinyl, (C$_{1-10}$)alkyl, halo (C$_{1-10}$)alkyl, alkoxy(C$_{1-10}$)alkyl, carbonyl(C$_{1-3}$)alkyl, thiocarbonyl(C$_{1-3}$)alkyl, sulfonyl(C$_{1-3}$)alkyl, sulfinyl (C$_{1-3}$)alkyl, amino(C$_{1-10}$)alkyl, imino(C$_{1-3}$)alkyl, (C$_{3-12}$)cycloalkyl(C$_{1-5}$)alkyl, hetero(C$_{2-12}$)cycloalkyl (C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{4-12}$)bicyclo aryl (C$_{1-5}$)alkyl, (C$_{3-12}$)cycloalkyl, hetero(C$_{2-12}$)cycloalkyl, (C$_{9-12}$)bicycloalkyl, hetero(C$_{2-12}$)bicycloalkyl, (C$_{5-12}$) aryl, hetero(C$_{2-10}$)aryl, (C$_{9-12}$)bicycloaryl and hetero (C$_{4-12}$)bicycloaryl, each substituted or unsubstituted;

R$_2$ is selected from the group consisting of hydrogen, alkoxy, aryloxy, heteroaryloxy, (C$_{1-10}$)alkyl, halo(C$_{1-10}$) alkyl, alkoxy(C$_{1-10}$)alkyl, carbonyl(C$_{1-3}$)alkyl, thiocarbonyl(C$_{1-3}$)alkyl, carboxamido(C$_{1-3}$)alkyl, amido(C$_{1-3}$) alkyl, sulfonyl(C$_{1-3}$)alkyl, sulfinyl(C$_{1-3}$)alkyl, amino (C$_{1-10}$)alkyl, imino(C$_{1-3}$)alkyl, (C$_{3-12}$)cycloalkyl(C$_{1-5}$) alkyl, hetero(C$_{2-12}$)cycloalkyl(C$_{1-5}$)alkyl, aryl(C$_{1-10}$)

alkyl, heteroaryl($C_{1-5}$)alkyl, ($C_{9-12}$)bicycloaryl($C_{1-5}$) alkyl, hetero($C_{4-12}$)bicycloaryl($C_{1-5}$)alkyl, ($C_{3-12}$) cycloalkyl, hetero($C_{2-12}$)cycloalkyl, ($C_{9-12}$) bicycloalkyl, hetero($C_{3-12}$)bicycloalkyl, ($C_{5-12}$)aryl, hetero($C_{2-10}$)aryl, ($C_{9-12}$)bicycloaryl and hetero($C_{4-12}$) bicycloaryl, each substituted or unsubstituted;

$R_3$ is selected from the group consisting of hydrogen, alkoxy, aryloxy, heteroaryloxy, ($C_{1-10}$)alkyl, halo($C_{1-10}$) alkyl, alkoxy($C_{1-10}$)alkyl, carbonyl($C_{1-3}$)alkyl, thiocarbonyl($C_{1-3}$)alkyl, carboxamido($C_{1-3}$)alkyl, sulfonyl ($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero ($C_{2-12}$)cycloalkyl($C_{1-5}$)alkyl, aryl($C_{1-10}$)alkyl, heteroaryl($C_{1-5}$)alkyl, ($C_{9-12}$)bicyclo aryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero ($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted; and each $R_4$ is independently selected from the group consisting of hydrogen, oxo, oxyalkyl, alkoxycarbonyl, carbonyl, thioalkyl, alkoxy, oxycarbonyl, aminocarbonyl, amino, amido, carboxamido, sulfonyl, sulfinyl, ($C_{1-10}$) alkyl, halo($C_{1-10}$)alkyl, oxyalkyl, alkoxyalkyl, alkylthioalkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$) alkyl, imino($C_{1-3}$)alkyl, carboxamido($C_{1-10}$)alkyl, amido($C_{1-10}$)alkyl, ($C_{3-12}$)cycloalkyl($C_{1-5}$)alkyl, hetero ($C_{2-12}$)cycloalkyl($C_{1-5}$)alkyl, aryl($C_{1-10}$)alkyl, heteroaryl($C_{1-5}$)alkyl, aryloxyalkyl, heteroarylalkyl, ($C_{9-12}$)bicycloaryl($C_{1-5}$)alkyl, hetero($C_{4-12}$)bicycloaryl ($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$) aryl, hetero($C_{2-10}$)aryl, ($C_{9-12}$)bicycloaryl, and hetero ($C_{4-12}$)bicycloaryl, each substituted or unsubstituted;

provided that $R_1$ and $R_3$ are not both hydrogen;

wherein the compound includes any hydrate, solvate, ester, tautomer, enantiomer, and pharmaceutically acceptable salt form of the compound.

In another embodiment, the compound has the formula

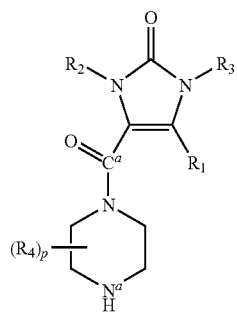

wherein $C_a$ denotes a carbon atom;

$N_a$ denotes a nitrogen atom;

p is 0, 1, 2, 3, or 4; and $R_1$ is selected from the group consisting of hydrogen, carbonyl, oxycarbonyl, aminocarbonyl, ($C_{1-10}$)alkylamino, sulfonamido, sulfonyl, sulfinyl, ($C_{1-10}$)alkyl, halo ($C_{1-10}$)alkyl, alkoxy($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl ($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl ($C_{1-5}$)alkyl, ($C_{3-12}$)cycloalkyl, hetero($C_{2-12}$)cycloalkyl, ($C_{9-12}$)bicycloalkyl, hetero($C_{2-12}$)bicycloalkyl, ($C_{5-12}$) aryl, hetero($C_{2-10}$)aryl, ($C_{9-12}$)bicycloaryl and hetero ($C_{4-12}$)bicycloaryl, each substituted or unsubstituted;

$R_2$ is selected from the group consisting of hydrogen, alkoxy, aryloxy, heteroaryloxy, ($C_{1-10}$)alkyl, halo($C_{1-10}$) alkyl, alkoxy($C_{1-10}$)alkyl, carbonyl($C_{1-3}$)alkyl, thiocarbonyl($C_{1-3}$)alkyl, carboxamido($C_{1-3}$)alkyl, amido($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$) alkyl, hetero($C_{2-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{4-12}$)bicycloaryl($C_{1-5}$)alkyl, ($C_{3-12}$) cycloalkyl, hetero($C_{2-12}$)cycloalkyl, ($C_{9-12}$) bicycloalkyl, hetero($C_{3-12}$)bicycloalkyl, ($C_{5-12}$)aryl, hetero($C_{2-10}$)aryl, ($C_{9-12}$)bicycloaryl and hetero($C_{4-12}$) bicycloaryl, each substituted or unsubstituted;

$R_3$ is selected from the group consisting of hydrogen, alkoxy, aryloxy, heteroaryloxy, ($C_{1-10}$)alkyl, halo($C_{1-10}$) alkyl, alkoxy($C_{1-10}$)alkyl, carbonyl($C_{1-3}$)alkyl, thiocarbonyl($C_{1-3}$)alkyl, carboxamido($C_{1-3}$)alkyl, sulfonyl ($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero ($C_{2-12}$)cycloalkyl($C_{1-5}$)alkyl, aryl($C_{1-10}$)alkyl, heteroaryl($C_{1-5}$)alkyl, ($C_{9-12}$)bicyclo aryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero ($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted; and each $R_4$ is independently selected from the group consisting of hydrogen, oxo, oxyalkyl, alkoxycarbonyl, carbonyl, thioalkyl, alkoxy, oxycarbonyl, aminocarbonyl, amino, amido, carboxamido, sulfonyl, sulfinyl, ($C_{1-10}$) alkyl, halo($C_{1-10}$)alkyl, oxyalkyl, alkoxyalkyl, alkylthioalkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$) alkyl, imino($C_{1-3}$)alkyl, carboxamido($C_{1-10}$)alkyl, amido($C_{1-10}$)alkyl, ($C_{3-12}$)cycloalkyl($C_{1-5}$)alkyl, hetero ($C_{2-12}$)cycloalkyl($C_{1-5}$)alkyl, aryl($C_{1-10}$)alkyl, heteroaryl($C_{1-5}$)alkyl, aryloxyalkyl, heteroarylalkyl, ($C_{9-12}$)bicycloaryl($C_{1-5}$)alkyl, hetero($C_{4-12}$)bicycloaryl ($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$) aryl, hetero($C_{2-10}$)aryl, ($C_{9-12}$)bicycloaryl, and hetero ($C_{4-12}$)bicycloaryl, each substituted or unsubstituted;

provided that $R_1$ and $R_3$ are not both hydrogen;

wherein the compound includes any hydrate, solvate, ester, tautomer, enantiomer, and pharmaceutically acceptable salt form of the compound.

In another embodiment, the compound has the formula

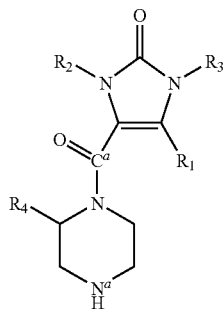

wherein
$C_a$ denotes a carbon atom;
$N_a$ denotes a nitrogen atom;
p is 0, 1, 2, 3, or 4; and
$R_1$ is selected from the group consisting of hydrogen, carbonyl, oxycarbonyl, aminocarbonyl, $(C_{1-10})$alkylamino, sulfonamido, sulfonyl, sulfinyl, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{2-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted;

$R_2$ is selected from the group consisting of hydrogen, alkoxy, aryloxy, heteroaryloxy, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, carboxamido$(C_{1-3})$alkyl, amido$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted;

$R_3$ is selected from the group consisting of hydrogen, alkoxy, aryloxy, heteroaryloxy, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, carboxamido$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicyclo aryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted; and each $R_4$ is independently selected from the group consisting of hydrogen, oxo, oxyalkyl, alkoxycarbonyl, carbonyl, thioalkyl, alkoxy, oxycarbonyl, aminocarbonyl, amino, amido, carboxamido, sulfonyl, sulfinyl, $(C_{1-10})$alkyl, halo$(C_{1-10})$alkyl, oxyalkyl, alkoxyalkyl, alkylthioalkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, carboxamido$(C_{1-10})$alkyl, amido$(C_{1-10})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, aryloxyalkyl, heteroarylalkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl, and hetero$(C_{4-12})$bicycloaryl, each substituted or unsubstituted;

provided that $R_1$ and $R_3$ are not both hydrogen;
wherein
the compound includes any hydrate, solvate, ester, tautomer, enantiomer, and pharmaceutically acceptable salt form of the compound.

In another embodiment, the compound has the formula

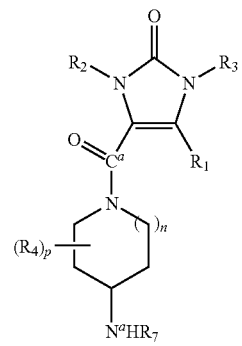

wherein:
$C_a$ denotes a carbon atom;
$N_a$ denotes a nitrogen atom;
n is 0, 1, or 2;
p is 0, 1, 2, 3, or 4;
$R_1$ is selected from the group consisting of hydrogen, carbonyl, oxycarbonyl, aminocarbonyl, $(C_{1-10})$alkylamino, sulfonamido, sulfonyl, sulfinyl, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{2-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted;

$R_2$ is selected from the group consisting of hydrogen, alkoxy, aryloxy, heteroaryloxy, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, carboxamido$(C_{1-3})$alkyl, amido$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted;

$R_3$ is selected from the group consisting of hydrogen, alkoxy, aryloxy, heteroaryloxy, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, carboxamido$(C_{1-3})$alkyl, sulfonyl$(C_{1-3})$alkyl, sulfinyl$(C_{1-3})$alkyl, amino$(C_{1-10})$alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicyclo aryl($C_{1-5}$)alkyl, hetero($C_{4-12}$)bicyclo aryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted;

each $R_4$ is independently selected from the group consisting of hydrogen, oxo, oxyalkyl, alkoxycarbonyl, carbonyl, thioalkyl, alkoxy, oxycarbonyl, aminocarbonyl, amino, amido, carboxamido, sulfonyl, sulfinyl, ($C_{1-10}$)alkyl, halo($C_{1-10}$)alkyl, oxyalkyl, alkoxyalkyl, alkylthio alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, carboxamido($C_{1-10}$)alkyl, amido($C_{1-10}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, aryloxyalkyl, heteroarylalkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl, and hetero($C_{4-12}$)bicycloaryl, each substituted or unsubstituted; and $R_7$ is selected from the group consisting of hydrogen, ($C_{1-10}$)alkyl, halo($C_{1-10}$)alkyl, carbonyl($C_{1-3}$)alkyl, carboxamido alkyl, amido alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, alkoxy($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero ($C_{2-12}$)cyclo alkyl, ($C_{9-12}$)bicyclo alkyl, hetero ($C_{3-12}$)bicyclo alkyl, ($C_{5-12}$)aryl, hetero($C_{2-10}$)aryl, ($C_{9-12}$)bicycloaryl and hetero($C_{4-12}$)bicycloaryl, each substituted or unsubstituted;

provided that $R_1$ and $R_3$ are not both hydrogen;
wherein
the compound includes any polymorph, solvate, ester, tautomer, enantiomer, and pharmaceutically acceptable salt form of the compound.

In another embodiment, the compound has the formula

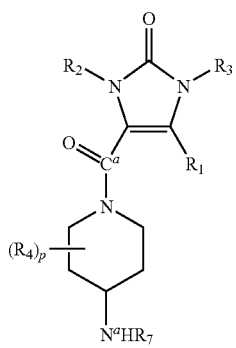

wherein:
$C_a$ denotes a carbon atom;
$N_a$ denotes a nitrogen atom;
p is 0, 1, 2, 3, or 4;
$R_1$ is selected from the group consisting of hydrogen, carbonyl, oxycarbonyl, aminocarbonyl, ($C_{1-10}$)alkylamino, sulfonamido, sulfonyl, sulfinyl, ($C_{1-10}$)alkyl, halo($C_{1-10}$)alkyl, alkoxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{2-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted;

$R_2$ is selected from the group consisting of hydrogen, alkoxy, aryloxy, heteroaryloxy, ($C_{1-10}$)alkyl, halo($C_{1-10}$)alkyl, alkoxy($C_{1-10}$)alkyl, carbonyl($C_{1-3}$)alkyl, thiocarbonyl($C_{1-3}$)alkyl, carboxamido($C_{1-3}$)alkyl, amido($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted;

$R_3$ is selected from the group consisting of hydrogen, alkoxy, aryloxy, heteroaryloxy, ($C_{1-10}$)alkyl, halo($C_{1-10}$)alkyl, alkoxy($C_{1-10}$)alkyl, carbonyl($C_{1-3}$)alkyl, thiocarbonyl($C_{1-3}$)alkyl, carboxamido($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicyclo aryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted;

each $R_4$ is independently selected from the group consisting of hydrogen, oxo, oxyalkyl, alkoxycarbonyl, carbonyl, thioalkyl, alkoxy, oxycarbonyl, aminocarbonyl, amino, amido, carboxamido, sulfonyl, sulfinyl, ($C_{1-10}$)alkyl, halo($C_{1-10}$)alkyl, oxyalkyl, alkoxyalkyl, alkylthioalkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, carboxamido($C_{1-10}$)alkyl, amido($C_{1-10}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, aryloxyalkyl, heteroarylalkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl, and hetero($C_{4-12}$)bicycloaryl, each substituted or unsubstituted; and $R_7$ is selected from the group consisting of hydrogen, ($C_{1-10}$)alkyl, halo($C_{1-10}$)alkyl, carbonyl($C_{1-3}$)alkyl, carboxamido alkyl, amido alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, alkoxy($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicyclo aryl($C_{1-5}$)alkyl, hetero($C_{4-12}$)bicycloaryl($C_{1-5}$)alkyl, ($C_{3-12}$)cyclo alkyl, hetero ($C_{2-12}$)cyclo alkyl, ($C_{9-12}$)bicyclo alkyl, hetero ($C_{3-12}$)bicyclo alkyl, ($C_{5-12}$)aryl, hetero($C_{2-10}$)aryl, ($C_{9-12}$)bicycloaryl and hetero($C_{4-12}$)bicycloaryl, each substituted or unsubstituted;

provided that $R_1$ and $R_3$ are not both hydrogen;

wherein
the compound includes any polymorph, solvate, ester, tautomer, enantiomer, and pharmaceutically acceptable salt form of the compound.

In another embodiment, the compound has the formula:

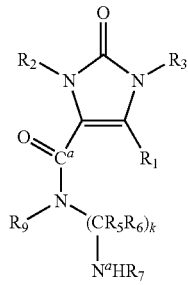

wherein:
$C_a$ denotes a carbon atom;
$N_a$ denotes a nitrogen atom;
k is 0, 1, 2, 3, 4 or 5;
$R_1$ is selected from the group consisting of hydrogen, carbonyl, oxycarbonyl, aminocarbonyl, $(C_{1-10})$alkylamino, sulfonamido, sulfonyl, sulfinyl, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{2-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted;
$R_2$ is selected from the group consisting of hydrogen, alkoxy, aryloxy, heteroaryloxy, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, carboxamido$(C_{1-3})$alkyl, amido$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted;
$R_3$ is selected from the group consisting of hydrogen, alkoxy, aryloxy, heteroaryloxy, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, carboxamido$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted;
each $R_4$ is independently selected from the group consisting of hydrogen, oxo, oxyalkyl, alkoxycarbonyl, carbonyl, thioalkyl, alkoxy, oxycarbonyl, aminocarbonyl, amino, amido, carboxamido, sulfonyl, sulfinyl, $(C_{1-10})$alkyl, halo$(C_{1-10})$alkyl, oxyalkyl, alkoxyalkyl, alkylthio alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, carboxamido$(C_{1-10})$alkyl, amido$(C_{1-10})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, aryloxyalkyl, heteroarylalkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl, and hetero$(C_{4-12})$bicycloaryl, each substituted or unsubstituted;
$R_5$ and $R_6$ are each independently selected from the group consisting of hydrogen, oxycarbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicyclo aryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl, and hetero$(C_{4-12})$bicycloaryl, each substituted or unsubstituted, and $R_5$ and $R_6$ on a given carbon may be taken together to form $=O$, $=S$, or $=NR_{10}$, where $R_{10}$ is selected from the group consisting of hydrogen, hydroxyl, alkoxy, aryloxy, heteroaryloxy, $(C_{1-10})$alkyl, halo$(C_{1-10})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{3-12})$cycloalkyl, hetero$(C_{2-12})$cycloalkyl, $(C_{5-12})$aryl, and hetero$(C_{2-10})$aryl, each substituted or unsubstituted, and $R_6$ is absent when the carbon to which it is bound forms part of a double bond;
$R_7$ is selected from the group consisting of hydrogen, $(C_{1-10})$alkyl, halo$(C_{1-10})$alkyl, carbonyl$(C_{1-3})$alkyl, carboxamidoalkyl, amidoalkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, alkoxy$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted, and
$R_9$ is selected from the group consisting of hydrogen, alkoxy, aryloxy, heteroaryloxy, $(C_{1-10})$alkyl, halo$(C_{1-10})$alkyl, carbonyl$(C_{1-3})$alkyl, aminocarbonylalkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, alkoxy$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicyclo aryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{4-12})$bicycloalkyl, $(C_{5-12})$aryl, hetero$(C_{2-10})$aryl, $(C_{9-12})$bicycloaryl, and hetero$(C_{4-12})$bicycloaryl, each substituted or unsubstituted;
provided that $R_1$ and $R_3$ are not both hydrogen;
wherein
the compound includes any hydrate, solvate, ester, tautomer, enantiomer, and pharmaceutically acceptable salt form of the compound.

In another embodiment, the compound has the formula:

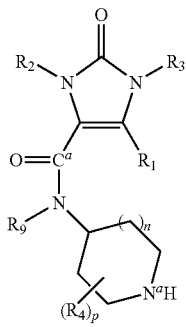

wherein
$C_a$ denotes a carbon atom;
$N_a$ denotes a nitrogen atom;
n is 0, 1, or 2;
p is 0, 1, 2, 3, or 4;
$R_1$ is selected from the group consisting of hydrogen, carbonyl, oxycarbonyl, aminocarbonyl, $(C_{1-10})$alkylamino, sulfonamido, sulfonyl, sulfinyl, $(C_{1-10})$alkyl, halo($C_{1-10}$)alkyl, alkoxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{2-10})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted;
$R_2$ is selected from the group consisting of hydrogen, alkoxy, aryloxy, heteroaryloxy, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, carboxamido$(C_{1-3})$alkyl, amido$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicyclo aryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted;
$R_3$ is selected from the group consisting of hydrogen, alkoxy, aryloxy, heteroaryloxy, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, carboxamido$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicyclo aryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted;
each $R_4$ is independently selected from the group consisting of hydrogen, oxo, oxyalkyl, alkoxycarbonyl, carbonyl, thioalkyl, alkoxy, oxycarbonyl, aminocarbonyl, amino, amido, carboxamido, sulfonyl, sulfinyl, $(C_{1-10})$alkyl, halo$(C_{1-10})$alkyl, oxyalkyl, alkoxyalkyl, alkylthioalkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, carboxamido$(C_{1-10})$alkyl, amido$(C_{1-10})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, aryloxyalkyl, heteroarylalkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl, and hetero$(C_{4-12})$bicycloaryl, each substituted or unsubstituted; and
$R_9$ is selected from the group consisting of hydrogen, alkoxy, aryloxy, heteroaryloxy, $(C_{1-10})$alkyl, halo$(C_{1-10})$alkyl, carbonyl$(C_{1-3})$alkyl, aminocarbonylalkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, alkoxy$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicyclo aryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{4-12})$bicycloalkyl, $(C_{5-12})$aryl, hetero$(C_{2-10})$aryl, $(C_{9-12})$bicycloaryl, and hetero$(C_{4-12})$bicycloaryl, each substituted or unsubstituted;
provided that $R_1$ and $R_3$ are not both hydrogen;
wherein
the compound includes any hydrate, solvate, ester, tautomer, enantiomer, and pharmaceutically acceptable salt form of the compound.
In another embodiment, the compound has the formula

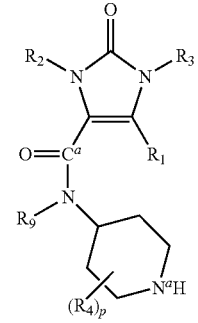

wherein:
$C_a$ denotes a carbon atom;
$N_a$ denotes a nitrogen atom;
p is 0, 1, 2, 3, or 4;
$R_1$ is selected from the group consisting of hydrogen, carbonyl, oxycarbonyl, aminocarbonyl, $(C_{1-10})$alkylamino, sulfonamido, sulfonyl, sulfinyl, $(C_{1-10})$alkyl, halo $(C_{1-10})$alkyl, alkoxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{2-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted;
$R_2$ is selected from the group consisting of hydrogen, alkoxy, aryloxy, heteroaryloxy, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, carboxamido$(C_{1-3})$alkyl, amido$(C_{1-3})$ alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$) alkyl, hetero($C_{2-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{4-12}$)bicycloaryl($C_{1-5}$)alkyl, ($C_{3-12}$) cycloalkyl, hetero($C_{2-12}$)cycloalkyl, ($C_{9-12}$) bicycloalkyl, hetero($C_{3-12}$)bicycloalkyl, ($C_{5-12}$)aryl, hetero($C_{2-10}$)aryl, ($C_{9-12}$)bicycloaryl and hetero($C_{4-12}$) bicycloaryl, each substituted or unsubstituted;

$R_3$ is selected from the group consisting of hydrogen, alkoxy, aryloxy, heteroaryloxy, ($C_{1-10}$)alkyl, halo($C_{1-10}$) alkyl, alkoxy($C_{1-10}$)alkyl, carbonyl($C_{1-3}$)alkyl, thiocarbonyl($C_{1-3}$)alkyl, carboxamido($C_{1-3}$)alkyl, sulfonyl ($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero ($C_{2-12}$)cycloalkyl($C_{1-5}$)alkyl, aryl($C_{1-10}$)alkyl, heteroaryl($C_{1-5}$)alkyl, ($C_{9-12}$)bicyclo aryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero ($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted;

each $R_4$ is independently selected from the group consisting of hydrogen, oxo, oxyalkyl, alkoxycarbonyl, carbonyl, thioalkyl, alkoxy, oxycarbonyl, aminocarbonyl, amino, amido, carboxamido, sulfonyl, sulfinyl, ($C_{1-10}$) alkyl, halo($C_{1-10}$)alkyl, oxyalkyl, alkoxyalkyl, alkylthioalkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$) alkyl, imino($C_{1-3}$)alkyl, carboxamido($C_{1-10}$)alkyl, amido($C_{1-10}$)alkyl, ($C_{3-12}$)cycloalkyl($C_{1-5}$)alkyl, hetero ($C_{2-12}$)cycloalkyl($C_{1-5}$)alkyl, aryl($C_{1-10}$)alkyl, heteroaryl($C_{1-5}$)alkyl, aryloxyalkyl, heteroarylalkyl, ($C_{9-12}$)bicycloaryl($C_{1-5}$)alkyl, hetero($C_{4-12}$)bicycloaryl ($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$) aryl, hetero($C_{2-10}$)aryl, ($C_{9-12}$)bicycloaryl, and hetero ($C_{4-12}$)bicycloaryl, each substituted or unsubstituted; and $R_9$ is selected from the group consisting of hydrogen, alkoxy, aryloxy, heteroaryloxy, ($C_{1-10}$)alkyl, halo($C_{1-10}$) alkyl, carbonyl($C_{1-3}$)alkyl, aminocarbonylalkyl, thiocarbonyl($C_{1-3}$)alkyl, sulfonyl($C_{1-3}$)alkyl, sulfinyl($C_{1-3}$) alkyl, amino($C_{1-10}$)alkyl, imino($C_{1-3}$)alkyl, alkoxy ($C_{1-3}$)alkyl, ($C_{3-12}$)cycloalkyl($C_{1-5}$)alkyl, hetero($C_{2-12}$) cycloalkyl($C_{1-5}$)alkyl, aryl($C_{1-10}$)alkyl, heteroaryl ($C_{1-5}$)alkyl, ($C_{9-12}$)bicyclo aryl($C_{1-5}$)alkyl, hetero ($C_{4-12}$)bicycloaryl($C_{1-5}$)alkyl, ($C_{3-12}$)cycloalkyl, hetero ($C_{2-12}$)cycloalkyl, ($C_{9-12}$)bicycloalkyl, hetero($C_{4-12}$)bicycloalkyl, ($C_{5-12}$)aryl, hetero($C_{2-10}$)aryl, ($C_{9-12}$)bicycloaryl, and hetero($C_{4-12}$)bicycloaryl, each substituted or unsubstituted;

provided that $R_1$ and $R_3$ are not both hydrogen;

wherein the compound includes any hydrate, solvate, ester, tautomer, enantiomer, and pharmaceutically acceptable salt form of the compound.

In one variation of any one of the preceding embodiments and variations, $R_1$ is selected from the group consisting of hydrogen, ($C_{1-10}$)alkyl, ($C_{3-12}$)cycloalkyl, hetero($C_{2-12}$)cycloalkyl, ($C_{3-12}$)cycloalkyl($C_{1-5}$)alkyl, hetero($C_{2-12}$)cycloalkyl($C_{1-5}$)alkyl, ($C_{5-12}$)aryl, hetero($C_{2-10}$)aryl, aryl ($C_{1-10}$)alkyl, and heteroaryl($C_{1-5}$)alkyl, each substituted or unsubstituted.

In another variation, $R_1$ is selected from the group consisting of ($C_{1-10}$)alkyl, ($C_{3-8}$)cycloalkyl and ($C_{3-8}$)cycloalkyl ($C_{1-3}$)alkyl.

In another variation, $R_1$ comprises an aromatic ring and is selected from a group consisting of phenyl, benzyl, hetero ($C_{2-5}$)aryl, hetero($C_{2-5}$)arylmethyl, each substituted or unsubstituted, where the hetero($C_{2-5}$)aryl and hetero($C_{2-5}$)arylmethyl may contain up to three heteroatoms as ring atoms, and each of the heteroatoms is independently selected from the group consisting of nitrogen, oxygen and sulfur atoms, and the aromatic ring may be unsubstituted or substituted with 1-4 substituents independently selected from the group consisting of alkyl, halo, and alkoxy, each substituted or unsubstituted.

In another variation, $R_1$ is selected from the group of consisting of

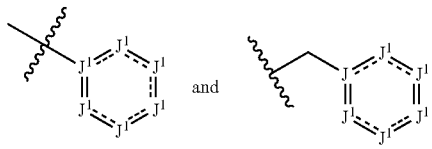

wherein each J is independently selected from the group consisting of —$CR_8$— and —N—;

each $J^1$ is independently selected from the group consisting of —$CR_8R_{8'}$— and —$NR_{11}$—; and not more than two ring atoms of $R_1$ is —N— or —$NR_{11}$—;

where each of $R_8$ and $R_{8'}$ is independently selected from the group consisting of hydrogen, halo, alkyl, and alkoxy, each substituted or unsubstituted, and $R_{8'}$ may be absent when the carbon to which it is bound forms a double bond, and each $R_{11}$ is independently selected from the group consisting of hydrogen, alkyl and alkoxy, each substituted or unsubstituted, and $R_{11}$ may be absent when the nitrogen to which it is bound forms a double bond.

In another variation, $R_1$ is selected from the group consisting of

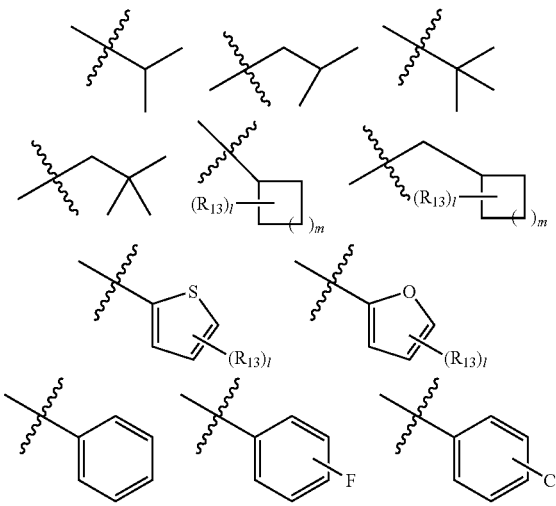

-continued

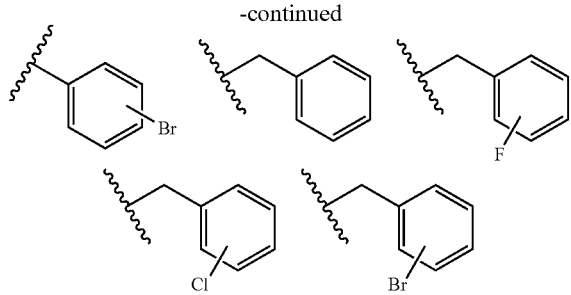

wherein
m is 0, 1, 2, 3 or 4;
l is 0, 1, 2 or 3;
each $R_{13}$ is selected from the group consisting of alkyl, halo, and alkoxy, each substituted or unsubstituted.

In another variation, $R_1$ is phenyl or benzyl. In another variation, $R_1$ is phenyl. In another variation, $R_1$ is benzyl.

In another variation, $R_1$ is a fluoro or chloro substituted phenyl or benzyl. In another variation, $R_1$ is a fluoro or chloro substituted phenyl. In another variation, $R_1$ is a fluoro or chloro substituted benzyl.

In another variation, $R_1$ is selected from the group consisting of isopropyl, cyclopropyl, and cyclopropylmethyl.

In one variation of the above embodiments and variations, $R_2$ is selected from the group consisting of $(C_{1-10})$alkyl, $(C_{1-10})$alkoxy$(C_{1-3})$alkyl, carboxamido$(C_{1-3})$alkyl, amido$(C_{1-3})$alkyl, alkylsulfonyl$(C_{1-3})$alkyl, arylsulfonyl$(C_{1-3})$alkyl, $(C_{1-10})$alkylcarbonyl$(C_{1-3})$alkyl, halo$(C_{1-10})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{5-12})$aryl, and hetero$(C_{2-10})$aryl, each substituted or unsubstituted.

In another variation of the above embodiments and variations, $R_2$ is selected from the group consisting of unsubstituted or substituted $(C_{1-10})$alkyl, halo$(C_{1-10})$alkyl, $(C_{1-6})$alkoxy$(C_{1-3})$alkyl, $(C_{5-8})$aryloxyalkoxy, $(C_{1-10})$alkylcarboxamido$(C_{1-3})$alkyl, $(C_{5-8})$arylcarboxamido$(C_{1-3})$alkyl, amido$(C_{1-3})$alkyl, $(C_{1-6})$alkylsulfonyl$(C_{1-3})$alkyl, $(C_{5-8})$arylsulfonyl$(C_{1-3})$alkyl, $(C_{5-8})$arylsulfonylamino$(C_{1-3})$alkyl, $(C_{1-10})$alkylsulfonylamino$(C_{1-3})$alkyl, and $(C_{1-6})$alkylcarbonyl$(C_{1-3})$alkyl.

In another variation, $R_2$ is selected from a group, the members of which comprise a three, four, five, six or seven membered ring, and said group consists of $(C_{3-7})$cycloalkyl, hetero$(C_{2-6})$cycloalkyl, phenyl, hetero$(C_{2-5})$aryl, $(C_{3-7})$cycloalkylmethyl, hetero$(C_{2-6})$cycloalkylmethyl, benzyl, and hetero$(C_{2-5})$arylmethyl, each substituted or unsubstituted;
where
the hetero$(C_{2-6})$cycloalkyl, hetero$(C_{2-6})$cycloalkylmethyl, hetero$(C_{2-5})$aryl, and hetero$(C_{2-5})$arylmethyl may contain up to three heteroatoms as ring atoms, where each of the heteroatoms is independently selected from the group consisting of nitrogen, oxygen and sulfur atoms, and
the three, four, five, six and seven membered rings is unsubstituted or optionally substituted with up to four substituents each of which is independently selected from the group consisting of halo, cyano, thio, amino, hydroxy, alkoxy, aryloxy, heteroaryloxy, carbonyl, oxycarbonyl, alkoxycarbonyl, aminocarbonyl, $(C_{1-10})$alkylamino, amido, carboxamido, sulfonamido, sulfonyl, sulfinyl, $(C_{1-10})$alkyl, halo$(C_{1-10})$alkyl, alkoxy$(C_{1-10})$alkyl, carbonyl$(C_{1-10})$alkyl, thiocarbonyl$(C_{1-5})$alkyl, sulfonyl$(C_{1-5})$alkyl, sulfinyl$(C_{1-5})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{2-12})$bicycloalkyl, $(C_{5-12})$aryl, hetero$(C_{2-10})$aryl, $(C_{9-12})$bicycloaryl, and hetero$(C_{4-12})$bicycloaryl, each substituted or unsubstituted.

In another variation, $R_2$ is

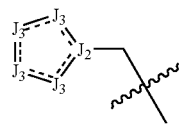

where
$J^2$ is selected from the group consisting of —$CR_{16}$—, —N—;
each $J^3$ is independently selected from the group consisting of —$CR_{16}XR_{14}$—, —$NR_{17}$—, —O—, and —S—; and not more than three $J^2$ and $J^3$s together are —N—, —$NR_{17}$—, —O—, or —S—,
where
each X is selected from a group consisting of a bond, —O—, —C(O)—, —$NR_{15}$—, —$NR_{15}C(O)$—, —$C(O)NR_{15}$—, —$S(O)_2NR_{15}$—, and —$NR_{15}S(O)_2$—; where $R_{15}$ is selected from the group consisting of hydrogen, alkoxy, aryloxy, heteroaryloxy, $(C_{1-10})$alkyl, halo$(C_{1-10})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{3-12})$cycloalkyl, hetero$(C_{2-12})$cycloalkyl, $(C_{5-12})$aryl, and hetero$(C_{2-10})$aryl, each substituted or unsubstituted,
each $R_{14}$ is independently selected from a group consisting of hydrogen, halo, cyano, thio, amino, hydroxy, alkoxy, aryloxy, heteroaryloxy, carbonyl, oxycarbonyl, alkoxycarbonyl, aminocarbonyl, $(C_{1-10})$alkylamino, amido, carboxamido, sulfonamido, sulfonyl, sulfinyl, $(C_{1-10})$alkyl, halo$(C_{1-10})$alkyl, alkoxy$(C_{1-10})$alkyl, carbonyl$(C_{1-10})$alkyl, thiocarbonyl$(C_{1-5})$alkyl, sulfonyl$(C_{1-5})$alkyl, sulfinyl$(C_{1-5})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{2-12})$bicycloalkyl, $(C_{5-12})$aryl, hetero$(C_{2-10})$aryl, $(C_{9-12})$bicycloaryl, and hetero$(C_{4-12})$bicycloaryl, each substituted or unsubstituted,
$R_{16}$ is independently selected from the group consisting of hydrogen, halo, alkyl, hydroxyl, and alkoxy, each substituted or unsubstituted, or $R_{16}$ may be absent when the carbon to which it is bound forms a double bond,
each $R_{17}$ is independently selected from the group consisting of hydrogen, alkyl, and alkoxy, each substituted or unsubstituted, or $R_{17}$ may be absent when the nitrogen to which it is bound forms a double bond, and
any two adjacent $R_{16}$, or $R_{17}$, or $R_{16}$ and $R_{17}$ may be taken together to form a substituted or unsubstituted ring.

In another variation, $R_2$ is

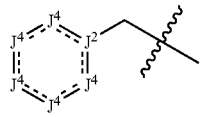

wherein
$J^2$ is selected from the group consisting of $-CR_{16}-$, $-N-$;
each $J^4$ is independently selected from the group consisting of $-CR_{16}XR_{14}-$ and $-NR_{17}-$; and
not more than two $J^2$ and $J^4$ together are $-N-$, or $-NR_{17}-$,
where
  each X is selected from a group consisting of a bond, $-O-$, $-S-$, $-C(O)-$, $-NR_{15}-$, $-NR_{15}C(O)-$, $-C(O)NR_{15}-$, $-S(O)_2NR_{15}-$, and $-NR_{15}S(O)_2-$, where $R_{15}$ is selected from the group consisting of hydrogen, alkoxy, aryloxy, heteroaryloxy, $(C_{1-10})$alkyl, halo$(C_{1-10})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{3-12})$cycloalkyl, hetero$(C_{2-12})$cycloalkyl, $(C_{5-12})$aryl, and hetero$(C_{2-10})$aryl, each substituted or unsubstituted,
  each $R_{14}$ is independently selected from a group consisting of hydrogen, halo, cyano, thio, amino, hydroxy, alkoxy, aryloxy, heteroaryloxy, carbonyl, oxycarbonyl, alkoxycarbonyl, aminocarbonyl, $(C_{1-10})$alkylamino, amido, carboxamido, sulfonamido, sulfonyl, sulfinyl, $(C_{1-10})$alkyl, halo$(C_{1-10})$alkyl, alkoxy$(C_{1-10})$alkyl, carbonyl$(C_{1-10})$alkyl, thiocarbonyl$(C_{1-5})$alkyl, sulfonyl$(C_{1-5})$alkyl, sulfinyl$(C_{1-5})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{2-12})$bicycloalkyl, $(C_{5-12})$aryl, hetero$(C_{2-10})$aryl, $(C_{9-12})$bicycloaryl, and hetero$(C_{4-12})$bicycloaryl, each substituted or unsubstituted;
  $R_{16}$ is independently selected from the group consisting of hydrogen, halo, alkyl, hydroxyl, and alkoxy, each substituted or unsubstituted, or $R_{16}$ may be absent when the carbon to which it is bond forms a double bond,
  each $R_{17}$ is independently selected from the group consisting of hydrogen, alkyl, and alkoxy, each substituted or unsubstituted, or $R_{17}$ may be absent when the nitrogen to which it is bond forms a double bond, and
  any two adjacent $R_{16}$s, or $R_{17}$s, or $R_{16}$ and $R_{17}$ may be taken together to form a ring.
In another variation, $R_2$ is selected from the group consisting of

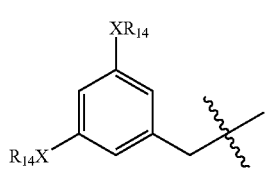 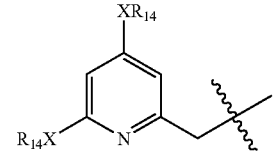

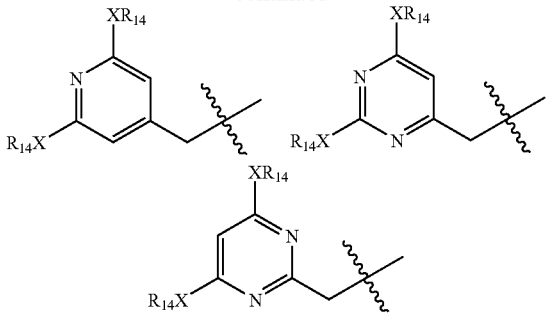

wherein
X is selected from the group consisting of a bond, $-O-$, $-S-$, $-C(O)-$, and $-NR_{15}-$; and
(i) when X is a bond, $R_{14}$ is selected from the group consisting of hydrogen, halo, cyano, alkyl, amino,

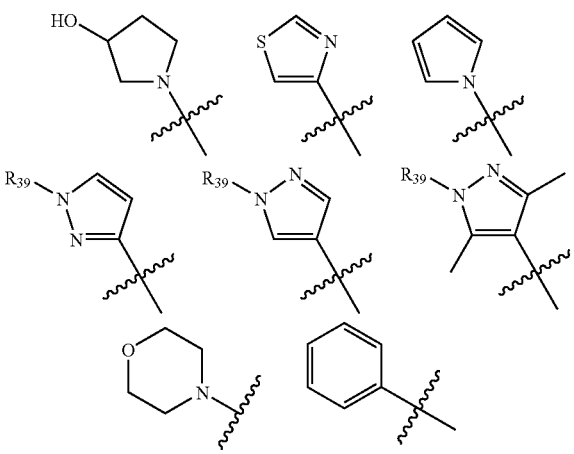

where
$R_{39}$ is selected from the group consisting of hydrogen, $(C_{1-6})$alkyl, halo$(C_{1-6})$alkyl, $(C_{1-6})$alkoxy, $(C_{4-6})$aryl, hetero$(C_{2-5})$aryl, each substituted or unsubstituted,
(ii) when X is $=O-$ or $-S-$, $R_{14}$ is selected from the group consisting of

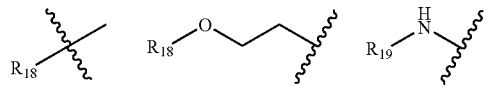

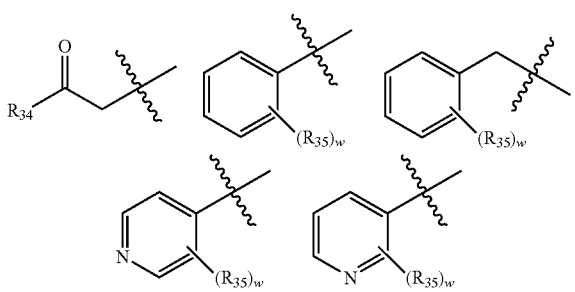

where
w is 0, 1 or 2,
R$_{18}$ is selected from the group consisting of hydrogen, (C$_{1-6}$)alkyl, (C$_{1-6}$)alkoxy, halo(C$_{1-6}$)alkyl, (C$_{4-6}$)aryl, hetero(C$_{2-5}$)aryl, each substituted or unsubstituted,
R$_{19}$ is selected from the group consisting of hydrogen, (C$_{1-6}$)alkyl, (C$_{3-12}$)cycloalkyl, hetero(C$_{2-12}$)cycloalkyl, (C$_{5-12}$)aryl, and hetero(C$_{2-10}$)aryl, each substituted or unsubstituted,
R$_{34}$ is selected from the group consisting of (C$_{1-6}$) alkyl, amino, (C$_{1-6}$)alkylamino, hetero(C$_{2-5}$)cycloalkyl, and
R$_{35}$ is selected from the group consisting of halo, (C$_{1-6}$)alkoxy;
(iii) when X is —C(O)—, R$_{14}$ is selected from the group consisting of

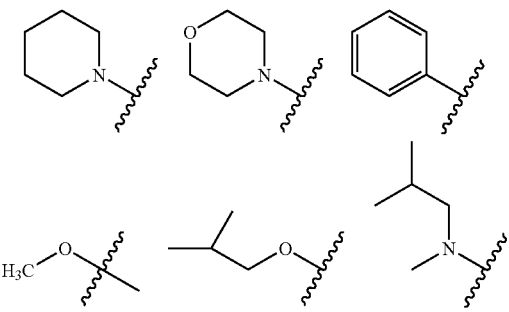

(iv) when X is —NR$_{15}$— and R$_{15}$ is hydrogen or alkyl, R$_{14}$ is selected from the group consisting of hydrogen and alkyl.

In another variation, R$_2$ is selected from the group consisting of —(CH$_2$)$_r$NHC(O)R$_{20}$, —(CH$_2$)$_r$NHS(O)$_2$R$_{20}$, —(CH$_2$)$_r$NHC(O)NHR$_{20}$, and —(CH$_2$)$_r$NHC(O)OR$_{20}$, wherein
r is 2 or 3, and
R$_{20}$ is selected from the group consisting of alkyl, cycloalkyl, heterocycloalkyl, aryl, heteroaryl, cycloalkylmethyl, heterocycloalkylmethyl, arylmethyl, and heteroarylmethyl, each unsubstituted or substituted.

In one variation of the above variation, R$_{20}$ is aryl or aryl methyl selected from the group consisting of unsubstituted or substituted pheny and unsubstituted or substituted benzyl, where the substituents on the phenyl and benzyl are selected from the group consisting of fluoro, chloro, methyl, ethyl, and methoxy. In other variations, R$_{20}$ is hetero(C$_{1-6}$)aryl.

In another variation of the above variation, R$_{20}$ is alkyl. In some variations, R$_{20}$ is (C$_{1-6}$)alkyl. In other variations, R$_{20}$ is selected from the group consisting of methyl, ethyl, isopropyl, and isobutyl. In another variation of the above variation, R$_{20}$ is cyclohexyl. In other variations, R$_{20}$ is heterocyclo (C$_{1-6}$) alkyl.

In another variation, R$_2$ is selected from the group consisting of methyl, isobutyl, —CH$_2$C(O)NH$_2$, —CH$_2$CH$_2$OCH$_3$, —CH$_2$CH$_2$=CH$_2$,

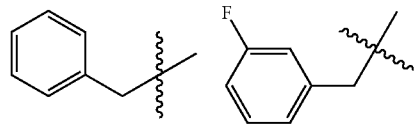

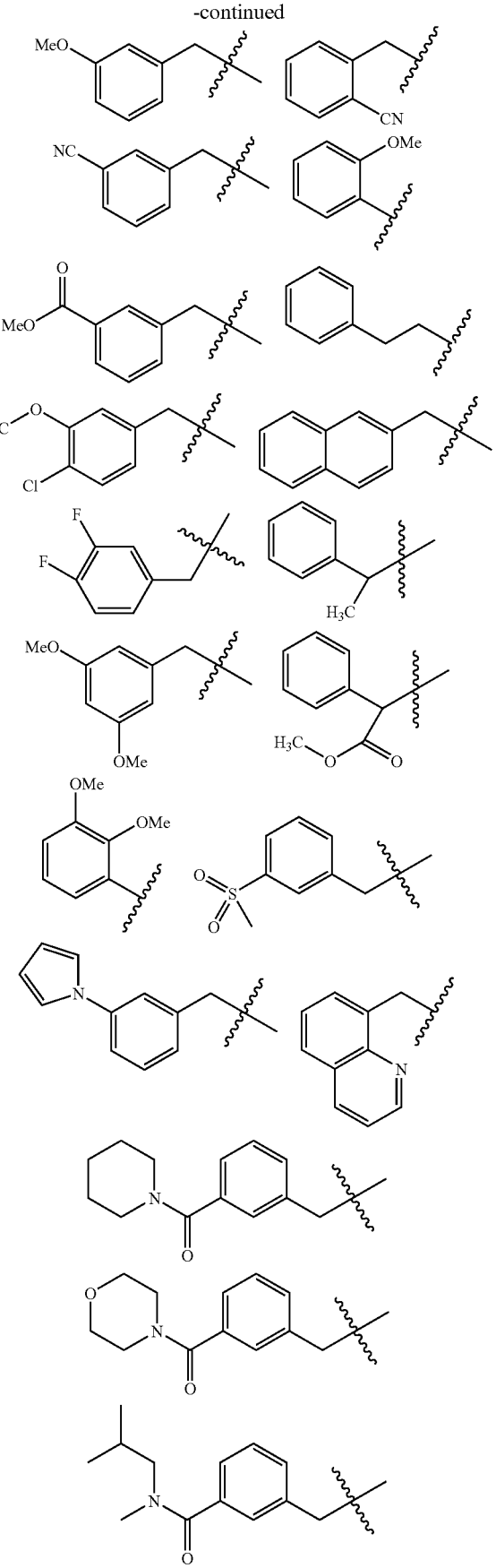

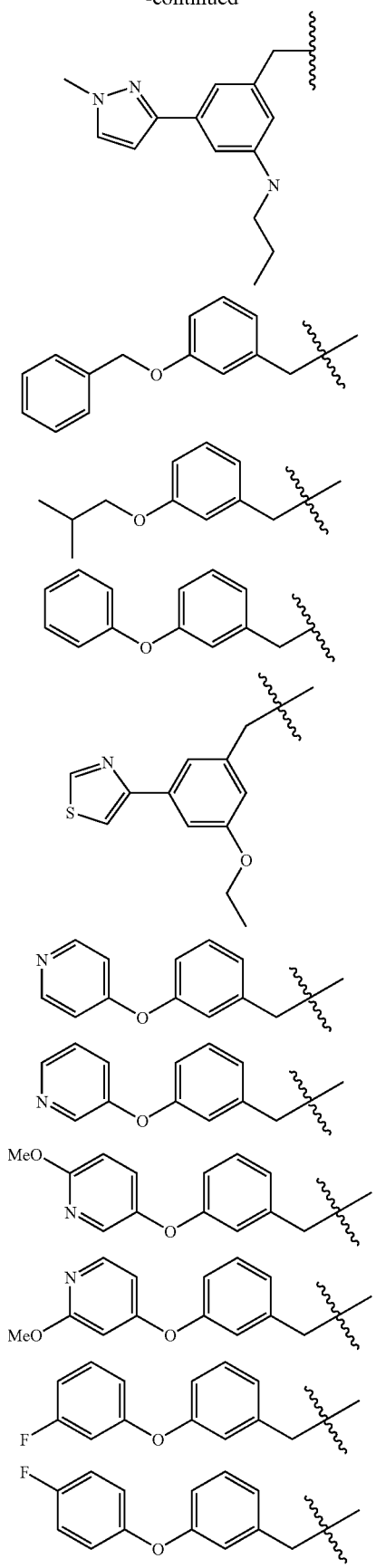
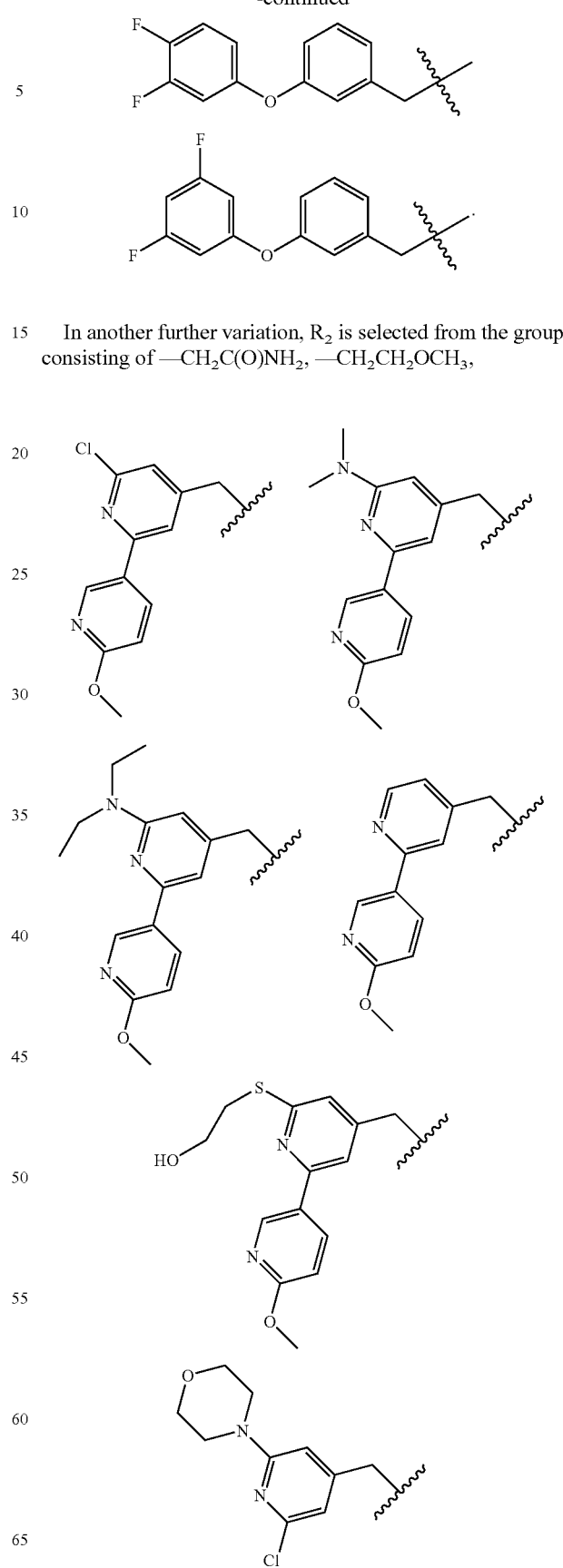
In another further variation, $R_2$ is selected from the group consisting of —$CH_2C(O)NH_2$, —$CH_2CH_2OCH_3$,

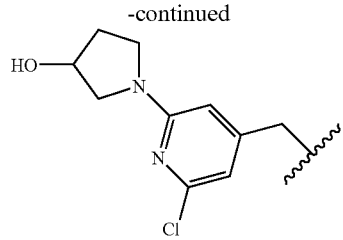
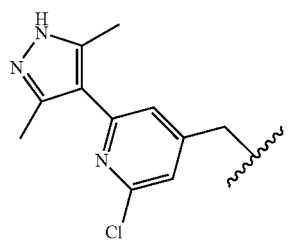
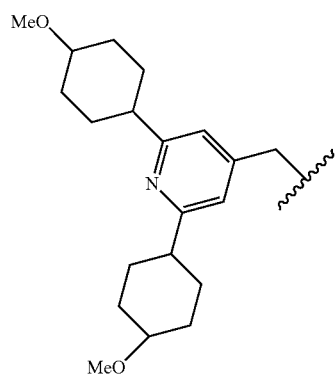
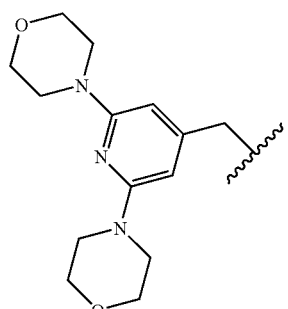
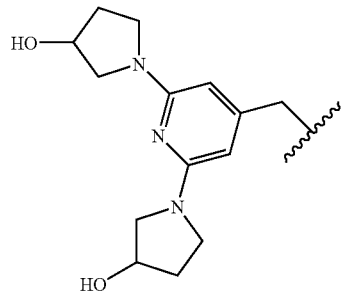
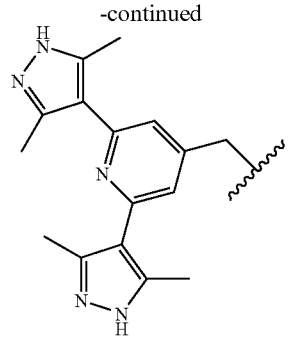
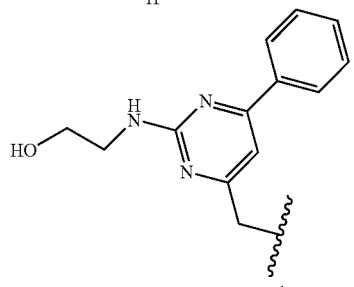
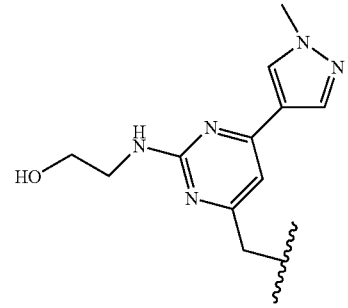
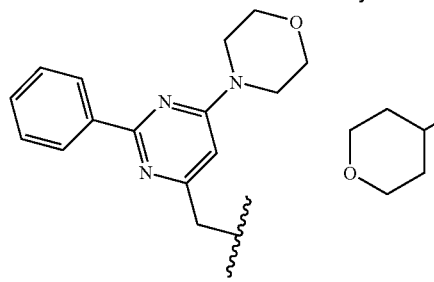
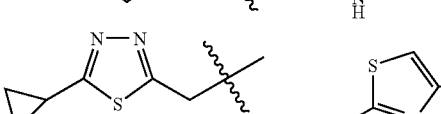
In another variation, R₂ is selected from the group consisting of
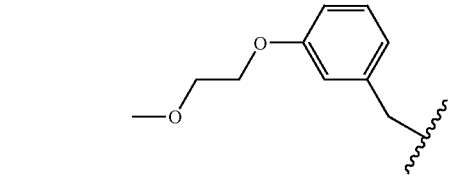

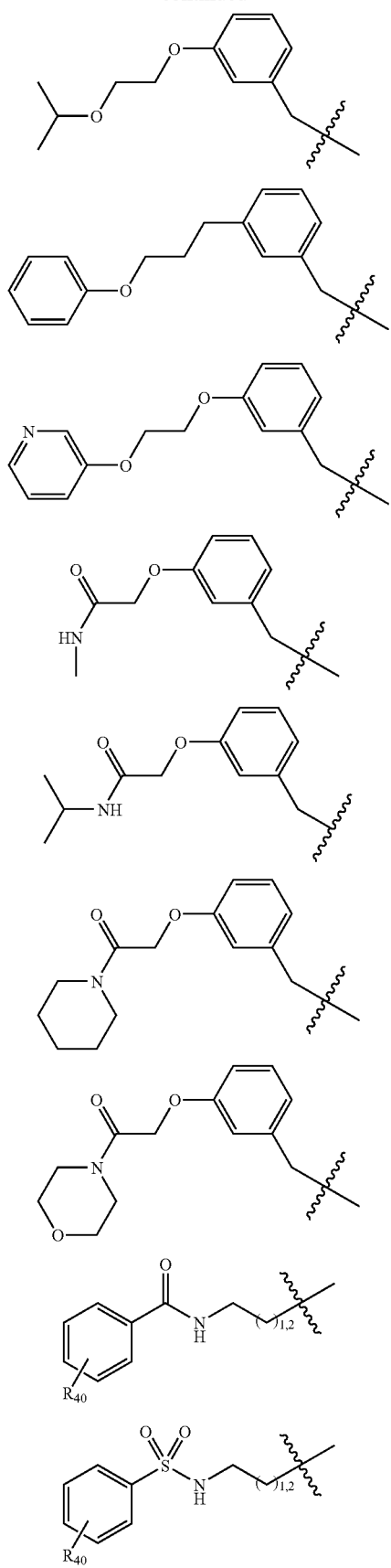
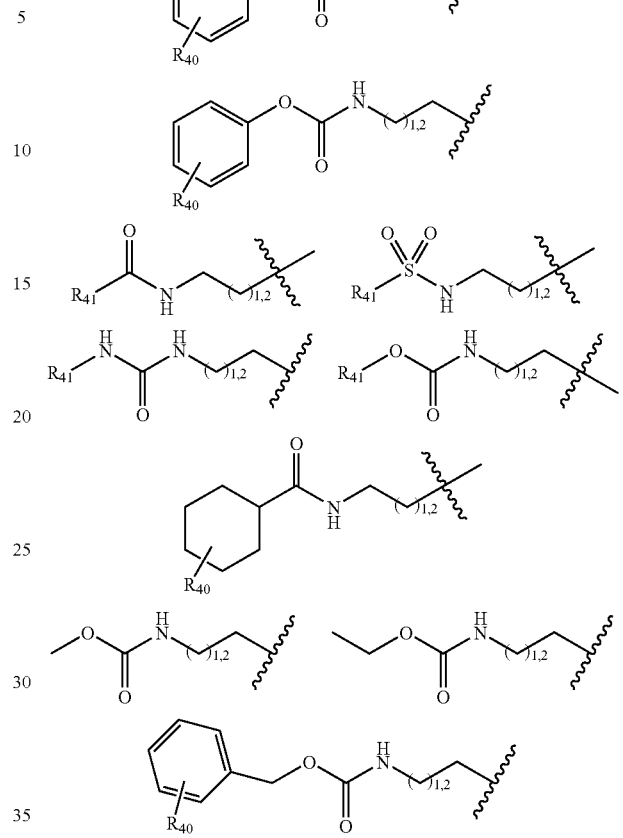
where
R$_{40}$ is H, fluoro, chloro, methyl, or methoxy; and
R$_{41}$ is isopropyl or isobutyl
In another variation, R$_2$ is selected from the group consisting of methyl, —CH$_2$CH$_2$=CH$_2$,
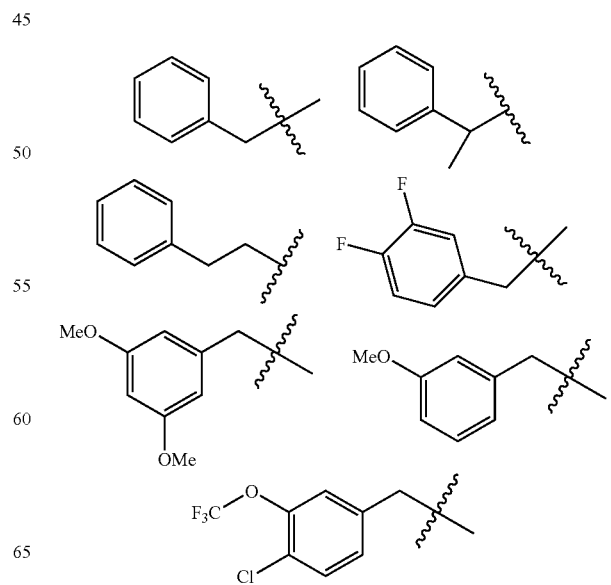

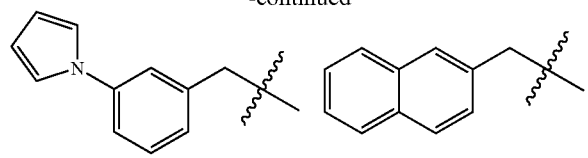
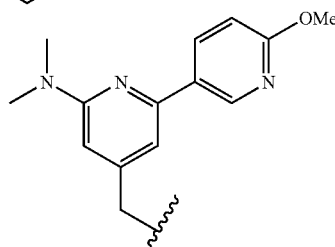
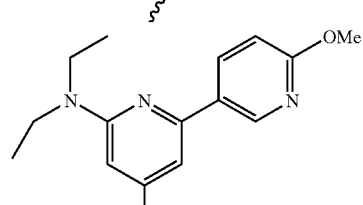
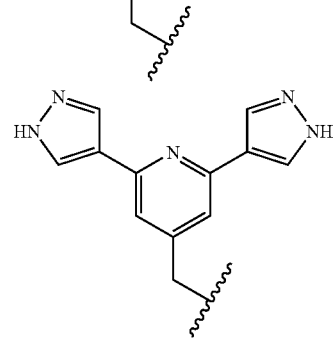
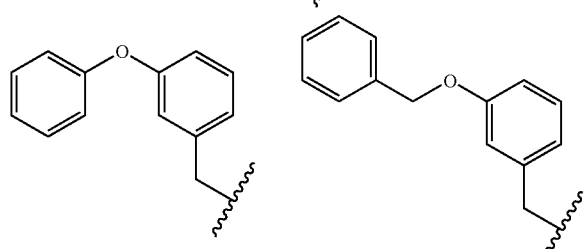
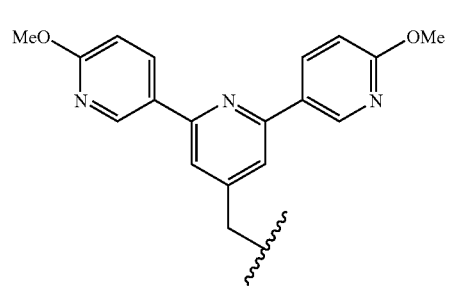
In another variation, R$_2$ is selected from the group consisting of isobutyl, —CH$_2$C(O)NH$_2$, —CH$_2$CH$_2$=CH$_2$,
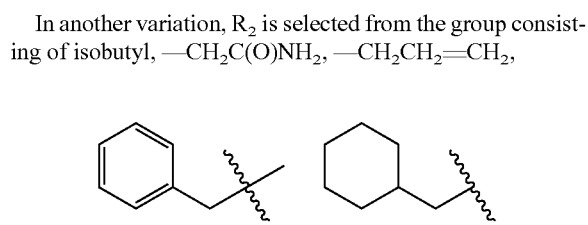
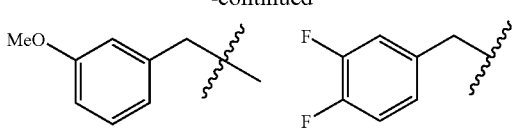
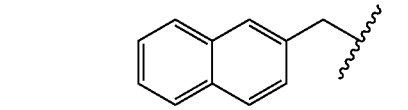
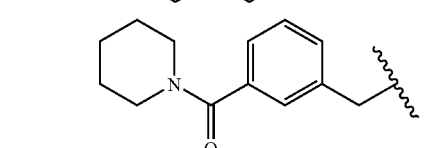
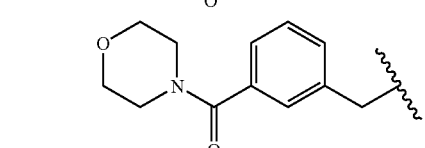
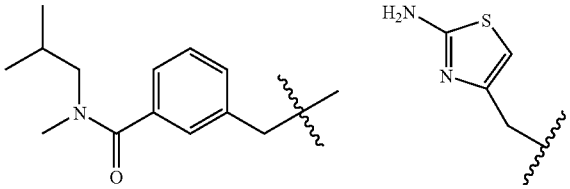
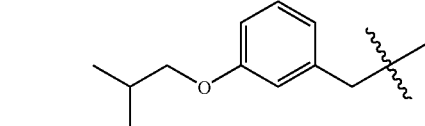
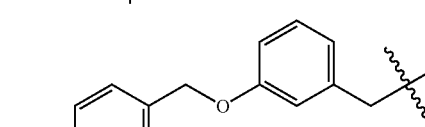
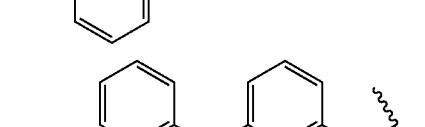
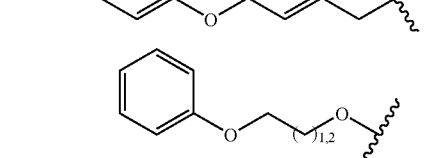
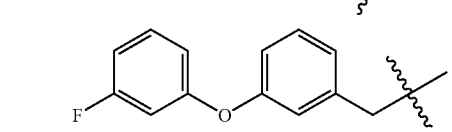
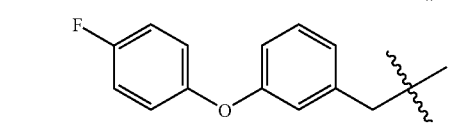
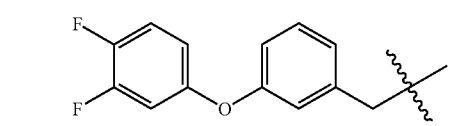

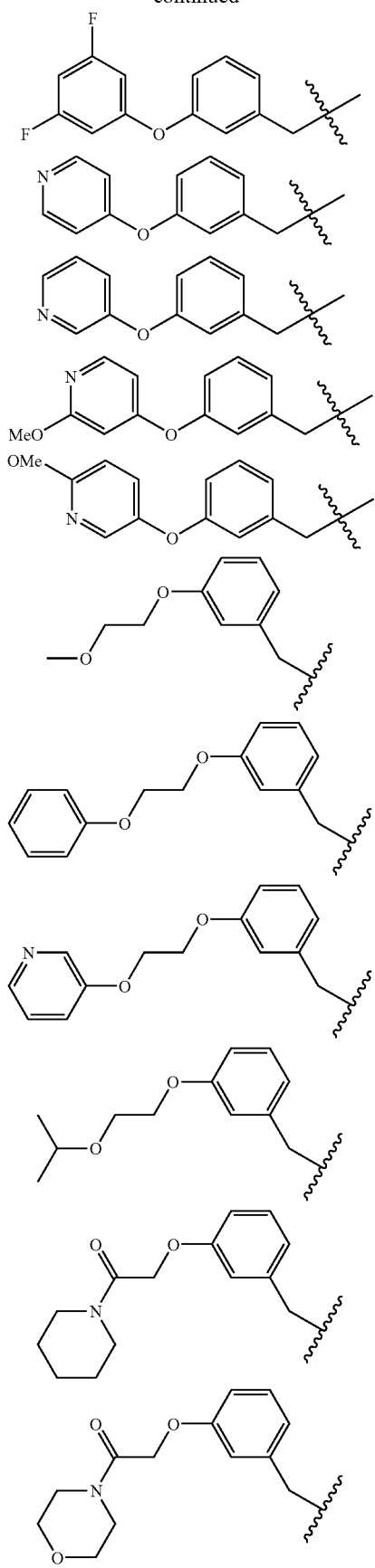
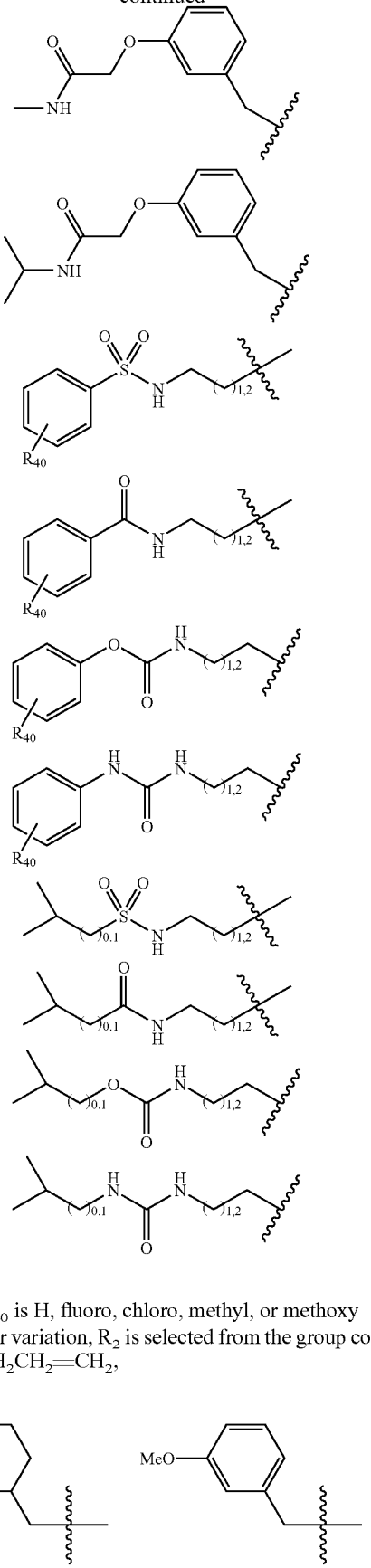
where $R_{40}$ is H, fluoro, chloro, methyl, or methoxy
In another variation, $R_2$ is selected from the group consisting of —CH$_2$CH$_2$=CH$_2$,
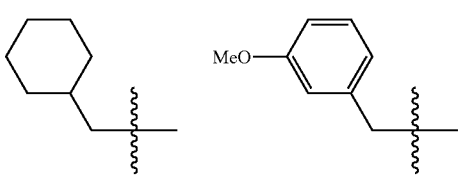

-continued
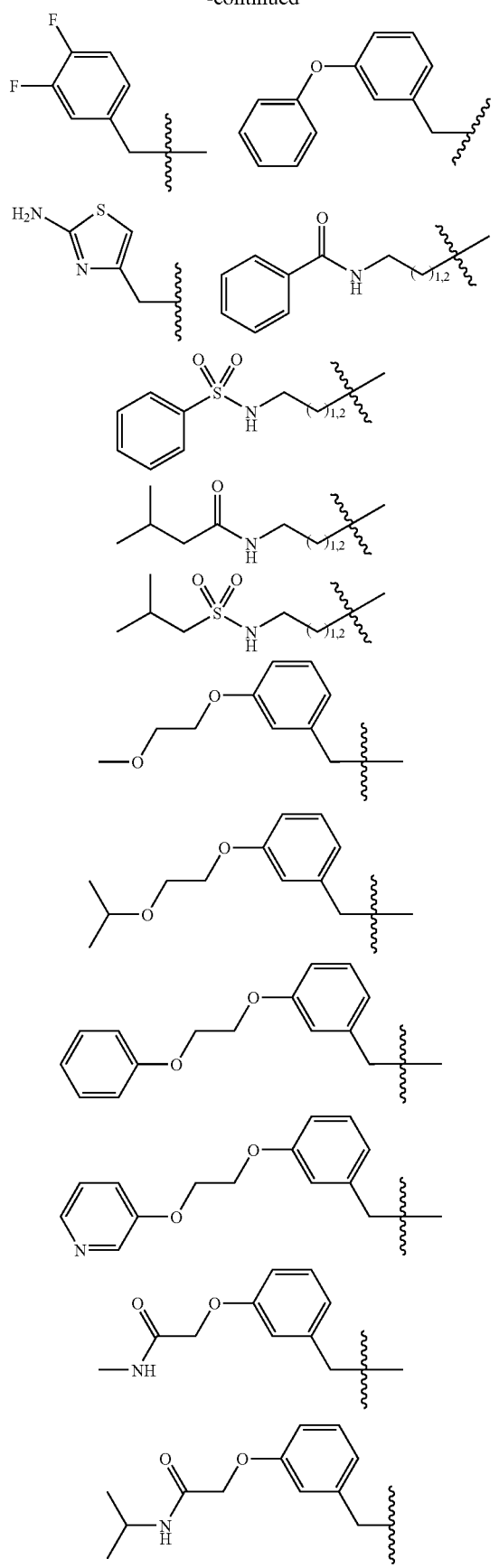
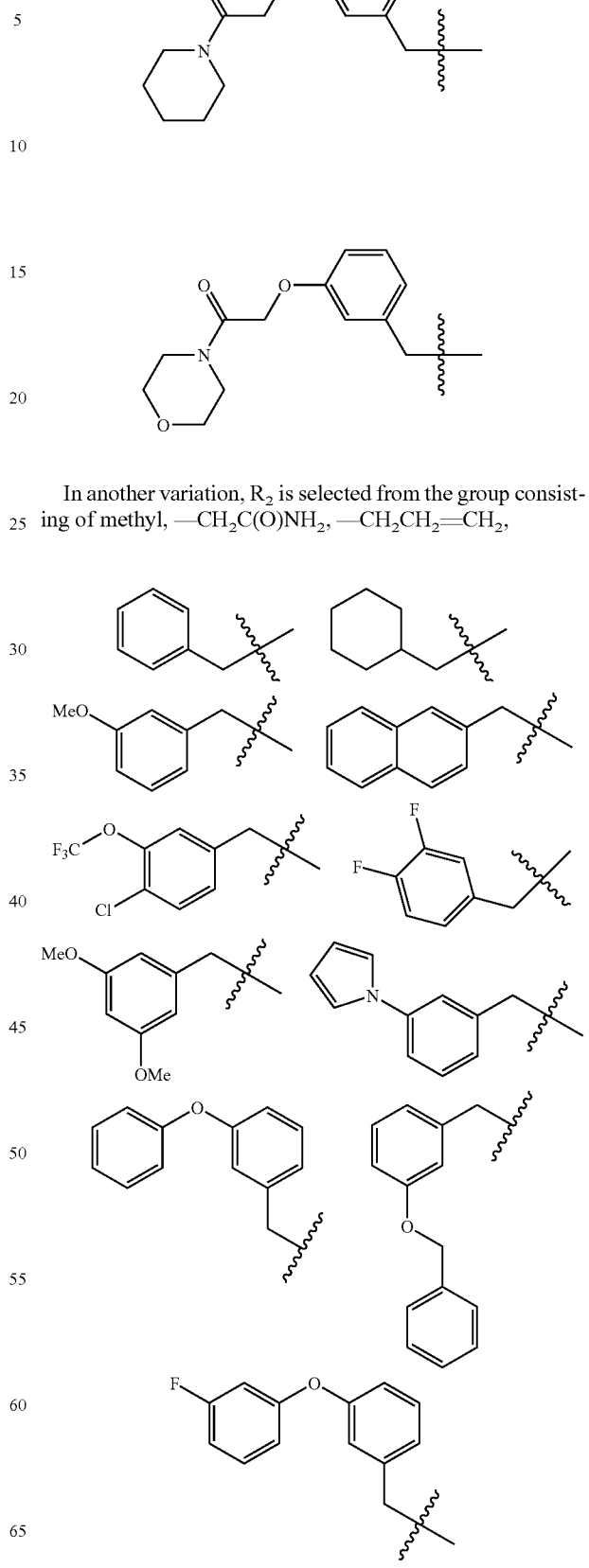
In another variation, $R_2$ is selected from the group consisting of methyl, —$CH_2C(O)NH_2$, —$CH_2CH=CH_2$, -continued

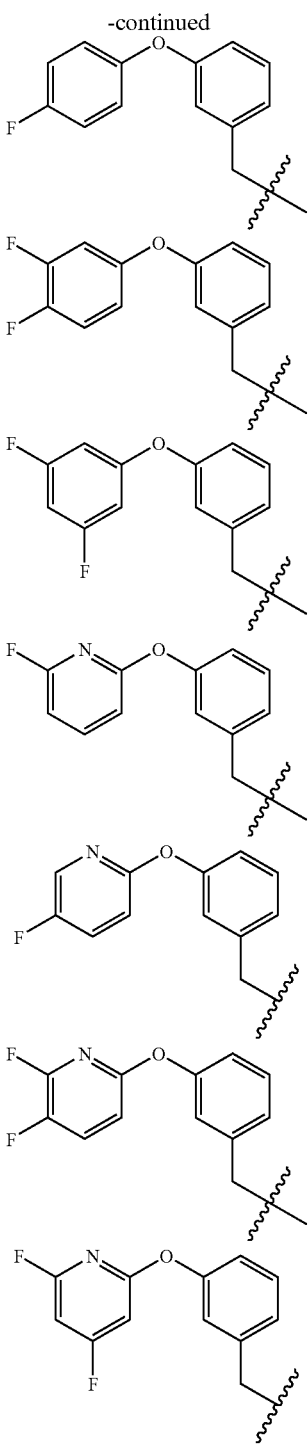

nitrogen, oxygen and sulfur atoms and where the five or six membered ring may be unsubstituted or substituted with up to four substituents. In another variation, $R_3$ is a six membered ring selected from the group consisting of $(C_6)$cycloalkyl, hetero$(C_{3-6})$cycloalkyl, $(C_6)$aryl, and hetero$(C_{3-6})$aryl, where the hetero$(C_6)$cycloalkyl and the hetero$(C_6)$aryl may contain up to three nitrogen atoms as ring atoms, and where six membered ring may be unsubstituted or substituted with up to four substituents. In another variation, $R_3$ is phenyl, an unsubstituted or substituted with up to four substituents. In another variation, $R_3$ is cyclohexyl, unsubstituted or substituted with up to four substituents.

In the above variations, the up to four substituents on $R_3$ are each independently selected from the group consisting of halo, cyano, thio, amino, hydroxy, alkoxy, aryloxy, heteroaryloxy, carbonyl, oxycarbonyl, alkoxycarbonyl, aminocarbonyl, $(C_{1-10})$alkylamino, amido, carboxamido, sulfonamido, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{2-12})$bicycloalkyl, $(C_{5-12})$aryl, hetero$(C_{2-10})$aryl, $(C_{9-12})$bicycloaryl, and hetero$(C_{4-12})$bicycloaryl, each substituted or unsubstituted, and any two adjacent substituents on $R_3$ may be taken together to form a five, six or seven membered ring, each substituted or unsubstituted.

In another variation, the up to four substituents on $R_3$ are each independently selected from the group consisting of hydrogen, nitro, hydroxy, alkoxy, alkyl, alkylsulfonyl, heteroalkyl, cycloalkyl, cycloheteroalkyl, alkoxyalkyl, alkoxyalkylthio, amidoalkyl, alkylamidoalkyl, carboxyamidoalkyl, alkylcarboxyamidoalkyl, and

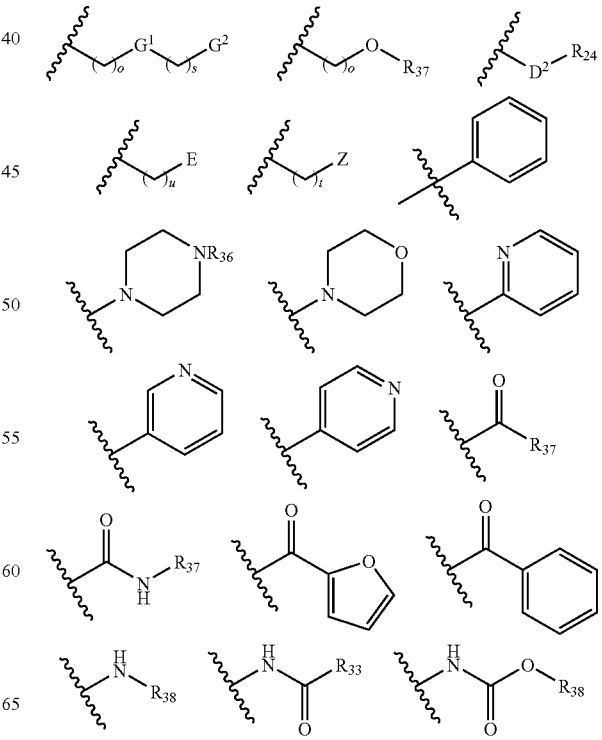

In one variation, $R_3$ is selected from the group consisting of hydrogen, $(C_{1-10})$alkyl, halo$(C_{1-10})$alkyl, $(C_{3-12})$cycloalkyl, hetero$(C_{2-12})$cycloalkyl, $(C_{5-12})$aryl, hetero$(C_{2-10})$aryl, $(C_{9-12})$bicycloaryl, and hetero$(C_{4-12})$bicycloaryl, each unsubstituted or substituted with up to four substituents.

In another variation, $R_3$ is a five or six membered ring selected from the group consisting of $(C_{5-6})$cycloalkyl, hetero$(C_{1-6})$cycloalkyl, $(C_{5-6})$aryl, and hetero$(C_{1-6})$aryl, where the hetero$(C_{1-6})$cycloalkyl and the hetero$(C_{1-6})$aryl may contain up to four heteroatoms as ring atoms, where the heteroatoms are each independently selected from the group consisting of

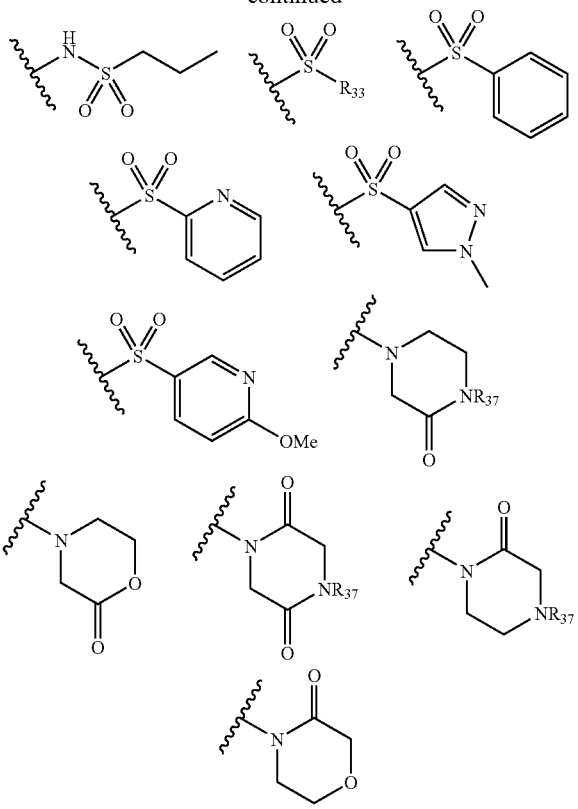

wherein
- o is 0, 1, or 2,
- s is 1, 2, 3, or 4,
- t is 0, 1, 2, 3, or 4,
- u is 0, 1, 2, 3, or 4,
- $D^2$ is —C(O)—, —S(O)— and —S(O)$_2$—,
- E is selected from the group consisting of hydrogen, hydroxyl and alkoxy,
- $G^1$ is selected from the group consisting of —CH$_2$—, —O—, and —S—,
- $G^2$ is selected from the group consisting of hydrogen, hydroxy, (C$_{1-10}$)alkoxy, aryl, heteroaryl, —C(O)R$_{21}$, —S(O)R$_{21}$, and —S(O)$_2$R$_{21}$, wherein R$_{21}$ is selected from the group consisting of hydrogen, hydroxyl, alkoxy, alkyl, aryl, and heteroaryl,
- Z is selected from the group consisting of hydrogen, hydroxyl, alkoxy, alkyl, and —NHC(O)alkyl,
- R$_{24}$ is selected from the group consisting of hydrogen, alkyl, alkoxy, aryl, and heteroaryl, each substituted or unsubstituted,
- R$_{33}$ is selected from the group consisting of hydrogen, (C$_{1-6}$)alkyl, hydroxy(C$_{1-6}$)alkyl, (C$_{1-6}$)alkoxy(C$_{1-6}$)alkyl, aryl, and heteroaryl, each substituted or unsubstituted,
- R$_{36}$ is selected from the group consisting of hydrogen, (C$_{1-6}$)alkyl, hydroxy(C$_{1-6}$)alkyl, (C$_{1-6}$)alkoxy(C$_{1-6}$)alkyl, each substituted or unsubstituted,
- each R$_{37}$ is independently selected from the group consisting of hydrogen, (C$_{1-8}$)alkyl, (C$_{1-4}$)alkoxy(C$_{1-8}$)alkyl, each substituted or unsubstituted, and
- each R$_{38}$ is independently selected from the group consisting of (C$_{1-8}$)alkyl, (C$_{1-8}$)alkoxy, (C$_{1-4}$)alkoxy(C$_{1-8}$)alkyl, and —(C$_{1-8}$)alkyl-NHC(O)(C$_{1-4}$)alkyl.

In another variation, R$_3$ is selected from the group consisting of

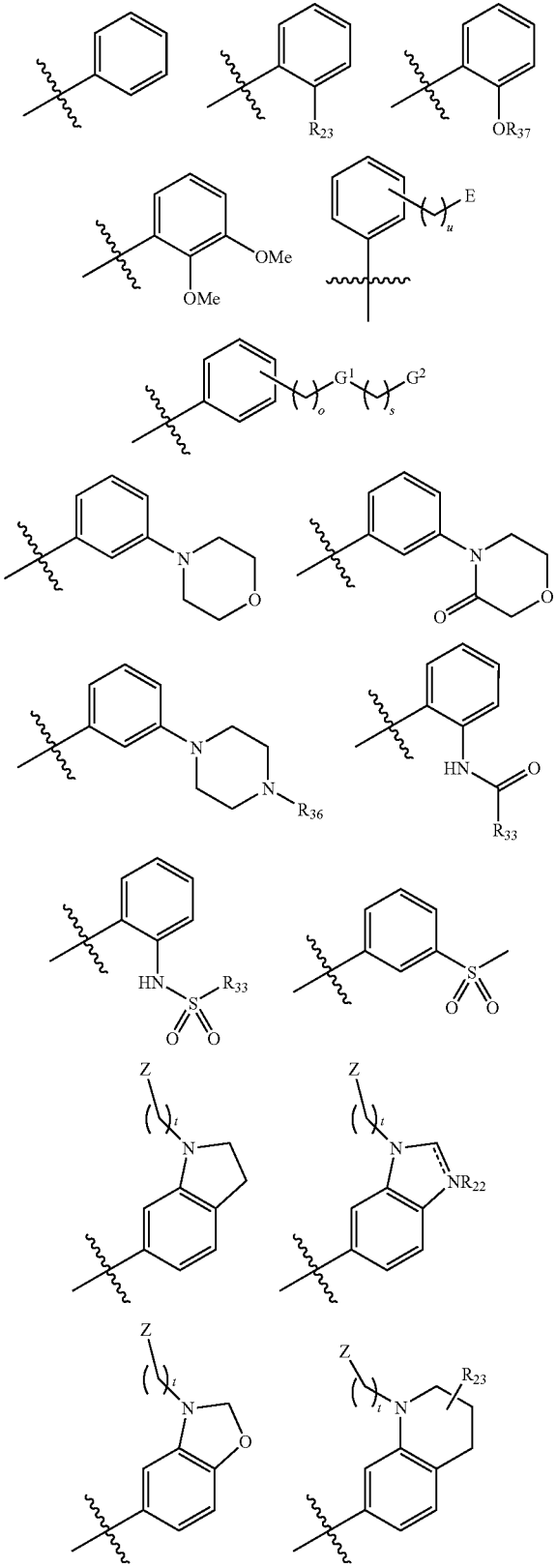

-continued

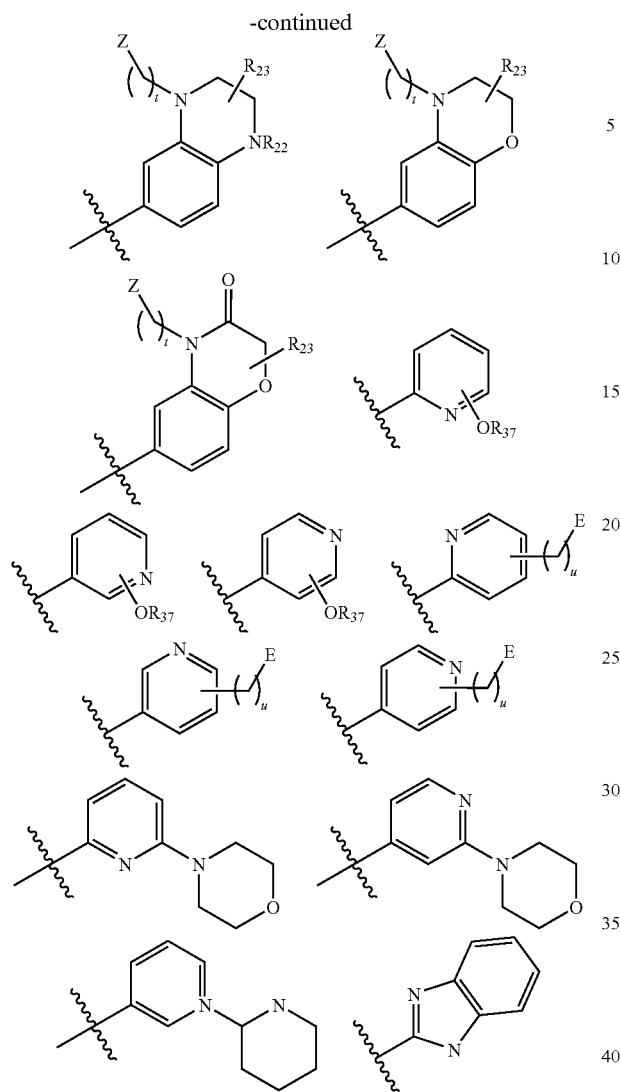

wherein
o is 0, 1, or 2,
s is 1, 2, 3, or 4,
t is 0, 1, 2, 3, or 4,
u is 0, 1, 2, 3, or 4,
E is selected from the group consisting of hydrogen, hydroxyl and alkoxy,
$G^1$ is selected from the group consisting of —CH$_2$—, —O—, and —S—,
$G^2$ is selected from the group consisting of hydrogen, hydroxy, (C$_{1-10}$)alkoxy, aryl, heteroaryl, —C(O)R$_{21}$, —S(O)R$_{21}$, and —S(O)$_2$R$_{21}$, wherein R$_{21}$ is selected from the group consisting of hydrogen, hydroxyl, alkoxy, alkyl, aryl, and heteroaryl,
Z is selected from the group consisting of hydrogen, hydroxyl, alkoxy, alkyl, and —NHC(O)alkyl,
R$_{22}$ is selected from the group consisting of hydrogen, alkyl, aryl, and heteroaryl,
R$_{23}$ is selected from the group consisting of hydrogen, alkyl, heteroalkyl, cycloalkyl, heterocycloalkyl, alkoxy, alkoxyalkyl, and alkoxyalkylthio,
R$_{33}$ is selected from the group consisting of hydrogen, (C$_{1-6}$)alkyl, (C$_{3-7}$)cycloalkyl, (C$_{1-6}$)heterocyclo alkyl, hydroxy(C$_{1-6}$)alkyl, (C$_{1-6}$)alkoxy(C$_{1-6}$)alkyl, aryl, and heteroaryl, R$_{36}$ is selected from the group consisting of hydrogen, (C$_{1-6}$)alkyl, hydroxy(C$_{1-6}$)alkyl, (C$_{1-6}$)alkoxy(C$_{1-6}$)alkyl, and
R$_{37}$ is selected from the group consisting of hydrogen, (C$_{1-8}$)alkyl, (C$_{1-4}$)alkoxy(C$_{1-8}$)alkyl.

In another variation, R$_3$ is selected from the group consisting of

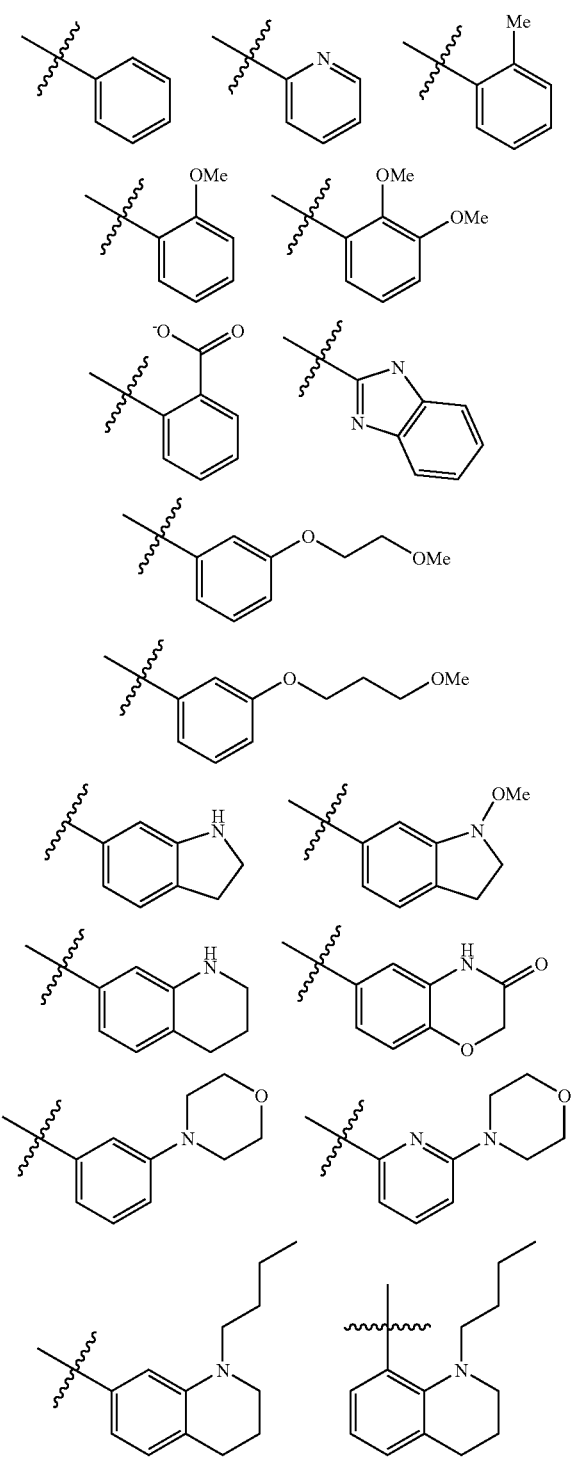

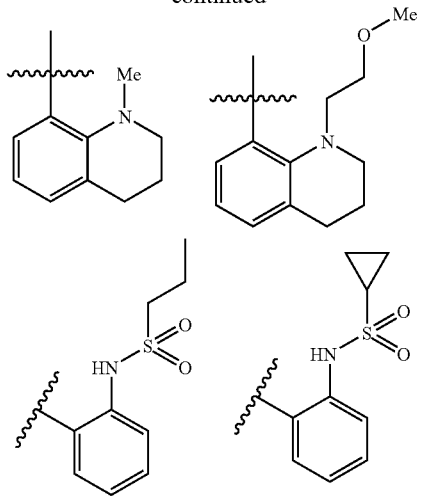

In another variation, R₃ is selected from the group consisting of

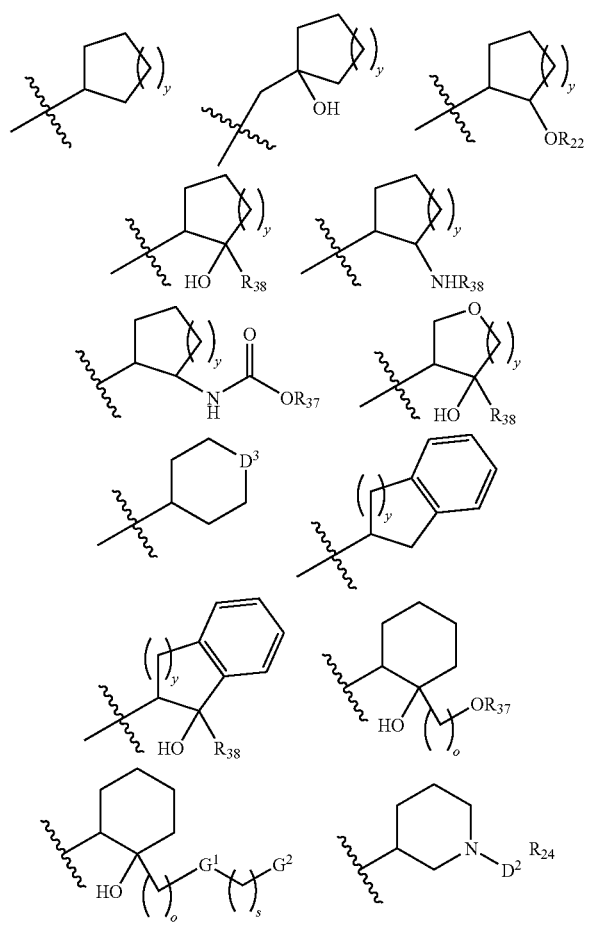

wherein
o is 0, 1, or 2;
s is 1, 2, 3, or 4;
y is 1 or 2;
D² is selected from the group consisting of —C(O)—, —S(O)— and —S(O)₂—;

D³ is selected from the group consisting of —C(=S)—, —C(=O)—, and —C(=NR₁₂)—, where R₁₂ is selected from the group consisting of hydrogen, hydroxyl, alkoxy, aryloxy, heteroaryloxy, $(C_{1-10})$alkyl, halo$(C_{1-10})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-4})$alkyl, $(C_{3-12})$cycloalkyl, hetero$(C_{2-12})$cycloalkyl, $(C_{5-12})$aryl, hetero$(C_{2-10})$aryl, each substituted or unsubstituted;

G¹ is selected from the group consisting of —CH₂—, —O—, and —S—;

G² is selected from the group consisting of hydrogen, hydroxy, $(C_{1-10})$alkoxy, aryl, heteroaryl, —C(O)R₂₁, —S(O)R₂₁, and —S(O)₂R₂₁, wherein R₂₁ is selected from the group consisting of hydrogen, hydroxyl, alkoxy, alkyl, aryl, and heteroaryl;

R₂₂ is selected from the group consisting of hydrogen, alkyl, aryl, and heteroaryl;

R₂₄ is selected from the group consisting of hydrogen, alkyl, alkoxy, aryl, and heteroaryl, each substituted or unsubstituted;

R₃₇ is selected from the group consisting of hydrogen, $(C_{1-8})$alkyl, $(C_{1-4})$alkoxy$(C_{1-8})$alkyl; and R₃₈ are independently selected from the group consisting of hydrogen, $(C_{1-8})$alkyl, $(C_{1-8})$alkoxy, $(C_{1-4})$alkoxy$(C_{1-8})$alkyl, and —$(C_{1-8})$alkyl-NHC(O)$(C_{1-4})$alkyl.

In another variation, R₃ is selected from the group consisting of

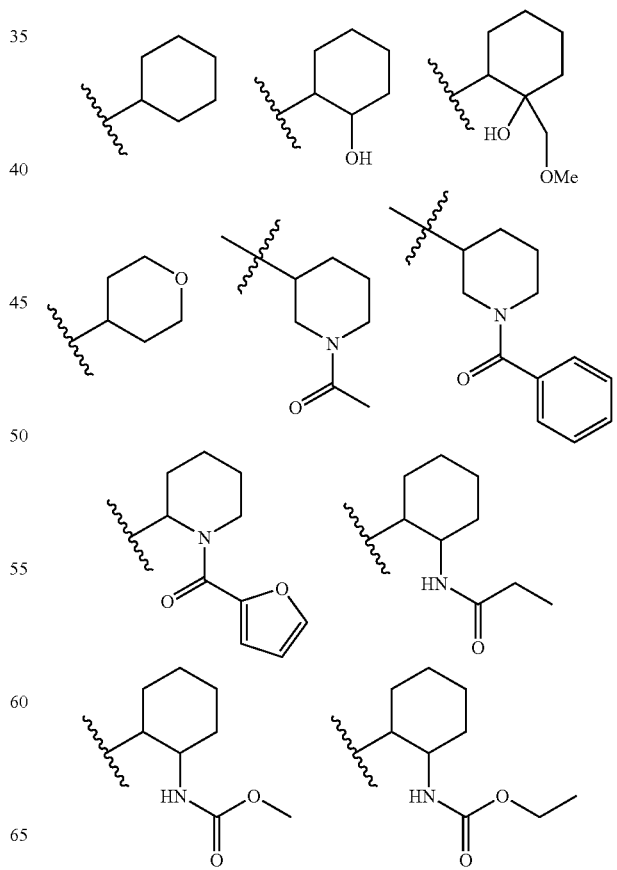

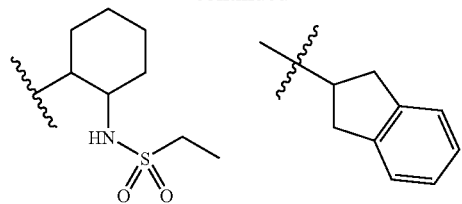
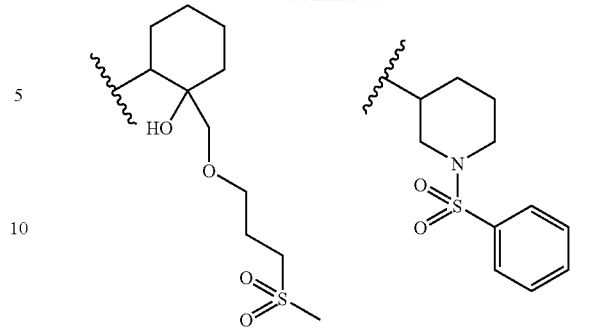
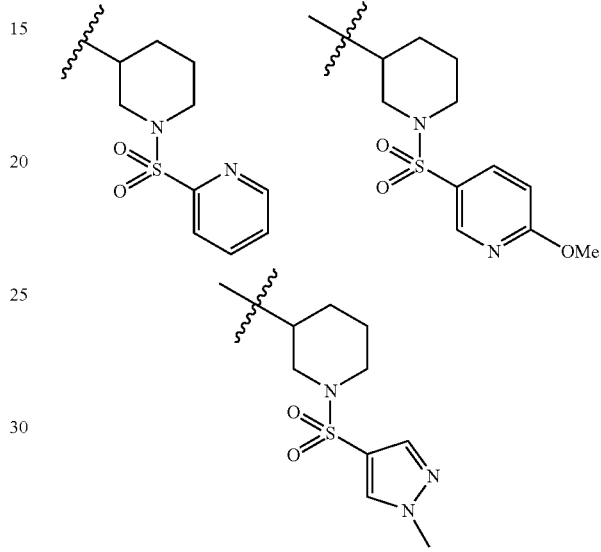
In another variation, R$_3$ is selected from the group consisting of
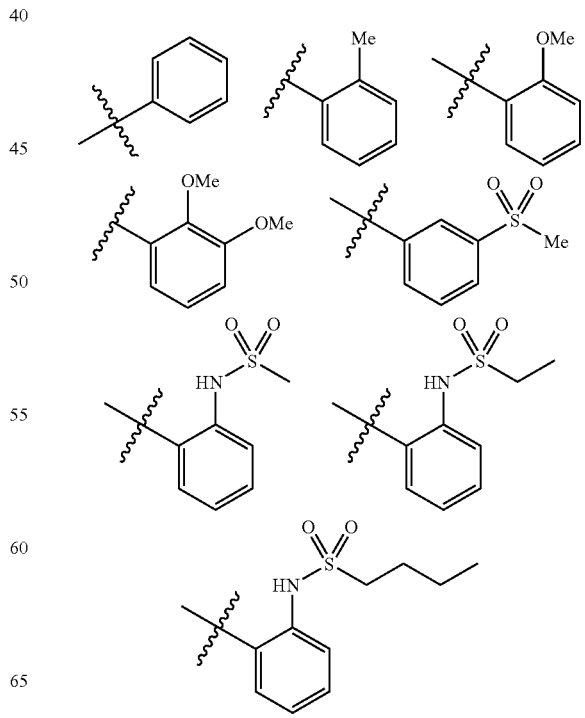

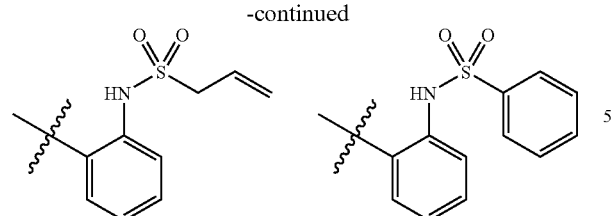
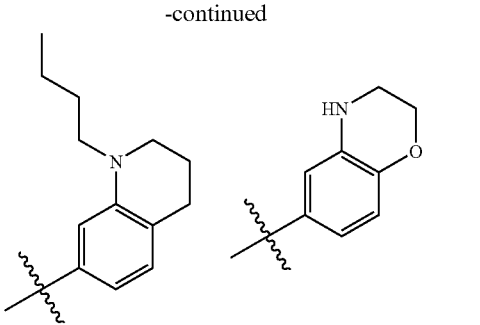
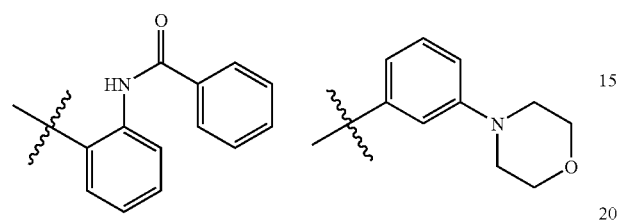
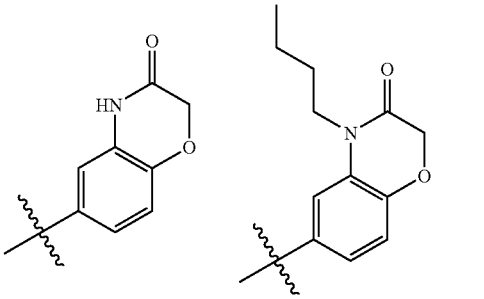
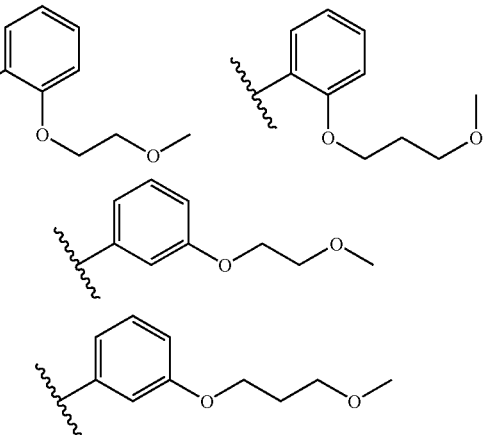
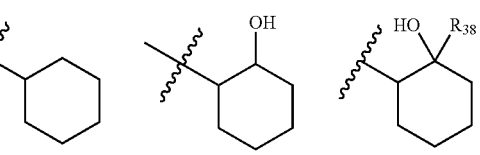
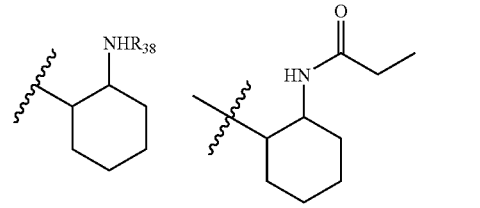
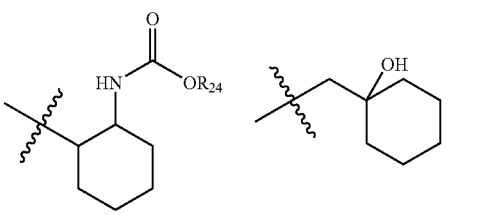

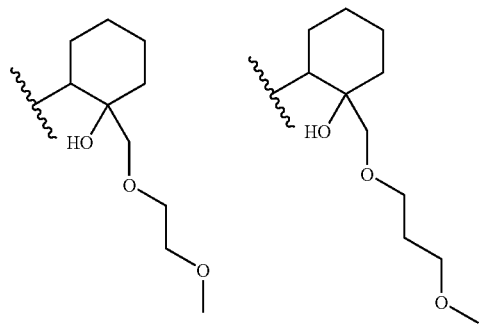
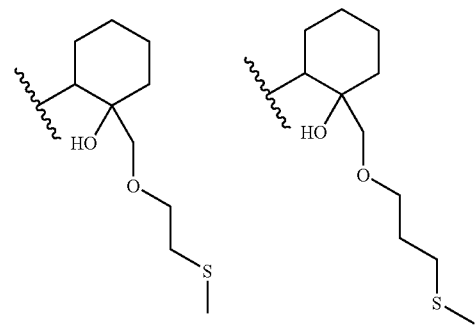
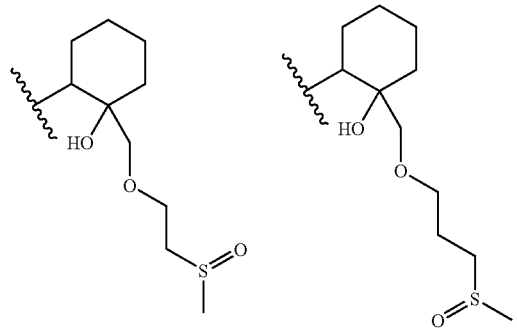
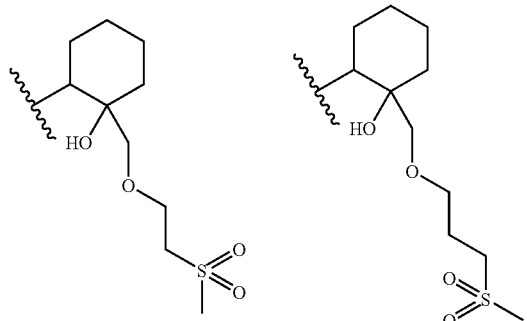
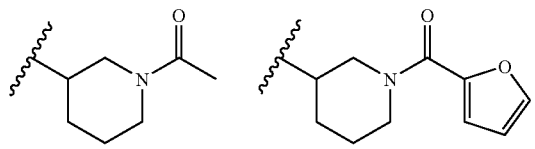

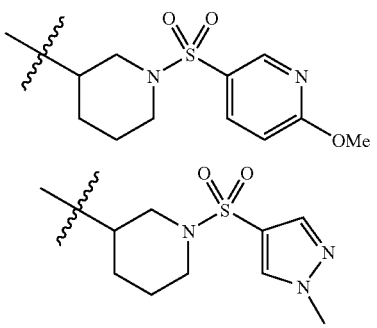

wherein

R$_{24}$ is selected from the group consisting of hydrogen, alkyl, aryl, and heteroaryl;

R$_{37}$ is selected from the group consisting of hydrogen, (C$_{1-8}$)alkyl, (C$_{1-4}$)alkoxy(C$_{1-8}$)alkyl; and R$_{38}$ are independently selected from the group consisting of (C$_{1-8}$)alkyl, (C$_{1-4}$)alkoxy(C$_{1-8}$)alkyl, and —(C$_{1-8}$)alkyl-NHC(O)(C$_{1-4}$)alkyl.

In another variation, R$_3$ is selected from the group consisting of:

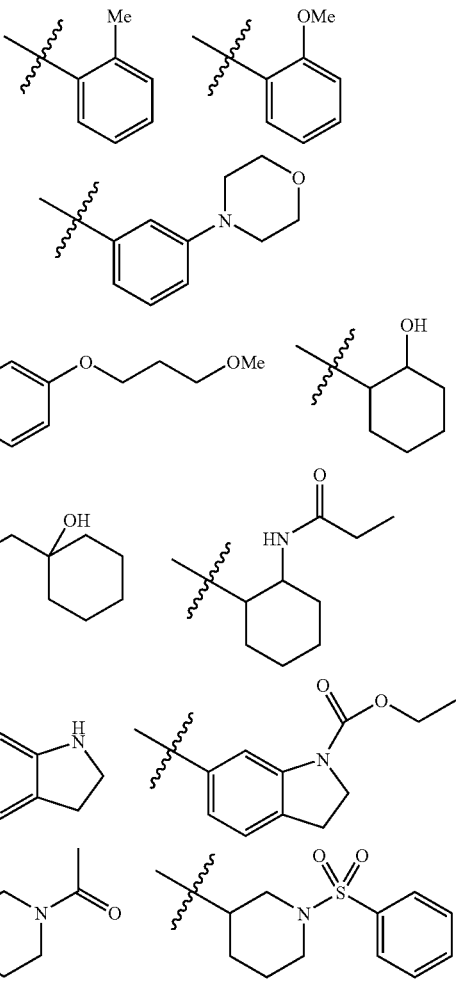

-continued

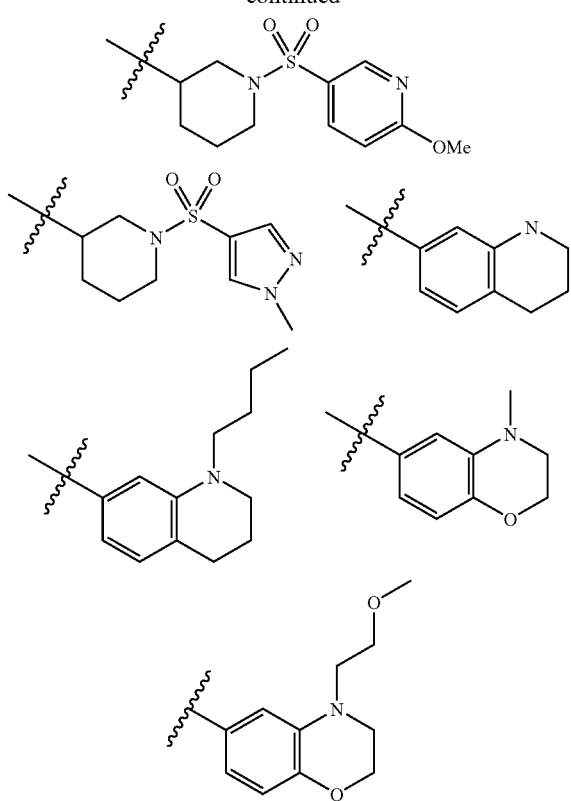

In another variation, $R_3$ is selected from the group consisting of:

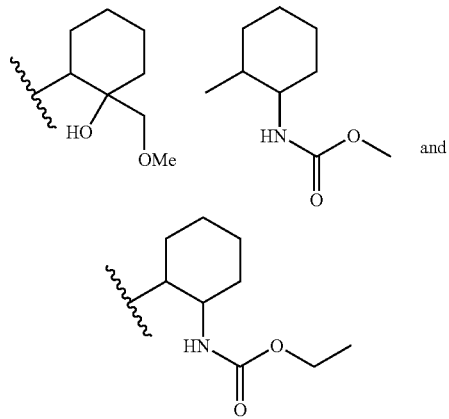

In one variation, $R_4$ when present is selected from the group consisting of hydrogen, oxo, $(C_{1-40})$alkoxy, $(C_{1-10})$alkoxy$(C_{1-3})$alkyl, $(C_{1-6})$alkylthio$(C_{1-3})$alkyl, $(C_{1-10})$alkoxycarbonyl, aminocarbonyl, $(C_{1-10})$alkyl, halo$(C_{1-10})$alkyl, oxyalkyl, $(C_{1-6})$alkylthio$(C_{1-3})$alkyl, carbonyl$(C_{1-3})$alkyl, thiocarbonyl$(C_{1-3})$alkyl, amino$(C_{1-10})$alkyl, amido$(C_{1-10})$alkyl, carboxamido$(C_{1-10})$alkyl, sulfonyl$(C_{1-3})$alkyl, sulfinyl$(C_{1-3})$alkyl, aryl$(C_{1-10})$alkyl, heteroaryl$(C_{1-5})$alkyl, aryloxy$(C_{1-5})$alkyl, heteroaryloxy$(C_{1-5})$alkyl, $(C_{3-12})$cycloalkyl, hetero$(C_{2-12})$cycloalkyl, $(C_{5-12})$aryl, and hetero$(C_{2-10})$aryl, each substituted or unsubstituted.

In another variation, $R_4$ when present is selected from the group consisting of hydrogen, $(C_{1-10})$alkyl, $(C_{1-10})$alkoxy, —CH$_2$—R$_{25}$,

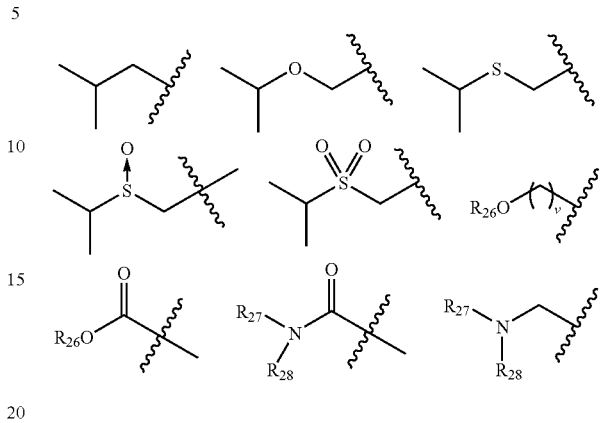

wherein:
v is 0, 1, 2, 3 or 4;
$R_{25}$ is a six membered saturated, unsaturated or aromatic ring which may contain up to four nitrogen atoms as ring atoms, and $R_{25}$ may be substituted with up to four substituents, wherein each of the substituent is independently selected from the group consisting of halo, $(C_{1-10})$alkoxy, aryloxy, heteroaryloxy, $(C_{1-10})$alkyl, $(C_{3-12})$cycloalkyl, hetero$(C_{2-12})$cycloalkyl, $(C_{5-12})$aryl, and hetero$(C_{2-10})$aryl, each substituted or unsubstituted;
$R_{26}$ is selected from the group consisting of hydrogen, $(C_{1-10})$alkyl, halo$(C_{1-10})$alkyl, $(C_{3-12})$cycloalkyl, hetero$(C_{2-12})$cycloalkyl, $(C_{9-12})$bicycloalkyl, hetero$(C_{4-12})$bicycloalkyl, $(C_{4-12})$aryl, and hetero$(C_{1-10})$aryl, each substituted or unsubstituted; and
$R_{27}$ and $R_{28}$ are each independently selected from the group consisting of hydrogen, $(C_{1-10})$alkyl, halo$(C_{1-10})$alkyl, $(C_{3-12})$cycloalkyl, carbonyl, hetero$(C_{2-12})$cycloalkyl, $(C_{5-12})$aryl, hetero$(C_{2-10})$aryl, $(C_{9-12})$bicycloaryl, and hetero$(C_{4-12})$bicycloaryl, each substituted or unsubstituted.

In another variation, wherein $R_4$ when present is selected from the group consisting of hydrogen, $(C_{1-6})$alkyl, —CH$_2$—R$_{25}$,

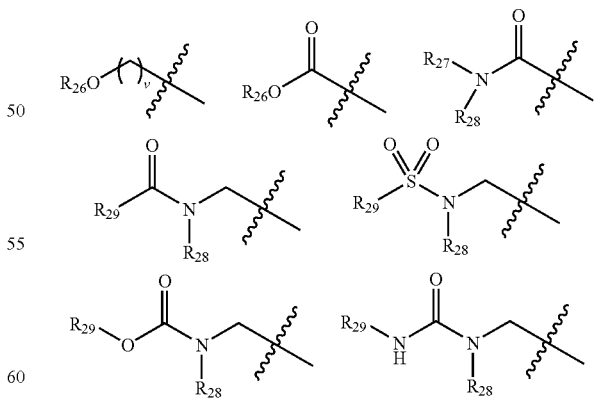

wherein
v is 0, 1, 2, 3 or 4;
$R_{25}$ is a 6-membered saturated, unsaturated or aromatic carbocycle which may be substituted with up to four substituents, wherein each substituent is independently selected from the group consisting of halo, $(C_{1-10})$alkoxy, aryloxy, heteroaryloxy, $(C_{1-10})$alkyl, $(C_{3-12})$cycloalkyl$(C_{1-5})$alkyl, hetero$(C_{2-12})$cycloalkyl$(C_{1-5})$alkyl, $(C_{5-12})$aryl$(C_{1-5})$alkyl, hetero$(C_{2-10})$aryl$(C_{1-5})$alkyl, $(C_{3-12})$cycloalkyl, hetero$(C_{2-12})$cycloalkyl, $(C_{5-12})$aryl, hetero$(C_{2-10})$aryl, each substituted or unsubstituted;

$R_{26}$ is selected from the group consisting of hydrogen, $(C_{1-10})$alkyl, halo$(C_{1-10})$alkyl, $(C_{3-12})$cycloalkyl$(C_{1-5})$alkyl, hetero$(C_{2-12})$cycloalkyl$(C_{1-5})$alkyl, $(C_{5-12})$aryl$(C_{1-5})$alkyl, hetero$(C_{2-10})$aryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, each substituted or unsubstituted;

$R_{27}$ and $R_{28}$ are each independently selected from the group consisting of hydrogen, $(C_{1-10})$alkyl, halo$(C_{1-10})$alkyl, carbonyl, $(C_{3-12})$cycloalkyl$(C_{1-5})$alkyl, hetero$(C_{2-12})$cycloalkyl$(C_{1-5})$alkyl, $(C_{5-12})$aryl$(C_{1-5})$alkyl, hetero$(C_{2-10})$aryl$(C_{1-5})$alkyl, $(C_{3-12})$cycloalkyl, hetero$(C_{2-12})$cycloalkyl, $(C_{5-12})$aryl, hetero$(C_{2-10})$aryl, $(C_{9-12})$bicycloaryl and hetero$(C_{4-12})$bicycloaryl, each substituted or unsubstituted; and $R_{29}$ is selected from the group consisting of hydrogen, alkyl, amidoalkyl carboxamidoalkyl, alkoxycarbonylalkyl, aryl, heteroaryl, cycloalkyl, heterocycloalkyl, arylalkyl, heterarylalkyl, cycloalkylalkyl, and heterocycloalkylalkyl, each substituted and unsubstituted.

In another variation, $R_4$ when present is selected from the group consisting of hydrogen, $(C_{1-6})$alkyl, —CH$_2$—R$_{25}$, —CH$_2$N(R$_{28}$)C(O)R$_{29}$,
wherein
$R_{25}$ is a 6-membered saturated, unsaturated or aromatic carbocycle which may be substituted with up to four substituents, wherein each substituent is independently selected from the group consisting of alkyl, halo and $(C_{1-10})$alkoxy, each substituted or unsubstituted;
$R_{28}$ is selected from the group consisting of hydrogen, $(C_{1-10})$alkyl, halo$(C_{1-10})$alkyl, $(C_{3-12})$cycloalkyl, hetero$(C_{2-12})$cycloalkyl, $(C_{5-12})$aryl, and hetero$(C_{2-10})$aryl, each substituted or unsubstituted; and
$R_{29}$ is selected from the group consisting of hydrogen, alkyl, amidoalkyl carboxamidoalkyl, alkoxycarbonylalkyl, $(C_{5-12})$aryl, hetero$(C_{2-10})$aryl, $(C_{3-12})$cycloalkyl, hetero$(C_{2-12})$cycloalkyl, $(C_{5-12})$aryl$(C_{1-5})$alkyl, heteraryl$(C_{2-10})$aryl$(C_{1-5})$alkyl, $(C_{3-12})$cycloalkyl$(C_{1-5})$alkyl, and hetero$(C_{2-12})$cycloalkyl$(C_{1-5})$alkyl, each substituted and unsubstituted.

In another variation, $R_4$ when present is selected from the group consisting of hydrogen, benzyl,

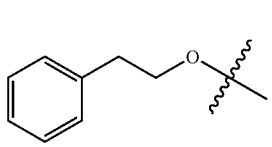 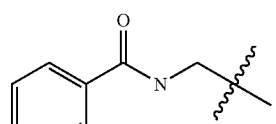

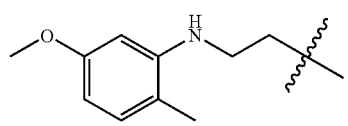 and

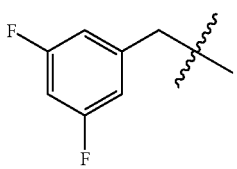

In another variation, $R_4$ when present is selected from the group consisting of hydrogen and benzyl.

In another variation, $R_4$ when present is benzyl.

In another variation, $R_4$ when present is hydrogen.

In another variation, $R_4$ when present is

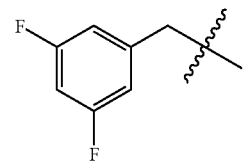

In another variation, $R_4$ when present is

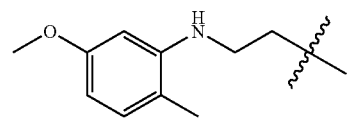

In another variation, $R_4$ when present is —CH$_2$-phenyl where the phenyl is substituted with up to two substituents and each of the substituents is independently selected from the group consisting of —OR$_{30}$, —NHR$_{31}$ and —C(O)NHR$_{31}$,
wherein
$R_{30}$ is selected from the group consisting of hydrogen, carbonyl, oxycarbonyl, aminocarbonyl, $(C_{1-10})$alkylamino, sulfonamido, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{3-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl, and hetero$(C_{4-12})$bicycloaryl, each substituted or unsubstituted, and $R_{31}$ is selected from the group consisting of hydrogen, $(C_{1-10})$alkyl, halo$(C_{1-10})$alkyl, carbonyl$(C_{1-3})$alkyl, thiocarbonyl$(C_{1-3})$alkyl, carboxamido$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, alkoxy$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl, and hetero$(C_{4-12})$bicycloaryl, each substituted or unsubstituted.

In another variation, $R_4$ when present is selected from the group consisting of hydrogen, —CH$_2$N(R$_{28}$)C(O)R$_{29}$, and —(CH$_2$)$_n$—O—R$_{28}$,
wherein
n is 1, 2, or 3;
$R_{28}$ is selected from the group consisting of hydrogen, $(C_{1-6})$alkyl and aryl, each substituted or unsubstituted; and
$R_{29}$ is selected from the group consisting of hydrogen, alkyl, aryl, —CH$_2$C(CH$_3$)$_2$C(O)OCH$_3$, and —CH$_2$C(CH$_3$)$_2$C(O)NR$_{32}$R$_{32'}$, wherein R$_{32}$ and R$_{32'}$ are each independently selected from the group consisting of hydrogen, alkyl, aryl, heteroaryl, cycloalkyl, and heterocyclic alkyl, each substituted or unsubstituted.

In one variation, $R_7$ when present is selected from the group consisting of hydrogen, $(C_{1-10})$alkyl, halo$(C_{1-10})$alkyl, ($C_{1-10}$)alkoxy, ($C_{5-12}$)aryloxy, hetero($C_{2-40}$)aryloxy, carbonyl($C_{1-3}$)alkyl, carboxamidoalkyl, amidoalkyl, sulfonyl($C_{1-3}$)alkyl, amino($C_{1-10}$)alkyl, ($C_{1-10}$)alkoxy($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{3-12}$)cycloalkyl, hetero($C_{2-12}$)cycloalkyl, ($C_{5-12}$)aryl, hetero($C_{2-10}$)aryl, each substituted or unsubstituted, or where $R_7$ and a substituent of L, Q, $C^a$, or A are taken together to form a ring.

In another variation, $R_7$ when present is selected from the group consisting of hydrogen, ($C_{1-10}$)alkyl, halo($C_{1-10}$)alkyl, ($C_{1-10}$)alkoxy, ($C_{5-8}$)aryloxy, hetero($C_{4-7}$)aryloxy, carbonyl($C_{1-3}$)alkyl, carboxamido($C_{1-5}$)alkyl, amino($C_{1-5}$)alkyl, ($C_{1-40}$)alkoxy($C_{1-3}$)alkyl, ($C_{3-8}$)cycloalkyl($C_{1-5}$)alkyl, hetero($C_{2-6}$)cycloalkyl($C_{1-5}$)alkyl, aryl($C_{5-8}$) alkyl, hetero($C_{4-7}$)aryl($C_{1-5}$)alkyl, ($C_{3-8}$)cycloalkyl, hetero($C_{2-6}$)cycloalkyl, ($C_{5-8}$)aryl, hetero($C_{4-7}$)aryl, each substituted or unsubstituted, or where $R_7$ and a substituent of L, Q, $C^a$, or A are taken together to form a ring.

In another variation, $R_7$ when present is selected from the group consisting of hydrogen and alkyl.

In another variation, $R_7$ when present is hydrogen.

In another variation, $R_9$ when present is selected from the group consisting of hydrogen and substituted or unsubstituted ($C_{1-10}$)alkyl.

In one embodiment, the compound of the invention consisting of the formula,

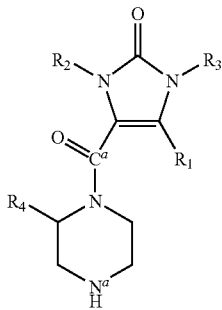

wherein
$R_1$ is phenyl;
$R_2$ is selected from all the variations disclosed above;
$R_3$ is selected from the group consisting of

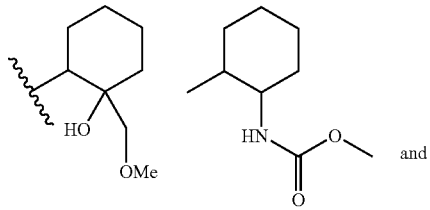

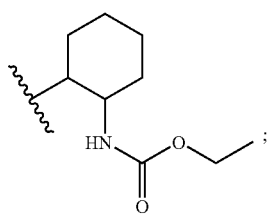

and
$R_4$ is selected from the group consisting of

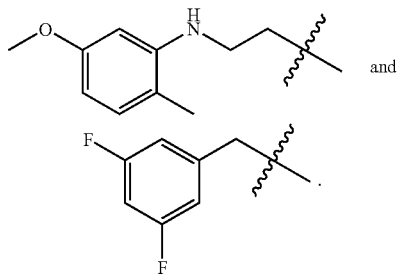

Examples of compounds according to the present invention include, but are not limited to:
(S)-1-((2-Chloro-6-(3-hydroxypyrrolidin-1-yl)pyridin-4-yl)methyl)-3-cyclohexyl-4-phenyl-5-(piperazine-1-carbonyl)-1H-imidazol-2(3H)-one;
(R)-1-((2-Chloro-6-(3-hydroxypyrrolidin-1-yl)pyridin-4-yl)methyl)-3-cyclohexyl-4-phenyl-5-(piperazine-1-carbonyl)-1H-imidazol-2(3H)-one;
1-((2,6-bis((R)-3-Hydroxypyrrolidin-1-yl)pyridin-4-yl)methyl)-3-cyclohexyl-4-phenyl-5-(piperazine-1-carbonyl)-1H-imidazol-2(3H)-one;
1-((2,6-bis((S)-3-Hydroxypyrrolidin-1-yl)pyridin-4-yl)methyl)-3-cyclohexyl-4-phenyl-5-(piperazine-1-carbonyl)-1H-imidazol-2(3H)-one;
1-Cyclohexyl-3((2,6-di(2methoxyl-pyridine-4-yl)pyridin-4-yl)methyl)-5-phenyl-4-(piperazine-1-carbonyl)-1H-imidazol-2(3H)-one;
1-Cyclohexyl-3((6'-methoxy-2,3'-bipyridin-4-yl)methyl)-5-phenyl-4-(piperazine-1-carbonyl)-1H-imidazol-2(3H)-one;
1((6-Chloro-6'-methoxy-2,3'-bipyridin-4-yl)methyl)-3-cyclohexyl-4-phenyl-5-(piperazine-1-carbonyl)-1H-imidazol-2(3H)-one;
1-Cyclohexyl-3((6-(dimethylamino)-6'-methoxy-2,3'-bipyridin-4-yl)methyl)-5-phenyl-4-(piperazine-1-carbonyl)-1H-imidazol-2(3H)-one;
1-Cyclohexyl-3((6-(diethylamino)-6'-methoxy-2,3'-bipyridin-4-yl)methyl)-5-phenyl-4-(piperazine-1-carbonyl)-1H-imidazol-2(3H)-one;
1,5-Diphenyl-4-(piperazine-1-carbonyl)-1H-imidazol-2(3H)-one;
5-Phenyl-4-(piperazine-1-carbonyl)-1-(pyridin-2-yl)-1H-imidazol-2(3H)-one;
4-(2-(Hydroxymethyl)piperazine-1-carbonyl)-1,5-diphenyl-1H-imidazol-2(3H)-one;
5-(3-Fluorophenyl)-1-phenyl-4-(piperazine-1-carbonyl)-1H-imidazol-2(3H)-one;
1-(3-Morpholinophenyl)-5-phenyl-4-(piperazine-1-carbonyl)-1H-imidazol-2(3H)-one;
5-Isopropyl-1-phenyl-4-(piperazine-1-carbonyl)-1H-imidazol-2(3H)-one;
5-Cyclopropyl-1-phenyl-4-(piperazine-1-carbonyl)-1H-imidazol-2(3H)-one;
5-(Cyclopropylmethyl)-1-phenyl-4-(piperazine-1-carbonyl)-1H-imidazol-2(3H)-one;
5-(2-Chlorophenyl)-1-phenyl-4-(piperazine-1-carbonyl)-1H-imidazol-2(3H)-one;
5-(3-Chlorophenyl)-1-phenyl-4-(piperazine-1-carbonyl)-1H-imidazol-2(3H)-one;
5-(4-Chlorophenyl)-1-phenyl-4-(piperazine-1-carbonyl)-1H-imidazol-2(3H)-one;

1-Cyclohexyl-5-phenyl-4-(piperazine-1-carbonyl)-1H-imidazol-2(3H)-one;
Benzyl 3-(2-oxo-5-phenyl-4-(piperazine-1-carbonyl)-2,3-dihydro-1H-imidazol-1-yl)piperidine-1-carboxylate;
1-((1R,2R)-2-(Benzyloxy)cyclohexyl)-5-phenyl-4-(piperazine-1-carbonyl)-1H-imidazol-2(3H)-one;
1-(2-(2-Methoxyethoxy)phenyl)-5-phenyl-4-(piperazine-1-carbonyl)-1H-imidazol-2(3H)-one;
1-(2-(3-Methoxypropoxy)phenyl)-5-phenyl-4-(piperazine-1-carbonyl)-1H-imidazol-2(3H)-one;
1-(3-(2-Methoxyethoxy)phenyl)-5-phenyl-4-(piperazine-1-carbonyl)-1H-imidazol-2(3H)-one;
1-(3-(3-Methoxypropoxy)phenyl)-5-phenyl-4-(piperazine-1-carbonyl)-1H-imidazol-2(3H)-one;
1-(6-(3-Methoxypropoxy)pyridin-2-yl)-5-phenyl-4-(piperazine-1-carbonyl)-1H-imidazol-2(3H)-one;
(R)-1-Cyclohexyl-4-(3-methylpiperazine-1-carbonyl)-5-phenyl-1H-imidazol-2(3H)-one;
1-Cyclohexyl-4-(3-methylpiperazine-1-carbonyl)-5-phenyl-1H-imidazol-2(3H)-one;
(S)-1-Cyclohexyl-4-(3-methylpiperazine-1-carbonyl)-5-phenyl-1H-imidazol-2(3H)-one;
1-Cyclohexyl-4-(3,5-dimethylpiperazine-1-carbonyl)-5-phenyl-1H-imidazol-2(3H)-one;
1-Cyclohexyl-4-(2,5-dimethylpiperazine-1-carbonyl)-5-phenyl-1H-imidazol-2(3H)-one;
5-(3-Chlorophenyl)-1-(3-(3-methoxypropoxy)phenyl)-4-(piperazine-1-carbonyl)-1H-imidazol-2(3H)-one;
5-(3-Chlorophenyl)-1-(3-(2-methoxyethoxy)phenyl)-4-(piperazine-1-carbonyl)-1H-imidazol-2(3H)-one;
1-(1H-Benzo[d]imidazol-2-yl)-5-phenyl-4-(piperazine-1-carbonyl)-1H-imidazol-2(3H)-one;
1-Benzyl-3,4-diphenyl-5-(piperazine-1-carbonyl)-1H-imidazol-2(3H)-one;
1-Benzyl-4-phenyl-5-(piperazine-1-carbonyl)-3-(pyridin-2-yl)-1H-imidazol-2(3H)-one;
1-((5-Methylisoxazol-3-yl)methyl)-3,4-diphenyl-5-(piperazine-1-carbonyl)-1H-imidazol-2(3H)-one;
1-((5-Cyclopropyl-1,3,4-thiadiazol-2-yl)methyl)-3,4-diphenyl-5-(piperazine-1-carbonyl)-1H-imidazol-2(3H)-one;
1-((1H-Imidazol-4-yl)methyl)-3,4-diphenyl-5-(piperazine-1-carbonyl)-1H-imidazol-2(3H)-one;
1-((2-Aminothiazol-4-yl)methyl)-3,4-diphenyl-5-(piperazine-1-carbonyl)-1H-imidazol-2(3H)-one;
1-(3-Fluorobenzyl)-3,4-diphenyl-5-(piperazine-1-carbonyl)-1H-imidazol-2(3H)-one;
1-(3,4-Difluorobenzyl)-3,4-diphenyl-5-(piperazine-1-carbonyl)-1H-imidazol-2(3H)-one;
1,5-Diphenyl-4-(piperazine-1-carbonyl)-3-((tetrahydro-2H-pyran-4-yl)methyl)-1H-imidazol-2(3H)-one;
1-Methyl-3,4-diphenyl-5-(piperazine-1-carbonyl)-1H-imidazol-2(3H)-one;
(R)-4-(2-Benzylpiperazine-1-carbonyl)-3-methyl-1-(3-morpholinophenyl)-5-phenyl-1H-imidazol-2(3H)-one;
1-Benzyl-3-(3-morpholinophenyl)-4-phenyl-5-(piperazine-1-carbonyl)-1H-imidazol-2(3H)-one;
1-(3-(Morpholine-4-carbonyl)benzyl)-3-(3-morpholinophenyl)-4-phenyl-5-(piperazine-1-carbonyl)-1H-imidazol-2(3H)-one;
1-(3-Morpholinophenyl)-5-phenyl-4-(piperazine-1-carbonyl)-3-(3-(piperidine-1-carbonyl)benzyl)-1H-imidazol-2(3H)-one;
2-(3-((3-(3-Morpholinophenyl)-2-oxo-4-phenyl-5-(piperazine-1-carbonyl)-2,3-dihydro-1H-imidazol-1-yl)methyl)phenoxy)acetic acid;
1-Cyclohexyl-3-methyl-5-phenyl-4-(piperazine-1-carbonyl)-1H-imidazol-2(3H)-one;
1-Allyl-3-cyclohexyl-4-phenyl-5-(piperazine-1-carbonyl)-1H-imidazol-2(3H)-one;
2-(3-Cyclohexyl-2-oxo-4-phenyl-5-(piperazine-1-carbonyl)-2,3-dihydro-1H-imidazol-1-yl)acetamide;
(R)-1-Allyl-5-(2-benzylpiperazine-1-carbonyl)-3-cyclohexyl-4-phenyl-1H-imidazol-2(3H)-one;
(R)-4-(2-Benzylpiperazine-1-carbonyl)-1-cyclohexyl-3-methyl-5-phenyl-1H-imidazol-2(3H)-one;
(R)-4-(2-Benzylpiperazine-1-carbonyl)-1-cyclohexyl-3-(2-methoxyethyl)-5-phenyl-1H-imidazol-2(3H)-one;
(R)-2-(5-(2-Benzylpiperazine-1-carbonyl)-3-cyclohexyl-2-oxo-4-phenyl-2,3-dihydro-1H-imidazol-1-yl)acetamide;
Methyl 2-(3-cyclohexyl-2-oxo-4-phenyl-5-(piperazine-1-carbonyl)-2,3-dihydro-1H-imidazol-1-yl)-2-phenylacetate;
1-Cyclohexyl-5-phenyl-3-(1-phenylethyl)-4-(piperazine-1-carbonyl)-1H-imidazol-2(3H)-one;
(R)-4-(2-Benzylpiperazine-1-carbonyl)-1-cyclohexyl-3-methyl-5-phenyl-1H-imidazol-2(3H)-one;
1-Cyclohexyl-3-phenethyl-5-phenyl-4-(piperazine-1-carbonyl)-1H-imidazol-2(3H)-one;
1-(3-(1H-Pyrrol-1-yl)benzyl)-3-cyclohexyl-4-phenyl-5-(piperazine-1-carbonyl)-1H-imidazol-2(3H)-one;
(R)-2-(5-(2-Benzylpiperazine-1-carbonyl)-2-oxo-3,4-diphenyl-2,3-dihydro-1H-imidazol-1-yl)acetamide;
1-(3-Morpholinophenyl)-3-(3-phenoxybenzyl)-5-phenyl-4-(piperazine-1-carbonyl)-1H-imidazol-2(3H)-one;
1-(3-(3-Methoxypropoxy)phenyl)-3-(3-phenoxybenzyl)-5-phenyl-4-(piperazine-1-carbonyl)-1H-imidazol-2(3H)-one;
1-(3-(Benzyloxy)benzyl)-3-(3-morpholinophenyl)-4-phenyl-5-(piperazine-1-carbonyl)-1H-imidazol-2(3H)-one;
1-(3-(1H-Pyrrol-1-yl)benzyl)-3-(3-morpholinophenyl)-4-phenyl-5-(piperazine-1-carbonyl)-1H-imidazol-2(3H)-one;
N-Isobutyl-N-methyl-3-((3-(3-morpholinophenyl)-2-oxo-4-phenyl-5-(piperazine-1-carbonyl)-2,3-dihydro-1H-imidazol-1-yl)methyl)benzamide;
3-((2-O-oxo-3,4-Diphenyl-5-(piperazine-1-carbonyl)-2,3-dihydro-1H-imidazol-1-yl)methyl)benzonitrile;
Methyl 3-((2-oxo-3,4-Diphenyl-5-(piperazine-1-carbonyl)-2,3-dihydro-1H-imidazol-1-yl)methyl)benzoate;
1-Benzyl-4-phenyl-5-(piperazine-1-carbonyl)-3-(tetrahydro-2H-pyran-4-yl)-1H-imidazol-2(3H)-one;
1,5-Diphenyl-4-(piperazine-1-carbonyl)-3-(quinolin-8-ylmethyl)-1H-imidazol-2(3H)-one;
1-(3-Methoxybenzyl)-3,4-diphenyl-5-(piperazine-1-carbonyl)-1H-imidazol-2(3H)-one;
1-(Naphthalen-2-ylmethyl)-3,4-diphenyl-5-(piperazine-1-carbonyl)-1H-imidazol-2(3H)-one;
2-((2-oxo-3,4-Diphenyl-5-(piperazine-1-carbonyl)-2,3-dihydro-1H-imidazol-1-yl)methyl)benzonitrile;
1-(3,5-Dimethoxybenzyl)-3,4-diphenyl-5-(piperazine-1-carbonyl)-1H-imidazol-2(3H)-one;
1-(4-Chloro-3-(trifluoromethoxy)benzyl)-3,4-diphenyl-5-(piperazine-1-carbonyl)-1H-imidazol-2(3H)-one;
1-(3-(1H-Pyrrol-1-yl)benzyl)-3,4-diphenyl-5-(piperazine-1-carbonyl)-1H-imidazol-2(3H)-one;
1-Cyclohexyl-4-(1,4-diazepane-1-carbonyl)-5-phenyl-1H-imidazol-2(3H)-one;
1-((2-Chloro-6-morpholinopyridin-4-yl)methyl)-3-cyclohexyl-4-phenyl-5-(piperazine-1-carbonyl)-1H-imidazol-2(3H)-one;
1-Cyclohexyl-3-((2,6-di(1H-pyrazol-4-yl)pyridin-4-yl)methyl)-5-phenyl-4-(piperazine-1-carbonyl)-1H-imidazol-2(3H)-one;

1-(1-Acetylpiperidin-3-yl)-3-(3-methoxybenzyl)-5-phenyl-4-(piperazine-1carbonyl)-1H-imidazol-2(3H)-one;
1-(1-Acetylpiperidin-3-yl)-3-benzyl-5-phenyl-4-(piperazine-1-carbonyl)-1H-imidazol-2(3H)-one;
1-(1-Acetylpiperidin-3-yl)-5-phenyl-4-(piperazine-1-carbonyl)-1H-imidazol-2(3H)-one;
1-(1-Benzoylpiperidin-3-yl)-3-benzyl-5-phenyl-4-(piperazine-1-carbonyl)-1H-imidazol-2(3H)-one;
1-Benzyl-4-phenyl-3-(1-(phenylsulfonyl)piperidin-3-yl)-5-(piperazine-1-carbonyl)-1H-imidazol-2(3H)-one;
1-Benzyl-3-(1-(furan-2-carbonyl)piperidin-3-yl)-4-phenyl-5-(piperazine-1-carbonyl)-1H-imidazol-2(3H)-one;
5-Phenyl-1-(1-(phenylsulfonyl)piperidin-3-yl)-4-(piperazine-1-carbonyl)-1H-imidazol-2(3H)-one;
1-(1-Acetylpiperidin-3-yl)-3-(3-phenoxybenzyl)-5-phenyl-4-(piperazine-1-carbonyl)-1H-imidazol-2(3H)-one;
1-Benzyl-4-phenyl-3-(1-(phenylsulfonyl)piperidin-3-yl)-5-(piperazine-1-carbonyl)-1H-imidazol-2(3H)-one;
1-Benzyl-4-phenyl-5-(piperazine-1-carbonyl)-3-(1-(pyridin-2-ylsulfonyl)piperidin-3-yl)-1H-imidazol-2(3H)-one;
1-(3-Phenoxybenzyl)-4-phenyl-3-(1-(phenylsulfonyl)piperidin-3-yl)-5-(piperazine-1-carbonyl)-1H-imidazol-2(3H)-one;
1-(3-Phenoxybenzyl)-4-phenyl-5-(piperazine-1-carbonyl)-3-(1-(pyridin-2-ylsulfonyl)piperidin-3-yl)-1H-imidazol-2(3H)-one;
1-(1-Acetylpiperidin-3-yl)-4-((R)-2-benzylpiperazine-1-carbonyl)-5-phenyl-1H-imidazol-2(3H)-one;
1-Benzyl-3-((1R,2R)-2-hydroxycyclohexyl)-4-phenyl-5-(piperazine-1-carbonyl)-1H-imidazol-2(3H)-one;
1-((1R,2R)-2-Hydroxycyclohexyl)-3-(3-phenoxybenzyl)-5-phenyl-4-(piperazine-1-carbonyl)-1H-imidazol-2(3H)-one;
N—(((S)-1-(1-((1R,2R)-2-Hydroxycyclohexyl)-2-oxo-5-phenyl-2,3-dihydro-1H-imidazole-4-carbonyl)piperazin-2-yl)methyl)benzamide;
(S)—N-((1-(1-Cyclohexyl-2-oxo-5-phenyl-2,3-dihydro-1H-imidazole-4-carbonyl)piperazin-2-yl)methyl)benzamide;
(R)-4-(2-Benzylpiperazine-1-carbonyl)-1,5-diphenyl-1H-imidazol-2(3H)-one;
(R)-4-(2-Benzylpiperazine-1-carbonyl)-1-(3-morpholinophenyl)-5-phenyl-1H-imidazol-2(3H)-one;
(R)-4-(2-Benzylpiperazine-1-carbonyl)-1-cyclohexyl-5-phenyl-1H-imidazol-2(3H)-one;
(R)-4-(2-Benzylpiperazine-1-carbonyl)-1-(2,3-dimethoxyphenyl)-5-phenyl-1H-imidazol-2(3H)-one;
(R)-4-(2-Benzylpiperazine-1-carbonyl)-1-(2-methoxyphenyl)-5-phenyl-1H-imidazol-2(3H)-one;
(R)-4-(2-Benzylpiperazine-1-carbonyl)-1-(3-(methylsulfonyl)phenyl)-5-phenyl-1H-imidazol-2(3H)-one;
1-(1-Acetylpiperidin-3-yl)-4-((R)-2-benzylpiperazine-1-carbonyl)-5-phenyl-1H-imidazol-2(3H)-one;
(R)-4-(2-Benzylpiperazine-1-carbonyl)-5-phenyl-1-o-tolyl-1H-imidazol-2(3H)-one;
(R)-4-(2-Benzylpiperazine-1-carbonyl)-1-(2-nitrophenyl)-5-phenyl-1H-imidazol-2(3H)-one;
(R)—N-(2-(4-(2-Benzylpiperazine-1-carbonyl)-2-oxo-5-phenyl-2,3-dihydro-1H-imidazol-1-yl)phenyl)methanesulfonamide;
(R)—N-(2-(4-(2-Benzylpiperazine-1-carbonyl)-2-oxo-5-phenyl-2,3-dihydro-1H-imidazol-1-yl)phenyl)propane-1-sulfonamide;
(R)—N-(2-(4-(2-Benzylpiperazine-1-carbonyl)-2-oxo-5-phenyl-2,3-dihydro-1H-imidazol-1-yl)phenyl)cyclopropanecarboxamide;
(R)—N-(2-(4-(2-Benzylpiperazine-1-carbonyl)-2-oxo-5-phenyl-2,3-dihydro-1H-imidazol-1-yl)phenyl)butyramide;
(R)—N-(2-(4-(2-Benzylpiperazine-1-carbonyl)-2-oxo-5-phenyl-2,3-dihydro-1H-imidazol-1-yl)phenyl)acetamide;
(R)—N-(2-(4-(2-Benzylpiperazine-1-carbonyl)-2-oxo-5-phenyl-2,3-dihydro-1H-imidazol-1-yl)phenyl)cyclopropanesulfonamide;
(R)—N-(2-(4-(2-Benzylpiperazine-1-carbonyl)-2-oxo-5-phenyl-2,3-dihydro-1H-imidazol-1-yl)phenyl)benzamide;
(R)—N-(2-(4-(2-Benzylpiperazine-1-carbonyl)-2-oxo-5-phenyl-2,3-dihydro-1H-imidazol-1-yl)phenyl)Benzenesulfonamide;
4-((R)-2-Benzylpiperazine-1-carbonyl)-14(1S,2S)-2-hydroxycyclohexyl)-5-phenyl-1H-imidazol-2(3H)-one;
(R)—N-(2-(4-(2-Benzylpiperazine-1-carbonyl)-2-oxo-5-phenyl-2,3-dihydro-1H-imidazol-1-yl)phenyl)ethanesulfonamide;
(R)—N-(2-(4-(2-Benzylpiperazine-1-carbonyl)-2-oxo-5-phenyl-2,3-dihydro-1H-imidazol-1-yl)phenyl)butane-1-sulfonamide;
(R)—N-(2-(4-(2-Benzylpiperazine-1-carbonyl)-2-oxo-5-phenyl-2,3-dihydro-1H-imidazol-1-yl)phenyl)prop-2-ene-1-sulfonamide;
(R)-4-(2-Benzylpiperazine-1-carbonyl)-1-((1-hydroxycyclohexyl)methyl)-5-phenyl-1H-imidazol-2(3H)-one;
(R)-4-(2-Benzylpiperazine-1-carbonyl)-5-phenyl-1-(1,2,3,4-tetrahydroquinolin-7-yl)-1H-imidazol-2(3H)-one;
(R)-4-(2-Benzylpiperazine-1-carbonyl)-5-phenyl-1-(1,2,3,4-tetrahydroquinolin-7-yl)-1H-imidazol-2(3H)-one;
(R)-4-(2-Benzylpiperazine-1-carbonyl)-1-(1-butyl-1,2,3,4-tetrahydroquinolin-7-yl)-5-cyclopropyl-1H-imidazol-2(3H)-one;
(R)-4-(2-Benzylpiperazine-1-carbonyl)-5-cyclopropyl-1-(1,2,3,4-tetrahydroquinolin-7-yl)-1H-imidazol-2(3H)-one;
(R)-4-(2-Benzylpiperazine-1-carbonyl)-1-(4-methyl-3,4-dihydro-2H-benzo[b][1,4]oxazin-6-yl)-5-phenyl-1H-imidazol-2(3H)-one;
(R)-4-(2-Benzylpiperazine-1-carbonyl)-1-(indolin-6-yl)-5-phenyl-1H-imidazol-2(3H)-one;
(R)-4-(2-Benzylpiperazine-1-carbonyl)-1-(4-(2-methoxyethyl)-3,4-dihydro-2H-benzo[b][1,4]oxazin-6-yl)-5-phenyl-1H-imidazol-2(3H)-one;
4-((R)-2-Benzylpiperazine-1-carbonyl)-1-(3-methoxy-2,3-dihydro-1H-inden-5-yl)-5-phenyl-1H-imidazol-2(3H)-one;
(S)-(6-(4-(2-Benzylpiperidine-1-carbonyl)-2-oxo-5-phenyl-2,3-dihydro-1H-imidazol-1-yl)indolin-1-yl)methyl acetate;
(R)-4-(2-(2-Phenoxyethyl)piperazine-1-carbonyl)-5-phenyl-1-(1,2,3,4-tetrahydroquinolin-7-yl)-1H-imidazol-2(3H)-one.
1-Allyl-4-phenyl-5-(piperazine-1-carbonyl)-3-o-tolyl-1H-imidazol-2(3H)-one;
1-(3-Phenoxybenzyl)-4-phenyl-5-(piperazine-1-carbonyl)-3-o-tolyl-1H-imidazol-2(3H)-one;
1-(3-Methoxybenzyl)-4-phenyl-5-(piperazine-1-carbonyl)-3-o-tolyl-1H-imidazol-2(3H)-one;
1-(3,4-Difluorobenzyl)-4-phenyl-5-(piperazine-1-carbonyl)-3-o-tolyl-1H-imidazol-2(3H)-one;
1-Allyl-3-(2-methoxyphenyl)-4-phenyl-5-(piperazine-1-carbonyl)-1H-imidazol-2(3H)-one;
1-(2-Methoxyphenyl)-3-(3-phenoxybenzyl)-5-phenyl-4-(piperazine-1-carbonyl)-1H-imidazol-2(3H)-one;
1-(3-Methoxybenzyl)-3-(2-methoxyphenyl)-4-phenyl-5-(piperazine-1-carbonyl)-1H-imidazol-2(3H)-one;

1-(3,4-Difluorobenzyl)-3-(2-methoxyphenyl)-4-phenyl-5-(piperazine-1-carbonyl)-1H-imidazol-2(3H)-one;

1-(3-(2-Phenoxyethoxy)benzyl)-4-phenyl-5-(piperazine-1-carbonyl)-3-o-tolyl-1H-imidazol-2(3H)-one;

1-Allyl-3-(3-morpholinophenyl)-4-phenyl-5-(piperazine-1-carbonyl)-1H-imidazol-2(3H)-one;

1-(3-Methoxybenzyl)-3-(3-morpholinophenyl)-4-phenyl-5-(piperazine-1-carbonyl)-1H-imidazol-2(3H)-one;

1-((1S,2R)-2-Hydroxycyclohexyl)-3-(3-phenoxybenzyl)-5-phenyl-4-(piperazine-1-carbonyl)-1H-imidazol-2(3H)-one;

1-((1S,2R)-2-Hydroxycyclohexyl)-3-(3-methoxybenzyl)-5-phenyl-4-(piperazine-1-carbonyl)-1H-imidazol-2(3H)-one;

1-(3,4-Difluorobenzyl)-3-((1S,2R)-2-hydroxycyclohexyl)-4-phenyl-5-(piperazine-1-carbonyl)-1H-imidazol-2(3H)-one;

N-(2-(2-oxo-4-Phenyl-5-(piperazine-1-carbonyl)-3-o-tolyl-2,3-dihydro-1H-imidazol-1-yl)ethyl)benzenesulfonamide;

N-(3-(2-oxo-4-Phenyl-5-(piperazine-1-carbonyl)-3-o-tolyl-2,3-dihydro-1H-imidazol-1-yl)propyl)benzamide;

1-(Cyclohexylmethyl)-3-((1S,2R)-2-hydroxycyclohexyl)-4-phenyl-5-(piperazine-1-carbonyl)-1H-imidazol-2(3H)-one;

N-(2-(3-(2-Methoxyphenyl)-2-oxo-4-phenyl-5-(piperazine-1-carbonyl)-2,3-dihydro-1H-imidazol-1-yl)ethyl)benzenesulfonamide;

N-(3-(3-(2-Methoxyphenyl)-2-oxo-4-phenyl-5-(piperazine-1-carbonyl)-2,3-dihydro-1H-imidazol-1-yl)propyl)benzamide;

1-(Cyclohexylmethyl)-3-(2-methoxyphenyl)-4-phenyl-5-(piperazine-1-carbonyl)-1H-imidazol-2(3H)-one;

N-(3-(3-(2-Methoxyphenyl)-2-oxo-4-phenyl-5-(piperazine-1-carbonyl)-2,3-dihydro-1H-imidazol-1-yl)propyl)benzenesulfonamide;

N-(3-(2-oxo-4-Phenyl-5-(piperazine-1-carbonyl)-3-o-tolyl-2,3-dihydro-1H-imidazol-1-yl)propyl)benzenesulfonamide;

1-(Cyclohexylmethyl)-4-phenyl-5-(piperazine-1-carbonyl)-3-o-tolyl-1H-imidazol-2(3H)-one;

1-(3,4-Difluorobenzyl)-3-(3-(3-methoxypropoxy)phenyl)-4-phenyl-5-(piperazine-1-carbonyl)-1H-imidazol-2(3H)-one;

3-Methyl-N-(3-(2-oxo-4-phenyl-5-(piperazine-1-carbonyl)-3-o-tolyl-2,3-dihydro-1H-imidazol-1-yl)propyl)butanamide;

N-(2-(2-oxo-4-Phenyl-5-(piperazine-1-carbonyl)-3-o-tolyl-2,3-dihydro-1H-imidazol-1-yl)ethyl)benzamide;

N-(3-(3-(2-Methoxyphenyl)-2-oxo-4-phenyl-5-(piperazine-1-carbonyl)-2,3-dihydro-1H-imidazol-1-yl)propyl)-3-methylbutanamide;

N-(2-(3-(2-Methoxyphenyl)-2-oxo-4-phenyl-5-(piperazine-1-carbonyl)-2,3-dihydro-1H-imidazol-1-yl)ethyl)benzamide;

N-(2-(3-(2-Methoxyphenyl)-2-oxo-4-phenyl-5-(piperazine-1-carbonyl)-2,3-dihydro-1H-imidazol-1-yl)ethyl)-3-methylbutanamide;

N-(3-(3-((2S)-2-Hydroxycyclohexyl)-2-oxo-4-phenyl-5-(piperazine-1-carbonyl)-2,3-dihydro-1H-imidazol-1-yl)propyl)benzamide;

N-(3-(3-((2S)-2-Hydroxycyclohexyl)-2-oxo-4-phenyl-5-(piperazine-1-carbonyl)-2,3-dihydro-1H-imidazol-1-yl)propyl)benzenesulfonamide;

N-(3-(3-((2S)-2-Hydroxycyclohexyl)-2-oxo-4-phenyl-5-(piperazine-1-carbonyl)-2,3-dihydro-1H-imidazol-1-yl)propyl)-3-methylbutanamide;

N-(2-(3-((2S)-2-Hydroxycyclohexyl)-2-oxo-4-phenyl-5-(piperazine-1-carbonyl)-2,3-dihydro-1H-imidazol-1-yl)ethyl)-3-methylbutanamide;

N-(3-(3-(3-Morpholinophenyl)-2-oxo-4-phenyl-5-(piperazine-1-carbonyl)imidazolidin-1-yl)propyl)benzamide;

N-(3-(3-(3-Morpholinophenyl)-2-oxo-4-phenyl-5-(piperazine-1-carbonyl)-2,3-dihydro-1H-imidazol-1-yl)propyl)benzenesulfonamide;

3-Methyl-N-(3-(3-(3-morpholinophenyl)-2-oxo-4-phenyl-5-(piperazine-1-carbonyl)-2,3-dihydro-1H-imidazol-1-yl)propyl)butanamide;

N-(2-(3-(3-Morpholinophenyl)-2-oxo-4-phenyl-5-(piperazine-1-carbonyl)-2,3-dihydro-1H-imidazol-1-yl)ethyl)benzamide;

3-Methyl-N-(2-(3-(3-morpholinophenyl)-2-oxo-4-phenyl-5-(piperazine-1-carbonyl)-2,3-dihydro-1H-imidazol-1-yl)ethyl)butanamide;

N-(3-(3-(3-(3-Methoxypropoxy)phenyl)-2-oxo-4-phenyl-5-(piperazine-1-carbonyl)-2,3-dihydro-1H-imidazol-1-yl)propyl)benzamide;

N-(3-(3-(3-(3-Methoxypropoxy)phenyl)-2-oxo-4-phenyl-5-(piperazine-1-carbonyl)-2,3-dihydro-1H-imidazol-1-yl)propyl)benzenesulfonamide;

N-(3-(3-(3-(3-Methoxypropoxy)phenyl)-2-oxo-4-phenyl-5-(piperazine-1-carbonyl)-2,3-dihydro-1H-imidazol-1-yl)propyl)-3-methylbutanamide;

N-(2-(3-(3-(3-Methoxypropoxy)phenyl)-2-oxo-4-phenyl-5-(piperazine-1-carbonyl)-2,3-dihydro-1H-imidazol-1-yl)ethyl)benzamide;

N-(2-(3-(3-(3-Methoxypropoxy)phenyl)-2-oxo-4-phenyl-5-(piperazine-1-carbonyl)-2,3-dihydro-1H-imidazol-1-yl)ethyl)benzenesulfonamide;

N-(2-(3-(3-(3-Methoxypropoxy)phenyl)-2-oxo-4-phenyl-5-(piperazine-1-carbonyl)-2,3-dihydro-1H-imidazol-1-yl)ethyl)-3-methylbutanamide;

N-(2-(3-(3-Morpholinophenyl)-2-oxo-4-phenyl-5-(piperazine-1-carbonyl)-2,3-dihydro-1H-imidazol-1-yl)ethyl)benzenesulfonamide;

1-(3-(2-Methoxyethoxy)benzyl)-4-phenyl-5-(piperazine-1-carbonyl)-3-o-tolyl-1H-imidazol-2(3H)-one;

1-(3-(2-Methoxyethoxy)benzyl)-3-(2-methoxyphenyl)-4-phenyl-5-(piperazine-1-carbonyl)-1H-imidazol-2(3H)-one;

1-(2-Methoxyphenyl)-3-(3-(2-phenoxyethoxy)benzyl)-5-phenyl-4-(piperazine-1-carbonyl)-1H-imidazol-2(3H)-one;

1-(Cyclohexylmethyl)-3-(3-morpholinophenyl)-4-phenyl-5-(piperazine-1-carbonyl)-1H-imidazol-2(3H)-one;

1-(3,4-Difluorobenzyl)-3-(3-morpholinophenyl)-4-phenyl-5-(piperazine-1-carbonyl)-1H-imidazol-2(3H)-one;

1-(3-Morpholinophenyl)-3-(3-(2-phenoxyethoxy)benzyl)-5-phenyl-4-(piperazine-1-carbonyl)-1H-imidazol-2(3H)-one;

1-(3-(2-Methoxyethoxy)benzyl)-3-(3-(3-methoxypropoxy)phenyl)-4-phenyl-5-(piperazine-1-carbonyl)-1H-imidazol-2(3H)-one;

2-Fluoro-N-(3-(3-(3-morpholinophenyl)-2-oxo-4-phenyl-5-(piperazine-1-carbonyl)-2,3-dihydro-1H-imidazol-1-yl)propyl)benzenesulfonamide;

2-Chloro-N-(3-(3-(3-morpholinophenyl)-2-oxo-4-phenyl-5-(piperazine-1-carbonyl)-2,3-dihydro-1H-imidazol-1-yl)propyl)benzenesulfonamide;

3-Chloro-N-(3-(3-(3-morpholinophenyl)-2-oxo-4-phenyl-5-(piperazine-1-carbonyl)-2,3-dihydro-1H-imidazol-1-yl)propyl)benzenesulfonamide;

N-(3-(3-(3-Morpholinophenyl)-2-oxo-4-phenyl-5-(piperazine-1-carbonyl)-2,3-dihydro-1H-imidazol-1-yl)propyl)propane-2-sulfonamide;

2-Methyl-N-(3-(3-(3-morpholinophenyl)-2-oxo-4-phenyl-5-(piperazine-1-carbonyl)-2,3-dihydro-1H-imidazol-1-yl)propyl)benzenesulfonamide;

3-Methoxy-N-(3-(3-(3-morpholinophenyl)-2-oxo-4-phenyl-5-(piperazine-1-carbonyl)-2,3-dihydro-1H-imidazol-1-yl)propyl)benzenesulfonamide;

4-Methoxy-N-(3-(3-(3-morpholinophenyl)-2-oxo-4-phenyl-5-(piperazine-1-carbonyl)-2,3-dihydro-1H-imidazol-1-yl)propyl)benzenesulfonamide;

1-(3-(3-(3-Morpholinophenyl)-2-oxo-4-phenyl-5-(piperazine-1-carbonyl)-2,3-dihydro-1H-imidazol-1-yl)propyl)-3-phenylurea;

1-Isopropyl-3-(3-(3-(3-morpholinophenyl)-2-oxo-4-phenyl-5-(piperazine-1-carbonyl)-2,3-dihydro-1H-imidazol-1-yl)propyl)urea;

4-Chloro-N-(3-(3-(3-morpholinophenyl)-2-oxo-4-phenyl-5-(piperazine-1-carbonyl)-2,3-dihydro-1H-imidazol-1-yl)propyl)benzenesulfonamide;

2-Fluoro-N-(2-(2-oxo-4-phenyl-5-(piperazine-1-carbonyl)-3-o-tolyl-2,3-dihydro-1H-imidazol-1-yl)ethyl)benzenesulfonamide;

2-Chloro-N-(2-(2-oxo-4-phenyl-5-(piperazine-1-carbonyl)-3-o-tolyl-2,3-dihydro-1H-imidazol-1-yl)ethyl)benzenesulfonamide;

3-Chloro-N-(2-(2-oxo-4-phenyl-5-(piperazine-1-carbonyl)-3-o-tolyl-2,3-dihydro-1H-imidazol-1-yl)ethyl)benzenesulfonamide;

4-Chloro-N-(2-(2-oxo-4-phenyl-5-(piperazine-1-carbonyl)-3-o-tolyl-2,3-dihydro-1H-imidazol-1-yl)ethyl)benzenesulfonamide;

N-(2-(2-oxo-4-phenyl-5-(piperazine-1-carbonyl)-3-o-tolyl-2,3-dihydro-1H-imidazol-1-yl)ethyl)propane-2-sulfonamide;

2-Methyl-N-(2-(2-oxo-4-phenyl-5-(piperazine-1-carbonyl)-3-o-tolyl-2,3-dihydro-1H-imidazol-1-yl)ethyl)benzenesulfonamide;

3-Methoxy-N-(2-(2-oxo-4-phenyl-5-(piperazine-1-carbonyl)-3-o-tolyl-2,3-dihydro-1H-imidazol-1-yl)ethyl)benzenesulfonamide;

4-Methoxy-N-(2-(2-oxo-4-phenyl-5-(piperazine-1-carbonyl)-3-o-tolyl-2,3-dihydro-1H-imidazol-1-yl)ethyl)benzenesulfonamide;

1-(2-(2-oxo-4-phenyl-5-(piperazine-1-carbonyl)-3-o-tolyl-2,3-dihydro-1H-imidazol-1-yl)ethyl)-3-phenylurea;

1-(2-Chlorophenyl)-3-(2-(2-oxo-4-phenyl-5-(piperazine-1-carbonyl)-3-o-tolyl-2,3-dihydro-1H-imidazol-1-yl)ethyl)urea;

1-(4-Chlorophenyl)-3-(2-(2-oxo-4-phenyl-5-(piperazine-1-carbonyl)-3-o-tolyl-2,3-dihydro-1H-imidazol-1-yl)ethyl)urea;

1-(2-Methoxyphenyl)-3-(2-(2-oxo-4-phenyl-5-(piperazine-1-carbonyl)-3-o-tolyl-2,3-dihydro-1H-imidazol-1-yl)ethyl)urea;

1-(3-Methoxyphenyl)-3-(2-(2-oxo-4-phenyl-5-(piperazine-1-carbonyl)-3-o-tolyl-2,3-dihydro-1H-imidazol-1-yl)ethyl)urea;

1-Isopropyl-3-(2-(2-oxo-4-phenyl-5-(piperazine-1-carbonyl)-3-o-tolyl-2,3-dihydro-1H-imidazol-1-yl)ethyl)urea;

2-Chloro-N-(3-(2-oxo-4-phenyl-5-(piperazine-1-carbonyl)-3-o-tolyl-2,3-dihydro-1H-imidazol-1-yl)propyl)benzenesulfonamide;

3-Chloro-N-(3-(2-oxo-4-phenyl-5-(piperazine-1-carbonyl)-3-o-tolyl-2,3-dihydro-1H-imidazol-1-yl)propyl)benzenesulfonamide;

4-Chloro-N-(3-(2-oxo-4-phenyl-5-(piperazine-1-carbonyl)-3-o-tolyl-2,3-dihydro-1H-imidazol-1-yl)propyl)benzenesulfonamide;

2-Methyl-N-(3-(2-oxo-4-phenyl-5-(piperazine-1-carbonyl)-3-o-tolyl-2,3-dihydro-1H-imidazol-1-yl)propyl)benzenesulfonamide;

3-Methoxy-N-(3-(2-oxo-4-phenyl-5-(piperazine-1-carbonyl)-3-o-tolyl-2,3-dihydro-1H-imidazol-1-yl)propyl)benzenesulfonamide;

4-Methoxy-N-(3-(2-oxo-4-phenyl-5-(piperazine-1-carbonyl)-3-o-tolyl-2,3-dihydro-1H-imidazol-1-yl)propyl)benzenesulfonamide;

1-(3-(2-Oxo-4-phenyl-5-(piperazine-1-carbonyl)-3-o-tolyl-2,3-dihydro-1H-imidazol-1-yl)propyl)-3-phenylurea;

1-(2-Chlorophenyl)-3-(3-(2-oxo-4-phenyl-5-(piperazine-1-carbonyl)-3-o-tolyl-2,3-dihydro-1H-imidazol-1-yl)propyl)urea;

1-(2-Methoxyphenyl)-3-(3-(2-oxo-4-phenyl-5-(piperazine-1-carbonyl)-3-o-tolyl-2,3-dihydro-1H-imidazol-1-yl)propyl)urea;

1-(3-Methoxyphenyl)-3-(3-(2-oxo-4-phenyl-5-(piperazine-1-carbonyl)-3-o-tolyl-2,3-dihydro-1H-imidazol-1-yl)propyl)urea;

1-Isopropyl-3-(3-(2-oxo-4-phenyl-5-(piperazine-1-carbonyl)-3-o-tolyl-2,3-dihydro-1H-imidazol-1-yl)propyl)urea;

1-(4-Methoxyphenyl)-3-(2-(2-oxo-4-phenyl-5-(piperazine-1-carbonyl)-3-o-tolyl-2,3-dihydro-1H-imidazol-1-yl)ethyl)urea;

2-Fluoro-N-(3-(2-oxo-4-phenyl-5-(piperazine-1-carbonyl)-3-o-tolyl-2,3-dihydro-1H-imidazol-1-yl)propyl)benzenesulfonamide;

2-Fluoro-N-(2-(2-oxo-4-phenyl-5-(piperazine-1-carbonyl)-3-o-tolyl-2,3-dihydro-1H-imidazol-1-yl)ethyl)benzamide;

2-Chloro-N-(2-(2-oxo-4-phenyl-5-(piperazine-1-carbonyl)-3-o-tolyl-2,3-dihydro-1H-imidazol-1-yl)ethyl)benzamide;

2-Chloro-N-(2-(2-oxo-4-phenyl-5-(piperazine-1-carbonyl)-3-o-tolyl-2,3-dihydro-1H-imidazol-1-yl)ethyl)benzamide;

3-Chloro-N-(2-(2-oxo-4-phenyl-5-(piperazine-1-carbonyl)-3-o-tolyl-2,3-dihydro-1H-imidazol-1-yl)ethyl)benzamide;

4-Chloro-N-(2-(2-oxo-4-phenyl-5-(piperazine-1-carbonyl)-3-o-tolyl-2,3-dihydro-1H-imidazol-1-yl)ethyl)benzamide;

2-Methoxy-N-(2-(2-oxo-4-phenyl-5-(piperazine-1-carbonyl)-3-o-tolyl-2,3-dihydro-1H-imidazol-1-yl)ethyl)benzamide;

4-Methoxy-N-(2-(2-oxo-4-phenyl-5-(piperazine-1-carbonyl)-3-o-tolyl-2,3-dihydro-1H-imidazol-1-yl)ethyl)benzamide;

N-(2-(2-Oxo-4-phenyl-5-(piperazine-1-carbonyl)-3-o-tolyl-2,3-dihydro-1H-imidazol-1-yl)ethyl)isobutyramide;

N-(2-(2-Oxo-4-phenyl-5-(piperazine-1-carbonyl)-3-o-tolyl-2,3-dihydro-1H-imidazol-1-yl)ethyl)cyclohexanecarboxamide 3-Methyl-N-(2-(2-oxo-4-phenyl-5-(piperazine-1-carbonyl)-3-o-tolyl-2,3-dihydro-1H-imidazol-1-yl)ethyl)butanamide;

N-(3-(2-Oxo-4-phenyl-5-(piperazine-1-carbonyl)-3-o-tolyl-2,3-dihydro-1H-imidazol-1-yl)propyl)propane-2-sulfonamide;

2-Fluoro-N-(3-(2-oxo-4-phenyl-5-(piperazine-1-carbonyl)-3-o-tolyl-2,3-dihydro-1H-imidazol-1-yl)propyl)benzamide;

2-Chloro-N-(3-(2-oxo-4-phenyl-5-(piperazine-1-carbonyl)-3-o-tolyl-2,3-dihydro-1H-imidazol-1-yl)propyl)benzamide;
3-Chloro-N-(3-(2-oxo-4-phenyl-5-(piperazine-1-carbonyl)-3-o-tolyl-2,3-dihydro-1H-imidazol-1-yl)propyl)benzamide;
4-Chloro-N-(3-(2-oxo-4-phenyl-5-(piperazine-1-carbonyl)-3-o-tolyl-2,3-dihydro-1H-imidazol-1-yl)propyl)benzamide;
2-Methoxy-N-(3-(2-oxo-4-phenyl-5-(piperazine-1-carbonyl)-3-o-tolyl-2,3-dihydro-1H-imidazol-1-yl)propyl)benzamide;
4-Methoxy-N-(3-(2-oxo-4-phenyl-5-(piperazine-1-carbonyl)-3-o-tolyl-2,3-dihydro-1H-imidazol-1-yl)propyl)benzamide;
N-(3-(2-Oxo-4-phenyl-5-(piperazine-1-carbonyl)-3-o-tolyl-2,3-dihydro-1H-imidazol-1-yl)propyl)isobutyramide;
N-(3-(2-Oxo-4-phenyl-5-(piperazine-1-carbonyl)-3-o-tolyl-2,3-dihydro-1H-imidazol-1-yl)propyl)cyclohexanecarboxamide;
Phenyl 2-(2-oxo-4-phenyl-5-(piperazine-1-carbonyl)-3-o-tolyl-2,3-dihydro-1H-imidazol-1-yl)ethylcarbamate;
Methyl 2-(2-oxo-4-phenyl-5-(piperazine-1-carbonyl)-3-o-tolyl-2,3-dihydro-1H-imidazol-1-yl)ethylcarbamate;
Ethyl 2-(2-oxo-4-phenyl-5-(piperazine-1-carbonyl)-3-o-tolyl-2,3-dihydro-1H-imidazol-1-yl)ethylcarbamate;
Benzyl 2-(2-oxo-4-phenyl-5-(piperazine-1-carbonyl)-3-o-tolyl-2,3-dihydro-1H-imidazol-1-yl)ethylcarbamate;
Phenyl 3-(2-oxo-4-phenyl-5-(piperazine-1-carbonyl)-3-o-tolyl-2,3-dihydro-1H-imidazol-1-yl)propylcarbamate;
Methyl 3-(2-oxo-4-phenyl-5-(piperazine-1-carbonyl)-3-o-tolyl-2,3-dihydro-1H-imidazol-1-yl)propylcarbamate;
Ethyl 3-(2-oxo-4-phenyl-5-(piperazine-1-carbonyl)-3-o-tolyl-2,3-dihydro-1H-imidazol-1-yl)propylcarbamate;
Benzyl 3-(2-oxo-4-phenyl-5-(piperazine-1-carbonyl)-3-o-tolyl-2,3-dihydro-1H-imidazol-1-yl)propylcarbamate;
1-(2-Methylphenyl)-5-phenyl-4-(piperazine-1-carbonyl)-3-prop-2-enyl-imidazol-2-one;
1-(Cyclohexylmethyl)-3-(2-methylphenyl)-4-phenyl-5-(piperazine-1-carbonyl)imidazol-2-one;
1-(2-Methylphenyl)-3-[(3-phenoxyphenyl)methyl]-5-phenyl-4-(piperazine-1-carbonyl)imidazol-2-one;
1-[(2-Amino1,3-thiazol-4-yl)methyl]-3-(2-methylphenyl)-4-phenyl-5-(piperazine-1-carbonyl)imidazol-2-one;
1-[(3-Methoxyphenyl)methyl]-3-(2-methylphenyl)-4-phenyl-5-(piperazine-1-carbonyl)imidazol-2-one;
1-[(3,4-Difluorophenyl)methyl]-3-(2-methylphenyl)-4-phenyl-5-(piperazine-1-carbonyl)imidazol-2-one;
N-[2-[3-(2-Methylphenyl)-2-oxo-4-phenyl-5-(piperazine-1-carbonyl)imidazol-1-yl]ethyl]benzamide;
N-[2-[3-(2-Methylphenyl)-2-oxo-4-phenyl-5-(piperazine-1-carbonyl)imidazol-1-yl]ethyl]benzenesulfonamide;
3-Methyl-N-[2-[3-(2-methylphenyl)-2-oxo-4-phenyl-5-(piperazine-1-carbonyl)imidazol-1-yl]ethyl]butanamide;
2-Methyl-N-[2-[3-(2-methylphenyl)-2-oxo-4-phenyl-5-(piperazine-1-carbonyl)imidazol-1-yl]ethyl]propane-1-sulfonamide;
N-[3-[3-(2-Methylphenyl)-2-oxo-4-phenyl-5-(piperazine-1-carbonyl)imidazol-1-yl]propyl]benzamide;
N-[3-[3-(2-Methylphenyl)-2-oxo-4-phenyl-5-(piperazine-1-carbonyl)imidazol-1-yl]propyl]benzenesulfonamide;
3-Methyl-N-[3-[3-(2-methylphenyl)-2-oxo-4-phenyl-5-(piperazine-1-carbonyl)imidazol-1-yl]propyl]butanamide;
2-Methyl-N-[3-[3-(2-methylphenyl)-2-oxo-4-phenyl-5-(piperazine-1-carbonyl)imidazol-1-yl]propyl]propane-1-sulfonamide;
1-[[3-(2-Methoxyethoxy)phenyl]methyl]-3-(2-methylphenyl)-4-phenyl-5-(piperazine-1-carbonyl)imidazol-2-one;
1-(2-Methylphenyl)-5-phenyl-4-(piperazine-1-carbonyl)-3-[[3-(2-pyridin-3-yloxyethoxy)phenyl]methyl]imidazol-2-one;
1-(2-Methylphenyl)-5-phenyl-4-(piperazine-1-carbonyl)-3-[[3-(2-propan-2-yloxyethoxy)phenyl]methyl]imidazol-2-one;
1-(2-Methylphenyl)-3-[[3-(2-phenoxyethoxy)phenyl]methyl]-5-phenyl-4-(piperazine-1-carbonyl)imidazol-2-one;
1-(2-Methylphenyl)-3-[[3-(2-morpholin-4-yl-2-oxo-ethoxy)phenyl]methyl]-5-phenyl-4-(piperazine-1-carbonyl)imidazol-2-one;
1-(2-Methylphenyl)-3-[[3-[2-oxo-2-(1-piperidyl)ethoxy]phenyl]methyl]-5-phenyl-4-(piperazine-1-carbonyl)imidazol-2-one;
N-Methyl-2-[3-[[3-(2-methylphenyl)-2-oxo-4-phenyl-5-(piperazine-1-carbonyl)imidazol-1-yl]methyl]phenoxy]acetamide;
2-[3-[[3-(2-Methylphenyl)-2-oxo-4-phenyl-5-(piperazine-1-carbonyl)imidazol-1-yl]methyl]phenoxy]-N-propan-2-yl-acetamide;
1-(2-Methoxyphenyl)-5-phenyl-4-(piperazine-1-carbonyl)-3-prop-2-enyl-imidazol-2-one;
1-(Cyclohexylmethyl)-3-(2-methoxyphenyl)-4-phenyl-5-(piperazine-1-carbonyl)imidazol-2-one;
1-(2-Methoxyphenyl)-3-[(3-phenoxyphenyl)methyl]-5-phenyl-4-(piperazine-1-carbonyl)imidazol-2-one;
1-[(2-Amino1,3-thiazol-4-yl)methyl]-3-(2-methoxyphenyl)-4-phenyl-5-(piperazine-1-carbonyl)imidazol-2-one;
1-(2-Methoxyphenyl)-3-[(3-methoxyphenyl)methyl]-5-phenyl-4-(piperazine-1-carbonyl)imidazol-2-one;
1-[(3,4-Difluorophenyl)methyl]-3-(2-methoxyphenyl)-4-phenyl-5-(piperazine-1-carbonyl)imidazol-2-one;
N-[2-[3-(2-Methoxyphenyl)-2-oxo-4-phenyl-5-(piperazine-1-carbonyl)imidazol-1-yl]ethyl]benzamide;
N-[2-[3-(2-Methoxyphenyl)-2-oxo-4-phenyl-5-(piperazine-1-carbonyl)imidazol-1-yl]ethyl]benzenesulfonamide;
N-[2-[3-(2-Methoxyphenyl)-2-oxo-4-phenyl-5-(piperazine-1-carbonyl)imidazol-1-yl]ethyl]-3-methyl-butanamide;
N-[2-[3-(2-Methoxyphenyl)-2-oxo-4-phenyl-5-(piperazine-1-carbonyl)imidazol-1-yl]ethyl]-2-methyl-propane-1-sulfonamide;
N-[3-[3-(2-Methoxyphenyl)-2-oxo-4-phenyl-5-(piperazine-1-carbonyl)imidazol-1-yl]propyl]benzamide;
N-[3-[3-(2-Methoxyphenyl)-2-oxo-4-phenyl-5-(piperazine-1-carbonyl)imidazol-1-yl]propyl]benzenesulfonamide;
N-[3-[3-(2-Methoxyphenyl)-2-oxo-4-phenyl-5-(piperazine-1-carbonyl)imidazol-1-yl]propyl]-3-methyl-butanamide;
N-[3-[3-(2-Methoxyphenyl)-2-oxo-4-phenyl-5-(piperazine-1-carbonyl)imidazol-1-yl]propyl]-2-methyl-propane-1-sulfonamide;
1-[[3-(2-Methoxyethoxy)phenyl]methyl]-3-(2-methoxyphenyl)-4-phenyl-5-(piperazine-1-carbonyl)imidazol-2-one;
1-(2-Methoxyphenyl)-5-phenyl-4-(piperazine-1-carbonyl)-3-[[3-(2-pyridin-3-yloxyethoxy)phenyl]methyl]imidazol-2-one;
1-(2-Methoxyphenyl)-5-phenyl-4-(piperazine-1-carbonyl)-3-[[3-(2-propan-2-yloxyethoxy)phenyl]methyl]imidazol-2-one;
1-(2-Methoxyphenyl)-3-[[3-(2-phenoxyethoxy)phenyl]methyl]-5-phenyl-4-(piperazine-1-carbonyl)imidazol-2-one;
1-(2-Methoxyphenyl)-3-[[3-(2-morpholin-4-yl-2-oxo-ethoxy)phenyl]methyl]-5-phenyl-4-(piperazine-1-carbonyl)imidazol-2-one;

1-(2-Methoxyphenyl)-3-[[3-[2-oxo-2-(1-piperidyl)ethoxy]phenyl]methyl]-5-phenyl-4-(piperazine-1-carbonyl)imidazol-2-one;

2-[3-[[3-(2-Methoxyphenyl)-2-oxo-4-phenyl-5-(piperazine-1-carbonyl)imidazol-1-yl]methyl]phenoxy]-N-methyl-acetamide;

2-[3-[[3-(2-Methoxyphenyl)-2-oxo-4-phenyl-5-(piperazine-1-carbonyl)imidazol-1-yl]methyl]phenoxy]-N-propan-2-yl-acetamide;

1-(3-Morpholin-4-ylphenyl)-5-phenyl-4-(piperazine-1-carbonyl)-3-prop-2-enyl-imidazol-2-one;

1-(Cyclohexylmethyl)-3-(3-morpholin-4-ylphenyl)-4-phenyl-5-(piperazine-1-carbonyl)imidazol-2-one;

1-(3-Morpholin-4-ylphenyl)-3-[(3-phenoxyphenyl)methyl]-5-phenyl-4-(piperazine-1-carbonyl)imidazol-2-one;

1-[(2-Amino 1,3-thiazol-4-yl)methyl]-3-(3-morpholin-4-ylphenyl)-4-phenyl-5-(piperazine-1-carbonyl)imidazol-2-one;

1-[(3-Methoxyphenyl)methyl]-3-(3-morpholin-4-ylphenyl)-4-phenyl-5-(piperazine-1-carbonyl)imidazol-2-one;

1-[(3,4-Difluorophenyl)methyl]-3-(3-morpholin-4-ylphenyl)-4-phenyl-5-(piperazine-1-carbonyl)imidazol-2-one;

N-[2-[3-(3-Morpholin-4-ylphenyl)-2-oxo-4-phenyl-5-(piperazine-1-carbonyl)imidazol-1-yl]ethyl]benzamide;

N-[2-[3-(3-Morpholin-4-ylphenyl)-2-oxo-4-phenyl-5-(piperazine-1-carbonyl)imidazol-1-yl]ethyl]benzenesulfonamide;

3-Methyl-N-[2-[3-(3-morpholin-4-ylphenyl)-2-oxo-4-phenyl-5-(piperazine-1-carbonyl)imidazol-1-yl]ethyl]butanamide;

2-Methyl-N-[2-[3-(3-morpholin-4-ylphenyl)-2-oxo-4-phenyl-5-(piperazine-1-carbonyl)imidazol-1-yl]ethyl]propane-1-sulfonamide;

N-[3-[3-(3-Morpholin-4-ylphenyl)-2-oxo-4-phenyl-5-(piperazine-1-carbonyl)imidazol-1-yl]propyl]benzamide;

N-[3-[3-(3-Morpholin-4-ylphenyl)-2-oxo-4-phenyl-5-(piperazine-1-carbonyl)imidazol-1-yl]propyl]benzenesulfonamide;

3-Methyl-N-[3-[3-(3-morpholin-4-ylphenyl)-2-oxo-4-phenyl-5-(piperazine-1-carbonyl)imidazol-1-yl]propyl]butanamide;

2-Methyl-N-[3-[3-(3-morpholin-4-ylphenyl)-2-oxo-4-phenyl-5-(piperazine-1-carbonyl)imidazol-1-yl]propyl]propane-1-sulfonamide;

1-[[3-(2-Methoxyethoxy)phenyl]methyl]-3-(3-morpholin-4-ylphenyl)-4-phenyl-5-(piperazine-1-carbonyl)imidazol-2-one;

1-(3-Morpholin-4-ylphenyl)-5-phenyl-4-(piperazine-1-carbonyl)-3-[[3-(2-pyridin-3-yloxyethoxy)phenyl]methyl]imidazol-2-one;

1-(3-Morpholin-4-ylphenyl)-5-phenyl-4-(piperazine-1-carbonyl)-3-[[3-(2-propan-2-yloxyethoxy)phenyl]methyl]imidazol-2-one 1-(3-Morpholin-4-ylphenyl)-3-[[3-(2-phenoxyethoxy)phenyl]methyl]-5-phenyl-4-(piperazine-1-carbonyl)imidazol-2-one;

1-[[3-(2-Morpholin-4-yl-2-oxo-ethoxy)phenyl]methyl]-3-(3-morpholin-4-ylphenyl)-4-phenyl-5-(piperazine-1-carbonyl)imidazol-2-one;

1-(3-Morpholin-4-ylphenyl)-3-[[3-[2-oxo-2-(1-piperidyl)ethoxy]phenyl]methyl]-5-phenyl-4-(piperazine-1-carbonyl)imidazol-2-one;

N-Methyl-2-[3-[[3-(3-morpholin-4-ylphenyl)-2-oxo-4-phenyl-5-(piperazine-1-carbonyl)imidazol-1-yl]methyl]phenoxy]acetamide;

2-[3-[[3-(3-Morpholin-4-ylphenyl)-2-oxo-4-phenyl-5-(piperazine-1-carbonyl)imidazol-1-yl]methyl]phenoxy]-N-propan-2-yl-acetamide;

1-[3-(3-Methoxypropoxy)phenyl]-5-phenyl-4-(piperazine-1-carbonyl)-3-prop-2-enyl-imidazol-2-one;

1-(Cyclohexylmethyly)-3-[3-(3-methoxypropoxy)phenyl]-4-phenyl-5-(piperazine-1-carbonyl)imidazol-2-one;

1-[3-(3-Methoxypropoxy)phenyl]-3-[(3-phenoxyphenyl)methyl]-5-phenyl-4-(piperazine-1-carbonyl)imidazol-2-one;

1-[(2-Amino 1,3-thiazol-4-yl)methyl]-3-[3-(3-methoxypropoxy)phenyl]-4-phenyl-5-(piperazine-1-carbonyl)imidazol-2-one;

1-[(3-Methoxyphenyl)methyl]-3-[3-(3-methoxypropoxy)phenyl]-4-phenyl-5-(piperazine-1-carbonyl)imidazol-2-one;

1-[(3,4-Difluorophenyl)methyl]-3-[3-(3-methoxypropoxy)phenyl]-4-phenyl-5-(piperazine-1-carbonyl)imidazol-2-one;

N-[2-[3-[3-(3-Methoxypropoxy)phenyl]-2-oxo-4-phenyl-5-(piperazine-1-carbonyl)imidazol-1-yl]ethyl]benzamide;

N-[2-[3-[3-(3-Methoxypropoxy)phenyl]-2-oxo-4-phenyl-5-(piperazine-1-carbonyl)imidazol-1-yl]ethyl]benzenesulfonamide;

N-[2-[3-[3-(3-Methoxypropoxy)phenyl]-2-oxo-4-phenyl-5-(piperazine-1-carbonyl)imidazol-1-yl]ethyl]-3-methyl-butanamide;

N-[2-[3-[3-(3-Methoxypropoxy)phenyl]-2-oxo-4-phenyl-5-(piperazine-1-carbonyl)imidazol-1-yl]ethyl]-2-methyl-propane-1-sulfonamide;

N-[3-[3-[3-(3-Methoxypropoxy)phenyl]-2-oxo-4-phenyl-5-(piperazine-1-carbonyl)imidazol-1-yl]propyl]benzamide;

N-[3-[3-[3-(3-Methoxypropoxy)phenyl]-2-oxo-4-phenyl-5-(piperazine-1-carbonyl)imidazol-1-yl]propyl]benzenesulfonamide;

N-[3-[3-[3-(3-Methoxypropoxy)phenyl]-2-oxo-4-phenyl-5-(piperazine-1-carbonyl)imidazol-1-yl]propyl]-3-methyl-butanamide;

N-[3-[3-[3-(3-Methoxypropoxy)phenyl]-2-oxo-4-phenyl-5-(piperazine-1-carbonyl)imidazol-1-yl]propyl]-2-methyl-propane-1-sulfonamide;

1-[[3-(2-Methoxyethoxy)phenyl]methyl]-3-[3-(3-methoxypropoxy)phenyl]-4-phenyl-5-(piperazine-1-carbonyl)imidazol-2-one;

1-[3-(3-Methoxypropoxy)phenyl]-5-phenyl-4-(piperazine-1-carbonyl)-3-[[3-(2-pyridin-3-yloxyethoxy)phenyl]methyl]imidazol-2-one;

1-[3-(3-Methoxypropoxy)phenyl]-5-phenyl-4-(piperazine-1-carbonyl)-3-[[3-(2-propan-2-yloxyethoxy)phenyl]methyl]imidazol-2-one;

1-[3-(3-Methoxypropoxy)phenyl]-3-[[3-(2-phenoxyethoxy)phenyl]methyl]-5-phenyl-4-(piperazine-1-carbonyl)imidazol-2-one;

1-[3-(3-Methoxypropoxy)phenyl]-3-[[3-(2-morpholin-4-yl-2-oxo-ethoxy)phenyl]methyl]-5-phenyl-4-(piperazine-1-carbonyl)imidazol-2-one;

1-[3-(3-Methoxypropoxy)phenyl]-3-[[3-[2-oxo-2-(1-piperidyl)ethoxy]phenyl]methyl]-5-phenyl-4-(piperazine-1-carbonyl)imidazol-2-one;

2-[3-[[3-[3-(3-Methoxypropoxy)phenyl]-2-oxo-4-phenyl-5-(piperazine-1-carbonyl)imidazol-1-yl]methyl]phenoxy]-N-methyl-acetamide;

2-[3-[[3-[3-(3-Methoxypropoxy)phenyl]-2-oxo-4-phenyl-5-(piperazine-1-carbonyl)imidazol-1-yl]methyl]phenoxy]-N-propan-2-yl-acetamide;

N-[(1S)-2-[2-oxo-5-Phenyl-4-(piperazine-1-carbonyl)-3-prop-2-enyl-imidazol-1-yl]cyclohexyl]propanamide;

N-[(1S)-2-[3-(Cyclohexylmethyly)-2-oxo-5-phenyl-4-(piperazine-1-carbonyl)imidazol-1-yl]cyclohexyl]propanamide;
N-[(1S)-2-[2-oxo-3-[(3-Phenoxyphenyl)methyl]-5-phenyl-4-(piperazine-1-carbonyl)imidazol-1-yl]cyclohexyl]propanamide;
N-[(1S)-2-[3-[(2-Amino1,3-thiazol-4-yl)methyl]-2-oxo-5-phenyl-4-(piperazine-1-carbonyl)imidazol-1-yl]cyclohexyl]propanamide;
N-[(1S)-2-[3-[(3-Methoxyphenyl)methyl]-2-oxo-5-phenyl-4-(piperazine-1-carbonyl)imidazol-1-yl]cyclohexyl]propanamide;
N-[(1S)-2-[3-[(3,4-Difluorophenyl)methyl]-2-oxo-5-phenyl-4-(piperazine-1-carbonyl)imidazol-1-yl]cyclohexyl]propanamide;
N-[2-[2-oxo-4-Phenyl-5-(piperazine-1-carbonyl)-3-[(2S)-2-(propanoylamino)cyclohexyl]imidazol-1-yl]ethyl]benzamide;
N-[(1S)-2-[3-[2-(Benzenesulfonamido)ethyl]-2-oxo-5-phenyl-4-(piperazine-1-carbonyl)imidazol-1-yl]cyclohexyl]propanamide;
3-Methyl-N-[2-[2-oxo-4-phenyl-5-(piperazine-1-carbonyl)-3-[(2S)-2-(propanoylamino)cyclohexyl]imidazol-1-yl]ethyl]butanamide;
N-[(1S)-2-[3-[2-(2-Methylpropylsulfonylamino)ethyl]-2-oxo-5-phenyl-4-(piperazine-1-carbonyl)imidazol-1-yl]cyclohexyl]propanamide;
N-[3-[2-oxo-4-Phenyl-5-(piperazine-1-carbonyl)-3-[(2S)-2-(propanoylamino)cyclohexyl]imidazol-1-yl]propyl]benzamide;
N-[(1S)-2-[3-[3-(Benzenesulfonamido)propyl]-2-oxo-5-phenyl-4-(piperazine-1-carbonyl)imidazol-1-yl]cyclohexyl]propanamide;
3-Methyl-N-[3-[2-oxo-4-phenyl-5-(piperazine-1-carbonyl)-3-[(2S)-2-(propanoylamino)cyclohexyl]imidazol-1-yl]propyl]butanamide;
N-[(1S)-2-[3-[3-(2-Methylpropylsulfonylamino)propyl]-2-oxo-5-phenyl-4-(piperazine-1-carbonyl)imidazol-1-yl]cyclohexyl]propanamide;
N-[(1S)-2-[3-[[3-(2-Methoxyethoxy)phenyl]methyl]-2-oxo-5-phenyl-4-(piperazine-1-carbonyl)imidazol-1-yl]cyclohexyl]propanamide;
N-[(1S)-2-[2-oxo-5-Phenyl-4-(piperazine-1-carbonyl)-3-[[3-(2-pyridin-3-yloxyethoxy)phenyl]methyl]imidazol-1-yl]cyclohexyl]propanamide;
N-[(1S)-2-[2-oxo-5-Phenyl-4-(piperazine-1-carbonyl)-3-[[3-(2-propan-2-yloxyethoxy)phenyl]methyl]imidazol-1-yl]cyclohexyl]propanamide;
N-[(1S)-2-[2-oxo-3-[[3-(2-Phenoxyethoxy)phenyl]methyl]-5-phenyl-4-(piperazine-1-carbonyl)imidazol-1-yl]cyclohexyl]propanamide;
N-[(1S)-2-[3-[[3-(2-Morpholin-4-yl-2-oxo-ethoxy)phenyl]methyl]-2-oxo-5-phenyl-4-(piperazine-1-carbonyl)imidazol-1-yl]cyclohexyl]propanamide;
N-[(1S)-2-[2-oxo-3-[[3-[2-oxo-2-(1-Piperidyl)ethoxy]phenyl]methyl]-5-phenyl-4-(piperazine-1-carbonyl)imidazol-1-yl]cyclohexyl]propanamide;
N-[(1S)-2-[3-[[3-(Methylcarbamoylmethoxy)phenyl]methyl]-2-oxo-5-phenyl-4-(piperazine-1-carbonyl)imidazol-1-yl]cyclohexyl]propanamide;
N-[(1S)-2-[2-oxo-5-Phenyl-4-(piperazine-1-carbonyl)-3-[[3-(propan-2-ylcarbamoylmethoxy)phenyl]methyl]imidazol-1-yl]cyclohexyl]propanamide;
1-(1-Acetyl-3-piperidyl)-5-phenyl-4-(piperazine-1-carbonyl)-3-prop-2-enyl-imidazol-2-one;
1-(1-Acetyl-3-piperidyl)-3-(cyclohexylmethyl)-5-phenyl-4-(piperazine-1-carbonyl)imidazol-2-one;
1-(1-Acetyl-3-piperidyl)-3-[(3-phenoxyphenyl)methyl]-5-phenyl-4-(piperazine-1-carbonyl)imidazol-2-one;
1-(1-Acetyl-3-piperidyl)-3-[(2-amino1,3-thiazol-4-yl)methyl]-5-phenyl-4-(piperazine-1-carbonyl)imidazol-2-one;
1-(1-Acetyl-3-piperidyl)-3-[(3-methoxyphenyl)methyl]-5-phenyl-4-(piperazine-1-carbonyl)imidazol-2-one;
1-(1-Acetyl-3-piperidyl)-3-[(3,4-difluorophenyl)methyl]-5-phenyl-4-(piperazine-1-carbonyl)imidazol-2-one;
N-[2-[3-(1-Acetyl-3-piperidyl)-2-oxo-4-phenyl-5-(piperazine-1-carbonyl)imidazol-1-yl]ethyl]benzamide;
N-[2-[3-(1-Acetyl-3-piperidyl)-2-oxo-4-phenyl-5-(piperazine-1-carbonyl)imidazol-1-yl]ethyl]benzenesulfonamide;
N-[2-[3-(1-Acetyl-3-piperidyl)-2-oxo-4-phenyl-5-(piperazine-1-carbonyl)imidazol-1-yl]ethyl]-3-methyl-butanamide;
N-[2-[3-(1-Acetyl-3-piperidyl)-2-oxo-4-phenyl-5-(piperazine-1-carbonyl)imidazol-1-yl]ethyl]-2-methyl-propane-1-sulfonamide;
N-[3-[3-(1-Acetyl-3-piperidyl)-2-oxo-4-phenyl-5-(piperazine-1-carbonyl)imidazol-1-yl]propyl]benzamide;
N-[3-[3-(1-Acetyl-3-piperidyl)-2-oxo-4-phenyl-5-(piperazine-1-carbonyl)imidazol-1-yl]propyl]benzenesulfonamide;
N-[3-[3-(1-Acetyl-3-piperidyl)-2-oxo-4-phenyl-5-(piperazine-1-carbonyl)imidazol-1-yl]propyl]-3-methyl-butanamide;
N-[3-[3-(1-Acetyl-3-piperidyl)-2-oxo-4-phenyl-5-(piperazine-1-carbonyl)imidazol-1-yl]propyl]-2-methyl-propane-1-sulfonamide;
1-(1-Acetyl-3-piperidyl)-3-[[3-(2-methoxyethoxy)phenyl]methyl]-5-phenyl-4-(piperazine-1-carbonyl)imidazol-2-one;
1-(1-Acetyl-3-piperidyl)-5-phenyl-4-(piperazine-1-carbonyl)-3-[[3-(2-pyridin-3-yloxyethoxy)phenyl]methyl]imidazol-2-one;
1-(1-Acetyl-3-piperidyl)-5-phenyl-4-(piperazine-1-carbonyl)-3-[[3-(2-propan-2-yloxyethoxy)phenyl]methyl]imidazol-2-one;
1-(1-Acetyl-3-piperidyl)-3-[[3-(2-phenoxyethoxy)phenyl]methyl]-5-phenyl-4-(piperazine-1-carbonyl)imidazol-2-one;
1-(1-Acetyl-3-piperidyl)-3-[[3-(2-morpholin-4-yl-2-oxo-ethoxy)phenyl]methyl]-5-phenyl-4-(piperazine-1-carbonyl)imidazol-2-one;
1-(1-Acetyl-3-piperidyl)-3-[[3-[2-oxo-2-(1-piperidyl)ethoxy]phenyl]methyl]-5-phenyl-4-(piperazine-1-carbonyl)imidazol-2-one;
2-[3-[[3-(1-Acetyl-3-piperidyl)-2-oxo-4-phenyl-5-(piperazine-1-carbonyl)imidazol-1-yl]methyl]phenoxy]-N-methyl-acetamide;
2-[3-[[3-(1-Acetyl-3-piperidyl)-2-oxo-4-phenyl-5-(piperazine-1-carbonyl)imidazol-1-yl]methyl]phenoxy]-N-propan-2-yl-acetamide;
1-[1-(Benzenesulfonyl)-3-piperidyl]-5-phenyl-4-(piperazine-1-carbonyl)-3-prop-2-enyl-imidazol-2-one;
1-[1-(Benzenesulfonyl)-3-piperidyl]-3-(cyclohexylmethyl)-5-phenyl-4-(piperazine-1-carbonyl)imidazol-2-one;
1-[1-(Benzenesulfonyl)-3-piperidyl]-3-[(3-phenoxyphenyl)methyl]-5-phenyl-4-(piperazine-1-carbonyl)imidazol-2-one;
1-[(2-Amino1,3-thiazol-4-yl)methyl]-3-[1-(benzenesulfonyl)-3-piperidyl]-4-phenyl-5-(piperazine-1-carbonyl)imidazol-2-one;
1-[1-(Benzenesulfonyl)-3-piperidyl]-3-[(3-methoxyphenyl)methyl]-5-phenyl-4-(piperazine-1-carbonyl)imidazol-2-one;

1-[1-(Benzenesulfonyl)-3-piperidyl]-3-[(3,4-difluorophenyl)methyl]-5-phenyl-4-(piperazine-1-carbonyl)imidazol-2-one;

N-[2-[3-[1-(Benzenesulfonyl)-3-piperidyl]-2-oxo-4-phenyl-5-(piperazine-1-carbonyl)imidazol-1-yl]ethyl]benzamide;

N-[2-[3-[1-(Benzenesulfonyl)-3-piperidyl]-2-oxo-4-phenyl-5-(piperazine-1-carbonyl)imidazol-1-yl]ethyl]benzenesulfonamide;

N-[2-[3-[1-(Benzenesulfonyl)-3-piperidyl]-2-oxo-4-phenyl-5-(piperazine-1-carbonyl)imidazol-1-yl]ethyl]-3-methyl-butanamide;

N-[2-[3-[1-(Benzenesulfonyl)-3-piperidyl]-2-oxo-4-phenyl-5-(piperazine-1-carbonyl)imidazol-1-yl]ethyl]-2-methyl-propane-1-sulfonamide;

N-[3-[3-[1-(Benzenesulfonyl)-3-piperidyl]-2-oxo-4-phenyl-5-(piperazine-1-carbonyl)imidazol-1-yl]propyl]benzamide;

N-[3-[3-[1-(Benzenesulfonyl)-3-piperidyl]-2-oxo-4-phenyl-5-(piperazine-1-carbonyl)imidazol-1-yl]propyl]benzenesulfonamide;

N-[3-[3-[1-(Benzenesulfonyl)-3-piperidyl]-2-oxo-4-phenyl-5-(piperazine-1-carbonyl)imidazol-1-yl]propyl]-3-methyl-butanamide;

N-[3-[3-[1-(Benzenesulfonyl)-3-piperidyl]-2-oxo-4-phenyl-5-(piperazine-1-carbonyl)imidazol-1-yl]propyl]-2-methyl-propane-1-sulfonamide;

1-[1-(Benzenesulfonyl)-3-piperidyl]-3-[[3-(2-methoxyethoxy)phenyl]methyl]-5-phenyl-4-(piperazine-1-carbonyl)imidazol-2-one;

1-[1-(Benzenesulfonyl)-3-piperidyl]-5-phenyl-4-(piperazine-1-carbonyl)-3-[[3-(2-pyridin-3-yloxyethoxy)phenyl]methyl]imidazol-2-one;

1-[1-(Benzenesulfonyl)-3-piperidyl]-5-phenyl-4-(piperazine-1-carbonyl)-3-[[3-(2-propan-2-yloxyethoxy)phenyl]methyl]imidazol-2-one;

1-[1-(Benzenesulfonyl)-3-piperidyl]-3-[[3-(2-phenoxyethoxy)phenyl]methyl]-5-phenyl-4-(piperazine-1-carbonyl)imidazol-2-one;

1-[1-(Benzenesulfonyl)-3-piperidyl]-3-[[3-(2-morpholin-4-yl-2-oxo-ethoxy)phenyl]methyl]-5-phenyl-4-(piperazine-1-carbonyl)imidazol-2-one;

1-[1-(Benzenesulfonyl)-3-piperidyl]-3-[[3-[2-oxo-2-(1-piperidyl)ethoxy]phenyl]methyl]-5-phenyl-4-(piperazine-1-carbonyl)imidazol-2-one;

2-[3-[[3-[1-(Benzenesulfonyl)-3-piperidyl]-2-oxo-4-phenyl-5-(piperazine-1-carbonyl)imidazol-1-yl]methyl]phenoxy]-N-methyl-acetamide;

2-[3-[[3-[1-(Benzenesulfonyl)-3-piperidyl]-2-oxo-4-phenyl-5-(piperazine-1-carbonyl)imidazol-1-yl]methyl]phenoxy]-N-propan-2-yl-acetamide;

N-[2-[2-oxo-5-Phenyl-4-(piperazine-1-carbonyl)-3-prop-2-enyl-imidazol-1-yl]phenyl]propane-1-sulfonamide;

N-[2-[3-(Cyclohexylmethyly)-2-oxo-5-phenyl-4-(piperazine-1-carbonyl)imidazol-1-yl]phenyl]propane-1-sulfonamide;

N-[2-[2-oxo-3-[(3-Phenoxyphenyl)methyl]-5-phenyl-4-(piperazine-1-carbonyl)imidazol-1-yl]phenyl]propane-1-sulfonamide;

N-[2-[3-[(2-Amino1,3-thiazol-4-yl)methyl]-2-oxo-5-phenyl-4-(piperazine-1-carbonyl)imidazol-1-yl]phenyl]propane-1-sulfonamide;

N-[2-[3-[(3-Methoxyphenyl)methyl]-2-oxo-5-phenyl-4-(piperazine-1-carbonyl)imidazol-1-yl]phenyl]propane-1-sulfonamide;

N-[2-[3-[(3,4-Difluorophenyl)methyl]-2-oxo-5-phenyl-4-(piperazine-1-carbonyl)imidazol-1-yl]phenyl]propane-1-sulfonamide;

N-[2-[2-oxo-4-Phenyl-5-(piperazine-1-carbonyl)-3-[2-(propylsulfonylamino)phenyl]imidazol-1-yl]ethyl]benzamide;

N-[2-[2-oxo-4-Phenyl-5-(piperazine-1-carbonyl)-3-[2-(propylsulfonylamino)phenyl]imidazol-1-yl]ethyl]benzenesulfonamide;

3-Methyl-N-[2-[2-oxo-4-phenyl-5-(piperazine-1-carbonyl)-3-[2-(propylsulfonylamino)phenyl]imidazol-1-yl]ethyl]butanamide;

2-Methyl-N-[2-[2-oxo-4-phenyl-5-(piperazine-1-carbonyl)-3-[2-(propylsulfonylamino)phenyl]imidazol-1-yl]ethyl]propane-1-sulfonamide;

N-[3-[2-oxo-4-Phenyl-5-(piperazine-1-carbonyl)-3-[2-(propylsulfonylamino)phenyl]imidazol-1-yl]propyl]benzamide;

N-[3-[2-oxo-4-Phenyl-5-(piperazine-1-carbonyl)-3-[2-(propylsulfonylamino)phenyl]imidazol-1-yl]propyl]benzenesulfonamide;

3-Methyl-N-[3-[2-oxo-4-phenyl-5-(piperazine-1-carbonyl)-3-[2-(propylsulfonylamino)phenyl]imidazol-1-yl]propyl]butanamide;

2-Methyl-N-[3-[2-oxo-4-phenyl-5-(piperazine-1-carbonyl)-3-[2-(propylsulfonylamino)phenyl]imidazol-1-yl]propyl]propane-1-sulfonamide;

N-[2-[3-[[3-(2-Methoxyethoxy)phenyl]methyl]-2-oxo-5-phenyl-4-(piperazine-1-carbonyl)imidazol-1-yl]phenyl]propane-1-sulfonamide;

N-[2-[2-oxo-5-Phenyl-4-(piperazine-1-carbonyl)-3-[[3-(2-pyridin-3-yloxyethoxy)phenyl]methyl]imidazol-1-yl]phenyl]propane-1-sulfonamide;

N-[2-[2-oxo-5-Phenyl-4-(piperazine-1-carbonyl)-3-[[3-(2-propan-2-yloxyethoxy)phenyl]methyl]imidazol-1-yl]phenyl]propane-1-sulfonamide;

N-[2-[2-oxo-3-[[3-(2-Phenoxyethoxy)phenyl]methyl]-5-phenyl-4-(piperazine-1-carbonyl)imidazol-1-yl]phenyl]propane-1-sulfonamide;

N-[2-[3-[[3-(2-Morpholin-4-yl-2-oxo-ethoxy)phenyl]methyl]-2-oxo-5-phenyl-4-(piperazine-1-carbonyl)imidazol-1-yl]phenyl]propane-1-sulfonamide;

N-[2-[2-oxo-3-[[3-[2-oxo-2-(1-Piperidyl)ethoxy]phenyl]methyl]-5-phenyl-4-(piperazine-1-carbonyl)imidazol-1-yl]phenyl]propane-1-sulfonamide;

N-Methyl-2-[3-[[2-oxo-4-phenyl-5-(piperazine-1-carbonyl)-3-[2-(propylsulfonylamino)phenyl]imidazol-1-yl]methyl]phenoxy]acetamide;

2-[3-[[2-oxo-4-Phenyl-5-(piperazine-1-carbonyl)-3-[2-(propylsulfonylamino)phenyl]imidazol-1-yl]methyl]phenoxy]-N-propan-2-yl-acetamide;

1-[1-(1-Methylpyrazol-4-yl)sulfonyl-3-piperidyl]-5-phenyl-4-(piperazine-1-carbonyl)-3-prop-2-enyl-imidazol-2-one;

1-(Cyclohexylmethyly)-3-[1-(1-methylpyrazol-4-yl)sulfonyl-3-piperidyl]-4-phenyl-5-(piperazine-1-carbonyl)imidazol-2-one;

1-[1-(1-Methylpyrazol-4-yl)sulfonyl-3-piperidyl]-3-[(3-phenoxyphenyl)methyl]-5-phenyl-4-(piperazine-1-carbonyl)imidazol-2-one;

1-[(2-Amino1,3-thiazol-4-yl)methyl]-3-[1-(1-methylpyrazol-4-yl)sulfonyl-3-piperidyl]-4-phenyl-5-(piperazine-1-carbonyl)imidazol-2-one;

1-[(3-Methoxyphenyl)methyl]-3-[1-(1-methylpyrazol-4-yl)sulfonyl-3-piperidyl]-4-phenyl-5-(piperazine-1-carbonyl)imidazol-2-one;

1-[(3,4-Difluorophenyl)methyl]-3-[1-(1-methylpyrazol-4-yl)sulfonyl-3-piperidyl]-4-phenyl-5-(piperazine-1-carbonyl)imidazol-2-one;

N-[2-[3-[1-(1-Methylpyrazol-4-yl)sulfonyl-3-piperidyl]-2-oxo-4-phenyl-5-(piperazine-1-carbonyl)imidazol-1-yl]ethyl]benzamide;

N-[2-[3-[1-(1-Methylpyrazol-4-yl)sulfonyl-3-piperidyl]-2-oxo-4-phenyl-5-(piperazine-1-carbonyl)imidazol-1-yl]ethyl]benzenesulfonamide;

3-Methyl-N-[2-[3-[1-(1-methylpyrazol-4-yl)sulfonyl-3-piperidyl]-2-oxo-4-phenyl-5-(piperazine-1-carbonyl)imidazol-1-yl]ethyl]butanamide;

2-Methyl-N-[2-[3-[1-(1-methylpyrazol-4-yl)sulfonyl-3-piperidyl]-2-oxo-4-phenyl-5-(piperazine-1-carbonyl)imidazol-1-yl]ethyl]propane-1-sulfonamide;

N-[3-[3-[1-(1-Methylpyrazol-4-yl)sulfonyl-3-piperidyl]-2-oxo-4-phenyl-5-(piperazine-1-carbonyl)imidazol-1-yl]propyl]benzamide;

N-[3-[3-[1-(1-Methylpyrazol-4-yl)sulfonyl-3-piperidyl]-2-oxo-4-phenyl-5-(piperazine-1-carbonyl)imidazol-1-yl]propyl]benzenesulfonamide;

3-Methyl-N-[3-[3-[1-(1-methylpyrazol-4-yl)sulfonyl-3-piperidyl]-2-oxo-4-phenyl-5-(piperazine-1-carbonyl)imidazol-1-yl]propyl]butanamide;

2-Methyl-N-[3-[3-[1-(1-methylpyrazol-4-yl)sulfonyl-3-piperidyl]-2-oxo-4-phenyl-5-(piperazine-1-carbonyl)imidazol-1-yl]propyl]propane-1-sulfonamide;

1-[[3-(2-Methoxyethoxy)phenyl]methyl]-3-[1-(1-methylpyrazol-4-yl)sulfonyl-3-piperidyl]-4-phenyl-5-(piperazine-1-carbonyl)imidazol-2-one;

1-[1-(1-Methylpyrazol-4-yl)sulfonyl-3-piperidyl]-5-phenyl-4-(piperazine-1-carbonyl)-3-[[3-(2-pyridin-3-yloxyethoxy)phenyl]methyl]imidazol-2-one;

1-[1-(1-Methylpyrazol-4-yl)sulfonyl-3-piperidyl]-5-phenyl-4-(piperazine-1-carbonyl)-3-[[3-(2-propan-2-yloxyethoxy)phenyl]methyl]imidazol-2-one;

1-[1-(1-Methylpyrazol-4-yl)sulfonyl-3-piperidyl]-3-[[3-(2-phenoxyethoxy)phenyl]methyl]-5-phenyl-4-(piperazine-1-carbonyl)imidazol-2-one;

1-[1-(1-Methylpyrazol-4-yl)sulfonyl-3-piperidyl]-3-[[3-(2-morpholin-4-yl-2-oxo-ethoxy)phenyl]methyl]-5-phenyl-4-(piperazine-1-carbonyl)imidazol-2-one;

1-[1-(1-Methylpyrazol-4-yl)sulfonyl-3-piperidyl]-3-[[3-[2-oxo-2-(1-piperidyl)ethoxy]phenyl]methyl]-5-phenyl-4-(piperazine-1-carbonyl)imidazol-2-one;

N-Methyl-2-[3-[[3-[1-(1-methylpyrazol-4-yl)sulfonyl-3-piperidyl]-2-oxo-4-phenyl-5-(piperazine-1-carbonyl)imidazol-1-yl]methyl]phenoxy]acetamide;

2-[3-[[3-[1-(1-Methylpyrazol-4-yl)sulfonyl-3-piperidyl]-2-oxo-4-phenyl-5-(piperazine-1-carbonyl)imidazol-1-yl]methyl]phenoxy]-N-propan-2-yl-acetamide;

1-[(2R)-2-Hydroxycyclohexyl]-5-phenyl-4-(piperazine-1-carbonyl)-3-prop-2-enyl-imidazol-2-one;

1-(Cyclohexylmethyly)-3-[(2R)-2-hydroxycyclohexyl]-4-phenyl-5-(piperazine-1-carbonyl)imidazol-2-one;

1-[(2R)-2-Hydroxycyclohexyl]-3-[(3-phenoxyphenyl)methyl]-5-phenyl-4-(piperazine-1-carbonyl)imidazol-2-one;

1-[(2-Amino1,3-thiazol-4-yl)methyl]-3-[(2R)-2-hydroxycyclohexyl]-4-phenyl-5-(piperazine-1-carbonyl)imidazol-2-one;

1-[(2R)-2-Hydroxycyclohexyl]-3-[(3-methoxyphenyl)methyl]-5-phenyl-4-(piperazine-1-carbonyl)imidazol-2-one;

1-[(3,4-Difluorophenyl)methyl]-3-[(2R)-2-hydroxycyclohexyl]-4-phenyl-5-(piperazine-1-carbonyl)imidazol-2-one;

N-[2-[3-[(2R)-2-Hydroxycyclohexyl]-2-oxo-4-phenyl-5-(piperazine-1-carbonyl)imidazol-1-yl]ethyl]benzamide;

N-[2-[3-[(2R)-2-Hydroxycyclohexyl]-2-oxo-4-phenyl-5-(piperazine-1-carbonyl)imidazol-1-yl]ethyl]benzenesulfonamide;

N-[2-[3-[(2R)-2-Hydroxycyclohexyl]-2-oxo-4-phenyl-5-(piperazine-1-carbonyl)imidazol-1-yl]ethyl]-3-methylbutanamide;

N-[2-[3-[(2R)-2-Hydroxycyclohexyl]-2-oxo-4-phenyl-5-(piperazine-1-carbonyl)imidazol-1-yl]ethyl]-2-methylpropane-1-sulfonamide;

N-[3-[3-[(2R)-2-Hydroxycyclohexyl]-2-oxo-4-phenyl-5-(piperazine-1-carbonyl)imidazol-1-yl]propyl]benzamide;

N-[3-[3-[(2R)-2-Hydroxycyclohexyl]-2-oxo-4-phenyl-5-(piperazine-1-carbonyl)imidazol-1-yl]propyl]benzenesulfonamide;

N-[3-[3-[(2R)-2-Hydroxycyclohexyl]-2-oxo-4-phenyl-5-(piperazine-1-carbonyl)imidazol-1-yl]propyl]-3-methylbutanamide;

N-[3-[3-[(2R)-2-Hydroxycyclohexyl]-2-oxo-4-phenyl-5-(piperazine-1-carbonyl)imidazol-1-yl]propyl]-2-methylpropane-1-sulfonamide;

1-[(2R)-2-Hydroxycyclohexyl]-3-[[3-(2-methoxyethoxy)phenyl]methyl]-5-phenyl-4-(piperazine-1-carbonyl)imidazol-2-one;

1-[(2R)-2-Hydroxycyclohexyl]-5-phenyl-4-(piperazine-1-carbonyl)-3-[[3-(2-pyridin-3-yloxyethoxy)phenyl]methyl]imidazol-2-one;

1-[(2R)-2-Hydroxycyclohexyl]-5-phenyl-4-(piperazine-1-carbonyl)-3-[[3-(2-propan-2-yloxyethoxy)phenyl]methyl]imidazol-2-one;

1-[(2R)-2-Hydroxycyclohexyl]-3-[[3-(2-phenoxyethoxy)phenyl]methyl]-5-phenyl-4-(piperazine-1-carbonyl)imidazol-2-one;

1-[(2R)-2-Hydroxycyclohexyl]-3-[[3-(2-morpholin-4-yl-2-oxo-ethoxy)phenyl]methyl]-5-phenyl-4-(piperazine-1-carbonyl)imidazol-2-one;

1-[(2R)-2-Hydroxycyclohexyl]-3-[[3-[2-oxo-2-(1-piperidyl)ethoxy]phenyl]methyl]-5-phenyl-4-(piperazine-1-carbonyl)imidazol-2-one;

2-[3-[[3-[(2R)-2-Hydroxycyclohexyl]-2-oxo-4-phenyl-5-(piperazine-1-carbonyl)imidazol-1-yl]methyl]phenoxy]-N-methyl-acetamide; and 2-[3-[[3-[(2R)-2-Hydroxycyclohexyl]-2-oxo-4-phenyl-5-(piperazine-1-carbonyl)imidazol-1-yl]methyl]phenoxy]-N-propan-2-yl-acetamide.

It is noted that the compounds of the present invention may be in the form of a pharmaceutically acceptable salt. It is further note that the compounds of the present invention may be in a mixture of stereoisomers, or the compound may comprise a single stereoisomer.

In another of its aspects, the present invention also directs to pharmaceutical compositions comprising as an active ingredient a compound according to any one of the preceding embodiments and variations. In one variation, the pharmaceutical composition is a solid formulation adapted for oral administration. In another variation, the pharmaceutical composition is a liquid formulation adapted for oral administration. In yet another variation, the pharmaceutical composition is a tablet. In still another variation, the pharmaceutical composition is a liquid formulation adapted for parenteral administration.

In yet another variation, the pharmaceutical composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

In yet another of its aspects, the invention is directed to kits comprising a compound of any one of the above embodiments and variations and instructions which comprise one or more forms of information selected from the group consisting of indicating a disease state for which the composition is to be administered, storage information for the composition, dosing information and instructions regarding how to administer the composition. In one variation, the kit comprises the compound in a multiple dose form.

In still another of its aspects, the invention is directed to an article of manufacture comprising a compound of any one of the above embodiments and variations; and packaging materials. In one variation, the packaging material comprises a container for housing the compound. In another variation, the container comprises a label indicating one or more members of the group consisting of a disease state for which the compound is to be administered, storage information, dosing information and/or instructions regarding how to administer the compound. In another variation, the article of manufacture comprises the compound in a multiple dose form.

In a further of its aspects, the invention is directed to a therapeutic method which comprises administering a compound of any one of the above embodiments and variations to a subject. In one embodiment, the subject is an animal. In another embodiment, the subject is a human.

In a further of its aspects, the invention is directed to a method for inhibiting renin. In one embodiment, the method comprises contacting renin with a compound of any one of the above embodiments and variations. In another embodiment, the method comprises causing a compound of any one of the above embodiments and variations to be present in a subject in order to inhibit renin in vivo. In yet another embodiment, the method comprises administering a first compound to a subject that is converted in vivo to a second compound wherein the second compound inhibits renin in vivo, the second compound being a compound according to any one of the above embodiments and variations. In one variation, the subject is an animal. In another variation, the subject is a human.

In yet another of its aspects, the invention is directed to a method for treating a disease state for which renin possesses activity that contributes to the pathology and/or symptomology of the disease state. In one embodiment, the method comprises causing a compound of any one of the above embodiments and variations to be present in a subject in a therapeutically effective amount for the disease state. In another embodiment, the method comprises administering a compound of any one of the above embodiments and variations to a subject, wherein the compound is present in the subject in a therapeutically effective amount for the disease state. In yet another embodiment, the method comprises administering a first compound to a subject that is converted in vivo to a second compound wherein the second compound inhibits renin in vivo, the second compound being a compound according to any one of the above embodiments and variations. It is noted that the disease state cited in the preceding embodiment and variations, is selected from the group consisting of cardiovascular disease, hypertension, congestive heart failure, myocardial infarction, renal protection, inflammation, neurological disease and cancer.

In another of its aspects, the invention is directed to methods for the preparation of the inhibitors of the invention. In one embodiment, the method comprises:

reacting a compound having the formula

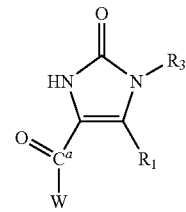

with a metalated compound of the formula

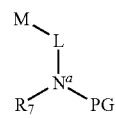

under conditions that form a compound of the formula

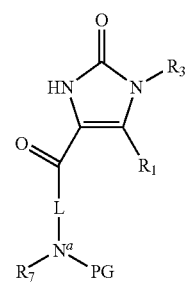

deprotecting the compound formed above under conditions to yield a compound having the formula

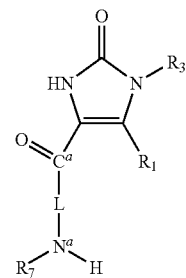

wherein
$C^a$ denotes a carbon atom;
$N^a$ denotes a nitrogen atom;
PG is a protecting group;
L is a linker moiety between 1-5 atoms in length as measured between $C^a$ and $N^a$;
M is lithium or magnesium halide;
W is selected from the group consisting of alkoxy, aryloxy, fluoro, chloro, and bromo;
$R_1$ is selected from the group consisting of hydrogen, carbonyl, oxycarbonyl, aminocarbonyl, $(C_{1-10})$alkylamino, sulfonamido, sulfonyl, sulfinyl, $(C_{1-10})$alkyl, halo$(C_{1-10})$alkyl, alkoxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-4}$alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{2-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted;

$R_3$ is selected from the group consisting of hydrogen, alkoxy, aryloxy, heteroaryloxy, ($C_{1-10}$)alkyl, halo($C_{1-10}$)alkyl, alkoxy($C_{1-10}$)alkyl, carbonyl($C_{1-3}$)alkyl, thiocarbonyl($C_{1-3}$)alkyl, carboxamido($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted; and $R_7$ is selected from the group consisting of hydrogen, ($C_{1-10}$)alkyl, halo($C_{1-10}$)alkyl, carbonyl($C_{1-3}$)alkyl, carboxamidoalkyl, amidoalkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, alkoxy($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted, or $R_7$ and a substituent of L are taken together to form a ring;

provided that $R_1$ and $R_3$ are not both hydrogen.

In another embodiment, the method comprises:

coupling an $R_2$-substituted compound having the formula

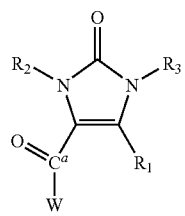

to a metalated compound having the formula

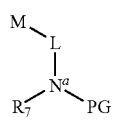

under conditions to form a compound having the formula

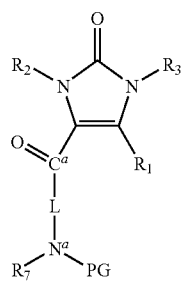

deprotecting the compound formed above under conditions to yield a compound having the formula

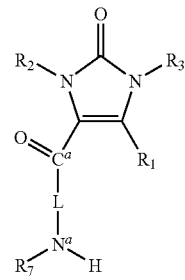

wherein $C^a$ denotes a carbon atom;

$N^a$ denotes a nitrogen atom;

PG is a protecting group;

L is a linker moiety between 1-5 atoms in length as measured between $C^a$ and $N^a$;

M is lithium or magnesium halide;

W is selected from the group consisting of alkoxy, aryloxy, fluoro, chloro, and bromo;

$R_1$ is selected from the group consisting of hydrogen, carbonyl, oxycarbonyl, aminocarbonyl, ($C_{1-10}$)alkylamino, sulfonamido, sulfonyl, sulfinyl, ($C_{1-10}$)alkyl, halo($C_{1-10}$)alkyl, alkoxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-4}$alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{2-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted;

$R_2$ is selected from the group consisting of hydrogen, alkoxy, aryloxy, heteroaryloxy, ($C_{1-10}$)alkyl, halo($C_{1-10}$)alkyl, alkoxy($C_{1-10}$)alkyl, carbonyl($C_{1-3}$)alkyl, thiocarbonyl($C_{1-3}$)alkyl, carboxamido($C_{1-3}$)alkyl, amido($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted;

$R_3$ is selected from the group consisting of hydrogen, alkoxy, aryloxy, heteroaryloxy, ($C_{1-10}$)alkyl, halo($C_{1-10}$)alkyl, alkoxy($C_{1-10}$)alkyl, carbonyl($C_{1-3}$)alkyl, thiocarbonyl($C_{1-3}$)alkyl, carboxamido($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted; and $R_7$ is selected from the group consisting of hydrogen, ($C_{1-10}$)alkyl, halo($C_{1-10}$)alkyl, carbonyl($C_{1-3}$)alkyl, carboxamidoalkyl, amidoalkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, alkoxy($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted, or $R_7$ and a substituent of L are taken together to form a ring;

provided that $R_1$ and $R_3$ are not both hydrogen.

In another embodiment, the method comprises:

coupling a halide compound having the formula $R_2$-halide to a compound having the formula

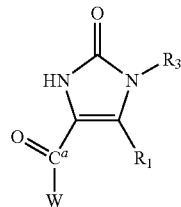

under conditions to form the $R_2$-substituted compound having the formula

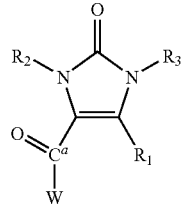

wherein $C^a$ denotes a carbon atom;

W is selected from the group consisting of alkoxy, aryloxy, fluoro, chloro, and bromo;

$R_1$ is selected from the group consisting of hydrogen, carbonyl, oxycarbonyl, aminocarbonyl, ($C_{1-10}$)alkylamino, sulfonamido, sulfonyl, sulfinyl, ($C_{1-10}$)alkyl, halo($C_{1-10}$)alkyl, alkoxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-4}$alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{2-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted;

$R_2$ is selected from the group consisting of hydrogen, alkoxy, aryloxy, heteroaryloxy, ($C_{1-10}$)alkyl, halo($C_{1-10}$)alkyl, alkoxy($C_{1-10}$)alkyl, carbonyl($C_{1-3}$)alkyl, thiocarbonyl($C_{1-3}$)alkyl, carboxamido($C_{1-3}$)alkyl, amido($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted; and $R_3$ is selected from the group consisting of hydrogen, alkoxy, aryloxy, heteroaryloxy, ($C_{1-10}$)alkyl, halo($C_{1-10}$)alkyl, alkoxy($C_{1-10}$)alkyl, carbonyl($C_{1-3}$)alkyl, thiocarbonyl($C_{1-3}$)alkyl, carboxamido($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted;

provided that $R_1$ and $R_3$ are not both hydrogen.

In another embodiment, the method comprises:

converting a compound having the formula

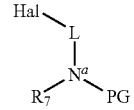

under conditions to produce the metalated compound having the formula

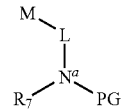

wherein $N^a$ denotes a nitrogen atom;

PG is a protecting group;

Hal is fluoro, chloro or bromo;

L is a linker moiety between 1-5 atoms in length as measured between $C^a$ and $N^a$; and $R_7$ is selected from the group consisting of hydrogen, ($C_{1-10}$)alkyl, halo($C_{1-10}$)alkyl, carbonyl($C_{1-3}$)alkyl, carboxamidoalkyl, amidoalkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, alkoxy($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted, or $R_7$ and a substituent of L are taken together to form a ring.

In one variation of the preceding embodiments and variations of the method of the invention, when present, M is Li and Hal is Br.

In another variation of the preceding embodiments and variations, W when present is ethoxy and PG is t-butoxycarbonyl (Boc).

In another variation, L is -(A)$_k$;
wherein
k is selected from the group consisting of 1, 2, 3, 4 and 5;
each A is independently selected from the group consisting of —NR$_9$—, —O—, —S—, and —CR$_5$R$_6$—,
where
$R_5$ and $R_6$ are each independently selected from the group consisting of hydrogen, oxycarbonyl, sulfonyl, sulfinyl, (C$_{1-10}$)alkyl, halo(C$_{1-10}$)alkyl, carbonyl (C$_{1-3}$)alkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino (C$_{1-3}$)alkyl, (C$_{3-12}$)cycloalkyl(C$_{1-5}$)alkyl, hetero (C$_{2-12}$)cycloalkyl(C$_{1-5}$)alkyl, aryl(C$_{1-10}$)alkyl, heteroaryl(C$_{1-5}$)alkyl, (C$_{9-12}$)bicyclo aryl(C$_{1-5}$)alkyl, hetero(C$_{4-12}$)bicycloaryl(C$_{1-5}$)alkyl, (C$_{3-12}$)cycloalkyl, hetero (C$_{2-12}$)cycloalkyl, (C$_{9-12}$)bicycloalkyl, hetero(C$_{3-12}$) bicycloalkyl, (C$_{5-12}$)aryl, hetero(C$_{2-10}$)aryl, (C$_{9-12}$) bicycloaryl, and hetero(C$_{4-12}$)bicycloaryl, each substituted or unsubstituted, and R$_6$ may be absent when the carbon to which it is bound forms part of a double bond, and R$_5$ and R$_6$ on a given carbon may be taken together to form =O, =S, or =NR$_{10}$, wherein R$_{10}$ is selected from the group consisting of hydrogen, hydroxyl, alkoxy, aryloxy, heteroaryloxy, (C$_{1-10}$) alkyl, halo(C$_{1-10}$)alkyl, (C$_{3-12}$)cycloalkyl(C$_{1-5}$)alkyl, hetero(C$_{2-12}$)cycloalkyl(C$_{1-5}$)alkyl, aryl(C$_{1-10}$)alkyl, heteroaryl(C$_{1-4}$alkyl, (C$_{3-12}$)cycloalkyl, hetero (C$_{2-12}$)cycloalkyl, (C$_{5-12}$)aryl, and hetero(C$_{2-10}$)aryl, each substituted or unsubstituted, $R_9$ is selected from the group consisting of hydrogen, alkoxy, aryloxy, heteroaryloxy, (C$_{1-10}$)alkyl, halo (C$_{1-10}$)alkyl, carbonyl(C$_{1-3}$)alkyl, aminocarbonylalkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$) alkyl, alkoxy(C$_{1-3}$)alkyl, (C$_{3-12}$)cycloalkyl(C$_{1-5}$) alkyl, hetero(C$_{2-12}$)cycloalkyl(C$_{1-5}$)alkyl, aryl(C$_{1-10}$) alkyl, heteroaryl(C$_{1-5}$)alkyl, (C$_{9-12}$)bicyclo aryl(C$_{1-5}$) alkyl, hetero(C$_{4-12}$)bicycloaryl(C$_{1-5}$)alkyl, (C$_{3-12}$) cycloalkyl, hetero(C$_{2-12}$)cycloalkyl, (C$_{9-12}$) bicycloalkyl, hetero(C$_{4-12}$)bicycloalkyl, (C$_{5-12}$)aryl, hetero(C$_{2-10}$)aryl, (C$_{9-12}$)bicycloaryl and hetero (C$_{4-12}$)bicycloaryl, each substituted or unsubstituted, and R$_9$ may be absent when the nitrogen to which it is attached forms part of a double bond, and any two adjacent R$_5$, R$_6$, R$_7$ and R$_9$ may be taken together to form a substituted or unsubstituted five, six, seven or eight membered ring.

In another variation, L is *—NR$_9$-(A)$_{k'}$—, wherein
* indicated the point of attachment of —NR$_9$-(A)$_{k'}$ to M;
k' is selected from the group consisting of 1, 2, 3 and 4; and
each A is independently selected from the group consisting of —NR$_9$—, —O—, —S—, and —CR$_5$R$_6$—,
where
$R_5$ and $R_6$ are each independently selected from the group consisting of hydrogen, oxycarbonyl, sulfonyl, sulfinyl, (C$_{1-10}$)alkyl, halo(C$_{1-10}$)alkyl, carbonyl (C$_{1-3}$)alkyl, thiocarbonyl(C$_{1-3}$)alkyl, sulfonyl(C$_{1-3}$) alkyl, sulfinyl(C$_{1-3}$)alkyl, amino(C$_{1-10}$)alkyl, imino (C$_{1-3}$)alkyl, (C$_{3-12}$)cycloalkyl(C$_{1-5}$)alkyl, hetero (C$_{2-12}$)cycloalkyl(C$_{1-5}$)alkyl, aryl(C$_{1-10}$)alkyl, heteroaryl(C$_{1-5}$)alkyl, (C$_{9-12}$)bicyclo aryl(C$_{1-5}$)alkyl, hetero(C$_{4-12}$)bicycloaryl(C$_{1-5}$)alkyl, (C$_{3-12}$)cycloalkyl, hetero(C$_{2-12}$)cycloalkyl, (C$_{9-12}$)bicycloalkyl, hetero(C$_{3-12}$)bicycloalkyl, (C$_{5-12}$)aryl, hetero(C$_{2-10}$)aryl, (C$_{9-12}$)bicycloaryl, and hetero(C$_{4-12}$) bicycloaryl, each substituted or unsubstituted, and R$_6$ may be absent when the carbon to which it is bound forms part of a double bond, and R$_5$ and R$_6$ on a given carbon may be taken together to form =O, =S, or =NR$_{10}$, wherein R$_{10}$ is selected from the group consisting of hydrogen, hydroxyl, alkoxy, aryloxy, heteroaryloxy, (C$_{1-10}$)alkyl, halo(C$_{1-10}$)alkyl, (C$_{3-12}$)cycloalkyl(C$_{1-5}$)alkyl, hetero(C$_{2-12}$)cycloalkyl(C$_{1-5}$)alkyl, hetero(C$_{2-12}$)cycloalkyl(C$_{1-5}$)alkyl, aryl(C$_{1-10}$)alkyl, heteroaryl(C$_{1-4}$alkyl, (C$_{3-12}$) cycloalkyl, hetero(C$_{2-12}$)cycloalkyl, (C$_{5-12}$)aryl, and hetero(C$_{2-10}$)aryl, each substituted or unsubstituted.

$R_9$ is selected from the group consisting of hydrogen, alkoxy, aryloxy, heteroaryloxy, (C$_{1-10}$)alkyl, halo (C$_{1-10}$)alkyl, carbonyl(C$_{1-3}$)alkyl, aminocarbonylalkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$) alkyl, alkoxy(C$_{1-3}$)alkyl, (C$_{3-12}$)cycloalkyl(C$_{1-5}$) alkyl, hetero(C$_{2-12}$)cycloalkyl(C$_{1-5}$)alkyl, aryl(C$_{1-10}$) alkyl, heteroaryl(C$_{1-5}$)alkyl, (C$_{9-12}$)bicyclo aryl(C$_{1-5}$) alkyl, hetero(C$_{4-12}$)bicycloaryl(C$_{1-5}$)alkyl, (C$_{3-12}$) cycloalkyl, hetero(C$_{2-12}$)cycloalkyl, (C$_{9-12}$) bicycloalkyl, hetero(C$_{4-12}$)bicycloalkyl, (C$_{5-12}$)aryl, hetero(C$_{2-10}$)aryl, (C$_{9-12}$)bicycloaryl, and hetero (C$_{4-12}$)bicycloaryl, each substituted or unsubstituted, and R$_9$ may be absent when the nitrogen to which it is attached forms part of a double bond, and any two adjacent R$_5$, R$_6$, R$_7$ and R$_9$ may be taken together to form a substituted or unsubstituted five, six, seven or eight membered ring.

In another variation, L is *—NR$_9$—(CR$_5$R$_6$)$_{k'}$—, wherein
* indicates the point of attachment of —NR$_9$—(CR$_5$ R$_6$)$_{k'}$— to M;
k' is 1, 2, 3, or 4;

$R_5$ and $R_6$ are each independently selected from the group consisting of hydrogen, oxycarbonyl, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, (C$_{3-12}$)cycloalkyl(C$_{1-5}$) alkyl, hetero(C$_{2-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero (C$_{4-12}$)bicycloaryl(C$_{1-5}$)alkyl, (C$_{3-12}$)cycloalkyl, hetero (C$_{2-12}$)cycloalkyl, (C$_{9-12}$)bicycloalkyl, hetero(C$_{3-12}$)bicycloalkyl, (C$_{5-12}$)aryl, hetero(C$_{2-10}$)aryl, (C$_{9-12}$)bicycloaryl, and hetero(C$_{4-12}$)bicycloaryl, each substituted or unsubstituted, and R$_6$ may be absent when the carbon to which it is bound forms part of a double bond, and R$_5$ and R$_6$ on a given carbon may be taken together to form =O, =S, or =NR$_{10}$, where R$_{10}$ is selected from the group consisting of hydrogen, hydroxyl, alkoxy, aryloxy, heteroaryloxy, (C$_{1-10}$)alkyl, halo (C$_{1-10}$)alkyl, (C$_{3-12}$)cycloalkyl(C$_{1-5}$)alkyl, hetero(C$_{2-12}$)cycloalkyl(C$_{1-5}$)alkyl, aryl(C$_{1-10}$)alkyl, heteroaryl(C$_{1-5}$)alkyl, (C$_{3-12}$)cycloalkyl, hetero(C$_{2-12}$)cycloalkyl, (C$_{5-12}$)aryl, and hetero(C$_{2-10}$)aryl, each substituted or unsubstituted;

$R_9$ is selected from the group consisting of hydrogen, alkoxy, aryloxy, heteroaryloxy, (C$_{1-10}$)alkyl, halo(C$_{1-10}$) alkyl, carbonyl(C$_{1-3}$)alkyl, aminocarbonylalkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, alkoxy(C$_{1-3}$)alkyl, (C$_{3-12}$)cycloalkyl(C$_{1-5}$)alkyl, hetero(C$_{2-12}$)cycloalkyl(C$_{1-5}$) alkyl, aryl(C$_{1-10}$)alkyl, heteroaryl(C$_{1-5}$)alkyl, (C$_{9-12}$)bicycloaryl(C$_{1-5}$)alkyl, hetero(C$_{4-12}$)bicycloaryl(C$_{1-5}$)alkyl, (C$_{3-12}$)cycloalkyl, hetero(C$_{2-12}$)cycloalkyl, (C$_{9-12}$)bicycloalkyl, hetero(C$_{4-12}$)bicycloalkyl, (C$_{5-12}$)aryl, hetero (C$_{2-10}$)aryl, (C$_{9-12}$)bicycloaryl and hetero(C$_{4-12}$)bicycloaryl, each substituted or unsubstituted, and $R_9$ may be absent when the nitrogen to which it is attached forms part of a double bond; and any two adjacent $R_5$, $R_6$, $R_7$ and $R_9$ may be taken together to form a substituted or unsubstituted five, six, seven or eight membered ring.

In another variation, -L-$N^a R_7$PG is selected from the group consisting of

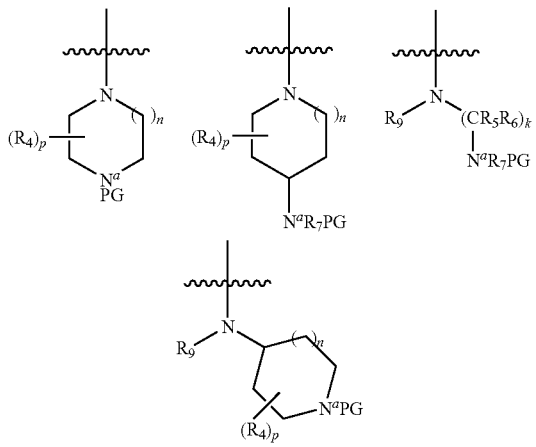

where k is 0, 1, 2, 3, 4 or 5;

n is 0, 1 or 2;

p is 0, 1, 2, 3 or 4;

$N^a$ denotes a nitrogen atom;

PG is a protected group;

each $R_4$ is independently selected from the group consisting of hydrogen, oxo, oxyalkyl, alkoxycarbonyl, carbonyl, thioalkyl, alkoxy, oxycarbonyl, aminocarbonyl, amino, amido, carboxamido, sulfonyl, sulfinyl, $(C_{1-10})$alkyl, halo $(C_{1-10})$alkyl, oxyalkyl, alkoxyalkyl, alkylthioalkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, carboxamido$(C_{1-40})$alkyl, amido$(C_{1-10})$alkyl, $(C_{3-12})$cycloalkyl$(C_{1-5})$alkyl, hetero$(C_{2-12})$cycloalkyl$(C_{1-5})$alkyl, aryl $(C_{1-10})$alkyl, heteroaryl$(C_{1-5})$alkyl, aryloxyalkyl, heteroarylalkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl, and hetero$(C_{4-12})$bicycloaryl, each substituted or unsubstituted;

$R_5$ and $R_6$ are each independently selected from the group consisting of hydrogen, oxycarbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$ alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero $(C_{4-12})$bicycloaryl$(C_{1-5})$alkyl, $(C_{3-12})$cycloalkyl, hetero $(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl, and hetero$(C_{4-12})$bicycloaryl, each substituted or unsubstituted, and $R_5$ and $R_6$ on a given carbon may be taken together to form =O, =S, or =N$R_{10}$, where $R_{10}$ is selected from the group consisting of hydrogen, hydroxyl, alkoxy, aryloxy, heteroaryloxy, $(C_{1-10})$alkyl, halo$(C_{1-10})$alkyl, $(C_{3-12})$cycloalkyl $(C_{1-5})$alkyl, hetero$(C_{2-12})$cycloalkyl$(C_{1-5})$alkyl, aryl$(C_{1-10})$ alkyl, heteroaryl$(C_{1-5})$alkyl, $(C_{3-12})$cycloalkyl, hetero$(C_{2-12})$ cycloalkyl, $(C_{5-12})$aryl, and hetero$(C_{2-10})$aryl, each substituted or unsubstituted, and $R_6$ is absent when the carbon to which it is bound forms part of a double bond;

$R_7$ is selected from the group consisting of hydrogen, $(C_{1-10})$alkyl, halo$(C_{1-10})$alkyl, carbonyl$(C_{1-3})$alkyl, carboxamidoalkyl, amidoalkyl, thiocarbonyl$(C_{1-3})$alkyl, sulfonyl $(C_{1-3})$alkyl, sulfinyl$(C_{1-3})$alkyl, amino$(C_{1-10})$alkyl, imino $(C_{1-3})$alkyl, alkoxy$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero $(C_{4-12})$bicycloaryl$(C_{1-5})$alkyl, $(C_{3-12})$cycloalkyl, hetero $(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted, or $R_7$ and a substituent of L are taken together to form a ring, and $R_9$ is selected from the group consisting of hydrogen, alkoxy, aryloxy, heteroaryloxy, $(C_{1-10})$alkyl, halo$(C_{1-10})$ alkyl, carbonyl$(C_{1-3})$alkyl, aminocarbonylalkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, alkoxy$(C_{1-3})$alkyl, $(C_{3-12})$cycloalkyl$(C_{1-5})$alkyl, hetero$(C_{2-12})$cycloalkyl$(C_{1-5})$ alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{4-12})$bicycloalkyl, $(C_{5-12})$aryl, hetero $(C_{2-10})$aryl, $(C_{9-12})$bicycloaryl, and hetero$(C_{4-12})$bicycloaryl, each substituted or unsubstituted.

In another embodiment, the method comprises:

coupling a compound having the formula

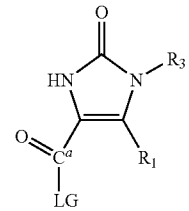

to a compound having the formula

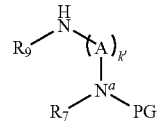

under conditions that form a compound of the formula

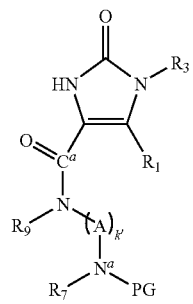

deprotecting the compound formed above under conditions that yield a compound of the formula

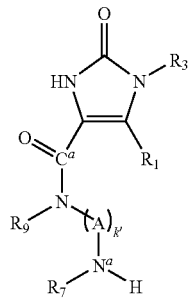

wherein
$C^a$ denotes a carbon atom;
$N^a$ denotes a nitrogen atom;
LG is a leaving group;
PG is a protecting group;
k' is selected from the group consisting of 1, 2, 3 and 4;
each A is independently selected from the group consisting of —$NR_9$—, —O—, —S—, and —$CR_5R_6$—;
$R_1$ is selected from the group consisting of hydrogen, carbonyl, oxycarbonyl, aminocarbonyl, ($C_{1-10}$)alkylamino, sulfonamido, sulfonyl, sulfinyl, ($C_{1-10}$)alkyl, halo($C_{1-10}$)alkyl, alkoxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{2-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted;
$R_3$ is selected from the group consisting of hydrogen, alkoxy, aryloxy, heteroaryloxy, ($C_{1-10}$)alkyl, halo($C_{1-10}$)alkyl, alkoxy($C_{1-10}$)alkyl, carbonyl($C_{1-3}$)alkyl, thiocarbonyl($C_{1-3}$)alkyl, carboxamido($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$) aryl, hetero($C_{2-10}$)aryl, ($C_{9-12}$)bicycloaryl and hetero($C_{4-12}$)bicycloaryl, each substituted or unsubstituted;
$R_5$ and $R_6$ are each independently selected from the group consisting of hydrogen, oxycarbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$) alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicyclo aryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl, and hetero($C_{4-12}$)bicycloaryl, each substituted or unsubstituted, and $R_6$ may be absent when the carbon to which it is bound forms part of a double bond, and $R_5$ and $R_6$ on a given carbon may be taken together to form =O, =S, or =$NR_{10}$, wherein $R_{10}$ is selected from the group consisting of hydrogen, hydroxyl, alkoxy, aryloxy, heteroaryloxy, ($C_{1-10}$)alkyl, halo($C_{1-10}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$) alkyl, ($C_{3-12}$)cycloalkyl, hetero($C_{2-12}$)cycloalkyl, ($C_{5-12}$) aryl, and hetero($C_{2-10}$)aryl, each substituted or unsubstituted;
$R_7$ is selected from the group consisting of hydrogen, ($C_{1-10}$)alkyl, halo($C_{1-10}$)alkyl, carbonyl($C_{1-3}$)alkyl, carboxamidoalkyl, amidoalkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, alkoxy($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted;
$R_9$ is selected from the group consisting of hydrogen, alkoxy, aryloxy, heteroaryloxy, ($C_{1-10}$)alkyl, halo($C_{1-10}$) alkyl, carbonyl($C_{1-3}$)alkyl, aminocarbonylalkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, alkoxy($C_{1-3}$)alkyl, ($C_{3-12}$)cycloalkyl($C_{1-5}$)alkyl, hetero($C_{2-12}$)cycloalkyl($C_{1-5}$) alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{4-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted, and $R_9$ may be absent when the nitrogen to which it is attached forms part of a double bond; and
any two adjacent $R_5$, $R_6$, $R_7$ and $R_9$ may be taken together to form a substituted or unsubstituted five, six, seven or eight membered ring;
provided that $R_1$ and $R_3$ are not both hydrogen.
In another embodiment, the method comprises:
coupling a compound having the formula

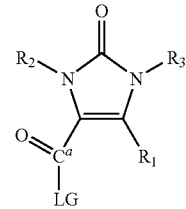

to a compound having the formula

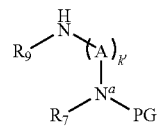

under conditions to form a compound having the formula

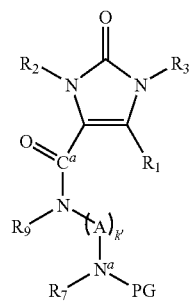

deprotecting the compound formed above to yield a compound having the formula

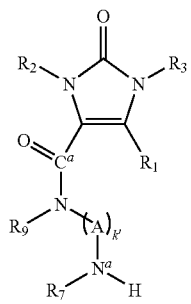

wherein
$C^a$ denotes a carbon atom;
$N^a$ denotes a nitrogen atom;
LG is a leaving group;
PG is a protecting group;
k' is selected from the group consisting of 1, 2, 3 and 4;
each A is independently selected from the group consisting of —$NR_9$—, —O—, —S—, and —$CR_5R_6$—;

$R_1$ is selected from the group consisting of hydrogen, carbonyl, oxycarbonyl, aminocarbonyl, ($C_{1-10}$)alkylamino, sulfonamido, sulfonyl, sulfonyl, ($C_{1-10}$)alkyl, halo($C_{1-10}$)alkyl, alkoxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-4}$alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{2-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted;

$R_2$ is selected from the group consisting of hydrogen, alkoxy, aryloxy, heteroaryloxy, ($C_{1-10}$)alkyl, halo($C_{1-10}$)alkyl, alkoxy($C_{1-10}$)alkyl, carbonyl($C_{1-3}$)alkyl, thiocarbonyl($C_{1-3}$)alkyl, carboxamido($C_{1-3}$)alkyl, amido($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted;

$R_3$ is selected from the group consisting of hydrogen, alkoxy, aryloxy, heteroaryloxy, ($C_{1-10}$)alkyl, halo($C_{1-10}$)alkyl, alkoxy($C_{1-10}$)alkyl, carbonyl($C_{1-3}$)alkyl, thiocarbonyl($C_{1-3}$)alkyl, carboxamido($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted;

$R_5$ and $R_6$ are each independently selected from the group consisting of hydrogen, oxycarbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicyclo aryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl, and hetero($C_{4-12}$)bicycloaryl, each substituted or unsubstituted, and $R_6$ may be absent when the carbon to which it is bound forms part of a double bond, and $R_5$ and $R_6$ on a given carbon may be taken together to form =O, =S, or =$NR_{10}$, wherein $R_{10}$ is selected from the group consisting of hydrogen, hydroxyl, alkoxy, aryloxy, heteroaryloxy, ($C_{1-10}$)alkyl, halo($C_{1-10}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{3-12}$)cycloalkyl, hetero($C_{2-12}$)cycloalkyl, ($C_{5-12}$)aryl, and hetero($C_{2-10}$)aryl, each substituted or unsubstituted;

$R_7$ is selected from the group consisting of hydrogen, ($C_{1-10}$)alkyl, halo($C_{1-10}$)alkyl, carbonyl($C_{1-3}$)alkyl, carboxamidoalkyl, amidoalkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, alkoxy($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted;

$R_9$ is selected from the group consisting of hydrogen, alkoxy, aryloxy, heteroaryloxy, ($C_{1-10}$)alkyl, halo($C_{1-10}$)alkyl, carbonyl($C_{1-3}$)alkyl, aminocarbonylalkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, alkoxy($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{4-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted, and $R_9$ may be absent when the nitrogen to which it is attached forms part of a double bond; and any two adjacent $R_5$, $R_6$, $R_7$ and $R_9$ may be taken together to form a substituted or unsubstituted five, six, seven or eight membered ring;

provided that $R_1$ and $R_3$ are not both hydrogen.

In another embodiment, the method comprises:
coupling a compound having the formula

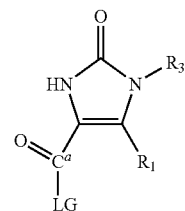

to a compound having the formula

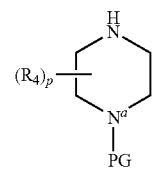

under conditions that form a compound of the formula

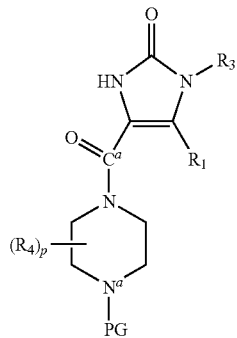

deprotecting the compound formed immediately above to form a compound having the formula

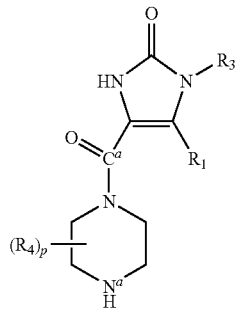

wherein $C^a$ denotes a carbon atom;

$N^a$ denotes a nitrogen atom;

LG is a leaving group;

PG is a protecting group;

p is 0, 1, 2, 3 or 4;

$R_1$ is selected from the group consisting of hydrogen, carbonyl, oxycarbonyl, aminocarbonyl, $(C_{1-10})$alkylamino, sulfonamido, sulfonyl, sulfinyl, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl $(C_{1-4})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{2-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted;

$R_3$ is selected from the group consisting of hydrogen, alkoxy, aryloxy, heteroaryloxy, $(C_{1-10})$alkyl, halo$(C_{1-10})$alkyl, alkoxy$(C_{1-10})$alkyl, carbonyl$(C_{1-3})$alkyl, thiocarbonyl $(C_{1-3})$alkyl, carboxamido$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted; and each $R_4$ is independently selected from the group consisting of hydrogen, oxo, oxyalkyl, alkoxycarbonyl, carbonyl, thioalkyl, alkoxy, oxycarbonyl, aminocarbonyl, amino, amido, carboxamido, sulfonyl, sulfinyl, $(C_{1-10})$alkyl, halo$(C_{1-10})$alkyl, oxyalkyl, alkoxyalkyl, alkylthioalkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, carboxamido$(C_{1-40})$alkyl, amido$(C_{1-10})$alkyl, $(C_{3-12})$cycloalkyl$(C_{1-5})$alkyl, hetero$(C_{2-12})$cycloalkyl$(C_{1-5})$alkyl, aryl $(C_{1-10})$alkyl, heteroaryl$(C_{1-5})$alkyl, aryloxyalkyl, heteroarylalkyl, $(C_{9-12})$bicycloaryl$(C_{1-5})$alkyl, hetero$(C_{4-12})$ bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl, and hetero$(C_{4-12})$bicycloaryl, each substituted or unsubstituted;

provided that $R_1$ and $R_3$ are not both hydrogen.

In another embodiment, the method comprises:

coupling a compound having the formula

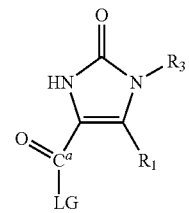

to a compound having the formula

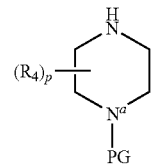

under conditions that form a compound having the formula

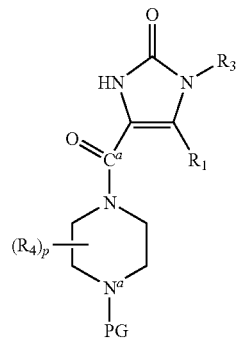

coupling a halide compound having the formula $R_2$-halide to the compound formed above to form a compound having the formula

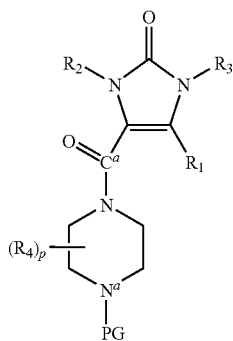

deprotecting the compound formed above to yield a compound having the formula

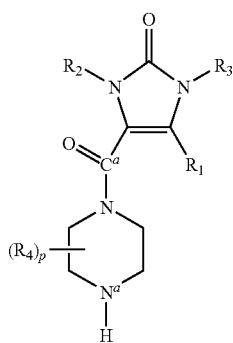

wherein $C^a$ denotes a carbon atom;

$N^a$ denotes a nitrogen atom;

LG is a leaving group;

PG is a protecting group;

p is 0, 1, 2, 3 or 4;

$R_1$ is selected from the group consisting of hydrogen, carbonyl, oxycarbonyl, aminocarbonyl, $(C_{1-10})$alkylamino, sulfonamido, sulfonyl, sulfinyl, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{2-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted;

$R_2$ is selected from the group consisting of hydrogen, alkoxy, aryloxy, heteroaryloxy, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, carboxamido$(C_{1-3})$alkyl, amido$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted;

$R_3$ is selected from the group consisting of hydrogen, alkoxy, aryloxy, heteroaryloxy, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, carboxamido$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted; and each $R_4$ is independently selected from the group consisting of hydrogen, oxo, oxyalkyl, alkoxycarbonyl, carbonyl, thioalkyl, alkoxy, oxycarbonyl, aminocarbonyl, amino, amido, carboxamido, sulfonyl, sulfinyl, $(C_{1-10})$alkyl, halo$(C_{1-10})$alkyl, oxyalkyl, alkoxyalkyl, alkylthioalkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, carboxamido$(C_{1-10})$alkyl, amido$(C_{1-10})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, aryloxyalkyl, heteroarylalkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl, and hetero$(C_{4-12})$bicycloaryl, each substituted or unsubstituted;

provided that $R_1$ and $R_3$ are not both hydrogen.

In another embodiment, the method comprises:

reacting a compound having the formula

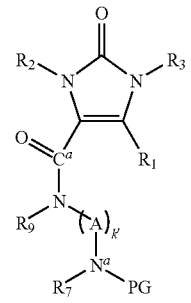

with a reagent selected from the group consisting of $P_2S_5$ and Lawesson's reagent under conditions to form a compound having the formula

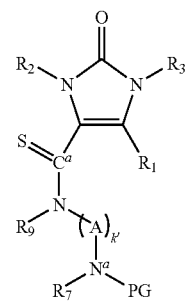

deprotecting the compound formed above under conditions to yield a compound having the formula

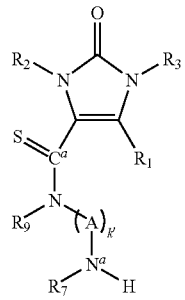

wherein

C$^a$ denotes a carbon atom;

N$^a$ denotes a nitrogen atom;

PG is a protecting group;

k' is selected from the group consisting of 1, 2, 3 and 4;

each A is independently selected from the group consisting of —NR$_9$—, —O—, —S—, and —CR$_5$R$_6$—;

R$_1$ is selected from the group consisting of hydrogen, carbonyl, oxycarbonyl, aminocarbonyl, (C$_{1-10}$)alkylamino, sulfonamido, sulfonyl, sulfinyl, (C$_{1-10}$)alkyl, halo(C$_{1-10}$)alkyl, alkoxy(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, (C$_{3-12}$)cycloalkyl(C$_{1-5}$)alkyl, hetero(C$_{2-12}$)cycloalkyl(C$_{1-5}$)alkyl, aryl(C$_{1-10}$)alkyl, heteroaryl(C$_{1-4}$alkyl, (C$_{9-12}$)bicycloaryl(C$_{1-5}$)alkyl, hetero(C$_{4-12}$)bicycloaryl(C$_{1-5}$)alkyl, (C$_{3-12}$)cycloalkyl, hetero(C$_{2-12}$)cycloalkyl, (C$_{9-12}$)bicycloalkyl, hetero(C$_{2-12}$)bicycloalkyl, (C$_{5-12}$)aryl, hetero(C$_{2-10}$)aryl, (C$_{9-12}$)bicycloaryl and hetero(C$_{4-12}$)bicycloaryl, each substituted or unsubstituted;

R$_2$ is selected from the group consisting of hydrogen, alkoxy, aryloxy, heteroaryloxy, (C$_{1-10}$)alkyl, halo(C$_{1-10}$)alkyl, alkoxy(C$_{1-10}$)alkyl, carbonyl(C$_{1-3}$)alkyl, thiocarbonyl(C$_{1-3}$)alkyl, carboxamido(C$_{1-3}$)alkyl, amido(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, (C$_{3-12}$)cycloalkyl(C$_{1-5}$)alkyl, hetero(C$_{2-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{4-12}$)bicycloaryl(C$_{1-5}$)alkyl, (C$_{3-12}$)cycloalkyl, hetero(C$_{2-12}$)cycloalkyl, (C$_{9-12}$)bicycloalkyl, hetero(C$_{3-12}$)bicycloalkyl, (C$_{5-12}$)aryl, hetero(C$_{2-10}$)aryl, (C$_{9-12}$)bicycloaryl and hetero(C$_{4-12}$)bicycloaryl, each substituted or unsubstituted;

R$_3$ is selected from the group consisting of hydrogen, alkoxy, aryloxy, heteroaryloxy, (C$_{1-10}$)alkyl, halo(C$_{1-10}$)alkyl, alkoxy(C$_{1-10}$)alkyl, carbonyl(C$_{1-3}$)alkyl, thiocarbonyl(C$_{1-3}$)alkyl, carboxamido(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, (C$_{3-12}$)cycloalkyl(C$_{1-5}$)alkyl, hetero(C$_{2-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{4-12}$)bicycloaryl(C$_{1-5}$)alkyl, (C$_{3-12}$)cycloalkyl, hetero(C$_{2-12}$)cycloalkyl, (C$_{9-12}$)bicycloalkyl, hetero(C$_{3-12}$)bicycloalkyl, (C$_{5-12}$) aryl, hetero(C$_{2-10}$)aryl, (C$_{9-12}$)bicycloaryl and hetero(C$_{4-12}$)bicycloaryl, each substituted or unsubstituted;

R$_5$ and R$_6$ are each independently selected from the group consisting of hydrogen, oxycarbonyl, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, (C$_{3-12}$)cycloalkyl(C$_{1-5}$) alkyl, hetero(C$_{2-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{4-12}$)bicyclo aryl(C$_{1-5}$)alkyl, (C$_{3-12}$)cycloalkyl, hetero(C$_{2-12}$)cycloalkyl, (C$_{9-12}$)bicycloalkyl, hetero(C$_{3-12}$)bicycloalkyl, (C$_{5-12}$)aryl, hetero(C$_{2-10}$)aryl, (C$_{9-12}$)bicycloaryl, and hetero(C$_{4-12}$)bicycloaryl, each substituted or unsubstituted, and R$_6$ may be absent when the carbon to which it is bound forms part of a double bond, and R$_5$ and R$_6$ on a given carbon may be taken together to form =O, =S, or =NR$_{10}$, wherein R$_{10}$ is selected from the group consisting of hydrogen, hydroxyl, alkoxy, aryloxy, heteroaryloxy, (C$_{1-10}$)alkyl, halo(C$_{1-10}$)alkyl, (C$_{3-12}$)cycloalkyl(C$_{1-5}$)alkyl, hetero(C$_{2-12}$)cycloalkyl(C$_{1-5}$)alkyl, aryl(C$_{1-10}$)alkyl, heteroaryl(C$_{1-5}$)alkyl, (C$_{3-12}$)cycloalkyl, hetero(C$_{2-12}$)cycloalkyl, (C$_{5-12}$)aryl, and hetero(C$_{2-10}$)aryl, each substituted or unsubstituted;

R$_7$ is selected from the group consisting of hydrogen, (C$_{1-10}$)alkyl, halo(C$_{1-10}$)alkyl, carbonyl(C$_{1-3}$)alkyl, carboxamidoalkyl, amidoalkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, alkoxy(C$_{1-3}$)alkyl, (C$_{3-12}$)cycloalkyl(C$_{1-5}$)alkyl, hetero(C$_{2-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{4-12}$)bicycloaryl(C$_{1-5}$)alkyl, (C$_{3-12}$)cycloalkyl, hetero(C$_{2-12}$)cycloalkyl, (C$_{9-12}$)bicycloalkyl, hetero(C$_{3-12}$)bicycloalkyl, (C$_{5-12}$)aryl, hetero(C$_{2-10}$)aryl, (C$_{9-12}$)bicycloaryl and hetero(C$_{4-12}$)bicycloaryl, each substituted or unsubstituted, R$_9$ is selected from the group consisting of hydrogen, alkoxy, aryloxy, heteroaryloxy, (C$_{1-10}$)alkyl, halo(C$_{1-10}$) alkyl, carbonyl(C$_{1-3}$)alkyl, aminocarbonylalkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, alkoxy(C$_{1-3}$)alkyl, (C$_{3-12}$)cycloalkyl(C$_{1-5}$)alkyl, hetero(C$_{2-12}$)cycloalkyl(C$_{1-5}$) alkyl, aryl(C$_{1-10}$)alkyl, heteroaryl(C$_{1-5}$)alkyl, (C$_{9-12}$)bicycloaryl(C$_{1-5}$)alkyl, hetero(C$_{4-12}$)bicycloaryl(C$_{1-5}$)alkyl, (C$_{3-12}$)cycloalkyl, hetero(C$_{2-12}$)cycloalkyl, (C$_{9-12}$)bicycloalkyl, hetero(C$_{4-12}$)bicycloalkyl, (C$_{5-12}$)aryl, hetero(C$_{2-10}$)aryl, (C$_{9-12}$)bicycloaryl and hetero(C$_{4-12}$)bicycloaryl, each substituted or unsubstituted, and R$_9$ may be absent when the nitrogen to which it is attached forms part of a double bond; and any two adjacent R$_5$, R$_6$, R$_7$ and R$_9$ may be taken together to form a substituted or unsubstituted five, six, seven or eight membered ring;

provided that R$_1$ and R$_3$ are not both hydrogen.

In one variation of the preceding embodiments, —NR$_9$-(A)$_{k'}$-N$^a$R$_7$PG when present is selected from the group consisting of

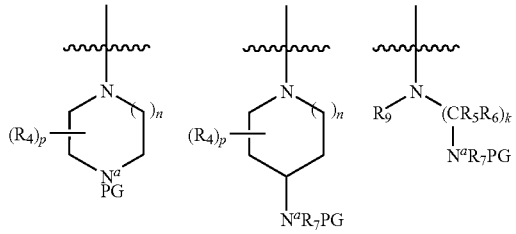

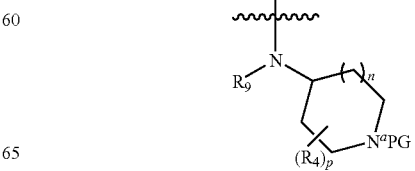

where
k is 0, 1, 2, 3, 4 or 5;
n is 0, 1 or 2;
p is 0, 1, 2, 3 or 4;
$N^a$ denotes a nitrogen atom;
PG is a protective group;
each $R_4$ is independently selected from the group consisting of hydrogen, oxo, oxyalkyl, alkoxycarbonyl, carbonyl, thioalkyl, alkoxy, oxycarbonyl, aminocarbonyl, amino, amido, carboxamido, sulfonyl, sulfinyl, $(C_{1-10})$alkyl, halo $(C_{1-10})$alkyl, oxyalkyl, alkoxyalkyl, alkylthioalkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, carboxamido$(C_{1-10})$alkyl, amido$(C_{1-10})$alkyl, $(C_{3-12})$cycloalkyl$(C_{1-5})$alkyl, hetero$(C_{2-12})$cycloalkyl$(C_{1-5})$alkyl, aryl $(C_{1-10})$alkyl, heteroaryl$(C_{1-5})$alkyl, aryloxyalkyl, heteroarylalkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl, and hetero $(C_{4-12})$bicycloaryl, each substituted or unsubstituted;
$R_5$ and $R_6$ are each independently selected from the group consisting of hydrogen, oxycarbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$ alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero $(C_{4-12})$bicyclo aryl$(C_{1-5})$alkyl, $(C_{3-12})$cycloalkyl, hetero $(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl, and hetero$(C_{4-12})$bicycloaryl, each substituted or unsubstituted, and $R_5$ and $R_6$ on a given carbon may be taken together to form =O, =S, or =$NR_{10}$, where $R_{10}$ is selected from the group consisting of hydrogen, hydroxyl, alkoxy, aryloxy, heteroaryloxy, $(C_{1-10})$alkyl, halo$(C_{1-10})$alkyl, $(C_{3-12})$cycloalkyl $(C_{1-5})$alkyl, hetero$(C_{2-12})$cycloalkyl$(C_{1-5})$alkyl, aryl$(C_{1-10})$ alkyl, heteroaryl$(C_{1-5})$alkyl, $(C_{3-12})$cycloalkyl, hetero$(C_{2-12})$ cycloalkyl, $(C_{5-12})$aryl, and hetero$(C_{2-10})$aryl, each substituted or unsubstituted, and $R_6$ is absent when the carbon to which it is bound forms part of a double bond;
$R_7$ is selected from the group consisting of hydrogen, $(C_{1-10})$alkyl, halo$(C_{1-10})$alkyl, carbonyl$(C_{1-3})$alkyl, carboxamidoalkyl, amidoalkyl, thiocarbonyl$(C_{1-3})$alkyl, sulfonyl $(C_{1-3})$alkyl, sulfinyl$(C_{1-3})$alkyl, amino$(C_{1-10})$alkyl, imino $(C_{1-3})$alkyl, alkoxy$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero $(C_{4-12})$bicycloaryl$(C_{1-5})$alkyl, $(C_{3-12})$cycloalkyl, hetero $(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted; and
$R_9$ is selected from the group consisting of hydrogen, alkoxy, aryloxy, heteroaryloxy, $(C_{1-10})$alkyl, halo$(C_{1-10})$ alkyl, carbonyl$(C_{1-3})$alkyl, aminocarbonylalkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, alkoxy$(C_{1-3})$alkyl, $(C_{3-12})$cycloalkyl$(C_{1-5})$alkyl, hetero$(C_{2-12})$cycloalkyl$(C_{1-5})$ alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{4-12})$bicycloalkyl, $(C_{5-12})$aryl, hetero $(C_{2-10})$aryl, $(C_{9-12})$bicycloaryl and hetero$(C_{4-12})$bicycloaryl, each substituted or unsubstituted, and $R_9$ may be absent when the nitrogen to which it is attached forms part of a double bond.

In another embodiment, the method further comprises:
reacting a primary urea having the formula

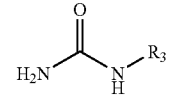

with a diazo compound having the formula

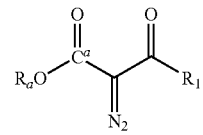

under conditions to form an insertion product having the formula

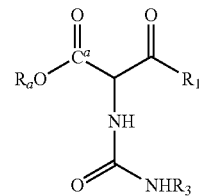

cyclizing the insertion product forming an imidazolone ester having the formula

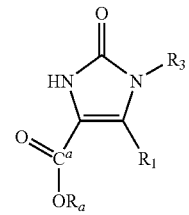

wherein
$C^a$ denotes a carbon atom;
$R_a$ is alkyl;
$R_1$ is selected from the group consisting of hydrogen, carbonyl, oxycarbonyl, aminocarbonyl, $(C_{1-10})$alkylamino, sulfonamido, sulfonyl, sulfinyl, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$ alkyl, sulfonyl$(C_{1-3})$alkyl, sulfinyl$(C_{1-3})$alkyl, amino$(C_{1-10})$ alkyl, imino$(C_{1-3})$alkyl, $(C_{3-12})$cycloalkyl$(C_{1-5})$alkyl, hetero $(C_{2-12})$cycloalkyl$(C_{1-5})$alkyl, aryl$(C_{1-10})$alkyl, heteroaryl $(C_{1-4}$alkyl, $(C_{9-12})$bicycloaryl$(C_{1-5})$alkyl, hetero$(C_{4-12})$ bicycloaryl$(C_{1-5})$alkyl, $(C_{3-12})$cycloalkyl, hetero$(C_{2-12})$ cycloalkyl, $(C_{9-12})$bicycloalkyl, hetero$(C_{2-12})$bicycloalkyl, $(C_{5-12})$aryl, hetero$(C_{2-10})$aryl, $(C_{9-12})$bicycloaryl and hetero $(C_{4-12})$bicycloaryl, each substituted or unsubstituted; and
$R_3$ is selected from the group consisting of hydrogen, alkoxy, aryloxy, heteroaryloxy, $(C_{1-10})$alkyl, halo$(C_{1-10})$ alkyl, alkoxy$(C_{1-10})$alkyl, carbonyl$(C_{1-3})$alkyl, thiocarbonyl $(C_{1-3})$alkyl, carboxamido$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$ alkyl, aryl$(C_{1-10})$alkyl, heteroaryl$(C_{1-5})$alkyl, $(C_{9-12})$bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted;

provided that $R_1$ and $R_3$ are not both hydrogen.

In another embodiment, the method further comprises:

reacting a dicarbonyl compound having the formula

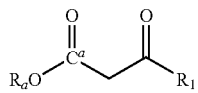

with an aryl sulfonylazide compound having the formula

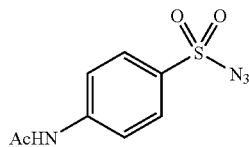

under conditions that form a diazo compound having the formula

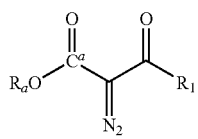

wherein $C^a$ denotes a carbon atom;

$R_a$ is alkyl; and $R_1$ is selected from the group consisting of hydrogen, carbonyl, oxycarbonyl, aminocarbonyl, ($C_{1-10}$)alkylamino, sulfonamido, sulfonyl, sulfonyl, ($C_{1-10}$)alkyl, halo($C_{1-10}$)alkyl, alkoxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-4}$alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{2-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted.

In another embodiment, the method further comprises:

reacting a amine compound having the formula $NH_2$—$R_3$ with potassium cyanate under the conditions to yield the primary urea having the formula

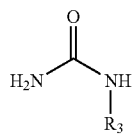

wherein $R_3$ is selected from the group consisting of hydrogen, alkoxy, aryloxy, heteroaryloxy, ($C_{1-10}$)alkyl, halo($C_{1-10}$)alkyl, alkoxy($C_{1-10}$)alkyl, carbonyl($C_{1-3}$)alkyl, thiocarbonyl($C_{1-3}$)alkyl, carboxamido($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted.

In another embodiment, the method further comprises:

converting a nitro derivative of $R_3$ having the formula $NO_2$—$R_3$ under reaction conditions to form the amine having the formula $NH_2$—$R_3$.

In another embodiment, the method further comprises:

hydrolyzing an imidazolone ester having the formula

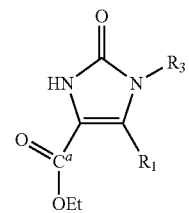

under conditions to form a carboxylic acid having the formula

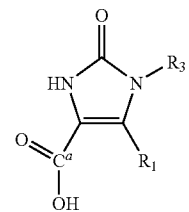

wherein $C^a$ denotes a carbon atom;

$R_1$ is selected from the group consisting of hydrogen, carbonyl, oxycarbonyl, aminocarbonyl, ($C_{1-10}$)alkylamino, sulfonamido, sulfonyl, sulfinyl, ($C_{1-10}$)alkyl, halo($C_{1-10}$)alkyl, alkoxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-4}$alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{2-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted; and $R_3$ is selected from the group consisting of hydrogen, alkoxy, aryloxy, heteroaryloxy, ($C_{1-10}$)alkyl, halo($C_{1-10}$)alkyl, alkoxy($C_{1-10}$)alkyl, carbonyl($C_{1-3}$)alkyl, thiocarbonyl($C_{1-3}$)alkyl, carboxamido($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted;

provided that $R_1$ and $R_3$ are not both hydrogen.

In another embodiment, the method comprises:
coupling an imidate compound having the formula

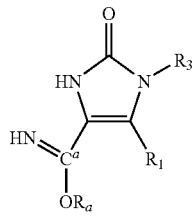

to a compound having the formula

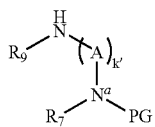

under condition to form an amidine having the formula

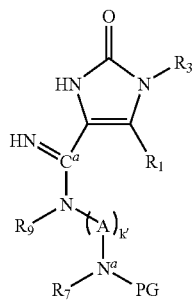

deprotecting the amidine compound to yield a compound having the formula

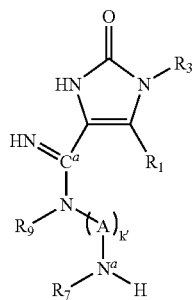

wherein
$C^a$ denotes a carbon atom;
$N^a$ denotes a nitrogen atom;
PG is a protecting group;
k' is selected from the group consisting of 1, 2, 3 and 4;
each A is independently selected from the group consisting of —$NR_9$—, —O—, —S—, and —$CR_5R_6$—;
$R_a$ is alkyl;
$R_1$ is selected from the group consisting of hydrogen, carbonyl, oxycarbonyl, aminocarbonyl, ($C_{1-10}$)alkylamino, sulfonamido, sulfonyl, sulfinyl, ($C_{1-10}$)alkyl, halo($C_{1-10}$)alkyl, alkoxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-4}$alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{2-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted;

$R_3$ is selected from the group consisting of hydrogen, alkoxy, aryloxy, heteroaryloxy, ($C_{1-10}$)alkyl, halo($C_{1-10}$)alkyl, alkoxy($C_{1-10}$)alkyl, carbonyl($C_{1-3}$)alkyl, thiocarbonyl($C_{1-3}$)alkyl, carboxamido($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted;

$R_5$ and $R_6$ are each independently selected from the group consisting of hydrogen, oxycarbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl, and hetero($C_{4-12}$)bicycloaryl, each substituted or unsubstituted, and $R_6$ may be absent when the carbon to which it is bound forms part of a double bond, and $R_5$ and $R_6$ on a given carbon may be taken together to form =O, =S, or =$NR_{10}$, wherein $R_{10}$ is selected from the group consisting of hydrogen, hydroxyl, alkoxy, aryloxy, heteroaryloxy, ($C_{1-10}$)alkyl, halo($C_{1-10}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{3-12}$)cycloalkyl, hetero($C_{2-12}$)cycloalkyl, ($C_{5-12}$)aryl, and hetero($C_{2-10}$)aryl, each substituted or unsubstituted;

$R_7$ is selected from the group consisting of hydrogen, ($C_{1-10}$)alkyl, halo($C_{1-10}$)alkyl, carbonyl($C_{1-3}$)alkyl, carboxamidoalkyl, amidoalkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, alkoxy($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted;

$R_9$ is selected from the group consisting of hydrogen, alkoxy, aryloxy, heteroaryloxy, ($C_{1-10}$)alkyl, halo($C_{1-10}$)alkyl, carbonyl($C_{1-3}$)alkyl, aminocarbonylalkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, alkoxy($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{4-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted, and $R_9$ may be absent when the nitrogen to which it is attached forms part of a double bond; and any two adjacent $R_5$, $R_6$, $R_7$ and $R_9$ may be taken together to form a substituted or unsubstituted five, six, seven or eight membered ring;

provided that $R_1$ and $R_3$ are not both hydrogen.

In the preceding embodiment, the method further comprises:

converting a cyano imidazolone compound having the formula

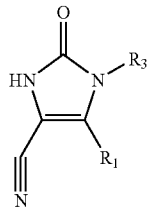

under conditions to produce the imidate having the formula

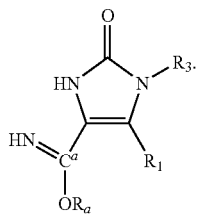

In another embodiment, the method comprises:

coupling an imidate compound having the formula

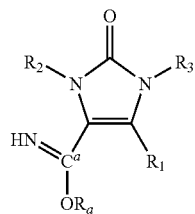

to a compound having the formula

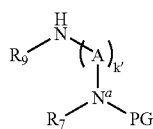

under condition to form an amidine having the formula

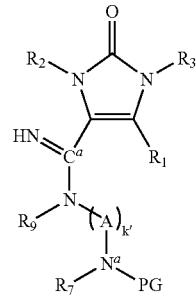

deprotecting the amidine compound to form a compound of the invention having the formula

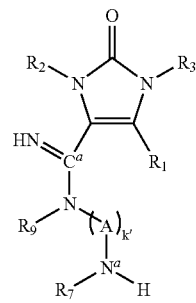

wherein $C^a$ denotes a carbon atom;

$N^a$ denotes a nitrogen atom;

PG is a protecting group;

k' is selected from the group consisting of 1, 2, 3 and 4;

each A is independently selected from the group consisting of —$NR_9$—, —O—, —S—, and —$CR_5R_6$—;

$R_a$ is alkyl;

$R_1$ is selected from the group consisting of hydrogen, carbonyl, oxycarbonyl, aminocarbonyl, ($C_{1-10}$)alkylamino, sulfonamido, sulfonyl, sulfinyl, ($C_{1-10}$)alkyl, halo($C_{1-10}$)alkyl, alkoxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-4}$alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{2-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted;

$R_2$ is selected from the group consisting of hydrogen, alkoxy, aryloxy, heteroaryloxy, ($C_{1-10}$)alkyl, halo($C_{1-10}$)alkyl, alkoxy($C_{1-10}$)alkyl, carbonyl($C_{1-3}$)alkyl, thiocarbonyl($C_{1-3}$)alkyl, carboxamido($C_{1-3}$)alkyl, amido($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted;

$R_3$ is selected from the group consisting of hydrogen, alkoxy, aryloxy, heteroaryloxy, ($C_{1-10}$)alkyl, halo($C_{1-10}$)

alkyl, alkoxy($C_{1-10}$)alkyl, carbonyl($C_{1-3}$)alkyl, thiocarbonyl ($C_{1-3}$)alkyl, carboxamido($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$) alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$) aryl, hetero ($C_{2-10}$)aryl, ($C_{9-12}$)bicycloaryl and hetero($C_{4-12}$)bicycloaryl, each substituted or unsubstituted;

$R_5$ and $R_6$ are each independently selected from the group consisting of hydrogen, oxycarbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$) alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero ($C_{4-12}$)bicyclo aryl($C_{1-5}$)alkyl, ($C_{3-12}$)cycloalkyl, hetero ($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl, and hetero($C_{4-12}$)bicycloaryl, each substituted or unsubstituted, and $R_6$ may be absent when the carbon to which it is bound forms part of a double bond, and $R_5$ and $R_6$ on a given carbon may be taken together to form =O, =S, or =$NR_{10}$, wherein $R_{10}$ is selected from the group consisting of hydrogen, hydroxyl, alkoxy, aryloxy, heteroaryloxy, ($C_{1-10}$)alkyl, halo($C_{1-10}$)alkyl, ($C_{3-12}$)cycloalkyl($C_{1-5}$)alkyl, hetero($C_{2-12}$) cycloalkyl($C_{1-5}$)alkyl, aryl($C_{1-10}$)alkyl, heteroaryl($C_{1-5}$) alkyl, ($C_{3-12}$)cycloalkyl, hetero($C_{2-12}$)cycloalkyl, ($C_{5-12}$) aryl, and hetero($C_{2-10}$)aryl, each substituted or unsubstituted;

$R_7$ is selected from the group consisting of hydrogen, ($C_{1-10}$)alkyl, halo($C_{1-10}$)alkyl, carbonyl($C_{1-3}$)alkyl, carboxamidoalkyl, amidoalkyl, thiocarbonyl($C_{1-3}$)alkyl, sulfonyl ($C_{1-3}$)alkyl, sulfinyl($C_{1-3}$)alkyl, amino($C_{1-10}$)alkyl, imino ($C_{1-3}$)alkyl, alkoxy($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero ($C_{4-12}$)bicycloaryl($C_{1-5}$)alkyl, ($C_{3-12}$)cycloalkyl, hetero ($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl and hetero($C_{4-12}$)bicycloaryl, each substituted or unsubstituted;

$R_9$ is selected from the group consisting of hydrogen, alkoxy, aryloxy, heteroaryloxy, ($C_{1-10}$)alkyl, halo($C_{1-10}$) alkyl, carbonyl($C_{1-3}$)alkyl, aminocarbonylalkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, alkoxy($C_{1-3}$)alkyl, ($C_{3-12}$)cycloalkyl($C_{1-5}$)alkyl, hetero($C_{2-12}$)cycloalkyl($C_{1-5}$) alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{4-12}$)bicycloalkyl, ($C_{5-12}$)aryl, hetero ($C_{2-10}$)aryl, ($C_{9-12}$)bicycloaryl and hetero($C_{4-12}$)bicycloaryl, each substituted or unsubstituted, and $R_9$ may be absent when the nitrogen to which it is attached forms part of a double bond; and any two adjacent $R_5$, $R_6$, $R_7$ and $R_9$ may be taken together to form a substituted or unsubstituted five, six, seven or eight membered ring;

provided that $R_1$ and $R_3$ are not both hydrogen.

In the preceding embodiment, the method further comprises:

coupling a halide compound having the formula $R_2$-halide to a cyano imidazolone compound having the formula

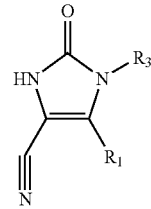

under conditions to produce an $R_2$-substituted cyano imidazolone

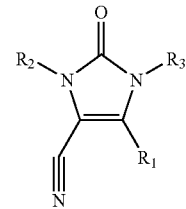

converting the $R_2$-substituted cyano imidazolone compound under conditions to produce an imidate having the formula

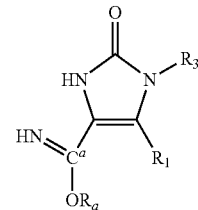

wherein $C_a$ denotes a nitrogen atom;

$R_a$ is alkyl;

$R_1$ is selected from the group consisting of hydrogen, carbonyl, oxycarbonyl, aminocarbonyl, ($C_{1-10}$)alkylamino, sulfonamido, sulfonyl, sulfinyl, ($C_{1-10}$)alkyl, halo($C_{1-10}$)alkyl, alkoxy($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino($C_{1-10}$) alkyl, imino($C_{1-3}$)alkyl, ($C_{3-12}$)cycloalkyl($C_{1-5}$)alkyl, hetero ($C_{2-12}$)cycloalkyl($C_{1-5}$)alkyl, aryl($C_{1-10}$)alkyl, heteroaryl ($C_{1-4}$alkyl, ($C_{9-12}$)bicycloaryl($C_{1-5}$)alkyl, hetero($C_{4-12}$) bicycloaryl($C_{1-5}$)alkyl, ($C_{3-12}$)cycloalkyl, hetero($C_{2-12}$) cycloalkyl, ($C_{9-12}$)bicycloalkyl, hetero($C_{2-12}$)bicycloalkyl, ($C_{5-12}$)aryl, hetero($C_{2-10}$)aryl, ($C_{9-12}$)bicycloaryl and hetero ($C_{4-12}$)bicycloaryl, each substituted or unsubstituted;

$R_2$ is selected from the group consisting of hydrogen, alkoxy, aryloxy, heteroaryloxy, ($C_{1-10}$)alkyl, halo($C_{1-10}$) alkyl, alkoxy($C_{1-10}$)alkyl, carbonyl($C_{1-3}$)alkyl, thiocarbonyl ($C_{1-3}$)alkyl, carboxamido($C_{1-3}$)alkyl, amido($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$) cycloalkyl($C_{1-5}$)alkyl, aryl($C_{1-10}$)alkyl, heteroaryl($C_{1-5}$) alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$) cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl and hetero ($C_{4-12}$)bicycloaryl, each substituted or unsubstituted; and $R_3$ is selected from the group consisting of hydrogen, alkoxy, aryloxy, heteroaryloxy, ($C_{1-10}$)alkyl, halo($C_{1-10}$)

alkyl, alkoxy($C_{1-10}$)alkyl, carbonyl($C_{1-3}$)alkyl, thiocarbonyl ($C_{1-3}$)alkyl, carboxamido($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$) alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{3-12}$)bicycloalkyl, ($C_{5-12}$)aryl, hetero ($C_{2-10}$)aryl, ($C_{9-12}$)bicycloaryl and hetero($C_{4-12}$)bicycloaryl, each substituted or unsubstituted;

provided that $R_1$ and $R_3$ are not both hydrogen.

In one variation of the preceding embodiments and variations, when present, $-NR_9-(A)_k-N^aR_7PG$ is selected from the group consisting of

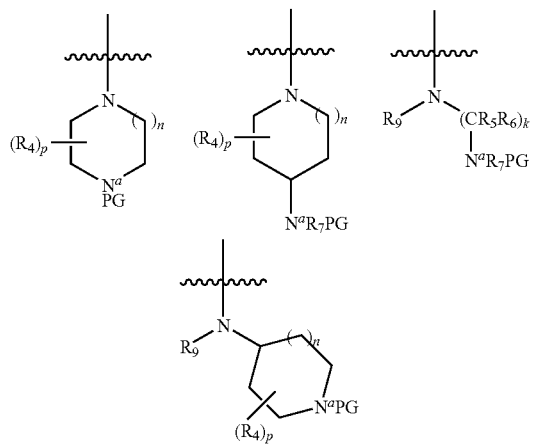

wherein
k is 0, 1, 2, 3, 4 or 5;
n is 0, 1 or 2;
p is 0, 1, 2, 3 or 4;
$N^a$ denotes a nitrogen atom;
PG is a protecting group;
each $R_4$ is independently selected from the group consisting of hydrogen, oxo, oxyalkyl, alkoxycarbonyl, carbonyl, thioalkyl, alkoxy, oxycarbonyl, aminocarbonyl, amino, amido, carboxamido, sulfonyl, sulfinyl, ($C_{1-10}$)alkyl, halo ($C_{1-10}$)alkyl, oxyalkyl, alkoxyalkyl, alkylthioalkyl, carbonyl ($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, carboxamido($C_{1-40}$)alkyl, amido($C_{1-10}$)alkyl, ($C_{3-12}$)cycloalkyl($C_{1-5}$)alkyl, hetero($C_{2-12}$)cycloalkyl($C_{1-5}$)alkyl, aryl ($C_{1-10}$)alkyl, heteroaryl($C_{1-5}$)alkyl, aryloxyalkyl, heteroarylalkyl, ($C_{9-12}$)bicycloaryl($C_{1-5}$)alkyl, hetero($C_{4-12}$) bicycloaryl($C_{1-5}$)alkyl, ($C_{3-12}$)cycloalkyl, hetero($C_{2-12}$) cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl, and hetero ($C_{4-12}$)bicycloaryl, each substituted or unsubstituted;

$R_5$ and $R_6$ are each independently selected from the group consisting of hydrogen, oxycarbonyl, sulfonyl, sulfinyl, ($C_{1-10}$)alkyl, halo($C_{1-10}$)alkyl, carbonyl($C_{1-3}$)alkyl, thiocarbonyl ($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{2-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero ($C_{4-12}$)bicyclo aryl($C_{1-5}$)alkyl, ($C_{3-12}$)cycloalkyl, hetero ($C_{2-12}$)cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl, and hetero($C_{4-12}$)bicycloaryl, each substituted or unsubstituted, and $R_5$ and $R_6$ on a given carbon may be taken together to form =O, =S, or =$NR_{10}$, where $R_{10}$ is selected from the group consisting of hydrogen, hydroxyl, alkoxy, aryloxy, heteroaryloxy, ($C_{1-10}$)alkyl, halo($C_{1-10}$)alkyl, ($C_{3-12}$)cycloalkyl ($C_{1-5}$)alkyl, hetero($C_{2-12}$)cycloalkyl($C_{1-5}$)alkyl, aryl($C_{1-10}$) alkyl, heteroaryl($C_{1-5}$)alkyl, ($C_{3-12}$)cycloalkyl, hetero($C_{2-12}$) cycloalkyl, ($C_{5-12}$)aryl, and hetero($C_{2-10}$)aryl, each substituted or unsubstituted, and $R_6$ is absent when the carbon to which it is bound forms part of a double bond;

$R_7$ is selected from the group consisting of hydrogen, ($C_{1-10}$)alkyl, halo($C_{1-10}$)alkyl, carbonyl($C_{1-3}$)alkyl, carboxamidoalkyl, amidoalkyl, thiocarbonyl($C_{1-3}$)alkyl, sulfonyl($C_{1-3}$) alkyl, sulfinyl($C_{1-3}$)alkyl, amino($C_{1-10}$)alkyl, imino($C_{1-3}$) alkyl, alkoxy($C_{1-3}$)alkyl, ($C_{3-12}$)cycloalkyl($C_{1-5}$)alkyl, hetero ($C_{2-12}$)cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero($C_{4-12}$) bicyclo aryl($C_{1-5}$)alkyl, ($C_{3-12}$)cycloalkyl, hetero($C_{2-12}$) cycloalkyl, ($C_{9-12}$)bicycloalkyl, hetero($C_{3-12}$)bicycloalkyl, ($C_{5-12}$)aryl, hetero($C_{2-10}$)aryl, ($C_{9-12}$)bicycloaryl and hetero ($C_{4-12}$)bicycloaryl, each substituted or unsubstituted; and $R_9$ is selected from the group consisting of hydrogen, alkoxy, aryloxy, heteroaryloxy, ($C_{1-10}$)alkyl, halo($C_{1-10}$) alkyl, carbonyl($C_{1-3}$)alkyl, aminocarbonylalkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, alkoxy($C_{1-3}$)alkyl, ($C_{3-12}$)cycloalkyl($C_{1-5}$)alkyl, hetero($C_{2-12}$)cycloalkyl($C_{1-5}$) alkyl, aryl($C_{1-10}$)alkyl, heteroaryl($C_{1-5}$)alkyl, ($C_{9-12}$)bicycloaryl($C_{1-5}$)alkyl, hetero($C_{4-12}$)bicycloaryl($C_{1-5}$)alkyl, ($C_{3-12}$)cycloalkyl, hetero($C_{2-12}$)cycloalkyl, ($C_{9-12}$)bicycloalkyl, hetero($C_{4-12}$)bicycloalkyl, ($C_{5-12}$)aryl, hetero ($C_{2-10}$)aryl, ($C_{9-12}$)bicycloaryl and hetero($C_{4-12}$)bicycloaryl, each substituted or unsubstituted;

provided that $R_1$ and $R_3$ are not both hydrogen.

In another embodiment, the method further comprises:
reacting a primary urea having the formula

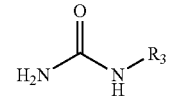

with a diazo compound having the formula

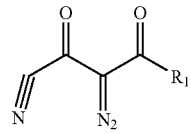

under conditions to form an insertion product having the formula

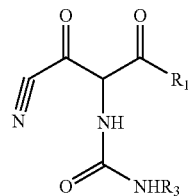

cyclizing the insertion product to yield the cyano imidazolone compound having the formula

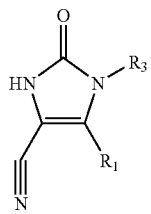

wherein $C_a$ denotes a nitrogen atom;

$R_a$ is alkyl;

$R_1$ is selected from the group consisting of hydrogen, carbonyl, oxycarbonyl, aminocarbonyl, $(C_{1-10})$alkylamino, sulfonamido, sulfonyl, sulfinyl, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-4}$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{2-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted; and $R_3$ is selected from the group consisting of hydrogen, alkoxy, aryloxy, heteroaryloxy, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, carboxamido$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted;

provided that $R_1$ and $R_3$ are not both hydrogen.

In another embodiment, the method further comprises reacting a compound having the formula

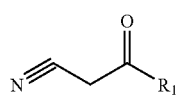

with an aryl sulfonylazide compound having the formula

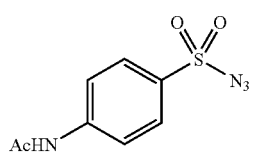

under conditions that form a compound having the formula

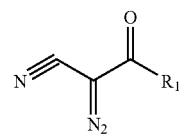

wherein $R_1$ is selected from the group consisting of hydrogen, carbonyl, oxycarbonyl, aminocarbonyl, $(C_{1-10})$alkylamino, sulfonamido, sulfonyl, sulfinyl, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-4}$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{2-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted.

In another embodiment, the method comprising:

coupling a carboxylic acid compound of the formula

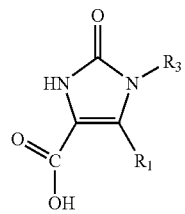

to a piperazine of the formula

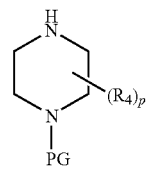

under conditions that form an intermediate of the formula

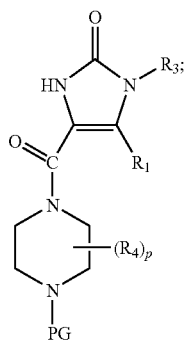

coupling the intermediate formed above to $R_2$-Hal, to form an initial product of the formula

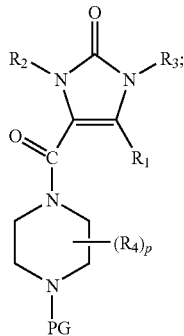

and deprotecting the initial product to yield a final product of the formula

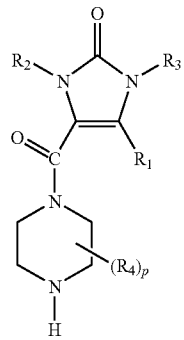

wherein

PG is a protecting group;

p is 0, 1, 2, 3 or 4;

$R_1$ is selected from the group consisting of hydrogen, carbonyl, oxycarbonyl, aminocarbonyl, $(C_{1-10})$alkylamino, sulfonamido, sulfonyl, sulfinyl, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{2-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted;

$R_2$ is selected from the group consisting of hydrogen, alkoxy, aryloxy, heteroaryloxy, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, carboxamido$(C_{1-3})$alkyl, amido$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted;

$R_3$ is selected from the group consisting of hydrogen, alkoxy, aryloxy, heteroaryloxy, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, carboxamido$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted; and each $R_4$ is independently selected from the group consisting of hydrogen, oxo, oxyalkyl, alkoxycarbonyl, carbonyl, thioalkyl, alkoxy, oxycarbonyl, aminocarbonyl, amino, amido, carboxamido, sulfonyl, sulfinyl, $(C_{1-10})$alkyl, halo$(C_{1-10})$alkyl, oxyalkyl, alkoxyalkyl, alkylthioalkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, carboxamido$(C_{1-40})$alkyl, amido$(C_{1-10})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, aryloxyalkyl, heteroarylalkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl, and hetero$(C_{4-12})$bicycloaryl, each substituted or unsubstituted;

provided that $R_1$ and $R_3$ are not both hydrogen.

In one variation of the above embodiment, the carboxylic acid compound is formed by the procedure comprising:

reacting a primary urea having the formula

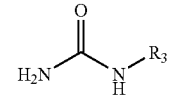

with a diazo compound having the formula

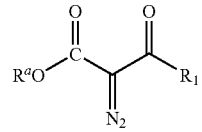

under conditions to form an insertion product having the formula

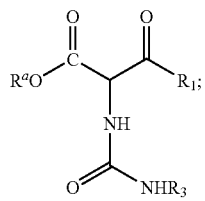

cyclizing the insertion product forming an imidazolone ester having the formula

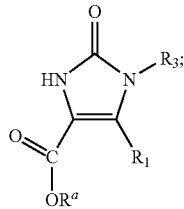

and hydrolyzing the imidazolone ester under conditions to form the carboxylic acid compound;

where $R^a$ is $(C_{1-3})$alkyl.

In another variation of the above embodiment, the diazo compound is formed by the procedure comprising:

reacting a dicarbonyl compound having the formula

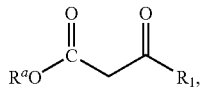

where $R^a$ is $(C_{1-3})$alkyl, with an aryl sulfonylazide compound having the formula

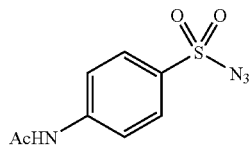

under conditions that form the diazo compound.

In another variation of the above embodiment, the primary urea is formed by a procedure comprising:

converting $NO_2$—$R_3$, a nitro derivative of $R_3$ under reaction conditions to an amine having the formula $NH_2$—$R_3$; and reacting the amine compound with potassium cyanate under the conditions to yield the primary urea.

In another embodiment, the method further comprises converting the product produced by the various embodiments and variations of the method into an acid or base addition salt. In one variation, the acid or base addition salt is selected from the group consisting of hydrochloride, trifluoroacetate, formate, acetate, toluenesulfonate, benzenesulfonate, methanesulfonate, oxalate, succinate, tartrate, citrate, lactate, maleate, fumarate, bisulfate, phosphorate, hydrobromate, benzoate, bis-hydrochloride, bis-trifluoroacetate, sulfate, aphthylene-2-sulfonate, propionate, hydroiodate, R-mandelate, and lithium salt, potassium salt, and sodium salt.

In another of its aspects, the invention is directed to reagents which are useful in the preparation of the compounds of the invention.

In one embodiment, the reagent is a carboxylic compound consisting of the formula

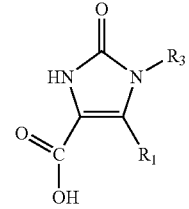

wherein $R_1$ is selected from the group consisting of hydrogen, carbonyl, oxycarbonyl, aminocarbonyl, $(C_{1-10})$alkylamino, sulfonamido, sulfonyl, sulfonyl, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{2-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted; and $R_3$ is selected from the group consisting of hydrogen, alkoxy, aryloxy, heteroaryloxy, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, carboxamido$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted.

Examples of useful carboxylic acid reagent include, but are not limited to:

2-Oxo-1,5-diphenyl-2,3-dihydro-1H-imidazole-4-carboxylic acid;

5-(3-Fluorophenyl)-2-oxo-1-phenyl-2,3-dihydro-1H-imidazole-4-carboxylic acid;

1-(3-Morpholinophenyl)-2-oxo-5-phenyl-2,3-dihydro-1H-imidazole-4-carboxylic acid;

1-(6-Morpholinopyridin-2-yl)-2-oxo-5-phenyl-2,3-dihydro-1H-imidazole-4-carboxylic acid;

5-Isopropyl-2-oxo-1-phenyl-2,3-dihydro-1H-imidazole-4-carboxylic acid;

5-Cyclopropyl-2-oxo-1-phenyl-2,3-dihydro-1H-imidazole-4-carboxylic acid;

5-(Cyclopropylmethyl)-2-oxo-1-phenyl-2,3-dihydro-1H-imidazole-4-carboxylic acid;

5-(2-Chlorophenyl)-2-oxo-1-phenyl-2,3-dihydro-1H-imidazole-4-carboxylic acid;

5-(3-Chlorophenyl)-2-oxo-1-phenyl-2,3-dihydro-1H-imidazole-4-carboxylic acid;

5-(4-Chlorophenyl)-2-oxo-1-phenyl-2,3-dihydro-1H-imidazole-4-carboxylic acid;

1-Cyclohexyl-2-oxo-5-phenyl-2,3-dihydro-1H-imidazole-4-carboxylic acid;

1-(1-(Benzyloxycarbonyl)piperidin-3-yl)-2-oxo-5-phenyl-2,3-dihydro-1H-imidazole-4-carboxylic acid;

1-((1R,2R)-2-(Benzyloxy)cyclohexyl)-2-oxo-5-phenyl-2,3-dihydro-1H-imidazole-4-carboxylic acid;

1-(2-(2-Methoxyethoxy)phenyl)-2-oxo-5-phenyl-2,3-dihydro-1H-imidazole-4-carboxylic acid;

1-(2-(3-Methoxypropoxy)phenyl)-2-oxo-5-phenyl-2,3-dihydro-1H-imidazole-4-carboxylic acid;
1-(3-(2-Methoxyethoxy)phenyl)-2-oxo-5-phenyl-2,3-dihydro-1H-imidazole-4-carboxylic acid; and
1-(3-(3-Methoxypropoxy)phenyl)-2-oxo-5-phenyl-2,3-dihydro-1H-imidazole-4-carboxylic acid.

In another embodiment, the reagent is a piperazine compound useful in the preparation of the compounds of the invention consisting of the formula

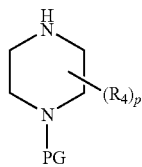

wherein
p is 0, 1, 2, 3 or 4;
PG is a protecting group;
each $R_4$ is independently selected from the group consisting of hydrogen, oxo, oxyalkyl, alkoxycarbonyl, carbonyl, thioalkyl, alkoxy, oxycarbonyl, aminocarbonyl, amino, amido, carboxamido, sulfonyl, sulfinyl, $(C_{1-10})$alkyl, halo$(C_{1-10})$alkyl, oxyalkyl, alkoxyalkyl, alkylthioalkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, carboxamido$(C_{1-10})$alkyl, amido$(C_{1-10})$alkyl, $(C_{3-12})$cycloalkyl$(C_{1-10})$alkyl, hetero$(C_{2-12})$cycloalkyl$(C_{1-5})$alkyl, aryl$(C_{1-10})$alkyl, heteroaryl$(C_{1-5})$alkyl, aryloxyalkyl, heteroarylalkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl, and hetero$(C_{4-12})$bicycloaryl, each substituted or unsubstituted.

In another embodiment, the reagent is an imidazolone initial product useful in the preparation of the compounds of the invention consisting of the formula

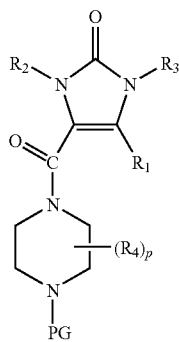

wherein
PG is a protecting group;
p is 0, 1, 2, 3 or 4;
$R_1$ is selected from the group consisting of hydrogen, carbonyl, oxycarbonyl, aminocarbonyl, $(C_{1-10})$alkylamino, sulfonamido, sulfonyl, sulfinyl, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{2-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted;

$R_2$ is selected from the group consisting of hydrogen, alkoxy, aryloxy, heteroaryloxy, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, carboxamido$(C_{1-3})$alkyl, amido$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted;

$R_3$ is selected from the group consisting of hydrogen, alkoxy, aryloxy, heteroaryloxy, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, carboxamido$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted; and each $R_4$ is independently selected from the group consisting of hydrogen, oxo, oxyalkyl, alkoxycarbonyl, carbonyl, thioalkyl, alkoxy, oxycarbonyl, aminocarbonyl, amino, amido, carboxamido, sulfonyl, sulfinyl, $(C_{1-10})$alkyl, halo$(C_{1-10})$alkyl, oxyalkyl, alkoxyalkyl, alkylthioalkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, carboxamido$(C_{1-10})$alkyl, amido$(C_{1-10})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, aryloxyalkyl, heteroarylalkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl, and hetero$(C_{4-12})$bicycloaryl, each substituted or unsubstituted;
provided that $R_1$ and $R_3$ are not both hydrogen.

Example of the imidazolone initial product reagent include, but are not limited to:
tert-Butyl 4-(5-cyclopropyl-2-oxo-1-phenyl-2,3-dihydro-1H-imidazole-4-carbonyl)piperazine-1-carboxylate;
tert-Butyl 4-(5-(cyclopropylmethyl)-2-oxo-1-phenyl-2,3-dihydro-1H-imidazole-4-carbonyl)piperazine-1-carboxylate;
tert-Butyl 4-(5-(2-chlorophenyl)-2-oxo-1-phenyl-2,3-dihydro-1H-imidazole-4-carbonyl)piperazine-1-carboxylate;
tert-Butyl 4-(5-(3-chlorophenyl)-2-oxo-1-phenyl-2,3-dihydro-1H-imidazole-4-carbonyl)piperazine-1-carboxylate;
tert-Butyl 4-(5-(4-chlorophenyl)-2-oxo-1-phenyl-2,3-dihydro-1H-imidazole-4-carbonyl)piperazine-1-carboxylate;
tert-Butyl 4-(1-cyclohexyl-2-oxo-5-phenyl-2,3-dihydro-1H-imidazole-4-carbonyl)piperazine-1-carboxylate;
tert-Butyl 4-(1-(1-(benzyloxycarbonyl)piperidin-3-yl)-2-oxo-5-phenyl-2,3-dihydro-1H-imidazole-4-carbonyl)piperazine-1-carboxylate;
tert-Butyl 4-(1-((1R,2R)-2-(benzyloxy)cyclohexyl)-2-oxo-5-phenyl-2,3-dihydro-1H-imidazole-4-carbonyl)piperazine-1-carboxylate;

tert-Butyl 4-(1-(2-(2-methoxyethoxy)phenyl)-2-oxo-5-phenyl-2,3-dihydro-1H-imidazole-4-carbonyl)piperazine-1-carboxylate;

tert-Butyl 4-(1-(2-(3-methoxypropoxy)phenyl)-2-oxo-5-phenyl-2,3-dihydro-1H-imidazole-4-carbonyl)piperazine-1-carboxylate;

tert-Butyl 4-(1-(3-(2-methoxyethoxy)phenyl)-2-oxo-5-phenyl-2,3-dihydro-1H-imidazole-4-carbonyl)piperazine-1-carboxylate;

tert-Butyl 4-(1-(3-(3-methoxypropoxy)phenyl)-2-oxo-5-phenyl-2,3-dihydro-1H-imidazole-4-carbonyl)piperazine-1-carboxylate;

tert-Butyl 4-(1-cyclohexyl-2-oxo-5-phenyl-2,3-dihydro-1H-imidazole-4-carbonyl)-3-methylpiperazine-1-carboxylate;

(R)-tert-Butyl 3-benzyl-4-(2-oxo-1,5-diphenyl-2,3-dihydro-1H-imidazole-4-carbonyl)piperazine-1-carboxylate;

tert-Butyl 4-(1-cyclohexyl-2-oxo-5-phenyl-2,3-dihydro-1H-imidazole-4-carbonyl)-2-methylpiperazine-1-carboxylate;

tert-Butyl 4-(1-cyclohexyl-2-oxo-5-phenyl-2,3-dihydro-1H-imidazole-4-carbonyl)-2,5-dimethylpiperazine-1-carboxylate; and tert-Butyl 3-(hydroxymethyl)-4-(2-oxo-1,5-diphenyl-2,3-dihydro-1H-imidazole-4-carbonyl)piperazine-1-carboxylate.

In another embodiment, the reagent useful in the preparation of the final product is a diazo compound consisting of the formula

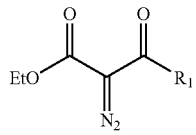

wherein $R_1$ is selected from the group consisting of hydrogen, carbonyl, oxycarbonyl, aminocarbonyl, $(C_{1-10})$alkylamino, sulfonamido, sulfonyl, sulfinyl, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-4}$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{2-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted.

Examples of the diazo compound useful for the production of the compounds of the invention includes, but are not limited to:

Ethyl 2-diazo-3-oxo-3-phenylpropanoate;

Ethyl 2-diazo-3-(3-fluorophenyl)-3-oxopropanoate;

Methyl 2-diazo-4-methyl-3-oxopentanoate;

Ethyl 3-(2-chlorophenyl)-2-diazo-3-oxopropanoate;

Ethyl 4-cyclopropyl-2-diazo-3-oxobutanoate; and

Ethyl 3-cyclopropyl-2-diazo-3-oxopropanoate.

In another embodiment, the reagent useful in the preparation of the compounds of the invention is a primary amine consisting of the formula

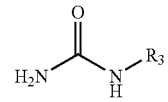

wherein $R_3$ is selected from the group consisting of hydrogen, alkoxy, aryloxy, heteroaryloxy, $(C_{1-10})$alkyl, halo$(C_{1-10})$alkyl, alkoxy$(C_{1-10})$alkyl, carbonyl$(C_{1-3})$alkyl, thiocarbonyl$(C_{1-3})$alkyl, carboxamido$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted.

In another embodiment, the reagent useful in the preparation of the compounds of the invention is an insertion product consisting of the formula

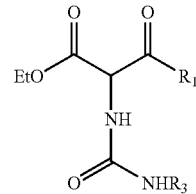

Examples of useful insertion product reagent include, but are not limited to:

Ethyl 2-oxo-1,5-diphenyl-2,3-dihydro-1H-imidazole-4-carboxylate;

Ethyl 5-(3-fluorophenyl)-2-oxo-1-phenyl-2,3-dihydro-1H-imidazole-4-carboxylate;

Ethyl 1-(3-morpholinophenyl)-2-oxo-5-phenyl-2,3-dihydro-1H-imidazole-4-carboxylate;

Ethyl 1-(6-Morpholinopyridin-2-yl)-2-oxo-5-phenyl-2,3-dihydro-1H-imidazole-4-carboxylate;

Ethyl 5-(3-fluorophenyl)-2-oxo-1-phenyl-2,3-dihydro-1H-imidazole-4-carboxylate;

Ethyl 5-cyclopropyl-2-oxo-1-phenyl-2,3-dihydro-1H-imidazole-4-carboxylate;

Ethyl 5-(cyclopropylmethyl)-2-oxo-1-phenyl-2,3-dihydro-1H-imidazole-4-carboxylate;

Ethyl 5-(2-chlorophenyl)-2-oxo-1-phenyl-2,3-dihydro-1H-imidazole-4-carboxylate;

Ethyl 5-(3-chlorophenyl)-2-oxo-1-phenyl-2,3-dihydro-1H-imidazole-4-carboxylate;

Ethyl 5-(4-chlorophenyl)-2-oxo-1-phenyl-2,3-dihydro-1H-imidazole-4-carboxylate;

Ethyl 1-cyclohexyl-2-oxo-5-phenyl-2,3-dihydro-1H-imidazole-4-carboxylate;

Benzyl 3-(4-(ethoxycarbonyl)-2-oxo-5-phenyl-2,3-dihydro-1H-imidazol-1-yl)piperidine-1-carboxylate;

Ethyl 1-((1R,2R)-2-(benzyloxy)cyclohexyl)-2-oxo-5-phenyl-2,3-dihydro-1H-imidazole-4-carboxylate;

Ethyl 1-(2-(2-methoxyethoxy)phenyl)-2-oxo-5-phenyl-2,3-dihydro-1H-imidazole-4-carboxylate;

Ethyl 1-(2-(3-methoxypropoxy)phenyl)-2-oxo-5-phenyl-2,3-dihydro-1H-imidazole-4-carboxylate;
Ethyl 1-(3-(2-methoxyethoxy)phenyl)-2-oxo-5-phenyl-2,3-dihydro-1H-imidazole-4-carboxylate; and
Ethyl 1-(3-(3-methoxypropoxy)phenyl)-2-oxo-5-phenyl-2,3-dihydro-1H-imidazole-4-carboxylate.

In another embodiment, the reagent is a diamine having a formula selected from the group consisting of

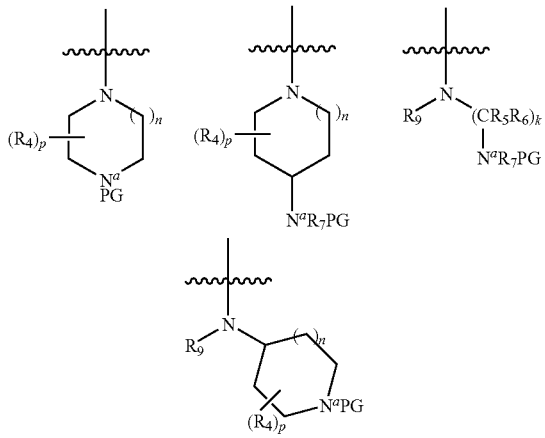

where
k is 0, 1, 2, 3, 4 or 5;
n is 0, 1 or 2;
p is 0, 1, 2, 3 or 4;
$N^a$ denotes a nitrogen atom;
PG is a protecting group;
each $R_4$ is independently selected from the group consisting of hydrogen, oxo, oxyalkyl, alkoxycarbonyl, carbonyl, thioalkyl, alkoxy, oxycarbonyl, aminocarbonyl, amino, amido, carboxamido, sulfonyl, sulfinyl, $(C_{1-10})$alkyl, halo$(C_{1-10})$alkyl, oxyalkyl, alkoxyalkyl, alkylthioalkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, carboxamido$(C_{1-40})$alkyl, amido$(C_{1-10})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, aryloxyalkyl, heteroarylalkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl, and hetero$(C_{4-12})$bicycloaryl, each substituted or unsubstituted;

$R_5$ and $R_6$ are each independently selected from the group consisting of hydrogen, oxycarbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicyclo aryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl, and hetero$(C_{4-12})$bicycloaryl, each substituted or unsubstituted, and $R_5$ and $R_6$ on a given carbon may be taken together to form $=O$, $=S$, or $=NR_{10}$, where $R_{10}$ is selected from the group consisting of hydrogen, hydroxyl, alkoxy, aryloxy, heteroaryloxy, $(C_{1-10})$alkyl, halo$(C_{1-10})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{3-12})$cycloalkyl, hetero$(C_{2-12})$cycloalkyl, $(C_{5-12})$aryl, and hetero$(C_{2-10})$aryl, each substituted or unsubstituted, and $R_6$ is absent when the carbon to which it is bound forms part of a double bond;

$R_7$ is selected from the group consisting of hydrogen, $(C_{1-10})$alkyl, halo$(C_{1-10})$alkyl, carbonyl$(C_{1-3})$alkyl, carboxamidoalkyl, amidoalkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, alkoxy$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{3-12})$bicycloalkyl, $(C_{5-12})$aryl, hetero$(C_{2-10})$aryl, $(C_{9-12})$bicycloaryl and hetero$(C_{4-12})$bicycloaryl, each substituted or unsubstituted; and $R_9$ is selected from the group consisting of hydrogen, alkoxy, aryloxy, heteroaryloxy, $(C_{1-10})$alkyl, halo$(C_{1-10})$alkyl, carbonyl$(C_{1-3})$alkyl, aminocarbonylalkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, alkoxy$(C_{1-3})$alkyl, $(C_{3-12})$cycloalkyl$(C_{1-5})$alkyl, hetero$(C_{2-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{4-12})$bicycloaryl$(C_{1-5})$alkyl, $(C_{3-12})$cycloalkyl, hetero$(C_{2-12})$cycloalkyl, $(C_{9-12})$bicycloalkyl, hetero$(C_{4-12})$bicycloalkyl, $(C_{5-12})$aryl, hetero$(C_{2-10})$aryl, $(C_{9-12})$bicycloaryl, and hetero$(C_{4-12})$bicycloaryl, each substituted or unsubstituted.

Salts, Hydrates, and Prodrugs of Renin Inhibitors

It should be recognized that the compounds of the present invention may be present and optionally administered in the form of salts, hydrates and prodrugs that are converted in vivo into the compounds of the present invention.

A "pharmaceutically acceptable salt", as used herein, is intended to encompass any compound according to the present invention that is utilized in the form of a salt thereof, especially where the salt confers on the compound improved pharmacokinetic properties as compared to the free form of compound or a different salt form of the compound. The pharmaceutically acceptable salt form may also initially confer desirable pharmacokinetic properties on the compound that it did not previously possess, and may even positively affect the pharmacodynamics of the compound with respect to its therapeutic activity in the body. An example of a pharmacokinetic property that may be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

It is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptaoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

Compounds of the present invention that comprise basic nitrogen-containing groups may be quaternized with such agents as $(C_{1-4})$alkyl halides, e.g., methyl, ethyl, iso-propyl and tert-butyl chlorides, bromides and iodides; di$(C_{1-4})$alkyl sulfates, e.g., dimethyl, diethyl and diamyl sulfates; $(C_{10-18})$ alkyl halides, e.g., decyl, dodecyl, lauryl, myristyl and stearyl chlorides, bromides and iodides; and aryl$(C_{1-4})$alkyl halides, e.g., benzyl chloride and phenethyl bromide. Such salts permit the preparation of both water-soluble and oil-soluble compounds of the present invention.

Compounds of the invention further include prodrug derivatives of the compounds. It is noted that in many instances, the prodrugs themselves also fall within the scope of the range of compounds according to the present invention.

Various forms of prodrugs are well known in the art. For examples of such prodrug derivatives, see, e.g., a) Design of Prodrugs, Bundgaard, A. Ed., Elsevier, 1985 and Method in Enzymology, Widder, K. et al., Ed.; Academic, 1985, vol. 42, p. 309-396;

b) Bundgaard, H. "Design and Application of Prodrugs" in A Textbook of Drug Design and Development, Krosgaard-Larsen and H. Bundgaard, Ed., 1991, Chapter 5, p. 113-191; and c) Bundgaard, H., Advanced Drug Delivery Review, 1992, 8, 1-38.

Each of which is incorporated herein by reference.

Pharmaceutically acceptable prodrugs of the compounds of this invention include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters.

Compounds of the present invention may also be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

Compositions Comprising Renin Inhibitors

A wide variety of compositions and administration methods may be used in conjunction with the compounds of the present invention. Such compositions may include, in addition to the compounds of the present invention, conventional pharmaceutical excipients, and other conventional, pharmaceutically inactive agents. Additionally, the compositions may include active agents in addition to the compounds of the present invention. These additional active agents may include additional compounds according to the invention, and/or one or more other pharmaceutically active agents.

The compositions may be in gaseous, liquid, semi-liquid or solid form, formulated in a manner suitable for the route of administration to be used. For oral administration, capsules and tablets are typically used. For parenteral administration, reconstitution of a lyophilized powder, prepared as described herein, is typically used.

Compositions comprising compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

The renin inhibitors and compositions comprising them may be administered or coadministered in any conventional dosage form. Co-administration in the context of this invention is intended to mean the administration of more than one therapeutic agent, one of which includes a renin inhibitor, in the course of a coordinated treatment to achieve an improved clinical outcome. Such co-administration may also be coextensive, that is, occurring during overlapping periods of time.

Solutions or suspensions used for parenteral, intradermal, subcutaneous, or topical application may optionally include one or more of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; agents for the adjustment of tonicity such as sodium chloride or dextrose, and agents for adjusting the acidity or alkalinity of the composition, such as alkaline or acidifying agents or buffers like carbonates, bicarbonates, phosphates, hydrochloric acid, and organic acids like acetic and citric acid. Parenteral preparations may optionally be enclosed in ampules, disposable syringes or single or multiple dose vials made of glass, plastic or other suitable material.

When compounds according to the present invention exhibit insufficient solubility, methods for solubilizing the compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as prodrugs of the compounds may also be used in formulating effective pharmaceutical compositions.

Upon mixing or adding compounds according to the present invention to a composition, a solution, suspension, emulsion or the like may be formed. The form of the resulting composition will depend upon a number of factors, including the intended mode of administration, and the solubility of the compound in the selected carrier or vehicle. The effective concentration needed to ameliorate the disease being treated may be empirically determined.

Compositions according to the present invention are optionally provided for administration to humans and animals in unit dosage forms, such as tablets, capsules, pills, powders, dry powders for inhalers, granules, sterile parenteral solutions or suspensions, and oral solutions or suspensions, and oil-water emulsions containing suitable quantities of the compounds, particularly the pharmaceutically acceptable salts, preferably the sodium salts, thereof. The pharmaceutically therapeutically active compounds and derivatives thereof are typically formulated and administered in unit-dosage forms or multiple-dosage forms. Unit-dose forms, as used herein, refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses that are not segregated in packaging.

In addition to one or more compounds according to the present invention, the composition may comprise: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to form a solution or suspension. If desired, the pharmaceutical composition to be administered may also contain minor amounts of auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known in the art, or will be apparent, to those skilled in this art; for example, see Remington's Pharmaceutical Sciences, Mack Publishing Company, Easton, Pa., 15th Edition, 1975. The composition or formulation to be administered will, in any event, contain a sufficient quantity of a inhibitor of the present invention to reduce renin activity in vivo, thereby treating the disease state of the subject.

Dosage forms or compositions may optionally comprise one or more compounds according to the present invention in the range of 0.005% to 100% (weight/weight) with the balance comprising additional substances such as those described herein. For oral administration, a pharmaceutically acceptable composition may optionally comprise any one or more commonly employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparing these formulations are known to those skilled in the art. The compositions may optionally contain 0.01%-100% (weight/weight) of one or more renin inhibitors, optionally 0.1-95%, and optionally 1-95%.

Salts, preferably sodium salts, of the inhibitors may be prepared with carriers that protect the compound against rapid elimination from the body, such as time release formulations or coatings. The formulations may further include other active compounds to obtain desired combinations of properties.

Formulations for Oral Administration

Oral pharmaceutical dosage forms may be as a solid, gel or liquid. Examples of solid dosage forms include, but are not limited to tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain embodiments, compounds according to the present invention are provided as solid dosage forms, preferably capsules or tablets. The tablets, pills, capsules, troches and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose and starch paste.

Examples of lubricants that may be used include, but are not limited to, talc, starch, magnesium or calcium stearate, lycopodium and stearic acid.

Examples of diluents that may be used include, but are not limited to, lactose, sucrose, starch, kaolin, salt, mannitol and dicalcium phosphate.

Examples of glidants that may be used include, but are not limited to, colloidal silicon dioxide.

Examples of disintegrating agents that may be used include, but are not limited to, crosscarmellose sodium, sodium starch glycolate, alginic acid, corn starch, potato starch, bentonite, methylcellulose, agar and carboxymethylcellulose.

Examples of coloring agents that may be used include, but are not limited to, any of the approved certified water-soluble FD and C dyes, mixtures thereof; and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate and polyoxyethylene lauryl ether.

Examples of anti-emetic coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, the salt of the compound may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compounds according to the present invention may also be administered as a component of an elixir, suspension, syrup, wafer, sprinkle, chewing gum or the like. A syrup may optionally comprise, in addition to the active compounds, sucrose as a sweetening agent and certain preservatives, dyes and colorings and flavors.

The compounds of the present invention may also be mixed with other active materials that do not impair the desired action, or with materials that supplement the desired action, such as antacids, $H_2$ blockers, and diuretics. For example, if a compound is used for treating asthma or hypertension, it may be used with other bronchodilators and antihypertensive agents, respectively.

Examples of pharmaceutically acceptable carriers that may be included in tablets comprising compounds of the present invention include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

Examples of liquid oral dosage forms that may be used include, but are not limited to, aqueous solutions, emulsions, suspensions, solutions and/or suspensions reconstituted from non-effervescent granules and effervescent preparations reconstituted from effervescent granules.

Examples of aqueous solutions that may be used include, but are not limited to, elixirs and syrups. As used herein, elixirs refer to clear, sweetened, hydroalcoholic preparations. Examples of pharmaceutically acceptable carriers that may be used in elixirs include, but are not limited to solvents. Particular examples of solvents that may be used include glycerin, sorbitol, ethyl alcohol and syrup. As used herein, syrups refer to concentrated aqueous solutions of a sugar, for example, sucrose. Syrups may optionally further comprise a preservative.

Emulsions refer to two-phase systems in which one liquid is dispersed in the form of small globules throughout another liquid. Emulsions may optionally be oil-in-water or water-in-oil emulsions. Examples of pharmaceutically acceptable carriers that may be used in emulsions include, but are not limited to non-aqueous liquids, emulsifying agents and preservatives.

Examples of pharmaceutically acceptable substances that may be used in non-effervescent granules, to be reconstituted into a liquid oral dosage form, include diluents, sweeteners and wetting agents.

Examples of pharmaceutically acceptable substances that may be used in effervescent granules, to be reconstituted into a liquid oral dosage form, include organic acids and a source of carbon dioxide.

Coloring and flavoring agents may optionally be used in all of the above dosage forms.

Particular examples of preservatives that may be used include glycerin, methyl and propylparaben, benzoic add, sodium benzoate and alcohol.

Particular examples of non-aqueous liquids that may be used in emulsions include mineral oil and cottonseed oil.

Particular examples of emulsifying agents that may be used include gelatin, acacia, tragacanth, bentonite, and surfactants such as polyoxyethylene sorbitan monooleate.

Particular examples of suspending agents that may be used include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Particular examples of wetting agents that may be used include propylene glycol monostearate, sorbitan monooleate, diethylene glycol monolaurate and polyoxyethylene lauryl ether.

Particular examples of organic acids that may be used include citric and tartaric acid.

Sources of carbon dioxide that may be used in effervescent compositions include sodium bicarbonate and sodium carbonate. Coloring agents include any of the approved certified water soluble FD and C dyes, and mixtures thereof.

Particular examples of flavoring agents that may be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603.

Injectables, Solutions, and Emulsions

The present invention is also directed to compositions designed to administer the compounds of the present invention by parenteral administration, generally characterized by subcutaneous, intramuscular or intravenous injection. Injectables may be prepared in any conventional form, for example as liquid solutions or suspensions, solid forms suitable for solution or suspension in liquid prior to injection, or as emulsions.

Examples of excipients that may be used in conjunction with injectables according to the present invention include, but are not limited to water, saline, dextrose, glycerol or ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

When administered intravenously, examples of suitable carriers include, but are not limited to physiological saline or phosphate buffered saline (PBS), and solutions containing thickening and solubilizing agents, such as glucose, polyethylene glycol, and polypropylene glycol and mixtures thereof.

Examples of pharmaceutically acceptable carriers that may optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles that may optionally be used include Sodium Chloride Injection, Ringers Injection, Isotonic Dextrose Injection, Sterile Water Injection, Dextrose and Lactated Ringers Injection.

Examples of nonaqueous parenteral vehicles that may optionally be used include fixed oils of vegetable origin, cottonseed oil, corn oil, sesame oil and peanut oil.

Antimicrobial agents in bacteriostatic or fungistatic concentrations may be added to parenteral preparations, particularly when the preparations are packaged in multiple-dose containers and thus designed to be stored and multiple aliquots to be removed. Examples of antimicrobial agents that may be used include phenols or cresols, mercurials, benzyl alcohol, chlorobutanol, methyl and propyl p-hydroxybenzoic acid esters, thimerosal, benzalkonium chloride and benzethonium chloride.

Examples of isotonic agents that may be used include sodium chloride and dextrose. Examples of buffers that may be used include phosphate and citrate. Examples of antioxidants that may be used include sodium bisulfate. Examples of local anesthetics that may be used include procaine hydrochloride. Examples of suspending and dispersing agents that may be used include sodium carboxymethylcellulose, hydroxypropyl methylcellulose and polyvinylpyrrolidone. Examples of emulsifying agents that may be used include Polysorbate 80 (TWEEN 80). Sequestering or chelating agents of metal ions include EDTA.

Pharmaceutical carriers may also optionally include ethyl alcohol, polyethylene glycol and propylene glycol for water miscible vehicles and sodium hydroxide, hydrochloric acid, citric acid or lactic acid for pH adjustment.

The concentration of an inhibitor in the parenteral formulation may be adjusted so that an injection administers a pharmaceutically effective amount sufficient to produce the desired pharmacological effect. The exact concentration of an inhibitor and/or dosage to be used will ultimately depend on the age, weight and condition of the patient or animal as is known in the art.

Unit-dose parenteral preparations may be packaged in an ampoule, a vial or a syringe with a needle. All preparations for parenteral administration should be sterile, as is know and practiced in the art.

Injectables may be designed for local and systemic administration. Typically a therapeutically effective dosage is formulated to contain a concentration of at least about 0.1% w/w up to about 90% w/w or more, preferably more than 1% w/w of the renin inhibitor to the treated tissue(s). The inhibitor may be administered at once, or may be divided into a number of smaller doses to be administered at intervals of time. It is understood that the precise dosage and duration of treatment will be a function of the location of where the composition is parenterally administered, the carrier and other variables that may be determined empirically using known testing protocols or by extrapolation from in vivo or in vitro test data. It is to be noted that concentrations and dosage values may also vary with the age of the individual treated. It is to be further understood that for any particular subject, specific dosage regimens may need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The renin inhibitor may optionally be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the disease state and may be empirically determined.

Lyophilized Powders

The compounds of the present invention may also be prepared as lyophilized powders, which can be reconstituted for administration as solutions, emulsions and other mixtures. The lyophilized powders may also be formulated as solids or gels.

Sterile, lyophilized powder may be prepared by dissolving the compound in a sodium phosphate buffer solution containing dextrose or other suitable excipient. Subsequent sterile filtration of the solution followed by lyophilization under standard conditions known to those of skill in the art provides the desired formulation. Briefly, the lyophilized powder may optionally be prepared by dissolving dextrose, sorbitol, fructose, corn syrup, xylitol, glycerin, glucose, sucrose or other suitable agent, about 1-20%, preferably about 5 to 15%, in a suitable buffer, such as citrate, sodium or potassium phosphate or other such buffer known to those of skill in the art at, typically, about neutral pH. Then, a renin inhibitor is added to the resulting mixture, preferably above room temperature, more preferably at about 30-35° C., and stirred until it dissolves. The resulting mixture is diluted by adding more buffer to a desired concentration. The resulting mixture is sterile filtered or treated to remove particulates and to insure sterility, and apportioned into vials for lyophilization. Each vial may contain a single dosage or multiple dosages of the inhibitor.

Topical Administration

The compounds of the present invention may also be administered as topical mixtures. Topical mixtures may be used for local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The renin inhibitors may be formulated as aerosols for topical application, such as by inhalation (see, U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The inhibitors may also be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the renin inhibitor alone or in combination with other pharmaceutically acceptable excipients can also be administered.

Formulations for Other Routes of Administrations

Depending upon the disease state being treated, other routes of administration, such as topical application, transdermal patches, and rectal administration, may also be used. For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration may be manufactured using the same pharmaceutically acceptable substance and by the same methods as for formulations for oral administration.

Examples of Formulations

The following are particular examples of oral, intravenous and tablet formulations that may optionally be used with compounds of the present invention. It is noted that these formulations may be varied depending on the particular compound being used and the indication for which the formulation is going to be used.

Oral Formulation

| | |
|---|---|
| Compound of the Present Invention | 10-100 mg |
| Citric Acid Monohydrate | 105 mg |
| Sodium Hydroxide | 18 mg |
| Flavoring | |
| Water | q.s. to 100 mL |

Intravenous Formulation

| | |
|---|---|
| Compound of the Present Invention | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

Tablet Formulation

| | |
|---|---|
| Compound of the Present Invention | 1% |
| Microcrystalline Cellulose | 73% |
| Stearic Acid | 25% |
| Colloidal Silica | 1%. |

Kits Comprising Renin Inhibitors

The invention is also directed to kits and other articles of manufacture for treating diseases associated with Renin. It is noted that diseases are intended to cover all conditions for which the renin possess activity that contributes to the pathology and/or symptomology of the condition.

In one embodiment, a kit is provided that comprises a composition comprising at least one inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

It is noted that the packaging material used in kits and articles of manufacture according to the present invention may form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

Combination Therapy

A wide variety of therapeutic agents may have a therapeutic additive or synergistic effect with renin inhibitors according to the present invention. Such therapeutic agents may additively or synergistically combine with the renin inhibitors to reduce or alleviate the effects and symptoms of cardiovascular disease.

In one embodiment, a method is provided for treating cardiovascular disease comprising treating cells with a compound according to the present invention in combination with an aldosterone receptor antagonist, wherein the cells are treated with the compound according to the present invention before, at the same time, and/or after the cells are treated with the aldosterone receptor antagonist, referred to herein as combination therapy. It is noted that treatment of one agent before another is referred to herein as sequential therapy, even if the agents are also administered together. It is noted that combination therapy is intended to cover when agents are administered before or after each other (sequential therapy) as well as when the agents are administered at the same time.

Preparation of Renin Inhibitors

Various methods may be developed for synthesizing compounds according to the present invention. General schemes for synthesizing these compounds are provided below and exemplified in the Examples. It is noted, however, that the compounds of the present invention may also be synthesized by other synthetic routes that others may devise.

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (i.e., enantiomers and diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) and can be readily separated by taking advantage of these dissimilarities.

For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet and Samuel H. Wilen, *Enantiomers, Racemates and Resolutions*, John Wiley & Sons, Inc. (1981).

Compounds according to the present invention can also be prepared as a pharmaceutically acceptable acid addition salt by reacting the free base form of the compound with a pharmaceutically acceptable inorganic or organic acid. Alternatively, a pharmaceutically acceptable base addition salt of a compound can be prepared by reacting the free acid form of the compound with a pharmaceutically acceptable inorganic or organic base. Inorganic and organic acids and bases suitable for the preparation of the pharmaceutically acceptable salts of compounds are set forth in the definitions section of this Application. Alternatively, the salt forms of the compounds can be prepared using salts of the starting materials or intermediates.

The free acid or free base forms of the compounds can be prepared from the corresponding base addition salt or acid addition salt form. For example, a compound in an acid addition salt form can be converted to the corresponding free base by treating with a suitable base (e.g., ammonium hydroxide solution, sodium hydroxide, and the like). A compound in a base addition salt form can be converted to the corresponding free acid by treating with a suitable acid (e.g., hydrochloric acid, etc).

The N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Compounds in an unoxidized form can be prepared from N-oxides of compounds by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds can be prepared by methods known to those of ordinary skill in the art. For example, appropriate prodrugs can be prepared by reacting a non-derivatized compound with a suitable carbamylating agent (e.g., 1,1-acyloxyalkylcarbonochloridate, para-nitrophenyl carbonate, or the like) or an acylating agent. Further examples of methods of making prodrugs are described in Saulnier et al. *Bioorganic and Medicinal Chemistry Letters*, 1994, Vol. 4, p. 1985. Those of ordinary skill in the art have the knowledge and means to accomplish this without undue experimentation.

Protected derivatives of the compounds can be made by methods known to those of ordinary skill in the art. A detailed description of the techniques applicable to the creation of protecting groups and their removal can be found in T. W. Greene, *Protecting Groups in Organic Synthesis*, 3rd edition, John Wiley & Sons, Inc. 1999.

Compounds according to the present invention may be conveniently prepared or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

Compounds according to the present invention can also be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diastereomeric derivatives of compounds, dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet and Samuel H. Wilen, *Enantiomers, Racemates and Resolutions*, John Wiley & Sons, Inc. (1981).

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

| | |
|---|---|
| μL (microliters) | Ac (acetyl) |
| atm (atmosphere) | ATP (Adenosine Triphophatase) |
| BOC (tert-butyloxycarbonyl) | BOP (bis(2-oxo-3-oxazolidinyl)phosphinic chloride) |
| Brij35 (polyoxyethyleneglycol dodecylether) | BSA (Bovine Serum Albumin) |
| CBZ (benzyloxycarbonyl) | CDI (1,1-carbonyldiimidazole) |
| DCC (dicyclohexylcarbodiimide) | DCE (dichloroethane) |
| DCM (dichloromethane) | DMAP (4-dimethylaminopyridine) |
| DME (1,2-dimethoxyethane) | DMF (N,N-dimethylformamide) |
| DMPU (N,N'-dimethylpropyleneurea) | DMSO (dimethylsulfoxide) |
| DTT (dithiothreitol) | EDCI (ethylcarbodiimide hydrochloride) |
| EDTA (Ethylenediaminetetraacetic acid) | Et (ethyl) |
| Et$_2$O (diethyl ether) | EtOAc (ethyl acetate) |

| | |
|---|---|
| FMOC (9-fluorenylmethoxycarbonyl) | g (grams) |
| h (hours) | HOAc or AcOH (acetic acid) |
| HOBT (1-hydroxybenzotriazole) | HOSu (N-hydroxysuccinimide) |
| HPLC (high pressure liquid chromatography) | Hz (Hertz) |
| i.v. (intravenous) | IBCF (isobutyl chloroformate) |
| i-PrOH (isopropanol) | L (liters) |
| LAH (lithium aluminum hydride) | M (molar) |
| mCPBA (meta-chloroperbenzoic acid) | Me (methyl) |
| MeOH (methanol) | mg (milligrams) |
| MHz (megahertz) | min (minutes) |
| mL (milliliters) | mM (millimolar) |
| mmol (millimoles) | mol (moles) |
| MOPS (Morpholinepropanesulfonic acid) | mp (melting point) |
| NaOAc (sodium acetate) | $NEt_3$ (triethylamine) |
| OMe (methoxy) | OTf (O-triflate) |
| OMs (O-mesylate) | psi (pounds per square inch) |
| RP (reverse phase) | RT (ambient temperature) |
| SPA (Scintillation Proximity Assay) | TBAF (tetra-n-butylammonium fluoride) |
| TBS (t-butyldimethylsilyl) | tBu (tert-butyl) |
| TEA (triethylamine) | TFA (trifluoroacetic acid) |
| TFAA (trifluoroacetic anhydride) | THF (tetrahydrofuran) |
| TIPS (triisopropylsilyl) | TLC (thin layer chromatography) |
| TMS (trimethylsilyl) | TMSE (2-(trimethylsilyl)ethyl) |
| Tr (retention time) | |

All references to ether or $Et_2O$ are to diethyl ether; and brine refers to a saturated aqueous solution of NaCl. Unless otherwise indicated, all temperatures are expressed in ° C. (degrees Centigrade). All reactions are conducted under an inert atmosphere at RT unless otherwise noted.

$^1H$ NMR spectra were recorded on a Bruker Avance 400. Chemical shifts are expressed in parts per million (ppm). Coupling constants are in units of Hertz (Hz). Splitting patterns describe apparent multiplicities and are designated as s (singlet), d (doublet), t (triplet), q (quartet), m (multiplet), br (broad). When two rotomers are observed, the combined NMR spectra are presented.

Low-resolution mass spectra (MS) and compound purity data were acquired on a Waters ZQ LC/MS single quadrupole system equipped with electrospray ionization (ESI) source, UV detector (220 and 254 nm), and evaporative light scattering detector (ELSD). Thin-layer chromatography was performed on 0.25 mm E. Merck silica gel plates (60F-254), visualized with UV light, 5% ethanolic phosphomolybdic acid, Ninhydrin or p-anisaldehyde solution. Flash column chromatography was performed on silica gel (230-400 mesh, Merck).

The starting materials and reagents used in preparing these compounds are either available from commercial suppliers such as the Aldrich Chemical Company (Milwaukee, Wis.), Bachem (Torrance, Calif.), Sigma (St. Louis, Mo.), or may be prepared by methods well known to a person of ordinary skill in the art, following procedures described in such standard references as Fieser and Fieser's Reagents for Organic Synthesis, vols. 1-17, John Wiley and Sons, New York, N.Y., 1991; Rodd's Chemistry of Carbon Compounds, vols. 1-5 and supps., Elsevier Science Publishers, 1989; Organic Reactions, vols. 1-40, John Wiley and Sons, New York, N.Y., 1991; March J.: Advanced Organic Chemistry, 4th ed., John Wiley and Sons, New York, N.Y.; and Larock: Comprehensive Organic Transformations, VCH Publishers, New York, 1989.

The entire disclosures of all documents cited throughout this application are incorporated herein by reference.

A. Synthetic Schemes for Compounds of the Present Invention

Compounds according to the present invention may be synthesized according to the reaction schemes shown below. Other reaction schemes could be readily devised by those skilled in the art. It should also be appreciated that a variety of different solvents, temperatures and other reaction conditions can be varied to optimize the yields of the reactions.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry*, John Wiley and Sons, 1991.

In describing the general synthetic routes for producing compounds of the present invention, the definitions of the various substituents are either specifically provided or they are the same as taught throughout the disclosure.

Scheme 1. Preparation of Imidazolone Ketone
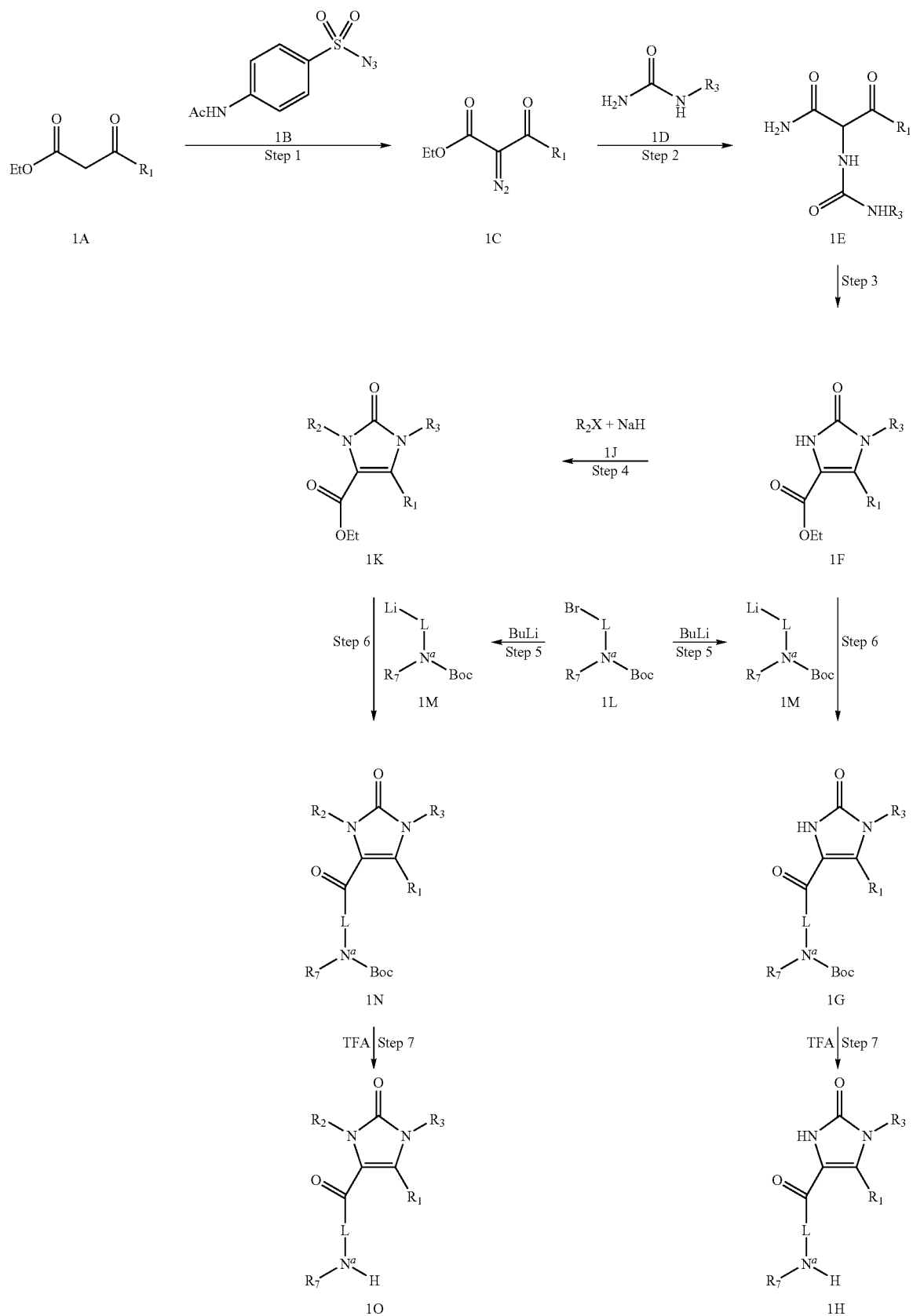

Scheme 1 provides a general procedure for the N—H insertion reaction of primary ureas with diazo compounds and the conversion of these products into imidazolones and ultimately into imidazolone ketones of the invention.

A dicarbonyl compound such as 3-carbonylacetate 1A may be treated with an aryl sulfonylazide 1B in the presence of a base such as triethylamine to give a diazocarbonyl compound 1C (Step 1). The diazocarbonyl compound 1C may be reacted with a primary urea 1D in the presence of a rhodium catalyst, such as rhodium (II) octanoate or rhodium (II) acetate, in a solvents such as a 1:1 mixture of 1,2-dichloroethane and toluene at elevated temperature (e.g., 80° C.) to yield an insertion product 1E (Step 2). In most cases, the insertion product 1E is formed very rapidly and the reaction can be completed within 1 hr of heating at 80° C. In cases where the urea 1D is sparingly soluble in the solvent mixture, it may be necessary to break down the urea into fine powder by grinding of the solid urea and/or sonicating the mixture prior to the reaction; otherwise, lower yield or slower reaction may result.

The insertion product 1E may be cyclized to the corresponding imidazolone ester 1F in the presence of an acid for example, trifluoroacetic acid (Step 3). The acid may be added to the reaction mixture directly; or in some instances, the solvent may be removed in vacuo first and the remaining residue can then be treated with trifluoroacetic acid to effect the formation of the imidazolone ester 1F. In some instances, heating the reaction mixture in TFA may also be necessary. The imidazolone ester 1F may be isolated by column chromatography from the concentrated crude product.

Imidazolone ester 1F may be N-alkylated under a basic condition (such as NaH in DMF) with an alkylating reagent 1J to give an alkylated imidazolone ester 1K (Step 4).

The imidazolone ester 1F or 1K may be treated with excess organolithium terminal amine reagent 1M (or Grignard reagent) to provide the corresponding imidazolone ketone 1G or 1N, respectively (Step 6). Typically, the reaction was carried out at temperature ranging from −78° C. to room temperature using solvents such as THF or ether. The reagent IM may be obtained by reaction of the corresponding protected terminal amine halide 1L with butyllithium or isopropylmagnesium bromide (Step 5).

The protected compound 1G or 1N can be deprotected by appropriate reagents to provide the desired imidazolone ketone renin inhibitors 1H or 1O, respectively. TFA may be used for the removal of a Boc group, and Pd-catalyzed hydrogenolysis may be used for the removal of a Bn group (Step 7).

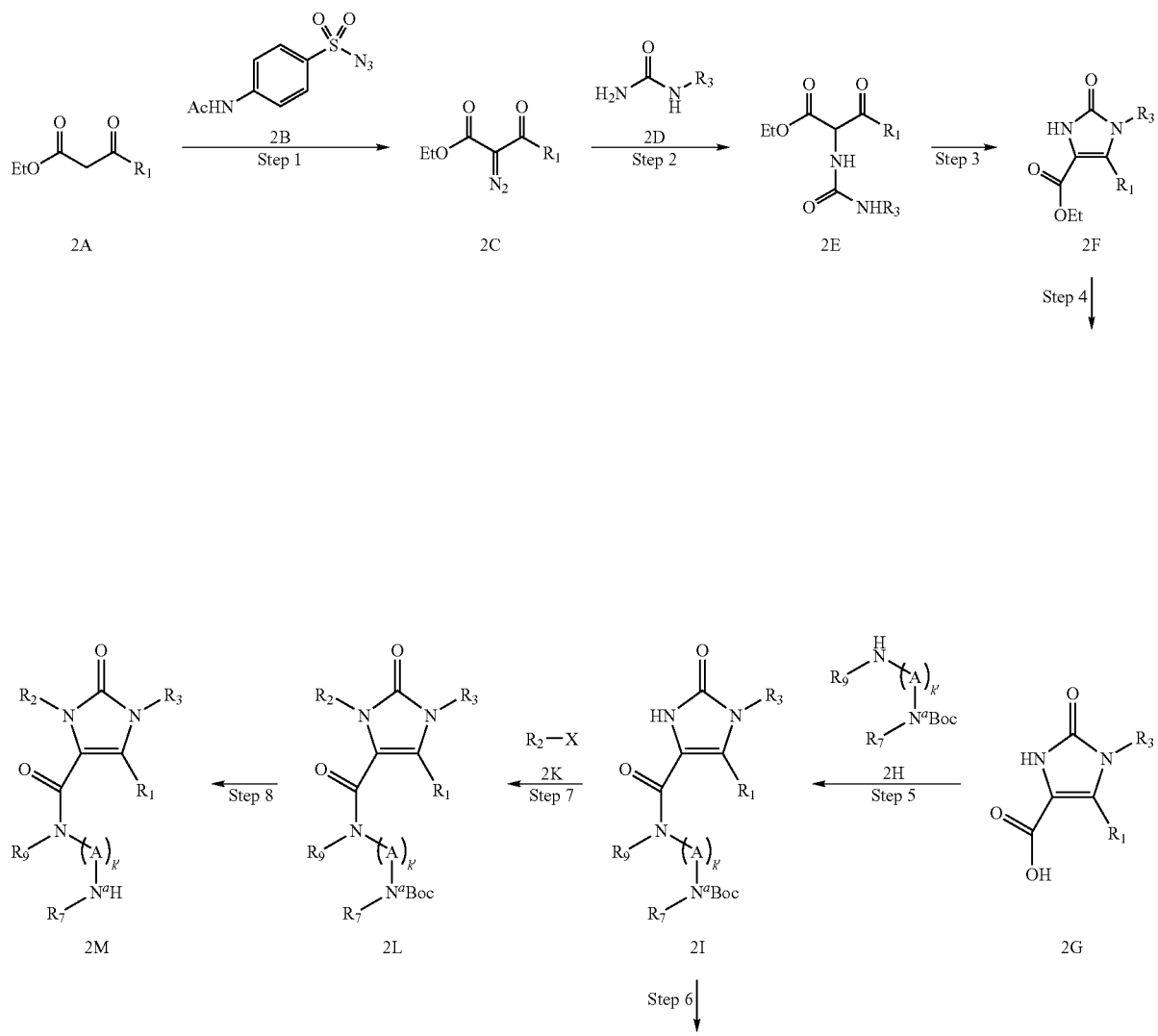

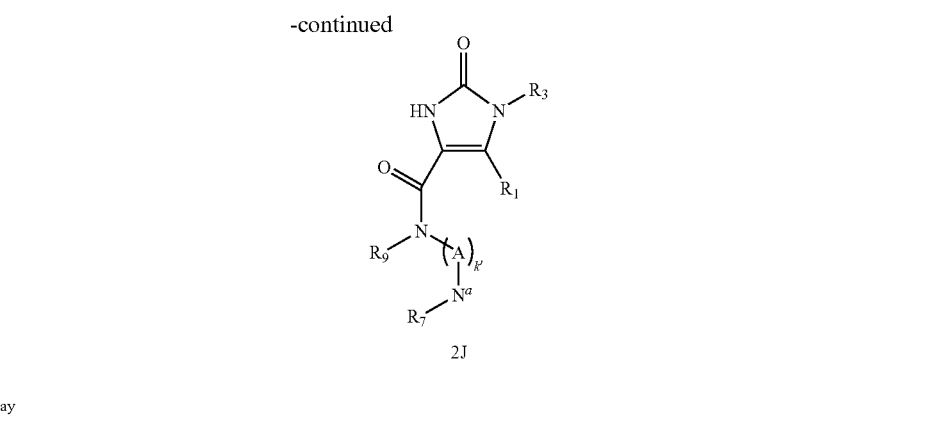

2J where
X is Cl, Br, OMs, or OTos
$R_7$, $R_9$ and any two substituents on A may be taken together to form a ring The preparation of a diazocarbonyl 2C from the treatment of a carbonylacetate 2A with aryl sulfonylazide 2B, its reaction with a primary ureas 2D to form an insertion product 2E, and the cyclization of the insert product 2E to the corresponding imidazolone ester 2F may proceed as described in Scheme 1, Steps 1-3.

The imidazolone ester 2F may be isolated by column chromatography from the concentrated crude product first and then hydrolyzed into the corresponding acid 2G (Step 4); or in some cases, the imidazolone ester 2F may be hydrolysized directly to the corresponding acid 2G.

The acid 2G may be purified and coupled with a diamine derivative 2H to provide the amide product 2I. The diamine derivatives 2H are typically monoprotected on one of the nitrogens by a protecting group such as a Boc or Bn group; however, unprotected piperazines such as 2,5-dimethyl piperazine can also be used directly for the coupling reaction.

The protected amide product 2I can be deprotected by appropriate reagents to provide the desired renin inhibitor 2J; TFA may be used for the removal of a Boc group, and Pd-catalyzed hydrogenolysis may be used for the removal of a Bn group (Step 6).

Further, the protected amide product 2I may be N-alkylated under a basic condition (such as NaH in DMF) with an alkylating reagent 2K (Step 7) to give a protect product 2L (Step 7), which upon deprotection (Step 8) to give the desired renin inhibitor 2M.

Scheme 3. Formation of Urea

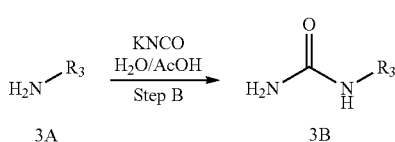

Ureas used in the insertion reaction (Scheme 1, step 2) that are not commercially available may be prepared by the reaction of KNCO with an amine in the presence of an acid, e.g., acetic acid.

An amine 3A (20 mmol) may be first mixed with KCNO (1 equivalent) in 24 mL of water, and the mixture chilled to 0° C. prior to the addition of an acid, such as glacial acetic acid (1.17 mL, 1 equivalent). The temperature of the reaction mixture may be allowed to rise to room temperature, and the corresponding ureas 3B may precipitate in about 2 hours. The reaction may be allowed to continue overnight while stirring at room temperature. The solid may be filtered; rinsed with water and dried under vacuum to provide primary ureas 3B.

Scheme 4. Formation of Amines

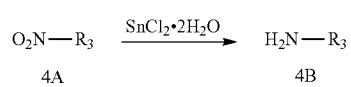

Amines may be prepared from the corresponding nitro derivatives in a reduction reaction by $SnCl_2$ dihydrate. Alternatively, the reaction may be catalyzed by Pd/C under a hydrogen atmosphere.

A nitro derivative 4A (~12 mmol) may be mixed in with tin chloride dihydrate (13.36 g, 5 equivalents) in 25 mL of ethyl acetate and heated at 60° C. for about two hours and then chilled at 0° C. Triethylamine (25-30 mL) may be added slowly until a white precipitate is formed. The white precipitate may be removed by filteration over a Celite plug. The filtrate may be washed with brine, dried over $MgSO_4$, and then concentrated and dried under vacuum to provide the amine derivative 4B.

Scheme 5. Preparation of Imidazolone Amidine

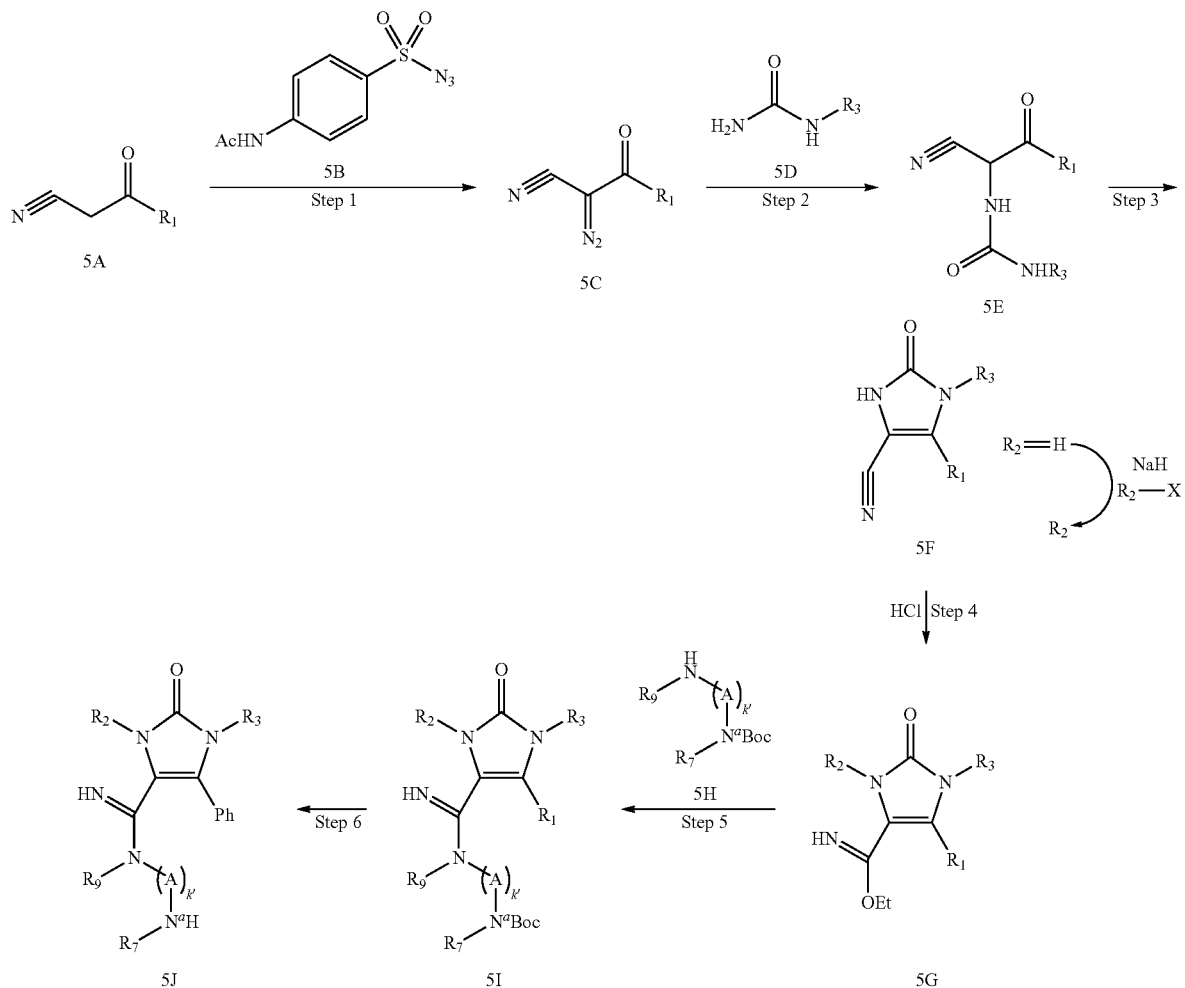

An imidazolone nitrile 5F can be synthesized using the same procedure as that described for the synthesis of imidazolone ester 1F (Scheme 1, Steps 1-3). Alkylation of 5F with $R_2$—X using similar procedure as that for conversion of 1F to 1K (Scheme 1, Step 4) to give an N-alkylated nitrile 5F.

The nitrile or N-alkylated nitrile 5F may be converted to the corresponding imidate 5G upon the treatment with HCl (Step 4). HCl gas may be bubbled through a solution of 2-imidazolone nitrile 5F (2 mmol) in anhydrous EtOH (5 mL) at 0° C. for 2 to 10 mins. The resulting mixture may be allowed to react for 2-72 hrs while stirring at room temperature. The imidate may be precipitate with ether, and the resulting precipitates collected by filtration (under nitrogen) or centrifugation, rinsed with ether and dried to give the desired imidates 5G as HCl salt.

Imidates may be reacted with amines (e.g., monoprotected piperazine) to yield protected products (Step 5). To a stirred solution of an imidate 5G (0.05 mmol) in anhydrous EtOH (200 µl) may be added mono-protected amine 5H (0.06 mmol) and diisopropylethylamine (0.15 mmol). The resulting mixture may be stirred for 1 to 24 h at room temperature. After removal of solvent under reduced pressure, the crude product may be purified by RP-HPLC to give the 2-imidazolone amidine 5I. Deprotection of 5I according to the procedure described in Scheme 2, Step 6 will give corresponding amidine product 5J (Step 6).

Scheme 6. Preparation of Imidazolone Thioamide

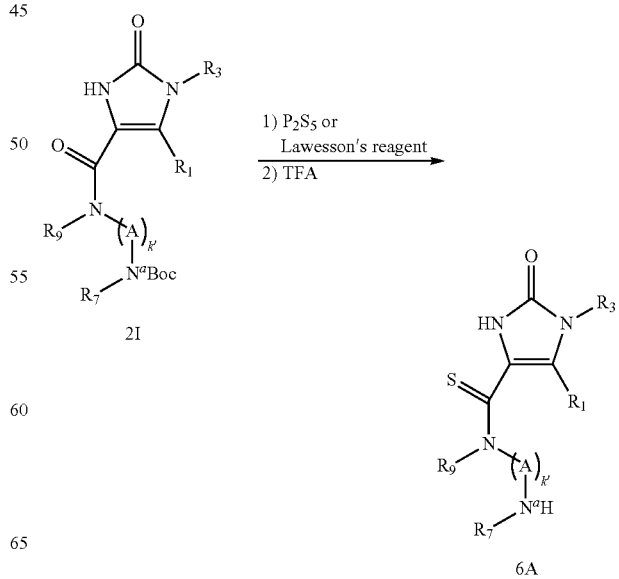

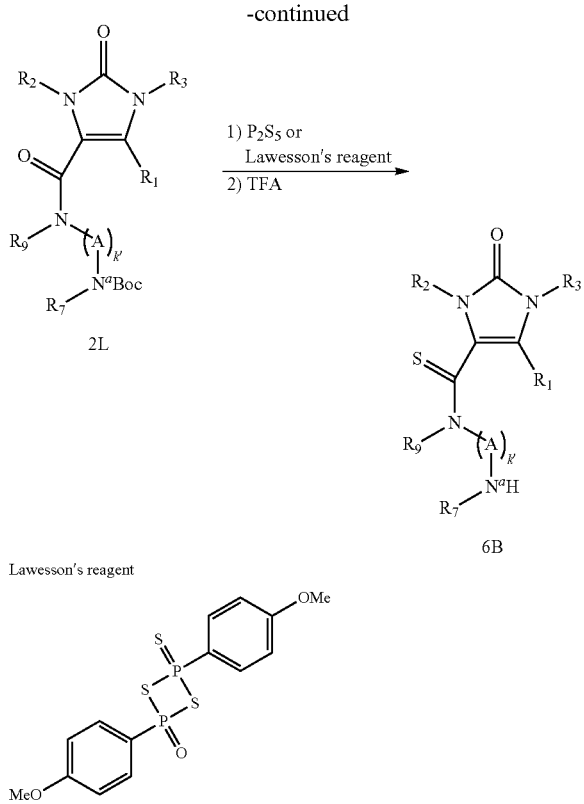

Imidazolone thioamides 6A or 6B may be prepared from imidazolones 2I or 2L (Scheme 2), respectively, by the reaction with Lawesson reagent or $P_2O_5$.

Lawesson reagent or $P_2O_5$ may be added to a solution of amide 2I or 2L in toluene (or dioxane). The resulting mixture may be stirred at room temperature or heated (up to reflux) for 2 hr to 48 hrs. After removal of the solvent under reduced pressure, the crude product may be purified by RP-HPLC to give the N-protected 2-imidazolone thioamide, which upon deprotection with an acid (e.g., TFA) to give the desired thioamide 6A or 6B.

It is understood that in each of the above reaction procedures or schemes, the various substituents may be selected from the various substituents taught herein.

Chiral components can be separated and purified using any of a variety of techniques known to those skilled in the art. For example, chiral components can be purified using supercritical fluid chromatography (SFC). In one particular variation, chiral analytical SFC/MS analyses are conducted using a Berger analytical SFC system (AutoChem, Newark, Del.) which consists of a Berger SFC dual pump fluid control module with a Berger FCM 1100/1200 supercritical fluid pump and FCM 1200 modifier fluid pump, a Berger TCM 2000 oven, and an Alcott 718 autosampler. The integrated system can be controlled by BI-SFC Chemstation software version 3.4. Detection can be accomplished with a Waters ZQ 2000 detector operated in positive mode with an ESI interface and a scan range from 200-800 Da with 0.5 second per scan. Chromatographic separations can be performed on a Chiral-Pak AD-H, ChiralPak AS-H, ChiralCel OD-H, or ChiralCel OJ-H column (5μ, 4.6×250 mm; Chiral Technologies, Inc. West Chester, Pa.) with 10 to 40% methanol as the modifier and with or without ammonium acetate (10 mM). Any of a variety of flow rates can be utilized including, for example, 1.5 or 3.5 mL/min with an inlet pressure set at about 100 bar. Additionally, a variety of sample injection conditions can be used including, for example, sample injections of either 5 or 10 μL in methanol at 0.1 mg/mL in concentration.

In another variation, preparative chiral separations are performed using a Berger MultiGram II SFC purification system. For example, samples can be loaded onto a ChiralPak AD column (21×250 mm, 10μ). In particular variations, the flow rate for separation can be 70 mL/min, the injection volume up to 2 mL, and the inlet pressure set at 130 bar. Stacked injections can be applied to increase the efficiency.

The present invention is further exemplified, but not limited, by examples provided in the EXAMPLE section below that describe the synthesis of particular compounds according to the invention.

Biological Testing

The activity of compounds as renin inhibitors may be assayed in vitro, in vivo or in a cell line. Example D below provides an in vitro enzymatic activity assay for activity against Renin.

Test compounds in varying concentrations may be reacted with recombinant human renin in the presence of a substrate, e.g., QXL520-γ-Abu-Ile-His-Pro-Phe-His-Leu-Val-Ile-His-Thr-Lys (HiLyteFluo488)-Arg-OH (Anaspec, San Jose, Calif.). The reaction can be followed kinetically using fluorescence (excitation λ=485 nm; emission λ=538 nm). Inhibition constants ($IC_{50}$) may be calculated by non-linear curve fitting of the compound concentrations and fluorescence intensities to the standard $IC_{50}$ equation. $IC_{50}$ values for selected compounds of the present invention are given in Table 1.

EXAMPLE

General Procedures for the Preparation of Imidazolone Amides of the Invention

Scheme A.

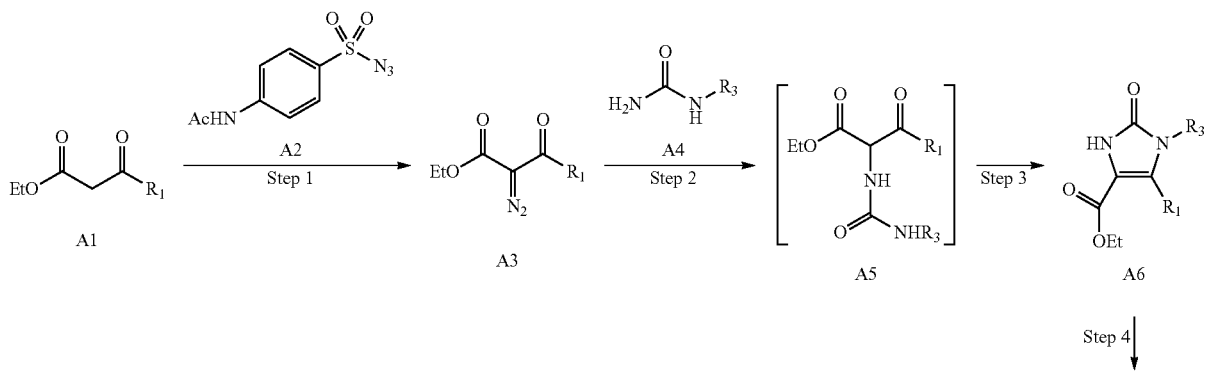

-continued

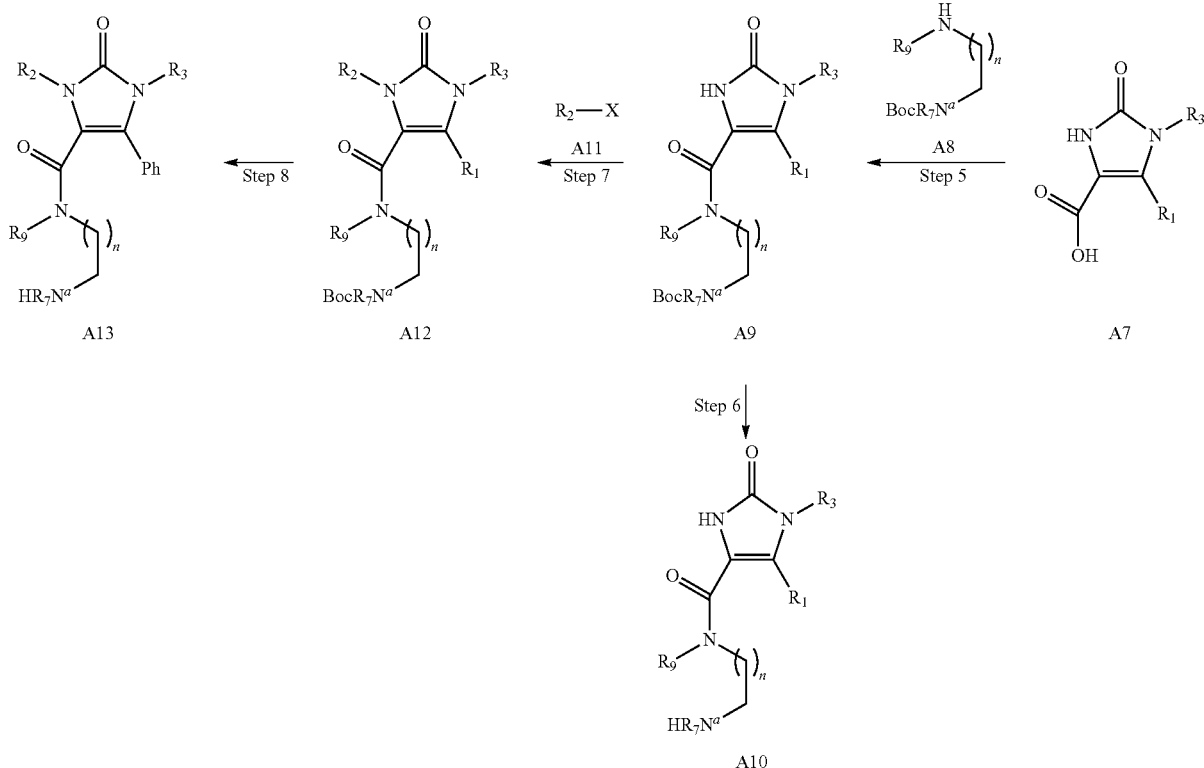

*n* is 0, 1, 2, or 3.
R₉ and R₇ may be taken together to form a ring.

A. General Procedure for Diazo Transfer (Scheme A, Step 1)

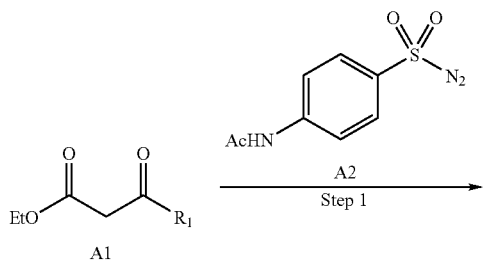

To a solution of the β-ketoester substrate A1 (10 mmol) and 4-acetamidobenzenesulfonyl azide A2 (11 mmol) in ethyl acetate (60 mL) at 0° C. is added triethylamine (30 mmol) dropwise. After stirring at room temperature for 16 h, the reaction mixture is concentrated in vacuo and the resultant solid is triturated with ether-light petroleum. The filtrate is concentrated in vacuo and purified by flash chromatography on silica gel eluting with ethyl acetate-light petroleum (1:4) to yield the desired product A3.

B. General Procedure for Rhodium-Catalyzed N—H Insertion Reaction (Scheme A, Step 2)

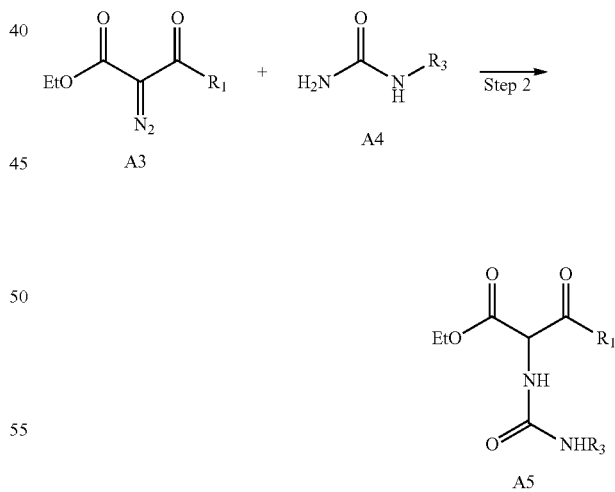

To a vigorously stirred and heated (80° C.) suspension of $R_1$-diazo compound A3 (2 mmol) and a finely powdered primary urea A4 (1.5 eq), for example phenyl urea in toluene-1,2-dichloroethane (1:1, 20 mL), a suspension of $Rh_2Oct_4$ (31 mg, 0.04 mmol) in toluene (4 mL) is added over 10 min. After addition of the catalyst, the mixture is stirred for an additional 60 min to 24 hrs to give the corresponding insertion product A5.

C. General Procedure for TFA-Promoted Cyclization Reaction (Scheme A, Step 3)

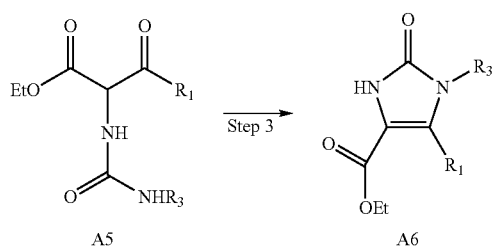

To the cooled insertion reaction mixture A5 is added TFA (1 mL), and the resulting solution is stirred for 1 h at room temperature. Alternatively, the insertion mixture A5 is evaporated, and then treated with neat TFA (10 mL) for 3 h to 24 h at 50 to 90° C. After removal of solvent under reduced pressure, the residue is purified by flash chromatography to give corresponding 2-imidazolone ester A6.

D. Hydrolysis of 2-Imidazolones Carboxyl Esters (Scheme A, Step 4)

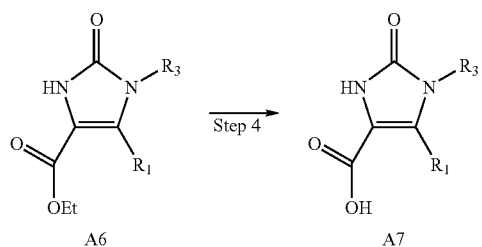

To a stirred mixture of 2-imidazolone ester A6 (1 mmol) in dioxane/EtOH (9 mL, 7:2) is added 5 eq of NaOH in 1 mL water (5 mmol) at room temperature under nitrogen, and the resulting suspension was stirred for 3 to 24 h at 50-80° C. After removal of solvent under reduced pressure, the crude product, 2-imidazolone acid, A7, is either used directly for the amide coupling reaction or purified by RP-HPLC.

E. Amide Coupling of 2-Imidazolones Carboxyl Acid (Scheme A, Step 5)

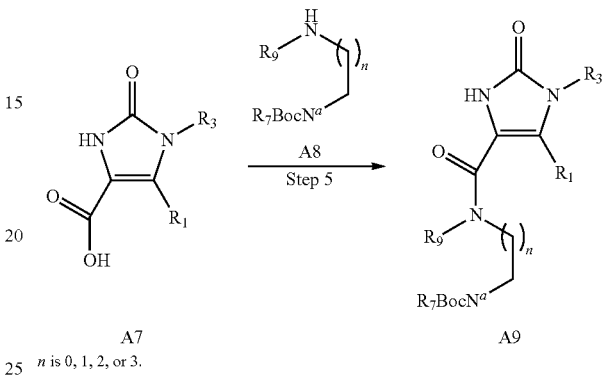

$n$ is 0, 1, 2, or 3.

To a stirred mixture of 2-imidazolone acid A7 (1 mmol) and EDCI in DCM or DMF (5 mL) was added 1.2 eq of the a mono-protected amine A8 in 2-5 mL of DCM or DMF (1.2 mmol) at 0° C. under nitrogen; diisopropylethylamine (3 mmol, 3 eq) was then added and the resulting suspension was stirred for 24 h at room temperature. After removal of solvent under reduced pressure, the crude product is purified by RP-HPLC to give the 2-imidazolone amide A9.

F. Alkylation at the N-3 Position of 2-Imidazolones and De-Protection, (Scheme A, Steps 6, 7 and 8)

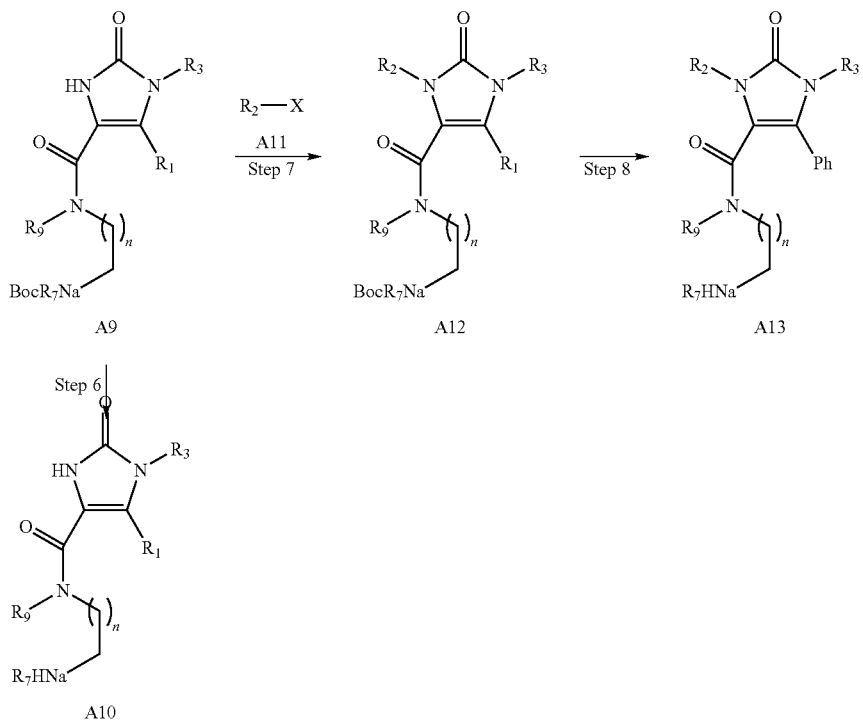

To a stirred mixture of 2-imidazolone amide A9 (0.2 mmol) in DMF (2 mL) is added 1.2 eq of 60% NaH at room temperature under nitrogen. The resulting suspension is stirred for 30 min at room temperature, and an alkyl halide A11 is added either neat or as a solution in DMF (1 mL). The mixture is stirred at room temperature or heated to 50-100° C. for 1 to 24 hrs. The solvent is removed under reduced pressure to provide compound A12.

The Boc protected group of compounds A9 and A12 may be removed by stirring with 20% TFA-DCM for 30 mins to 24 hrs at room temperature. The solvent is then removed under reduced pressure, and the crude products is purified by RP-HPLC to afford analytically pure, imidazolones A10 and A13.

General Procedure for the Preparation of Alkyloxyalkyloxyphenyl Urea slowly until a white precipitate is formed; the white precipitate is removed by filtration. The filtrate is washed with brine then dried over MgSO$_4$. The aniline B4 is collected by concentrating the filtrate in vacuo and dried under vacuum (Step 2). Alternatively, the aniline B4 is prepared from B3 by a reduction reaction catalyzed by Pd/C in a hydrogen atmosphere.

To a flask containing the aniline B4 (2.00 g, 11.04 mmol) is charged a 100 mL solution of 80% glacial acetic acid and 20% water; the mixture is chilled to 0° C. A solution of potassium cyanate (1.5 eq) in 5 mL of water is slowly added portionwise to the reaction mixture. The glacial acetic acid is removed under reduced pressure after the reaction mixture has been stirred for about 1 hour at RT. The resulting white

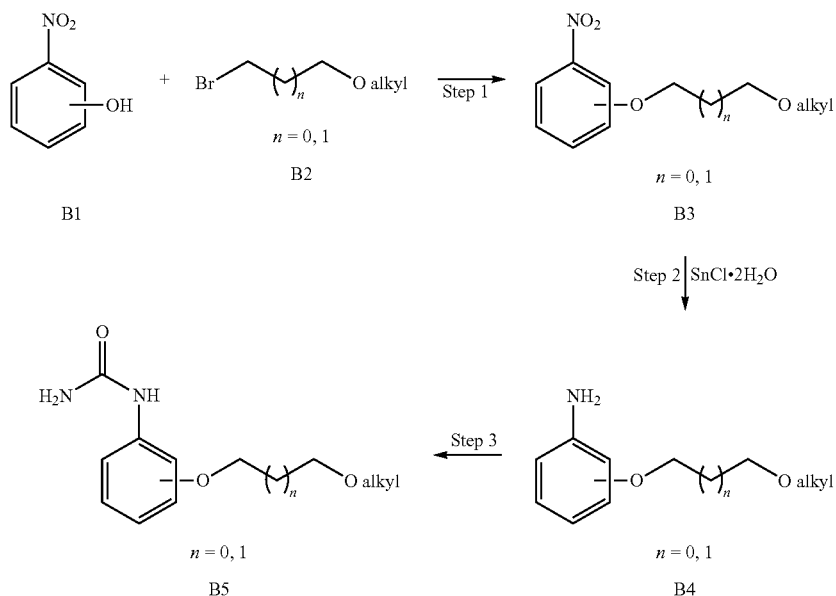

Scheme B

Alkyloxyalkyloxyphenyl ureas may be prepared from nitrophenols via the three-step reaction route (Scheme B) above.

A solution of a nitrophenol B1 (2.0 g, 14.377 mmol) in anhydrous DMF (5 mL) is added slowly to a solution of sodium hydride (95%, 0.4141 g, 17.253 mmol) in anhydrous DMF (50 mL) that has been stirring at 0° C. under nitrogen for about 10 minutes. To the mixture, a solution of a 1-bromoalkyoxyalkane B2 (1.1 eq) in anhydrous DMF (5 mL) is added dropwise. The reaction mixture is then allowed to reach room temperature and stirred for about 18 hours under nitrogen. The reaction is quenched in water, and the product extracted into organic solvent such as ethyl acetate. The organic layer is washed with brine, dried over MgSO$_4$, and concentrated in vacuo to give alkyoxyalkoxynitrobenzene B3 as an amber oil (Step 1).

The alkyoxyalkoxynitrobenzene B3 (11.84 mmol) is combined with tin chloride dihydrate (5 eq) in ethyl acetate (25 mL). The mixture is heated at 60° C. for about two hours and then chilled at 0° C. Triethylamine (25-30 mL) is added solid residue is collected by filtration and rinsed with copious amounts of water then dried under vacuum to give the urea B5 (Step 3).

Example 1

Ethyl 2-diazo-3-oxo-3-phenylpropanoate

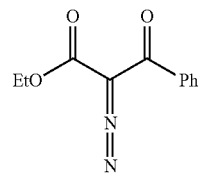

The title compound was prepared according to Scheme A, Step 1, and was obtained as a yellow oil (83%). ESI-MS: m/z 219.3 (M+H)$^+$.

Other compounds prepared by Scheme A, Step 1:

| Name | Structure | MS |
| --- | --- | --- |
| Ethyl 2-diazo-3-(3-fluorophenyl)-3-oxopropanoate | 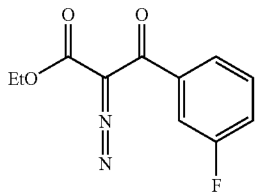 | ESI-MS: m/z 237.3 $(M + H)^+$. |
| Methyl 2-diazo-4-methyl-3-oxopentanoate | 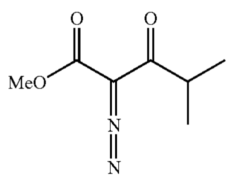 | ESI-MS: m/z 171.1 $(M + H)^+$. |
| Ethyl 3-(2-chlorophenyl)-2-diazo-3-oxopropanoate | 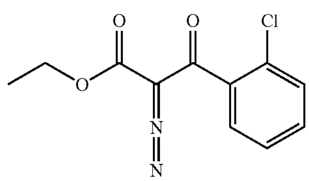 | ESI-MS: m/z 253.10 $(M + H)^+$. |
| Ethyl 4-cyclopropyl-2-diazo-3-oxobutanoate | 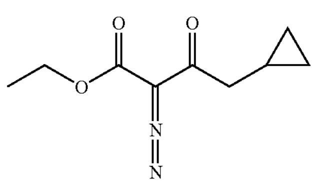 | ESI-MS: m/z 197.10 $(M + H)^+$. |
| Ethyl 3-cyclopropyl-2-diazo-3-oxopropanoate | 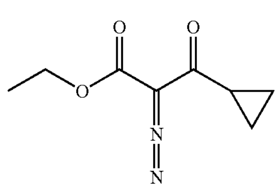 | ESI-MS: m/z 183.10 $(M + H)^+$. |

Example 2
Ethyl 2-oxo-1,5-diphenyl-2,3-dihydro-1H-imidazole-4-carboxylate
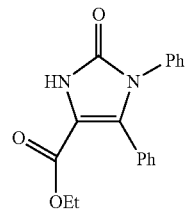
The title compound was prepared according to Scheme A, Steps 1-3, and was obtained as a yellow oil (83%) ESI-MS: m/z 309.3 (M+H)$^+$.
Other compounds prepared by Scheme A, Steps 1-3:
| Structure/MS |
|---|
| 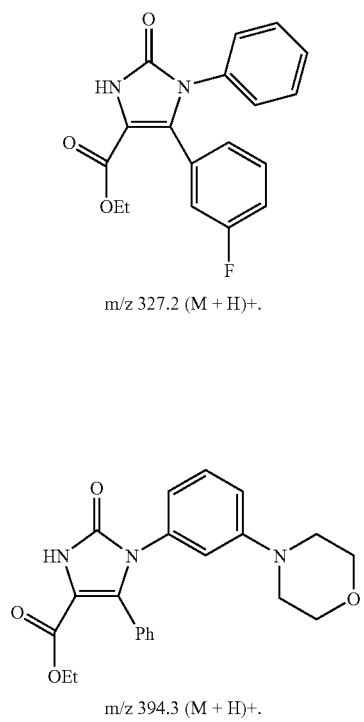 m/z 327.2 (M + H)+. |
| 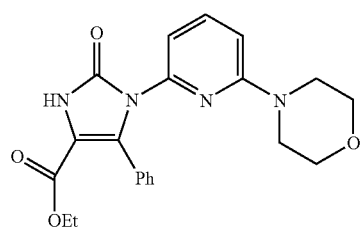 m/z 394.3 (M + H)+. |
|  m/z 395.3 (M + H)+. |
-continued
| Structure/MS |
|---|
|  m/z 275.2 (M + H)+. |
| 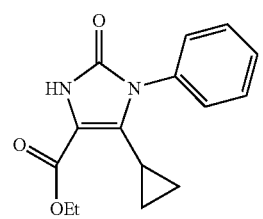 m/z 273.2 (M + H)+. |
| 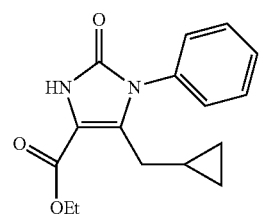 m/z 287.2 (M + H)+. |
| 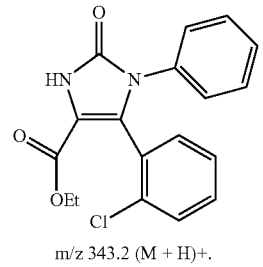 m/z 343.2 (M + H)+. |
| 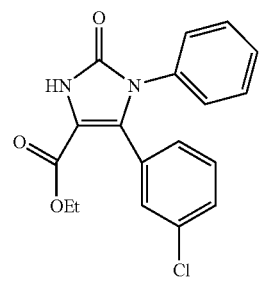 m/z 343.2 (M + H)+. |

| Structure/MS |
|---|
| 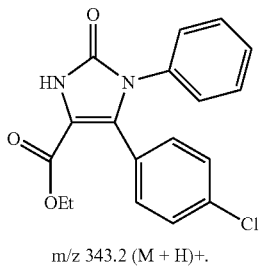<br>m/z 343.2 (M + H)+. |
| 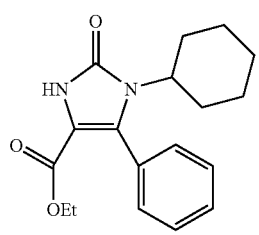<br>m/z 315.3 (M + H)+. |
| 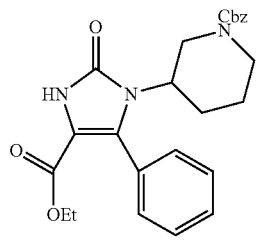<br>m/z 450.1 (M + H)+. |
| 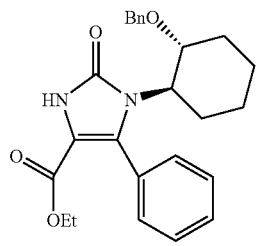<br>m/z 421.4 (M + H)+. |
| 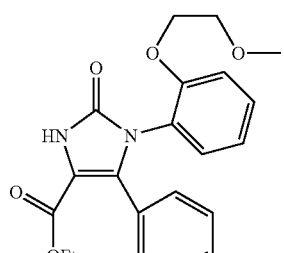<br>m/z 383.2 (M + H)+. |
| Structure/MS |
|---|
| 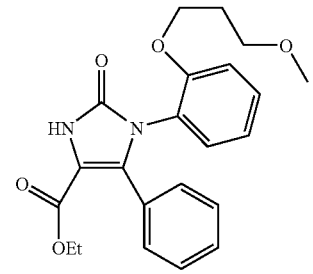<br>m/z 397.3 (M + H)+. |
| 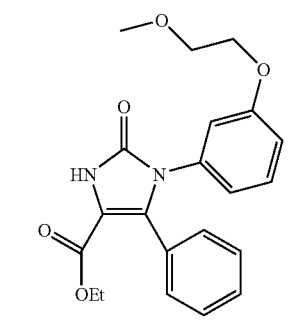<br>m/z 383.2 (M + H)+. |
| 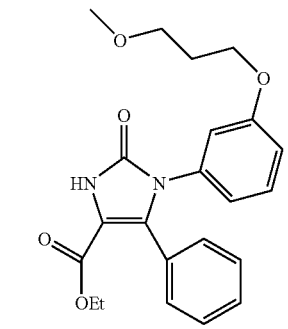<br>m/z 397.3 (M + H)+. |
Example 3
2-Oxo-1,5-diphenyl-2,3-dihydro-1H-imidazole-4-carboxylic acid
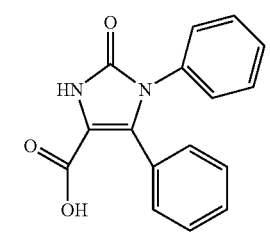
The title compound was prepared according to Scheme A, Steps 1-4 and was obtained as a yellow oil (90%). ESI-MS: m/z 281.1 (M+H)$^+$.

Other compounds prepared by Scheme A, Steps 1-4 are:
| Structure/MS |
|---|
| 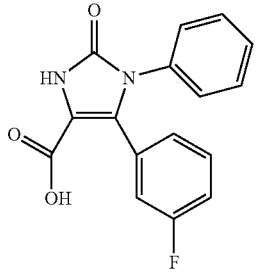 m/z 299.2 (M + H)+. |
| 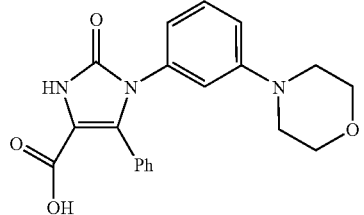 m/z 366.3 (M + H)+. |
| 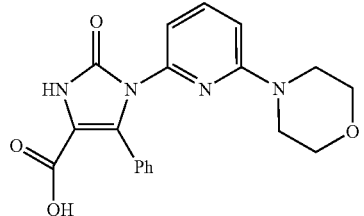 m/z 366.3 (M + H)+. |
| 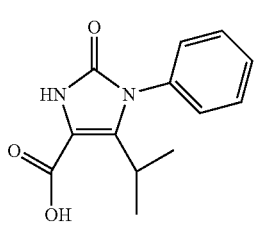 m/z 247.2 (M + H)+. |
| 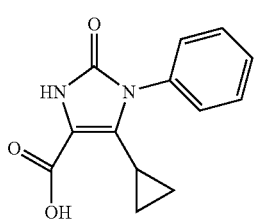 m/z 245.2 (M + H)+. |
-continued
| Structure/MS |
|---|
| 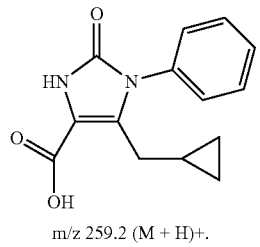 m/z 259.2 (M + H)+. |
| 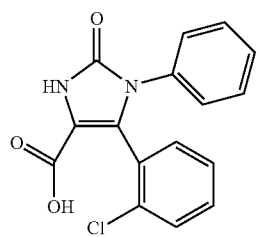 m/z 315.2 (M + H)+. |
| 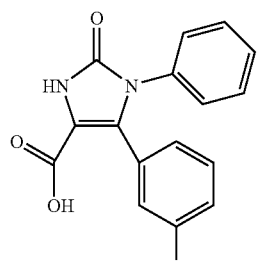 m/z 315.2 (M + H)+. |
| 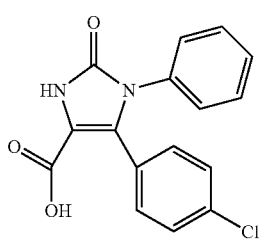 m/z 315.2 (M + H)+. |
| 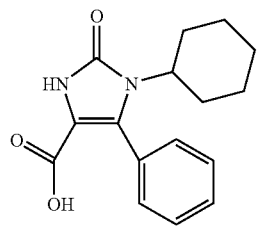 m/z 387.3 (M + H)+. |

| Structure/MS |
|---|
| 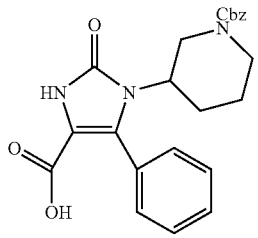
m/z 422.1 (M + H)+. |
| 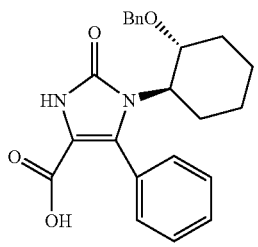
m/z 355.2 (M + H)+. |
| 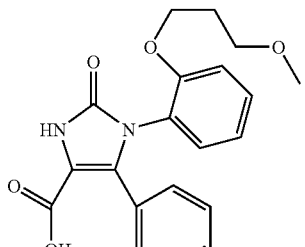
m/z 355.2 (M + H)+. |
| 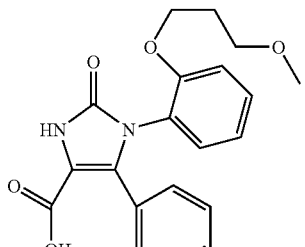
m/z 369.3 (M + H)+. |
| 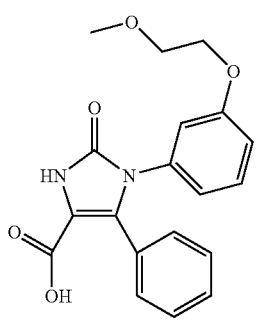
m/z 355.2 (M + H)+. |
| Structure/MS |
|---|
| 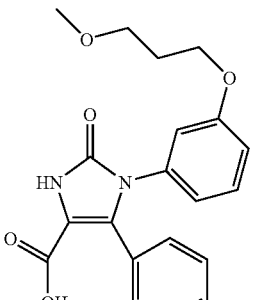
m/z 369.3 (M + H)+. |
Example 4
tert-Butyl 4-(2-oxo-1,5-diphenyl-2,3-dihydro-1H-imidazole-4-carbonyl)piperazine-1-carboxylate
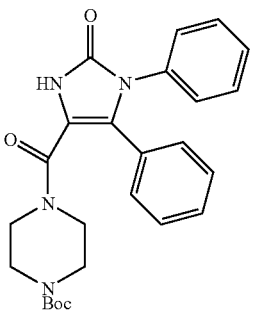
The title compound was prepared according to Scheme A, Steps 1-5, and was obtained as a yellow oil (75%). ESI-MS: m/z 449.4 (M+H)$^+$.
Other compounds prepared by Scheme A Steps 1-5 are:
| Structure/MS |
|---|
| 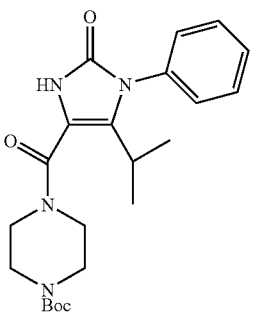
m/z 415.3 (M + H)+. |

| 177 -continued | 178 -continued |
|---|---|
| Structure/MS | Structure/MS |
| 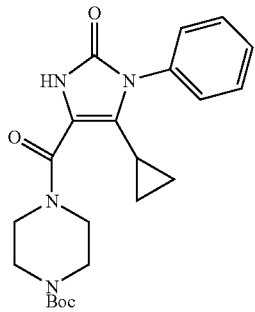 m/z 413.2 (M + H)+. | 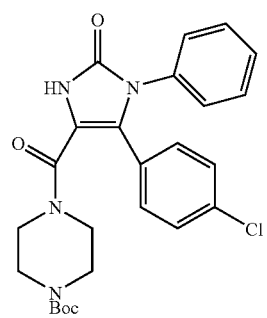 m/z 483.2 (M + H)+. |
| 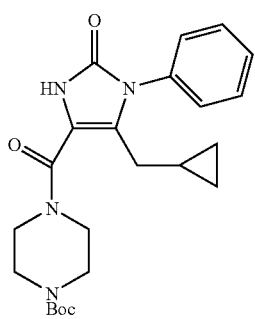 m/z 427.3 (M + H)+. | 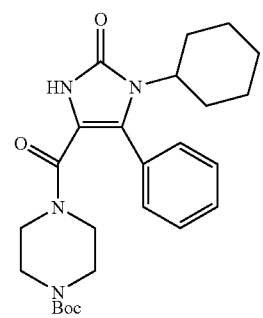 m/z 455.3 (M + H)+. |
| 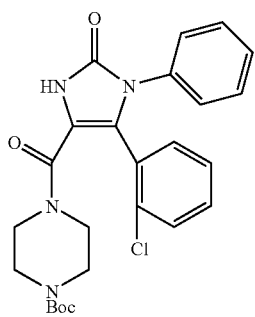 m/z 483.2 (M + H)+. | 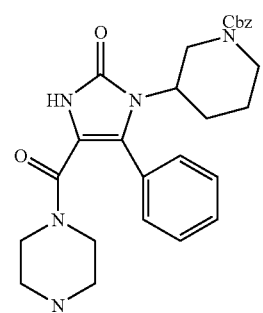 m/z 590.1 (M + H)+. |
| 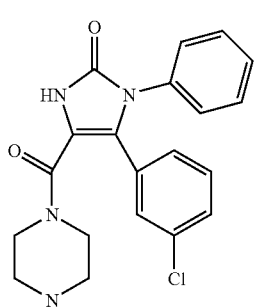 m/z 483.2 (M + H)+. | 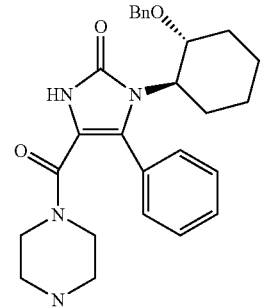 m/z 561.3 (M + H)+. |

| 179 -continued | 180 -continued |
|---|---|
| Structure/MS | Structure/MS |
| 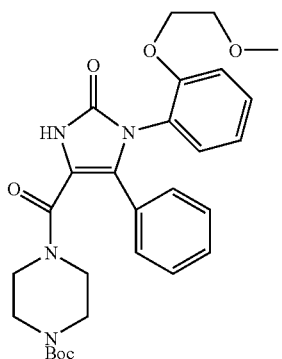 m/z 523.2 (M + H)+. | 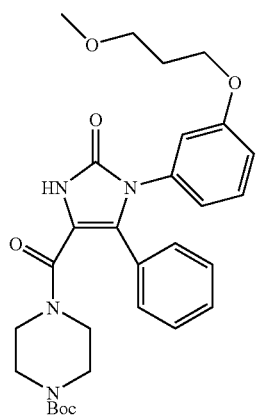 m/z 537.3 (M + H)+. |
| 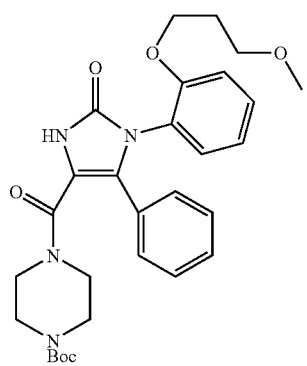 m/z 537.2 (M + H)+. | 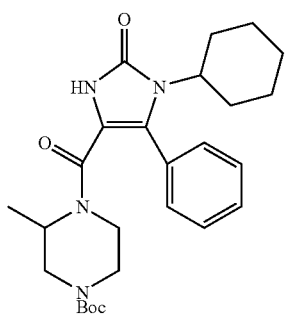 m/z 468.3 (M + H)+. |
| | 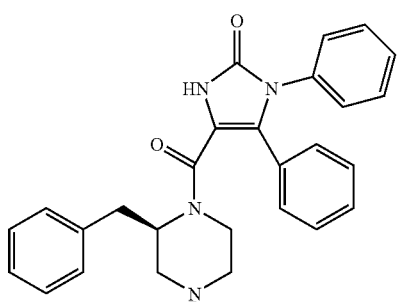 m/z 539.3 (M + H)+. |
| 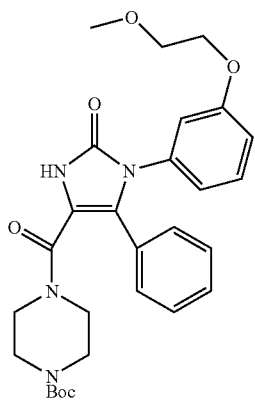 m/z 523.2 (M + H)+. | 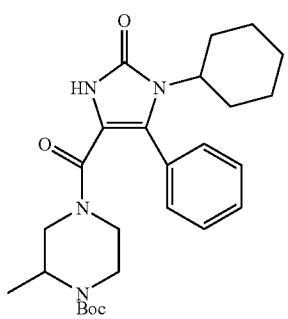 m/z 468.3 (M + H)+. |

| Structure/MS |
|---|
| 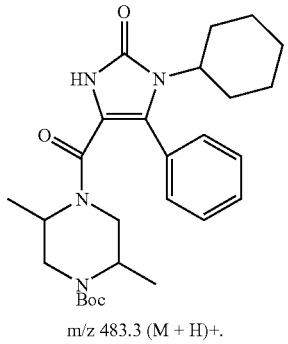 |
| m/z 483.3 (M + H)+. |
| 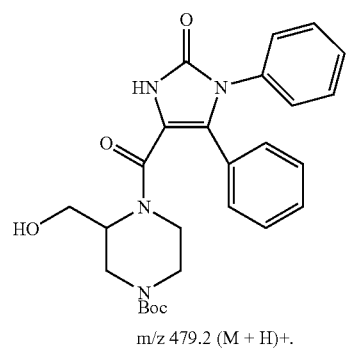 |
| m/z 479.2 (M + H)+. |

Example 5

Synthesis of 6-morpholinopyridin-2-amine

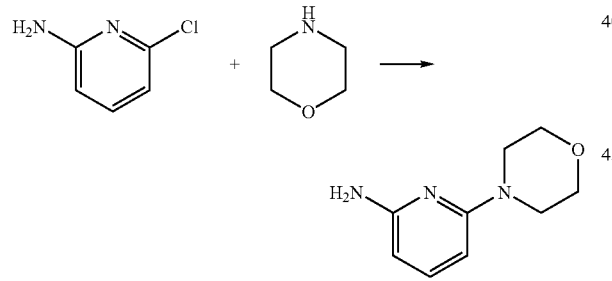

A mixture of 2-amino-6-chloropyridine in 100 mL of morpholine was heated at 225° C. for 60 mins. The mixture was cooled and precipitate filtered off, the filtrate was concentrated to give the 17 gram product as a brown oil.

Example 6

Synthesis of 6-(3-methoxypropoxy)pyridin-2-amine

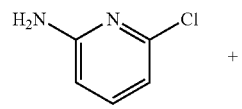

+

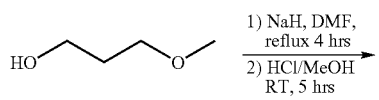

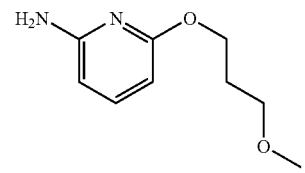

Into a 250 mL round bottom flask was added 3-methoxypropanol (5.26 g, 58.4 mmol) and DMF (156 mL). Sodium hydride (60%, 4.67 g, 3 eq) was added slowly to the solution. After addition the mixture was heated to 90° C. for one hour. 2-chloro-6-amino-pyridine was added and the mixture was heated to reflux for four hours. LCMS showed conversion to product. The reaction was cooled to room temperature and solvent was removed under vacuum. The residue was partitioned between water and ethyl acetate. Organic layer was separated and the aqueous was extracted three times with ethyl acetate (3×50 mL). Organic layer dried over sodium sulfate and filtered; the solvent was removed under vacuum. The residue was dissolved with 2N HCl in MeOH and stirred for five hours at room temperature; the solvent was removed and the residue was purified by column chromatography with 20% ethyl acetate in hexanes yielding 3.12 g (45%) of the title compound as a yellow oil.

Example 7

Synthesis of 1-(6-(3-Methoxypropoxy)pyridin-2-yl) urea (7B)

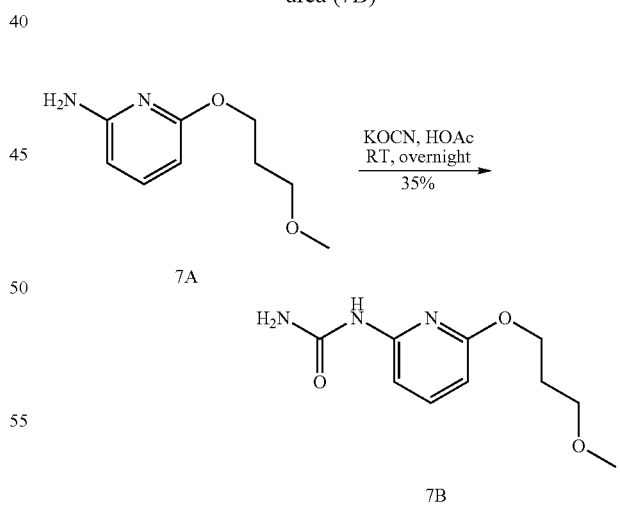

Into a 200 mL round bottom flask was added 7A (3.12 g, 17.1 mmol), acetic acid (1.03 g, 1 eq) and water (90 mL). The flask was cooled to 0° C. with an ice bath. Potassium cyanate (2.08 g, 1.5 eq) in water (1.7 mL) was slowly syringed into the reaction flask. After addition the reaction was stirred at room temperature overnight. The white precipitate that formed was isolated by filtration on a Buchner funnel. The solid was washed with cold water and dried under vacuum to give the product 7B (1.36 g, 35% yield).

Example 8

Synthesis of (3-(bromomethyl)phenyl)(piperidin-1-yl)methanone

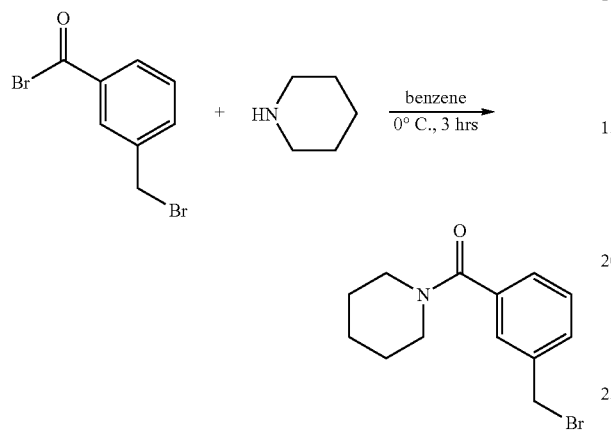

Into a 25 mL round bottom flask was added 3-bromomethyl-benzoyl bromide (1.39 g, 5 mmol) and benzene (5 mL). The flask was cooled to 0° C. with an ice bath and piperidine (852 mg, 2 eq) in benzene (3.3 mL) was added slowly. The reaction was stirred at 0° C. for three hours. The precipitate was removed by filtration on a Buchner funnel. The filtrate was concentrated to an oil which was purified by column chromatography with 20% ethyl acetate in hexanes to give the titled compound as a clear oil (578 mg, 41% yield).

Example 9

Synthesis of 1-(3-methoxypropxy)-3-nitrobenzene

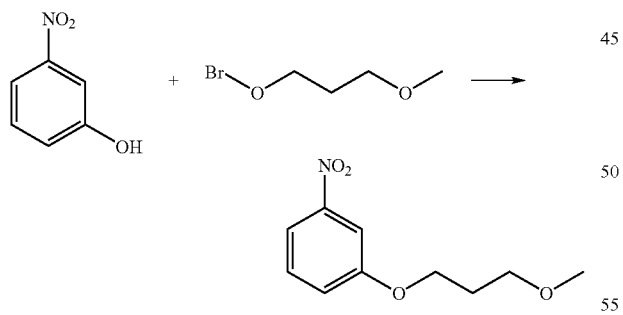

Sodium hydride (95%, 0.4141 g, 17.253 mmol) and anhydrous DMF (50 mL) was stirred at 0° C. under nitrogen for about 10 minutes. A solution of 3-nitrophenol (2.0 g, 14.377 mmol) in anhydrous DMF (5 mL) was added dropwise via addition funnel over 10 minutes. To the mixture, a solution of 1-bromo-3-methoxypropane (1.613 mL, 15.815 mmol) in anhydrous DMF (5 mL) was added dropwise via an addition funnel over 10 minutes. The ice bath was removed and the reaction was stirred at RT for about 18 hours under nitrogen. The reaction was poured into about 500 mL of ice water and stirred until mixture reached RT and extracted with ethyl acetate (3×50 mL). The combined organic layers were washed with brine, dried over MgSO$_4$ and concentrated in vacuo to give the title compound as an amber oil (2.5 g, 83% yield). $^1$H NMR (400 MHz, DMSO-d$_6$) δ ppm 3.31 (s, 3H) 3.66-3.70 (m, 2H) 4.21-4.25 (m, 2H) 7.41-7.45 (m, 1H) 7.57 (t, J=8.34 Hz, 1H) 7.72 (t, J=2.27 Hz, 1H) 7.81 (dd, J=8.08, 1.52 Hz, 1H). ESI-MS: m/z 198.3 (M+H)$^+$.

Example 10

Synthesis of 3-(3-methoxypropoxy)aniline (10B)

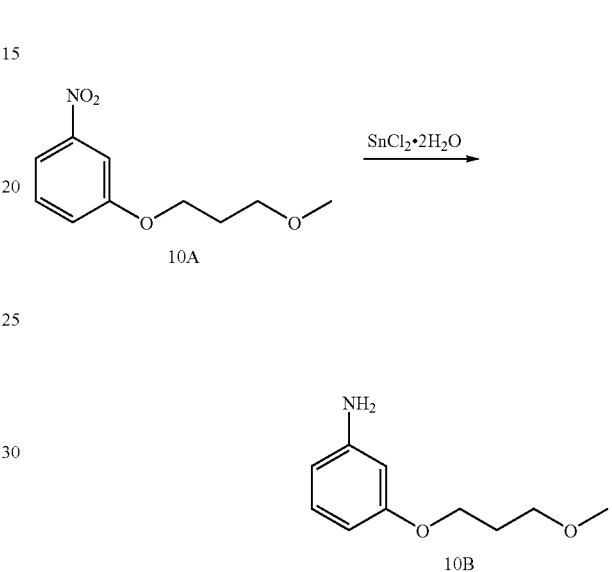

1-(3-methoxypropoxy)-3-nitrobenzene (10A) (2.0 g, 11.84 mmol) and tin chloride dihydrate (13.36 g, 59.18 mmol) in 25 mL of ethyl acetate was combined. The mixture was heated at 60° C. for about two hours. The reaction was then chilled at 0° C. Triethylamine (25-30 mL) was added slowly until a white precipitate formed. The white precipitate was filtered over a Celite plug, washed with brine, and then dried over MgSO$_4$. The dried filtrate was then concentrated in vacuo and dried under vacuum to provide 10B (2.0 g, 93%). $^1$H NMR (400 MHz, DMSO-d$_6$) δ ppm 1.90 (q, J=6.32 Hz, 2H) 3.24 (s, 3 H) 3.44 (t, J=6.32 Hz, 2H) 3.89 (t, J=6.44 Hz, 2H) 5.02 (br. s., 2H) 6.05 (dd, J=8.08, 1.26 Hz, 1H) 6.11-6.14 (m, 2H) 6.87 (t, J=8.21 Hz, 1H). ESI-MS: m/z 182.3 (M+H)$^+$.

Example 11

Synthesis 1-(3-(3-methoxypropoxy)phenyl)urea (11B)

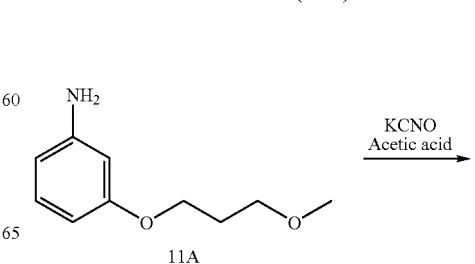

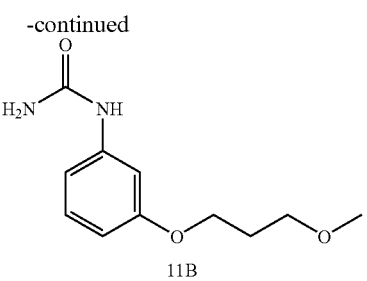
11B

To a flask containing 3-(3-methoxypropoxy)aniline (11A) (2.00 g, 11.04 mmol) was charged a 100 mL solution of 80% glacial acetic acid and 20% water. This mixture was chilled to 0° C. A solution of potassium cyanate (1.34 g, 16.56 mmol) in 5 mL of water was slowly added portion-wise to the reaction mixture. The reaction was then stirred for about 1 hour at RT. The glacial acetic acid was then removed under reduced pressure. The resulting white solid residue was then rinsed with copious amounts of water then dried under vacuum to give title compound 11B (1.70 g, 70%). $^1$H NMR (400 MHz, DMSO-$d_6$) δ ppm 1.86-1.95 (m, 2H) 3.24 (s, 3H) 3.46 (t, J=6.32 Hz, 2H) 3.94 (t, J=6.32 Hz, 2H) 5.82 (br. s., 2H) 6.45 (dd, J=8.08, 2.27 Hz, 1H) 6.81 (d, J=7.33 Hz, 1H) 7.00-7.17 (m, 2H) 8.49 (s, 1H). ESI-MS: m/z 225.3 (M+H)$^+$.

Example 12

Boc-Piperazine Amide Formation

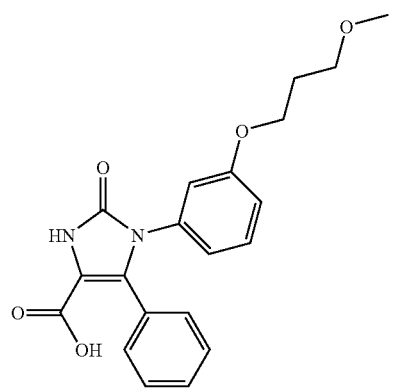

Acid 12A (200 mg, 543 μmol), Boc-piperazine (121 mg, 652 μmol) and EDC (135 mg, 706 μmol) was dissolved with dichloromethane (3.1 mL) and cooled to 0° C. in an ice bath. Diisopropylethylamine (284 μL, 1.63 mmol) was added slowly. The ice bath was removed and the reaction mixture was stirred at room temperature overnight. LCMS confirmed the formation of the desired amide and the solvent was removed under vacuum. The residue was purified by column chromatography with 5% MeOH in dichloromethane to give 78 mg of the Boc amide 12B (27%).

Example 13

1-(3-(3-methoxypropoxy)phenyl)-3-(3-phenoxybenzyl)-5-phenyl-4-(piperazine-1-carbonyl)-1H-imidazol-2(3H)-one (13C)

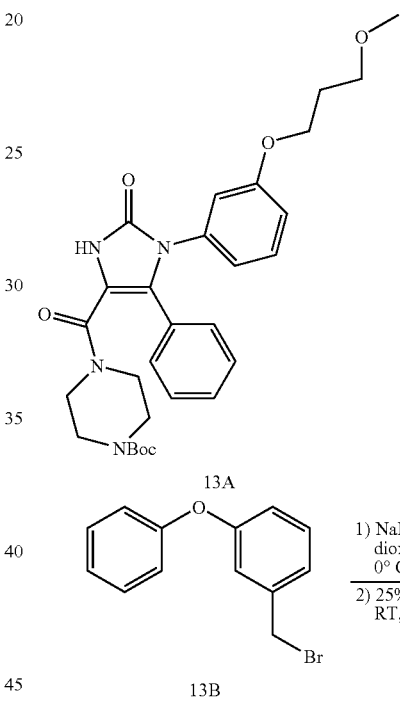

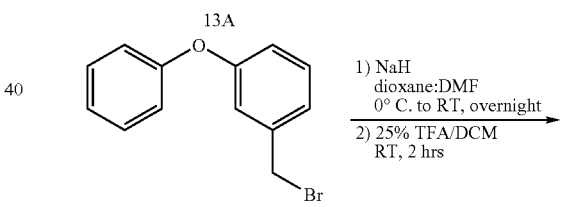

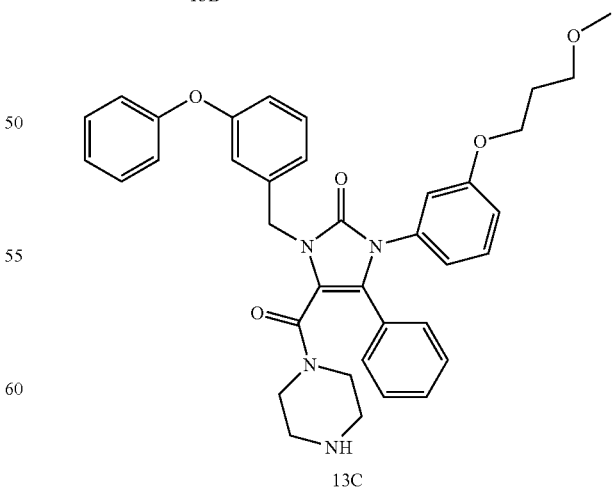

Amide 13A (79 mg, 147 μmol) was added to a flamed dried round bottom flask under nitrogen and dissolved with 3.9 mL of 1:1 DMF:dioxane. The solution was cooled to 0° C. with an ice bath. Sodium hydride (60%, 18 mg, 442 µmol) was added at once to the amide solution and stirred at 0° C. for 30 minutes. The ice bath was removed and the reaction mixture was continuously stirred at room temperature overnight. LCMS confirmed the formation of the alkylated product. Solvent was removed under vacuum (Step 1).

To the residue, 25% TFA/DCM (3 mL) was slowly added and the solution was stirred at room temperature for 3 hours. Solvent was removed under vacuum and the residue was redissolved in methanol (2 mL) and purified on a PREP LCMS (acetonitrile:water) to obtain 72 mg (45%) of the TFA salt of 13C.

Example 14

Preparation of 1-(3-morpholinophenyl)-3-(3-phenoxybenzyl)-5-phenyl-4-(piperazine-1-carbonyl)-1H-imidazol-2(3H)-one (14J)

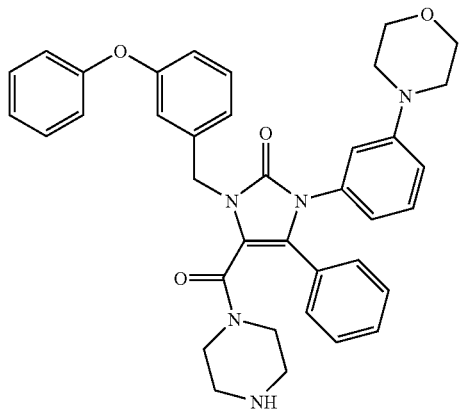

A. Urea synthesis

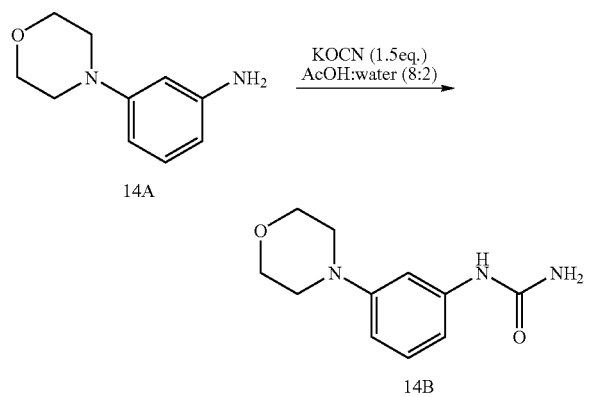

Aniline 14A (7.29 g, 40.9 mmol) was dissolved with 220 mL of 8:2 AcOH:water and cooled to 0° C. with an ice bath. Potassium isocyanate (4.98 g, 61.4 mmol) in 4 mL of water was slowly added to the aniline solution. After addition, the ice bath was removed and the reaction mixture was stirred at room temperature for one hour. After removing most of the solvent under vacuum, the residue was made basic by addition of saturated sodium bicarbonate. The precipitate formed was isolated by filtration on Buchner funnel, and was washed with diethyl ether. A tan solid 14B was obtained (6.25 g, 69%) which was used in the next step without further purification.

B. Urea Insertion to Diazocarbonyl

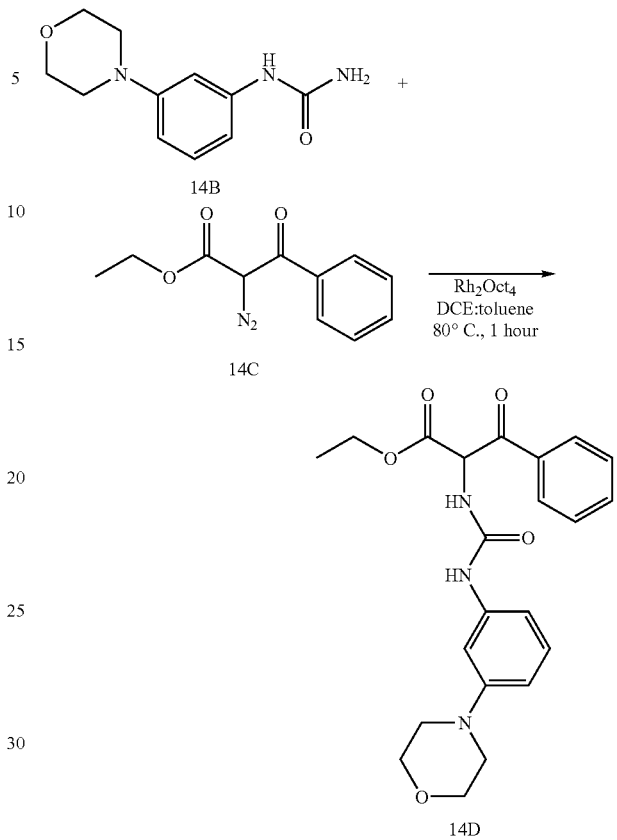

Urea 14B (2.65 g, 12 mmol) was ground into a fine powder with a mortar and pestle and suspended in 90 mL of 1:1 dichloroethane:toluene in a 250 mL flask. Diazocarbonyl 14C (1.74 g, 8 mmol) was added and the mixture was degassed by bubbling nitrogen through the solution for 15 minutes. After degassing, the flask was fitted with a reflux condenser connected to nitrogen source, the flask was heated to 80° C. Rhodium catalyst (125 mg, 0.16 mmol) was suspended in 18 mL of toluene and sonicated to make a fine suspension. The suspension was taken up in a syringe and added slowly to the urea 14B and diazocarbonyl 14C solution over 15 minutes. After addition, the flask was heated for one hour. The flask was cooled and the solvent was removed under vacuum to leave an oily residue 14D which was used in the next step without further purification.

C. Urea Cyclization

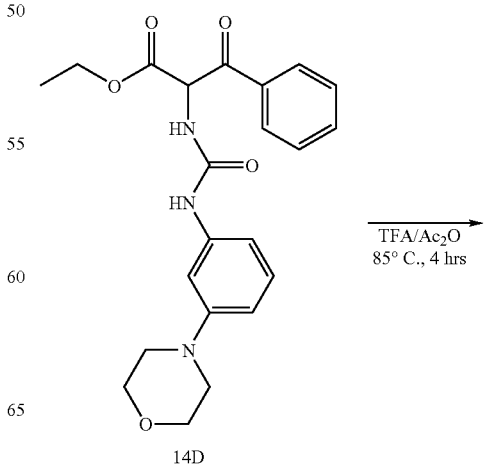

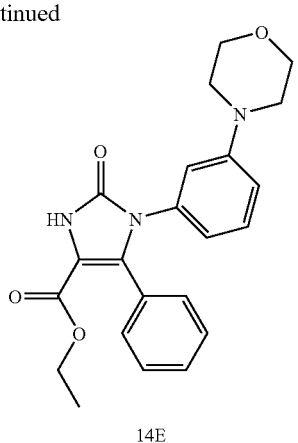

14E

The residue 14D obtained from the previous step was dissolved with trifluoroacetic acid (50 mL) and acetic anhydride (25 mL). The mixture was heated to 85° C. for 4 hours. Solvent was removed under vacuum to leave a residue 14E which was used in the next step without further purification.

D. Ester Hydrolysis

14E

The residue 14E from the previous step was dissolved with 1,4-dioxane (30 mL) and ethanol (15 mL). Sodium hydroxide (3 g) in water (5 mL) was added to the solution and the mixture was heated at 80° C. for 2 hours. The reaction was cooled and solvent was removed under vacuum. The residue was redissolved with water (15 mL) and acidified with 6N HCl to pH=5.

The aqueous layer was extracted with ethyl acetate (2×30 mL). The aqueous was acidified to pH=3 and extracted with ethyl acetate (2×30 mL). The aqueous layer was acidified to pH=1 and extracted with ethyl acetate (2×30 mL). The organic layers are combined and washed with brine (1×) and dried over sodium sulfate. The solvent was removed under vacuum to leave a brown oil (3.38 g). The residue was purified by column chromatography with 5% MeOH/DCM to give 1.15 g (39%) of a brown solid 14F.

E. Boc-Piperazine Amide Formation

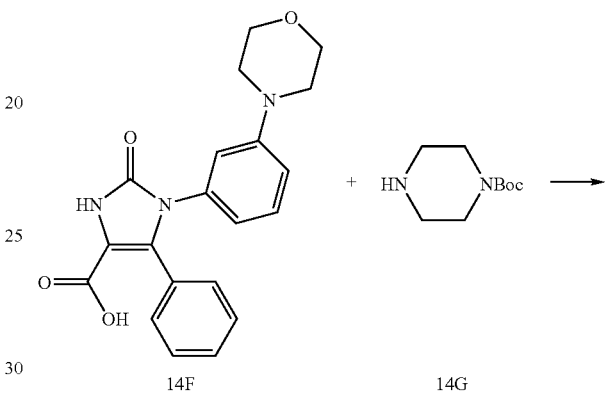

14F            14G

14F

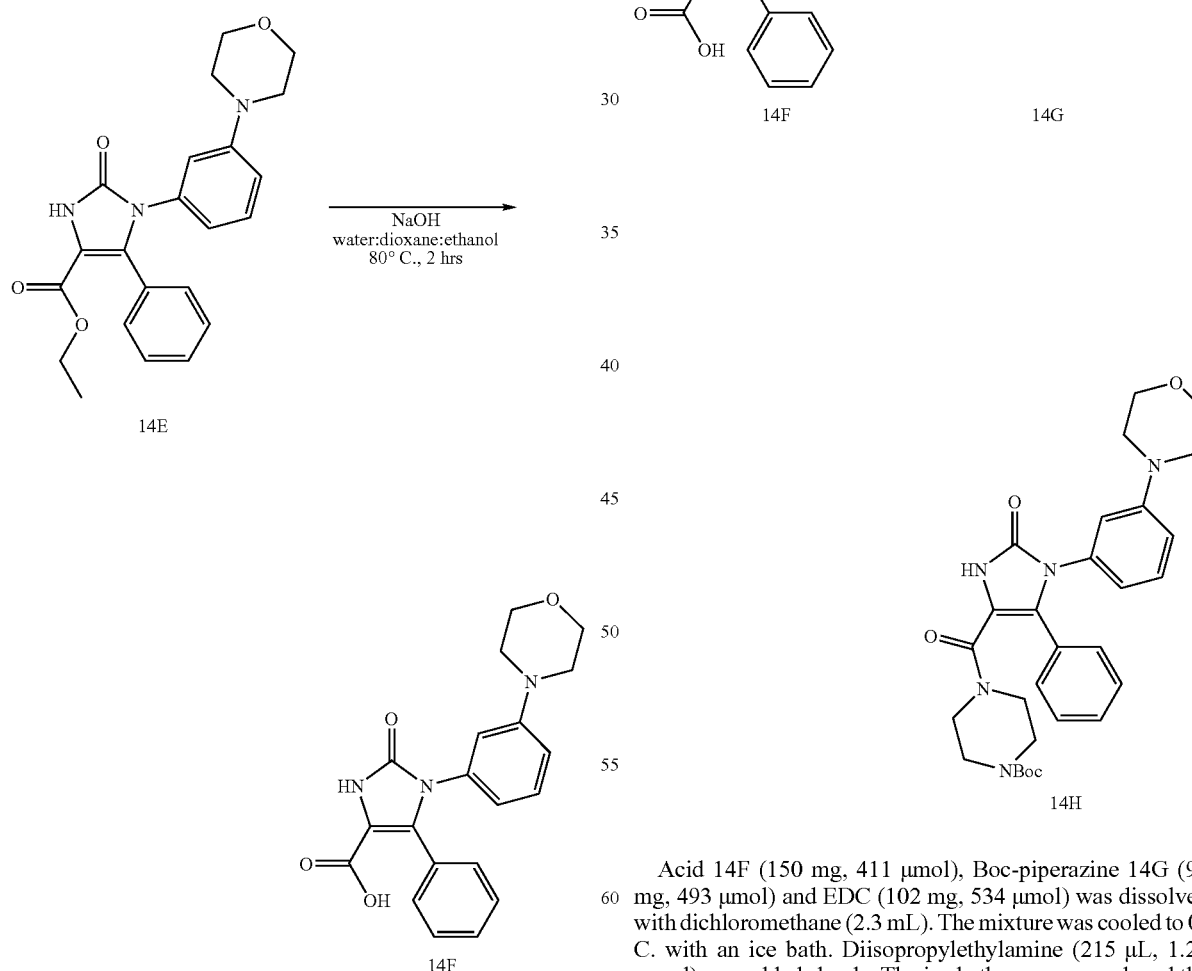

14H

Acid 14F (150 mg, 411 µmol), Boc-piperazine 14G (92 mg, 493 µmol) and EDC (102 mg, 534 µmol) was dissolved with dichloromethane (2.3 mL). The mixture was cooled to 0° C. with an ice bath. Diisopropylethylamine (215 µL, 1.23 mmol) was added slowly. The ice bath was removed, and the reaction mixture was stirred overnight at room temperature. Solvent was removed under vacuum and the residue was purified on a preparative LCMS (water:acetonitrile) to give the amide 14H (104 mg, 47%).

F. Alkylation and Deprotection

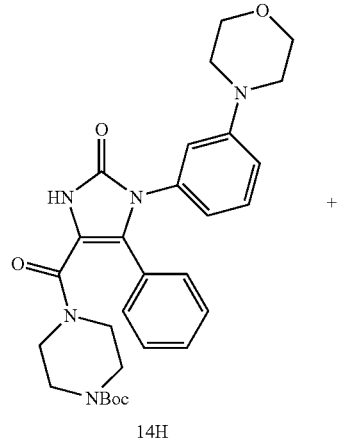

14H

+

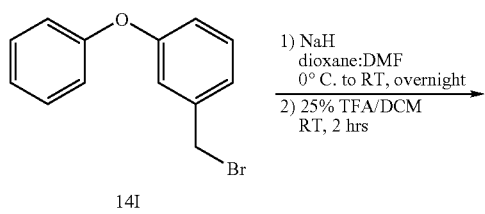

14I

1) NaH
dioxane:DMF
0° C. to RT, overnight
2) 25% TFA/DCM
RT, 2 hrs

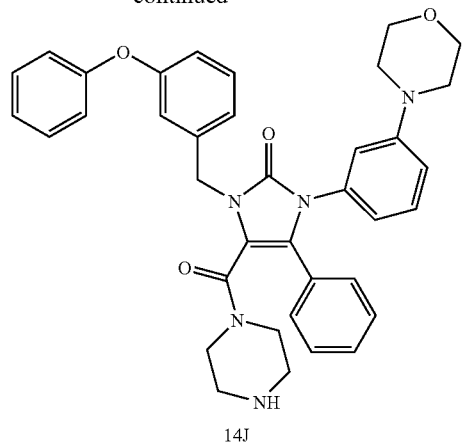

14J

Amide 14H (53 mg, 99 μmol) was added to a flamed dried round bottom flask under nitrogen. The amide was dissolved with 2.6 mL of 1:1 DMF:dioxane. The solution was cooled to 0° C. with an ice bath. Sodium hydride (60%, 12 mg, 298 μmol) was added at once to the amide solution and stirred at 0° C. for 30 minutes. The ice bath was removed and stirred at room temperature overnight. LCMS confirmed the formation of the alkylated product. Solvent was removed under vacuum. To the residue, 25% TFA/DCM (3 mL) was slowly added, and the solution was stirred at room temperature for 3 hours. Solvent was removed under vacuum and the residue was redissolved in methanol (2 mL) and purified on a preparative LCMS (acetonitrile:water) to obtain 72 mg (67%) of the TFA salt of 14J.

Example 15

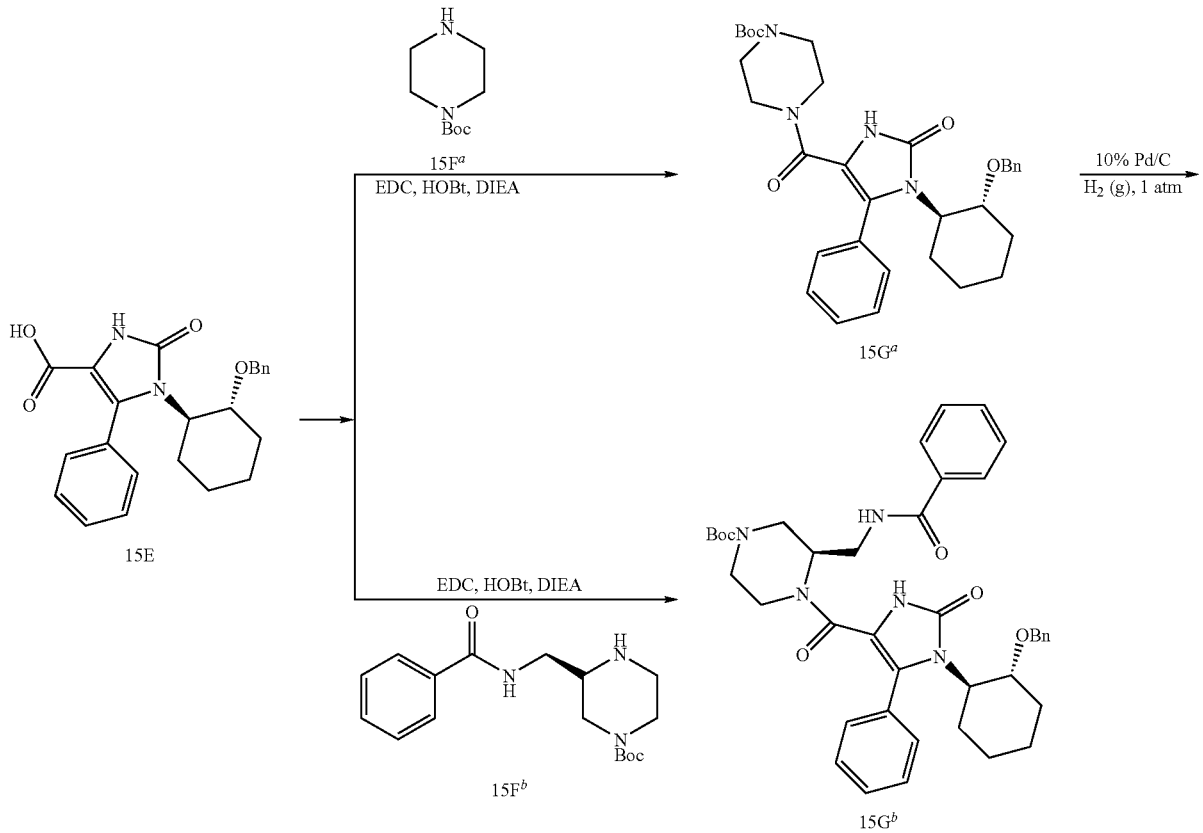

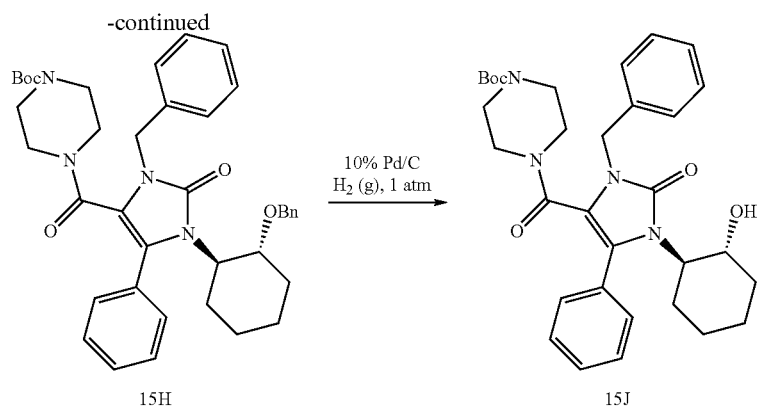

A. Synthesis of 1-((1R,2R)-2-(benzyloxy)cyclohexyl)-2-oxo-5-phenyl-2,3-dihydro-1H-imidazole-4-carboxylic acid (15E)

A.1: Synthesis of 1-((1R,2R)-2-(benzyloxy)cyclohexyl)urea (15B)

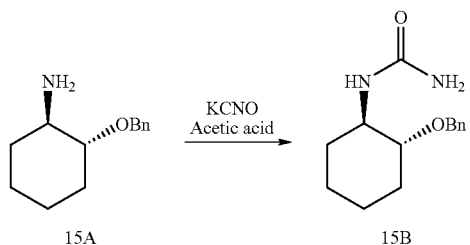

Combined (1R,2R)-2-(benzyloxy)cyclohexanamine 15A (4.0 g, 19.48 mmol) and KCNO (1.58 g, 19.48 mmol) in 24 mL of water. The mixture was chilled to 0° C. and then glacial acetic acid (1.17 mL, 19.48 mmol) was added. The ice bath was removed and a precipitate was observed after 2 hours. The reaction was stirred overnight at RT. The white solid was filtered, rinsed with water and dried under vacuum to provide 15B (3.20 g, 66%). $^1$H NMR (400 MHz, DMSO-$d_6$) δ ppm 1.15-1.27 (m, 2H) 1.50 (d, J=3.03 Hz, 1H) 1.61 (dd, J=5.68, 2.91 Hz, 1H) 1.81 (dd, J=8.59, 2.78 Hz, 1H) 1.91 (dd, J=14.27, 4.17 Hz, 1H) 3.18 (td, J=8.27, 3.92 Hz, 1H) 3.32 (s, 2H) 3.42-3.51 (m, 1H) 4.45-4.56 (m, 1H) 4.50 (d, J=19.71 Hz, 1H) 5.37 (s, 2H) 5.93 (d, J=8.08 Hz, 1H) 7.25 (td, J=5.31, 2.78 Hz, 1H) 7.32 (d, J=4.80 Hz, 4H). ESI-MS: m/z 249.4 (M+H)$^+$.

A.2: Synthesis of 1-((1R,2R)-2-(benzyloxy)cyclohexyl)-2-oxo-5-phenyl-2,3-dihydro-1H-imidazole-4-carboxylic acid (15E)

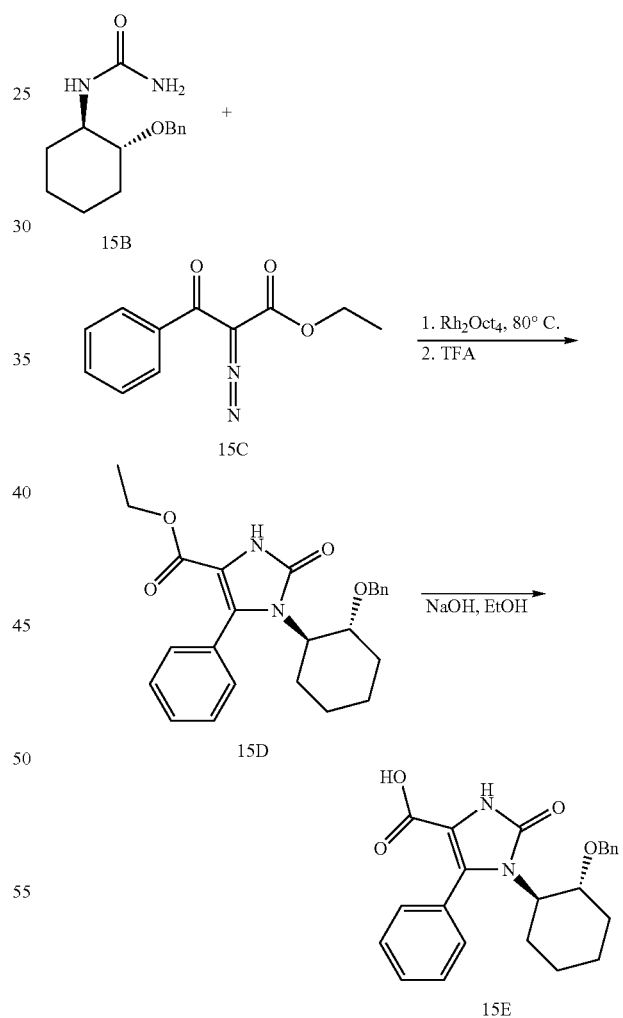

A flask containing a mixture of 15B (3.20 g, 12.87 mmol), ethyl 2-diazo-3-oxo-3-phenylpropanoate (15C) (2.25 g, 10.31 mmol), and 103 mL of 1:1 toluene:dichloroethane was heated at 80° C. for about 10 minutes. A suspension of rhodium octanoate dimer (0.16 g, 0.21 mmol) in 25 mL toluene was added dropwise to the reaction mixture via addition funnel. The reaction was held at 80° C. for an additional hour after addition was completed. After the disappearance of 15C, the reaction was cooled to RT. Approximately 8 mL of TFA was then added and the reaction was allowed to stir overnight at RT. The reaction mixture was concentrated to a green oil then purified by flash chromatography on silica gel using 5-40% ethyl acetate/hexanes to afford the desired product ethyl 1-((1R,2R)-2-(benzyloxy)cyclohexyl)-2-oxo-5-phenyl-2,3-dihydro-1H-imidazole-4-carboxylate as a tan solid (15D) (2.20 g, 49%). $^1$H NMR (400 MHz, DMSO-d$_6$) δ ppm 0.96 (t, J=7.07 Hz, 4H) 1.16 (d, J=12.13 Hz, 1H) 1.56-1.67 (m, 2H) 1.72 (d, J=12.13 Hz, 1H) 2.11 (d, J=6.82 Hz, 1H) 2.32 (d, J=8.84 Hz, 1H) 3.25 (br. s., 1H) 3.98 (q, J=7.07 Hz, 2H) 4.19-4.31 (m, 3H) 4.51 (d, J=11.87 Hz, 1H) 7.15 (d, J=7.33 Hz, 2H) 7.23-7.34 (m, 1H) 7.28 (dd, J=7.71, 1.64 Hz, 4H) 7.43 (br. s., 3H) 10.86 (s, 1H). ESI-MS: m/z 421.4 (M+H)$^+$.

Combined 15D (1.0 g, 2.38 mmol), 9 mL of ethyl alcohol and 9 mL of 1N NaOH. The mixture was heated at 90° C. overnight. After the disappearance of the starting materials by LC/MS, the reaction was cooled to RT and approximately 20 mL of 1N HCl was added directly. The aqueous mixture was extracted with ethyl acetate (3×20 mL), washed with brine, dried over MgSO$_4$ and concentrated in vacuo to afford 1-((1R,2R)-2-(benzyloxy)cyclohexyl)-2-oxo-5-phenyl-2,3-dihydro-1H-imidazole-4-carboxylic acid (15E) as an oil (0.8 g, 86%). This oil was used in next step without purification. ESI-MS: m/z 393.2 (M+H)$^+$.

B. Synthesis of tert-butyl 4-((1R,2R)-2-(benzyloxy) cyclohexyl)-2-oxo-5-phenyl-2,3-dihydro-1H-1-imidazole-4-carbonyl)piperazine-1-carboxylate (15G$^a$)

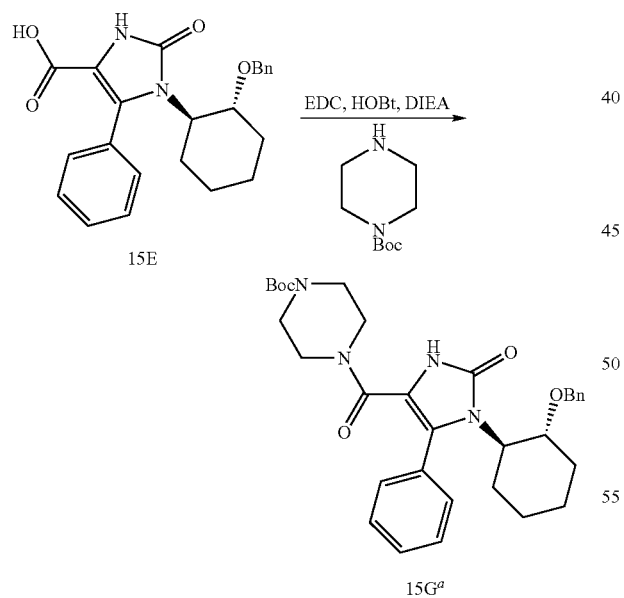

Dissolved 15E (1.5 g, 3.82 mmol) in 15 mL of DMF and added EDC (1.28 g, 6.68 mmol) and HOBt (0.88 g, 6.49 mmol). The mixture was stirred for at least 15 minutes. Next, DIEA (2.0 mL, 11.4 mmol) was added along with tert-butyl piperazine-1-carboxylate (0.85 g, 4.58 mmol). This reaction mixture was then stirred overnight at RT. After the disappearance of 15E, this mixture was poured into 150 mL of water. The white solid was filtered, rinsed with water and dried under vacuum to provide tert-butyl 4-(1-((1R,2R)-2-(benzyloxy)cyclohexyl)-2-oxo-5-phenyl-2,3-dihydro-1H-imidazole-4-carbonyl)piperazine-1-carboxylate (15G$^a$) (1.6 g, 75%). ESI-MS: m/z 561.6 (M+H)$^+$.

C. Synthesis of tert-butyl 4-(3-benzyl-1-((1R,2R)-2-(benzyloxy)cyclohexyl)-2-oxo-5-phenyl-2,3-dihydro-1H-1-imidazole-4-carbonyl)piperazine-1-carboxylate (15H)

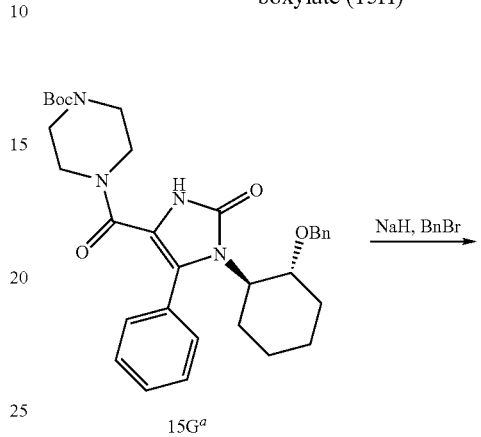

Sodium hydride (0.02 g, 0.86 mmol) was added to a 50 mL flask under blanket of nitrogen; to this, 4 mL of anhydrous DMF was added. While stirring, 15G$^a$ (0.4 g, 0.71 mmol) was added along with the remaining 4 mL of anhydrous DMF. After the reaction mixture was chilled at 0° C. for 15 mins, a solution benzyl bromide (0.10 mL, 0.86 mmol) in 1 mL was added slowly. The mixture was stirred in the ice bath for about two hours. At this time point, LC/MS and TLC showed at least 30% of the starting material remained. The reaction was stirred overnight under nitrogen. The next day, LC/MS shows about 10% of the starting material remained. Reaction was quenched by pouring into 50 mL of ice water. This aqueous mixture was extracted with ethyl acetate, washed with brine and dried over MgSO$_4$ to give crude product. The crude product was purified by flash chromatography using 5% MeOH in DCM to afford 15H as an oil (0.21 g, 45%). ESI-MS: m/z 651.4 (M+H)$^+$.

D. Synthesis of tert-butyl 4-(3-benzyl-1-((1R,2R)-2-hydroxycyclohexyl)-2-oxo-5-phenyl-2,3-dihydro-1H-1-imidazole-4-carbonyl)piperazine-1-carboxylate (15J)

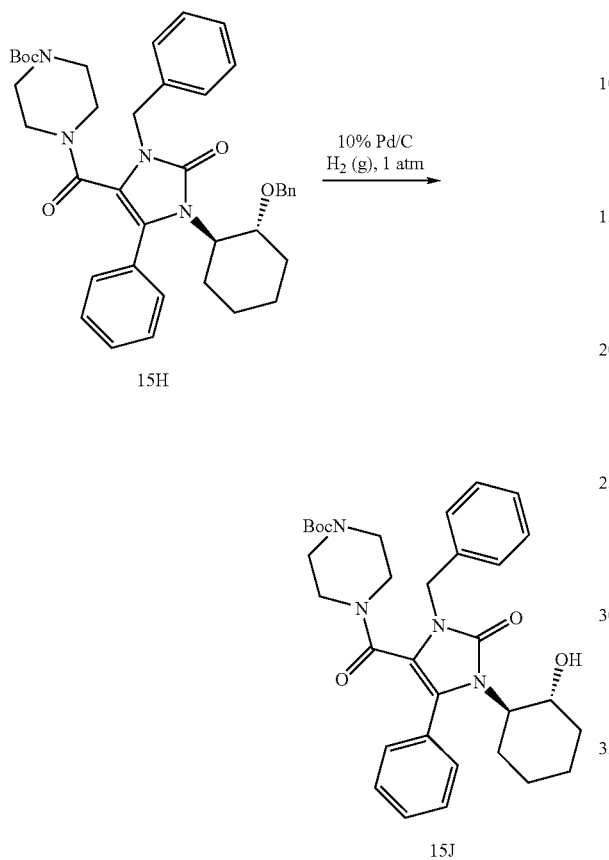

10 mL of methanol was added to a flask containing 15H (0.21 g, 0.32 mmol) and 10% Pd/C (0.02 g). The reaction flask was evacuated and purged with hydrogen then stirred under a balloon of hydrogen at RT. After about two hours, the reaction had fully converted to desired product as confirmed by LC/MS and TLC. The mixture was filtered over a pad of Celite and filtrate was concentrated in vacuo. The residue was reconstituted in ethyl acetate, washed with brine, dried over MgSO₄ and concentrated to give 15J, as a glassy oil in quantitative yield. ESI-MS: m/z 561.4 (M+H)$^+$.

E. Synthesis of (R)-tert-butyl 3-(benzamidomethyl)piperazine-1-carboxylate (15F$^b$)

E1: (S)-tert-butyl 3-(hydroxymethyl)piperazine-1-carboxylate (15L)

Into a 200 mL round bottom flask was added (S)-(4-benzylpiperazin-2-yl)methanol (15K) (10.3 g, 50 mmol) and methanol (100 mL). Palladium hydroxide on carbon (3.0 g) was added and the flask was cycled with hydrogen and vacuum five times. The flask was stirred at room temperature with atmospheric hydrogen overnight. The reaction was filtered through Celite with a Buchner funnel. The filtrate was cooled to −15° C. Boc anhydride (10.9 g, 1 eq) was slowly added to the methanol solution. Upon complete addition the flask was warmed to 0° C. and stirred for two hours. The flask was warmed to room temperature and solvent was removed under vacuum. The residue was purified by column chromatography using 4:2 ethyl acetate:methanol to give 15L as an oil (11.01 g, 85%).

E2: (S)-tert-butyl 4-benzyl-3-(hydroxymethyl)piperazine-1-carboxylate (15N)

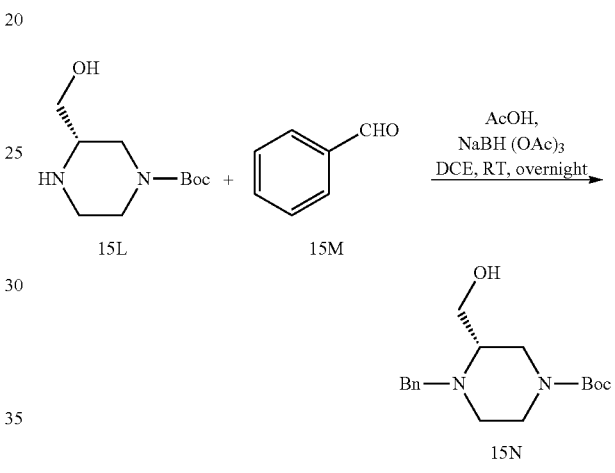

Into a 250 mL round bottom flask was added 15L (10.93 g, 50.5 mmol) and 1,2-dichloroethane (144 mL). Acetic acid (3.03 g, 1 eq) was added and the flask was cooled to 0° C. Sodium triacetoxyborohydride (13.91 g, 1.3 eq) was slowly added. The flask was warmed to room temperature and stirred overnight at room temperature. The reaction mixture was poured onto saturated sodium bicarbonate. The organic layer was separated and the aqueous was extracted two times with ethyl acetate. The organic were combined and washed once with brine. The organics were dried over sodium sulfate and filtered. Solvent was removed under vacuum. The residue was purified by column chromatography with 50% ethyl acetate in hexanes to give a white solid 15N (13.07 g, 84%).

E3: (R)-tert-butyl 4-benzyl-3-((1,3-dioxoisoindolin-2-yl)methyl)piperazine-1-carboxylate (15R)

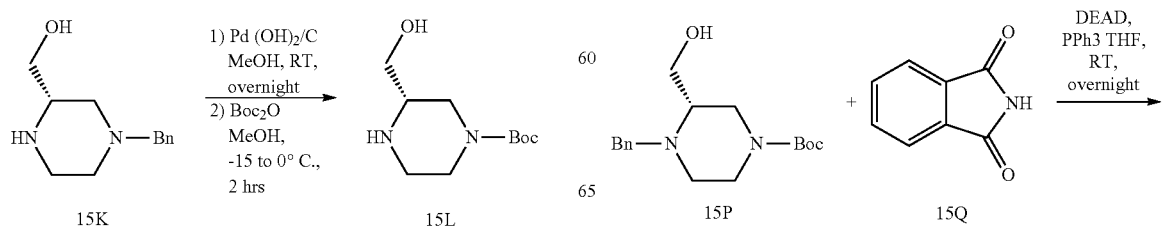

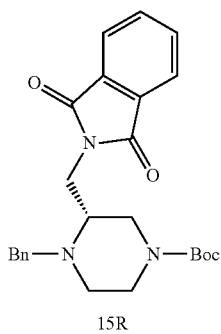

15R

Into a 100 mL round bottom flask was added 15P (3.5 g, 11.4 mmol) and THF (52 mL). DEAD (2.98 g, 1.5 eq), triphenylphosphine (4.49 g, 1.5 eq) and phthalimide 15Q (2.52 g, 10.5 eq) were added in succession. The reaction was stirred overnight at room temperature. The solvent was removed under vacuum and the residue was purified by column chromatography with 5% methanol in dichloromethane to give 15R as a white solid (5.87 g, 92%).

E4: (R)-tert-butyl 3-(aminomethyl)-4-benzylpiperazine-1-carboxylate (15S)

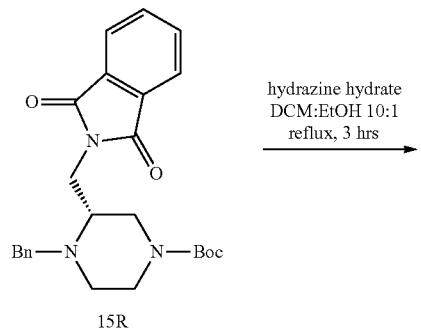

Into a 200 mL round bottom flask was added 15R (6.66 g, 15.3 mmol) and 110 mL of 10:1 dichloromethane:ethanol. Hydrazine hydrate (7.66 g, 10 equiv.) was added and the reaction was heated to reflux for three hours. The precipitate which had formed was removed by filtration through Celite. The filtrate was concentrated under high vacuum and temperature (to remove hydrazine). The residue was resuspended in dichloromethane and the resultant precipitate was removed by filtration through a Buchner funnel. The filtrate was concentrated to leave a clear oil 15S (3.27 g, 73%) which was analytically pure.

E5: (R)-tert-butyl 3-(benzamidomethyl)-4-benzylpiperazine-1-carboxylate (15U)

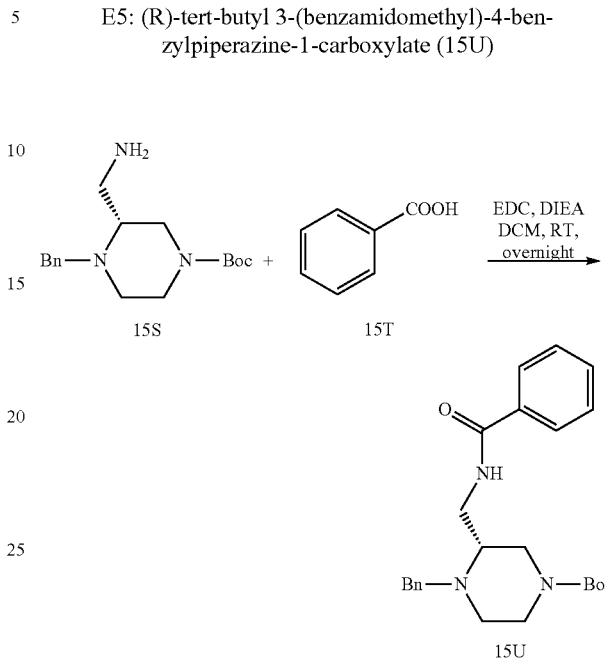

Into a 50 mL round bottom flask was added 15S (820 mg, 2.68 mmol) and dichloromethane (15 mL). Benzoic acid (15T) (426 mg, 1.3 eq) and EDC (669 mg, 1.3 eq) was added and the flask was cooled to 0° C. DIEA (1.04 g, 3 equiv.) was slowly added and the reaction was stirred at room temperature overnight. The solvent was removed under vacuum and the residue was purified by column chromatography with 5% methanol in dichloromethane to give 15U as a solid (865 mg, 79%).

E6: (R)-tert-butyl 3-(benzamidomethyl)piperazine-1-carboxylate (15F$^b$)

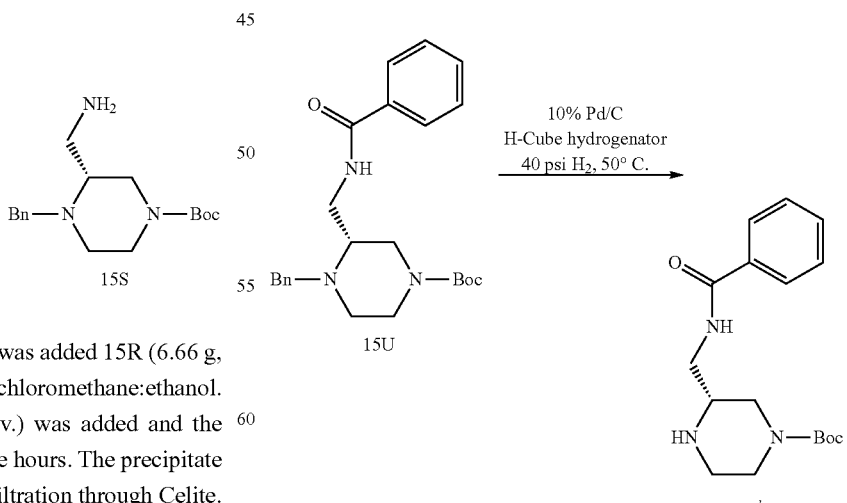

Into a 40 mL scintillation vial was added 15U (865 mg, 2.11 mmol) and methanol (21 mL). The solution was passed through the H-Cube hydrogentator three times at 40 psi of hydrogen pressure at 50° C. The resultant solution was concentrated under vacuum and the residue was purified by column chromatography with 5% methanol in dichloromethane to give (R)-tert-butyl 3-(benzamidomethyl)piperazine-1-carboxylate (15F[b]) as an oil (550 mg, 81%).

F. Synthesis of tert-butyl 4-(3-benzyl-1-((1R,2R)-2-hydroxycyclohexyl)-2-oxo-5-phenyl-2,3-dihydro-1H-imidazole-4-carbonyl)piperazine-1-carboxylate (15G[b])

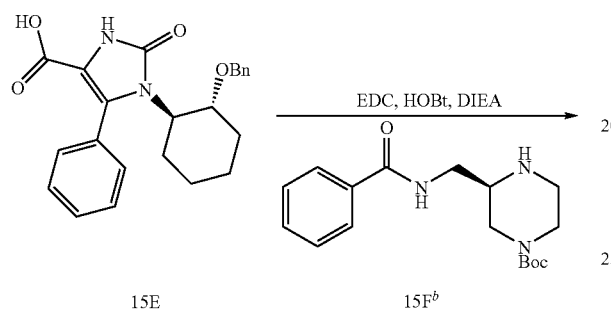

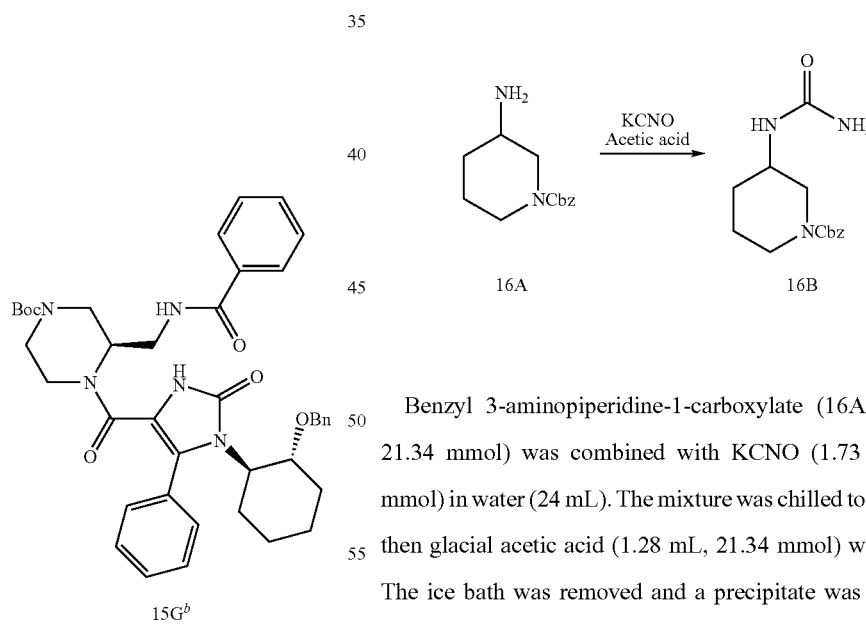

Dissolved 15E (0.20 g, 0.48 mmol) in 2.5 mL of DMF and added EDC (0.16 g, 0.83 mmol) and HOBt (0.11 g, 0.81 mmol). The mixture was stirred for at least 15 minutes. Next, DIEA (0.25 mL, 1.47 mmol) was added along with 15F[b] (0.16 g, 0.50 mmol). This reaction mixture was then stirred at RT for about two hours. After the disappearance of 15E, this mixture was poured into 40 mL of water. The white solid was filtered, rinsed with water and dried under vacuum to provide 15G[b] (0.21 g, 64%). ESI-MS: m/z 693.5 (M+H)$^+$.

Example 16

Synthesis of tert-butyl 4-(1-(1-acetylpiperidin-3-yl)-2-oxo-5-phenyl-2,3-dihydro-1H-imidazole-4-carbonyl)piperazine-1-carboxylate (16F)

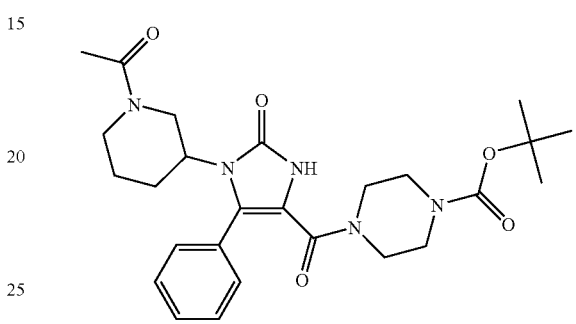

A. Synthesis of benzyl 3-ureidopiperidine-1-carboxylate (16B)

Benzyl 3-aminopiperidine-1-carboxylate (16A) (5.0 g, 21.34 mmol) was combined with KCNO (1.73 g, 21.34 mmol) in water (24 mL). The mixture was chilled to 0° C. and then glacial acetic acid (1.28 mL, 21.34 mmol) was added. The ice bath was removed and a precipitate was observed after 2 hours. The reaction mixture was stirred overnight at RT. The white solid was filtered, rinsed with water and dried under vacuum to provide benzyl 3-ureidopiperidine-1-carboxylate (16B) (2.90 g, 49%). $^1$H NMR (400 MHz, DMSO-d$_6$) δ ppm 1.20-1.44 (m, 2H) 1.53-1.69 (m, 1H) 1.75 (dd, J=11.87, 3.28 Hz, 1H) 2.63-3.14 (m, 2H) 3.40-3.83 (m, 3H)

5.06 (d, J=3.03 Hz, 2H) 5.43 (s, 2H) 6.02 (br. s., 1H) 7.25-7.41 (m, 5H) ESI-MS: m/z 278.2 (M+H)+.

B. Synthesis of benzyl 3-(4-(ethoxycarbonyl)-2-oxo-5-phenyl-2,3-dihydro-1H-imidazol-1-yl)piperidine-1-carboxylate (16D)

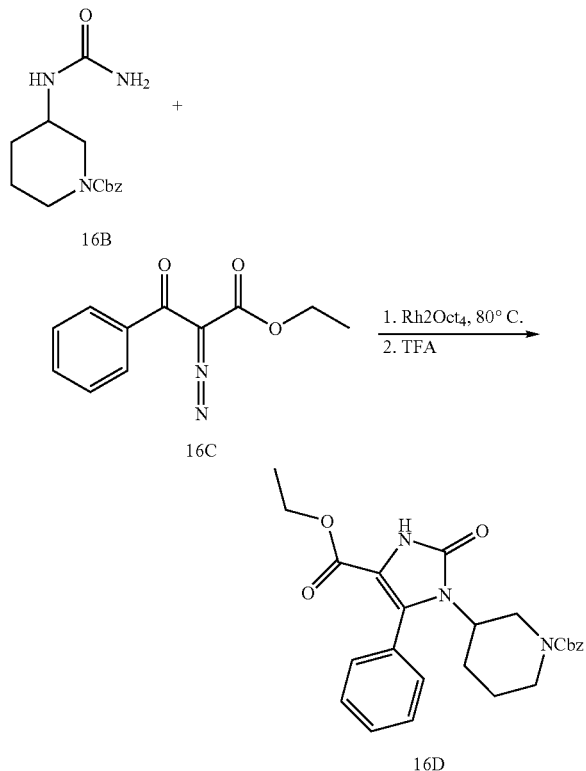

A flask containing a mixture of ethyl 2-diazo-3-oxo-3-phenylpropanoate (16C) (2.80 g, 12.84 mmol), 16B (4.45 g, 16.05 mmol) from previous step, and 128 mL of 1:1 toluene:dichloroethane was heated at 80° C. for about 10 minutes. A suspension of rhodium octanoate dimer (0.20 g, 0.26 mmol) in 25 mL toluene was added dropwise to the reaction mixture via an addition funnel. The reaction was held at 80° C. for an additional hour after the addition was completed. After the disappearance of 16C, the reaction was cooled to RT. Approximately 8 mL of TFA was then added and the reaction was allowed to stir overnight at RT. The reaction mixture was concentrated to a green oil then purified by flash chromatography on silica gel using 5% methanol/DCM to afford benzyl 3-(4-(ethoxycarbonyl)-2-oxo-5-phenyl-2,3-dihydro-1H-imidazol-1-yl)piperidine-1-carboxylate (16D) as a tan solid (2.50 g, 42%). $^1$H NMR (400 MHz, DMSO-d$_6$) δ ppm 0.94 (t, J=7.07 Hz, 3H) 1.07-1.18 (m, 2H) 1.24 (br. s., 1H) 1.62-1.78 (m, 2H) 2.36-2.43 (m, 1H) 2.59-2.68 (m, 1H) 3.46-3.58 (m, 2H) 3.96 (q, J=6.91 Hz, 2H) 4.99 (s, 1H) 7.26-7.51 (m, 11H) 10.97 (s, 1H) ESI-MS: m/z 450.1 (M+H)+.

C. Synthesis of 1-(1-(benzyloxycarbonyl)piperidin-3-yl)-2-oxo-5-phenyl-2,3-dihydro-1H-imidazole-4-carboxylic acid, (16E)

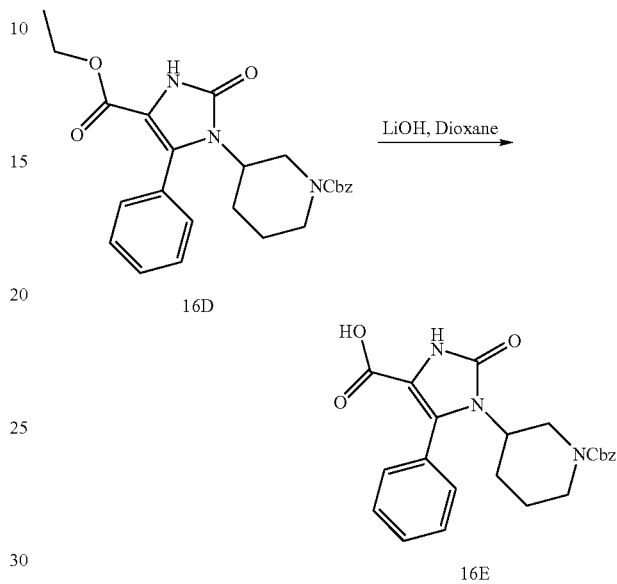

(16D) (2.6 g, 5.78 mmol) prepared in the previous step was combined with 26 mL of dioxane and 29 mL of 1N LiOH. The mixture was heated at 55° C. overnight. After the disappearance of 16D as monitored by LC/MS, the reaction was cooled to RT and approximately 50 mL of 1N HCl was added directly. The aqueous mixture was extracted with ethyl acetate (3×40 mL), washed with brine, dried over MgSO$_4$, and concentrated in vacuo to afford 1-(1-(benzyloxycarbonyl)piperidin-3-yl)-2-oxo-5-phenyl-2,3-dihydro-1H-imidazole-4-carboxylic acid as an oil (16E) (2.43 g, quantitative yield). $^1$H NMR (400 MHz, DMSO-d$_6$) δ ppm 1.13 (d, J=9.60 Hz, 1H) 1.25 (br. s., 1H) 1.61-1.77 (m, 2H) 2.60 (br. s., 1H) 3.25 (br. s., 1H) 3.84-4.00 (m, 2H) 4.99 (s, 2H) 7.27-7.47 (m, 10H) 7.92-7.97 (m, 1H) 10.79 (s, 1H) 12.43 (br. s., 1H). This was used in next step without purification. ESI-MS: m/z 422.3 (M+H)+.

D. Synthesis of tert-butyl 4-(1-(1-(benzyloxycarbonyl)piperidin-3-yl)-2-oxo-5-phenyl-2,3-dihydro-1H-imidazole-4-carbonyl)piperazine-1-carboxylate (16F)

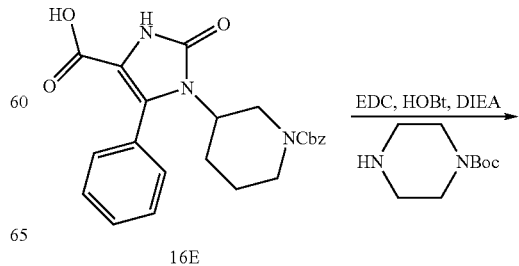

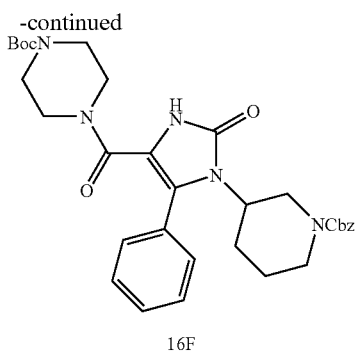

16F

Dissolved 16E (3.0 g, 7.118 mmol) prepared in the previous step in 30 mL of DMF and added EDC (2.39 g, 12.46 mmol) and HOBt (1.65 g, 12.01 mmol). The mixture was stirred for at least 15 minutes. Next, DIEA (2.76 mL, 21.35 mmol) was added along with tert-butyl piperazine-1-carboxylate (1.39 g, 7.47 mmol). This reaction mixture was then stirred at RT for about four hours. After the disappearance of 16E, this mixture was poured into 300 mL of water, a white precipitate was formed. The white solid was filtered, rinsed with water and dried under vacuum to provide tert-butyl 4-(1-(1-(benzyloxycarbonyl)piperidin-3-yl)-2-oxo-5-phenyl-2,3-dihydro-1H-imidazole-4-carbonyl)piperazine-1-carboxylate (16F) (3.2 g, 76%). $^1$H NMR (400 MHz, DMSO-$d_6$) δ ppm 1.34 (s, 9H) 1.40 (s, 2H) 1.65-1.80 (m, 4H) 2.34 (br. s., 1H) 2.83 (br. s., 4H) 3.13-3.19 (m, 4H) 3.94-4.07 (m, 2H) 5.03 (s, 2H) 7.23-7.50 (m, 10H) 10.73 (s, 1H). ESI-MS: m/z 590.1 (M+H)$^+$.

E. Synthesis of tert-butyl 4-(2-oxo-5-phenyl-1-(piperidin-3-yl)-2,3-dihydro-1H-imidazole-4-carbonyl)piperazine-1-carboxylate (16G)

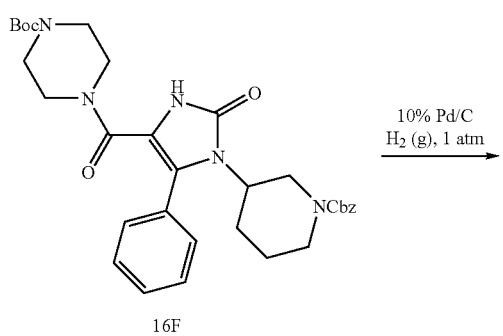

16F

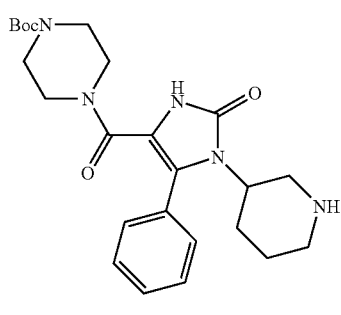

16G 10 mL of methanol was added to a flask containing 16F (0.50 g, 0.85 mmol) prepared in the previous step and 10% Pd/C (0.05 g). The reaction flask was evacuated and purged with hydrogen, then stirred under a balloon of hydrogen overnight at RT. The mixture was filtered over a pad of Celite and the filtrate was concentrated in vacuo. The residue was reconstituted in ethyl acetate, washed with brine, dried over MgSO$_4$, and concentrated to give tert-butyl 4-(2-oxo-5-phenyl-1-(piperidin-3-yl)-2,3-dihydro-1H-imidazole-4-carbonyl)piperazine-1-carboxylate (16H), as a glassy oil in quantitative yield. ESI-MS: m/z 456.4 (M+H)$^+$.

F. Synthesis of tert-butyl 4-(1-(1-acetylpiperidin-3-yl)-2-oxo-5-phenyl-2,3-dihydro-1H-imidazole-4-carbonyl)piperazine-1-carboxylate (16H)

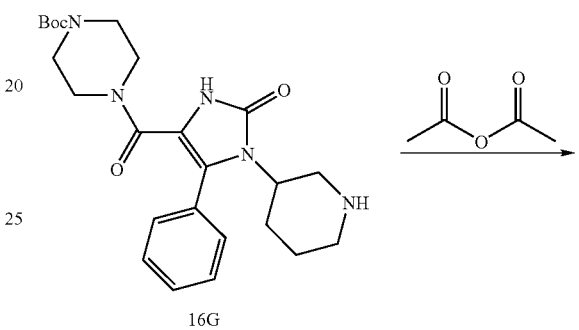

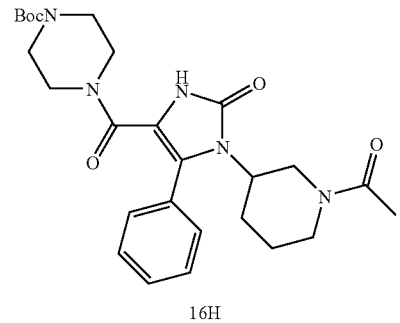

16H 16G (0.39 g, 0.85 mmol) prepared in the previous step was dissolved in 3 mL of anhydrous DCM. TEA (0.36 mL, 2.54 mmol) was added and the mixture was chilled to 0° C. To this chilled mixture, acetic anhydride (0.08 mL, 0.85 mmol) was added slowly. After about 30 minutes, TLC and LC/MS showed no signs of 16G. At this point, the mixture was concentrated to give tert-butyl 4-(1-(1-acetylpiperidin-3-yl)-2-oxo-5-phenyl-2,3-dihydro-1H-imidazole-4-carbonyl)piperazine-1-carboxylate (16H) as an oil (0.42 g, quantitative yield). ESI-MS: m/z 498.4 (M+H)$^+$.

Example 17

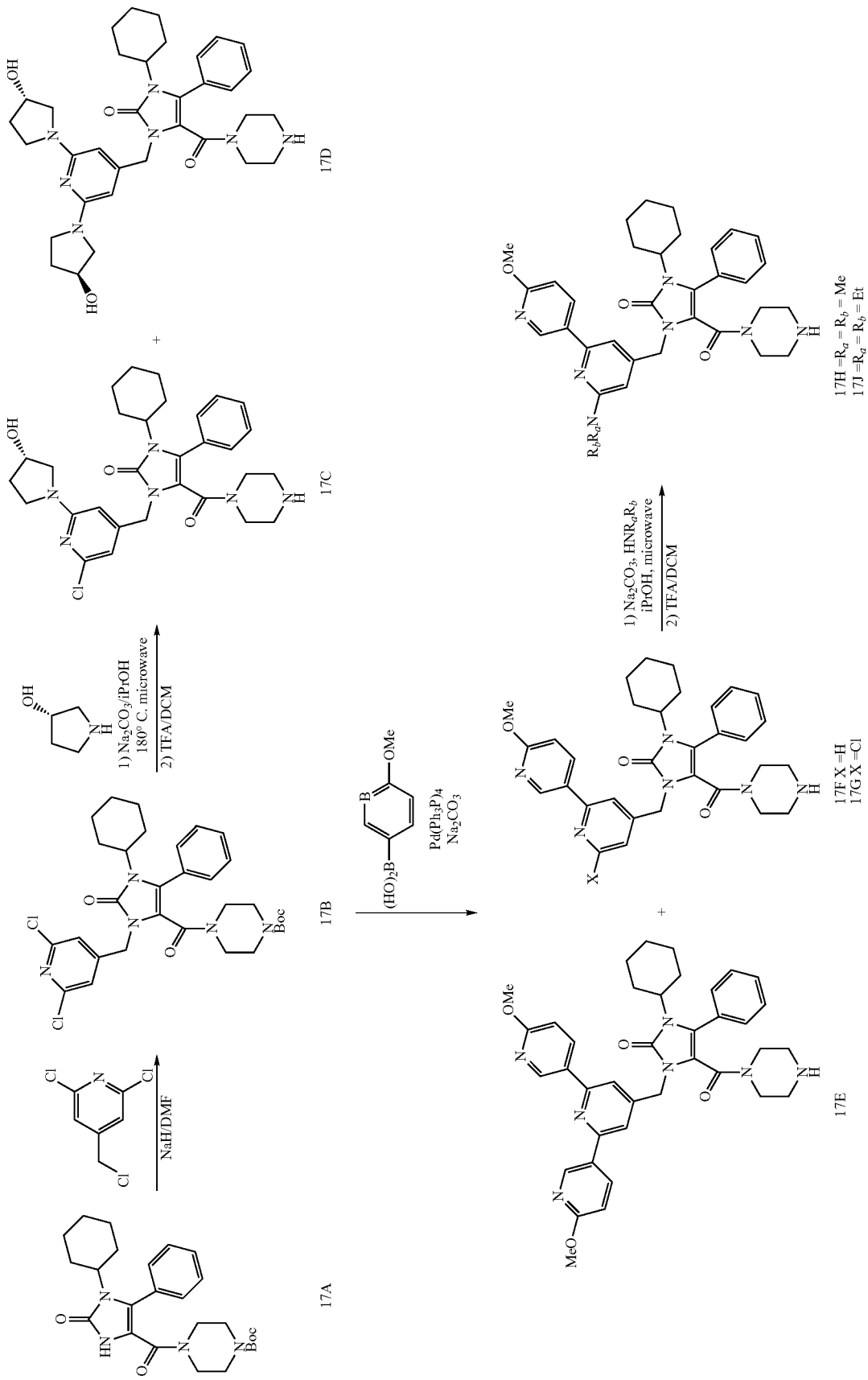

2,6-dichloro-4-(chloromethyl)pyridine was alkylated to 17A according to general procedure, Scheme A, Step 7, to afford tert-butyl 4-(1-cyclohexyl-3-((2,6-dichloropyridin-4-yl)methyl)-2-oxo-5-phenyl-2,3-dihydro-1H-imidazole-4-carbonyl)piperazine-1-carboxylate 17B.

17B was treated with 1.5 eq of (R)-pyrrolidin-3-ol and 5 equiv. of $Na_2CO_3$ in isopropanol under micro-wave condition at 180° C. for 30 min. The crude mixture was then treated with TAF-DCM (1:1) for 2 hr, purified by LCMS to give both 17C and 17D and their associated stereoisomers.

17C[1]: (S)-1-((2-Chloro-6-(3-hydroxypyrrolidin-1-yl)pyridin-4-yl)methyl)-3-cyclohexyl-4-phenyl-5-(piperazine-1-carbonyl)-1H-imidazol-2(3H)-one. $^1$H NMR (400 MHz, CHLOROFORM-d) δ ppm 7.42 (m, H), 7.15 (m, 2H), 6.26 (s, 1H), 6.04 (s, 1H), 4.81 (br. s., 2H), 4.44 (br. s., 2H), 3.41 (m, 4H), 3.32 (s, 1H), 2.26 (m, 4H), 2.00 (m, 2H), 1.75-1.65 (m, 4H), 1.53 (d, J=11.87 Hz, 1H), 1.12 (m, 4H). ESI-MS: calc'd for $C_{30}H_{38}ClN_6O_3$, 565.3. found 565.3 (M+H)$^+$.

17C[2]: (R)-1-((2-Chloro-6-(3-hydroxypyrrolidin-1-yl)pyridin-4-yl)methyl)-3-cyclohexyl-4-phenyl-5-(piperazine-1-carbonyl)-1H-imidazol-2(3H)-one. $^1$H-NMR (400 MHz, $CDCl_3$-$CD_3OD$ 10:1) δ ppm 7.42 (m, 3H), 7.15 (m, 2H), 6.26 (s, 1H), 6.04 (s, 1H), 4.44 (br. s., 2H), 3.52 (ddd, J=12.1, 8.4, 3.5 Hz, 2H), 3.40 (m., 4H), 2.28 (m., 5H), 1.95-2.15 (m, 2H), 1.75-1.65 (m., 4H), 1.51 (d., J=8.0 Hz, 1H), 1.10-125 (m, 4H). ESI-MS: calc'd for $C_{30}H_{38}ClN_6O_3$, 565.3. found 565.3 (M+H)$^+$.

17D[1]: 1-((2,6-bis((S)-3-Hydroxypyrrolidin-1-yl)pyridin-4-yl)methyl)-3-cyclohexyl-4-phenyl-5-(piperazine-1-carbonyl)-1H-imidazol-2(3H)-one. $^1$H NMR (400 MHz, CHLOROFORM-d) δ ppm 7.44 (m, 3H), 7.17 (m, 2H), 4.76 (br. s., 2H), 4.47 (br. s., 2H), 3.17 (br. s., 2H), 2.27 (m., 2H), 2.04 (br. s., 4H), 1.75 (m, 2H), 1.65 (m, 2H), 1.53 (m, 2H), 1.03-1.25 (m, 4H). ESI-MS: calc'd for $C_{34}H_{46}N_7O_4$, 616.4. found 616.4, (M+H)$^+$.

17D[2]: 1-((2,6-bis((R)-3-Hydroxypyrrolidin-1-yl)pyridin-4-yl)methyl)-3-cyclohexyl-4-phenyl-5-(piperazine-1-carbonyl)-1H-imidazol-2(3H)-one. $^1$H-NMR (400 MHz, $CDCl_3$-$CD_3OD$ 10:1) δ ppm 7.42 (m, 3H), 7.16 (m, 2H), 6.4, 6.2 (1H each), 4.5 (s, 2H), 2.26 (m, 2H), 2.03 (m, 4H), 1.75 (m, 2H), 1.66 (m, 1H), 1.05-123 (m., 4H). ESI-MS: calc'd for $C_{34}H_{46}N_7O_4$, 616.4. found 616.4, (M+H)$^+$.

A mixture of 1.0 eq of compound 17B, 1.2 eq of 6-methoxypyridin-3-ylboronic acid, 5 eq of $Na_2CO_3$ and tetrakis (triphenyl phosphine) palladium (0.01 equiv.) in dioxane-$H_2O$ (20:1) was treated under micro-wave condition at 160° C. for 20 min, purified by LCMS to give 17E, 17F, and 17G.

17E: 1-Cyclohexyl-3-((2,6-di(2-methoxyl-pyridine-4-yl)pyridin-4-yl)methyl)-5-phenyl-4-(piperazine-1-carbonyl)-1H-imidazol-2(3H)-one. $^1$H NMR (400 MHz, CHLOROFORM-d) δ ppm 8.68 (d, J=2.0 Hz, 2H), 8.25 (dd, J=8.8, 2.5 Hz, 2H), 7.43 (s, 2H), 7.37 (m, 3H), 7.14 (m, 2H), 6.77 (d, J=8.8 Hz, 2H), 5.17 (s, 1H), 4.92 (s, 2H), 3.85 (s, 6H), 3.33-3.56 (m, 1H), 3.09 (m, 4H), 2.06-2.30 (m, 4H), 1.68 1.59 (m, 4H), 1.45 (m, 1H), 0.94-1.17 (m, 4H). ESI-MS: calc'd for $C_{38}H_{42}N_7O_4$, 660.3. found 660.3, (M+H)$^+$.

17F: 1-Cyclohexyl-3-((6'-methoxy-2,3'-bipyridin-4-yl)methyl)-5-phenyl-4-(piperazine-1-carbonyl)-1H-imidazol-2(3H)-one. $^1$H NMR (400 MHz, CHLOROFORM-d) δ ppm 8.52 (dd, J=2.5, 0.8 Hz, 1H), 8.43 (dd, J=5.3, 0.5 Hz, 1H), 8.04 (dd, J=2.6, 8.9 Hz, 1H), 7.55 (s, 1H), 7.39 (m, 3H), 7.13 (m, 2H), 7.06 (dd, J=5.2, 1.6 Hz, 1H), 6.75 (dd, J=9.9, 1.8 Hz, 1H), 4.90 (s, 2H), 3.83 (m, 3H), 3.22 (s, 3H), 2.24 (m, 4H), 1.57-1.69 (m, 4H), 1.45 (m, 1H), 1.03 (m, 4H). ESI (MS) calc'd for $C_{32}H_{37}N_6O_3$, 553.3. found 553.3, (M+H)$^+$.

17G: 1-((6-chloro-6'-methoxy-2,3'-bipyridin-4-yl)methyl)-3-cyclohexyl-4-phenyl-5-(piperazine-1-carbonyl)-1H-imidazol-2(3H)-one. MS (ES) [m+H] calc'd for $C_{32}H_{36}N_6O_3Cl$, 587.3. found 587.3.

17G (0.2 mmol) was treated with (1 mmol, 1.5 eq) of either dimethyamine or diethylamine and 5 equiv. of $Na_2CO_3$ in 2 mL of isopropanol under micro-wave condition at 180° C. for 30 min. The crude mixture was then treated with TFA-DCM (1:1) for 2 h, purified by LCMS to give either the dimethyl substituted 17H or the diethyl substituted 17J.

17H: 1-cyclohexyl-3-((6-(dimethylamino)-6'-methoxy-2,3'-bipyridin-4-yl)methyl)-5-phenyl-4-(piperazine-1-carbonyl)-1H-imidazol-2(3H)-one. $^1$H NMR (400 MHz, CHLOROFORM-d) δ ppm 8.55 (d, J=2.6 Hz, 1H), 8.07 (dd, J=2.6, 8.6 Hz, 1H), 7.34 (m, 1H), 7.26 (m, 1H), 7.09 (m, 1H), 6.65 (m, 1H), 6.18 (s, 1H), 4.78 (s, 2H), 3.80 (s, 3H), 2.96 (s, 6H), 2.23 (m, 4H), 1.56-1.71 (m, 4H), 1.45 (m, 1H), 1.03 (m, 4H). ESI-MS: calc'd for $C_{34}H_{42}N_7O_3$, 596.3. found 596.3, (M+H)$^+$.

17J: 1-cyclohexyl-3-((6-(diethylamino)-6'-methoxy-2,3'-bipyridin-4-yl)methyl)-5-phenyl-4-(piperazine-1-carbonyl)-1H-imidazol-2(3H)-one. $^1$H NMR (400 MHz, CHLOROFORM-d) δ ppm 8.44 (d, J=2.5 Hz, 1H), 7.98 (dd, J=2.5, 8.8 Hz, 1H), 7.37 (m, 3H), 7.11 (m, 2H), 6.71 (d, J=8.5 Hz, 1H), 6.64 (s, 1H), 6.39 (s, 1H), 4.77 (br. s., 2H), 3.83 (s, 3H), 3.45 (q, J=7 Hz, 4H), 3.11 (m, 3H), 2.20 (m., 1H), 1.68 (m, 2H), 1.60 (m, 2H), 1.45 (m, 1H), 1.08 (t, J=7.07 Hz, 6H), 1.03 (m, 4H). ESI-MS: calc'd for $C_{36}H_{46}N_7O_3$, 624.4. found 624.4, (M+H)$^+$.

Example 18

1,5-Diphenyl-4-(piperazine-1-carbonyl)-1H-imidazol-2(3H)-one

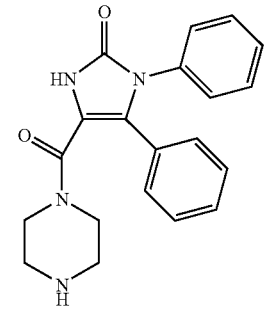

The title compound was prepared according to general procedure, Scheme A, Steps 1-6. $^1$H NMR (400 MHz, MeOD) δ ppm 2.7 (br s, 4H) 3.6 (br s, 4H) 7.17 (m, 4H) 7.36 (m, 6H). ESI-MS: m/z 349.4 (M+H)$^+$.

Example 19

5-Phenyl-4-(piperazine-1-carbonyl)-1-(pyridin-2-yl)-1H-imidazol-2(3H)-one

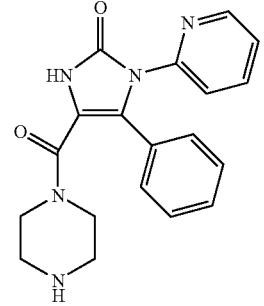

The title compound was prepared according to general procedure, Scheme A, Steps 1-6. $^1$H NMR (400 MHz, DMSO-d6) δ ppm 2.73 (br s, 4H), 3.48 (br s, 4H), 7.03 (m, 2H), 7.26-7.36 (m, 4H), 7.55 (d, 1H), 7.94 (t, 1H), 8.30 (d, 1H), 8.77 (br s, 1H), 11.07 (s, 1H). ESI-MS: m/z 350.4 (M+H)$^+$.

Example 20

4-(2-(Hydroxymethyl)piperazine-1-carbonyl)-1,5-diphenyl-1H-imidazol-2(3H)-one

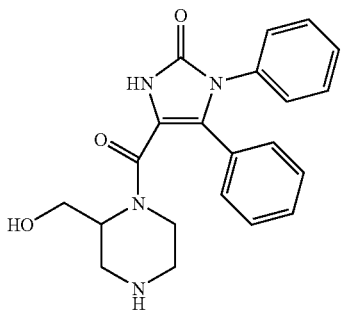

The title compound was prepared according to general procedure, Scheme A, Steps 1-6. $^1$H NMR (400 MHz, MeOD) δ ppm 2.7-3.3 (m, 9H) 7.17-7.43 (m, 10H). ESI-MS: m/z 379.4 (M+H)$^+$.

Example 21

5-(3-Fluorophenyl)-1-phenyl-4-(piperazine-1-carbonyl)-1H-imidazol-2(3H)-one

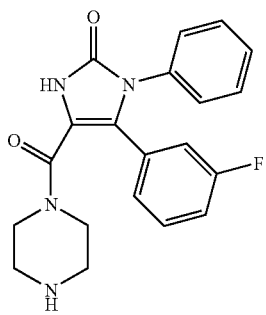

The title compound was prepared according to general procedure, Scheme A, Steps 1-6. $^1$H NMR (400 MHz, MeOD) δ ppm 2.8 (br s, 4H) 3.6 (br s, 4H) 6.95 (m, 2H) 7.3-7.45 (m, 7H); ESI-MS: m/z 367.4 (M+H)$^+$.

Example 22

1-(3-Morpholinophenyl)-5-phenyl-4-(piperazine-1-carbonyl)-1H-imidazol-2(3H)-one

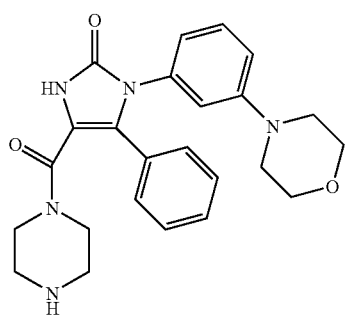

The title compound was prepared according to general procedure, Scheme A, Steps 1-6. ESI-MS: m/z 434.4 (M+H)$^+$.

Example 23

5-Isopropyl-1-phenyl-4-(piperazine-1-carbonyl)-1H-imidazol-2(3H)-one

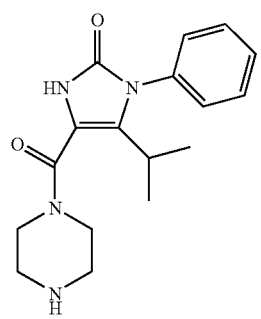

The title compound was prepared according to general procedure, Scheme A, Steps 1-6. $^1$H NMR (400 MHz, MeOD) δ ppm 1.12 (d, J=7.07 Hz, 6H) 2.63-2.85 (m, 1H) 3.23-3.27 (m, 2H) 3.34-3.38 (m, 2H) 3.77-3.99 (m, 3H) 7.35 (dd, J=8.08, 1.52 Hz, 2H) 7.45-7.64 (m, 3H). ESI-MS: m/z 315.4 (M+H)$^+$.

Example 24

5-Cyclopropyl-1-phenyl-4-(piperazine-1-carbonyl)-1H-imidazol-2(3H)-one

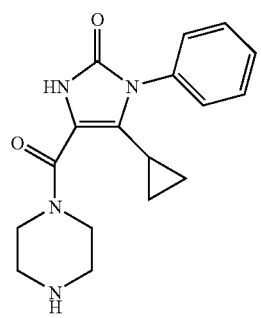

The title compound was prepared according to general procedure, Scheme A, Steps 1-6. $^1$H NMR (400 MHz, MeOD) δ ppm 0.28-0.51 (m, 2H) 0.60-0.85 (m, 2H) 1.51-

1.79 (m, 1H) 3.75-4.15 (m, 8H) 7.39-7.49 (m, 3H) 7.49-7.59 (m, 2H). ESI-MS: m/z 313.2 (M+H)$^+$.

Example 25

5-(Cyclopropylmethyl)-1-phenyl-4-(piperazine-1-carbonyl)-1H-imidazol-2(3H)-one

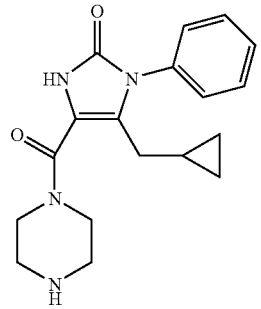

The title compound was prepared according to general procedure, Scheme A, Steps 1-6. $^1$H NMR (400 MHz, MeOD) δ ppm 0.10-0.44 (m, 4H) 0.49-0.72 (m, 1H) 2.45 (d, J=6.82 Hz, 2H) 3.71-4.08 (m, 8H) 7.23-7.46 (m, 2H) 7.44-7.76 (m, 3H). ESI-MS: m/z 327.2 (M+H)$^+$.

Example 26

5-(2-Chlorophenyl)-1-phenyl-4-(piperazine-1-carbonyl)-1H-imidazol-2(3H)-one

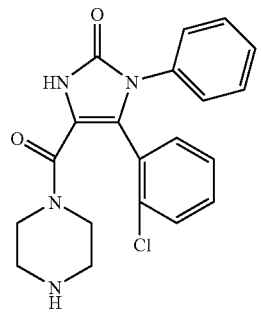

The title compound was prepared according to general procedure, Scheme A, Steps 1-6. $^1$H NMR (400 MHz, MeOD) δ ppm 2.65-2.96 (m, 4H) 3.45-3.74 (m, 4H) 7.08-7.18 (m, 2H) 7.24-7.52 (m, 7H). ESI-MS: m/z 383.2 (M+H)$^+$.

Example 27

1-(3-(2-methoxyethoxy)benzyl)-4-phenyl-5-(piperazine-1-carbonyl)-3-o-tolyl-1H-imidazol-2(3H)-one

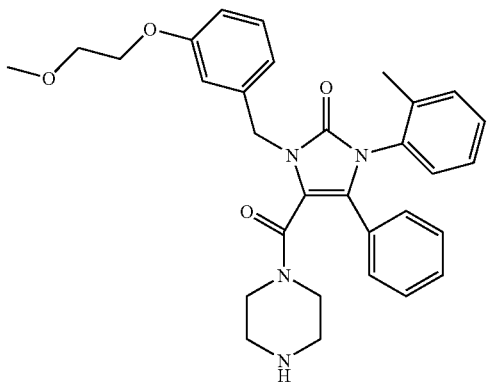

A. (3-(2-methoxyethoxy)phenyl)methanol, 27C

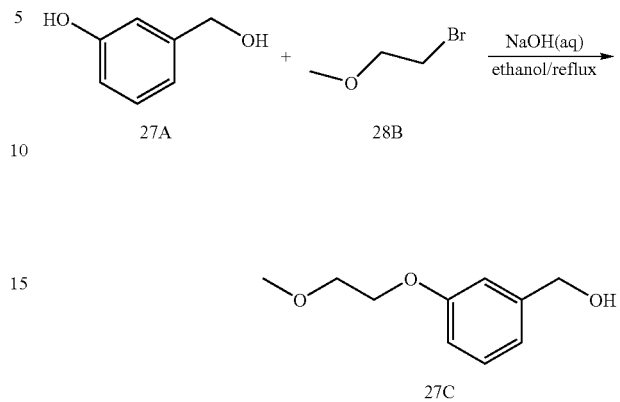

To a solution of 3-hydroxybenzyl alcohol (27A) (12.41 g, 100 mmol) in ethanol (150 mL) was added aqueous NaOH (10 N, 10 mL), followed by 1-bromo-2-methoxyethane (27B) (13.9 g). The reaction mixture was heated to reflux overnight. Then the reaction mixture was allowed to cool to RT, and diluted with water. The mixture was subsequently extracted with CH$_2$Cl$_2$, and the combined organic phase was dried with anhydrous MgSO$_4$ filtered, and concentrated in vacuum to give the product (27C) a yellow oil, which was used for the next reaction without further purification. $^1$H NMR (300 MHz, CDCl$_3$): δ 1.82 (br, 1H), 3.44 (s, 3H), 3.74 (t, 2H, J=4.8 Hz), 4.12 (t, 2H, J=4.8 Hz), 4.65 (s, 2H), 6.84-6.95 (m, 3H), 7.22-7.26 (m, 1H). LCMS: purity >94%. ESI-MS: M/Z 183 (M+H)$^+$.

B. 1-(bromomethyl)-3-(2-methoxyethoxy)benzene, 27D

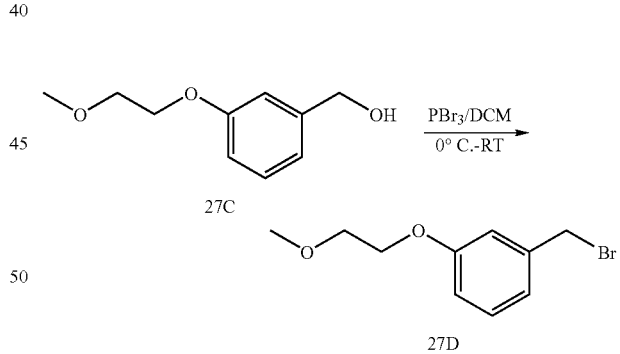

To a solution of 27C (18.2 g, 100 mmol) in CH$_2$Cl$_2$ (300 mL) was added PBr$_3$ (4.5 mL, 48 mmol) at 0° C., then the resulting mixture was allowed to warm to RT overnight. The reaction mixture was quenched with saturated NaHCO$_3$ (50 mL) and stirred at RT for an addition 0.5 h. The mixture was extracted with CH$_2$Cl$_2$, and the combined extracted were dried (MgSO$_4$), filtered, and evaporated in vacuum to give the product as a yellow oil (20.2 g, 82%, two steps). $^1$H NMR (300 MHz, CDCl$_3$): δ 3.45 (s, 1H), 3.75 (t, 2H, J=4.8 Hz), 4.12 (t, 2H, J=4.8 Hz), 4.45 (s, 2H), 6.85-6.99 (m, 3H), 7.21-7.26 (m, 1H). LC-MS: purity >95%, ESI-MS: M/Z 245 (M+H)$^+$, 247 (M+2+H)$^+$.

C. 1-(3-(2-methoxyethoxy)benzyl)-4-phenyl-5-(piperazine-1-carbonyl)-3-o-tolyl-1H-imidazol-2(3H)-one

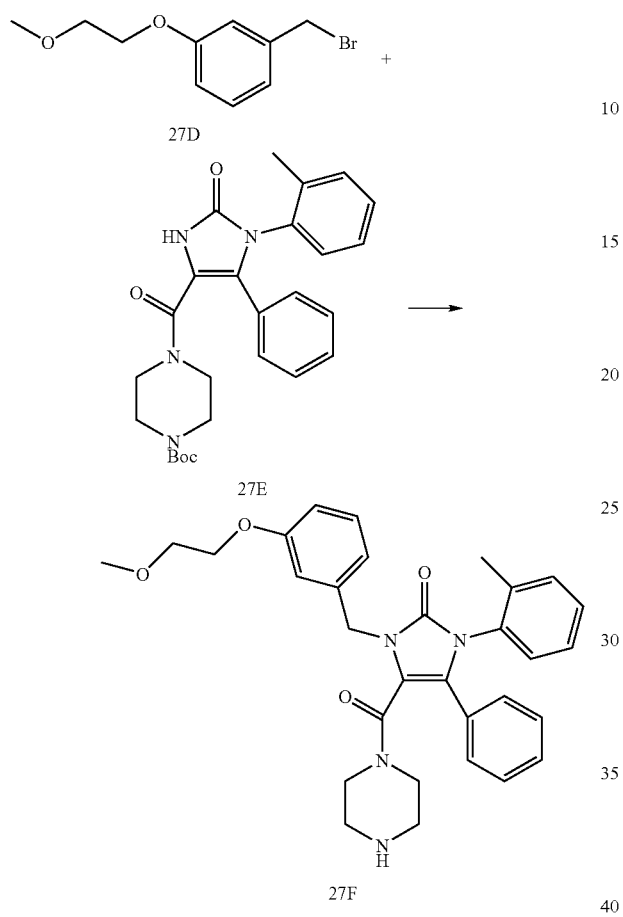

The title compound 27F was prepared according to general procedure, Scheme A, Steps 7 and 8. ESI-MS: m/z 527.2 (M+H)$^+$.

Example 28

5-(4-Chlorophenyl)-1-phenyl-4-(piperazine-1-carbonyl)-1H-imidazol-2(3H)-one

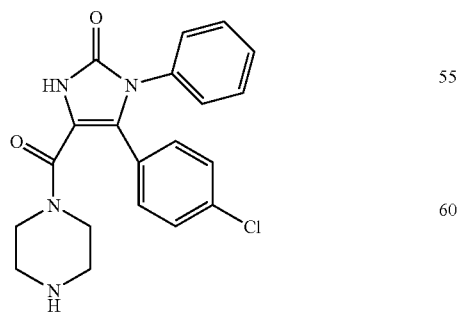

The title compound was prepared according to general procedure, Scheme A, Steps 1-6. $^1$H NMR (400 MHz, MeOD) δ ppm 2.74-3.01 (m, 4H) 3.49-3.70 (m, 4H) 7.06-7.25 (m, 5H) 7.28-7.45 (m, 2H). ESI-MS: m/z 383.2 (M+H)$^+$.

Example 29

1-Cyclohexyl-5-phenyl-4-(piperazine-1-carbonyl)-1H-imidazol-2(3H)-one

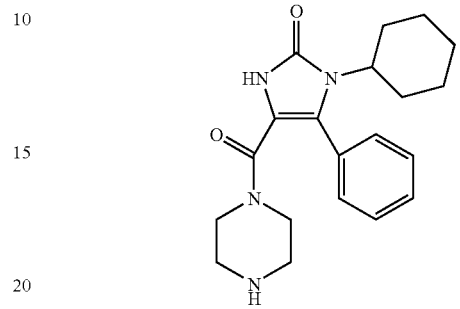

The title compound was prepared according to general procedure, Scheme A, Steps 1-6. $^1$H NMR (400 MHz, MeOD) δ ppm 0.96-1.31 (m, 4H) 1.59-1.88 (m, 4H) 2.18-2.44 (m, 2H) 3.16-3.29 (m, 4H) 3.40-3.68 (m, 4H) 7.26-7.49 (m, 2H) 7.48-7.70 (m, 3H). ESI-MS: m/z 355.3 (M+H)$^+$.

Example 30

Benzyl 3-(2-oxo-5-phenyl-4-(piperazine-1-carbonyl)-2,3-dihydro-1H-imidazol-1-yl)piperidine-1-carboxylate

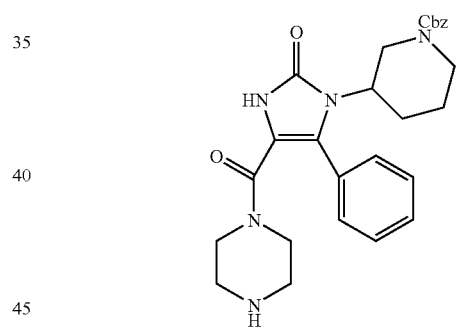

The title compound was prepared according to general procedure, Scheme A, Steps 1-6. ESI-MS: m/z 490.1 (M+H)$^+$.

Example 31

1-((1R,2R)-2-(Benzyloxy)cyclohexyl)-5-phenyl-4-(piperazine-1-carbonyl)-1H-imidazol-2(3H)-one

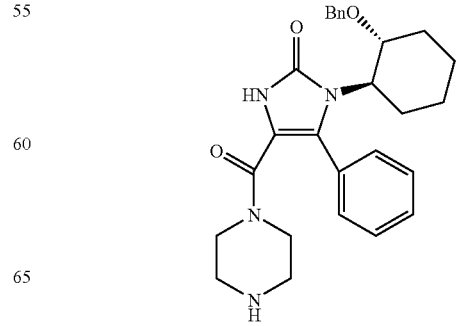

The title compound was prepared according to general procedure, Scheme A, Steps 1-6. ESI-MS: m/z 461.3 (M+H)+.

Example 32

1-(2-(2-Methoxyethoxy)phenyl)-5-phenyl-4-(piperazine-1-carbonyl)-1H-imidazol-2(3H)-one 5.3/5.4

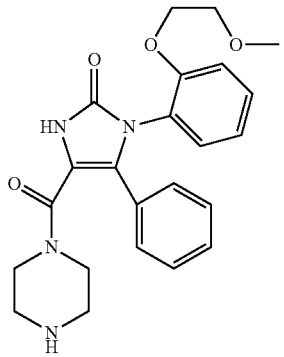

The title compound was prepared according to general procedure, Scheme A, Steps 1-6. $^1$H NMR (400 MHz, MeOD) δ ppm 3.34 (s, 3H) 3.49-3.70 (m, 8H) 3.81-3.94 (m, 2H) 4.00-4.09 (m, 2H) 6.92-7.08 (m, 4H) 7.20 (dd, J=7.96, 1.64 Hz, 2H) 7.24-7.40 (m, 5H). ESI-MS: m/z 423.2 (M+H)+.

Example 33

1-(2-(3-Methoxypropoxy)phenyl)-5-phenyl-4-(piperazine-1-carbonyl)-1H-imidazol-2(3H)-one

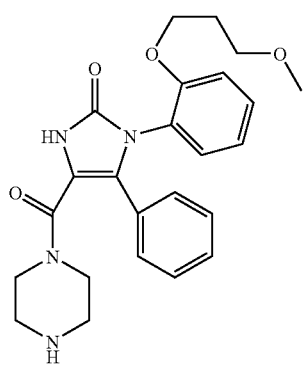

The title compound was prepared according to general procedure, Scheme A, Steps 1-6. $^1$H NMR (400 MHz, MeOD) δ ppm 1.76-1.93 (m, 2H) 2.64 (br. s., 2H) 2.76 (br. s., 2H) 3.31 (s, 3H) 3.42 (t, J=6.19 Hz, 2H) 3.49-3.71 (m, 4H) 3.76-4.03 (m, 4H) 6.91-7.06 (m, 2H) 7.17 (dd, J=7.96, 1.64 Hz, 2H) 7.26-7.42 (m, 5H). ESI-MS: m/z 437.3 (M+H)+.

Example 34

1-(3-(2-Methoxyethoxy)phenyl)-5-phenyl-4-(piperazine-1-carbonyl)-1H-imidazol-2(3H)-one

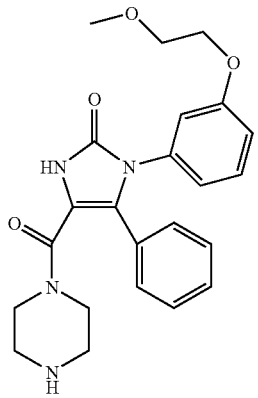

The title compound was prepared according to general procedure, Scheme A, Steps 1-6. $^1$H (400 MHz, DMSO-d$_6$) δ ppm 1.24 (s, 1H), 2.27 (d, J=9.60 Hz, 4H), 3.16 (s, 4H), 3.26 (s, 3H), 3.56 (dd, J=3.79, 2.27 Hz, 2H), 3.96 (dd, J=5.31, 3.79 Hz, 2H), 6.66 (dd, J=8.08, 1.01 Hz, 1H), 6.73 (t, J=2.15 Hz, 1H), 6.85 (dd, J=8.08, 2.27 Hz, 1H), 7.04 (dd, J=7.20, 2.40 Hz, 2H), 7.21 (t, J=8.08 Hz, 1H), 7.26-7.32 (m, 3H), 10.91 (s, 1H). ESI-MS: m/z 423.4 (M+H)+.

Example 35

1-(3-(3-Methoxypropoxy)phenyl)-5-phenyl-4-(piperazine-1-carbonyl)-1H-imidazol-2(3H)-one

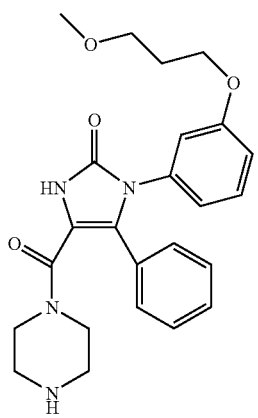

The title compound was prepared according to general procedure, Scheme A, Steps 1-6. $^1$H (400 MHz, DMSO-d$_6$) δ ppm 0.85 (d, J=6.82 Hz, 1H), 1.24 (s, 2H), 1.78-1.88 (m, J=6.32, 6.32, 6.32, 6.32 Hz, 2H), 2.28 (ddd, J=14.27, 4.17, 4.04 Hz, 3H), 3.18 (dd, J=8.59, 4.80 Hz, 3H), 3.23 (s, 3H), 3.40 (t, J=6.19 Hz, 2H), 3.90 (t, J=6.44 Hz, 2H), 6.64 (dd, J=7.96, 0.63 Hz, 1H), 6.73 (t, J=2.02 Hz, 1H), 6.83 (dd, J=8.21, 2.15 Hz, 1H), 7.04 (d, J=9.60 Hz, 1H), 7.04 (d, J=3.28

Hz, 1H), 7.20 (t, J=8.08 Hz, 1H), 7.24-7.32 (m, 1H), 7.28 (d, J=1.77 Hz, 2H), 10.91 (s, 1H). ESI-MS: m/z 437.4 (M+H)+.

Example 36

1-(6-(3-Methoxypropoxy)pyridin-2-yl)-5-phenyl-4-(piperazine-1-carbonyl)-1H-imidazol-2(3H)-one

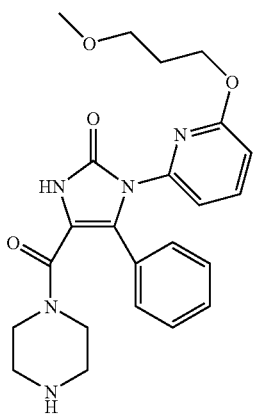

The title compound was prepared according to general procedure, Scheme A, Steps 1-6. ¹H NMR (400 MHz, MeOD) δ ppm 1.65 (m, 2H), 2.73 (br s, 4H), 3.29 (s, 3H), 3.34 (m, 2H), 3.60 (br s, 4H), 3.69 (m, 2H), 6.67 (d, 1H), 7.19 (m, 3H), 7.38 (m, 3H), 7.77 (t, 1H). ESI-MS: m/z 438.2 (M+H)+.

Example 37

(R)-1-Cyclohexyl-4-(3-methylpiperazine-1-carbonyl)-5-phenyl-1H-imidazol-2(3H)-one

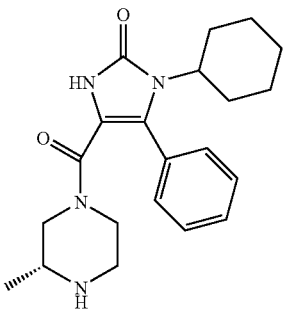

The title compound was prepared according to general procedure, Scheme A, Steps 1-6. ¹H NMR (400 MHz, MeOD) δ ppm 1.15 (m, 6H), 1.59-1.79 (m, 5H), 2.30 (m, 4H), 2.71 (dd, 1H), 2.88 (m, 1H), 3.11 (d, 1H), 3.57 (m, 1H), 4.06 (m, 2H), 7.41 (m, 2H), 7.59 (m, 3H). ESI-MS: m/z 369.2 (M+H)+.

Example 38

1-Cyclohexyl-4-(3-methylpiperazine-1-carbonyl)-5-phenyl-1H-imidazol-2(3H)-one

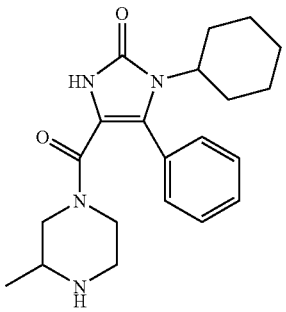

The title compound was prepared according to general procedure, Scheme A, Steps 1-6. ¹H NMR (400 MHz, MeOD) δ ppm 1.03-1.28 (m, 6H) 1.49-1.89 (m, 5H) 2.22-2.44 (m, 4H) 2.60-2.75 (m, 1H) 2.80-2.96 (m, 1H) 3.11 (d, J=12.88 Hz, 1H) 3.47-3.64 (m, 1H) 3.97-4.18 (m, 2H) 7.31-7.46 (m, 2H) 7.51-7.66 (m, 3H) ESI-MS: m/z 369.30 (M+H)+.

Example 39

(S)-1-Cyclohexyl-4-(3-methylpiperazine-1-carbonyl)-5-phenyl-1H-imidazol-2(3H)-one

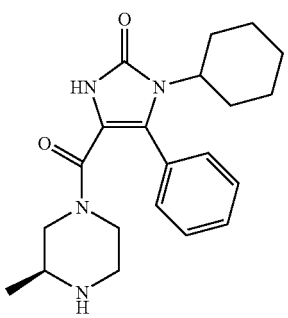

The title compound was prepared according to general procedure, Scheme A, Steps 1-6. ¹H NMR (400 MHz, MeOD) δ ppm 1.16 (m, 6H), 1.59-1.79 (m, 6H), 2.32 (m, 4H), 2.69 (dd, 1H), 2.89 (m, 1H), 3.11 (m, 1H), 3.57 (m, 1H), 4.18 (m, 1H). ESI-MS: m/z 369.2 (M+H)+.

Example 40

1-Cyclohexyl-4-(3,5-dimethylpiperazine-1-carbonyl)-5-phenyl-1H-imidazol-2(3H)-one

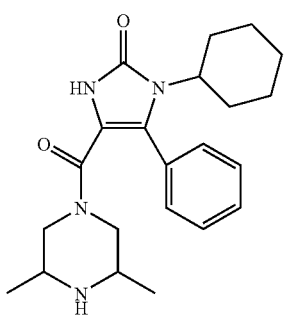

The title compound was prepared according to general procedure, Scheme A, Steps 1-6. ¹H NMR (400 MHz, MeOD) δ ppm 0.93-1.32 (m, 11H) 1.45-1.93 (m, 6H) 2.14-2.44 (m, 6H) 7.32-7.51 (m, 4H) 7.50-7.77 (m, 6H). ESI-MS: m/z 383.10 (M+H)+.

Example 41

1-Cyclohexyl-4-(2,5-dimethylpiperazine-1-carbonyl)-5-phenyl-1H-imidazol-2(3H)-one

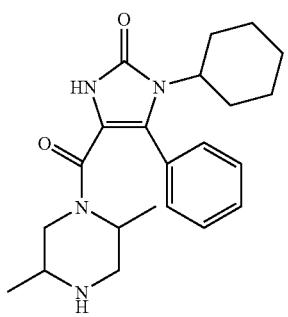

The title compound was prepared according to general procedure, Scheme A, Steps 1-6. $^1$H NMR (400 MHz, MeOD) δ ppm 0.95-1.39 (m, 10H) 1.60 (br. s., 2H) 1.69-1.99 (m, 4H) 2.16-2.40 (m, 2H) 2.71-2.83 (m, 1H) 2.83-2.95 (m, 1H) 3.04 (dd, J=14.65, 3.28 Hz, 1H) 3.38-3.67 (m, 2H) 7.29-7.46 (m, 2H) 7.47-7.65 (m, 3H). ESI-MS: m/z 383.35 (M+H)$^+$.

Example 42

5-(3-Chlorophenyl)-1-(3-(3-methoxypropoxy)phenyl)-4-(piperazine-1-carbonyl)-1H-imidazol-2(3H)-one

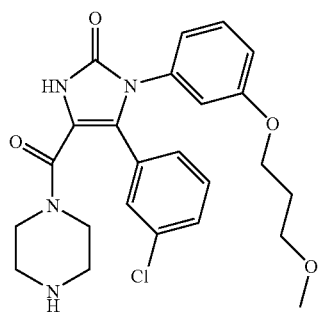

The title compound was prepared according to general procedure, Scheme A, Steps 1-6. $^1$H (400 MHz, DMSO-d$_6$) δ ppm 0.86 (m, 1H), 1.25 (s, 2H), 1.81-1.88 (m, J=6.32, 6.32, 6.32, 6.32 Hz, 2H), 2.33 (s, 3H), 3.16-3.22 (m, 3H), 3.22 (s, 3H), 3.40 (t, J=6.19 Hz, 2H), 3.93 (t, J=6.32 Hz, 2H), 6.67 (dd, J=7.83, 1.01 Hz, 1H), 6.79 (t, J=2.15 Hz, 1H), 6.86 (dd, J=8.08, 2.27 Hz, 1H), 6.95 (dt, J=7.39, 1.48 Hz, 1H), 7.11 (t, J=1.64 Hz, 1H), 7.23 (t, J=8.08 Hz, 1H), 7.28-7.36 (m, 2H), 11.02 (s, 1H). ESI-MS: m/z 471.4 (M+H)$^+$.

Example 43

5-(3-Chlorophenyl)-1-(3-(2-methoxyethoxy)phenyl)-4-(piperazine-1-carbonyl)-1H-imidazol-2(3H)-one

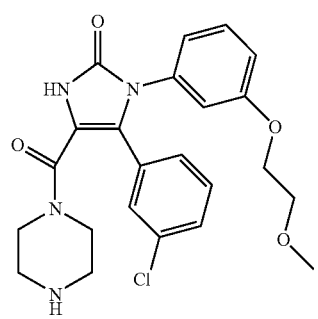

The title compound was prepared according to general procedure, Scheme A, Steps 1-6. $^1$H (400 MHz, DMSO-d$_6$) δ ppm 1.24 (s, 1H), 2.33 (s, 4H), 3.21 (s, 4H), 3.27 (s, 3H), 3.57 (dd, J=3.79, 2.02 Hz, 2H), 4.00 (dd, J=5.18, 3.92 Hz, 2H), 6.69 (dd, J=7.83, 1.01 Hz, 1H), 6.80 (t, J=2.15 Hz, 1H), 6.88 (dd, J=8.21, 2.15 Hz, 1H), 6.93-6.98 (m, 1H), 6.95 (d, J=7.33 Hz, 1H), 7.12 (t, J=1.64 Hz, 1H), 7.24 (t, J=8.08 Hz, 1H), 7.29-7.37 (m, 2H), 11.03 (s, 1H). ESI-MS: m/z 457.3 (M+H)$^+$.

Example 44

1-(1H-benzo[d]imidazol-2-yl)-5-phenyl-4-(piperazine-1-carbonyl)-1H-imidazol-2(3H)-one

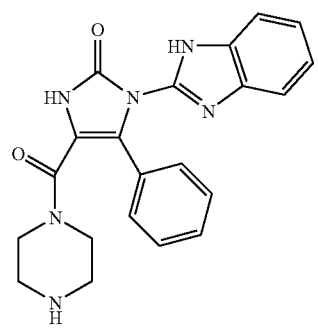

The title compound was prepared according to general procedure, Scheme A, Steps 1-6. ESI-MS: m/z 389.2 (M+H)+.

Example 45

1-Benzyl-3,4-diphenyl-5-(piperazine-1-carbonyl)-1H-imidazol-2(3H)-one

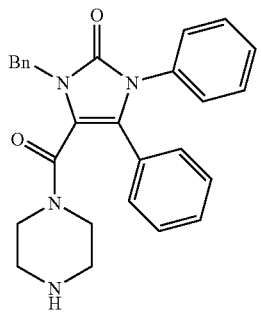

According to the general procedure, Scheme A, Steps 1-5 and 7-8, the title compound was obtained as a yellow oil (83%). 1H NMR (400 MHz, MeOD) δ ppm 2.7 (br s, 4H) 3.6 (br s, 4H), 5 (br, s, 2H), 7.10 (m, 2H) 7.25 (m, 2H), 7.28-7.42 (m, 11H). ESI-MS: m/z 439.4 (M+H)+.

Example 46

1-Benzyl-4-phenyl-5-(piperazine-1-carbonyl)-3-(pyridin-2-yl)-1H-imidazol-2(3H)-one

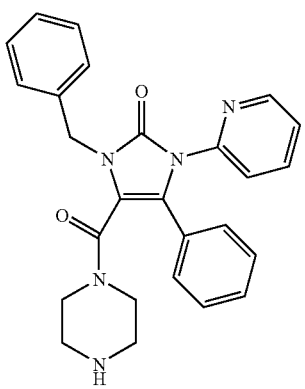

The title compound was prepared according to general procedure, Scheme A, Steps 1-5 and 7-8. 1H NMR (400 MHz, DMSO-d6) δ ppm 2.74 (b, 4H), 3.43 (b, 4H), 6.99 (m, 2H), 7.30 (m, 6H), 7.38 (m, 3H), 7.65 (d, 1H), 7.99 (t, 1H), 8.34 (d, 1H), 8.48 (br s, 1H), 8.60 (br s, 1H). ESI-MS: m/z 440.2 (M+H)+.

Example 47

1-((5-Methylisoxazol-3-yl)methyl)-3,4-diphenyl-5-(piperazine-1-carbonyl)-1H-imidazol-2(3H)-one

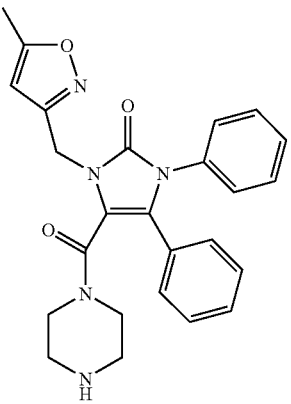

The title compound was prepared according to general procedure, Scheme A, Steps 1-5 and 7-8. 1H NMR (400 MHz, MeOD) δ ppm 2.43 (s, 3H), 2.7 (br s, 4H) 3.6 (br s, 4H), 3.3 (2H), 5.18 (br s, 2H), 6.24 (s, 1H), 7.17 (m, 4H) 7.37 (m, 6H). ESI-MS: m/z 444.4 (M+H)+.

Example 48

1-((5-Cyclopropyl-1,3,4-thiadiazol-2-yl)methyl)-3,4-diphenyl-5-(piperazine-1-carbonyl)-1H-imidazol-2(3H)-one

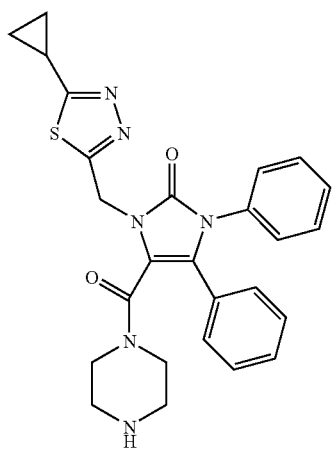

The title compound was prepared according to general procedure, Scheme A, Steps 1-5 and 7-8. 1H NMR (400 MHz, MeOD) δ ppm 1.1 (m, 2H), 1.3 (m, 2H), 2.4 (m, 1H), 2.9 (br s, 4H), 3.6 (br s, 4H), 5.5 (br s, 2H), 7.17 (m, 4H) 7.37 (m, 6H). ESI-MS: m/z 487.4 (M+H)+.

Example 49

1-((1H-Imidazol-4-yl)methyl)-3,4-diphenyl-5-(piperazine-1-carbonyl)-1H-imidazol-2(3H)-one

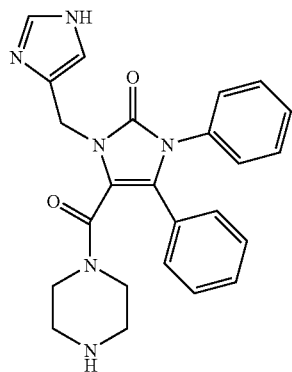

The title compound was prepared according to general procedure, Scheme A, Steps 1-5 and 7-8. ¹H NMR (400 MHz, MeOD) δ ppm 2.9 (br s, 4H), 3.6 (br s, 4H), 5.11 (br s, 2H), 7.17 (m, 4H) 7.38 (m, 6H), 7.63 (s, 1H), 8.80 (s, 1H). ESI-MS: m/z 429.4 (M+H)+.

Example 50

1-((2-Aminothiazol-4-yl)methyl)-3,4-diphenyl-5-(piperazine-1-carbonyl)-1H-imidazol-2(3H)-one

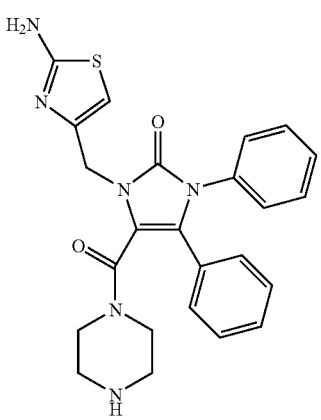

The title compound was prepared according to general procedure, Scheme A, Steps 1-5 and 7-8. ¹H NMR (400 MHz, MeOD) δ ppm 2.9 (br s, 4H), 3.8 (br s, 4H), 5.0 (br s, 2H), 7.17 (m, 5H) 7.38 (m, 6H). ESI-MS: m/z 461.3 (M+H)+.

Example 51

1-(3-Fluorobenzyl)-3,4-diphenyl-5-(piperazine-1-carbonyl)-1H-imidazol-2(3H)-one

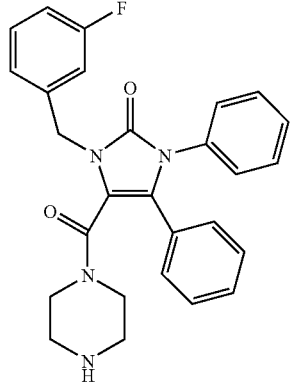

The title compound was prepared according to general procedure, Scheme A, Steps 1-5 and 7-8. ¹H NMR (400 MHz, MeOD) δ ppm 2.6 (br s, 4H) 3.4 (br s, 4H), 5.11 (br s, 2H), 7.06-7.43 (m, 14H). ESI-MS: m/z 457.3 (M+H)+.

Example 52

1-(3,4-Difluorobenzyl)-3,4-diphenyl-5-(piperazine-1-carbonyl)-1H-imidazol-2(3H)-one

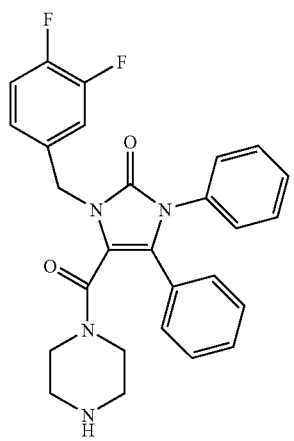

The title compound was prepared according to general procedure, Scheme A, Steps 1-5 and 7-8. ¹H NMR (400 MHz, MeOD) δ ppm 2.8 (br s, 4H) 3.4 (br s, 4H), 5.05 (br s, 2H), 7.1-7.43 (m, 13H). ESI-MS: m/z 475.4 (M+H)+.

Example 53

1,5-Diphenyl-4-(piperazine-1-carbonyl)-3-((tetrahydro-2H-pyran-4-yl)methyl)-1H-imidazol-2(3H)-one

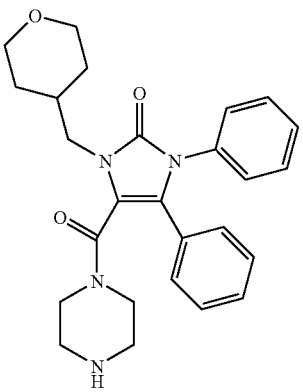

The title compound was prepared according to general procedure, Scheme A, Steps 1-5 and 7-8. ¹H NMR (400 MHz, MeOD) δ ppm 1.37 (m, 2H), 1.62 (m, 2H), 2.06 (m, 1H), 3.0 (m, 4H), 3.41 (t, 2H), 3.45 (m, 4H), 7.17 (m, 4H) 7.38 (m, 6H). ESI-MS: m/z 447.4 (M+H)+.

Example 54

1-Methyl-3,4-diphenyl-5-(piperazine-1-carbonyl)-1H-imidazol-2(3H)-one

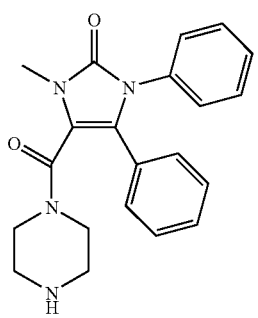

The title compound was prepared according to general procedure, Scheme A, Steps 1-5 and 7-8. ¹H NMR (400 MHz, MeOD) δ ppm 2.7 (br s, 4H), 3.40 (s, 3H), 3.6 (br s, 4H) 7.15 (m, 4H) 7.36 (m, 6H). ESI-MS: m/z 363.4 (M+H)+.

Example 55

(R)-4-(2-Benzylpiperazine-1-carbonyl)-3-methyl-1-(3-morpholinophenyl)-5-phenyl-1H-imidazol-2(3H)-one

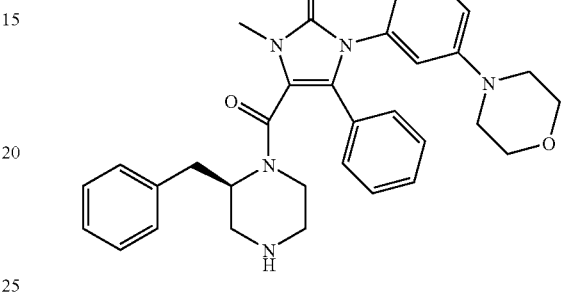

The title compound was prepared according to general procedure, Scheme A, Steps 1-5 and 7-8. ¹H NMR (400 MHz, MeOD) δ ppm 2.4 (m, 2H), 2.6-3.2 (m, 11H), 3.0 (s, 3H), 6.66 (m, 2H), 6.94 (m, 1H), 7.19-7.50 (m, 11H). ESI-MS: m/z 538.5 (M+H)+.

Example 56

1-Benzyl-3-(3-morpholinophenyl)-4-phenyl-5-(piperazine-1-carbonyl)-1H-imidazol-2(3H)-one

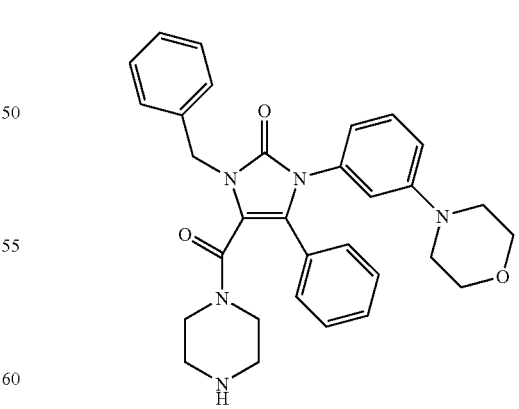

The title compound was prepared according to general procedure, Scheme A, Steps 1-5 and 7-8. ¹H NMR (400 MHz, DMSO-d6) δ ppm 2.99 (s, 4H), 3.67 (s, 4H), 4.97 (br s, 2H), 6.62 (d, 1H), 6.77 (s, 1H), 6.89 (d, 1H), 7.05 (m, 2H), 7.20 (t, 1H), 7.27-7.40 (m, 9H), 8.58 (br d, 2H). ESI-MS: m/z 524.3 (M+H)+

Example 57

1-(3-(Morpholine-4-carbonyl)benzyl)-3-(3-morpholinophenyl)-4-phenyl-5-(piperazine-1-carbonyl)-1H-imidazol-2(3H)-one

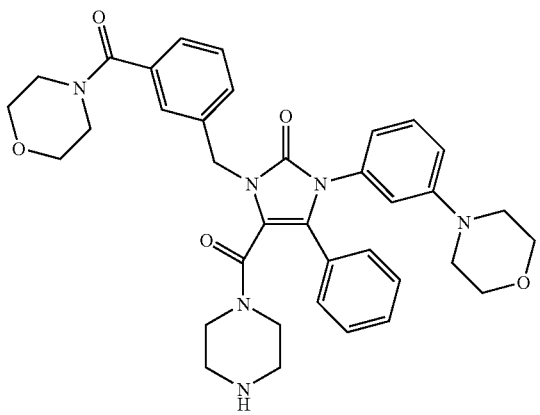

The title compound was prepared according to general procedure, Scheme A, Steps 1-5 and 7-8. ¹H NMR (400 MHz, MeOD) δ ppm 3.03 (m, 4h), 3.44 (br s, 2H), 3.63 (br s, 2H), 3.75 (m, 6H), 6.69 (m, 2H), 6.78 (m, 1H), 6.94 (m, 1H), 7.14 (m, 2H), 7.26 (m, 1H), 7.35 (m, 5H), 7.52 (m, 3H). ESI-MS: m/z 637.3 (M+H)+.

Example 58

1-(3-Morpholinophenyl)-5-phenyl-4-(piperazine-1-carbonyl)-3-(3-(piperidine-1-carbonyl)benzyl)-1H-imidazol-2(3H)-one

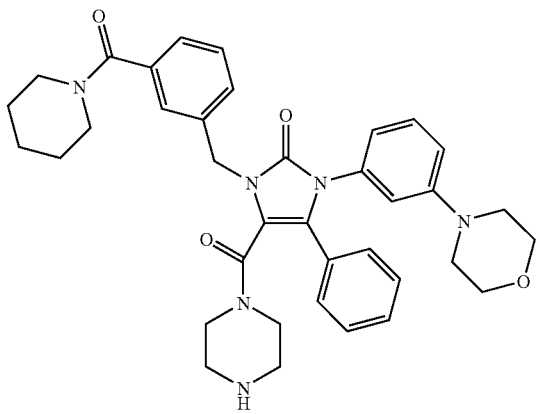

The title compound was prepared according to general procedure, Scheme A, Steps 1-5 and 7-8. ¹H NMR (400 MHz, MeOD) δ ppm 1.55-1.74 (br s, 10H), 3.03 (m, 6H), 3.37 (m, 4H), 3.75 (m, 9H), 6.71 (m, 2H), 6.79 (m, 1H), 6.97 (m, 1H), 7.14 (m, 2H), 7.25 (m, 1H), 7.31-7.42 (m, 6H), 7.49-7.57 (m, 3H). ESI-MS: m/z 635.3 (M+H)+.

Example 59

2-(3-((3-(3-Morpholinophenyl)-2-oxo-4-phenyl-5-(piperazine-1-carbonyl)-2,3-dihydro-1H-imidazol-1-yl)methyl)phenoxy)acetic acid

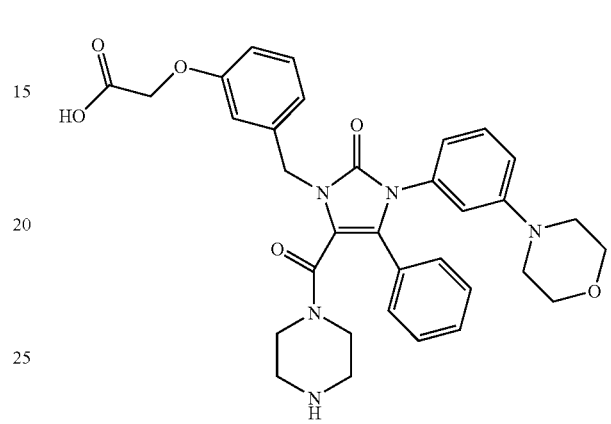

The title compound was prepared according to general procedure, Scheme A, Steps 1-5 and 7-8. ¹H NMR (400 MHz, MeOD) δ ppm 3.05 (m, 4H), 3.77 (m, 4H), 3.98 (s, 2H), 4.75 (s, 2H), 6.71 (m, 1H), 6.82 (m, 2H), 6.88 (m, 1H), 6.97 (m, 2H), 7.12 (m, 2H), 7.26 (t, 2H), 7.32 (m, 3H). ESI-MS: m/z 598.3 (M+H)+.

Example 60

1-Cyclohexyl-3-methyl-5-phenyl-4-(piperazine-1-carbonyl)-1H-imidazol-2(3H)-one

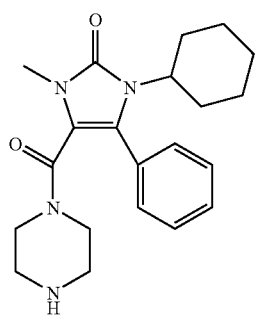

The title compound was prepared according to general procedure, Scheme A, Steps 1-5 and 7-8. ¹H NMR (400 MHz, MeOD) δ ppm 1.05-1.27 (m, 3H) 1.61 (br. s., 1H) 1.64-1.88 (m, 4H) 2.21-2.45 (m, 3H) 3.32 (br. s., 1H) 3.54 (br. s., 4H)

3.61 (dd, J=11.37, 7.83 Hz, 2H) 3.62-3.69 (m, 4H) 7.26-7.44 (m, 2H) 7.46-7.70 (m, 3H). ESI-MS: m/z 369.30 (M+H)+.

Example 61

1-Isopropyl-3-(3-(3-(3-morpholinophenyl)-2-oxo-4-phenyl-5-(piperazine-1-carbonyl)-2,3-dihydro-1H-imidazol-1-yl)propyl)urea

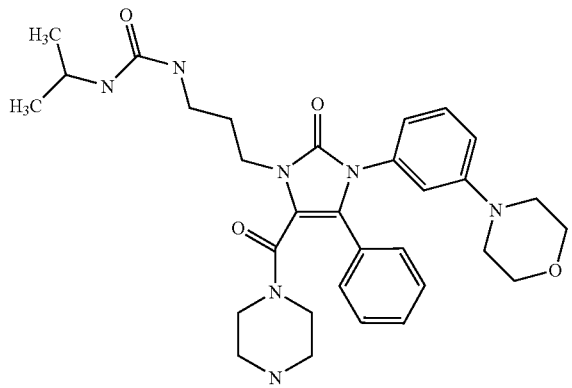

The title compound was prepared according to general procedure, Scheme A, Steps 1-5 and 7-8. ESI-MS: m/z 576.3 (M+H)+.

Example 62

1-Allyl-3-cyclohexyl-4-phenyl-5-(piperazine-1-carbonyl)-1H-imidazol-2(3H)-one

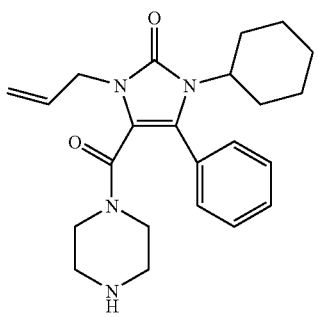

The title compound was prepared according to general procedure, Scheme A, Steps 1-5 and 7-8. $^1$H NMR (400 MHz, MeOD) δ ppm 1.17 (d, J=7.83 Hz, 3H) 1.47-2.00 (m, 6H) 2.33 (d, J=11.87 Hz, 3H) 2.66-3.22 (m, 2H) 3.35-3.78 (m, 5H) 4.42 (d, J=4.29 Hz, 2H) 5.08 (d, J=17.18 Hz, 1H) 5.18 (d, J=10.36 Hz, 1H) 5.73-5.97 (m, 1H) 7.23-7.46 (m, 2H) 7.47-7.71 (m, 3H) 7.51-7.71 (m, 3H). ESI-MS: m/z 395.30 (M+H)+.

Example 63

2-(3-Cyclohexyl-2-oxo-4-phenyl-5-(piperazine-1-carbonyl)-2,3-dihydro-1H-imidazol-1-yl)acetamide

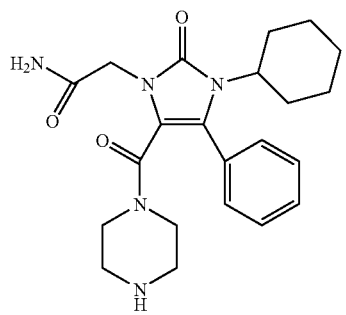

The title compound was prepared according to general procedure, Scheme A, Steps 1-5 and 7-8. $^1$H NMR (400 MHz, MeOD) δ ppm 1.07-1.23 (m, 3H) 1.60 (br. s., 1H) 1.68-1.88 (m, 4H) 2.21-2.40 (m, 2H) 2.86 (s, 2H) 3.00 (s, 2H) 3.35 (s, 1H) 3.46 (br. s., 3H) 3.98 (s, 1H) 4.58 (br. s., 2H) 7.28-7.46 (m, 2H) 7.50-7.67 (m, 3H). ESI-MS: m/z 412.30 (M+H)+.

Example 64

(R)-1-Allyl-5-(2-benzylpiperazine-1-carbonyl)-3-cyclohexyl-4-phenyl-1H-imidazol-2(3H)-one

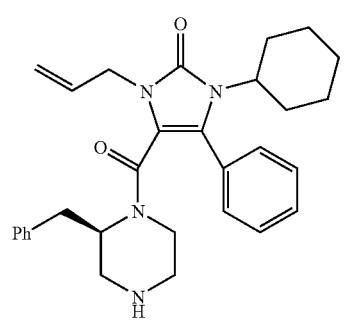

The title compound was prepared according to general procedure, Scheme A, Steps 1-5 and 7-8. $^1$H NMR (400 MHz, MeOD) δ ppm 1.16 (br. s., 5H) 1.61 (br. s., 3H) 1.82 (br. s., 4H) 2.31 (br. s., 4H) 3.54-3.72 (m, 2H) 3.98 (s, 2H) 5.12 (br.

s., 2H) 5.75 (br. s., 1H) 7.04-7.47 (m, 6H) 7.59 (br. s., 4H). ESI-MS: m/z 485.40 (M+H)$^+$.

Example 65

(R)-4-(2-Benzylpiperazine-1-carbonyl)-1-cyclohexyl-3-methyl-5-phenyl-1H-imidazol-2(3H)-one

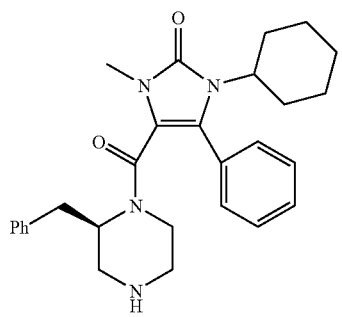

The title compound was prepared according to general procedure, Scheme A, Steps 1-5 and 7-8. $^1$H NMR (400 MHz, CHLOROFORM-d) δ ppm 1.16 (br. s., 5H) 1.59 (br. s., 3H) 1.81 (br. s., 4H) 2.20-2.53 (m, 2H) 3.40-3.73 (m, 6H) 3.99 (s, 3H) 7.28 (br. s., 6H) 7.54 (br. s., 4H). ESI-MS: m/z 459.40 (M+H)$^+$.

Example 66

(R)-4-(2-Benzylpiperazine-1-carbonyl)-1-cyclohexyl-3-(2-methoxyethyl)-5-phenyl-1H-imidazol-2(3H)-one

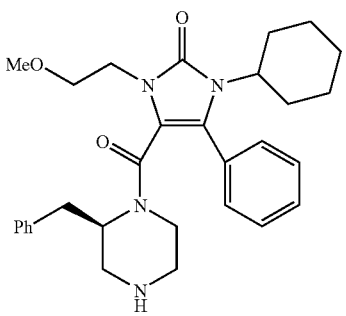

The title compound was prepared according to general procedure, Scheme A, Steps 1-5 and 7-8. $^1$H NMR (400 MHz, CHLOROFORM-d) δ ppm 0.96-1.22 (m, 5H) 1.37-1.63 (m, 4H) 1.66-1.93 (m, 4H) 2.18-2.42 (m, 3H) 3.33-3.57 (m, 8H) 3.96 (s, 2H) 7.26-7.40 (m, 6H) 7.41-7.58 (m, 4H). ESI-MS: m/z 503.40 (M+H)$^+$.

Example 67

(R)-2-(5-(2-Benzylpiperazine-1-carbonyl)-3-cyclohexyl-2-oxo-4-phenyl-2,3-dihydro-1H-imidazol-1-yl)acetamide

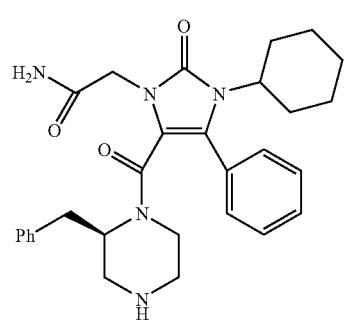

The title compound was prepared according to general procedure, Scheme A, Steps 1-5 and 7-8. $^1$H NMR (400 MHz, CHLOROFORM-d) δ ppm 1.00-1.35 (m, 5H) 1.48-1.98 (m, 5H) 2.22 (br. s., 2H) 2.98 (s, 2H) 3.08 (s, 2H) 3.79 (s, 2H) 3.99 (s, 2H) 7.54 (br. s., 2H) 9.20 (br. s., 8H). ESI-MS: m/z 502.3 (M+H)$^+$.

Example 68

Methyl 2-(3-cyclohexyl-2-oxo-4-phenyl-5-(piperazine-1-carbonyl)-2,3-dihydro-1H-imidazol-1-yl)-2-phenylacetate

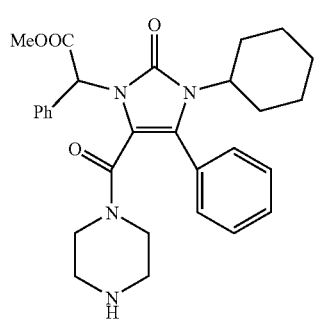

The title compound was prepared according to general procedure, Scheme A, Steps 1-5 and 7-8. $^1$H NMR (400 MHz, MeOD) δ ppm 1.05-1.45 (m, 4H) 1.55-1.68 (m, 1H) 1.70-1.93 (m, 4H) 2.23-2.47 (m, 4H) 2.66-2.76 (m, 3H) 3.08-3.30

(m, 2H) 3.56-3.78 (m, 2H) 7.27-7.42 (m, 6H) 7.48-7.64 (m, 4H). ESI-MS: m/z 503.30 (M+H)⁺.

Example 69

1-Cyclohexyl-5-phenyl-3-(1-phenylethyl)-4-(piperazine-1-carbonyl)-1H-imidazol-2(3H)-one

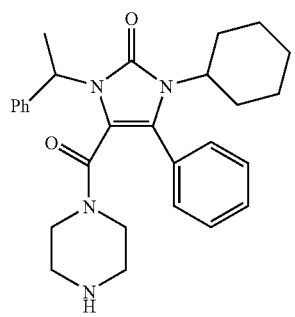

The title compound was prepared according to general procedure, Scheme A, Steps 1-5 and 7-8. ¹H NMR (400 MHz, MeOD) δ ppm 1.01-1.42 (m, 4H) 1.49-1.70 (m, 4H) 1.78 (d, J=14.91 Hz, 1H) 1.88-2.00 (m, 4H) 2.21-2.55 (m, 4H) 2.68-3.07 (m, 2H) 3.52-3.81 (m, 2H) 5.60 (br. s., 2H) 7.24-7.35 (m, 5H) 7.47-7.62 (m, 5H). ESI-MS: m/z 459.20 (M+H)⁺.

Example 70

(R)-4-(2-Benzylpiperazine-1-carbonyl)-1-cyclohexyl-3-methyl-5-phenyl-1H-imidazol-2(3H)-one

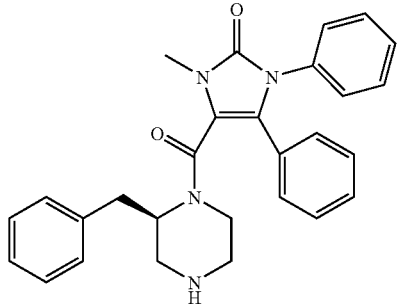

The title compound was prepared according to general procedure, Scheme A, Steps 1-5 and 7-8. ¹H NMR (400 MHz, CHLOROFORM-d) δ ppm 1.16 (br. s., 5H) 1.59 (br. s., 3H) 1.81 (br. s., 4H) 2.20-2.53 (m, 2H) 3.40-3.73 (m, 6H) 3.99 (s, 3H) 7.28 (br. s., 6H) 7.54 (br. s., 4H). ESI-MS: m/z 459.40 (M+H)⁺.

Example 71

1-Cyclohexyl-3-phenethyl-5-phenyl-4-(piperazine-1-carbonyl)-1H-imidazol-2(3H)-one

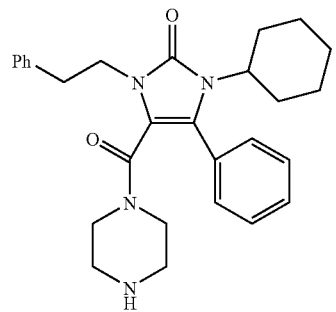

The title compound was prepared according to general procedure, Scheme A, Steps 1-5 and 7-8. ¹H NMR (400 MHz, MeOD) δ ppm 0.96-1.47 (m, 6H) 1.50-2.10 (m, 6H) 2.15-2.52 (m, 2H) 2.80-3.26 (m, 4H) 3.39-3.83 (m, 3H) 4.04 (t, J=6.95 Hz, 2H) 7.04-7.43 (m, 6H) 7.47-7.74 (m, 4H). ESI-MS: m/z 459.20 (M+H)⁺.

Example 72

1-(3-(1H-Pyrrol-1-yl)benzyl)-3-cyclohexyl-4-phenyl-5-(piperazine-1-carbonyl)-1H-imidazol-2(3H)-one

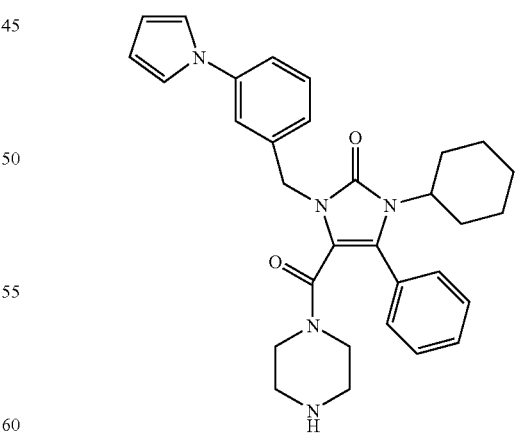

The title compound was prepared according to general procedure, Scheme A, Steps 1-5 and 7-8. ¹H NMR (400 MHz, MeOD) δ ppm 1.03-1.42 (m, 5H) 1.53-1.95 (m, 5H) 2.19-2.54 (m, 4H) 3.02-3.25 (m, 3H) 3.56-3.75 (m, 2H) 4.97-5.14 (m, 2H) 6.23-6.34 (m, 2H) 7.17-7.23 (m, 2H) 7.31-7.37 (m, 2H) 7.38-7.41 (m, 1H) 7.41-7.46 (m, 2H) 7.52-7.60 (m, 4H). ESI-MS: m/z 510.20 (M+H)$^+$.

Example 73

1-(3-(2-Phenoxyethoxy)benzyl)-4-phenyl-5-(piperazine-1-carbonyl)-3-o-tolyl-1H-imidazol-2(3H)-one

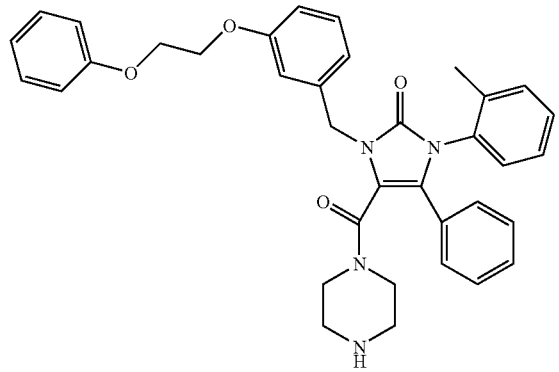

A. 1-Methyl-3-(2-phenoxyethoxy)benzene

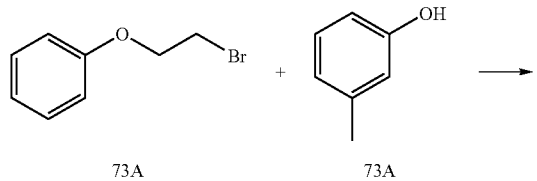

To a solution of m-cresol (73B) (5.4 mL, 50 mmol) in EtOH (72 mL) was added aqueous 10M NaOH (2.14 g, 53.5 mmol), followed by 73A (7.59 g, 37 mmol). The reaction mixture was refluxed for 24 hrs. The solvents were removed under reduced pressure. The residue was dissolved in ethyl acetate, washed with 10% NaOH, and then filtered. The aqueous phase was washed with saturated brine, dried over Na$_2$SO$_4$ and evaporated to give the (73C) as white solid. $^1$H-NMR: δ ppm 2.33 (s, 3H), 4.32 (s, 4H), 6.78-7.30 (m, 9H).

B. 1-(Bromomethyl)-3-(2-phenoxyethoxy)benzene (73D)

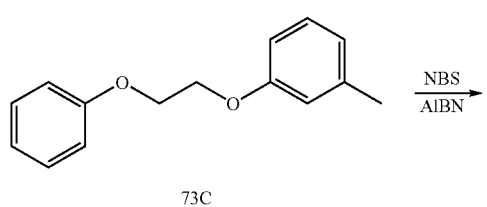

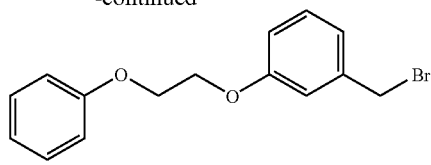

To a solution of 73C (6.5 g, 28.5 mmol) and NBS (6.1 g, 28.5 mmol) in dry CCl$_4$ (120 mL), catalytic amount of AIBN (0.46 g, 2.8 mmol) was added and refluxed at 78° C. for 24 hrs. The hot solution was filtered and the filtrate was concentrated under reduced pressure. The crude product was chromatographed over silica gel using a mixture of ethyl acetate and PE which gave (73D) as white powder. $^1$H NMR (300 MHz, CDCl$_3$): δ ppm 4.33 (s, 4H), 4.46 (s, 2H), 6.93-7.25 (m, 9H).

C. 1-(3-(2-Phenoxyethoxy)benzyl)-4-phenyl-5-(piperazine-1-carbonyl)-3-o-tolyl-1H-imidazol-2(3H)-one (73F)

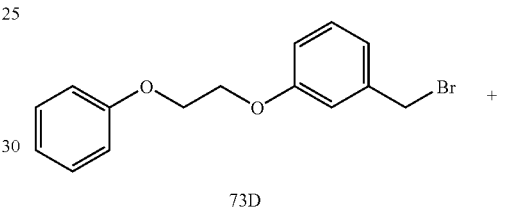

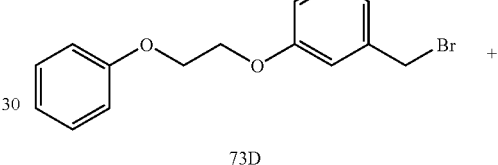

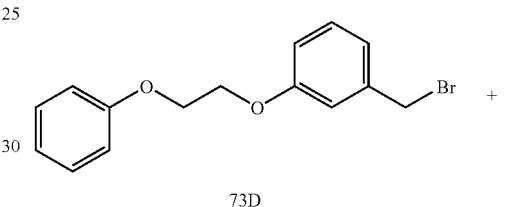

The title compound was prepared by the coupling of 73D to 73E followed by deprotection according to general procedure, Scheme A, Steps 7-8. ESI-MS: m/z 589.8 (M+H)+.

Example 74

1-(3-Morpholinophenyl)-3-(3-phenoxybenzyl)-5-phenyl-4-(piperazine-1-carbonyl)-1H-imidazol-2(3H)-one

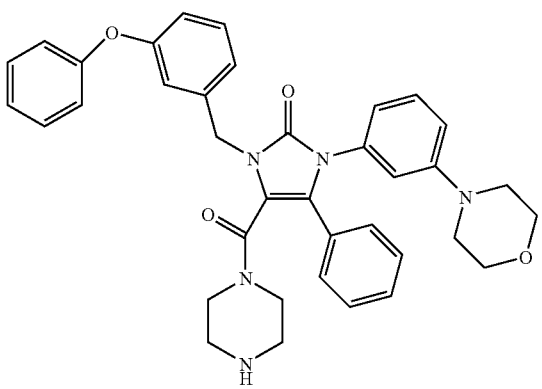

The title compound was prepared according to general procedure, Scheme A, Steps 1-5 and 7-8. $^1$H NMR (400 MHz, MeOD) δ ppm 3.02 (m, 4H), 3.76 (m, 4H), 5.1 (br s, 4H), 6.67 (dd, 1H), 6.74 (m, 1H), 6.95 (m, 3H), 7.01 (m, 2H), 7.08 (m, 1H), 7.12 (m, 3H), 7.17 (m, 1H), 7.25 (t, 1H), 7.36 (m, 6H). ESI-MS: m/z 616.3 (M+H)+.

Example 75

1-(3-(3-Methoxypropoxy)phenyl)-3-(3-phenoxybenzyl)-5-phenyl-4-(piperazine-1-carbonyl)-1H-imidazol-2(3H)-one

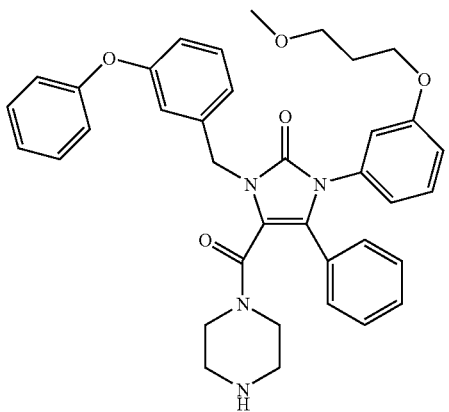

The title compound was prepared according to general procedure, Scheme A, Steps 1-5 and 7-8. $^1$H NMR (400 MHz, MeOD) δ ppm 1.95 (p, 2H), 3.34 (s, 3H), 3.52 (t, 2H), 3.98 (t, 2H), 6.75 (m, 1H), 6.79 (m, 1H), 7.02 (m, 3H), 7.04 (m, 2H), 7.13 (m, 1H), 7.15 (m, 2H), 7.20 (m, 1H), 7.28 (t, 1H), 7.39 (m, 6H). ESI-MS: m/z 619.3 (M+H)+.

Example 76

1-(3-(Benzyloxy)benzyl)-3-(3-morpholinophenyl)-4-phenyl-5-(piperazine-1-carbonyl)-1H-imidazol-2(3H)-one

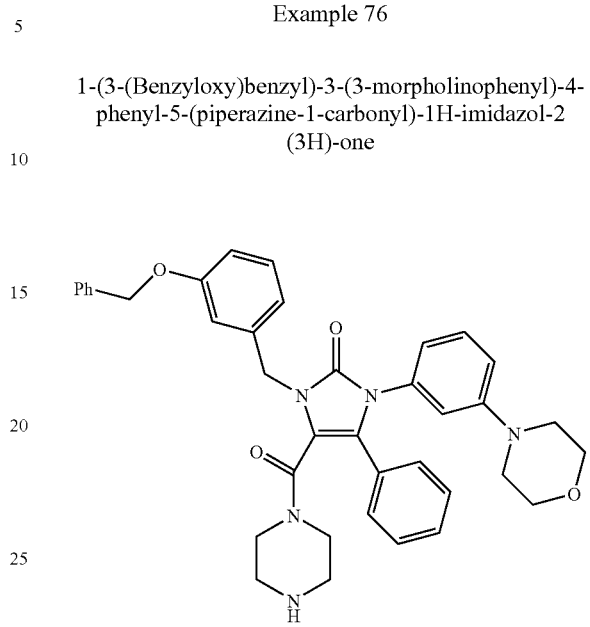

The title compound was prepared according to general procedure, Scheme A, Steps 1-5 and 7-8. $^1$H NMR (400 MHz, MeOD) δ ppm 3.03 (m, 4H), 3.75 (m, 4H), 6.75 (m, 2H), 6.89 (m, 1H), 6.97 (mm 4H), 7.10 (m, 2H), 7.25-7.39 (m, 11H), 7.46 (m, 2H). ESI-MS: m/z 630.3 (M+H)+.

Example 77

1-(3-(1H-Pyrrol-1-yl)benzyl)-3-(3-morpholinophenyl)-4-phenyl-5-(piperazine-1-carbonyl)-1H-imidazol-2(3H)-one

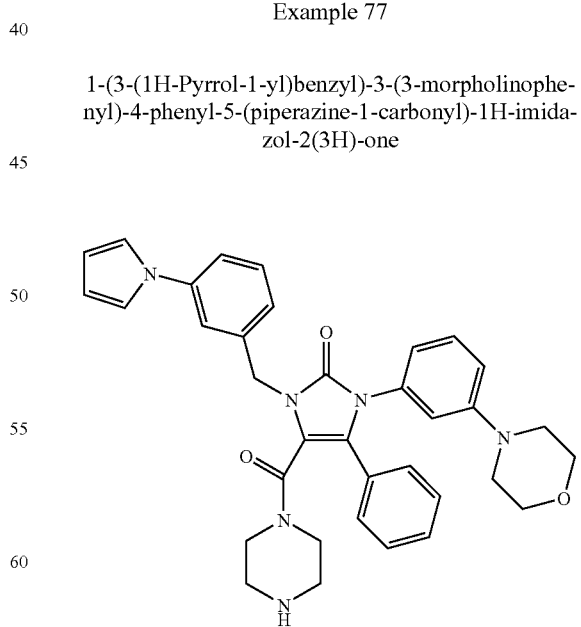

The title compound was prepared according to general procedure, Scheme A, Steps 1-5 and 7-8. $^1$H NMR (400 MHz, MeOD) δ ppm 3.05 (m, 4H), 3.76 (m, 4H), 6.31 (m, 2H), 6.73

(m, 1H), 6.79 (m, 1H), 6.96 (dd, 1H), 7.13 (m, 2H), 7.24 (m, 4H), 7.34 (m, 3H), 7.47 (m, 3H). ESI-MS: m/z 589.3 (M+H)+.

Example 78

N-isobutyl-N-methyl-3-((3-(3-morpholinophenyl)-2-oxo-4-phenyl-5-(piperazine-1-carbonyl)-2,3-dihydro-1H-imidazol-1-yl)methyl)benzamide

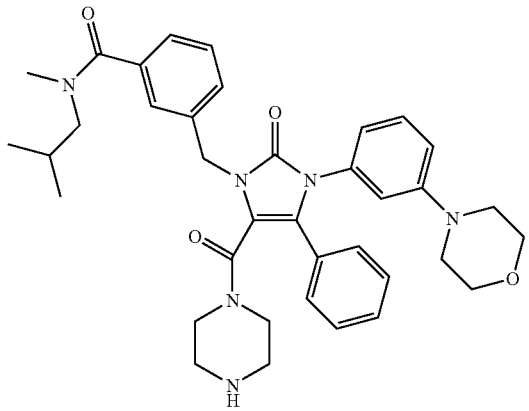

The title compound was prepared according to general procedure, Scheme A, Steps 1-5 and 7-8. ESI-MS: m/z 637.4 (M+H)+.

Example 79

3-((2-oxo-3,4-diphenyl-5-(piperazine-1-carbonyl)-2,3-dihydro-1H-imidazol-1-yl)methyl)benzonitrile

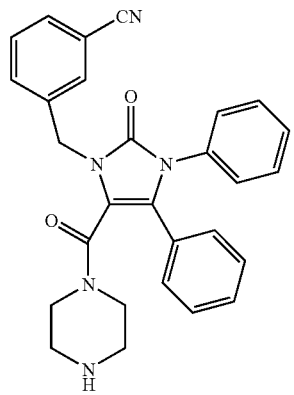

The title compound was prepared according to general procedure, Scheme A, Steps 1-5 and 7-8. $^1$H NMR (400 MHz, CDCl$_3$-CD$_3$OD 10:1) δ ppm 7.52 (br. s., 1H) 7.43 (m, 2H) 7.33 (t, J=7.9 Hz, 1H) 7.09-7.18 (m, 6H) 6.96 (bt. J=6.3, 2.0 Hz, 2H) 6.85 (bdd. J=6.4, 1.5 Hz, 2H), 4.90 (bs. s., 1H) 2.95 (m, 4H) 2.45 (m, 4H). ESI-MS: m/z 464.3 (M+H)+.

Example 80

Methyl 3-((2-oxo-3,4-diphenyl-5-(piperazine-1-carbonyl)-2,3-dihydro-1H-imidazol-1-yl)methyl)benzoate

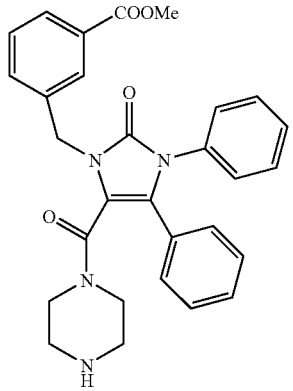

The title compound was prepared according to general procedure, Scheme A, Steps 1-5 and 7-8. $^1$H NMR (400 MHz, CDCl$_3$-CD$_3$OD 10:1) δ ppm 7.77 (dt, J=7.8, 1.3 Hz, 2H) 7.73 (t, J=1.5 Hz, 1H) 7.42 (ddd, J=7.7, 1.4, 1.3 Hz, 3H) 7.29 (t, J=7.7 Hz, 1H) 7.07-7.18 (m, 6H) 6.96 (m, 1H) 6.84 (m, 1H) 2.95 (bm, 4H) 2.45 (bm, 4H) 3.72 (s, 3H). ESI-MS: m/z 497.2 (M+H)+.

Example 81

1-Benzyl-4-phenyl-5-(piperazine-1-carbonyl)-3-(tetrahydro-2H-pyran-4-yl)-1H-imidazol-2(3H)-one

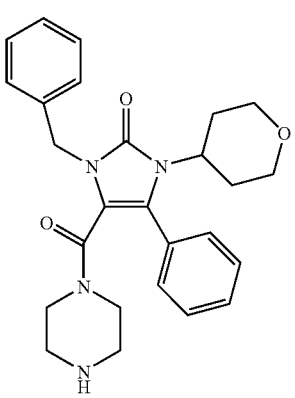

The title compound was prepared according to general procedure, Scheme A, Steps 1-5 and 7-8. $^1$H NMR (400 MHz, DMSO-d$_6$) δ ppm 1.46-1.78 (m, 2H) 2.00 (s, 2H) 2.51-2.68 (m, 2H) 2.92-3.31 (m, 6H) 3.44-3.87 (m, 6H) 4.86 (br. s., 1H)

7.17 (d, J=7.58 Hz, 2H) 7.22-7.41 (m, 5H) 7.46-7.63 (m, 3H) 8.63 (br. s., 1H). ESI-MS: m/z 447.20 (M+H)$^+$.

Example 82

1,5-Diphenyl-4-(piperazine-1-carbonyl)-3-(quinolin-8-ylmethyl)-1H-imidazol-2(3H)-one

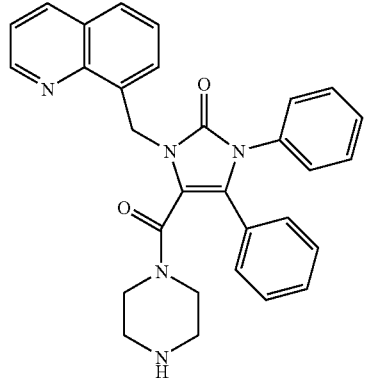

The title compound was prepared according to general procedure, Scheme A, Steps 1-5 and 7-8. $^1$H NMR (400 MHz, CDCl$_3$-CD$_3$OD 10:1) δ ppm 8.96 (dd, J=4.7, 1.6 Hz, 1H) 8.43 (dd, J=8.3, 1.5 Hz, 1H) 7.88 (d, J=8.8 Hz, 2H) 7.61 (m, 2H) 7.15-7.26 (m, 25H) 7.04 (dd, J=8.0, 1.6 Hz, 1H) 6.89 (dd, J=8.0, 1.6, 1H) 5.57 (s, 1H). ESI-MS: m/z 490.2 (M+H)$^+$.

Example 83

1-(3-methoxybenzyl)-3,4-diphenyl-5-(piperazine-1-carbonyl)-1H-imidazol-2(3H)-one

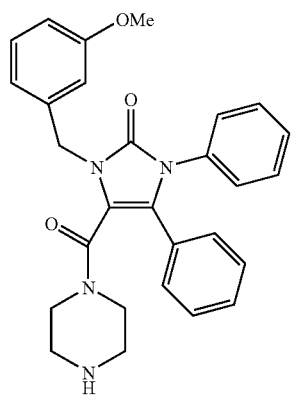

The title compound was prepared according to general procedure, Scheme A, Steps 1-5 and 7-8. $^1$H NMR (400 MHz, CDCl$_3$-CD$_3$OD 10:1) δ ppm 7.01-7.17 (m, 7H) 6.97 (d, J=7.1 Hz, 2H) 6.80 (dd, J=7.7, 1.4 Hz, 2H) 6.68-6.71 (m, 2H) 6.71 (s, 2H) 6.63 (dd, J=8.2, 2.4 Hz, 3H) 5.13 (s, 1H) 4.53 (bs, 1H) 3.61 (s., 3H) 3.17 (bs., 1H) 2.32 (bs., 2H) 2.22 (bs., 1H) 1.58 (bs, 1H) 1.29 (bs, 1H). ESI-MS: m/z 469.2 (M+H)$^+$.

Example 84

1-(Naphthalen-2-ylmethyl)-3,4-diphenyl-5-(piperazine-1-carbonyl)-1H-imidazol-2(3H)-one

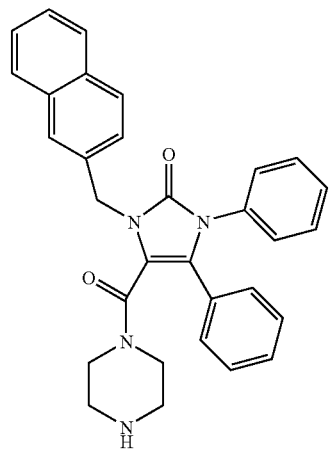

The title compound was prepared according to general procedure, Scheme A, Steps 1-5 and 7-8. $^1$H NMR (400 MHz, CDCl$_3$-CD$_3$OD 10:1) δ ppm 7.67-7.76 (m, 4H) 7.36-7.43 (m, 2H) 7.33 (dd, J=8.3, 1.8 Hz, 1H) 7.10-7.28 (m, 6H) 7.09 (d, J=6.8 Hz, 2H) 6.88 (d, J=6.6 Hz, 2H). ESI-MS: m/z 489.2 (M+H)$^+$.

Example 85

2-((2-Oxo-3,4-diphenyl-5-(piperazine-1-carbonyl)-2,3-dihydro-1H-imidazol-1-yl)methyl)benzonitrile

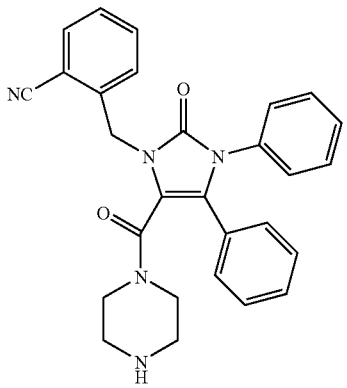

The title compound was prepared according to general procedure, Scheme A, Steps 1-5 and 7-8. $^1$H NMR (400 MHz, CDCl$_3$-CD$_3$OD 10:1) δ ppm 7.60 (d, J=7.6 Hz, 1H) 7.46-7.56 (m, 3H) 7.34 (t, J=7.6 Hz, 1H) 7.17-7.29 (m, 5H) 7.06 (bd, J=8.1 Hz, 2H) 6.94 (bd, J=6.8 Hz, 2H). ESI-MS: m/z 464.2 (M+H)$^+$.

Example 86

1-(3,5-Dimethoxybenzyl)-3,4-diphenyl-5-(piperazine-1-carbonyl)-1H-imidazol-2(3H)-one

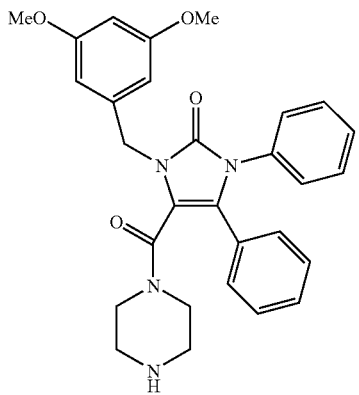

$^1$H NMR (400 MHz, CDCl$_3$-CD$_3$OD 10:1) δ ppm 7.06-7.18 (m, 6H) 6.96 (d, J=6.6 Hz, 2H) 6.81 (d, J=6.2 Hz, 2H) 6.26 (d, J=2.0 Hz, 2H) 6.21 (t, J=2.1 Hz, 1H) 3.59 (s, 6H). ESI-MS: m/z 499.2 (M+H)$^+$.

Example 87

1-(4-Chloro-3-(trifluoromethoxy)benzyl)-3,4-diphenyl-5-(piperazine-1-carbonyl)-1H-imidazol-2(3H)-one

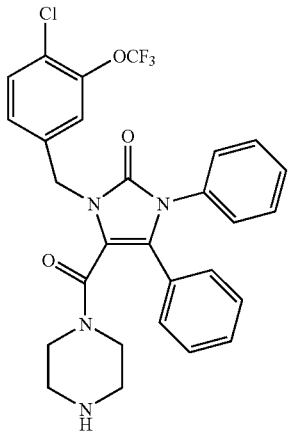

1H-NMR (400 MHz, CDCl3-CD3OD 10:1) δ ppm 7.39 (d, J=8.3 Hz, 1H) 7.17-7.27 (m, 8H) 7.03 (d, J=6.3 Hz, 2H) 6.93 (d, J=7.1 Hz, 2H) 4.96 (bs, 1H). ESI-MS: m/z 557.2 (M+H)$^+$.

Example 88

1-(3-(1H-Pyrrol-1-yl)benzyl)-3,4-diphenyl-5-(piperazine-1-carbonyl)-1H-imidazol-2(3H)-one

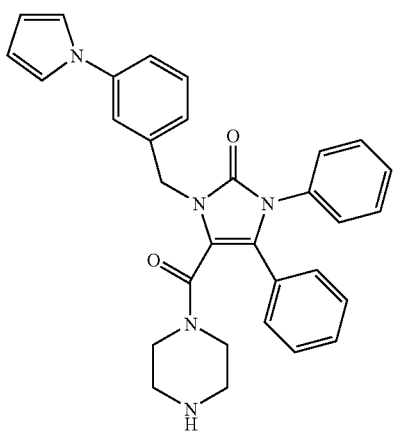

$^1$H-NMR (400 MHz, CDCl$_3$-CD$_3$OD 10:1) δ ppm 7.05-7.34 (m, 14H) 6.90 (d, J=6.8 Hz, 2H) 6.25 (t, J=1.9 Hz, 2H). ESI-MS: m/z 504.2 (M+H)$^+$.

Example 89

1-Cyclohexyl-4-(1,4-diazepane-1-carbonyl)-5-phenyl-1H-imidazol-2(3H)-one

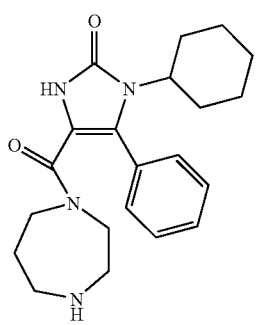

$^1$H NMR (400 MHz, CHLOROFORM-d) δ ppm 7.40 (m, 3H) 7.17 (m., 2H) 3.03 (m., 3H) 2.94 (m., 2H) 2.21 (m 2H) 1.87 (m 2H) 1.70 (m., 2H) 1.60 (m., 2H) 1.50 (m, 1H) 1.05 (m., 3H). ESI-MS: calc'd for C$_{21}$H$_{29}$N$_4$O$_2$, 369.2. found 469.2, (M+H)$^+$.

Example 90

1-((2-Chloro-6-morpholinopyridin-4-yl)methyl)-3-cyclohexyl-4-phenyl-5-(piperazine-1-carbonyl)-1H-imidazol-2(3H)-one

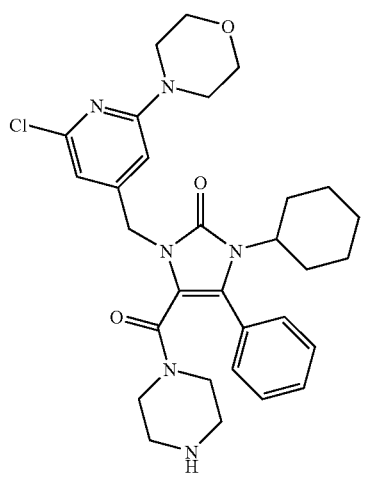

¹H NMR (400 MHz, CDCl3-d) δ ppm 7.43 (m., 3H), 7.16 (m, 2H), 6.14, 6.30 (s, 1H each), 4.79 (brs, 2H), 3.70 (t, J=4.6 Hz, 4H), 3.51 (m, 2H), 3.42 (dd, J=5.3, 4.3 Hz, 4H), 3.38-3.46 (m, 1H), 3.25 (br. s., 3H), 2.24 (m, 3H), 2.15-2.37 (m, 4H), 1.73 (d, J=11.6 Hz, 2H), 1.65 (d, J=11.7 Hz, 2H), 1.52 (d, J=9.9 Hz, 1H), 1 1.04-1.16 (m, 4H). ESI-MS: calc'd for $C_{30}H_{38}ClN_6O_3$, 565.3. found 565.3. (M+H)⁺.

Example 91

1-Cyclohexyl-3-((2,6-di(1H-pyrazol-4-yl)pyridin-4-yl)methyl)-5-phenyl-4-(piperazine-1-carbonyl)-1H-imidazol-2(3H)-one

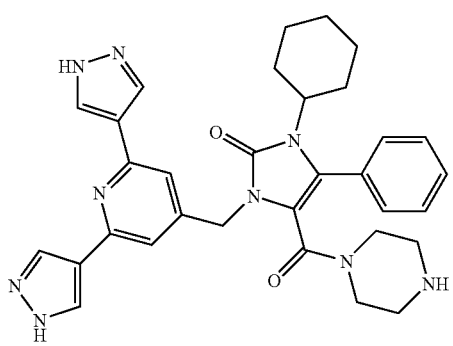

¹H NMR (400 MHz, CHLOROFORM-d) δ ppm 8.18 (s, 4H), 7.43 (m, 3H), 7.31 (s, 2H), 7.18 (m, 2H), 5.23 (s, 1H), 4.97 (br. s., 2H), 3.08 (m, 4H), 2.34 (br. s., 1H), 2.28 (br. s., 2H), 2.19 (br. s., 2H), 1.77 (m, 2H), 1.70 (m, 2H), 1.53 (m, 1H), 1.25-1.0 (m, 4H). ESI-MS: calc'd for $C_{32}H_{36}N_9O_2$, 578.3. found 578.3, (M+H)⁺.

Example 92

1-(1-Acetylpiperidin-3-yl)-3-(3-methoxybenzyl)-5-phenyl-4-(piperazine-1 carbonyl)-1H-imidazol-2(3H)-one

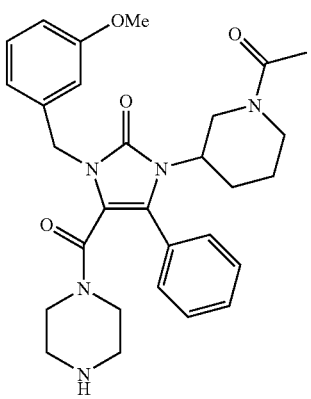

¹H NMR (400 MHz, DMSO-d₆) δ ppm 1.15 (d, J=10.11 Hz, 1H) 1.26-1.40 (m, 1H) 1.67-1.78 (m, 2H) 1.89 (br. s., 2H) 1.97 (s, 3H) 2.32-2.42 (m, 2H) 2.53-2.61 (m, 1H) 2.88-2.97 (m, 1H) 3.09 (br. s., 3H) 3.34 (t, J=11.37 Hz, 2H) 3.40-3.50 (m, 2H) 3.63 (d, J=2.02 Hz, 2H) 4.28-4.35 (m, 1H) 4.54 (br. s., 1H) 4.84 (br. s., 2H) 6.71-6.76 (m, 2H) 6.83-6.89 (m, 1H) 7.22-7.39 (m, 3H) 7.48-7.58 (m, 3H) 8.55 (br. s., 1H). ESI-MS: m/z 518.5 (M+H)⁺.

Example 93

1-(1-Acetylpiperidin-3-yl)-3-benzyl-5-phenyl-4-(piperazine-1-carbonyl)-1H-imidazol-2(3H)-one

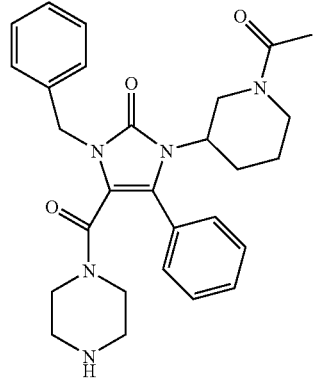

¹H NMR (400 MHz, DMSO-d₆) δ ppm 1.09-1.22 (m, 1H) 1.24-1.39 (m, 1H) 1.67-1.78 (m, 2H) 1.89 (br. s., 2H) 1.97 (s, 3H) 2.32-2.43 (m, 2H) 2.89-2.96 (m, 2H) 2.99-3.11 (m, 2H) 3.34 (t, J=11.75 Hz, 2H) 3.40-3.52 (m, 2H) 3.75 (d, J=13.39 Hz, 1H) 4.75-4.99 (m, 2H) 7.18 (t, J=6.95 Hz, 2H) 7.25-7.42 (m, 5H) 7.46-7.58 (m, 3H) 8.45 (br. s., 1H). ESI-MS: m/z 488.4 (M+H)⁺.

Example 94

1-(1-Acetylpiperidin-3-yl)-5-phenyl-4-(piperazine-1-carbonyl)-1H-imidazol-2(3H)-one

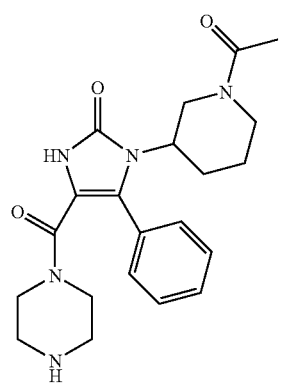

¹H NMR (400 MHz, DMSO-d₆) δ ppm 1.04-1.16 (m, 1H) 1.20-1.36 (m, 1H) 1.62-1.81 (m, 2H) 1.85 (s, 1H) 1.95 (s, 3H) 2.31-2.39 (m, 1H) 2.56-2.71 (m, 3H) 2.88 (t, J=13.39 Hz, 1H) 3.24-3.34 (m, 2H) 3.67-3.87 (m, 2H) 4.29 (d, J=12.63 Hz, 2H) 4.40 (d, J=8.59 Hz, 2H) 7.32 (dd, J=7.07, 2.27 Hz, 1H)

7.38 (dd, J=7.20, 1.89 Hz, 1H) 7.46-7.57 (m, 2H) 8.59 (br. s., 1H) 10.76-10.84 (m, 1H). ESI-MS: m/z 398.4 (M+H)+.

Example 95

1-(1-Benzoylpiperidin-3-yl)-3-benzyl-5-phenyl-4-(piperazine-1-carbonyl)-1H-imidazol-2(3H)-one

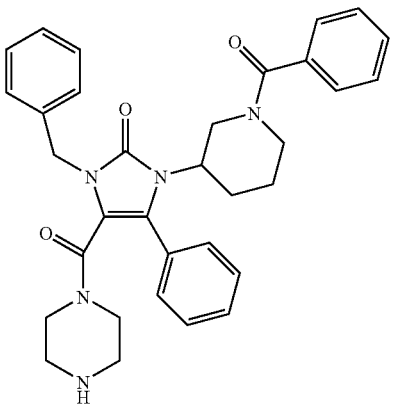

¹H NMR (400 MHz, DMSO-d₆) δ ppm 1.25-1.45 (m, 1H) 1.58-1.97 (m, 3H) 2.31-2.35 (m, 1H) 2.57-2.69 (m, 4H) 2.90-3.20 (m, 6H) 3.80-3.93 (m, 1H) 4.42 (br. s., 1H) 4.75-5.00 (m, 2H) 7.02-7.22 (m, 4H) 7.23-7.49 (m, 8H) 7.54 (br. s., 3H) 8.40 (br. s., 1H). ESI-MS: m/z 550.4 (M+H)+.

Example 96

1-Benzyl-4-phenyl-3-(1-(phenylsulfonyl)piperidin-3-yl)-5-(piperazine-1-carbonyl)-1H-imidazol-2(3H)-one

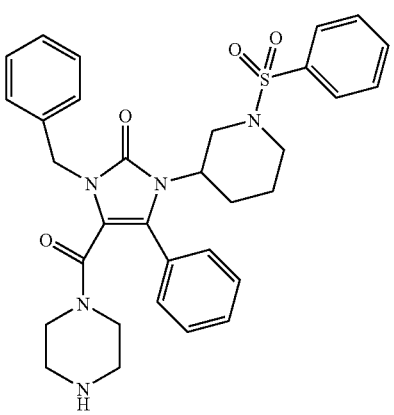

ESI-MS: m/z 550.4 (M+H)+.

Example 97

1-Benzyl-3-(1-(furan-2-carbonyl)piperidin-3-yl)-4-phenyl-5-(piperazine-1-carbonyl)-1H-imidazol-2(3H)-one

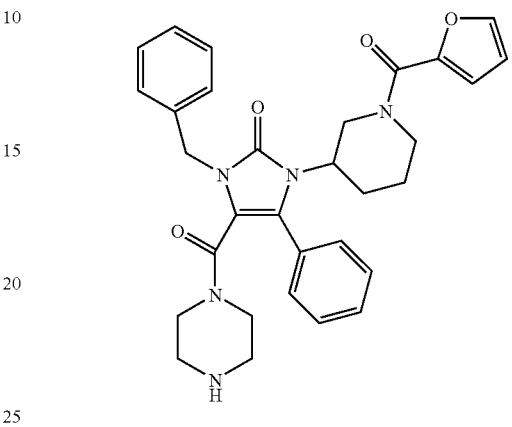

¹H NMR (400 MHz, DMSO-d₆) δ ppm 1.34 (dd, J=22.61, 10.48 Hz, 2H) 1.79 (d, J=11.37 Hz, 3H) 2.12-2.38 (m, 2H) 2.65 (dd, J=22.74, 7.83 Hz, 3H) 2.93-3.20 (m, 3H) 3.53-3.66 (m, 3H) 4.28 (d, J=12.38 Hz, 2H) 4.84 (d, J=127.07 Hz, 2H) 6.60 (br. s., 1H) 6.96 (br. s., 1H) 7.14-7.36 (m, 7H) 7.45 (br. s., 3H) 7.82 (br. s., 1H). ESI-MS: m/z 540.4 (M+H)+.

Example 98

5-Phenyl-1-(1-(phenylsulfonyl)piperidin-3-yl)-4-(piperazine-1-carbonyl)-1H-imidazol-2(3H)-one

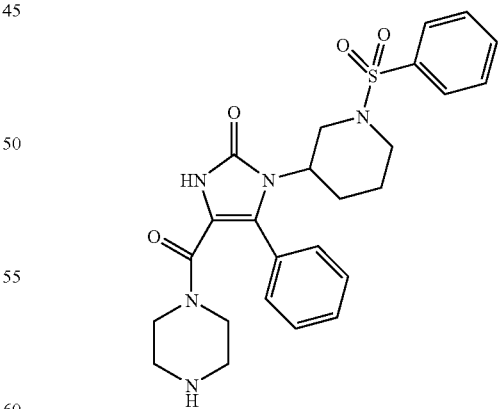

¹H NMR (400 MHz, DMSO-d₆) δ ppm 1.14-1.22 (m, 1H) 1.26-1.44 (m, 1H) 1.74 (d, J=10.61 Hz, 2H) 2.09 (t, J=11.24 Hz, 1H) 2.16-2.31 (m, 4H) 2.96 (t, J=10.99 Hz, 1H) 3.09 (br. s., 4H) 3.51-3.70 (m, 4H) 7.24-7.33 (m, 2H) 7.46-7.56 (m, 3H) 7.63 (t, J=7.71 Hz, 2H) 7.68-7.77 (m, 3H) 10.66 (br. s., 1H). ESI-MS: m/z 496.4 (M+H)$^+$.

Example 99

1-(1-Acetylpiperidin-3-yl)-3-(3-phenoxybenzyl)-5-phenyl-4-(piperazine-1-carbonyl)-1H-imidazol-2(3H)-one

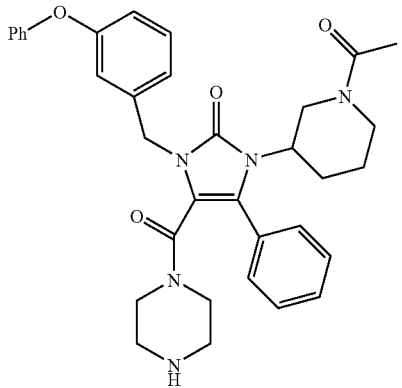

$^1$H NMR (400 MHz, DMSO-d$_6$) δ ppm 1.22-1.40 (m, 1H) 1.64-1.78 (m, 2H) 1.97 (br. s., 2H) 1.99 (s, 3H) 2.14 (br. s., 2H) 2.30-2.41 (m, 1H) 2.58-2.70 (m, 1H) 2.90 (t, J=12.25 Hz, 1H) 2.98-3.14 (m, 1H) 3.20-3.31 (m, 1H) 3.39-3.50 (m, 1H) 3.73 (d, J=13.64 Hz, 1H) 4.31 (d, J=12.13 Hz, 1H) 4.64-5.02 (m, 2H) 6.64-6.79 (m, 2H) 6.86-6.95 (m, 2H) 6.99 (dd, J=7.96, 2.40 Hz, 2H) 7.14-7.26 (m, 2H) 7.28-7.37 (m, 2H) 7.38-7.55 (m, 5H). ESI-MS: m/z 580.4 (M+H)$^+$.

Example 100

1-Benzyl-4-phenyl-3-(1-(phenylsulfonyl)piperidin-3-yl)-5-(piperazine-1-carbonyl)-1H-imidazol-2(3H)-one

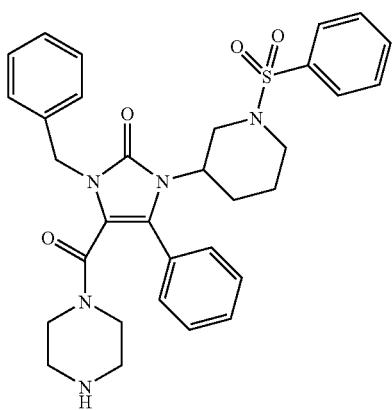

$^1$H NMR (400 MHz, DMSO-d$_6$) δ ppm 1.25-1.50 (m, 2H) 1.66-1.84 (m, 2H) 2.04-2.37 (m, 5H) 2.55-2.69 (m, 1H) 2.81-3.22 (m, 4H) 3.30 (s, 2H) 3.58-3.72 (m, 2H) 4.51-5.01 (m, 2H) 7.12 (d, J=7.07 Hz, 2H) 7.23-7.36 (m, 5H) 7.46-7.54 (m, 3H) 7.56-7.83 (m, 5H). ESI-MS: m/z 586.4 (M+H)$^+$.

Example 101

1-Benzyl-4-phenyl-5-(piperazine-1-carbonyl)-3-(1-(pyridin-2-ylsulfonyl)piperidin-3-yl)-1H-imidazol-2(3H)-one

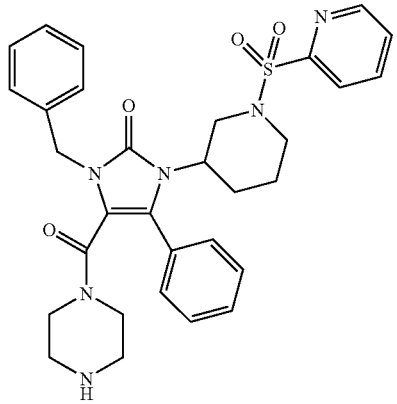

$^1$H NMR (400 MHz, DMSO-d$_6$) δ ppm 1.00-1.43 (m, 4H) 1.46-1.82 (m, 4H) 2.23-2.39 (m, 4H) 2.52-2.67 (m, 2H) 2.88-3.12 (m, 2H) 3.38-3.76 (m, 4H) 4.31-5.14 (m, 2H) 6.81-7.52 (m, 8H) 7.68 (br. s., 1H) 8.00 (d, J=71.24 Hz, 2H) 8.64 (br. s., 1H). ESI-MS: m/z 587.5 (M+H)$^+$.

Example 102

1-(3-Phenoxybenzyl)-4-phenyl-3-(1-(phenylsulfonyl)piperidin-3-yl)-5-(piperazine-1-carbonyl)-1H-imidazol-2(3H)-one

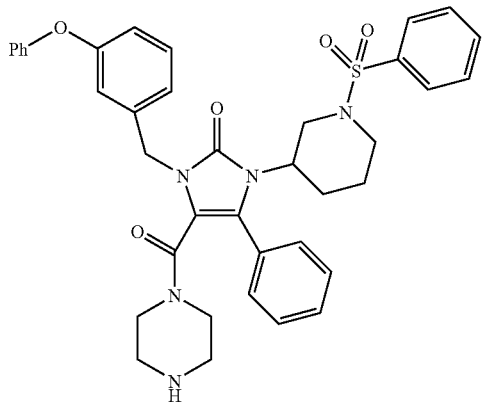

$^1$H NMR (400 MHz, DMSO-d$_6$) δ ppm 1.25-1.45 (m, 2H) 1.69-1.84 (m, 2H) 2.06-2.28 (m, 5H) 2.28-2.36 (m, 1H) 2.58-2.69 (m, 1H) 2.92-3.19 (m, 4H) 3.30 (s, 1H) 3.56-3.67 (m, 3H) 4.59-4.96 (m, 2H) 6.67 (s, 1H) 6.88 (dd, J=7.83, 2.02 Hz, 1H) 6.98 (d, J=7.83 Hz, 2H) 7.18 (t, J=7.33 Hz, 1H) 7.22-7.27

(m, 2H) 7.32 (t, J=7.83 Hz, 1H) 7.41 (t, J=7.83 Hz, 2H) 7.48-7.56 (m, 3H) 7.63 (br. s., 2H) 7.72 (d, J=6.57 Hz, 3H). ESI-MS: m/z 678.4 (M+H)+.

Example 103

1-(3-Phenoxybenzyl)-4-phenyl-5-(piperazine-1-carbonyl)-3-(1-(pyridin-2-ylsulfonyl)piperidin-3-yl)-1H-imidazol-2(3H)-one

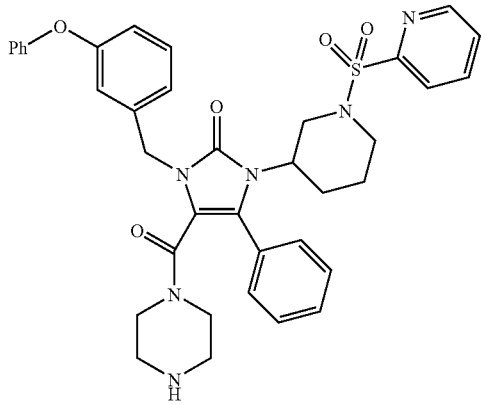

$^1$H NMR (400 MHz, DMSO-d$_6$) δ ppm 1.22-1.36 (m, 2H) 1.67-1.80 (m, 2H) 2.27 (br. s., 2H) 2.55-2.69 (m, 2H) 2.90-3.16 (m, 2H) 3.27-3.30 (m, 2H) 3.44-3.55 (m, 2H) 3.53-3.74 (m, 4H) 4.62-4.95 (m, 2H) 6.65 (s, 1H) 6.85-6.93 (m, 2H) 6.98 (d, J=8.08 Hz, 2H) 7.10-7.26 (m, 3H) 7.32 (t, J=7.96 Hz, 1H) 7.41 (t, J=7.96 Hz, 2H) 7.48-7.57 (m, 3H) 7.69 (br. s., 1H) 7.92 (br. s., 1H) 8.10 (br. s., 1H) 8.64 (br. s., 1H). ESI-MS: m/z 679.4 (M+H)+.

Example 104

1-(1-Acetylpiperidin-3-yl)-4-((R)-2-benzylpiperazine-1-carbonyl)-5-phenyl-1H-imidazol-2(3H)-one

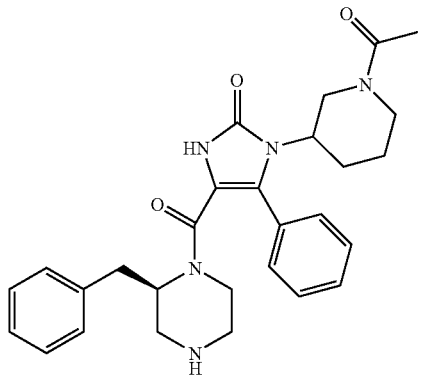

$^1$H NMR (400 MHz, DMSO-d$_6$) δ ppm 1.06-1.16 (m, 1H) 1.24-1.38 (m, 1H) 1.76-1.83 (m, 2H) 1.94 (s, 3H) 2.08 (dd, J=13.64, 6.06 Hz, 1H) 2.29-2.39 (m, 1H) 2.64-2.76 (m, 1H) 2.85-3.08 (m, 2H) 3.25-3.39 (m, 2H) 3.68-3.78 (m, 1H) 3.83-3.94 (m, 1H) 4.25-4.38 (m, 2H) 4.43-4.58 (m, 2H) 7.15-7.36 (m, 7H) 7.42-7.53 (m, 3H) 8.77 (d, J=52.80 Hz, 2H) 10.68 (br. s., 1H). ESI-MS: m/z 488.4 (M+H)+.

Example 105

1-Benzyl-3-((1R,2R)-2-hydroxycyclohexyl)-4-phenyl-5-(piperazine-1-carbonyl)-1H-imidazol-2(3H)-one

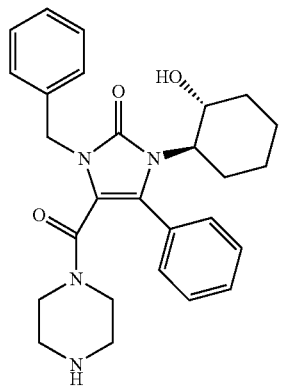

$^1$H NMR (400 MHz, DMSO-d$_6$) δ ppm 0.90-1.10 (m, 4H) 1.21-1.28 (m, 2H) 1.52-1.75 (m, 4H) 1.76-1.95 (m, 2H) 2.09-2.45 (m, 6H) 2.90-3.20 (m, 2H) 4.20-4.49 (m, 2H) 4.58-5.16 (m, 2H) 7.12-7.57 (m, 8H). ESI-MS: m/z 461.4 (M+H)+.

Example 106

1-((1R,2R)-2-Hydroxycyclohexyl)-3-(3-phenoxybenzyl)-5-phenyl-4-(piperazine-1-carbonyl)-1H-imidazol-2(3H)-one

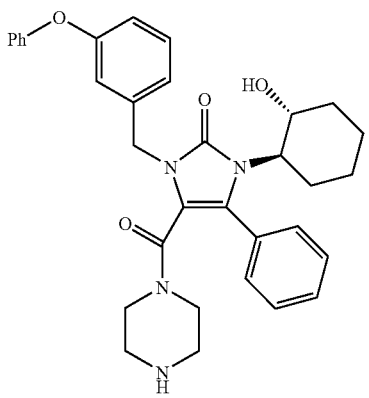

$^1$H NMR (400 MHz, DMSO-d$_6$) δ ppm 0.92-1.11 (m, 4H) 1.19-1.27 (m, 2H) 1.53-1.76 (m, 4H) 1.83-1.92 (m, 3H) 2.07-2.42 (m, 4H) 2.87-3.15 (m, 2H) 4.30 (d, J=11.87 Hz, 1H) 4.58-5.05 (m, 2H) 6.74-6.83 (m, 1H) 6.86 (d, J=8.34 Hz, 1H)

6.93 (d, J=7.58 Hz, 1H) 6.98 (d, J=8.59 Hz, 2H) 7.16 (t, J=7.45 Hz, 1H) 7.28-7.51 (m, 8H). ESI-MS: m/z 553.4 (M+H)+.

Example 107

N—(((S)-1-(1-((1R,2R)-2-Hydroxycyclohexyl)-2-oxo-5-phenyl-2,3-dihydro-1H-imidazole-4-carbonyl)piperazin-2-yl)methyl)benzamide

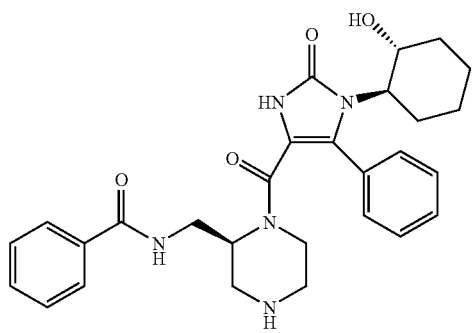

¹H NMR (400 MHz, DMSO-d₆) δ ppm 0.81-0.88 (m, 1H) 1.10-1.29 (m, 4H) 1.49-1.67 (m, 4H) 1.91 (dd, J=6.95, 3.92 Hz, 1H) 1.95-2.07 (m, 1H) 2.20-2.34 (m, 2H) 2.57-2.69 (m, 2H) 3.08-3.17 (m, 1H) 3.45-3.65 (m, 2H) 4.25-4.44 (m, 2H) 5.01 (d, J=3.79 Hz, 1H) 7.35-7.56 (m, 8H) 7.79 (d, J=7.33 Hz, 2H) 8.49 (t, J=5.18 Hz, 1H) 10.43 (br. s., 1H). ESI-MS: m/z 504.4 (M+H)+.

Example 108

(S)—N-((1-(1-Cyclohexyl-2-oxo-5-phenyl-2,3-dihydro-1H-imidazole-4-carbonyl)piperazin-2-yl)methyl)benzamide

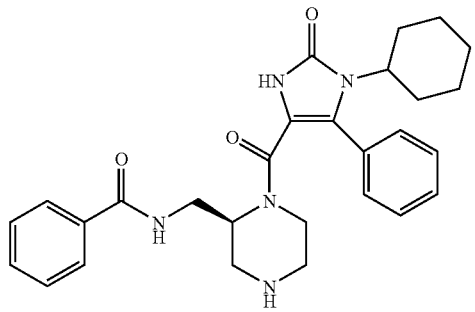

¹H NMR (400 MHz, MeOD) δ ppm 1.17 (m, 3H), 1.31 (m, 1H), 1.60 (m, 2H), 1.82 (m, 4H), 2.72 (m, 3H), 3.05-3.28 (m, 4H), 3.45-3.57 (m, 3H), 7.41 (m, 2H), 7.47 (m, 2H), 7.59 (m, 4H), 7.79 (m, 2H). ESI-MS: m/z 488.3 (M+H)+.

Example 109

(R)-4-(2-Benzylpiperazine-1-carbonyl)-1,5-diphenyl-1H-imidazol-2(3H)-one

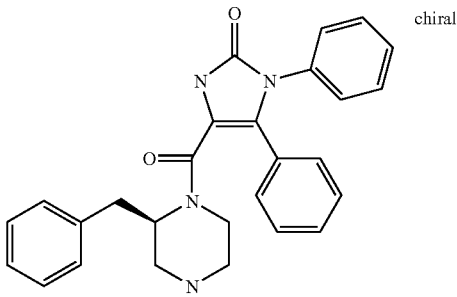

¹H NMR (400 MHz, MeOD) d ppm 2.5 (m, 2H), 2.6-3.5 (m, 7H), 7.15 (m, 4H), 7.36 (m, 6H); ESI-MS: m/z 439.3 (M+H)+.

Example 110

(R)-4-(2-Benzylpiperazine-1-carbonyl)-1-(3-morpholinophenyl)-5-phenyl-1H-imidazol-2(3H)-one

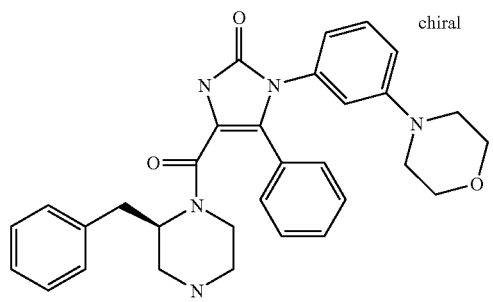

¹H NMR (400 MHz, MeOD) d ppm 2.78 (m, 1H), 2.96 (br s, 4H), 3.0 (t, 4.8 Hz, 4H), 3.21 (br s, 2H), 3.74 (t, 4.8 Hz, 4H), 6.60 (m, 2H), 6.93 (m, 1H), 7.12-7.42 (m, 11H); ESI-MS: m/z 524.4 (M+H)+.

Example 111

(R)-4-(2-Benzylpiperazine-1-carbonyl)-1-cyclohexyl-5-phenyl-1H-imidazol-2(3H)-one

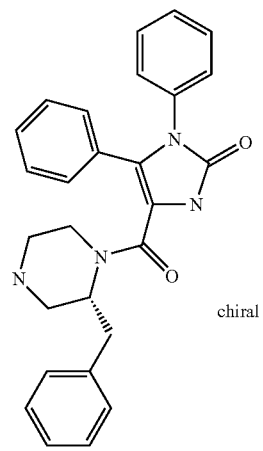

¹H NMR (400 MHz, MeOD) d ppm 1.04-1.31 (m, 4H) 1.44-1.70 (m, 4H) 2.65-2.87 (m, 2H) 2.86-3.06 (m, 4H) 3.05-3.25 (m, 4H) 3.42-3.61 (m, 2H) 7.13 (dd, J=6.95, 1.89 Hz, 2H) 7.21-7.45 (m, 5H) 7.51-7.70 (m, 3H) ESI-MS: m/z 445.2 (M+H)⁺.

Example 112

(R)-4-(2-Benzylpiperazine-1-carbonyl)-1-(2,3-dimethoxyphenyl)-5-phenyl-1H-imidazol-2(3H)-one

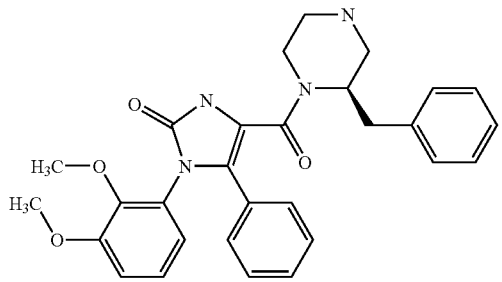

Example 113

(R)-4-(2-Benzylpiperazine-1-carbonyl)-1-(2-methoxyphenyl)-5-phenyl-1H-imidazol-2(3H)-one

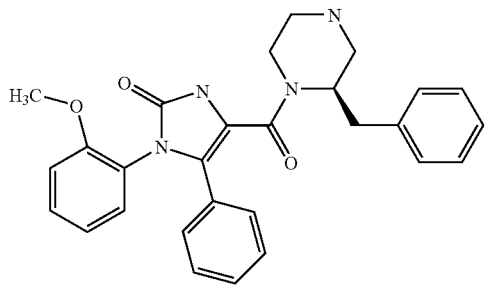

Example 114

(R)-4-(2-Benzylpiperazine-1-carbonyl)-1-(3-(methylsulfonyl)phenyl)-5-phenyl-1H-imidazol-2(3H)-one

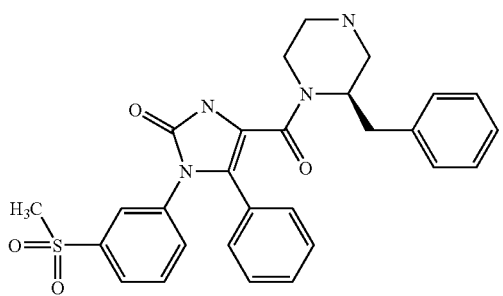

Example 115

1-(1-Acetylpiperidin-3-yl)-4-((R)-2-benzylpiperazine-1-carbonyl)-5-phenyl-1H-imidazol-2(3H)-one

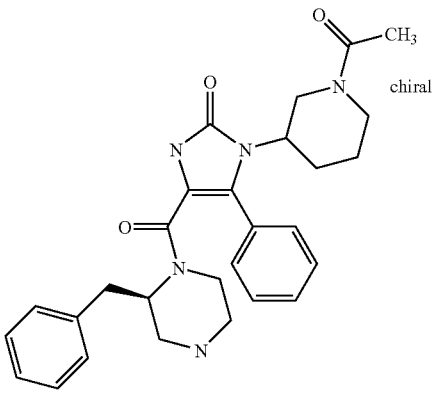

ESI-MS: m/z 488.3 (M+H)⁺.

Example 116

(R)-4-(2-Benzylpiperazine-1-carbonyl)-5-phenyl-1-o-tolyl-1H-imidazol-2(3H)-one

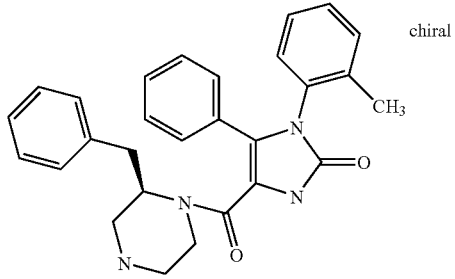

ESI-MS: m/z 453.02 (M+H)⁺.

Example 117

(R)-4-(2-Benzylpiperazine-1-carbonyl)-1-(2-nitrophenyl)-5-phenyl-1H-imidazol-2(3H)-one

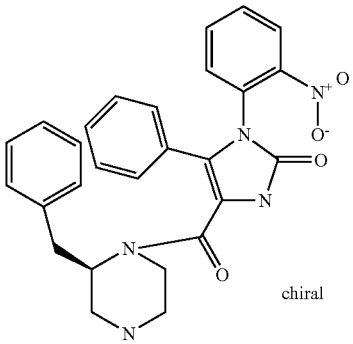

ESI-MS: m/z 484.03 (M+H)⁺.

Example 118

(R)—N-(2-(4-(2-Benzylpiperazine-1-carbonyl)-2-oxo-5-phenyl-2,3-dihydro-1H-imidazol-1-yl)phenyl)methanesulfonamide

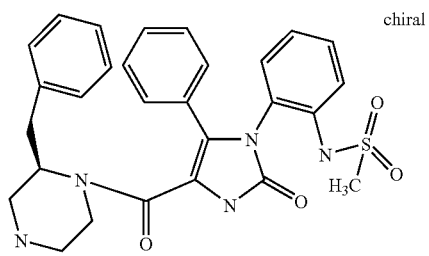

ESI-MS: m/z 532.05 (M+H)$^+$.

Example 119

(R)—N-(2-(4-(2-Benzylpiperazine-1-carbonyl)-2-oxo-5-phenyl-2,3-dihydro-1H-imidazol-1-yl)phenyl)propane-1-sulfonamide

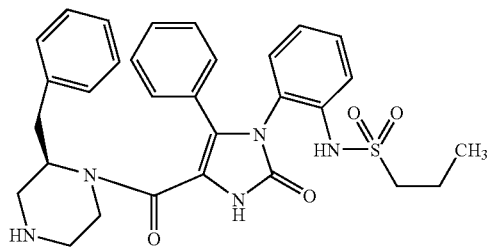

ESI-MS: m/z 560.09 (M+H)$^+$.

Example 120

(R)—N-(2-(4-(2-Benzylpiperazine-1-carbonyl)-2-oxo-5-phenyl-2,3-dihydro-1H-imidazol-1-yl)phenyl)cyclopropanecarboxamide

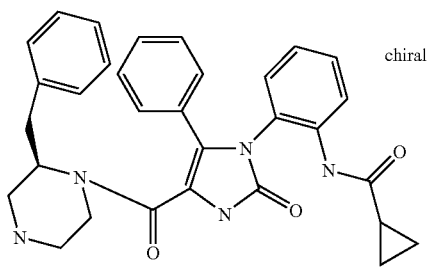

ESI-MS: m/z 522.10 (M+H)$^+$.

Example 121

(R)—N-(2-(4-(2-Benzylpiperazine-1-carbonyl)-2-oxo-5-phenyl-2,3-dihydro-1H-imidazol-1-yl)phenyl)butyramide

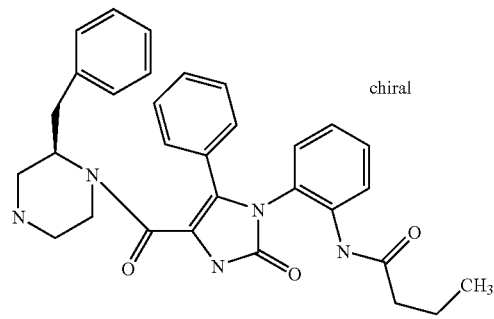

ESI-MS: m/z 524.11 (M+H)$^+$.

Example 122

(R)—N-(2-(4-(2-Benzylpiperazine-1-carbonyl)-2-oxo-5-phenyl-2,3-dihydro-1H-imidazol-1-yl)phenyl)acetamide

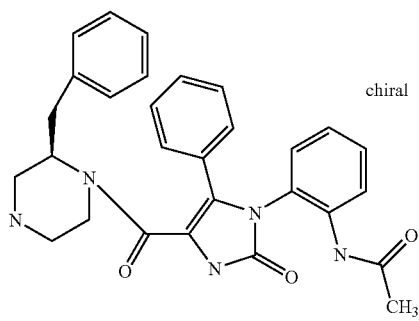

ESI-MS: m/z 496.06 (M+H)$^+$.

Example 123

(R)—N-(2-(4-(2-Benzylpiperazine-1-carbonyl)-2-oxo-5-phenyl-2,3-dihydro-1H-imidazol-1-yl)phenyl)cyclopropanesulfonamide

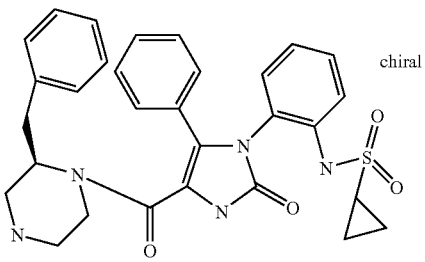

ESI-MS: m/z 558.06 (M+H)$^+$.

Example 124

(R)—N-(2-(4-(2-Benzylpiperazine-1-carbonyl)-2-oxo-5-phenyl-2,3-dihydro-1H-imidazol-1-yl)phenyl)benzamide

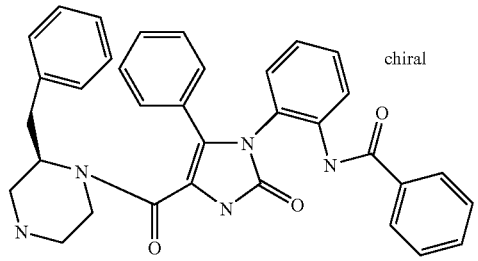

ESI-MS: m/z 558.11 (M+H)$^+$.

Example 125

(R)—N-(2-(4-(2-benzylpiperazine-1-carbonyl)-2-oxo-5-phenyl-2,3-dihydro-1H-imidazol-1-yl)phenyl)Benzenesulfonamide

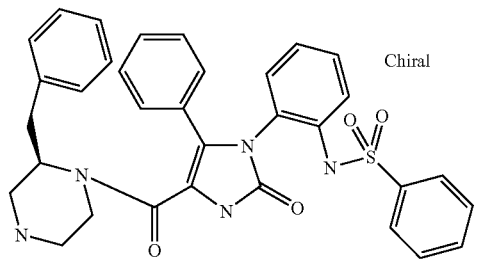

ESI-MS: m/z 594.05 (M+H)$^+$.

Example 126

4-((R)-2-Benzylpiperazine-1-carbonyl)-1-((1S,2S)-2-hydroxycyclohexyl)-5-phenyl-1H-imidazol-2(3H)-one

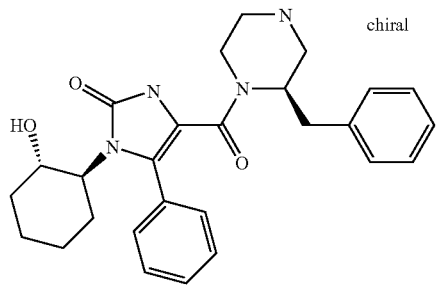

ESI-MS: m/z 461.09 (M+H)$^+$.

Example 127

(R)—N-(2-(4-(2-Benzylpiperazine-1-carbonyl)-2-oxo-5-phenyl-2,3-dihydro-1H-imidazol-1-yl)phenyl)ethanesulfonamide

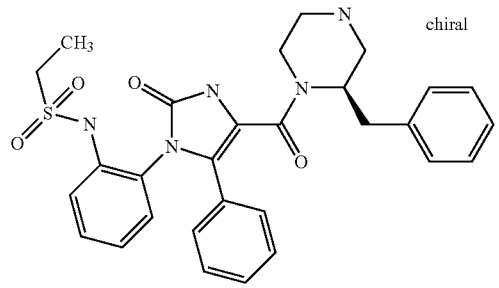

Example 128

(R)—N-(2-(4-(2-Benzylpiperazine-1-carbonyl)-2-oxo-5-phenyl-2,3-dihydro-1H-imidazol-1-yl)phenyl)butane-1-sulfonamide

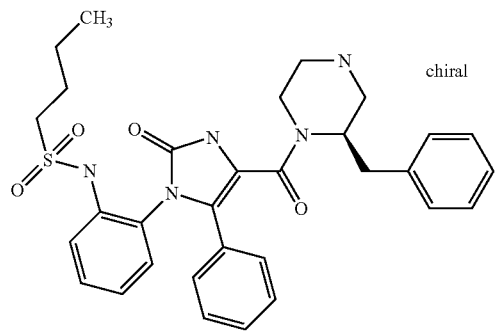

Example 129

(R)—N-(2-(4-(2-Benzylpiperazine-1-carbonyl)-2-oxo-5-phenyl-2,3-dihydro-1H-imidazol-1-yl)phenyl)prop-2-ene-1-sulfonamide

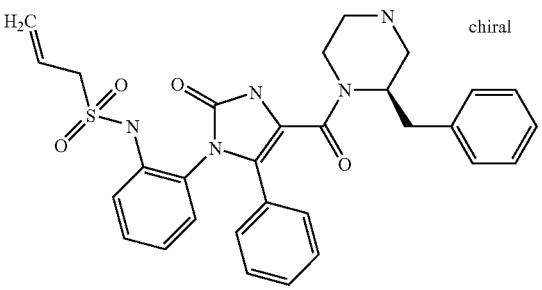

ESI-MS: m/z 558.12 (M+H)$^+$.

Example 130

(R)-4-(2-Benzylpiperazine-1-carbonyl)-1-((1-hydroxycyclohexyl)methyl)-5-phenyl-1H-imidazol-2(3H)-one

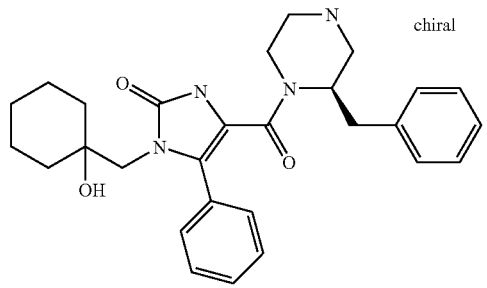

ESI-MS: m/z 475.15 (M+H)+.

Example 131

(R)-4-(2-Benzylpiperazine-1-carbonyl)-5-phenyl-1-(1,2,3,4-tetrahydroquinolin-7-yl)-1H-imidazol-2(3H)-one

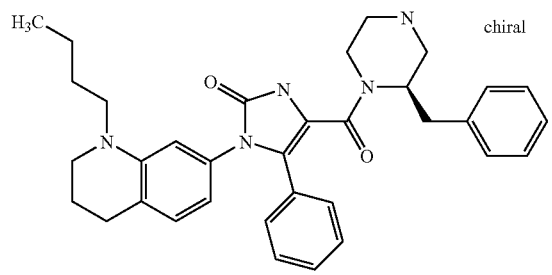

ESI-MS: m/z 550.1 (M+H)+.

Example 132

(R)-4-(2-Benzylpiperazine-1-carbonyl)-5-phenyl-1-(1,2,3,4-tetrahydroquinolin-7-yl)-1H-imidazol-2(3H)-one

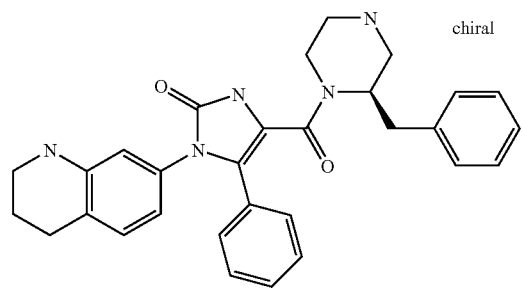

ESI-MS: m/z 494.1 (M+H)+.

Example 133

(R)-4-(2-Benzylpiperazine-1-carbonyl)-1-(1-butyl-1,2,3,4-tetrahydroquinolin-7-yl)-5-cyclopropyl-1H-imidazol-2(3H)-one

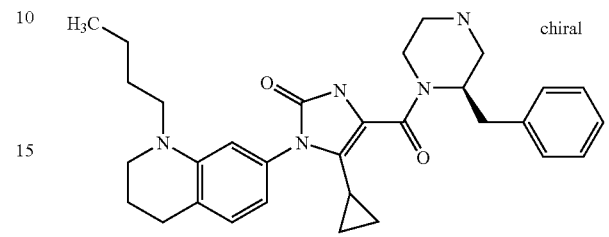

ESI-MS: m/z 514.19 (M+H)+.

Example 134

(R)-4-(2-Benzylpiperazine-1-carbonyl)-5-cyclopropyl-1-(1,2,3,4-tetrahydroquinolin-7-yl)-1H-imidazol-2(3H)-one

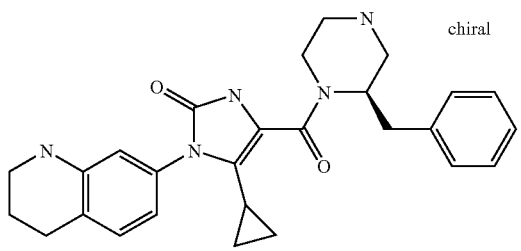

ESI-MS: m/z 458.11 (M+H)+.

Example 135

(R)-4-(2-Benzylpiperazine-1-carbonyl)-1-(4-methyl-3,4-dihydro-2H-benzo[b][1,4]oxazin-6-yl)-5-phenyl-1H-imidazol-2(3H)-one

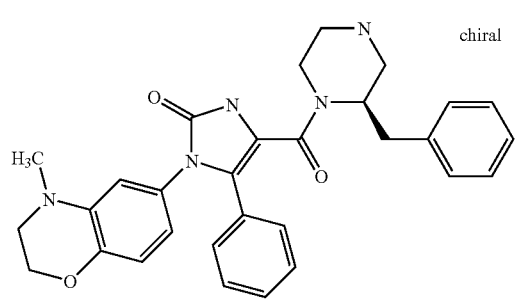

Example 136

(R)-4-(2-Benzylpiperazine-1-carbonyl)-1-(indolin-6-yl)-5-phenyl-1H-imidazol-2(3H)-one

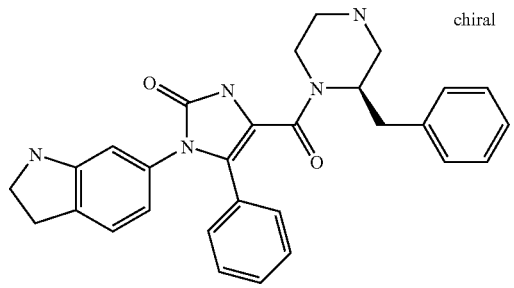

ESI-MS: m/z 480.1 (M+H)$^+$.

Example 137

(R)-4-(2-Benzylpiperazine-1-carbonyl)-1-(4-(2-methoxyethyl)-3,4-dihydro-2H-benzo[b][1,4]oxazin-6-yl)-5-phenyl-1H-imidazol-2(3H)-one

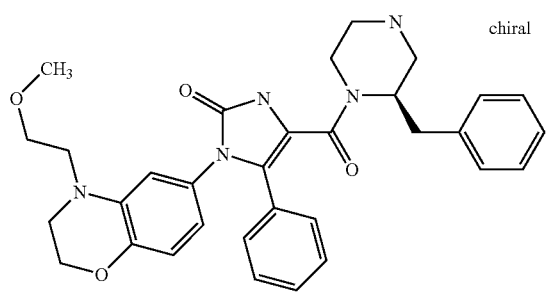

ESI-MS: m/z 554.1 (M+H)$^+$.

Example 138

4-((R)-2-Benzylpiperazine-1-carbonyl)-1-(3-methoxy-2,3-dihydro-1H-inden-5-yl)-5-phenyl-1H-imidazol-2(3H)-one

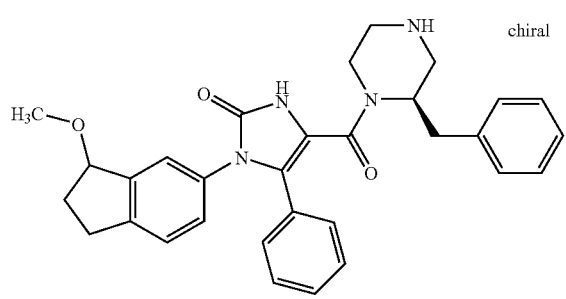

ESI-MS: m/z 509.2 (M+H)$^+$.

Example 139

(R)-Ethyl 6-(4-(2-benzylpiperazine-1-carbonyl)-2-oxo-5-phenyl-2,3-dihydro-1H-imidazol-1-yl)indoline-1-carboxylate

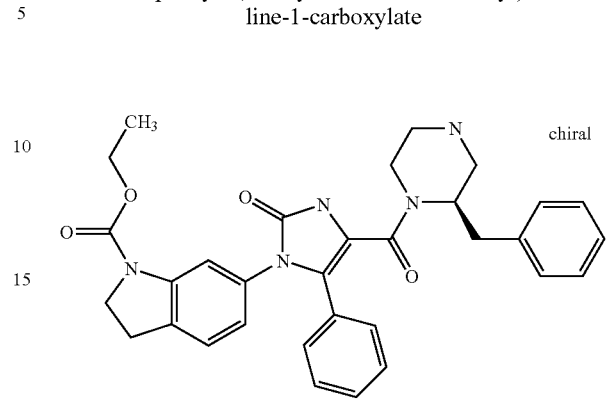

ESI-MS: m/z 552.11 (M+H)$^+$.

Example 140

(R)-4-(2-(2-Phenoxyethyl)piperazine-1-carbonyl)-5-phenyl-1-(1,2,3,4-tetrahydroquinolin-7-yl)-1H-imidazol-2(3H)-one

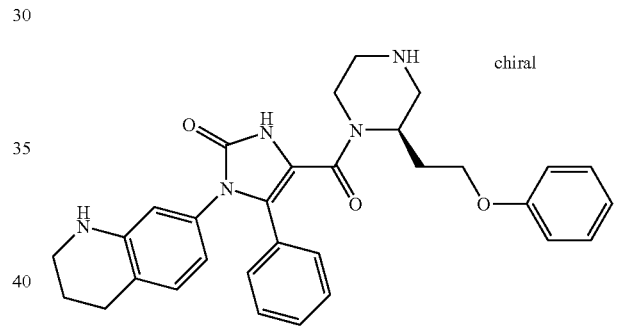

ESI-MS: m/z 524.10 (M+H)$^+$.

Example 141

1-Allyl-4-phenyl-5-(piperazine-1-carbonyl)-3-o-tolyl-1H-imidazol-2(3H)-one

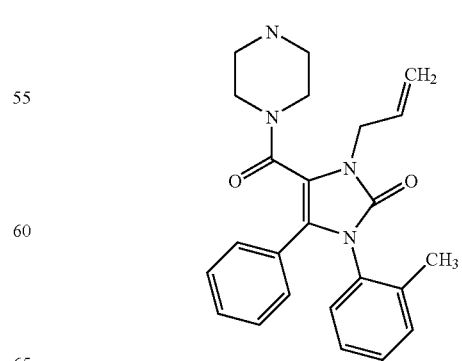

ESI-MS: m/z 403.2 (M+H)$^+$.

Example 142
1-(3-Phenoxybenzyl)-4-phenyl-5-(piperazine-1-carbonyl)-3-o-tolyl-1H-imidazol-2(3H)-one

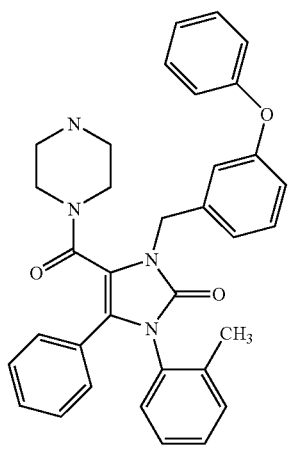

ESI-MS: m/z 545.2 (M+H)$^+$.

Example 143
1-(3-Methoxybenzyl)-4-phenyl-5-(piperazine-1-carbonyl)-3-o-tolyl-1H-imidazol-2(3H)-one

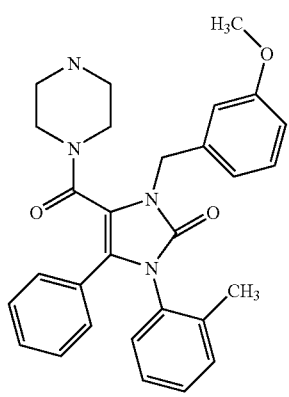

ESI-MS: m/z 483.2 (M+H)$^+$.

Example 144
1-(3,4-Difluorobenzyl)-4-phenyl-5-(piperazine-1-carbonyl)-3-o-tolyl-1H-imidazol-2(3H)-one

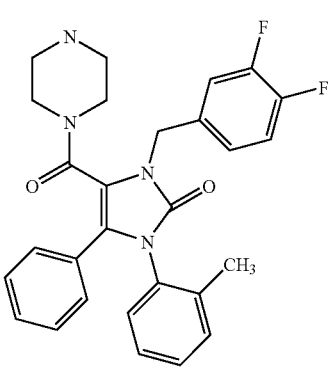

ESI-MS: m/z 489.1 (M+H)$^+$.

Example 145
1-Allyl-3-(2-methoxyphenyl)-4-phenyl-5-(piperazine-1-carbonyl)-1H-imidazol-2(3H)-one

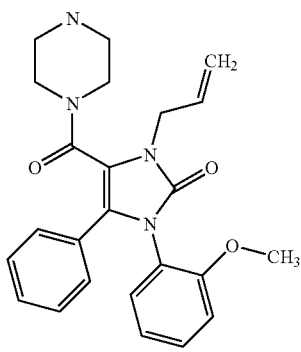

ESI-MS: m/z 419.1 (M+H)$^+$.

Example 146
1-(2-Methoxyphenyl)-3-(3-phenoxybenzyl)-5-phenyl-4-(piperazine-1-carbonyl)-1H-imidazol-2(3H)-one

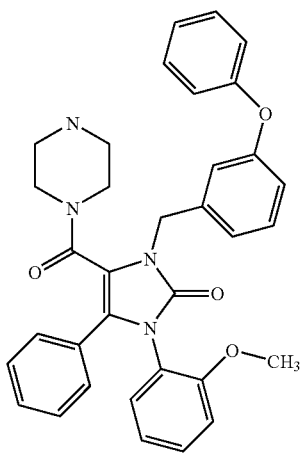

ESI-MS: m/z 561.2 (M+H)$^+$.

Example 147
1-(3-Methoxybenzyl)-3-(2-methoxyphenyl)-4-phenyl-5-(piperazine-1-carbonyl)-1H-imidazol-2(3H)-one

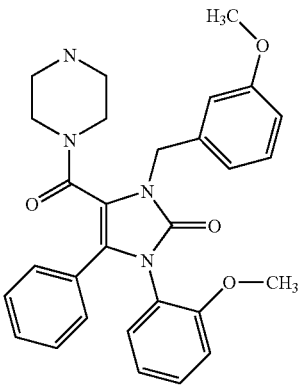

ESI-MS: m/z 499.1 (M+H)+.

Example 148
1-(3,4-Difluorobenzyl)-3-(2-methoxyphenyl)-4-phenyl-5-(piperazine-1-carbonyl)-1H-imidazol-2(3H)-one

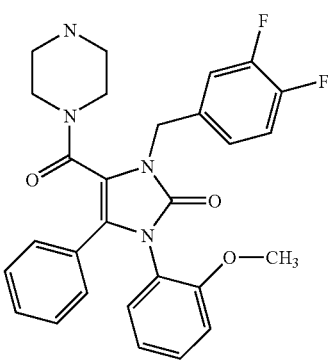

ESI-MS: m/z 505.1 (M+H)+.

Example 149
1-(3-(2-Phenoxyethoxy)benzyl)-4-phenyl-5-(piperazine-1-carbonyl)-3-o-tolyl-1H-imidazol-2(3H)-one

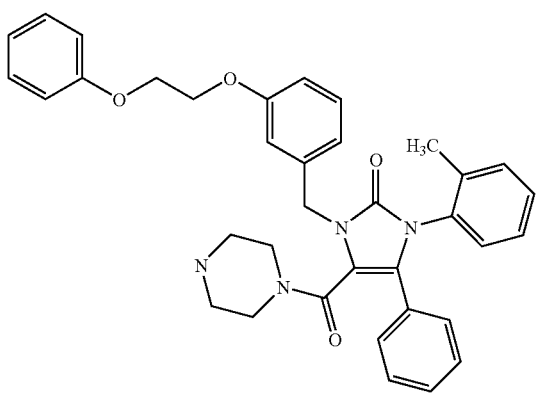

ESI-MS: m/z 589.8 (M+H)+.

Example 150
1-Allyl-3-(3-morpholinophenyl)-4-phenyl-5-(piperazine-1-carbonyl)-1H-imidazol-2(3H)-one

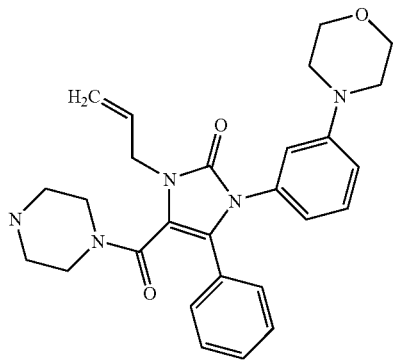

ESI-MS: m/z 474.2 (M+H)+.

Example 151
1-(3-Methoxybenzyl)-3-(3-morpholinophenyl)-4-phenyl-5-(piperazine-1-carbonyl)-1H-imidazol-2(3H)-one

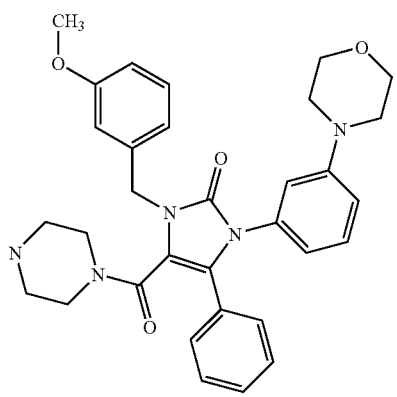

ESI-MS: m/z 554.2 (M+H)+.

Example 152
1-((1S,2R)-2-Hydroxycyclohexyl)-3-(3-phenoxybenzyl)-5-phenyl-4-(piperazine-1-carbonyl)-1H-imidazol-2(3H)-one

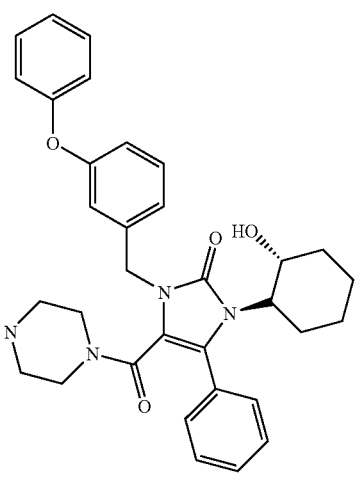

ESI-MS: m/z 553.1 (M+H)+.

Example 153

1-((1S,2R)-2-Hydroxycyclohexyl)-3-(3-methoxybenzyl)-5-phenyl-4-(piperazine-1-carbonyl)-1H-imidazol-2(3H)-one

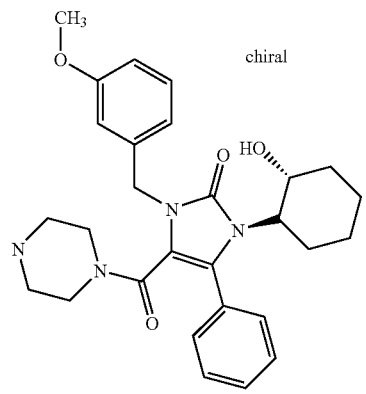

ESI-MS: m/z 491.1 (M+H)$^+$.

Example 154

1-(3,4-Difluorobenzyl)-3-((1S,2R)-2-hydroxycyclohexyl)-4-phenyl-5-(piperazine-1-carbonyl)-1H-imidazol-2(3H)-one

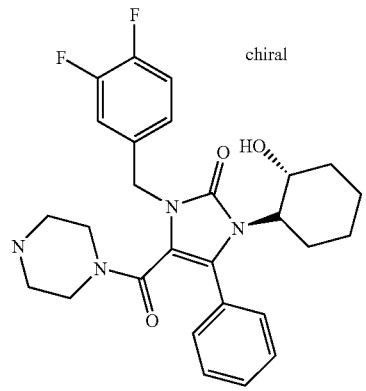

ESI-MS: m/z 497.1 (M+H)$^+$.

Example 155

N-(2-(2-oxo-4-Phenyl-5-(piperazine-1-carbonyl)-3-o-tolyl-2,3-dihydro-1H-imidazol-1-yl)ethyl)benzenesulfonamide

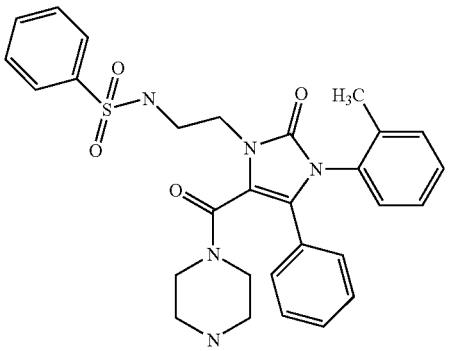

ESI-MS: m/z 546.1 (M+H)$^+$.

Example 156

N-(3-(2-oxo-4-Phenyl-5-(piperazine-1-carbonyl)-3-o-tolyl-2,3-dihydro-1H-imidazol-1-yl)propyl)benzamide

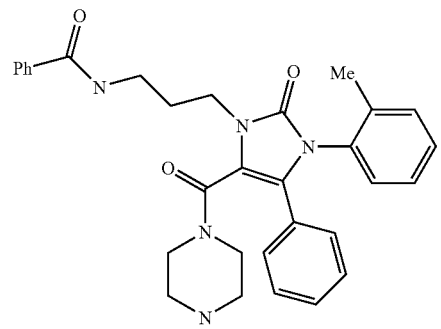

ESI-MS: m/z 524.2 (M+H)$^+$.

Example 157

1-(Cyclohexylmethyl)-3-((1S,2R)-2-hydroxycyclohexyl)-4-phenyl-5-(piperazine-1-carbonyl)-1H-imidazol-2(3H)-one

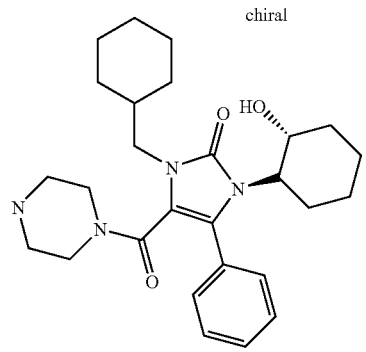

ESI-MS: m/z 467.3 (M+H)$^+$.

Example 158

N-(2-(3-(2-Methoxyphenyl)-2-oxo-4-phenyl-5-(piperazine-1-carbonyl)-2,3-dihydro-1H-imidazol-1-yl)ethyl)benzenesulfonamide

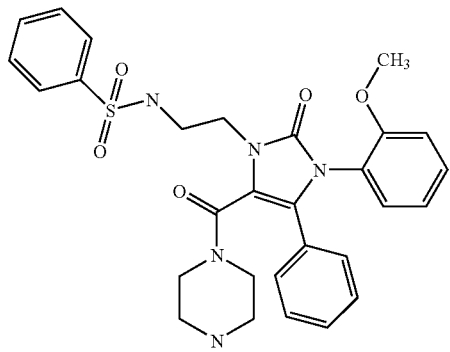

ESI-MS: m/z 562.2 (M+H)$^+$.

Example 159

N-(3-(3-(2-Methoxyphenyl)-2-oxo-4-phenyl-5-(piperazine-1-carbonyl)-2,3-dihydro-1H-imidazol-1-yl)propyl)benzamide

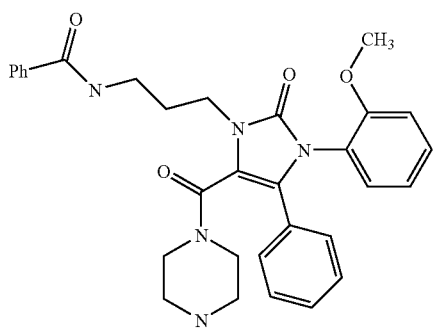

ESI-MS: m/z 562.2 (M+H)$^+$.

Example 160

1-(Cyclohexylmethyl)-3-(2-methoxyphenyl)-4-phenyl-5-(piperazine-1-carbonyl)-1H-imidazol-2(3H)-one

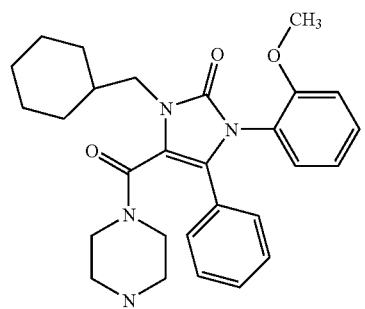

ESI-MS: m/z 475.2 (M+H)$^+$.

Example 161

N-(3-(3-(2-Methoxyphenyl)-2-oxo-4-phenyl-5-(piperazine-1-carbonyl)-2,3-dihydro-1H-imidazol-1-yl)propyl)benzenesulfonamide

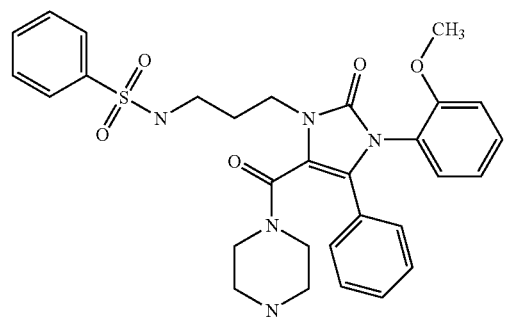

ESI-MS: m/z 576.2 (M+H)$^+$.

Example 162

N-(3-(2-oxo-4-Phenyl-5-(piperazine-1-carbonyl)-3-o-tolyl-2,3-dihydro-1H-imidazol-1-yl)propyl)benzenesulfonamide

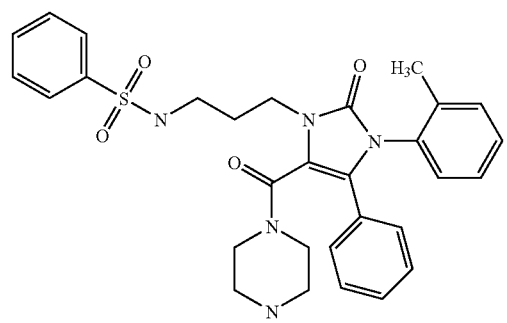

ESI-MS: m/z 560.2 (M+H)$^+$.

Example 163

1-(Cyclohexylmethyl)-4-phenyl-5-(piperazine-1-carbonyl)-3-o-tolyl-1H-imidazol-2(3H)-one

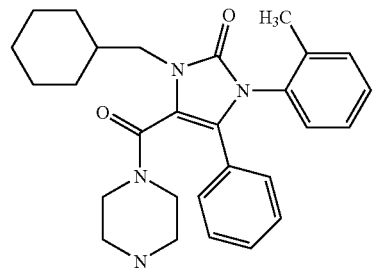

ESI-MS: m/z 459.1 (M+H)+.

Example 164

1-(3,4-Difluorobenzyl)-3-(3-(3-methoxypropoxy)phenyl)-4-phenyl-5-(piperazine-1-carbonyl)-1H-imidazol-2(3H)-one

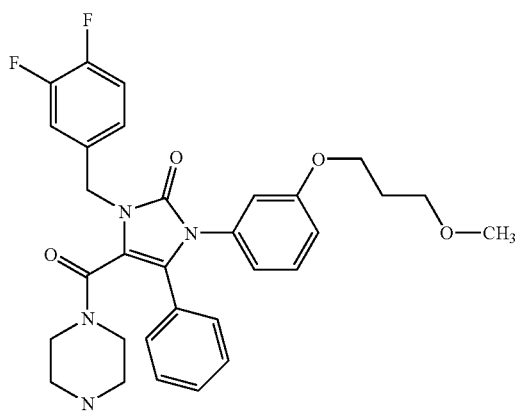

ESI-MS: m/z 459.1 (M+H)+.

Example 165

3-Methyl-N-(3-(2-oxo-4-phenyl-5-(piperazine-1-carbonyl)-3-o-tolyl-2,3-dihydro-1H-imidazol-1-yl)propyl)butanamide

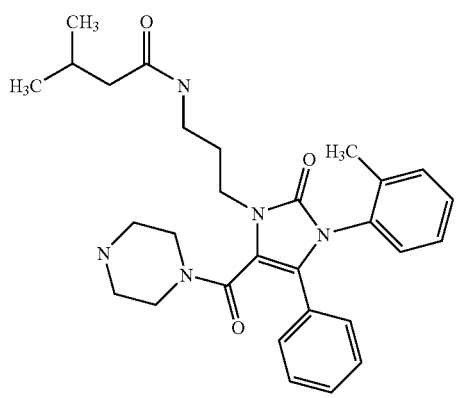

ESI-MS: m/z 504.2 (M+H)+.

Example 166

N-(2-(2-oxo-4-Phenyl-5-(piperazine-1-carbonyl)-3-o-tolyl-2,3-dihydro-1H-imidazol-1-yl)ethyl)benzamide

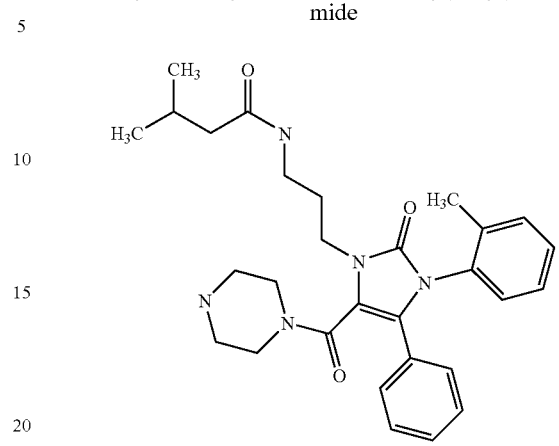

ESI-MS: m/z 510.1 (M+H)+.

Example 167

N-(3-(3-(2-Methoxyphenyl)-2-oxo-4-phenyl-5-(piperazine-1-carbonyl)-2,3-dihydro-1H-imidazol-1-yl)propyl)-3-methylbutanamide

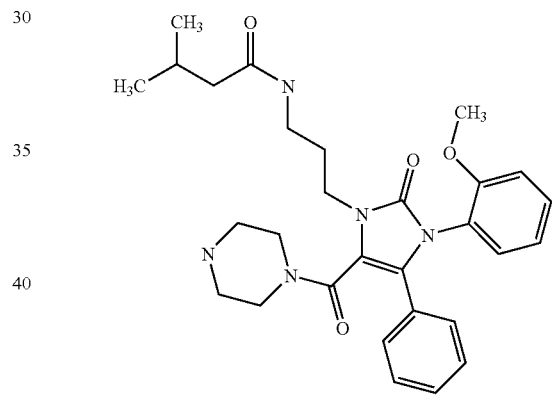

ESI-MS: m/z 520.2 (M+H)+.

Example 168

N-(2-(3-(2-Methoxyphenyl)-2-oxo-4-phenyl-5-(piperazine-1-carbonyl)-2,3-dihydro-1H-imidazol-1-yl)ethyl)benzamide

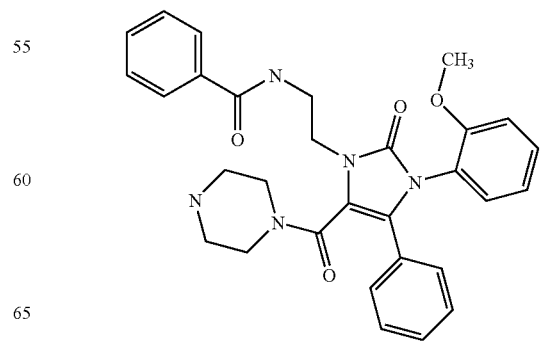

ESI-MS: m/z 526.2 (M+H)+.

Example 169

N-(2-(3-(2-Methoxyphenyl)-2-oxo-4-phenyl-5-(piperazine-1-carbonyl)-2,3-dihydro-1H-imidazol-1-yl)ethyl)-3-methylbutanamide

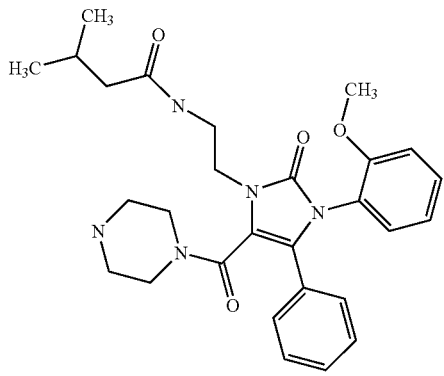

ESI-MS: m/z 506.2 (M+H)⁺.

Example 170

N-(3-(3-((2S)-2-Hydroxycyclohexyl)-2-oxo-4-phenyl-5-(piperazine-1-carbonyl)-2,3-dihydro-1H-imidazol-1-yl)propyl)benzamide

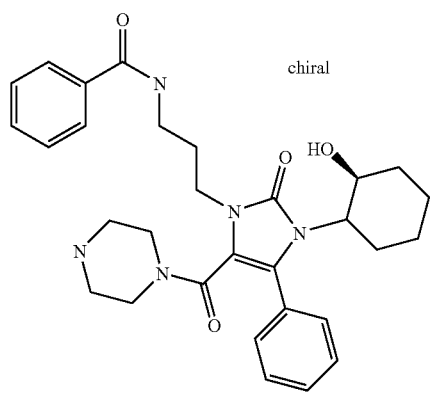

ESI-MS: m/z 532.3 (M+H)⁺.

Example 171

N-(3-(3-((2S)-2-Hydroxycyclohexyl)-2-oxo-4-phenyl-5-(piperazine-1-carbonyl)-2,3-dihydro-1H-imidazol-1-yl)propyl)benzenesulfonamide

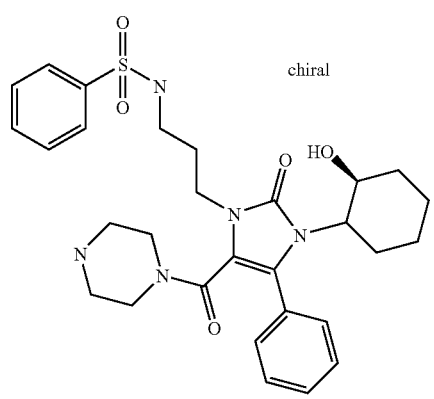

ESI-MS: m/z 506.2 (M+H)⁺.

Example 172

N-(3-(3-((2S)-2-Hydroxycyclohexyl)-2-oxo-4-phenyl-5-(piperazine-1-carbonyl)-2,3-dihydro-1H-imidazol-1-yl)propyl)-3-methylbutanamide

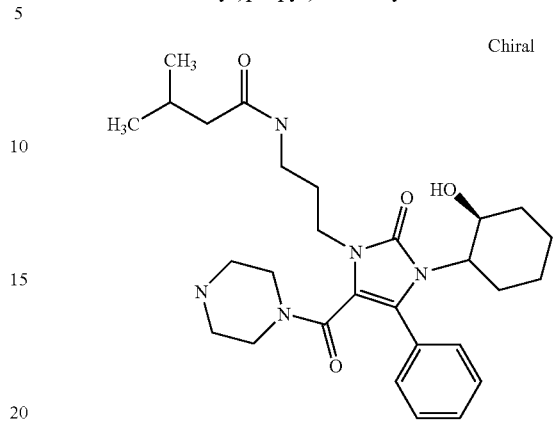

ESI-MS: m/z 512.2 (M+H)⁺.

Example 173

N-(2-(3-((2S)-2-Hydroxycyclohexyl)-2-oxo-4-phenyl-5-(piperazine-1-carbonyl)-2,3-dihydro-1H-imidazol-1-yl)ethyl)-3-methylbutanamide

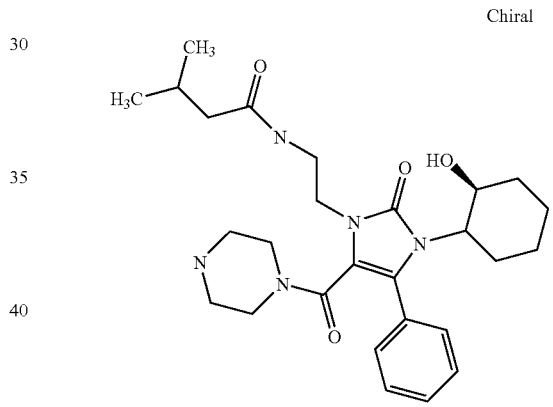

ESI-MS: m/z 498.2 (M+H)⁺.

Example 174

N-(3-(3-(3-Morpholinophenyl)-2-oxo-4-phenyl-5-(piperazine-1-carbonyl)imidazolidin-1-yl)propyl)benzamide

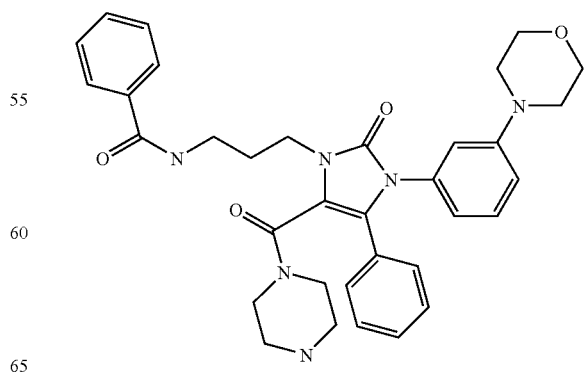

ESI-MS: m/z 595.2 (M+H)⁺.

Example 175
N-(3-(3-(3-Morpholinophenyl)-2-oxo-4-phenyl-5-(piperazine-1-carbonyl)-2,3-dihydro-1H-imidazol-1-yl)propyl)benzenesulfonamide

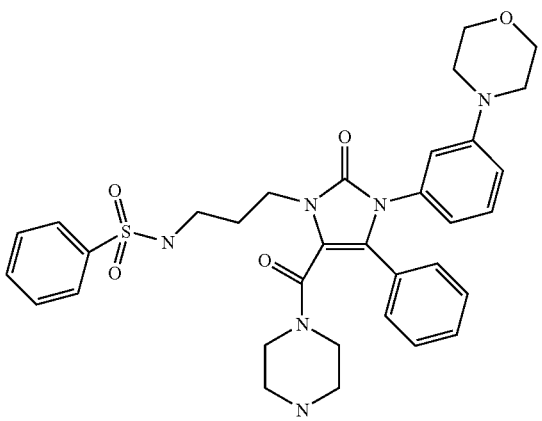

ESI-MS: m/z 631.2 (M+H)$^+$.

Example 176
3-Methyl-N-(3-(3-(3-morpholinophenyl)-2-oxo-4-phenyl-5-(piperazine-1-carbonyl)-2,3-dihydro-1H-imidazol-1-yl)propyl)butanamide

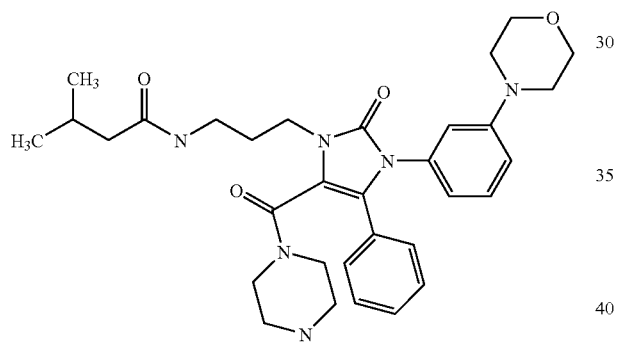

ESI-MS: m/z 575.3 (M+H)$^+$.

Example 177
N-(2-(3-(3-Morpholinophenyl)-2-oxo-4-phenyl-5-(piperazine-1-carbonyl)-2,3-dihydro-1H-imidazol-1-yl)ethyl)benzamide

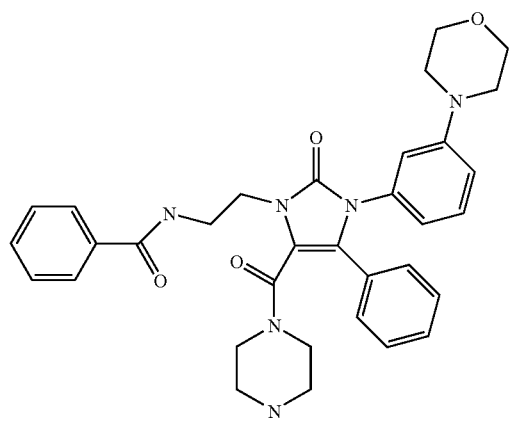

ESI-MS: m/z 581.3 (M+H)$^+$.

Example 178
3-Methyl-N-(2-(3-(3-morpholinophenyl)-2-oxo-4-phenyl-5-(piperazine-1-carbonyl)-2,3-dihydro-1H-imidazol-1-yl)ethyl)butanamide

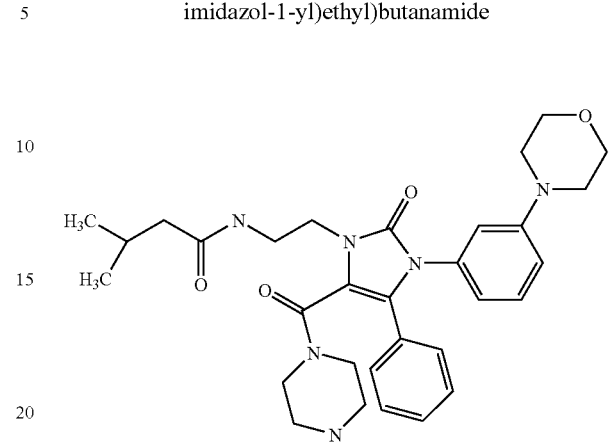

ESI-MS: m/z 561.3 (M+H)$^+$.

Example 179
N-(3-(3-(3-(3-Methoxypropoxy)phenyl)-2-oxo-4-phenyl-5-(piperazine-1-carbonyl)-2,3-dihydro-1H-imidazol-1-yl)propyl)benzamide

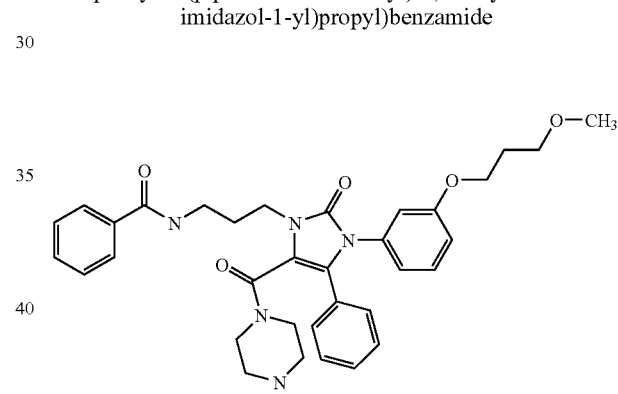

ESI-MS: m/z 598.3 (M+H)$^+$.

Example 180
N-(3-(3-(3-(3-Methoxypropoxy)phenyl)-2-oxo-4-phenyl-5-(piperazine-1-carbonyl)-2,3-dihydro-1H-imidazol-1-yl)propyl)benzenesulfonamide

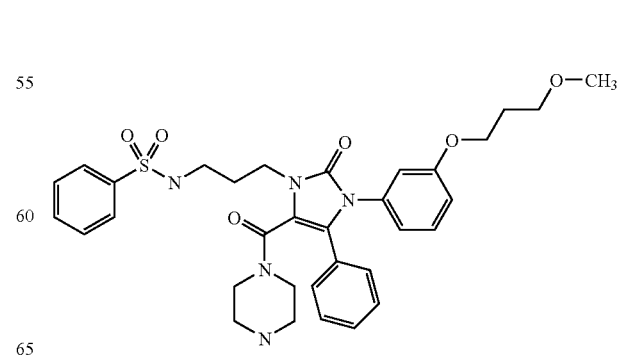

ESI-MS: m/z 634.2 (M+H)$^+$.

Example 181

N-(3-(3-(3-(3-Methoxypropoxy)phenyl)-2-oxo-4-phenyl-5-(piperazine-1-carbonyl)-2,3-dihydro-1H-imidazol-1-yl)propyl)-3-methylbutanamide

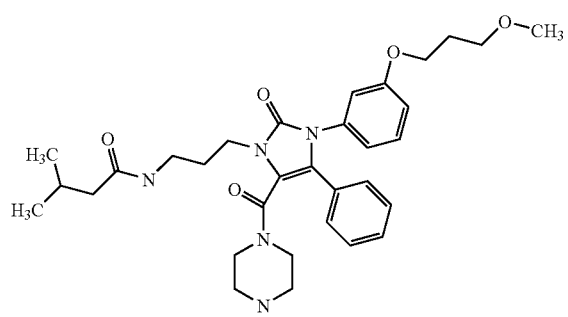

ESI-MS: m/z 578.3 (M+H)$^+$.

Example 182

N-(2-(3-(3-(3-Methoxypropoxy)phenyl)-2-oxo-4-phenyl-5-(piperazine-1-carbonyl)-2,3-dihydro-1H-imidazol-1-yl)ethyl)benzamide

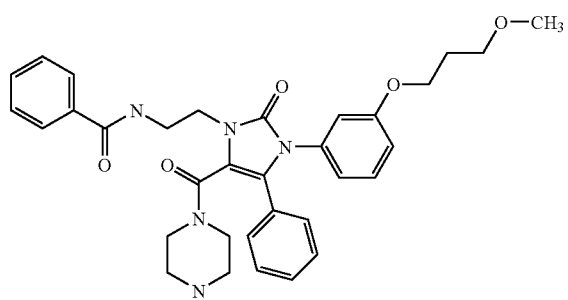

ESI-MS: m/z 584.3 (M+H)$^+$.

Example 183

N-(2-(3-(3-(3-Methoxypropoxy)phenyl)-2-oxo-4-phenyl-5-(piperazine-1-carbonyl)-2,3-dihydro-1H-imidazol-1-yl)ethyl)benzenesulfonamide

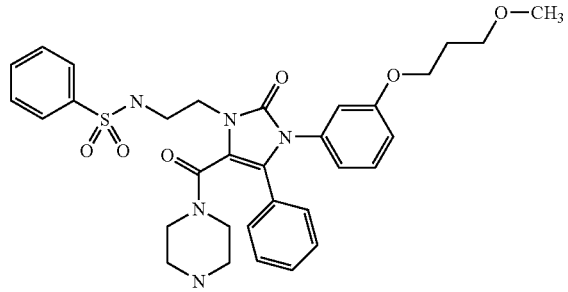

ESI-MS: m/z 620.2 (M+H)$^+$.

Example 184

N-(2-(3-(3-(3-Methoxypropoxy)phenyl)-2-oxo-4-phenyl-5-(piperazine-1-carbonyl)-2,3-dihydro-1H-imidazol-1-yl)ethyl)-3-methylbutanamide

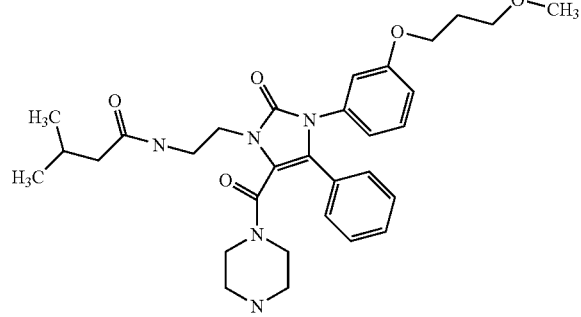

ESI-MS: m/z 564.3 (M+H)$^+$.

Example 185

N-(2-(3-(3-Morpholinophenyl)-2-oxo-4-phenyl-5-(piperazine-1-carbonyl)-2,3-dihydro-1H-imidazol-1-yl)ethyl)benzenesulfonamide

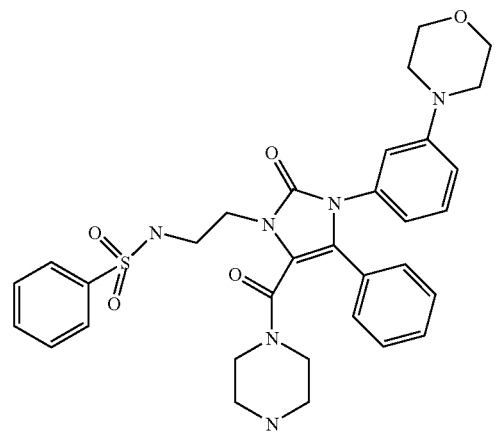

ESI-MS: m/z 617.2 (M+H)$^+$.

Example 186

1-(3-(2-Methoxyethoxy)benzyl)-4-phenyl-5-(piperazine-1-carbonyl)-3-o-tolyl-1H-imidazol-2(3H)-one

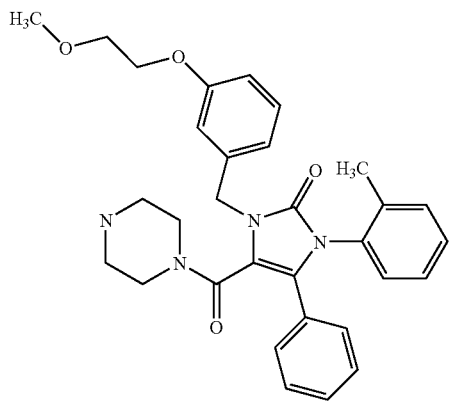

ESI-MS: m/z 527.2 (M+H)$^+$.

Example 187

1-(3-(2-Methoxyethoxy)benzyl)-3-(2-methoxyphenyl)-4-phenyl-5-(piperazine-1-carbonyl)-1H-imidazol-2(3H)-one

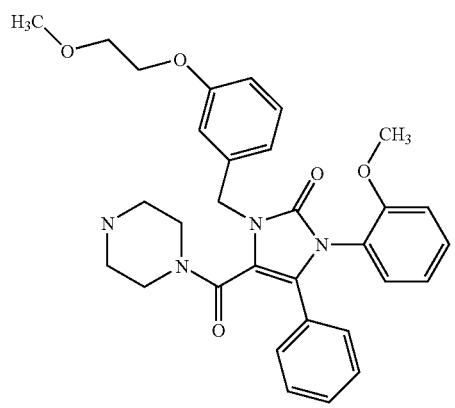

ESI-MS: m/z 543.2 (M+H)$^+$.

Example 188

1-(2-Methoxyphenyl)-3-(3-(2-phenoxyethoxy)benzyl)-5-phenyl-4-(piperazine-1-carbonyl)-1H-imidazol-2(3H)-one

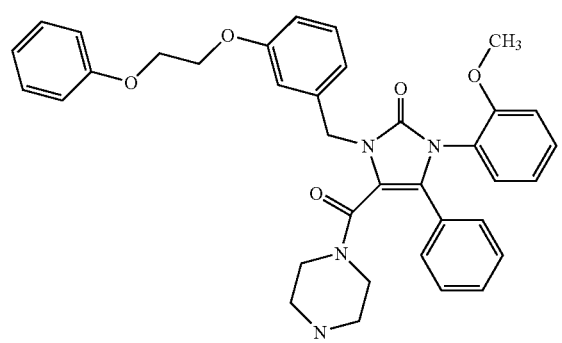

ESI-MS: m/z 605.3 (M+H)$^+$.

Example 189

1-(Cyclohexylmethyl)-3-(3-morpholinophenyl)-4-phenyl-5-(piperazine-1-carbonyl)-1H-imidazol-2(3H)-one

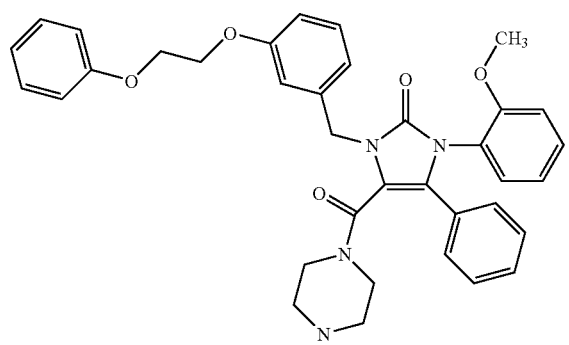

ESI-MS: m/z 530.2 (M+H)$^+$.

Example 190

1-(3,4-Difluorobenzyl)-3-(3-morpholinophenyl)-4-phenyl-5-(piperazine-1-carbonyl)-1H-imidazol-2(3H)-one

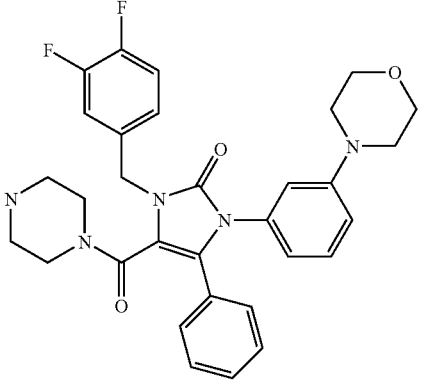

ESI-MS: m/z 560.2 (M+H)$^+$.

Example 191

1-(3-Morpholinophenyl)-3-(3-(2-phenoxyethoxy)benzyl)-5-phenyl-4-(piperazine-1-carbonyl)-1H-imidazol-2(3H)-one

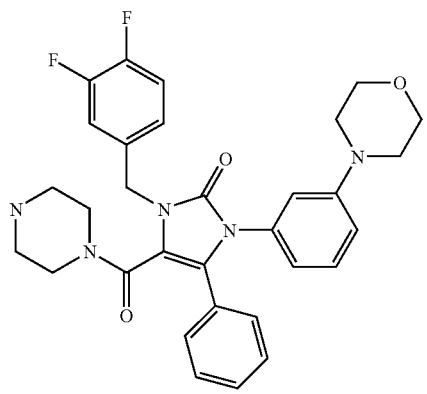

ESI-MS: m/z 660.3 (M+H)$^+$.

Example 192

1-(3-(2-Methoxyethoxy)benzyl)-3-(3-(3-methoxypropoxy)phenyl)-4-phenyl-5-(piperazine-1-carbonyl)-1H-imidazol-2(3H)-one

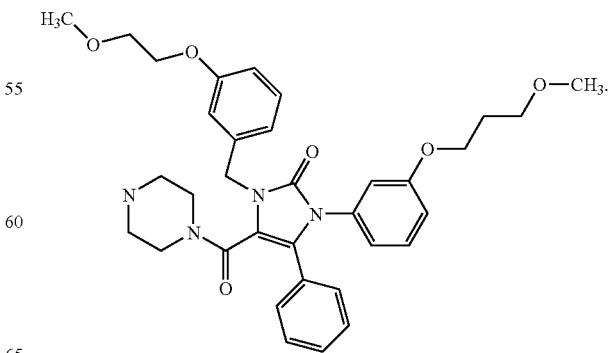

ESI-MS: m/z 601.3 (M+H)$^+$.

Example 193

2-Fluoro-N-(3-(3-(3-morpholinophenyl)-2-oxo-4-phenyl-5-(piperazine-1-carbonyl)-2,3-dihydro-1H-imidazol-1-yl)propyl)benzenesulfonamide

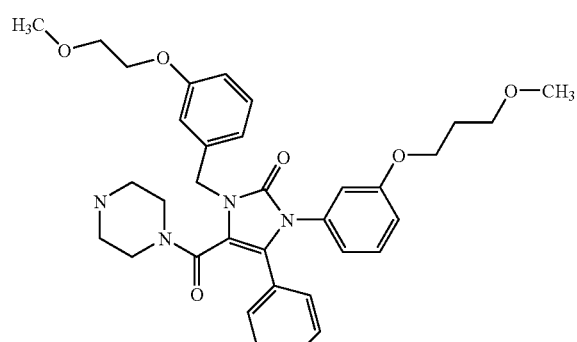

ESI-MS: m/z 649.2 (M+H)+.

Example 194

2-Chloro-N-(3-(3-(3-morpholinophenyl)-2-oxo-4-phenyl-5-(piperazine-1-carbonyl)-2,3-dihydro-1H-imidazol-1-yl)propyl)benzenesulfonamide

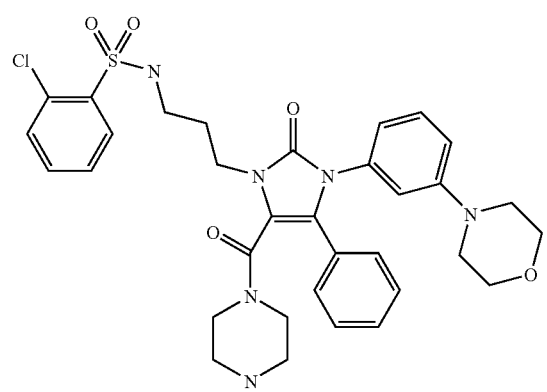

ESI-MS: m/z 665.2 (M+H)+.

Example 195

3-Chloro-N-(3-(3-(3-morpholinophenyl)-2-oxo-4-phenyl-5-(piperazine-1-carbonyl)-2,3-dihydro-1H-imidazol-1-yl)propyl)benzenesulfonamide

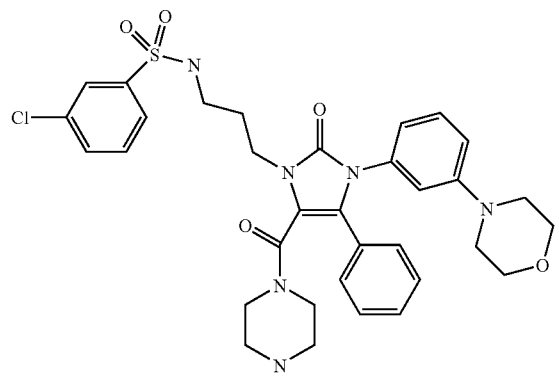

ESI-MS: m/z 665.2 (M+H)+.

Example 196

N-(3-(3-(3-Morpholinophenyl)-2-oxo-4-phenyl-5-(piperazine-1-carbonyl)-2,3-dihydro-1H-imidazol-1-yl)propyl)propane-2-sulfonamide

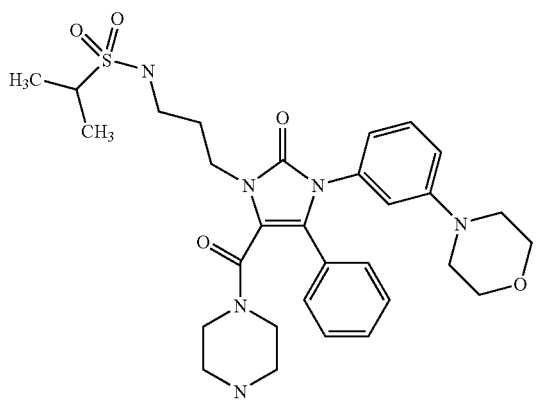

ESI-MS: m/z 597.3 (M+H)+.

Example 197

2-Methyl-N-(3-(3-(3-morpholinophenyl)-2-oxo-4-phenyl-5-(piperazine-1-carbonyl)-2,3-dihydro-1H-imidazol-1-yl)propyl)benzenesulfonamide

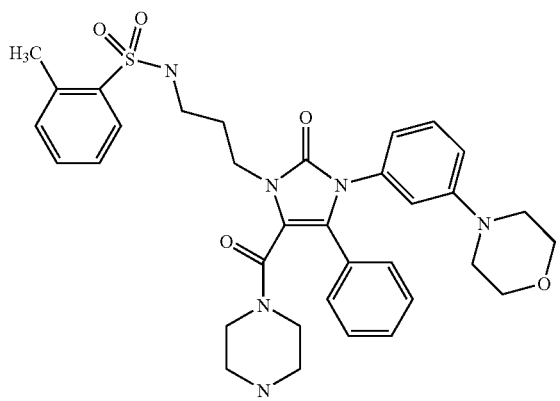

ESI-MS: m/z 645.3 (M+H)$^+$.

Example 198

3-Methoxy-N-(3-(3-(3-morpholinophenyl)-2-oxo-4-phenyl-5-(piperazine-1-carbonyl)-2,3-dihydro-1H-imidazol-1-yl)propyl)benzenesulfonamide

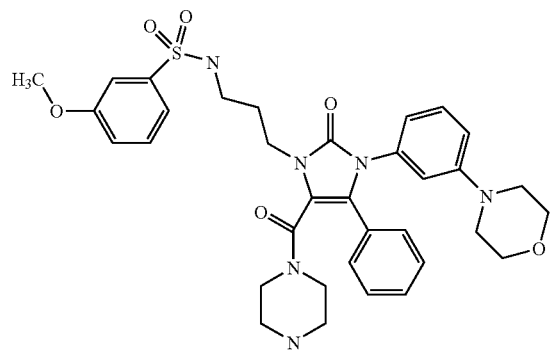

ESI-MS: m/z 661.2 (M+H)$^+$.

Example 199

4-Methoxy-N-(3-(3-(3-morpholinophenyl)-2-oxo-4-phenyl-5-(piperazine-1-carbonyl)-2,3-dihydro-1H-imidazol-1-yl)propyl)benzenesulfonamide

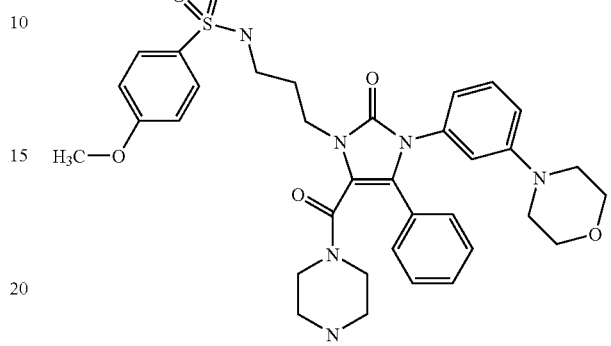

ESI-MS: m/z 661.2 (M+H)$^+$.

Example 200

1-(3-(3-(3-Morpholinophenyl)-2-oxo-4-phenyl-5-(piperazine-1-carbonyl)-2,3-dihydro-1H-imidazol-1-yl)propyl)-3-phenylurea

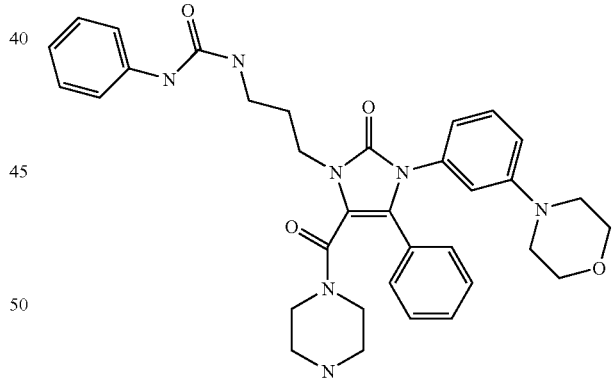

ESI-MS: m/z 610.2 (M+H)$^+$.

Example 201

General procedure for the preparation of tert-Butyl 4-(3-(3-aminopropyl)-2-oxo-5-phenyl-1-o-tolyl-2,3-dihydro-1H-imidazole-4-carbonyl)piperazine-1-carboxylate (201) and other imidazolone analogs

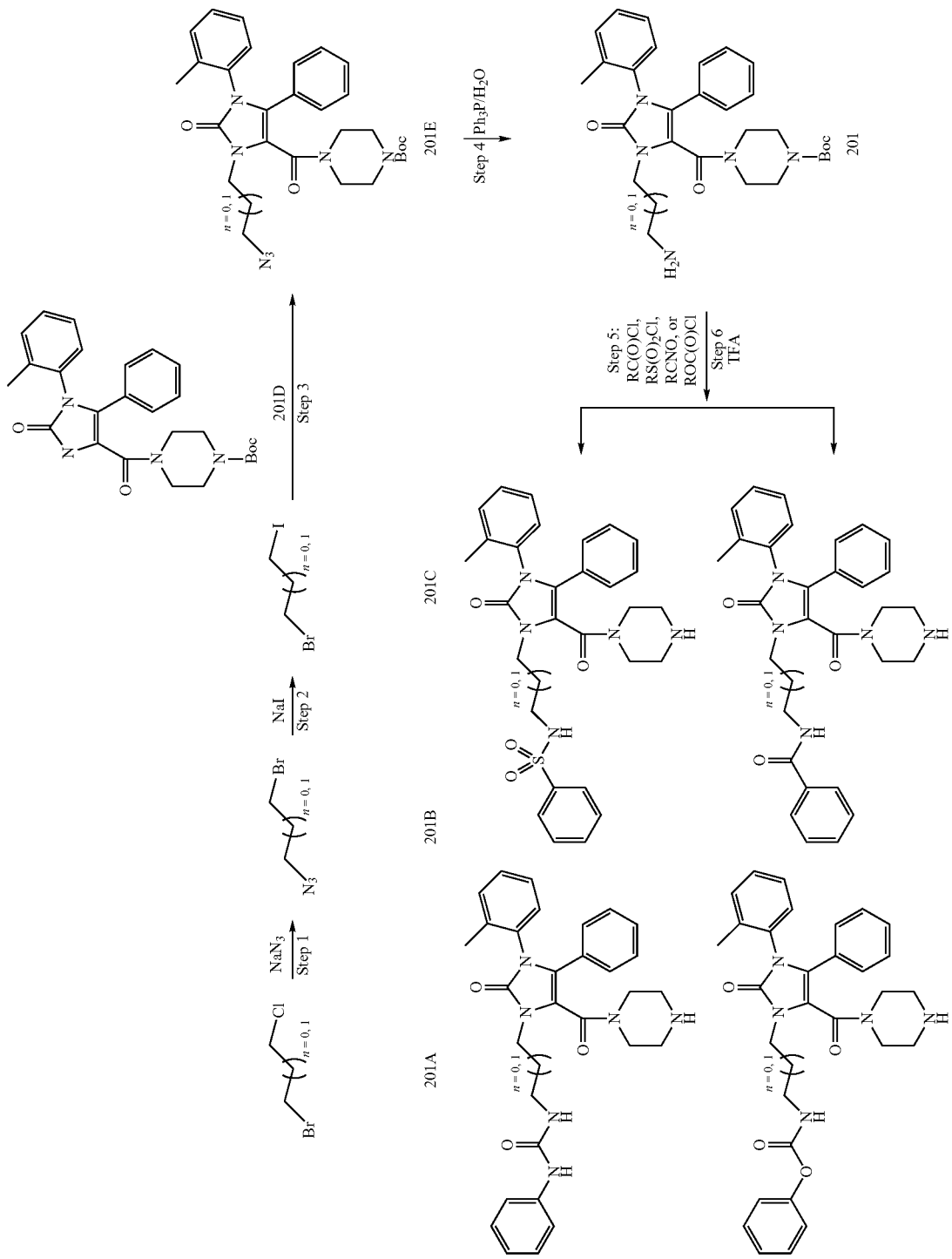

A. 1-Azido-3-iodopropane (201A)

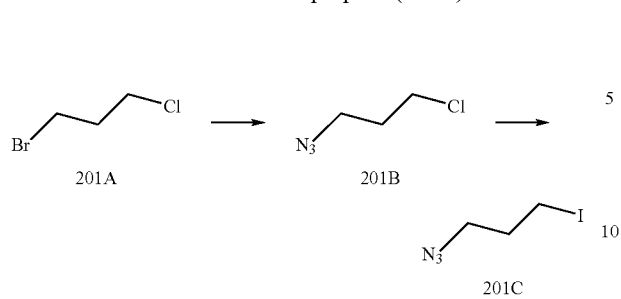

NaN3 (13.0 g, 0.2 mol) was added to a solution of 1-bromo-3-chloropropane (201A) (19.7 mL, 0.2 mol) in 500 mL of DMF at room temperature. The reaction mixture was allowed to stir for 24 hrs. The reaction mixture was partitioned between ether and water, and the organic layer was washed with water 3×, dried over $Na_2SO_4$ and concentrated to give 1-azido-3-chloropropane (201B) as a light yellow oil, which was carried into next reaction without further purification. $^1$H-NMR (300 MHz, $CDCl_3$): δ ppm 2.03 (m, 2H), 3.51 (t, 2H, J=6.6 Hz), 3.65 (t, 2H, J=6.6 Hz).

NaI (59.9 g, 400 mmol) was added to a solution of 201B (~200 mmol) in 600 mL of acetone and heated to reflux for 24 h. The reaction mixture was partitioned between EtOAc and water. Aqueous layer was extracted with EtOAc (3×100 mL). The combined organic layers were dried over $Na_2SO_4$ and concentrated to give an oil. Flash chromatography (5%, EtOAc/hexane) afforded 1-azido-3-iodopropane (201C) (23 g, 55%, two steps) as a yellow oil. $^1$H-NMR (300 MHz, $CDCl_3$): δ ppm 2.08 (m, 2H), 3.27 (t, 2H, J=6.9 Hz), 3.46 (t, 2H, J=6.6 Hz).

B. tert-Butyl 4-(3-(3-aminopropyl)-2-oxo-5-phenyl-1-o-tolyl-2,3-dihydro-1H-imidazole-4-carbonyl)piperazine-1-carboxylate (201)

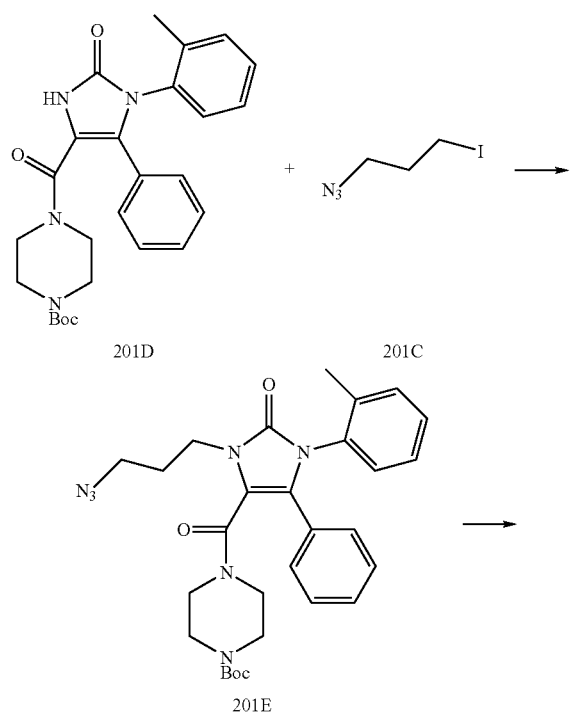

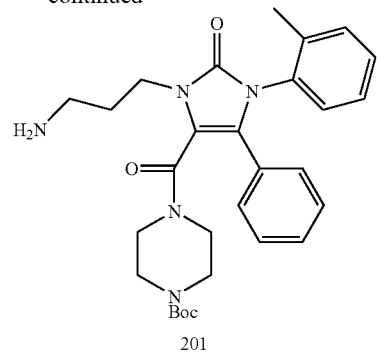

To a solution of 201D (324 mg, 0.7 mmol) in 5 mL DMF was added NaH (30 mg, 0.74 mmol). The reaction mixture was stirred at RT for 30 mins. 201C (155 mg, 0.74 mmol) was added to the reaction mixture; the resulting mixture was stirred at RT overnight. The mixture was diluted with ethyl acetate and $H_2O$. The aqueous phase was extracted with ethyl acetate; the combined organic phase was washed with water, dried with anhydrous $MgSO_4$, filtered, and concentrated in vacuo, leaving a yellow oil which was purified by flash chromatography (elution: PE/EA=10/1~0/1) giving 201E, (264 mg, 69%) as a light yellow solid. LCMS: purity=100% MS (EZ, m/e): 546 (M+H)$^+$.

A mixture of 201E (260 mg, 0.48 mmol) and triphenylphosphine (137 mg, 0.52 mmol) in THF (wet, 10 mL) was stirred at RT overnight. The mixture was concentrated in vacuo, and the residue was purified by flash chromatography, and afforded 201, (184 mg, 74%), as a white solid. LCMS: purity=99%. (MS (EZ, m/e:) 520(M+H)$^+$.

C. N-(3-(2-Oxo-4-phenyl-5-(piperazine-1-carbonyl)-3-o-tolyl-2,3-dihydro-1H-imidazol-1-yl)propyl)benzenesulfonamide (162)

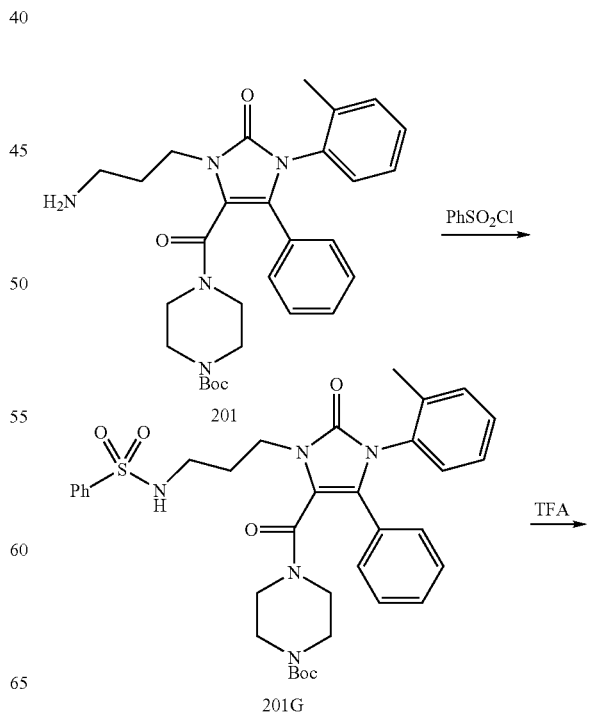

293

-continued

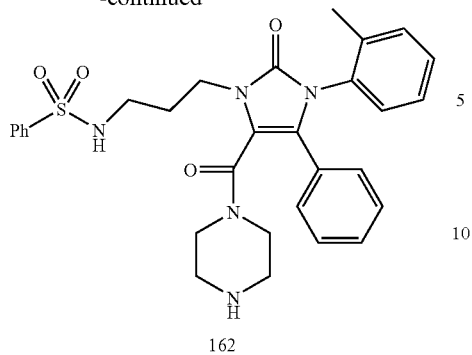

162

To a stirred solution of 201 (31 mg, 0.059 mmol) and DIPEA (11.5 mg) in THF (3 mL) was added benzenesulfonyl chloride (15.7 mg, 0.089 mmol) at 0° C. The reaction mixture was warmed to RT overnight, then extracted with ethyl acetate. The organic phase was washed with water, dried with anhydrous MgSO$_4$, filtered, and concentrated in vacuo. The residue was purified by flash chromatography, afforded 201G, (17 mg, 44%), as a light yellow solid. $^1$H NMR (300 MHz, CDCl3) δ ppm 1.27 (s, 9H), 1.96 (m, 2H), 2.03 (s, 3H), 3.0 (m, 4H), 3.2-3.5 (m, 4H), 3.8-4.2 (m, 4H), 6.9 (m, 2H), 7.25 (m, 6H), 7.44 (m, 4H), 7.85 (m, 2H); ESI-MS: m/z 660.2 (M+H)$^+$.

The protected group of 201G was removed by stirring in 20% TFA-DCM and stirred for 30 mins to 24 hrs at room temperature (Scheme A, Step 8) which afforded the title compound 162, after purified by RP-HPLC, as TFA salt. ESI-MS: m/z 560.2 (M+H)$^+$.

D. 1-(3-(2-oxo-4-phenyl-5-(piperazine-1-carbonyl)-3-o-tolyl-2,3-dihydro-1H-imidazol-1-yl)propyl)-3-phenylurea (223)

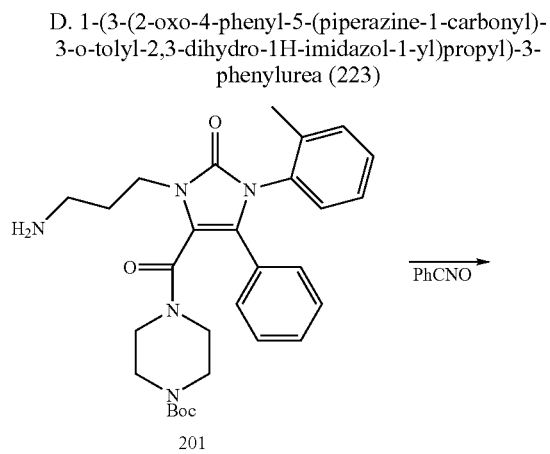

294

-continued

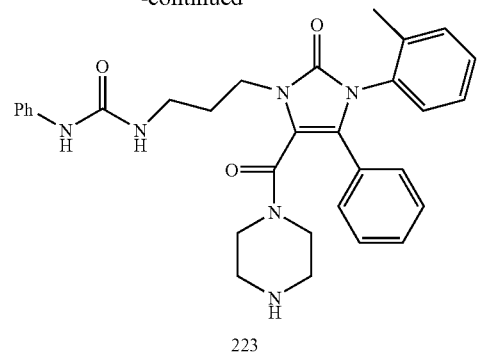

223

To a solution of 201 (27 mg, 0.05 mmol) in CH$_2$Cl$_2$ (1 mL), which was stirred at room temperature and was added phenyl isocyanate (6.5 mg, 0.055 mmol). The reaction mixture was stirred for 1.5 hours at 30° C., and was evaporated under reduced pressure. The residue was purified by flash chromatography, afforded 201H (21 mg) as a white solid. LCMS: purity=96%. MS (EZ, m/e): 639.2 (M+H)$^+$.

The protected group of 201H was removed by stirring in 20% TFA-DCM for 30 mins to 24 hrs at room temperature (Scheme A, Step 8) which afforded the title compound 223, after purified by RP-HPLC, as TFA salt. ESI-MS: m/z 539.2 (M+H)$^+$ E. N-(3-(2-oxo-4-phenyl-5-(piperazine-1-carbonyl)-3-o-tolyl-2,3-dihydro-1H-imidazol-1-yl)propyl)benzamide (156)

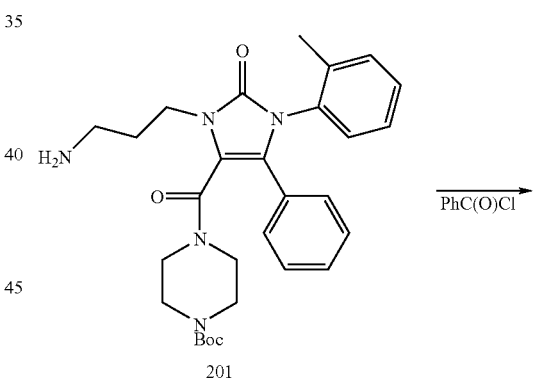

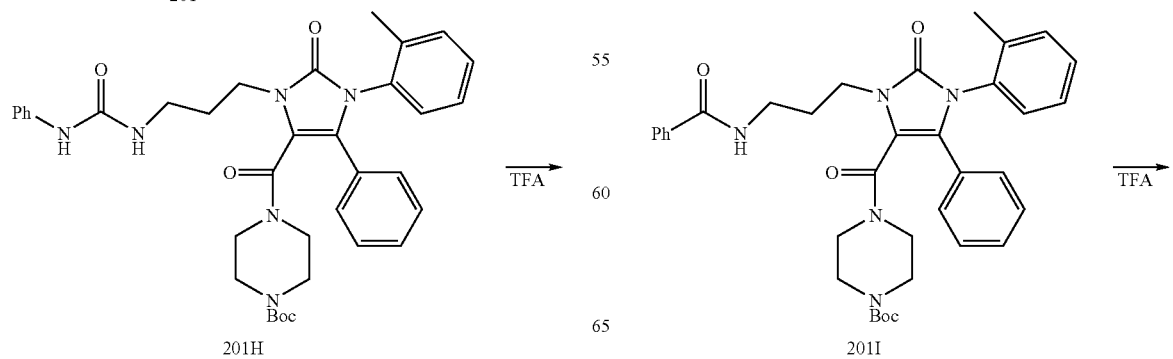

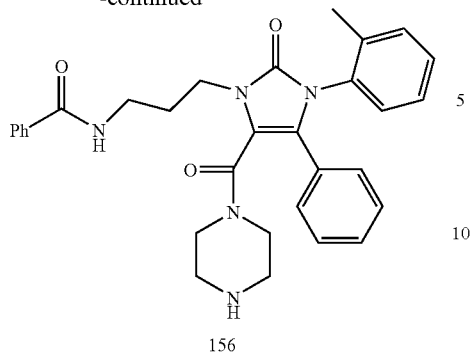

156

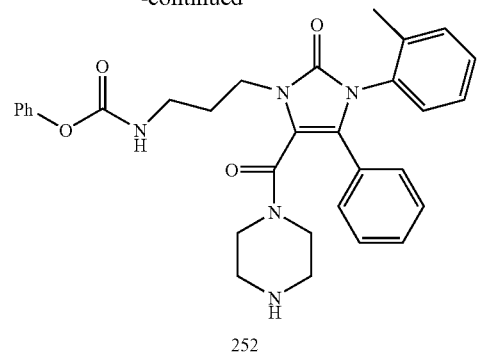

252

To a stirred solution of 201 (31 mg, 0.059 mmol) and DIPEA (11.5 mg) in THF (3 mL) was added benzoyl chloride (12.5 mg, 0.089 mmol) at 0° C. The reaction mixture was warmed to RT overnight, then extracted with ethyl acetate. The organic phase was washed with water, dried with anhydrous MgSO$_4$, filtered, and concentrated in vacuo. The residue was purified by flash chromatography, afforded 201I, (16 mg, 43%) as a light yellow solid. $^1$H NMR (300 MHz, CDCl$_3$) δ ppm 1.27 (s, 9H), 1.9 (m, 2H), 2.03 (s, 3H), 3.2 (m, 4H), 3.4 (m, 4H), 4.1 (m, 4H), 7.0 (m, 2H), 7.25 (m, 6H), 7.43 (m, 4H), 7.91 (m, 2H); ESI-MS: m/z 624.2 (M+H)$^+$.

The protected group of 201I was removed by stirring in 20% TFA-DCM for 30 mins to 24 hrs at room temperature (Scheme A, Step 8) which afforded the title compounds 156, after purified by RP-HPLC, as TFA salt. ESI-MS: m/z 524.2 (M+H)$^+$.

F. Phenyl 3-(2-oxo-4-phenyl-5-(piperazine-1-carbonyl)-3-o-tolyl-2,3-dihydro-1H-imidazol-1-yl)propyl-carbamate (252)

To a stirred solution of 201F (52 mg, 0.1 mmol) and DIPEA (54 mL, 3 eq) in THF (3 mL) was added phenyl carbonochloridate (18.8 mg, 15.1 mL, 0.12 mmol) at 0° C. The reaction mixture was warmed to RT overnight, then extracted with ethyl acetate. The organic phase was washed with water, dried with anhydrous MgSO$_4$, filtered, and concentrated in vacuo. The residue was purified by flash chromatography to afford 201J (17 mg 27%) as a light yellow solid. ESI-MS: m/z 640.3 (M+H)$^+$.

The protected group of 201J was removed by stirring in 20% TFA-DCM for 30 mins to 24 hrs at room temperature (Scheme A, Step 8) which afforded the title compound 252, after purified by RP-HPLC, as TFA salt. ESI-MS: m/z 540.3 (M+H)$^+$.

Example 202

4-Chloro-N-(3-(3-(3-morpholinophenyl)-2-oxo-4-phenyl-5-(piperazine-1-carbonyl)-2,3-dihydro-1H-imidazol-1-yl)propyl)benzenesulfonamide

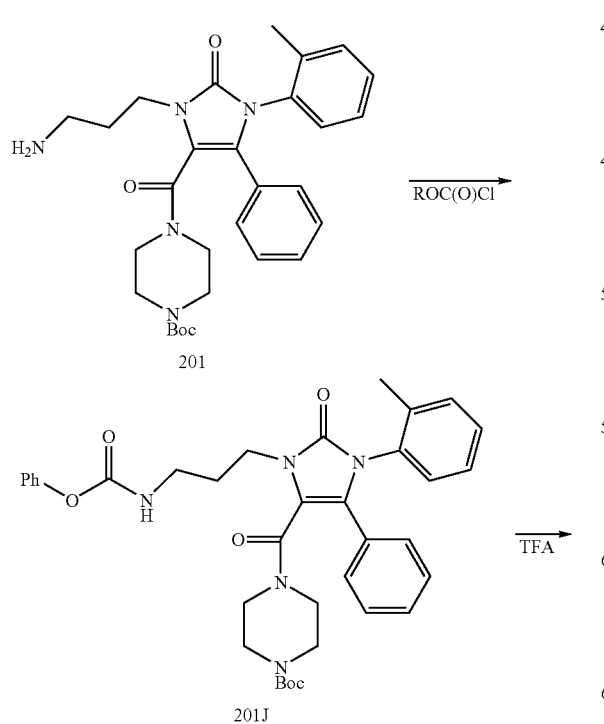

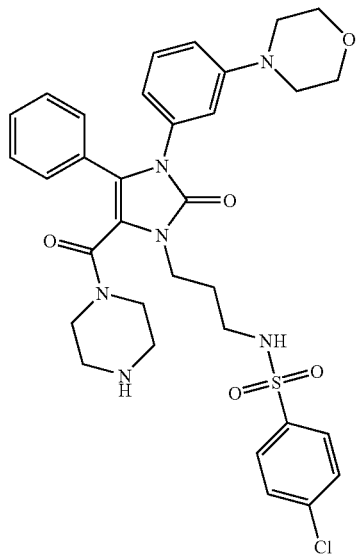

The titled compound was prepared by a procedure analogous to that described in Example 201. ESI-MS: m/z 666.2 (M+H)+.

Example 203

2-Fluoro-N-(2-(2-oxo-4-phenyl-5-(piperazine-1-carbonyl)-3-o-tolyl-2,3-dihydro-1H-imidazol-1-yl)ethyl)benzenesulfonamide

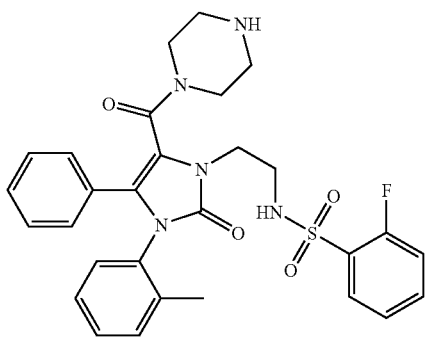

The titled compound was prepared by a procedure analogous to that described in Example 201. ESI-MS: m/z 564.2 (M+H)+.

Example 204

2-Chloro-N-(2-(2-oxo-4-phenyl-5-(piperazine-1-carbonyl)-3-o-tolyl-2,3-dihydro-1H-imidazol-1-yl)ethyl)benzenesulfonamide

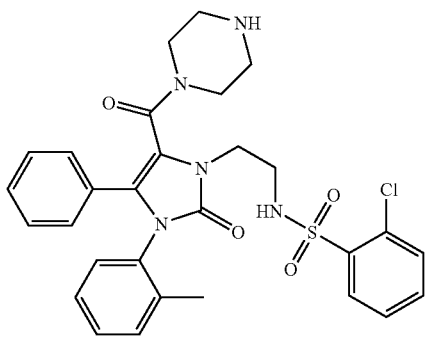

The titled compound was prepared by a procedure analogous to that described in Example 201. ESI-MS: m/z 581.2 (M+H)+.

Example 205

3-Chloro-N-(2-(2-oxo-4-phenyl-5-(piperazine-1-carbonyl)-3-o-tolyl-2,3-dihydro-1H-imidazol-1-yl)ethyl)benzenesulfonamide

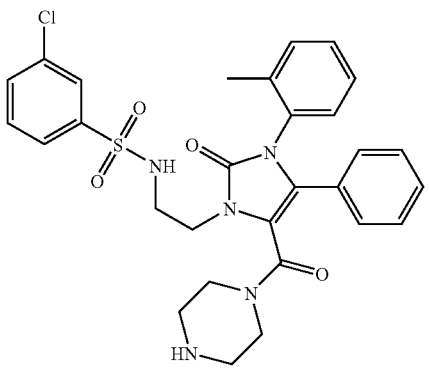

The titled compound was prepared by a procedure analogous to that described in Example 201. ESI-MS: m/z 581.2 (M+H)+.

Example 207

N-(2-(2-Oxo-4-phenyl-5-(piperazine-1-carbonyl)-3-o-tolyl-2,3-dihydro-1H-imidazol-1-yl)ethyl)propane-2-sulfonamide

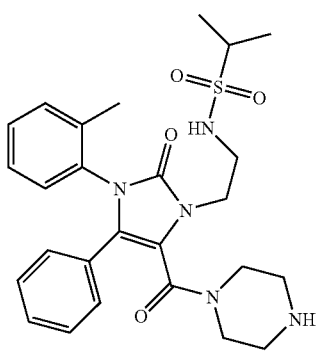

The titled compound was prepared by a procedure analogous to that described in Example 201. ESI-MS: m/z 581.2 (M+H)+.

Example 207

4-Chloro-N-(2-(2-oxo-4-phenyl-5-(piperazine-1-carbonyl)-3-o-tolyl-2,3-dihydro-1H-imidazol-1-yl)ethyl)benzenesulfonamide

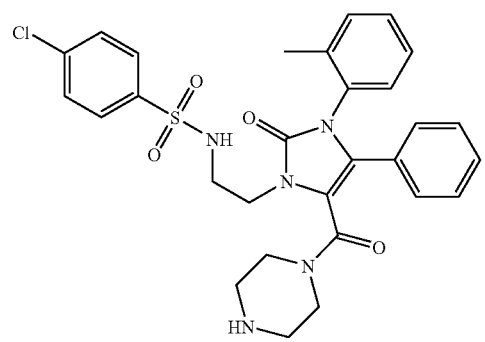

The titled compound was prepared by a procedure analogous to that described in Example 201. ESI-MS: m/z 512.2 (M+H)+.

Example 208

2-Methyl-N-(2-(2-oxo-4-phenyl-5-(piperazine-1-carbonyl)-3-o-tolyl-2,3-dihydro-1H-imidazol-1-yl)ethyl)benzenesulfonamide

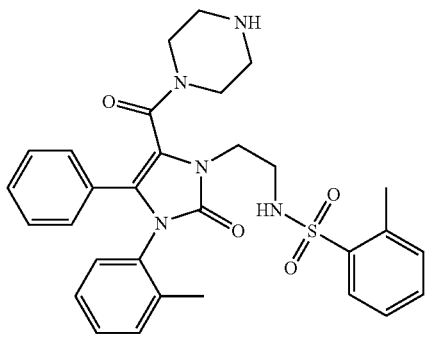

The titled compound was prepared by a procedure analogous to that described in Example 201. ESI-MS: m/z 560.2 (M+H)$^+$.

Example 209

3-Methoxy-N-(2-(2-oxo-4-phenyl-5-(piperazine-1-carbonyl)-3-o-tolyl-2,3-dihydro-1H-imidazol-1-yl)ethyl)benzenesulfonamide

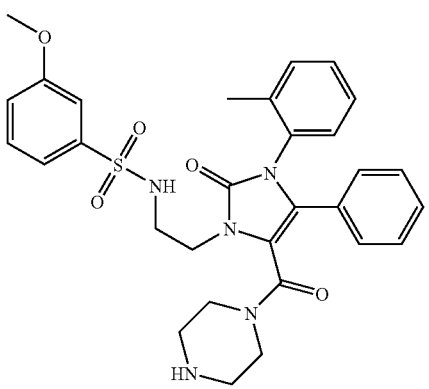

The titled compound was prepared by a procedure analogous to that described in Example 201. ESI-MS: m/z 576.2 (M+H)$^+$.

Example 210

4-Methoxy-N-(2-(2-oxo-4-phenyl-5-(piperazine-1-carbonyl)-3-o-tolyl-2,3-dihydro-1H-imidazol-1-yl)ethyl)benzenesulfonamide

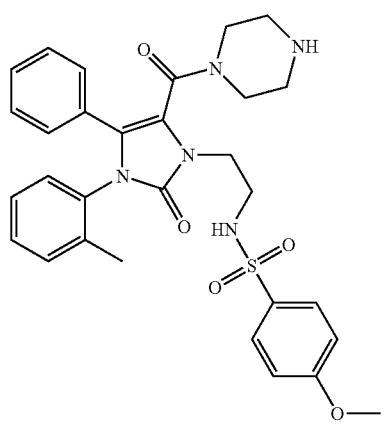

The titled compound was prepared by a procedure analogous to that described in Example 201. ESI-MS: m/z 576.2 (M+H)$^+$.

Example 211

1-(2-(2-Oxo-4-phenyl-5-(piperazine-1-carbonyl)-3-o-tolyl-2,3-dihydro-1H-imidazol-1-yl)ethyl)-3-phenylurea

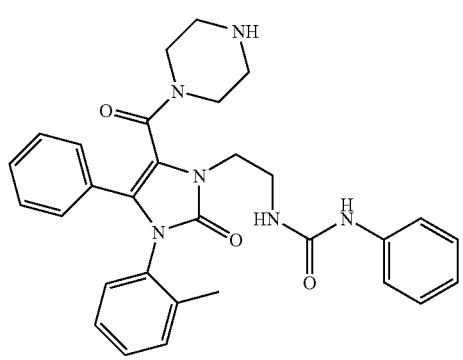

The titled compound was prepared by a procedure analogous to that described in Example 201. ESI-MS: m/z 525.3 (M+H)$^+$.

Example 212

1-(2-Chlorophenyl)-3-(2-(2-oxo-4-phenyl-5-(piperazine-1-carbonyl)-3-o-tolyl-2,3-dihydro-1H-imidazol-1-yl)ethyl)urea

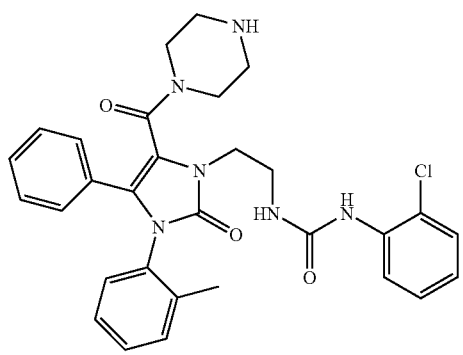

The titled compound was prepared by a procedure analogous to that described in Example 201. ESI-MS: m/z 560.3 (M+H)$^+$.

Example 213

1-(4-Chlorophenyl)-3-(2-(2-oxo-4-phenyl-5-(piperazine-1-carbonyl)-3-o-tolyl-2,3-dihydro-1H-imidazol-1-yl)ethyl)urea

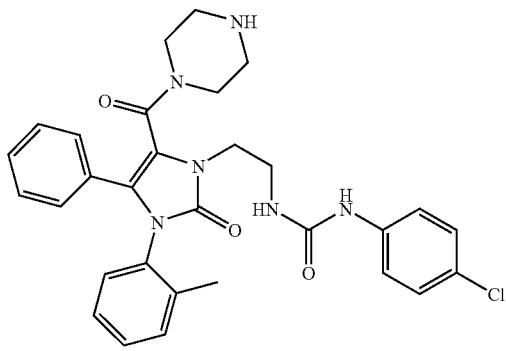

The titled compound was prepared by a procedure analogous to that described in Example 201. ESI-MS: m/z 560.2 (M+H)⁺.

Example 214

1-(2-Methoxyphenyl)-3-(2-(2-oxo-4-phenyl-5-(piperazine-1-carbonyl)-3-o-tolyl-2,3-dihydro-1H-imidazol-1-yl)ethyl)urea

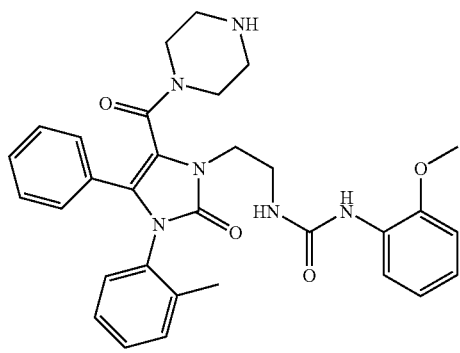

The titled compound was prepared by a procedure analogous to that described in Example 201. ESI-MS: m/z 555.3 (M+H)⁺.

Example 215

1-(3-Methoxyphenyl)-3-(2-(2-oxo-4-phenyl-5-(piperazine-1-carbonyl)-3-o-tolyl-2,3-dihydro-1H-imidazol-1-yl)ethyl)urea

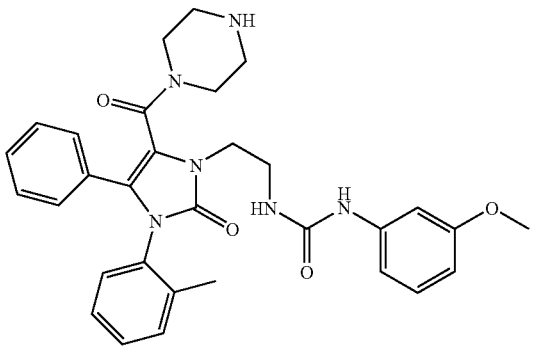

The titled compound was prepared by a procedure analogous to that described in Example 201. ESI-MS: m/z 555.3 (M+H)⁺.

Example 216

1-Isopropyl-3-(2-(2-oxo-4-phenyl-5-(piperazine-1-carbonyl)-3-o-tolyl-2,3-dihydro-1H-imidazol-1-yl)ethyl)urea

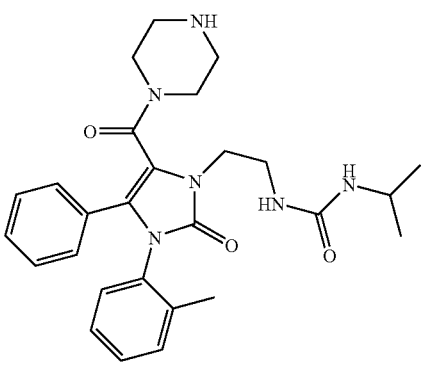

The titled compound was prepared by a procedure analogous to that described in Example 201. ESI-MS: m/z 491.3 (M+H)⁺.

Example 217

2-Chloro-N-(3-(2-oxo-4-phenyl-5-(piperazine-1-carbonyl)-3-o-tolyl-2,3-dihydro-1H-imidazol-1-yl)propyl)benzenesulfonamide

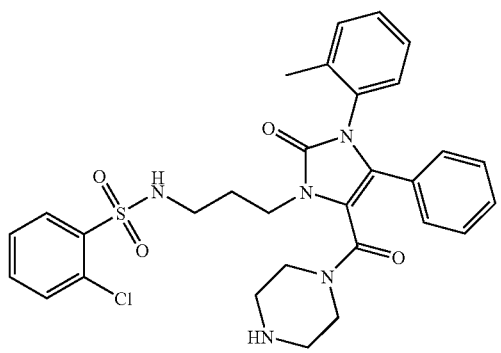

The titled compound was prepared by a procedure analogous to that described in Example 201. ESI-MS: m/z 595.2 (M+H)⁺.

Example 218

3-Chloro-N-(3-(2-oxo-4-phenyl-5-(piperazine-1-carbonyl)-3-o-tolyl-2,3-dihydro-1H-imidazol-1-yl)propyl)benzenesulfonamide

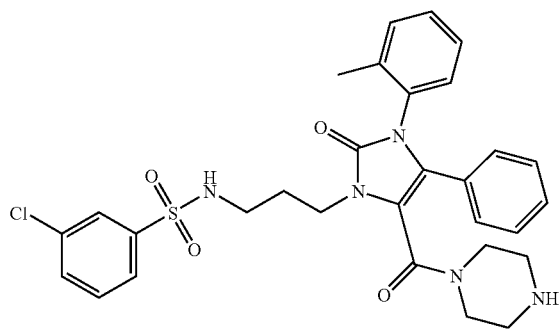

The titled compound was prepared by a procedure analogous to that described in Example 201. ESI-MS: m/z 595.2 (M+H)$^+$.

Example 219

4-Chloro-N-(3-(2-oxo-4-phenyl-5-(piperazine-1-carbonyl)-3-o-tolyl-2,3-dihydro-1H-imidazol-1-yl)propyl)benzenesulfonamide

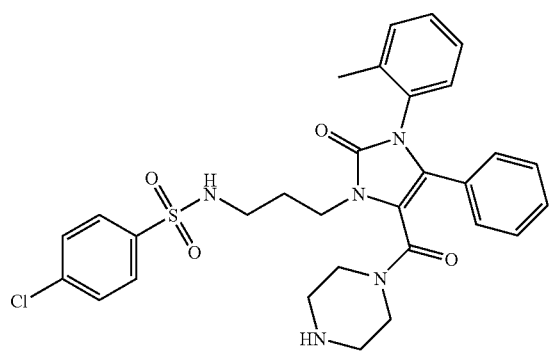

The titled compound was prepared by a procedure analogous to that described in Example 201. ESI-MS: m/z 595.3 (M+H)$^+$.

Example 220

2-Methyl-N-(3-(2-oxo-4-phenyl-5-(piperazine-1-carbonyl)-3-o-tolyl-2,3-dihydro-1H-imidazol-1-yl)propyl)benzenesulfonamide

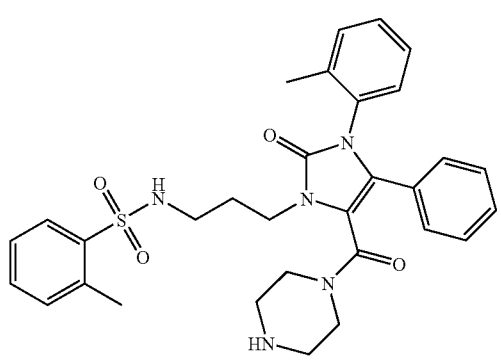

The titled compound was prepared by a procedure analogous to that described in Example 201. ESI-MS: m/z 574.3 (M+H)$^+$.

Example 221

3-Methoxy-N-(3-(2-oxo-4-phenyl-5-(piperazine-1-carbonyl)-3-o-tolyl-2,3-dihydro-1H-imidazol-1-yl)propyl)benzenesulfonamide

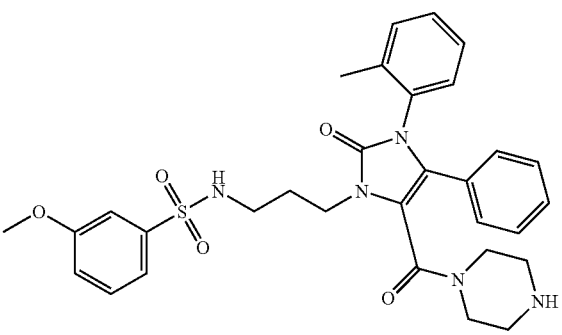

The titled compound was prepared by a procedure analogous to that described in Example 201. ESI-MS: m/z 590.3 (M+H)$^+$.

Example 222

4-Methoxy-N-(3-(2-oxo-4-phenyl-5-(piperazine-1-carbonyl)-3-o-tolyl-2,3-dihydro-1H-imidazol-1-yl)propyl)benzenesulfonamide

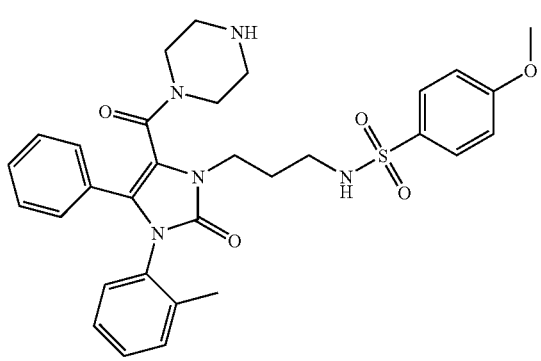

The titled compound was prepared by a procedure analogous to that described in Example 201. ESI-MS: m/z 590.3 (M+H)$^+$.

Example 223

1-(3-(2-Oxo-4-phenyl-5-(piperazine-1-carbonyl)-3-o-tolyl-2,3-dihydro-1H-imidazol-1-yl)propyl)-3-phenylurea

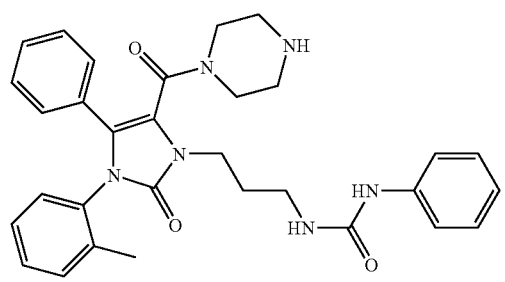

The titled compound was prepared by a procedure analogous to that described in Example 201. ESI-MS: m/z 539.3 (M+H)$^+$.

Example 224
1-(2-Chlorophenyl)-3-(3-(2-oxo-4-phenyl-5-(piperazine-1-carbonyl)-3-o-tolyl-2,3-dihydro-1H-imidazol-1-yl)propyl)urea

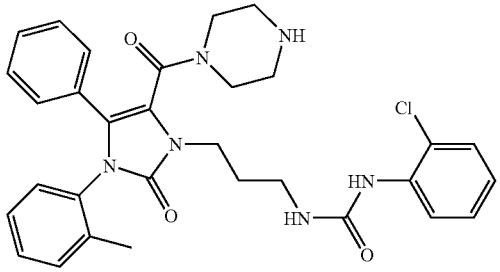

The titled compound was prepared by a procedure analogous to that described in Example 201. ESI-MS: m/z 574.3 (M+H)⁺.

Example 225
1-(2-Methoxyphenyl)-3-(3-(2-oxo-4-phenyl-5-(piperazine-1-carbonyl)-3-o-tolyl-2,3-dihydro-1H-imidazol-1-yl)propyl)urea

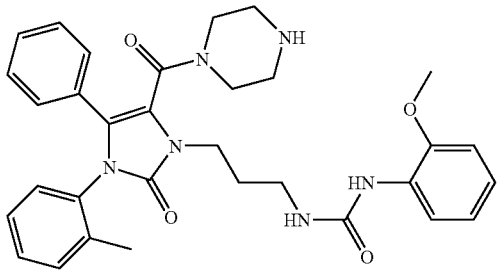

The titled compound was prepared by a procedure analogous to that described in Example 201. ESI-MS: m/z 569.3 (M+H)⁺.

Example 226
1-(3-Methoxyphenyl)-3-(3-(2-oxo-4-phenyl-5-(piperazine-1-carbonyl)-3-o-tolyl-2,3-dihydro-1H-imidazol-1-yl)propyl)urea

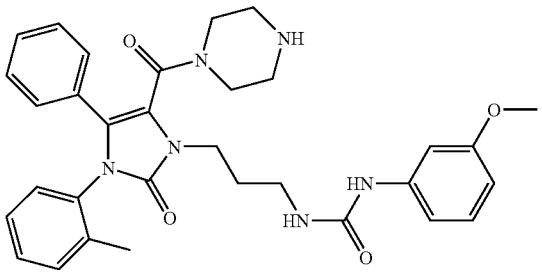

The titled compound was prepared by a procedure analogous to that described in Example 201. ESI-MS: m/z 569.3 (M+H)⁺.

Example 227
1-Isopropyl-3-(3-(2-oxo-4-phenyl-5-(piperazine-1-carbonyl)-3-o-tolyl-2,3-dihydro-1H-imidazol-1-yl)propyl)urea

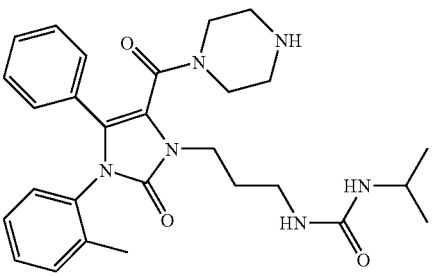

The titled compound was prepared by a procedure analogous to that described in Example 201. ESI-MS: m/z 505.4 (M+H)⁺.

Example 228
1-(4-Methoxyphenyl)-3-(2-(2-oxo-4-phenyl-5-(piperazine-1-carbonyl)-3-o-tolyl-2,3-dihydro-1H-imidazol-1-yl)ethyl)urea

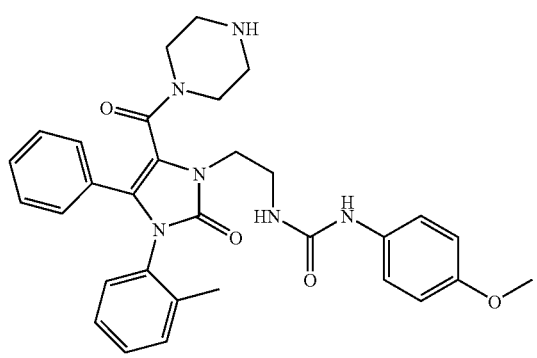

The titled compound was prepared by a procedure analogous to that described in Example 201. ESI-MS: m/z 555.3 (M+H)⁺.

Example 229
2-Fluoro-N-(3-(2-oxo-4-phenyl-5-(piperazine-1-carbonyl)-3-o-tolyl-2,3-dihydro-1H-imidazol-1-yl)propyl)benzenesulfonamide

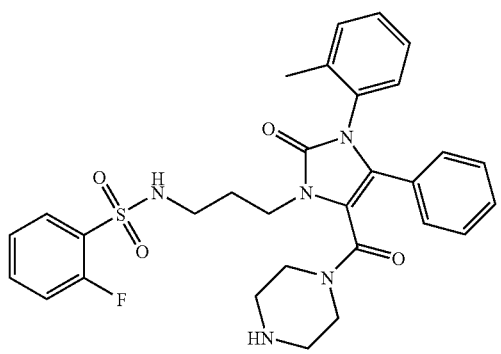

The titled compound was prepared by a procedure analogous to that described in Example 201. ESI-MS: m/z 578.2 (M+H)⁺.

Example 230

2-Fluoro-N-(2-(2-oxo-4-phenyl-5-(piperazine-1-carbonyl)-3-o-tolyl-2,3-dihydro-1H-imidazol-1-yl)ethyl)benzamide

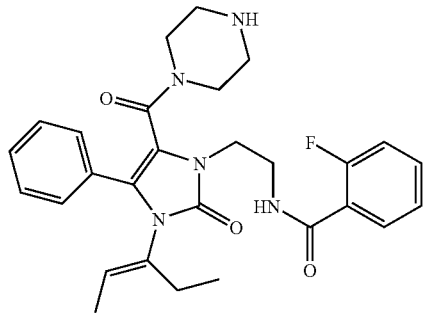

The titled compound was prepared by a procedure analogous to that described in Example 201. ESI-MS: m/z 528.3 (M+H)$^+$.

Example 231

2-Chloro-N-(2-(2-oxo-4-phenyl-5-(piperazine-1-carbonyl)-3-o-tolyl-2,3-dihydro-1H-imidazol-1-yl)ethyl)benzamide

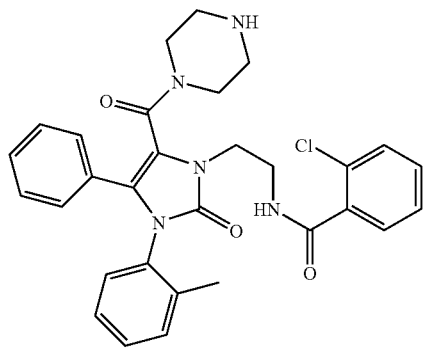

The titled compound was prepared by a procedure analogous to that described in Example 201. ESI-MS: m/z 545.3 (M+H)$^+$.

Example 232

3-Chloro-N-(2-(2-oxo-4-phenyl-5-(piperazine-1-carbonyl)-3-o-tolyl-2,3-dihydro-1H-imidazol-1-yl)ethyl)benzamide

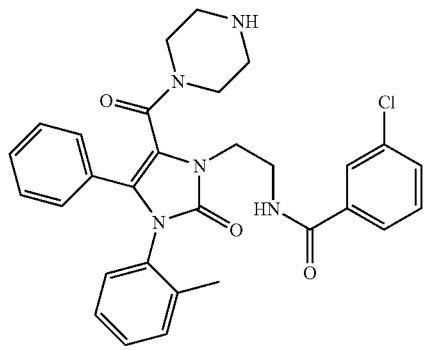

The titled compound was prepared by a procedure analogous to that described in Example 201. ESI-MS: m/z 545.2 (M+H)$^+$.

Example 233

4-Chloro-N-(2-(2-oxo-4-phenyl-5-(piperazine-1-carbonyl)-3-o-tolyl-2,3-dihydro-1H-imidazol-1-yl)ethyl)benzamide

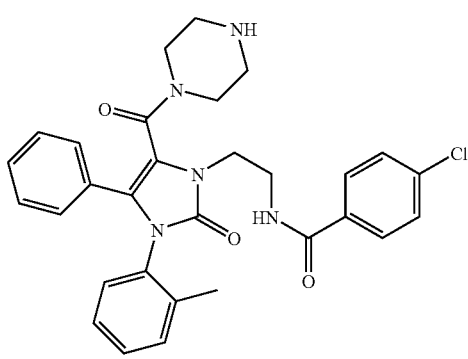

The titled compound was prepared by a procedure analogous to that described in Example 201. ESI-MS: m/z 545.2 (M+H)$^+$.

Example 234

2-Methoxy-N-(2-(2-oxo-4-phenyl-5-(piperazine-1-carbonyl)-3-o-tolyl-2,3-dihydro-1H-imidazol-1-yl)ethyl)benzamide

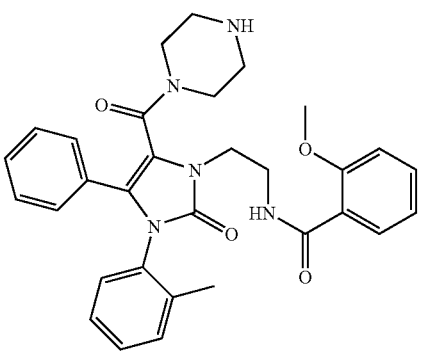

The titled compound was prepared by a procedure analogous to that described in Example 201. ESI-MS: m/z 540.3 (M+H)$^+$.

Example 235

4-Methoxy-N-(2-(2-oxo-4-phenyl-5-(piperazine-1-carbonyl)-3-o-tolyl-2,3-dihydro-1H-imidazol-1-yl)ethyl)benzamide

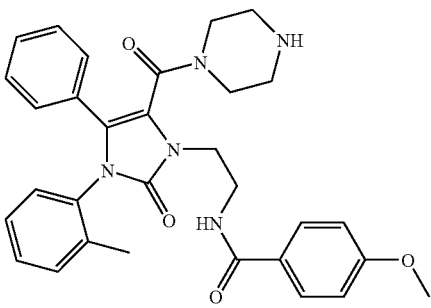

The titled compound was prepared by a procedure analogous to that described in Example 201. ESI-MS: m/z 540.3 (M+H)⁺.

Example 236

N-(2-(2-oxo-4-phenyl-5-(piperazine-1-carbonyl)-3-o-tolyl-2,3-dihydro-1H-imidazol-1-yl)ethyl)isobutyramide

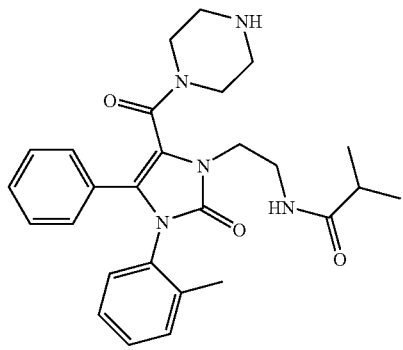

The titled compound was prepared by a procedure analogous to that described in Example 201. ESI-MS: m/z 476.4 (M+H)⁺.

Example 237

N-(2-(2-oxo-4-phenyl-5-(piperazine-1-carbonyl)-3-o-tolyl-2,3-dihydro-1H-imidazol-1-yl)ethyl)cyclohexanecarboxamide

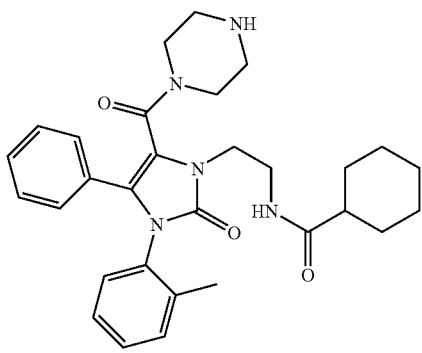

The titled compound was prepared by a procedure analogous to that described in Example 201. ESI-MS: m/z 516.4 (M+H)⁺.

Example 238

3-Methyl-N-(2-(2-oxo-4-phenyl-5-(piperazine-1-carbonyl)-3-o-tolyl-2,3-dihydro-1H-imidazol-1-yl)ethyl)butanamide

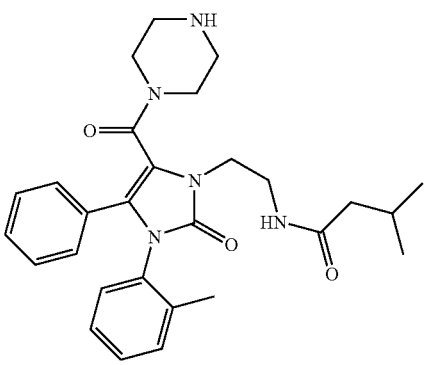

The titled compound was prepared by a procedure analogous to that described in Example 201. ESI-MS: m/z 590.3 (M+H)⁺.

Example 239

N-(3-(2-oxo-4-phenyl-5-(piperazine-1-carbonyl)-3-o-tolyl-2,3-dihydro-1H-imidazol-1-yl)propyl)propane-2-sulfonamide

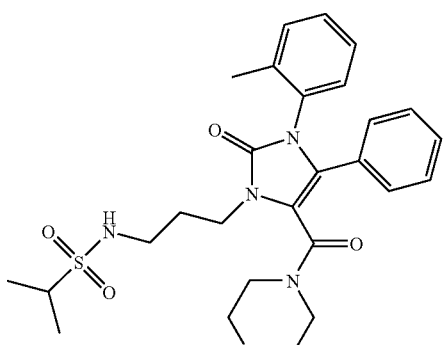

The titled compound was prepared by a procedure analogous to that described in Example 201. ESI-MS: m/z 526.3 (M+H)⁺.

Example 240

2-Fluoro-N-(3-(2-oxo-4-phenyl-5-(piperazine-1-carbonyl)-3-o-tolyl-2,3-dihydro-1H-imidazol-1-yl)propyl)benzamide

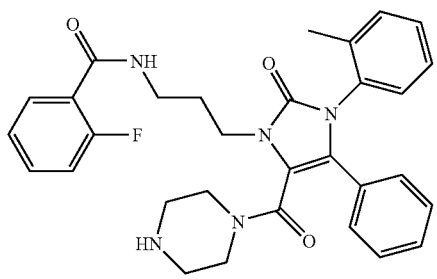

The titled compound was prepared by a procedure analogous to that described in Example 201. ESI-MS: m/z 542.3 (M+H)$^+$.

Example 241

2-Chloro-N-(3-(2-oxo-4-phenyl-5-(piperazine-1-carbonyl)-3-o-tolyl-2,3-dihydro-1H-imidazol-1-yl)propyl)benzamide

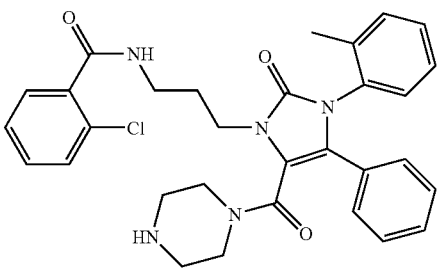

The titled compound was prepared by a procedure analogous to that described in Example 201. ESI-MS: m/z 559.2 (M+H)$^+$.

Example 242

3-Chloro-N-(3-(2-oxo-4-phenyl-5-(piperazine-1-carbonyl)-3-o-tolyl-2,3-dihydro-1H-imidazol-1-yl)propyl)benzamide

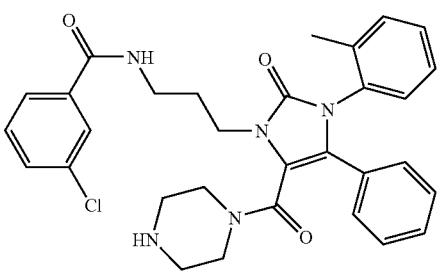

The titled compound was prepared by a procedure analogous to that described in Example 201. ESI-MS: m/z 559.3 (M+H)$^+$.

Example 243

4-Chloro-N-(3-(2-oxo-4-phenyl-5-(piperazine-1-carbonyl)-3-o-tolyl-2,3-dihydro-1H-imidazol-1-yl)propyl)benzamide

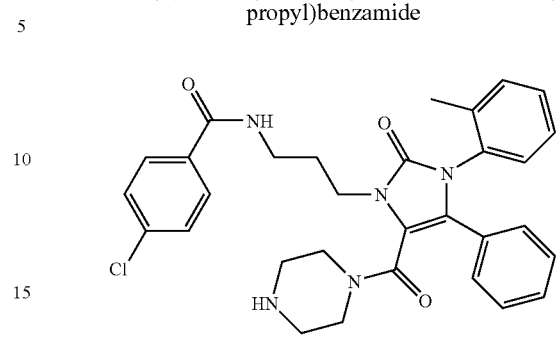

The titled compound was prepared by a procedure analogous to that described in Example 201. ESI-MS: m/z 559.3 (M+H)$^+$.

Example 244

2-Methoxy-N-(3-(2-oxo-4-phenyl-5-(piperazine-1-carbonyl)-3-o-tolyl-2,3-dihydro-1H-imidazol-1-yl)propyl)benzamide

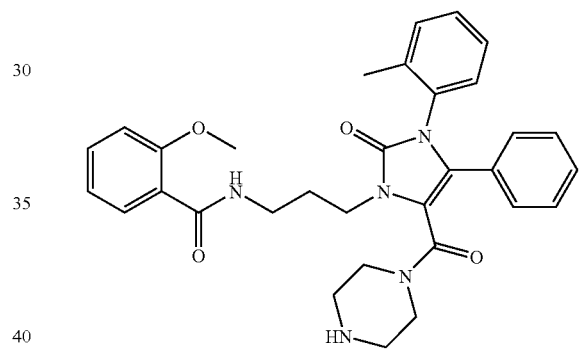

The titled compound was prepared by a procedure analogous to that described in Example 201. ESI-MS: m/z 554.3 (M+H)$^+$.

Example 245

4-Methoxy-N-(3-(2-oxo-4-phenyl-5-(piperazine-1-carbonyl)-3-o-tolyl-2,3-dihydro-1H-imidazol-1-yl)propyl)benzamide

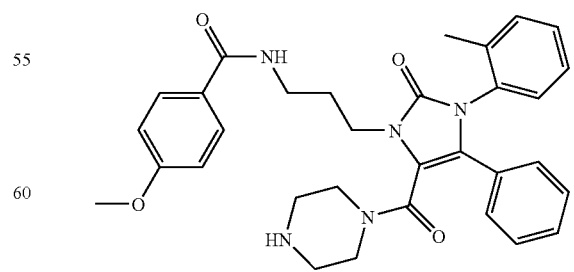

The titled compound was prepared by a procedure analogous to that described in Example 201. ESI-MS: m/z 554.3 (M+H)$^+$.

Example 246

N-(3-(2-oxo-4-phenyl-5-(piperazine-1-carbonyl)-3-o-tolyl-2,3-dihydro-1H-imidazol-1-yl)propyl)isobutyramide

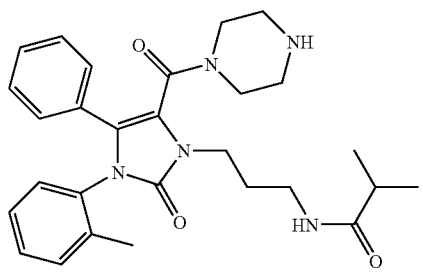

The titled compound was prepared by a procedure analogous to that described in Example 201. ESI-MS: m/z 490.3 (M+H)$^+$.

Example 247

N-(3-(2-oxo-4-phenyl-5-(piperazine-1-carbonyl)-3-o-tolyl-2,3-dihydro-1H-imidazol-1-yl)propyl)cyclohexanecarboxamide

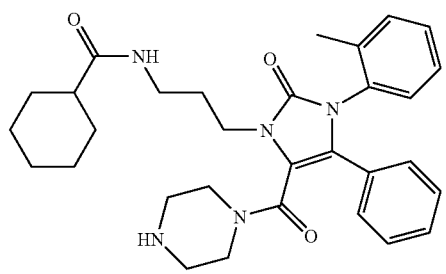

The titled compound was prepared by a procedure analogous to that described in Example 201. ESI-MS: m/z 530.3 (M+H)$^+$.

Example 248

Phenyl 2-(2-oxo-4-phenyl-5-(piperazine-1-carbonyl)-3-o-tolyl-2,3-dihydro-1H-imidazol-1-yl)ethylcarbamate

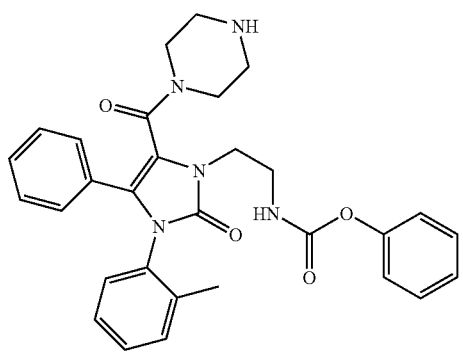

The titled compound was prepared by a procedure analogous to that described in Example 201. ESI-MS: m/z 526.2 (M+H)$^+$.

Example 249

Methyl 2-(2-oxo-4-phenyl-5-(piperazine-1-carbonyl)-3-o-tolyl-2,3-dihydro-1H-imidazol-1-yl)ethylcarbamate

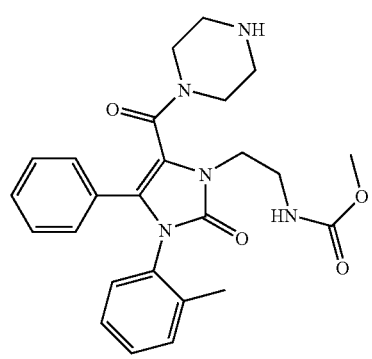

The titled compound was prepared by a procedure analogous to that described in Example 201. ESI-MS: m/z 464.2 (M+H)$^+$.

Example 250

Ethyl 2-(2-oxo-4-phenyl-5-(piperazine-1-carbonyl)-3-o-tolyl-2,3-dihydro-1H-imidazol-1-yl)ethylcarbamate

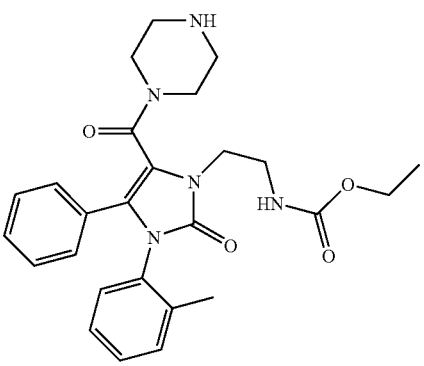

The titled compound was prepared by a procedure analogous to that described in Example 201. ESI-MS: m/z 478.3 (M+H)$^+$.

Example 251

Benzyl 2-(2-oxo-4-phenyl-5-(piperazine-1-carbonyl)-3-o-tolyl-2,3-dihydro-1H-imidazol-1-yl)ethylcarbamate

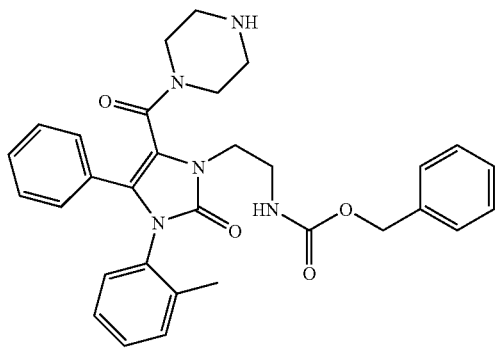

The titled compound was prepared by a procedure analogous to that described in Example 201. ESI-MS: m/z 540.3 (M+H)+.

Example 252

Phenyl 3-(2-oxo-4-phenyl-5-(piperazine-1-carbonyl)-3-o-tolyl-2,3-dihydro-1H-imidazol-1-yl)propylcarbamate

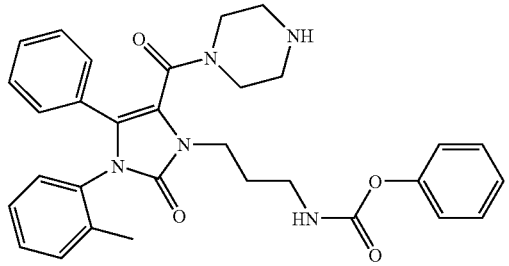

The titled compound was prepared by a procedure analogous to that described in Example 201. ESI-MS: m/z 540.3 (M+H)+.

Example 253

Methyl 3-(2-oxo-4-phenyl-5-(piperazine-1-carbonyl)-3-o-tolyl-2,3-dihydro-1H-imidazol-1-yl)propylcarbamate

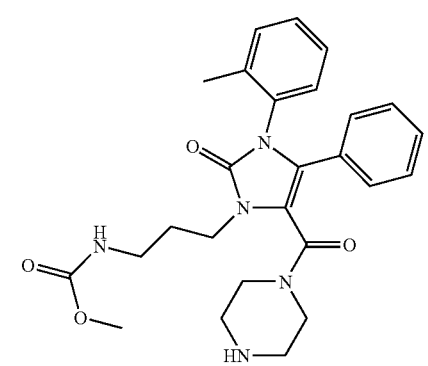

The titled compound was prepared by a procedure analogous to that described in Example 201. ESI-MS: m/z 478.2 (M+H)+.

Example 254

Ethyl 3-(2-oxo-4-phenyl-5-(piperazine-1-carbonyl)-3-o-tolyl-2,3-dihydro-1H-imidazol-1-yl)propylcarbamate

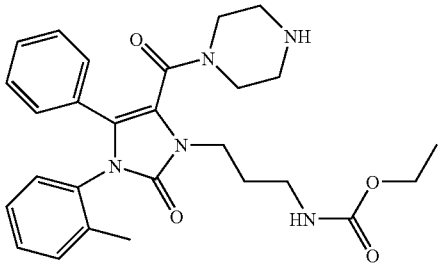

The titled compound was prepared by a procedure analogous to that described in Example 201. ESI-MS: m/z 492.3 (M+H)+.

Example 255

Benzyl 3-(2-oxo-4-phenyl-5-(piperazine-1-carbonyl)-3-o-tolyl-2,3-dihydro-1H-imidazol-1-yl)propylcarbamate

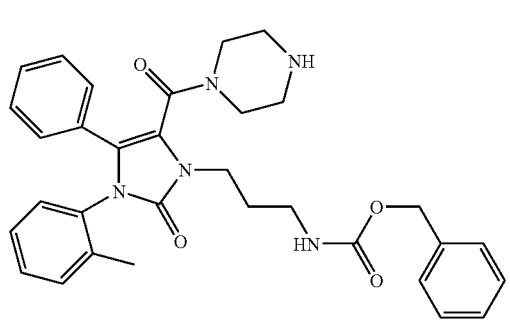

The titled compound was prepared by a procedure analogous to that described in Example 201. ESI-MS: m/z 554.3 (M+H)+.

In addition to the examples described above, the following non-limiting group of compounds can be prepared utilizing the above reaction schemes, and variations thereof, with the appropriate selection of substituents.

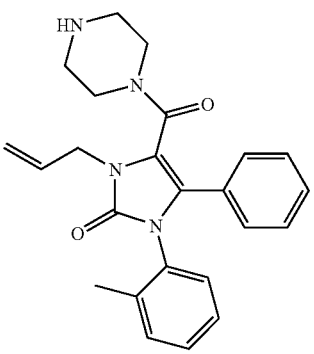

1-(2-methylphenyl)-5-phenyl-4-(piperazine-1-carbonyl)-3-prop-2-enyl-imidazol-2-one

317

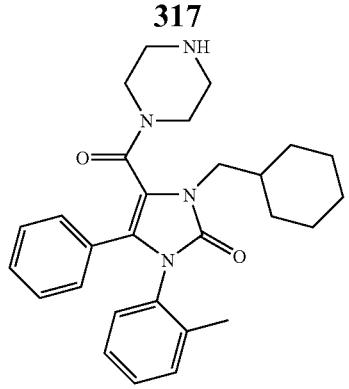

1-(cyclohexylmethyl)-3-(2-methylphenyl)-4-phenyl-5-(piperazine-1-carbonyl)imidazol-2-one

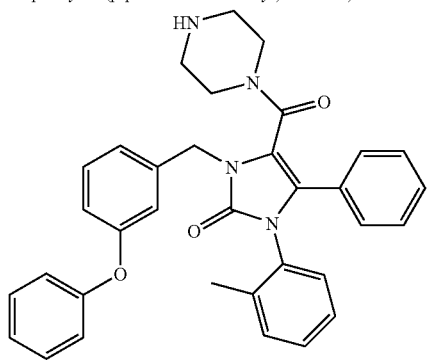

1-(2-methylphenyl)-3-[(3-phenoxyphenyl)methyl]-5-phenyl-4-(piperazine-1-carbonyl)imidazol-2-one

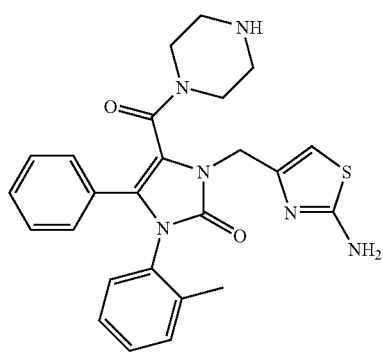

1-[(2-amino1,3-thiazol-4-yl)methyl]-3-(2-methylphenyl)-4-phenyl-5-(piperazine-1-carbonyl)imidazol-2-one

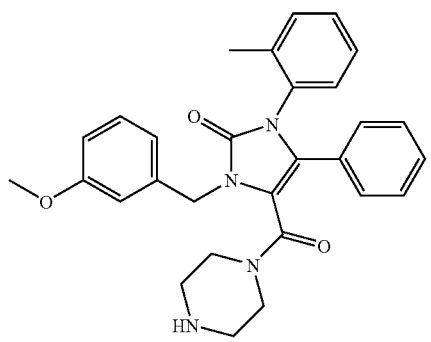

1-[(3-methoxyphenyl)methyl]-3-(2-methylphenyl)-4-phenyl-5-(piperazine-1-carbonyl)imidazol-2-one

318

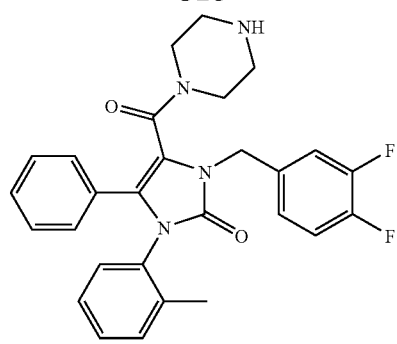

1-[(3,4-difluorophenyl)methyl]-3-(2-methylphenyl)-4-phenyl-5-(piperazine-1-carbonyl)imidazol-2-one

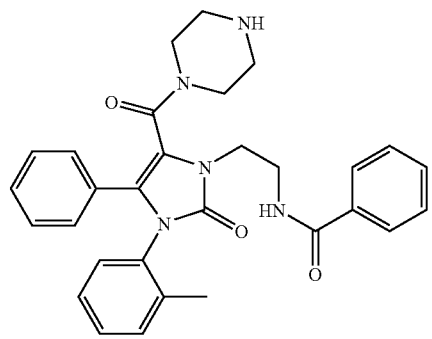

N-[2-[3-(2-methylphenyl)-2-oxo-4-phenyl-5-(piperazine-1-carbonyl)imidazol-1-yl]ethyl]benzamide

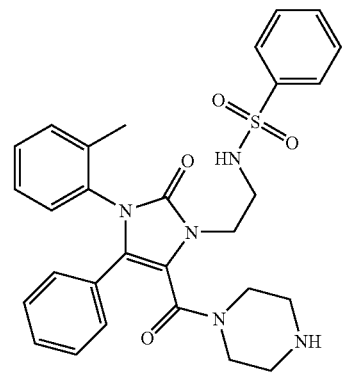

N-[2-[3-(2-methylphenyl)-2-oxo-4-phenyl-5-(piperazine-1-carbonyl)imidazol-1-yl]ethyl]benzenesulfonamide

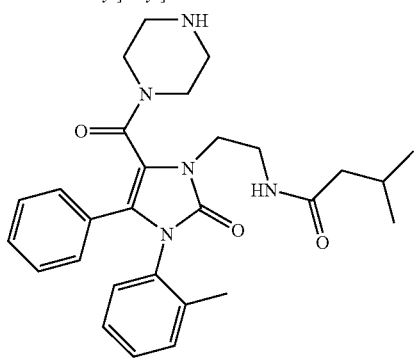

3-methyl-N-[2-[3-(2-methylphenyl)-2-oxo-4-phenyl-5-(piperazine-1-carbonyl)imidazol-1-yl]ehtyl]butanamide

319

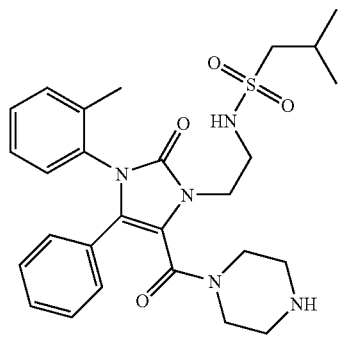

2-methyl-N-[2-[3-(2-methylphenyl)-2-oxo-4-phenyl-5-(piperazine-1-carbonyl)imidazol-1-yl]ethyl]propane-1-sulfonamide

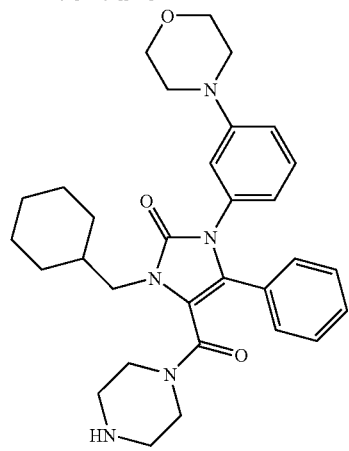

1-(cyclohexylmethyl)-3-(3-morpholin-4-ylphenyl)-4-phenyl-5-(piperazine-1-carbonyl)imidazol-2-one

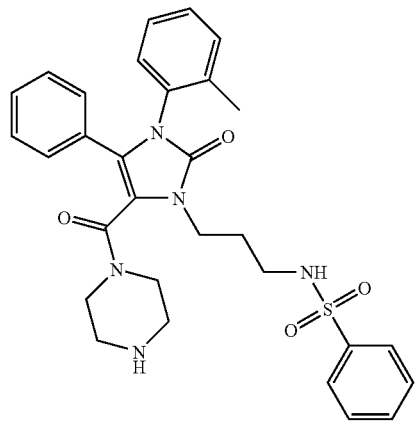

N-[3-[3-(2-methylohenyl)-2-oxo-4-phenyl-5-(piperazine-1-carbonyl)imidazol-1-yl]propyl]benzenesulfonamide

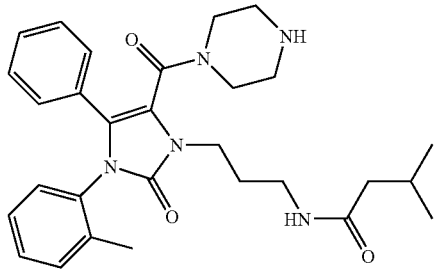

3-methyl-N-[3-[3-(2-methylphenyl)-2-oxo-4-phenyl-5-(piperazine-1-carbonyl)imidazol-1-yl]propyl]butanamide

320

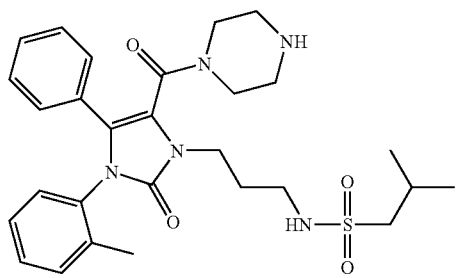

2-methyl-N-[3-[3-(2-methylphenyl)-2-oxo-4-phenyl-5-(piperazine-1-carbonyl)imidazol-1-yl]propyl]propane-1-sulfonamide

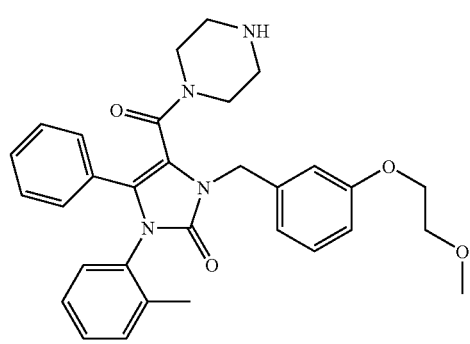

1-[[3-(2-methoxyethoxy)pheynyl]methyl]-3-(2-methylphenyl)-4-phenyl-5-(piperazine-1-carbonyl)imidazol-2-one

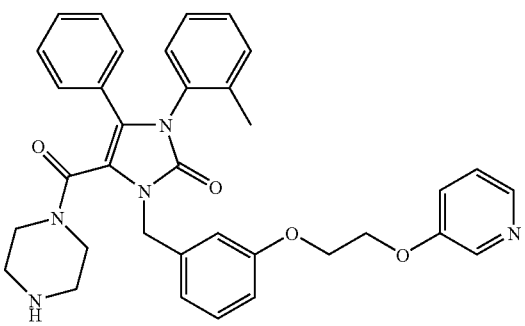

1-(2-methylphenyl)-5-phenyl-4-(piperazine-1-carbonyl)-3-[[3-(2-pyridin-3-yloxyethoxy)phenyl]methyl]imidazol-2-one

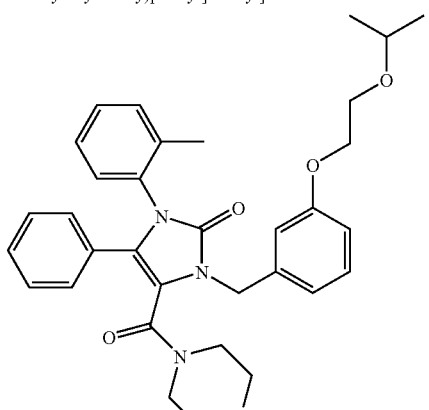

1-(2-methylphenyl)-5-phenyl-4-(piperazine-1-carbonyl)-3-[[3-(2-propan-2-yloxyethoxy)phenyl]methyl]imidazol-2-one

321

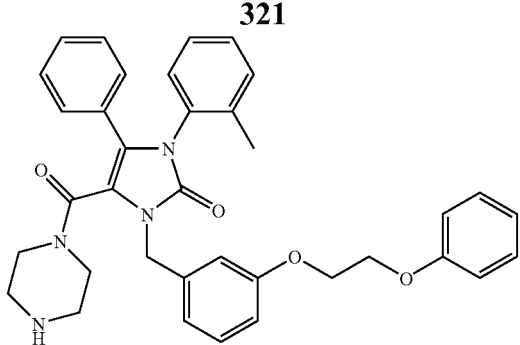

1-(2-methylphenyl)-3-[[3-(2-phenoxyethoxy)phenyl]methyl]-5-phenyl-4-(piperazine-1-carbonyl)imidazol-2-one

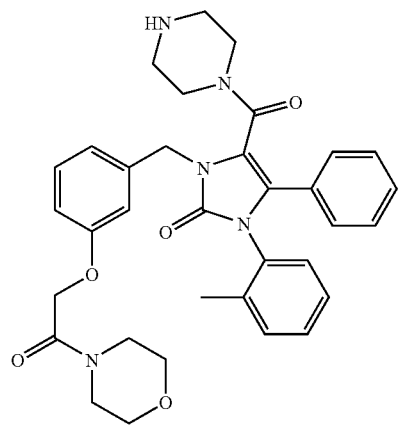

1-(2-methylphenyl)-3-[[3-(2-morpholin-4-yl-2-oxo-ethoxy)phenyl]methyl]-5-phenyl-4-(piperazine-1-carbonyl)imidazol-2-one

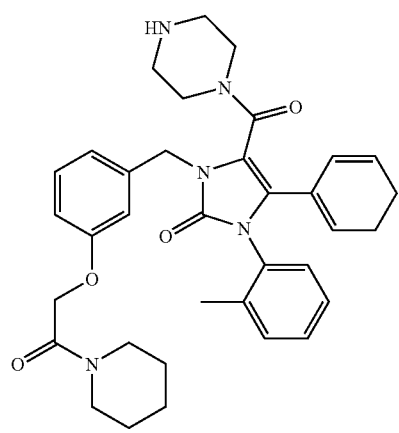

1-(2-methylphenyl)-3-[[3-[2-oxo-2-(1-piperidyl)ethoxy]phenyl]methyl]-5-phenyl-4-(piperazine-1-carbonyl)imidazol-2-one

322

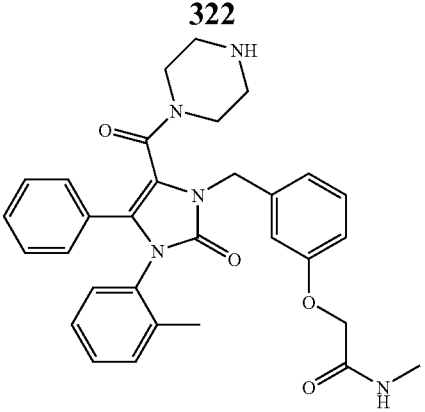

N-methyl-2-[3-[[3-(2-methylphenyl)-2-oxo-4-phenyl-5-(piperazine-1-carbonyl)imidazol-1-yl]methyl]phenoxy]acetamide

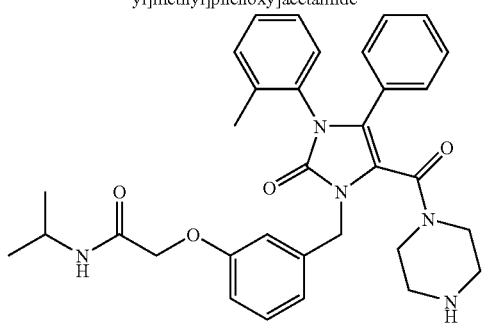

2-[3-[[3-(2-methylphenyl)-2-oxo-4-phenyl-5-(piperazine-1-carbonyl)imidazol-1-yl]methyl]phenoxy]-N-propan-2-yl-acetamide

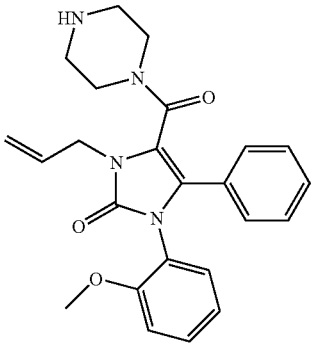

1-(2-methoxyphenyl)-5-phenyl-4-(piperazine-1-carbonyl)-3-prop-2-enyl-imidazol-2-one

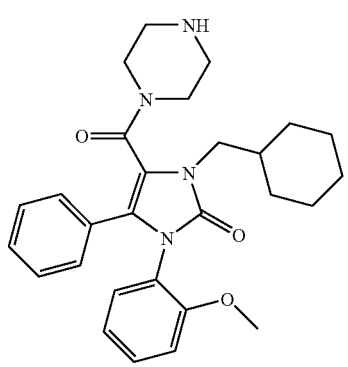

1-(cyclohexylmethyl)-3-(2-methoxyphenyl)-4-phenyl-5-(piperazine-1-carbonyl)imidazol-2-one

323

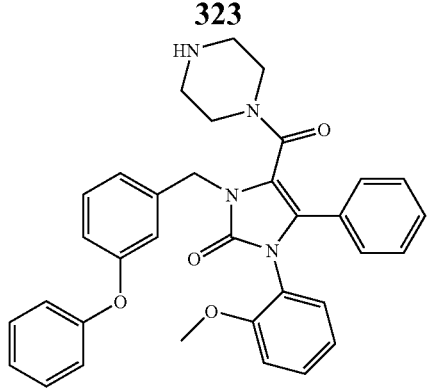

1-(2-methoxyphenyl)-3-[(3-phenoxyphenyl)methyl]-5-phenyl-4-(piperazine-1-carbonyl)imidazol-2-one

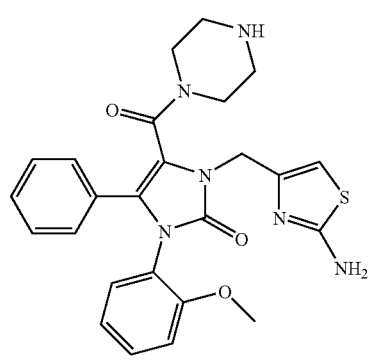

1-[(2-amino,3-thiazol-4-yl)methyl]-3-(2-methoxyphenyl)-4-phenyl-5-(piperazine-1-carbonyl)imidazol-2-one

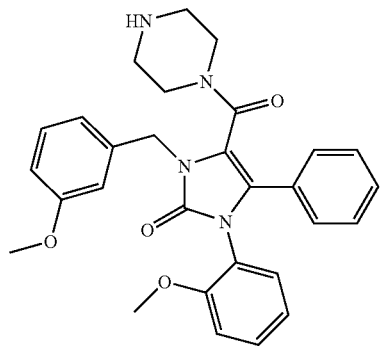

1-(2-methoxyphenyl)-3-[(3-methoxyphenyl)methyl]-5-phenyl-4-(piperazine-1-carbonyl)imidazol-2-one

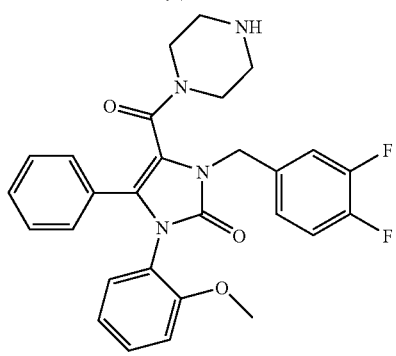

1-[(3,4-difluorophenyl)methyl]-3-(2-methoxyphenyl)-4-phenyl-5-(piperazine-1-carbonyl)imidazol-2-one

324

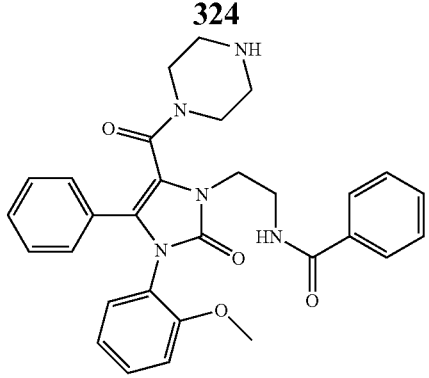

N-[2-[3-(2-methoxyphenyl)-2-oxo-4-phenyl-5-(piperazine-1-carbonyl)imidazol-1-yl]ethyl]benzamide

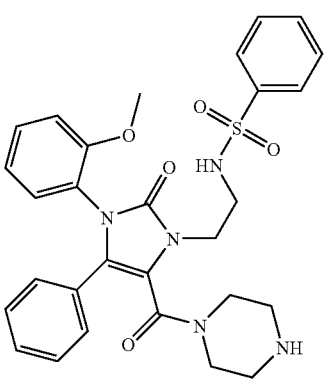

N-[2-[3-(2-methoxyphenyl)-2-oxo-4-phenyl-5-(piperazine-1-carbonyl)imidazol-1-yl]ethyl]benzenesulfonamide

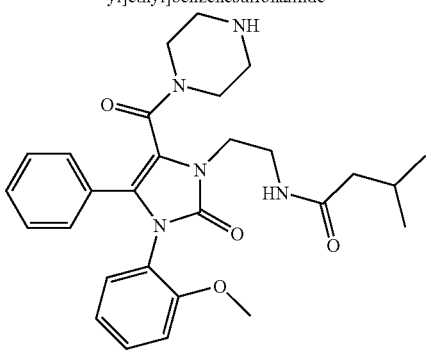

N-[2-[3-(2-methoxyphenyl)-2-oxo-4-phenyl-5-(piperazine-1-carbonyl)imidazol-1-yl]ethyl]-3-methyl-butanamide

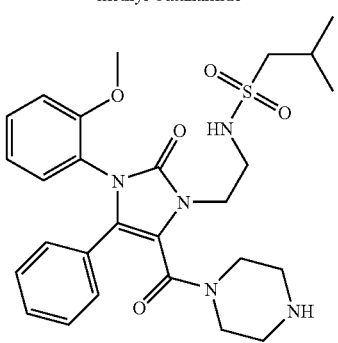

N-[2-[3-(2-methoxyphenyl)-2-oxo-4-phenyl-5-(piperazine-1-carbonyl)imidazol-1-yl]ethyl]-2-mehtyl-propane-1-sulfonamide

325

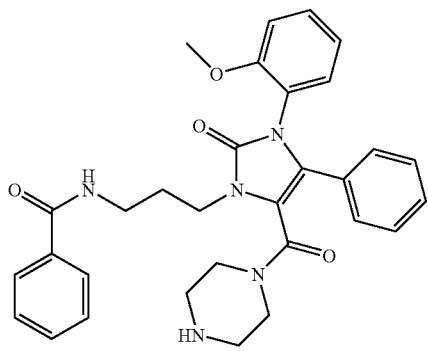

N-[3-[3-(2-methoxyphenyl)-2-oxo-4-phenyl-5-
(piperazine-1-carbonyl)imidazol-1-
yl]propyl]benzamide

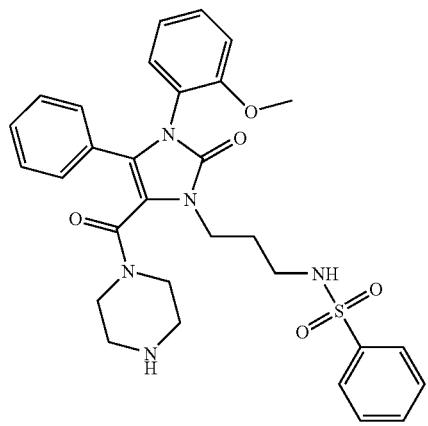

N-[3-[3-(2-methoxyphenyl)-2-oxo-4-phenyl-5-
(piperazine-1-carbonyl)imidazol-1-
yl]propyl]benzenesulfonamide

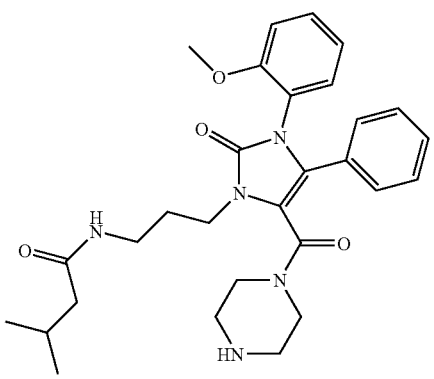

N-[3-[3-(2-methoxyphenyl)-2-oxo-4-phenyl-5-
(piperazine-1-carbonyl)imidazol-1-yl]propyl]-3-
methyl-butanamide

326

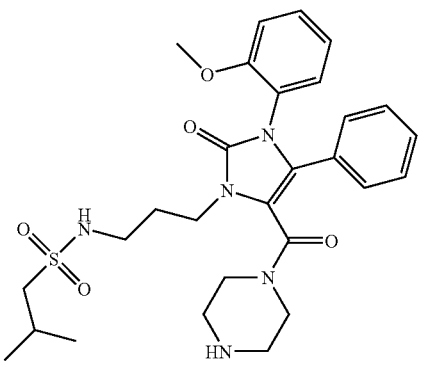

N-[3-[3-(2-methoxyphenyl)-2-oxo-4-phenyl-5-
(piperazine-1-carbonyl)imidazol-1-yl]propyl]-2-
methyl-propane-1-sulfonamide

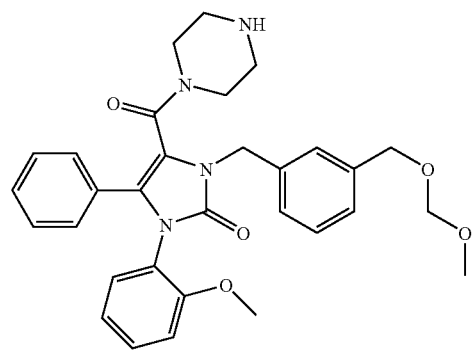

1-[[3-(2-methoxyethoxy)phenyl]methyl]-3-(2-
methoxyphenyl)-4-phenyl-5-(piperazine-1-
carbonyl)imidazol-2-one

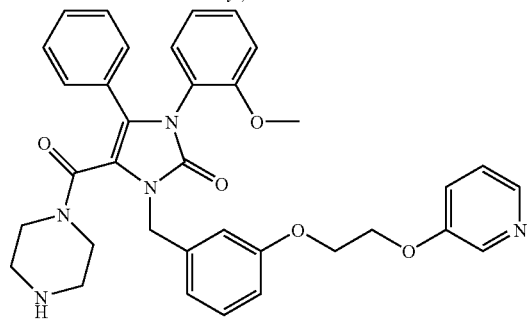

1-(2-methoxyphenyl)-5-phenyl-4-(piperazine-1-
carbonyl)-3-[[3-(2-pyridin-3-
yloxyethoxy)phenyl]methyl]imidazol-2-one

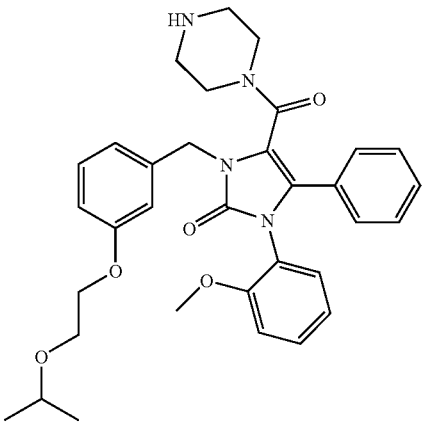

1-(2-methoxyphenyl)-5-phenyl-4-(piperazine-1-
carbonyl)-3-[[3-(2-propan-2-
yloxyethoxy)phenyl]methyl]imidazol-2-one

327

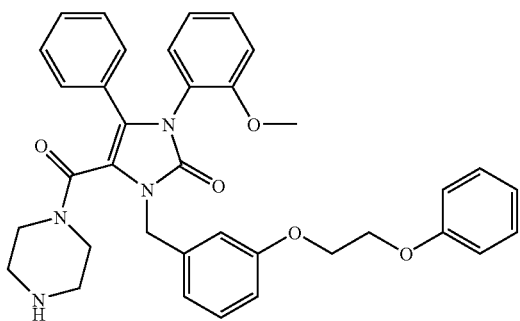

1-(2-methoxyphenyl)-3-[[3-(2-phenoxyethoxy)phenyl]methyl]-5-phenyl-4-(piperazine-1-carbonyl)imidazol-2-one

328

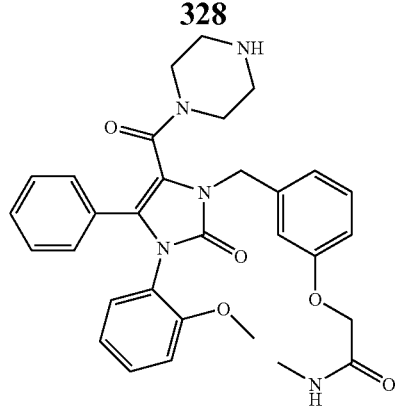

2-[3-[[3-(2-methoxyphenyl)-2-oxo-4-phenyl-5-(piperazine-1-carbonyl)imidazol-1-yl]methyl]phenoxy]-N-methyl-acetamide

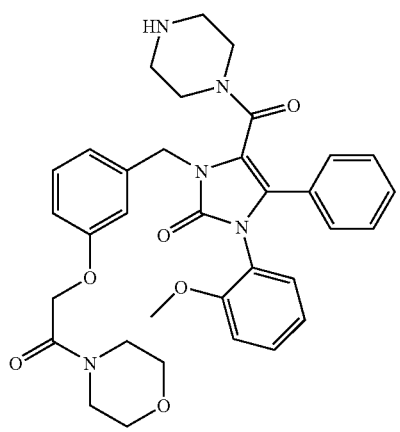

1-(2-methoxyphenyl)-3-[[3-(2-morpholin-4-yl-2-oxo-ethoxy)phenyl]methyl]-5-phenyl-4-(piperazine-1-carbonyl)imidazol-2-one

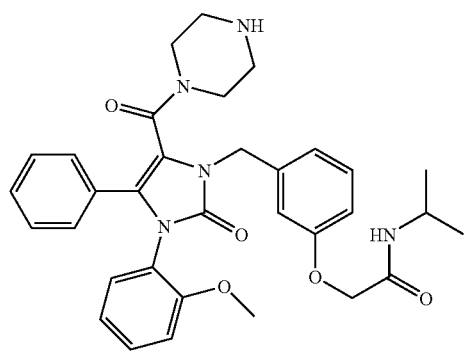

2-[3-[[3-(2-methoxyphenyl)-2-oxo-4-phenyl-5-(piperazine-1-carbonyl)imidazol-1-yl]methyl]phenoxy]-N-propan-2-yl-acetamide

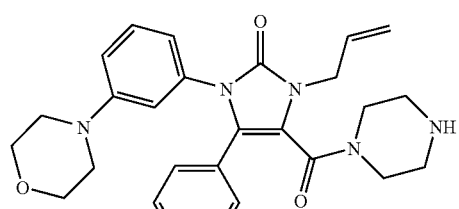

1-(3-morpholin-4-ylphenyl)-5-phenyl-4-(piperazine-1-carbonyl)-3-prop-2-enyl-imidazol-2-one

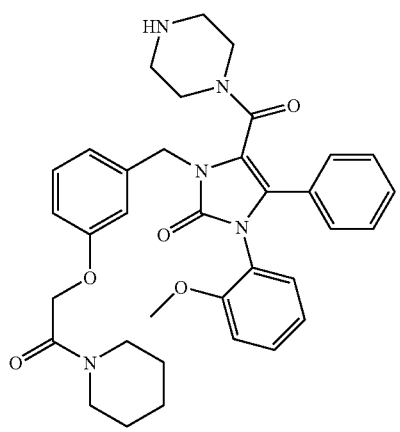

1-(2-methoxyphenyl)-3-[[3-[2-oxo-2-(1-piperidyl)ethoxy]phenyl]methyl]-5-phenyl-4-(piperazine-1-carbonyl)imidazol-2-one

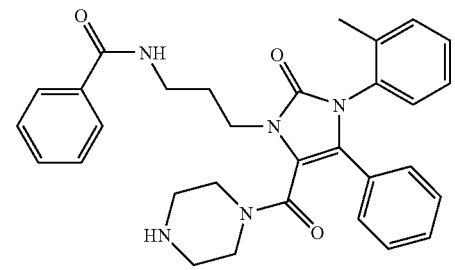

N-[3-[3-(2-methylphenyl)-2-oxo-4-phenyl-5-(piperazine-1-carbonyl)imidazol-1-yl]propyl]benzamide

329

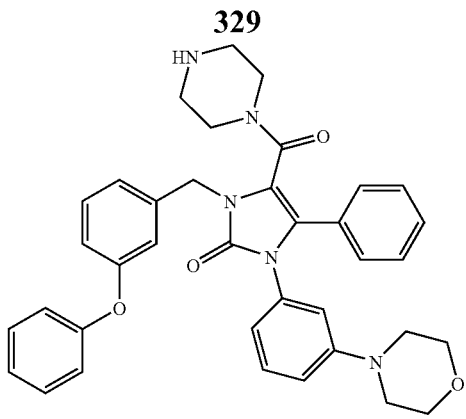

1-(3-morpholin-4-ylphenyl)-3-[(3-phenoxyphenyl)methyl]-5-phenyl-4-(piperazine-1-carbonyl)imidazol-2-one

330

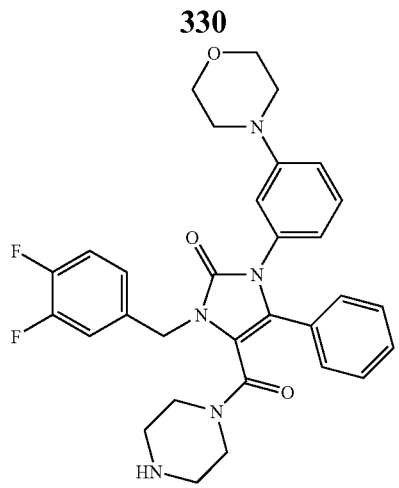

1-[(3,4-difluorophenyl)methyl]-3-(3-morpholin-4-ylphenyl)-4-phenyl-5-(piperazine-1-carbonyl)imidazol-2-one

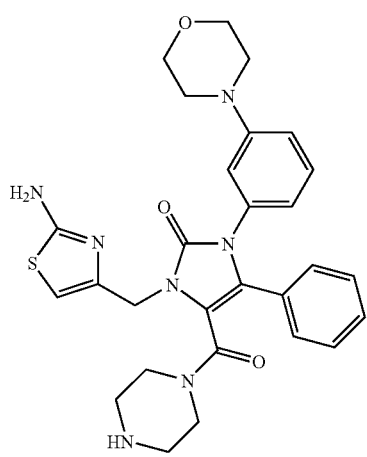

1-[(2-amino1,3-thiazol-4-yl)methyl]-3-(3-morpholin-4-ylphenyl)-4-phenyl-5-(piperazine-1-carbonyl)imidazol-2-one

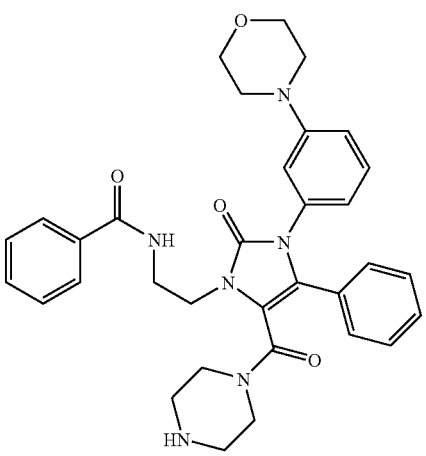

N-[2-[3-(3-morpholin-4-ylphenyl)-2-oxo-4-phenyl-5-(piperazine-1-carbonyl)imidazol-1-yl]ethyl]benzamide

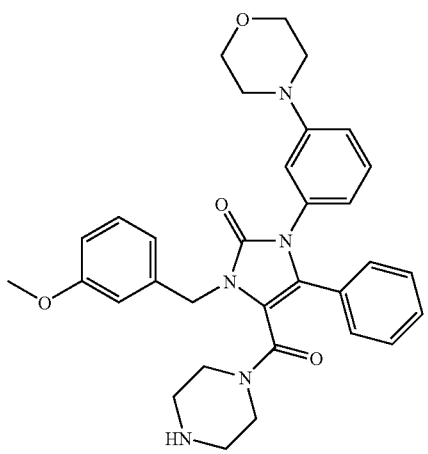

1-[(3-methoxyphenyl)methyl]-3-(3-morpholin-4-ylphenyl)-4-phenyl-5-(piperazine-1-carbonyl)imidazol-2-one

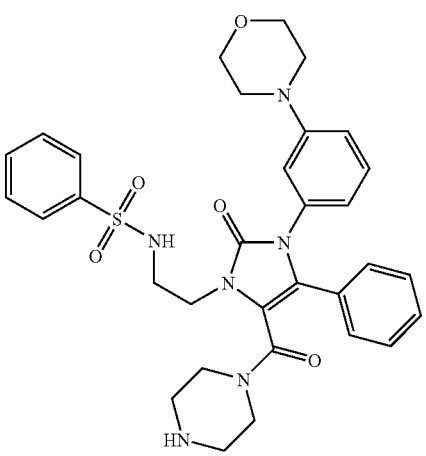

N-[2-[3-(3-morpholin-4-ylphenyl)-2-oxo-4-phenyl-5-(piperazine-1-carbonyl)imidazol-1-yl]ethyl]benzenesulfonamide

331

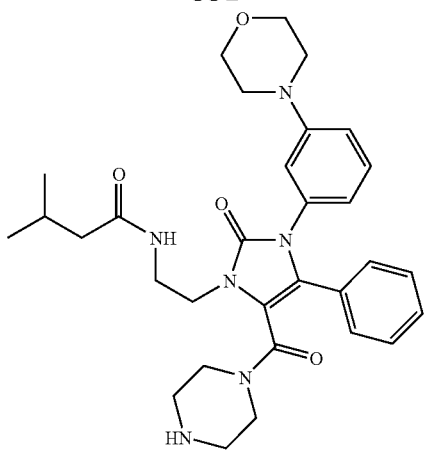

3-methyl-N-[2-[3-(3-morpholin-4-ylphenyl)-2-oxo-4-phenyl-5-(piperazine-1-carbonyl)imidazol-1-yl]ethyl]butanamide

332

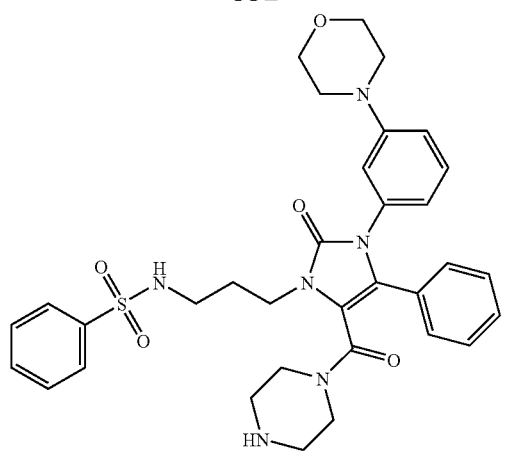

N-[3-[3-(3-morpholin-4-ylphenyl)-2-oxo-4-phenyl-5-(piperazine-1-carbonyl)imidazol-1-yl]propyl]benzenesulfonamide

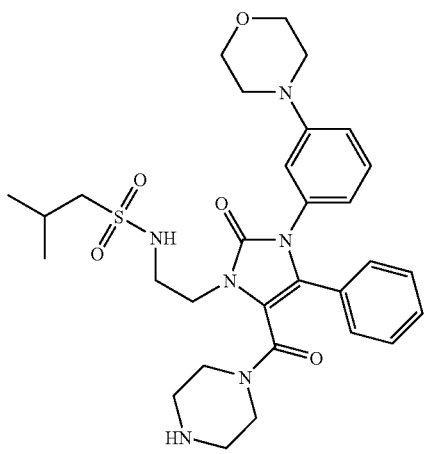

2-methyl-N-[2-[3-(3-morpholin-4-ylphenyl)-2-oxo-4-phenyl-5-(piperazine-1-carbonyl)imidazol-1-yl] ethyl]propane-1-sulfonamide

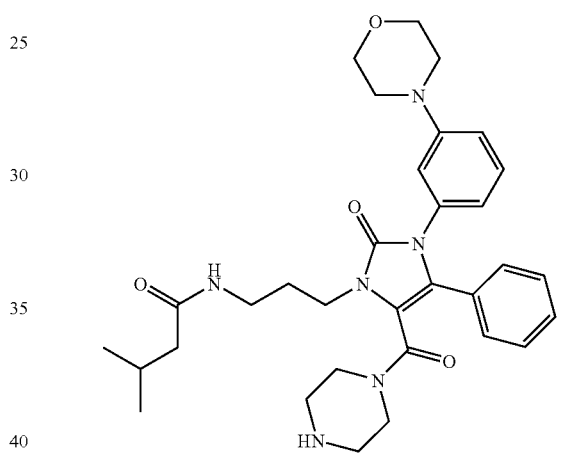

3-methyl-N-[3-[3-(3-morpholin-4-ylphenyl)-2-oxo-4-phenyl-5-(piperazine-1-carbonyl)imidazol-1-yl]propyl]butanamide

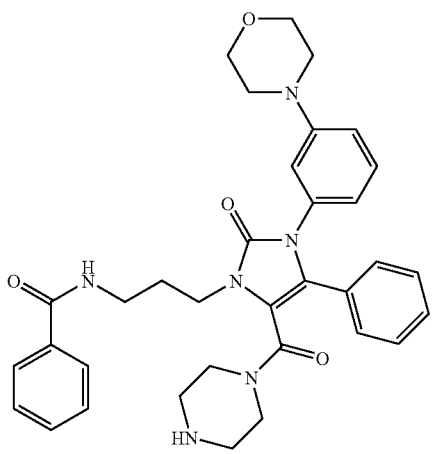

N-[3-[3-(3-morpholin-4-ylphenyl)-2-oxo-4-phenyl-5-(piperazine-1-carbonyl)imidazol-1-yl]propyl]benzamide

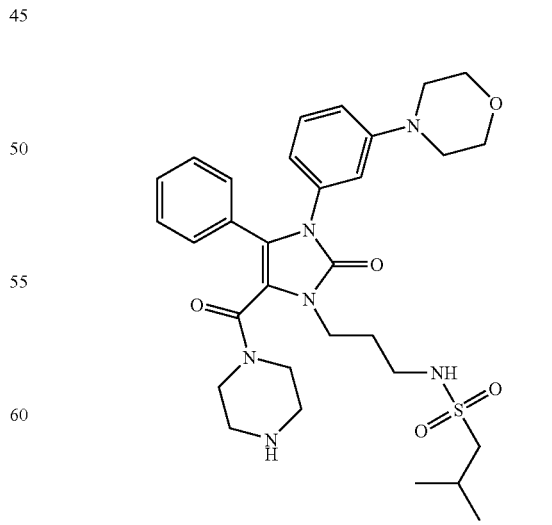

2-methyl-N-[3-[3-(3-morpholin-4-ylphenyl)-2-oxo-4-phenyl-5-(piperazine-1-carbonyl)imidazol-1-yl]propyl]propane-1-sulfonamide

333

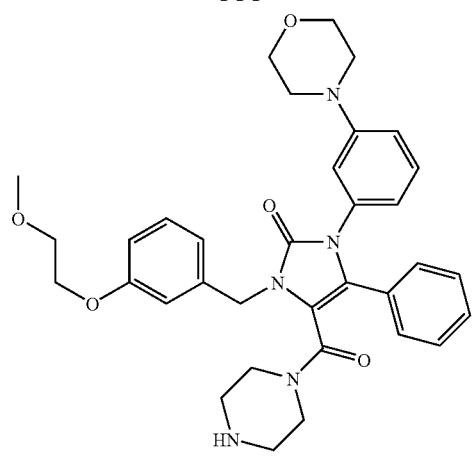

1-[[3-(2-methoxyethoxy)phenyl]methyl]-3-(3-morpholin-4-ylphenyl)-4-phenyl-5-(piperazine-1-carbonyl)imidazol-2-one

334

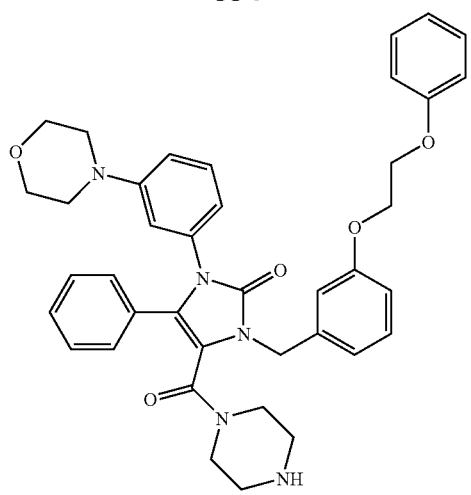

1-(3-morpholin-4-ylphenyl)-3-[[3-(2-phenoxyethoxy)phenyl]methyl]-5-phenyl-4-(piperazine-1-carbonyl)imidazol-2-one

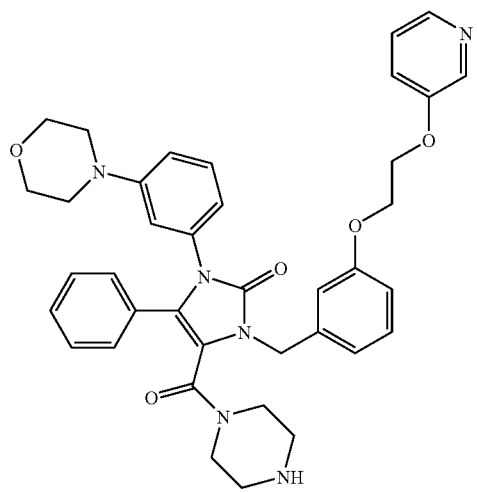

1-(3-morpholin-4-ylphenyl)-5-phenyl-4-(piperazine-1-carbonyl)-3-[[3-(2-pyridin-3-yloxyethoxy)phenyl]methyl]imidazol-2-one

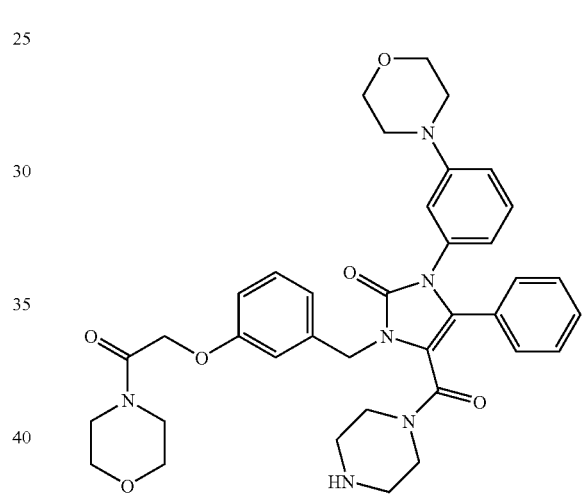

1-[[3-(2-morpholin-4-yl-2-oxo-ethoxy)phenyl]methyl]-3-(3-morpholin-4-ylphenyl)-4-phenyl-5-(piperazine-1-carbonyl)imidazol-2-one

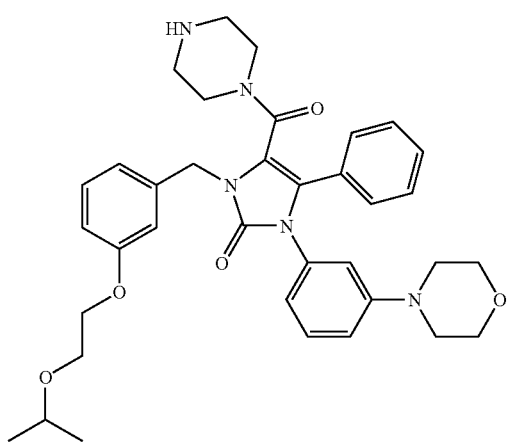

1-(3-morpholin-4-ylphenyl)-5-phenyl-4-(piperazine-1-carbonyl)-3-[[3-(2-propan-2-yloxyethoxy)phenyl]methyl]imidazol-2-one

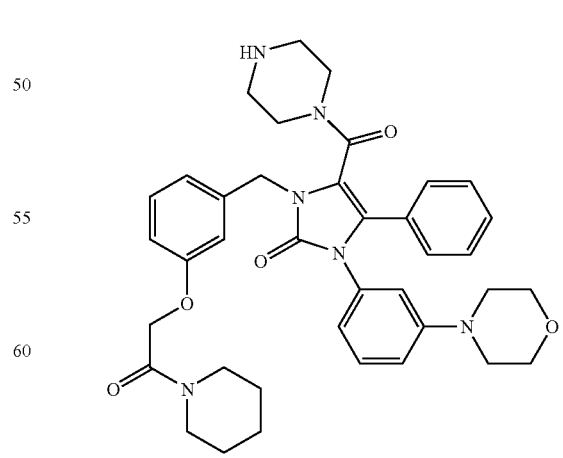

1-(3-morpholin-4-ylphenyl)-3-[[3-[2-oxo-2-(1-piperidyl)ethoxy]phenyl]methyl]-5-phenyl-4-(piperazine-1-carbonyl)imidazol-2-one

335

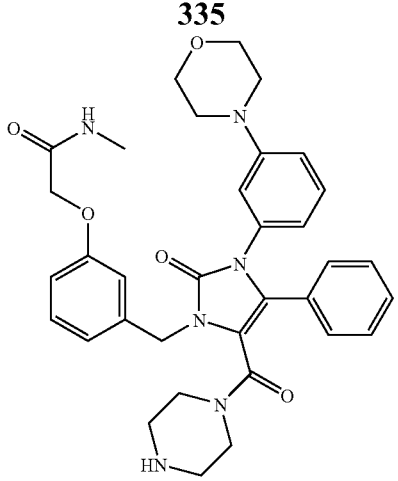

N-methyl-2-[3-[[3-(3-morpholin-4-ylphenyl)-2-oxo-4-phenyl-5-(piperazine-1-carbonyl)imidazol-1-yl]methyl]phenoxy]acetamide

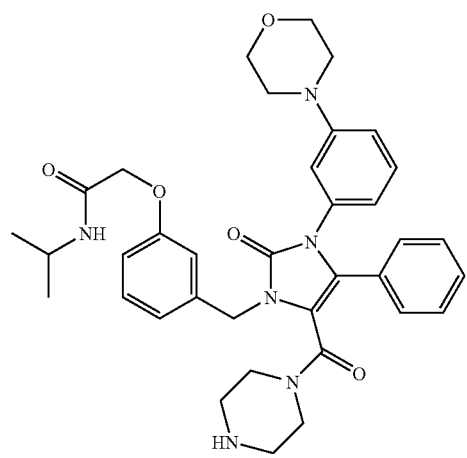

2-[3-[[3-(3-morpholin-4-ylphenyl)-2-oxo-4-phenyl-5-(piperazine-1-carbonyl)imidazol-1-yl]methyl]phenoxy]-N-propan-2-yl-acetamide

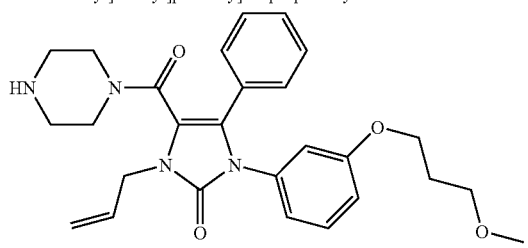

1-[3-(3-methoxypropoxy)phenyl]-5-phenyl-4-(piperazine-1-carbonyl)-3-prop-2-enyl-imidazol-2-one

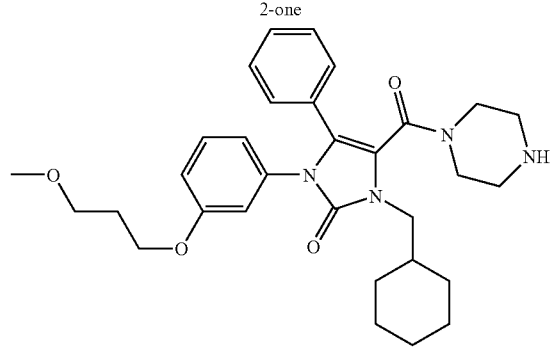

1-(cyclohexylmethyl)-3-[3-(3-methoxypropoxy)phenyl]-4-phenyl-5-(piperazine-1-carbonyl)imidazol-2-one

336

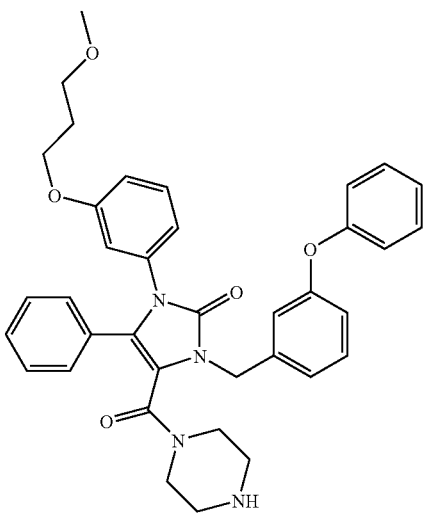

1-[3-(3-methoxypropoxy)phenyl]-3-[(3-phenoxyphenyl)methyl]-5-phenyl-4-(piperazine-1-carbonyl)imidazol-2-one

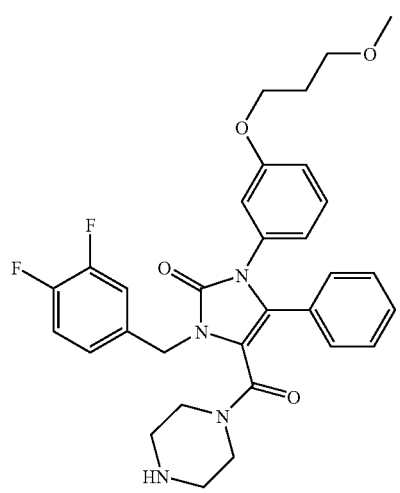

1-[(3,4-difluorophenyl)methyl]-3-[3-(3-methoxypropoxy)phenyl]-4-phenyl-5-(piperazine-1-carbonyl)imidazol-2-one

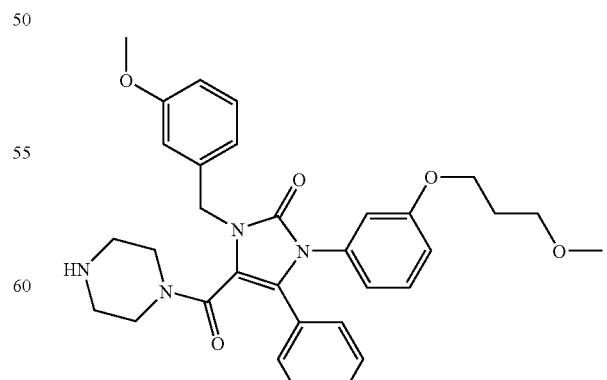

1-[(3-methoxyphenyl)methyl]-3-[3-(3-methoxypropoxy)phenyl]-4-phenyl-5-(piperazine-1-carbonyl)imidazol-2-one

337

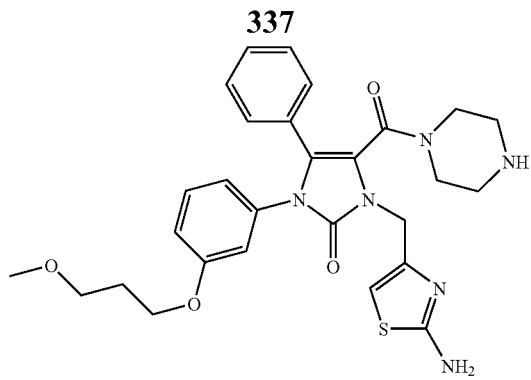

1-[(2-amino1,3-thiazol-4-yl)methyl]-3-[3-(3-methoxypropoxy)phenyl]-4-phenyl-5-(piperazine-1-carbonyl)imidazol-2-one

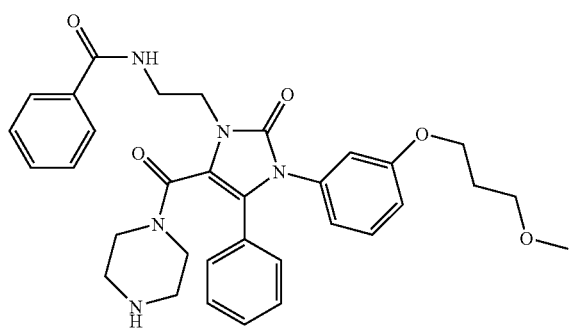

N-[2-[3-[3-(3-methoxypropoxy)phenyl]-2-oxo-4-phenyl-5-(piperazine-1-carbonyl)imidazol-1-yl]ethyl]benzamide

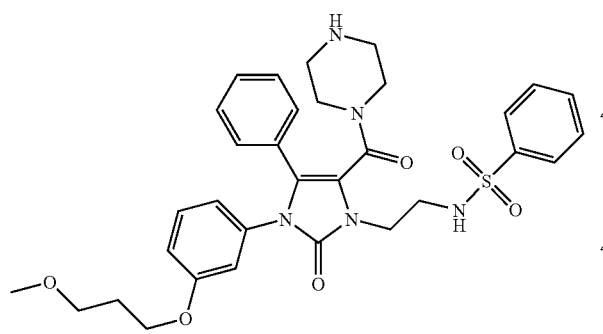

N-[2-[3-[3-(3-methoxypropoxy)phenyl]-2-oxo-4-phenyl-5-(piperazine-1-carbonyl)imidazol-1-yl]ethyl]benzenesulfonamide

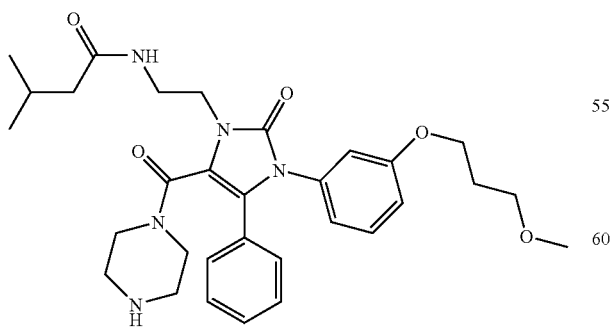

N-[2-[3-[3-(3-methoxypropoxy)phenyl]-2-oxo-4-phenyl-5-(piperazine-1-carbonyl)imidazol-1-yl]ethyl]-3-methyl-butanamide

338

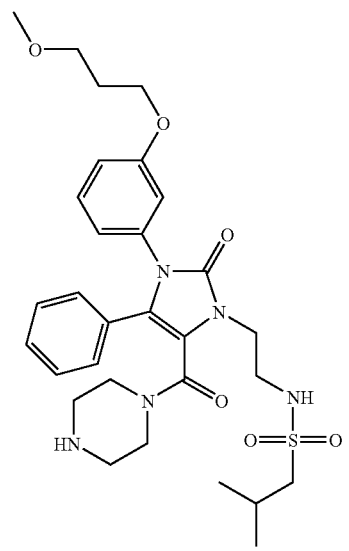

N-[2-[3-[3-(3-methoxypropoxy)phenyl]-2-oxo-4-phenyl-5-(piperazine-1-carbonyl)imidazol-1-yl]ethyl]-2-methyl-propane-1-sulfonamide

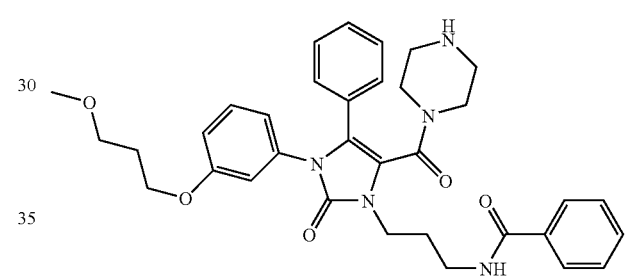

N-[3-[3-[3-(3-methoxypropoxy)phenyl]-2-oxo-4-phenyl-5-(piperazine-1-carbonyl)imidazol-1-yl]propyl]benzamide

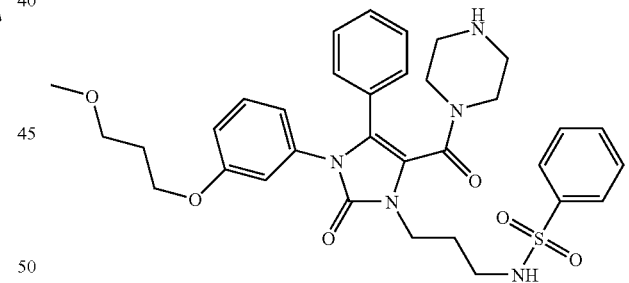

N-[3-[3-[3-(3-methoxypropoxy)phenyl]-2-oxo-4-phenyl-5-(piperazine-1-carbonyl)imidazol-1-yl]propyl]benzenesulfonamide

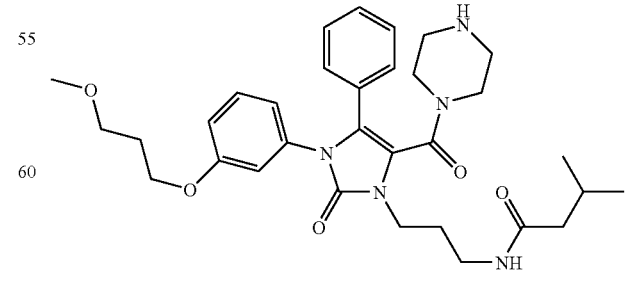

N-[3-[3-[3-(3-methoxypropoxy)phenyl]-2-oxo-4-phenyl-5-(piperazine-1-carbonyl)imidazol-1-yl]propyl]-3-methyl-butanamide

339

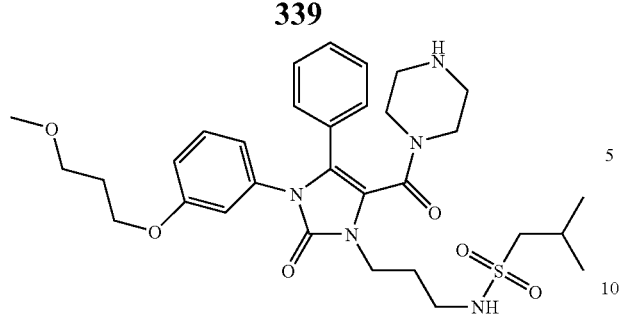

N-[3-[3-[3-(3-methoxypropoxy)phenyl]-2-oxo-4-phenyl-5-(piperazine-1-carbonyl)imidazol-1-yl]propyl]-2-methyl-propane-1-sulfonamide

340

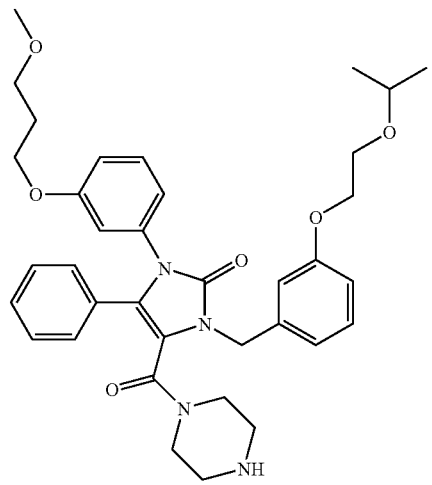

1-[3-(3-methoxypropoxy)phenyl]-5-phenyl-4-(piperazine-1-carbonyl)-3-[[3-(2-propan-2-yloxyethoxy)phenyl]methyl]imidazol-2-one

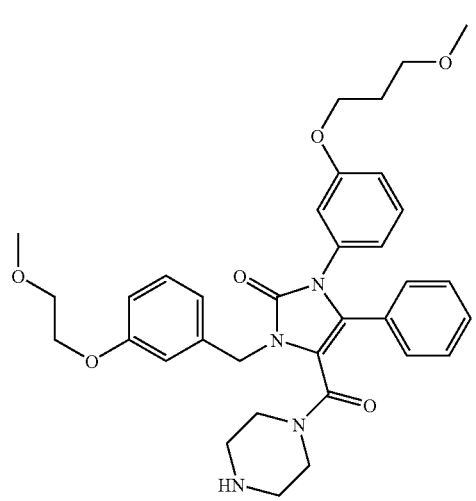

1-[[3-(2-methoxyethoxy)phenyl]methyl]-3-[3-(3-methoxypropoxy)phenyl]-4-phenyl-5-(piperazine-1-carbonyl)imidazol-2-one

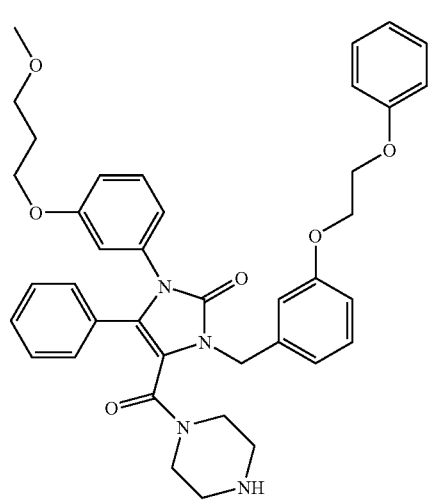

1-[3-(3-methoxypropoxy)phenyl]-3-[[3-(2-phenoxyethoxy)phenyl]methyl]-5-phenyl-4-(piperazine-1-carbonyl)imidazol-2-one

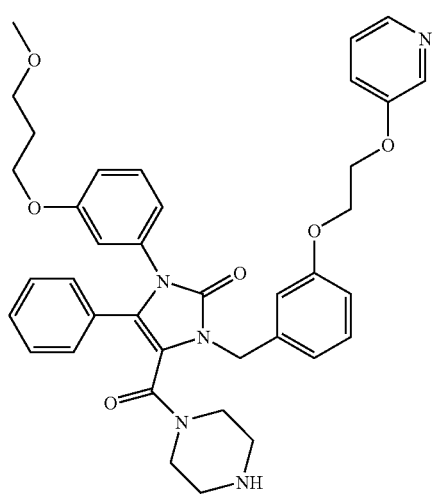

1-[3-(3-methoxypropoxy)phenyl]-5-phenyl-4-(piperazine-1-carbonyl)-3-[[3-(2-pyridin-3-yloxyethoxy)phenyl]methyl]imidazol-2-one

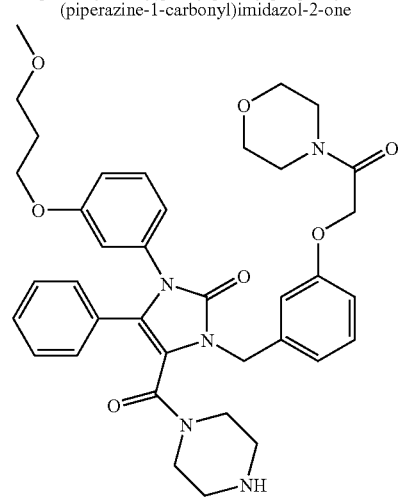

1-[3-(3-methoxypropoxy)phenyl]-3-[[3-(2-morpholin-4-yl-2-oxo-ethoxy)phenyl]methyl]-5-phenyl-4-(piperazine-1-carbonyl)imidazol-2-one

341

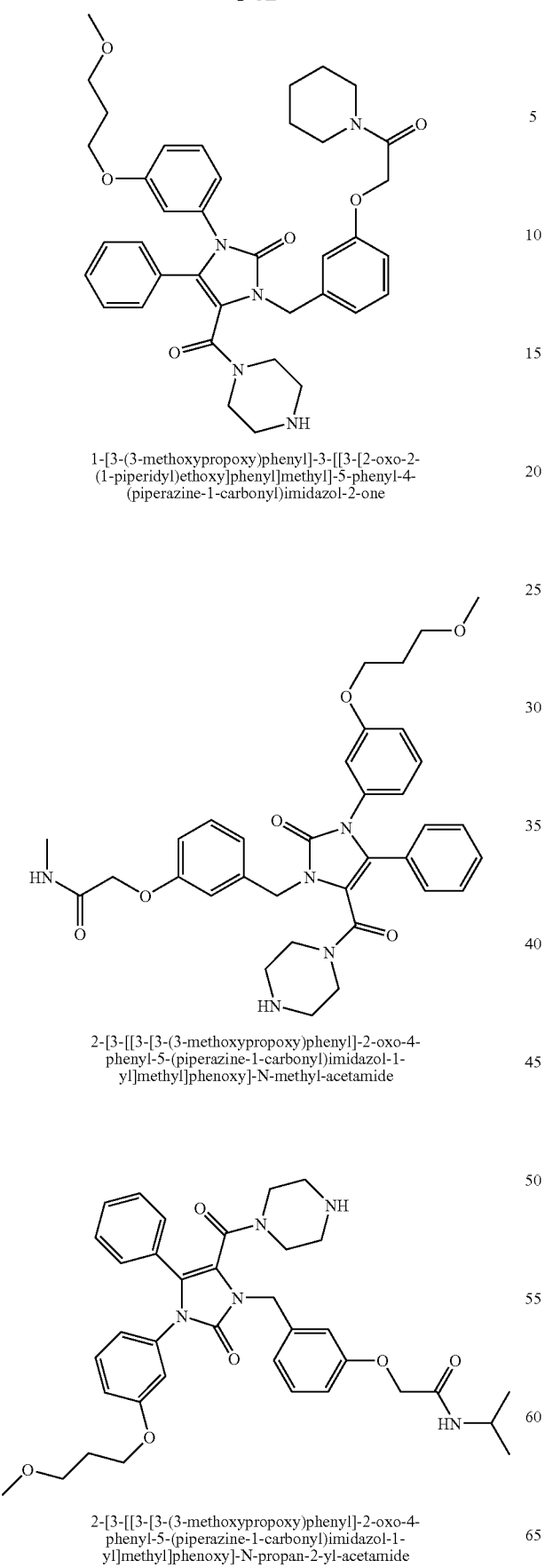

1-[3-(3-methoxypropoxy)phenyl]-3-[[3-[2-oxo-2-(1-piperidyl)ethoxy]phenyl]methyl]-5-phenyl-4-(piperazine-1-carbonyl)imidazol-2-one 2-[3-[[3-[3-(3-methoxypropoxy)phenyl]-2-oxo-4-phenyl-5-(piperazine-1-carbonyl)imidazol-1-yl]methyl]phenoxy]-N-methyl-acetamide 2-[3-[[3-[3-(3-methoxypropoxy)phenyl]-2-oxo-4-phenyl-5-(piperazine-1-carbonyl)imidazol-1-yl]methyl]phenoxy]-N-propan-2-yl-acetamide

342

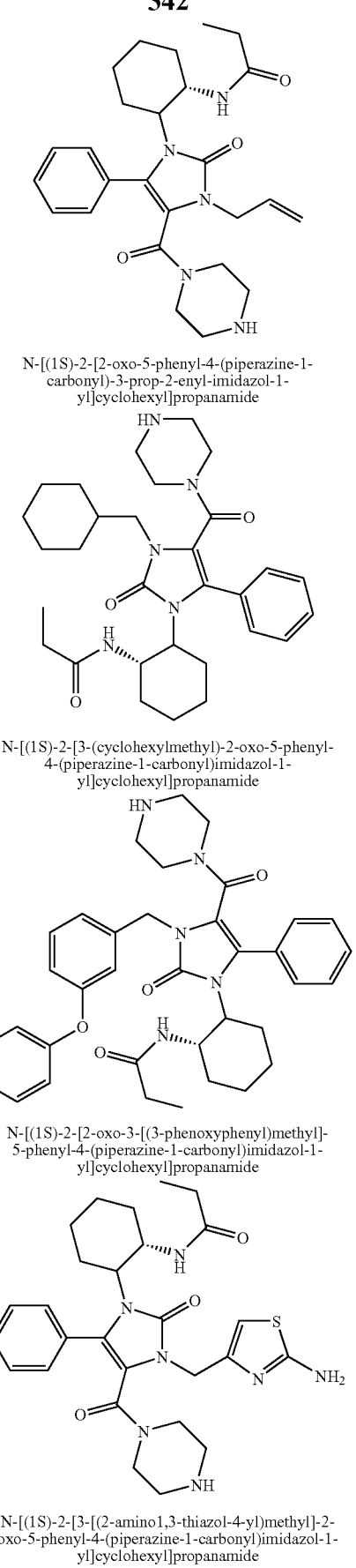

N-[(1S)-2-[2-oxo-5-phenyl-4-(piperazine-1-carbonyl)-3-prop-2-enyl-imidazol-1-yl]cyclohexyl]propanamide N-[(1S)-2-[3-(cyclohexylmethyl)-2-oxo-5-phenyl-4-(piperazine-1-carbonyl)imidazol-1-yl]cyclohexyl]propanamide N-[(1S)-2-[2-oxo-3-[(3-phenoxyphenyl)methyl]-5-phenyl-4-(piperazine-1-carbonyl)imidazol-1-yl]cyclohexyl]propanamide N-[(1S)-2-[3-[(2-amino1,3-thiazol-4-yl)methyl]-2-oxo-5-phenyl-4-(piperazine-1-carbonyl)imidazol-1-yl]cyclohexyl]propanamide

343

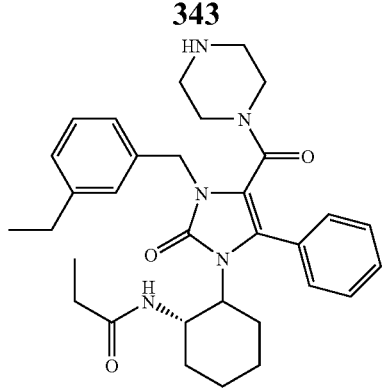

N-[(1S)-2-[3-[(3-methoxyphenyl)methyl]-2-oxo-
5-phenyl-4-(piperazine-1-carbonyl)imidazol-1-
yl]cyclohexyl]propanamide

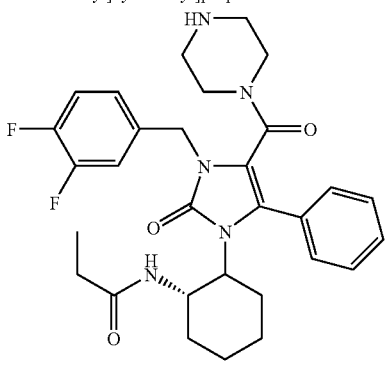

N-[(1S)-2-[3-[(3,4-difluorophenyl)methyl]-2-oxo-
5-phenyl-4-(piperazine-1-carbonyl)imidazol-1-
yl]cyclohexyl]propanamide

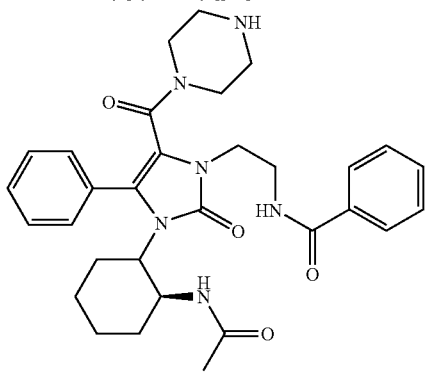

N-[2-[2-oxo-4-phenyl-5-(piperazine-1-carbonyl)-
3-[(2S)-2-(propanoylamino)cyclohexyl]imidazol-
1-yl]ethyl]benzamide

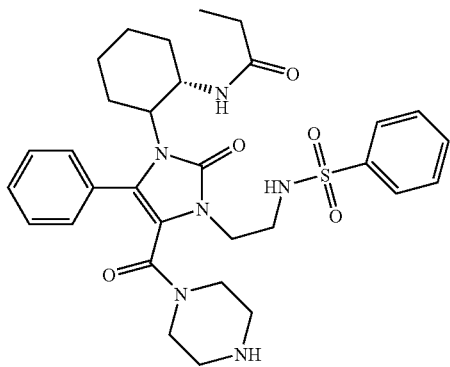

N-[(1S)-2-[3-[2-(benzenesulfonamido)ethyl]-2-
oxo-5-phenyl-4-(piperazine-1-carbonyl)imidazol-1-
yl]cyclohexyl]propanamide

344

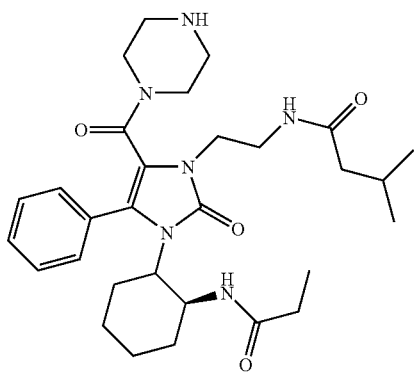

3-methyl-N-[2-[2-oxo-4-phenyl-5-(piperazine-1-
carbonyl)-3-[(2S)-2-
(propanoylamino)cyclohexyl]imidazol-1-
yl]ethyl]butanamide

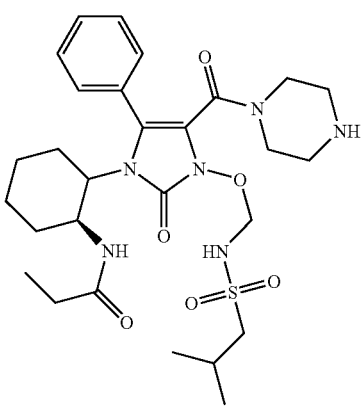

N-[(1S)-2-[3-[2-(2-
methylpropylsulfonylamino)ethyl]-2-oxo-5-phenyl-
4-(piperazine-1-carbonyl)imidazol-1-
yl]cyclohexyl]propanamide

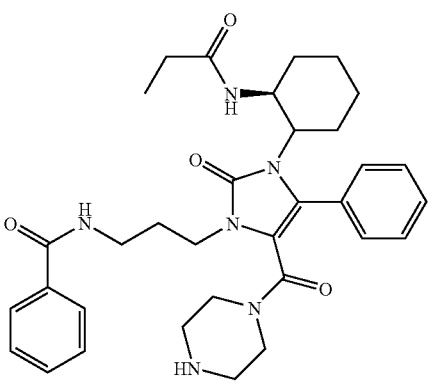

N-[3-[2-oxo-4-phenyl-5-(piperazine-1-carbonyl)-
3-[(2S)-2-(propanoylamino)cyclohexyl]imidazol-
1-yl]propyl]benzamide

345

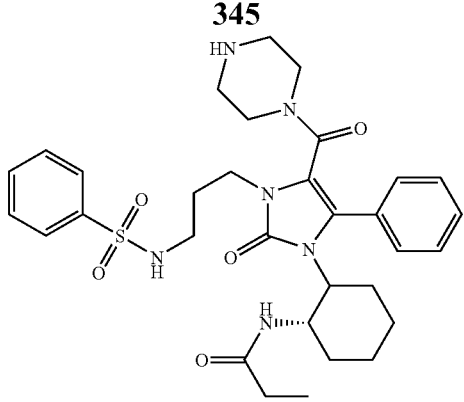

N-[(1S)-2-[3-[3-(benzenesulfonamido)propyl]-2-oxo-5-phenyl-4-(piperazine-1-carbonyl)imidazol-1-yl]cyclohexyl]propanamide

346

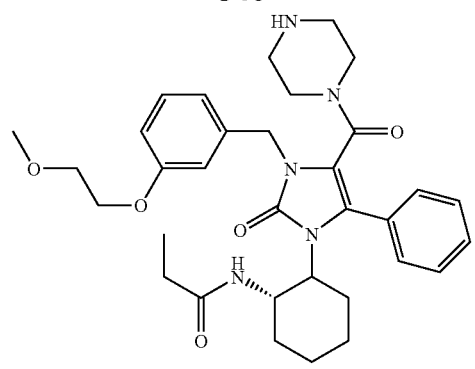

N-[(1S)-2-[3-[[3-(2-methoxyethoxy)phenylmethyl-2-oxo-5-phenyl-4-(piperazine-1-carbonyl)imidazol-1-yl]cyclohexyl]propanamide

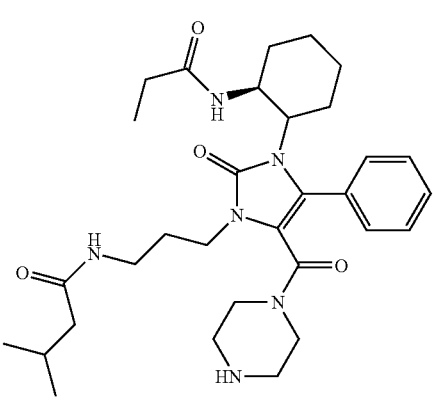

3-methyl-N-[3-[2-oxo-4-phenyl-5-(piperazine-1-carbonyl-3-[(2S)-2-(propanoylamino)cyclohexyl]imidazol-1-yl]propyl]butanamide

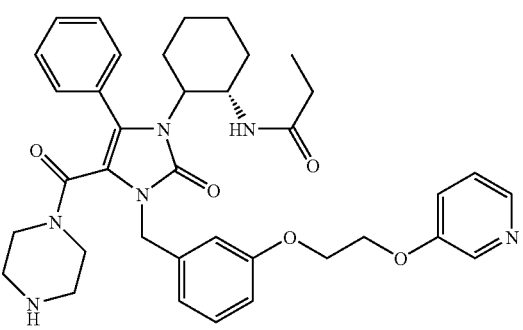

N-[(1S)-2-[2-oxo-5-phenyl-4-(piperazine-1-carbonyl)-3-[[3-(2-pyridin-3-yloxyethoxy)phenyl]methyl]imidazol-1-yl]cyclohexyl]propanamide

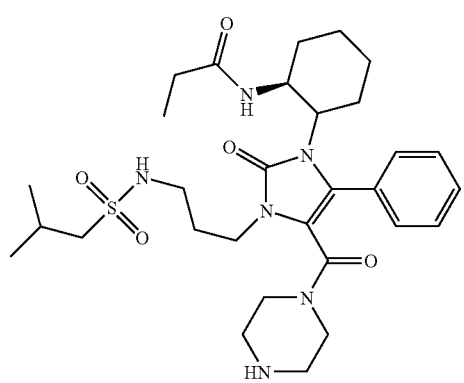

N-[(1S)-2-[3-[3-(2-methylpropylsulfonylamino)propyl]-2-oxo-5-phenyl-4-(piperazine-1-carbonyl)imidazol-1-yl]cyclohexyl]propanamide

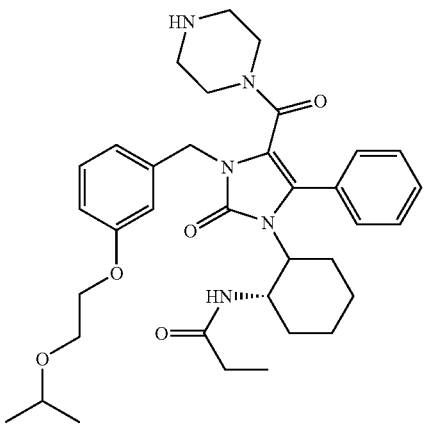

N-[(1S)-2-[2-oxo-5-phenyl-4-(piperazine-1-carbonyl)-3-[[3-(2-propan-2-yloxyethoxy)phenyl]methyl]imidazol-1-yl] cyclohexyl]propanamide

347

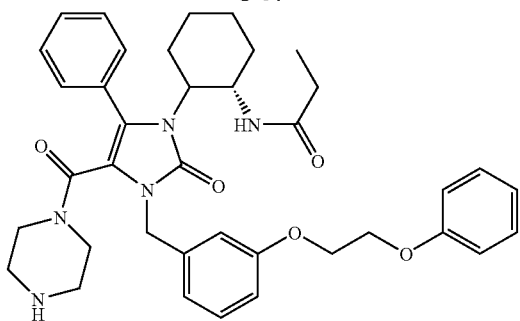

N-[(1S)-2-[2-oxo-3-[[3-(2-phenoxyethoxy)phenyl]methyl]-5-phenyl-4-(piperazine-1-carbonyl)imidazol-1-yl]cyclohexyl]propanamide

348

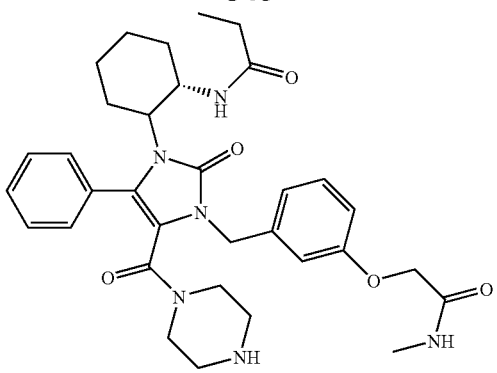

N-[(1S)-2-[3-[[3-(methylcarbamoylmethoxy)phenyl]methyl]-2-oxo-5-phenyl-4-(piperazine-1-carbonyl)imidazol-1-yl]cyclohexyl]propanamide

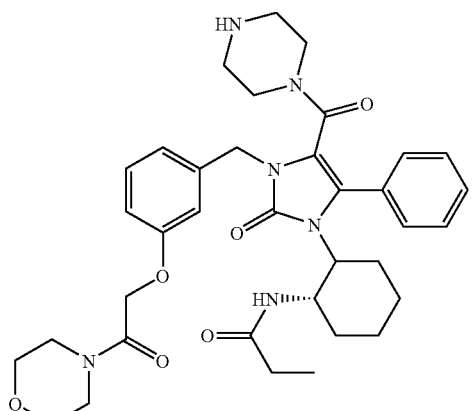

N-[(1S)-2-[3-[[3-(2-morpholin-4-yl-2-oxo-ethoxy)phenyl]methyl]-2-oxo-5-phenyl-4-(piperazine-1-carbonyl)imidazol-1-yl]cyclohexyl]propanamide

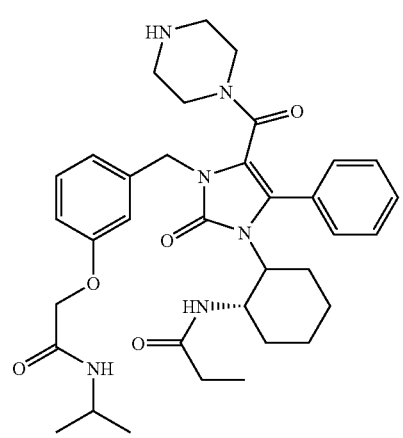

N-(1S)-2-[2-oxo-5-phenyl-4-(piperazine-1-carbonyl)-3-[[3-(propan-2-ylcarbamoylmethoxy)phenyl]methyl]imidazol-1-yl]cyclohexyl]propanamide

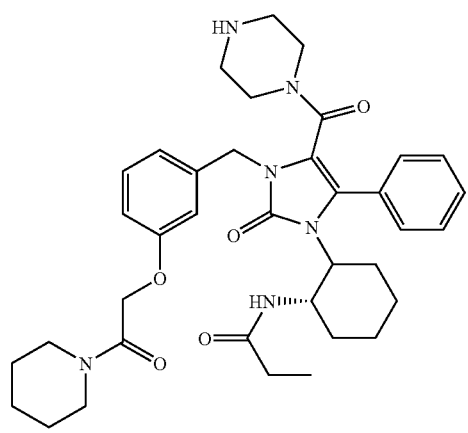

N-[(1S)-2-[2-oxo-3-[[3-[2-oxo-2-(1-piperidyl)ethoxy]phenyl]methyl]-5-phenyl-4-(piperazine-1-carbonyl)imidazol-1-yl]cyclohexyl]propanamide

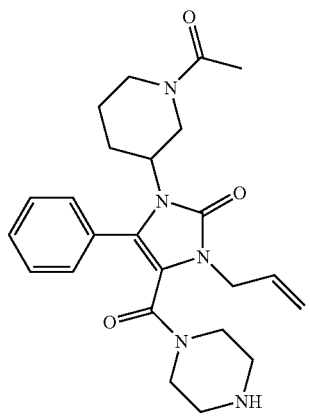

1-(1-acetyl-3-piperidyl)-5-phenyl-4-(piperazine-1-carbonyl)-3-prop-2-enyl-imidazol-2-one

349

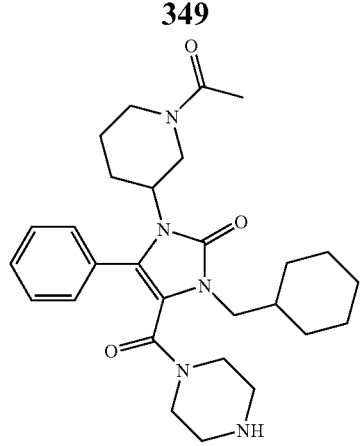

1-(1-acetyl-3-piperidyl)-3-(cyclohexylmethyl)-5-phenyl-4-(piperazine-1-carbonyl)imidazol-2-one

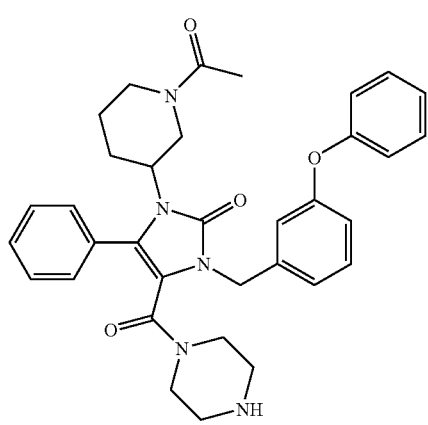

1-(1-acetyl-3-piperidyl)-3-[(3-phenoxyphenyl)methyl]-5-phenyl-4-(piperazine-1-carbonyl)imidazol-2-one

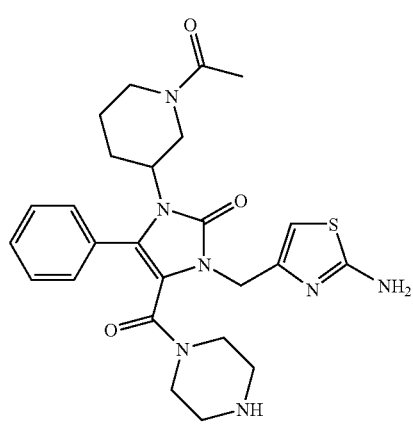

1-(1-acetyl-3-piperidyl)-3-[(2-amino1,3-thiazol-4-yl)methyl]-5-phenyl-4-(piperazine-1-carbonyl)imidazol-2-one

350

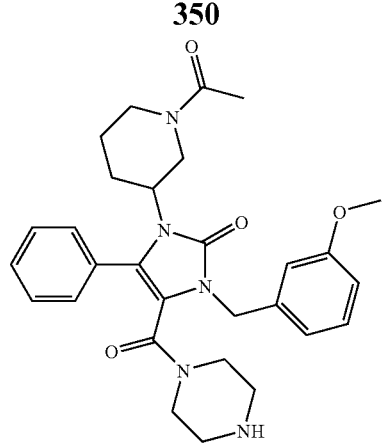

1-(1-acetyl-3-piperidyl)-3-[(3-methoxyphenyl)methyl]-5-phenyl-4-(piperazine-1-carbonyl)imidazol-2-one

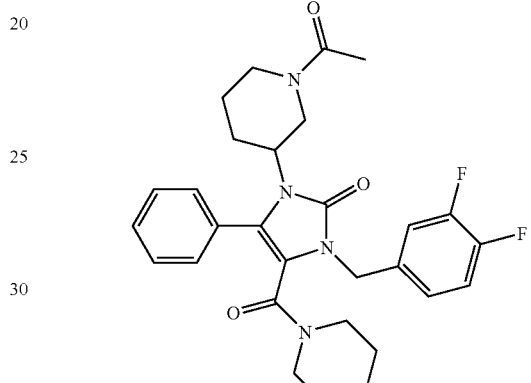

1-(1-acetyl-3-piperidyl)-3-[(3,4-difluorophenyl)methyl]-5-phenyl-4-(piperazine-1-carbonyl)imidazol-2-one

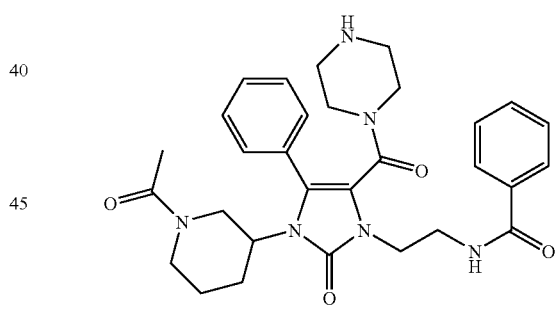

N-[2-[3-(1-acetyl-3-piperidyl)-2-oxo-4-phenyl-5-(piperazine-1-carbonyl)imidazol-1-yl]ethyl]benzamide

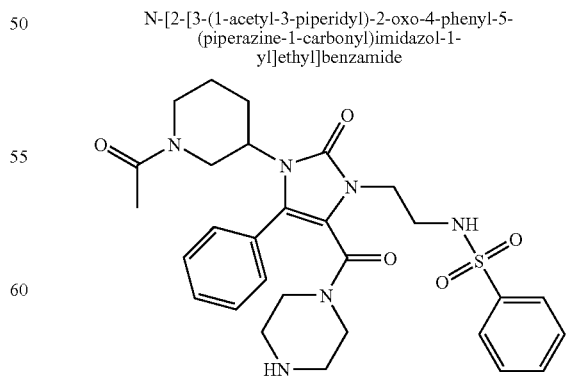

N-[2-[3-(1-acetyl-3-piperidyl)-2-oxo-4-phenyl-5-(piperazine-1-carbonyl)imidazol-1-yl]ethyl]benzenesulfonamide

351

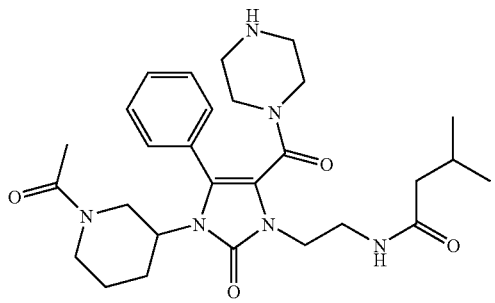

N-[2-[3-(1-acetyl-3-piperidyl)-2-oxo-4-phenyl-5-
(piperazine-1-carbonyl)imidazol-1-yl]ethyl]-3-
methyl-butanamide

352

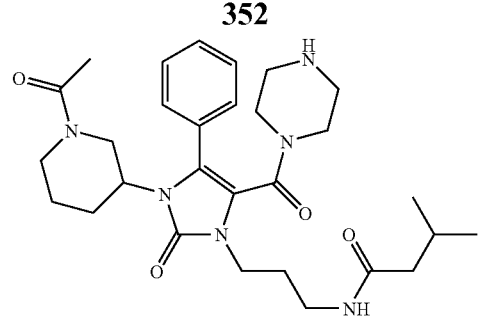

N-[3-[3-(1-acetyl-3-piperidyl)-2-oxo-4-phenyl-5-
(piperazine-1-carbonyl)imidazol-1-yl]propyl]-3-
methyl-butanamide

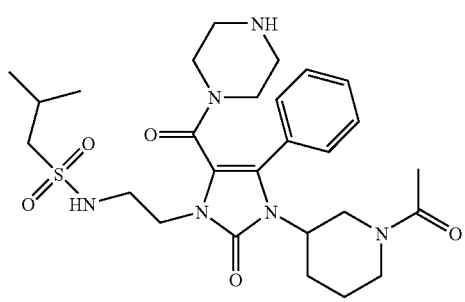

N-[2-[3-(1-acetyl-3-piperidyl)-2-oxo-4-phenyl-5-
(piperazine-1-carbonyl)imidazol-1-yl] ethyl]-2-
methyl-propane-i-sulfonamide

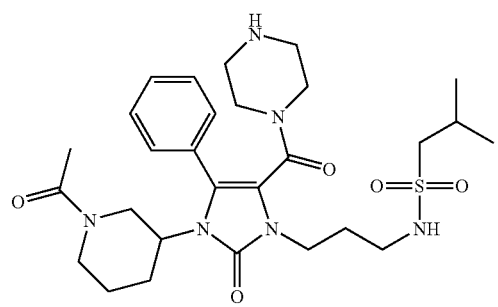

N-[2-[3-(1-acetyl-3-piperidyl)-2-oxo-4-phenyl-5-
(piperazine-1-carbonyl)imidazol-1-yl] propyl]-2-
methyl-propane-1-sulfonamide

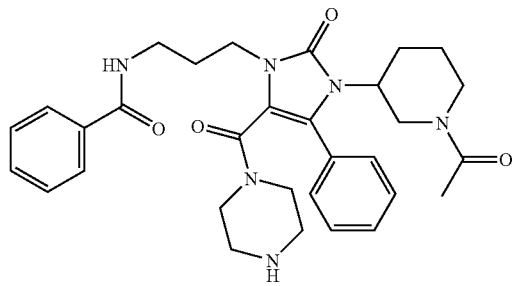

N-[3-[3-(1-acetyl-3-piperidyl)-2-oxo-4-phenyl-5-
(piperazine-1-carbonyl)imidazol-1-
yl]propyl]benzamide

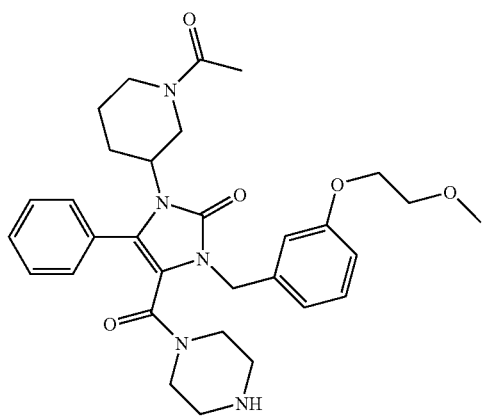

1-(1-acetyl-3-piperidyl)-3-[[3-(2-
methoxyethoxy)phenyl]methyl]-5-phenyl-4-
(piperazine-1-carbonyl)imidazol-2-one

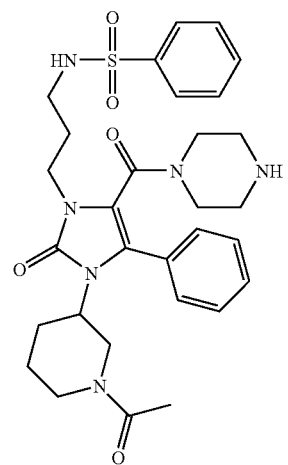

N-[3-[3-(1-acetyl-3-piperidyl)-2-oxo-4-phenyl-5-
(piperazine-1-carbonyl)imidazol-1-
yl]propyl]benzenesulfonamide

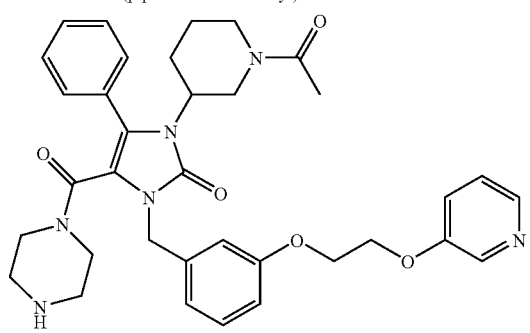

1-(1-acetyl-3-piperidyl)-5-phenyl-4-(piperazine-1-
carbonyl)-3-[[3-(2-pyridin-3-
yloxyethoxy)phenyl]methyl]imidazol-2-one

353

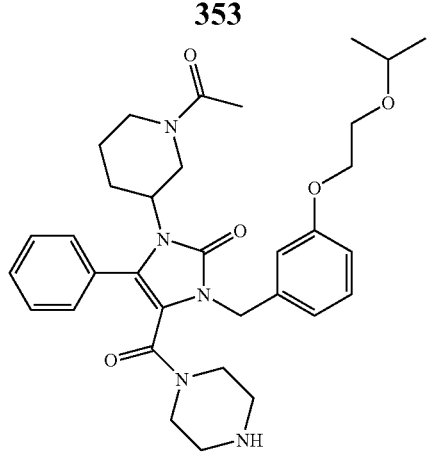

1-(1-acetyl-3-piperidyl)-5-phenyl-4-(piperazine-1-carbonyl)-3-[[3-(2-propan-2-yloxyethoxy)phenyl]methyl]imidazol-2-one

354

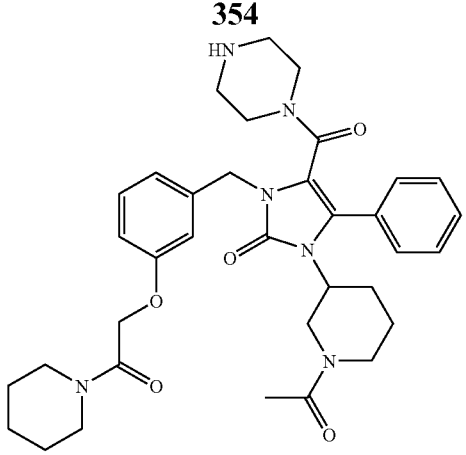

1-(1-acetyl-3-piperidyl)-3-[[3-[2-oxo-2-(1-piperidyl)ethoxy]phenyl]methyl]-5-phenyl-4-(piperazine-1-carbonyl)imidazol-2-one

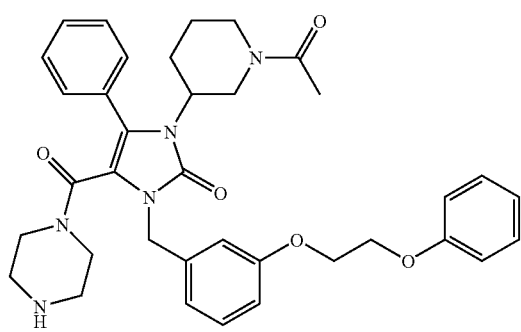

1-(1-acetyl-3-piperidyl)-3-[[3-(2-phenoxyethoxy)phenyl]methyl]-5-phenyl-4-(piperazine-1-carbonyl)imidazol-2-one

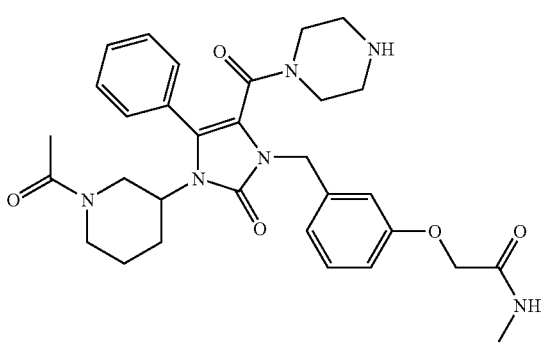

2-[3-[[3-(1-acetyl-3-piperidyl)-2-oxo-4-phenyl-5-(piperazine-1-carbonyl)imidazol-1-yl]methyl]phenoxy]-N-methyl-acetamide

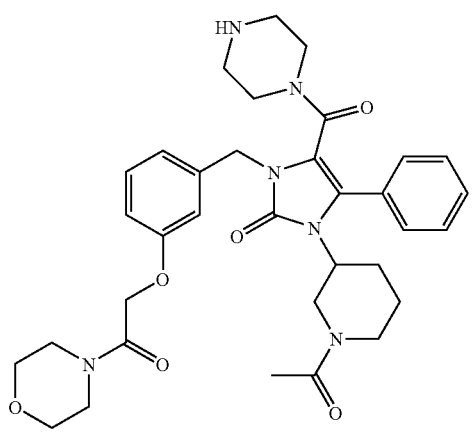

1-(1-acetyl-3-piperidyl)-3-[[3-(2-morpholin-4-yl-2-oxo-ethoxy)phenyl]methyl]-5-phenyl-4-(piperazine-1-carbonyl)imidazol-2-one

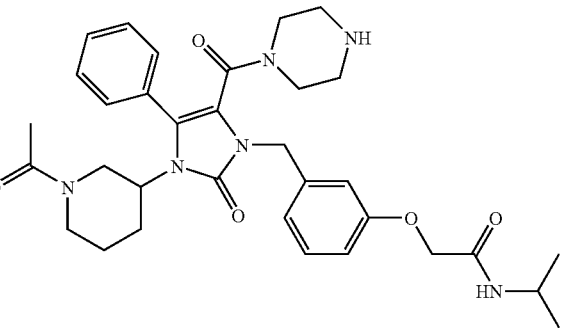

2-[3-[[3-(1-acetyl-3-piperidyl)-2-oxo-4-phenyl-5-(piperazine-1-carbonyl)imidazol-1-yl]methyl]phenoxy]-N-propan-2-yl-acetamide

355

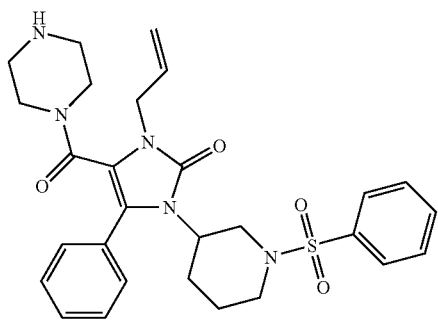

1-[1-(benzenesulfonyl)-3-piperidyl]-5-phenyl-4-(piperazine-1-carbonyl)-3-prop-2-enyl-imidazol-2-one

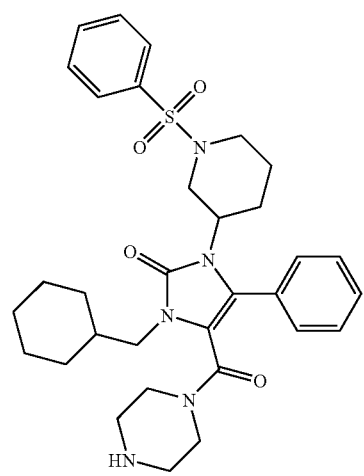

1-[1-(benzenesulfonyl)-3-piperidyl]-3-(cyclohexylmethyl)-5-phenyl-4-(piperazine-1-carbonyl)imidazol-2-one

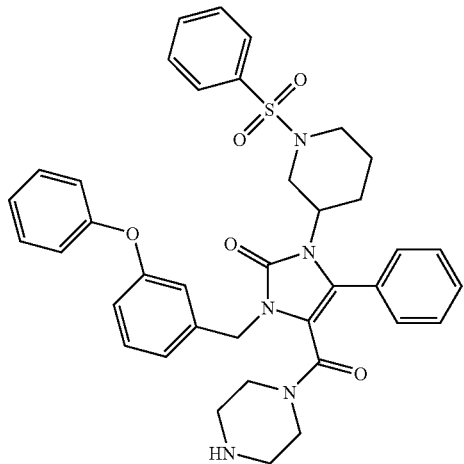

1-[1-(benzenesulfonyl)-3-piperidyl]-3-[(3-phenoxyphenyl)methyl]-5-phenyl-4-(piperazine-1-carbonyl)imidazol-2-one

356

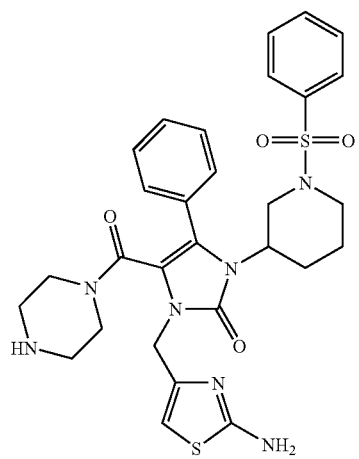

1-[(2-amino1,3-thiazol-4-yl)methyl]-3-[1-(benzenesulfonyl)-3-piperidyl]-4-phenyl-5-(piperazine-1-carbonyl)imidazol-2-one

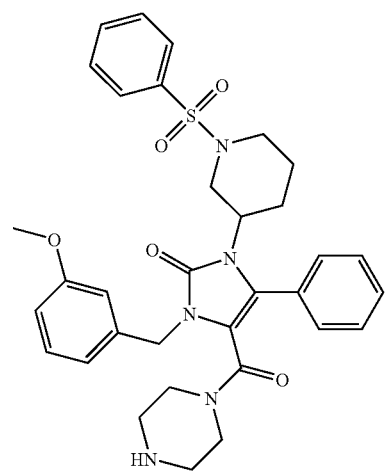

1-[1-(benzenesulfonyl)-3-piperidyl]-3-[(3-methoxyphenyl)methyl]-5-phenyl-4-(piperazine-1-carbonyl)imidazol-2-one

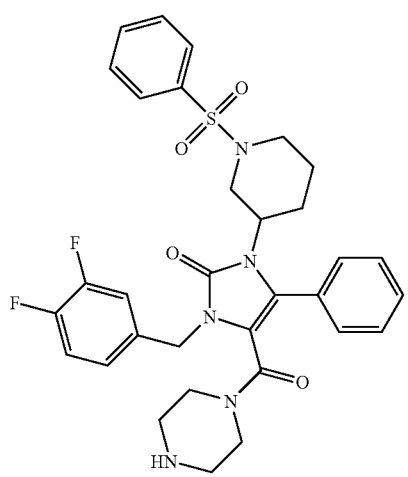

1-[1-(benzenesulfonyl)-3-piperidyl]-3-[(3,4-difluorophenyl)methyl]-5-phenyl-4-(piperazine-1-carbonyl)imidazol-2-one

357

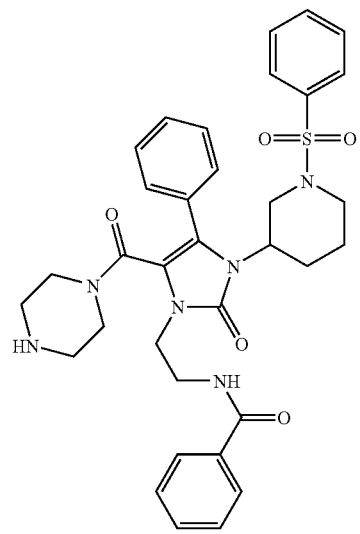

N-[2-[3-[1-(benzenesulfonyl)-3-piperidyl]-2-oxo-
4-phenyl-5-(piperazine-1-carbonyl)imidazol-1-
yl]ethyl]benzamide

358

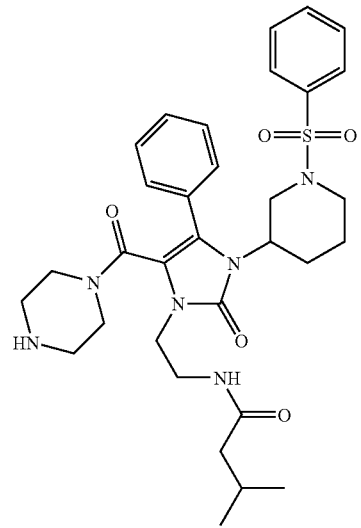

N-[2-[3-[1-(benzenesulfonyl)-3-piperidyl]-2-oxo-
4-phenyl-5-(piperazine-1-carbonyl)imidazol-1-
yl]ethyl]-3-methyl-butanamide

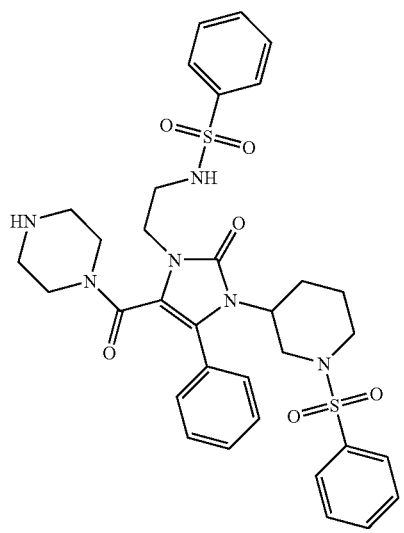

N-[2-[3-[1-(benzenesulfonyl)-3-piperidyl]-2-oxo-4-
phenyl-5-(piperazine-1-carbonyl)imidazol-1-
yl]ethyl]benzenesulfonamide

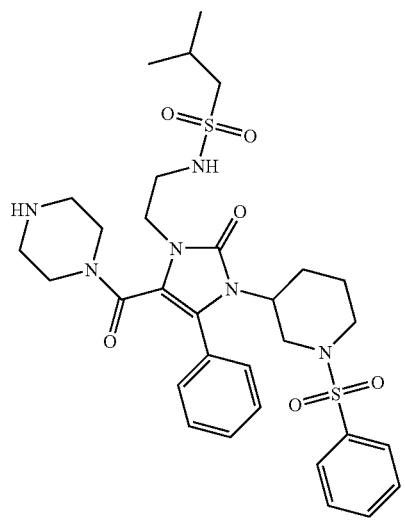

N-[2-[3-[1-(benzenesulfonyl)-3-piperidyl]-2-oxo-4-
phenyl-5-(piperazine-1-carbonyl)imidazol-1-
yl]ethyl]-2-methyl-propane-1-sulfonamide

359 360

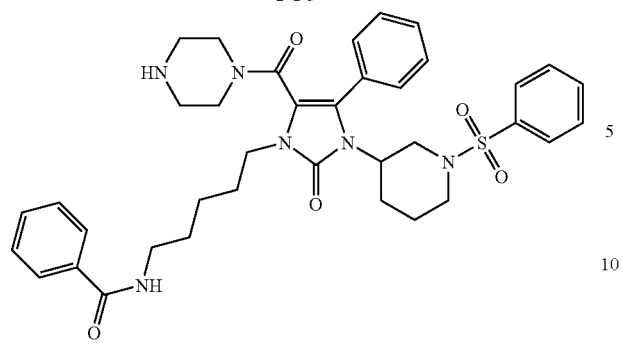

N-[3-[3-[1-(benzenesulfonyl)-3-piperidyl]-2-oxo-
4-phenyl-5-(piperazine-1-carbonyl)imidazol-1-
yl]propyl]benzamide

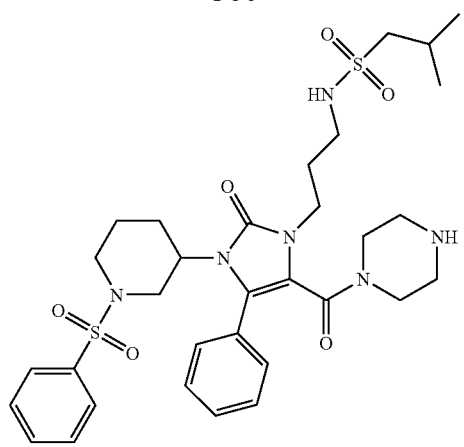

N-[3-[3-[1-(benzenesulfonyl)-3-piperidyl]-2-oxo-4-
phenyl-5-(piperazine-1-carbonyl)imidazol-1-
yl]propyl]-2-methyl-propane-1-sulfonamide

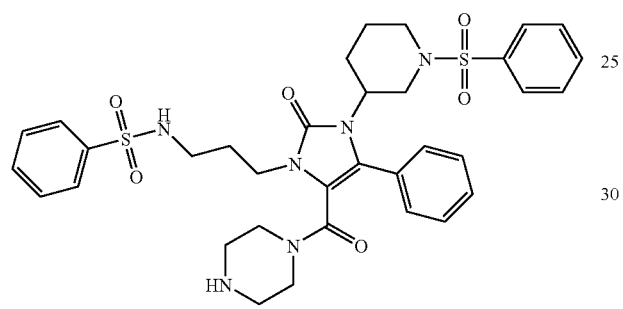

N-[3-[3-[1-(benzenesulfonyl)-3-piperidyl]-2-oxo-4-
phenyl-5-(piperazine-1-carbonyl)imidazol-1-
yl]propyl]benzenesulfonamide

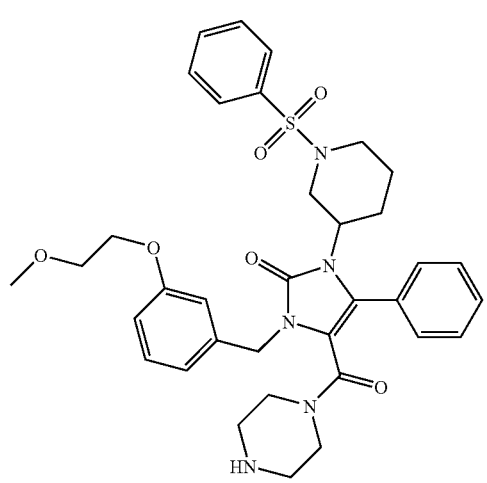

1-[1-(benzenesulfonyl)-3-piperidyl]-3-[[3-(2-
methoxyethoxy)phenyl]methyl]-5-phenyl-4-
(piperazine-1-carbonyl)imidazol-2-one

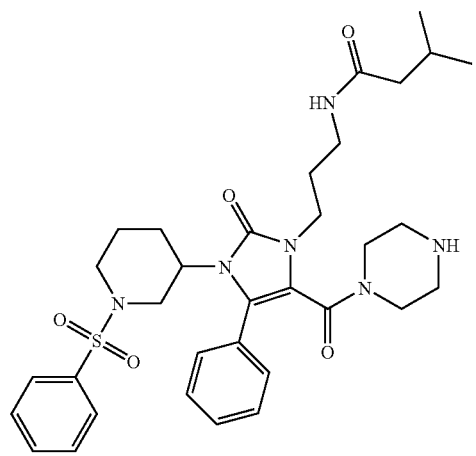

N-[3-[3-[1-(benzenesulfonyl)-3-piperidyl]-2-oxo-
4-phenyl-5-(piperazine-1-carbonyl)imidazol-1-
yl]propyl]-3-methyl-butanamide

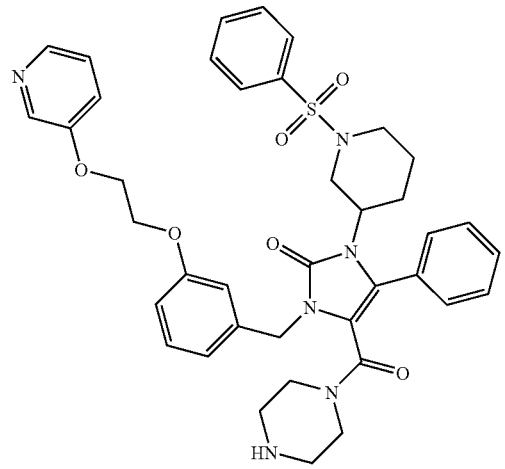

1-[1-(benzenesulfonyl)-3-piperidyl]-5-phenyl-4-
(piperazine-1-carbonyl)-3-[[3-(2-pyridin-3-
yloxyethoxy)phenyl]methyl]imidazol-2-one

361

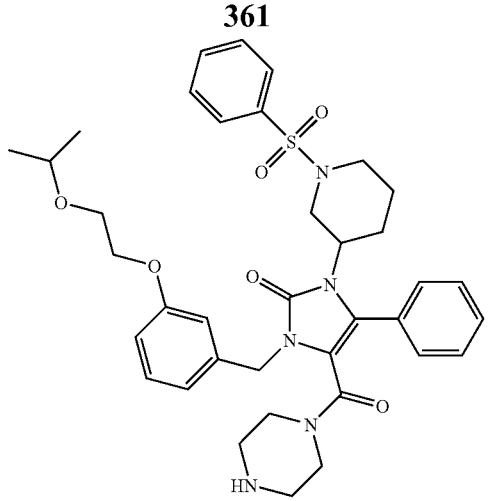

1-[1-(benzenesulfonyl)-3-piperidyl]-5-phenyl-4-
(piperazine-1-carbonyl)-3-[[3-(2-propan-2-
yloxyethoxy)phenyl]methyl]imidazol-2-one

362

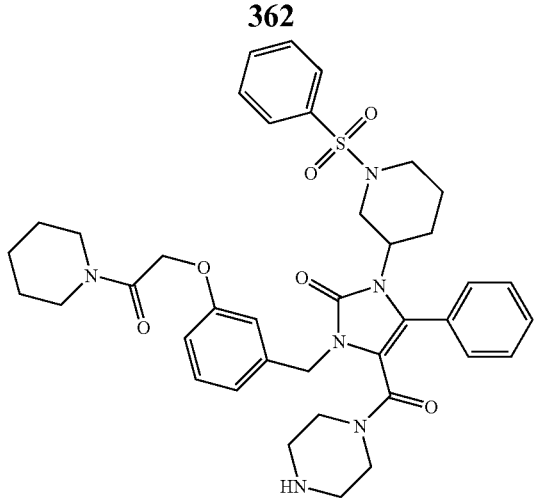

1-[1-(benzenesulfonyl)-3-piperidyl]-3-[[3-[2-oxo-2-
(1-piperidyl)ethoxy]phenyl]methyl]-5-phenyl-4-
(piperazine-1-carbonyl)imidazol-2-one

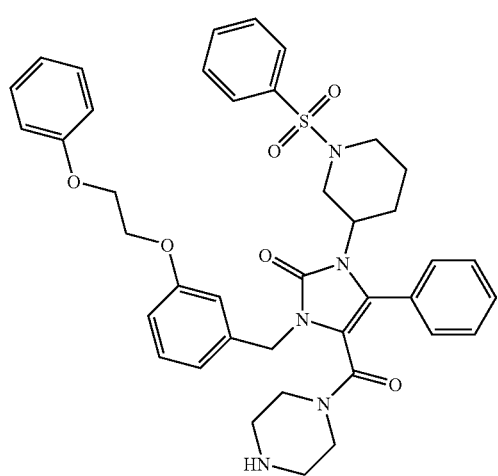

1-[1-(benzenesulfonyl)-3-piperidyl]-3-[[3-(2-
phenoxyethoxy)phenyl]methyl]-5-phenyl-4-
(piperazine-1-carbonyl)imidazol-2-on

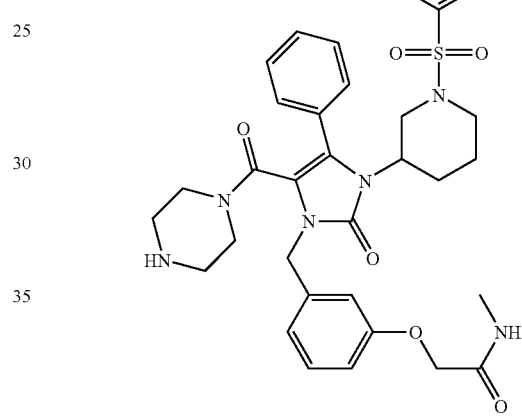

2-[3-[[3-[1-(benzenesulfonyl)-3-piperidyl]-2-oxo-
4-phenyl-5-(piperazine-1-carbonyl)imidazol-1-
yl]methyl]phenoxy]-N-methyl-acetamide

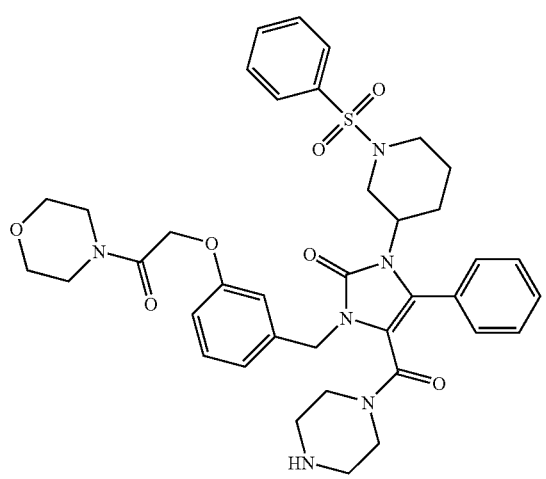

1-[1-(benzenesulfonyl)-3-piperidyl]-3-[[3-(2-
morpholin-4-yl-2-oxo-ethoxy)phenyl]methyl]-5-
phenyl-4-(piperazine-1-carbonyl)imidazol-2-one

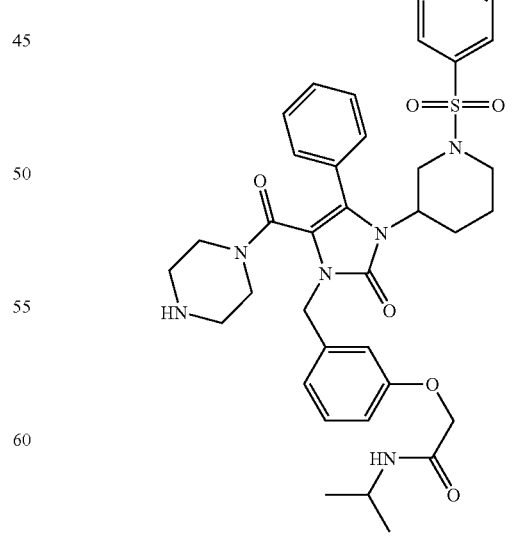

2-[3-[[3-[1-(benzenesulfonyl)-3-piperidyl]-2-oxo-4-
phenyl-5-(piperazine-1-carbonyl)imidazol-1-
yl]methyl]phenoxy]-N-propan-2-yl-acetamide

363

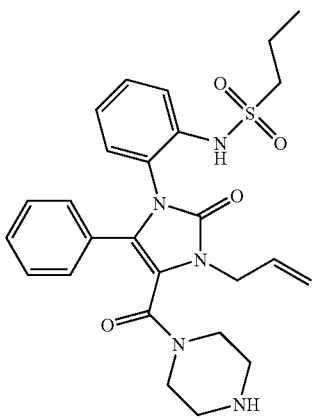

N-[2-[2-oxo-5-phenyl-4-(piperazine-1-carbonyl)-
3-prop-2-enyl-imidazol-1-yl]phenyl]propane-1-
sulfonamide

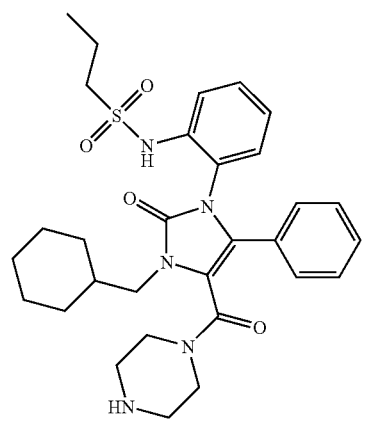

N-[2-[3-(cyclohexylmethyl)-2-oxo-5-phenyl-4-
(piperazine-1-carbonyl)imidazol-1-
yl]phenyl]propane-1-sulfonamide

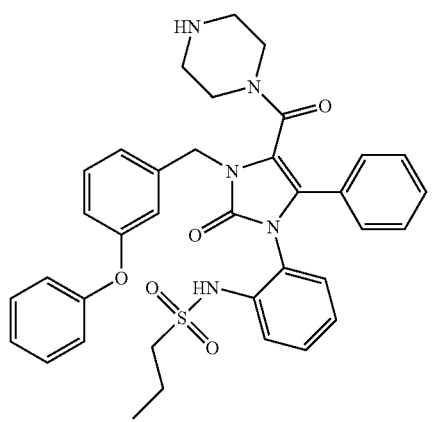

N-[2-[2-oxo-3-[(3-phenoxyphenyl)methyl]-5-
phenyl-4-(piperazine-1-carbonyl)imidazol-1-
yl]phenyl]propane-1-sulfonamide

364

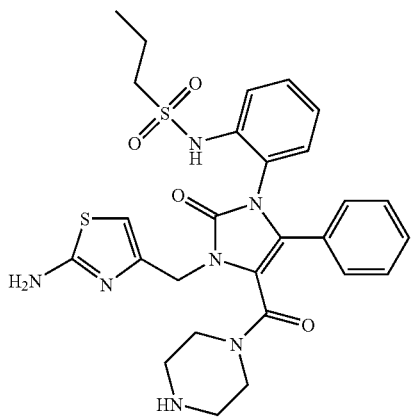

N-[2-[3-[(2-amino1,3-thiazol-4-yl)methyl]-2-oxo-
5-phenyl-4-(piperazine-1-carbonyl)imidazol-1-
yl]phenyl]propane-1-sulfonamide

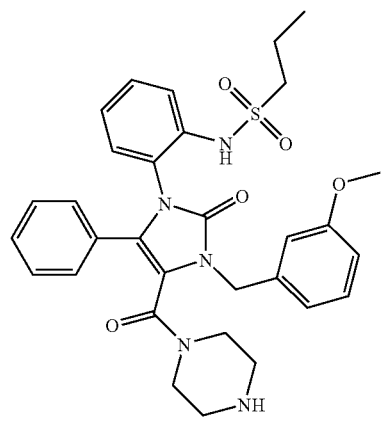

N-[2-[3-[(3-methoxyphenyl)methyl]-2-oxo-5-
phenyl-4-(piperazine-1-carbonyl)imidazol-1-
yl]phenyl]propane-1-sulfonamide

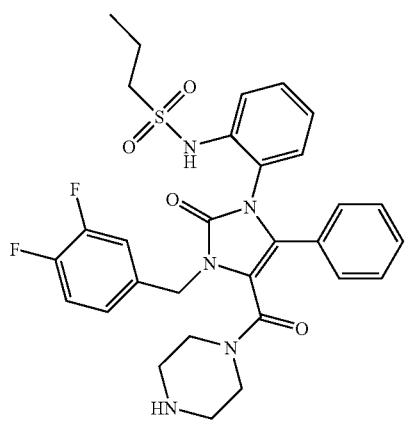

N-[2-[3-[(3,4-difluorophenyl)methyl]-2-oxo-5-
phenyl-4-(piperazine-1-carbonyl)imidazol-1-
yl]phenyl]propane-1-sulfonamide

365

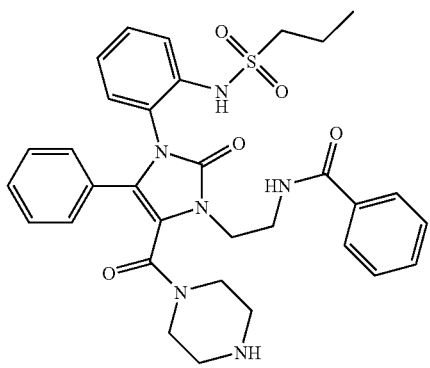

N-[2-[2-oxo-4-phenyl-5-(piperazine-1-carbonyl)-
3-[2-(propylsulfonylamino)phenyl]imidazol-1-
yl]ethyl]benzamide

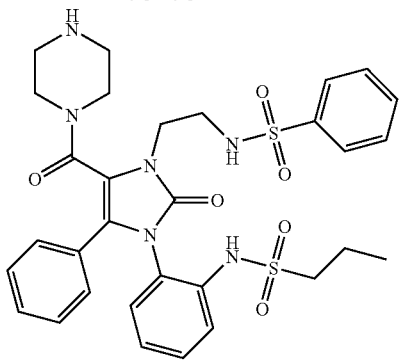

N-[2-[2-oxo-4-phenyl-5-(piperazine-1-carbonyl)-3-
[2-(propylsulfonylamino)phenyl]imidazol-1-
yl]ethyl]benzenesulfonamide

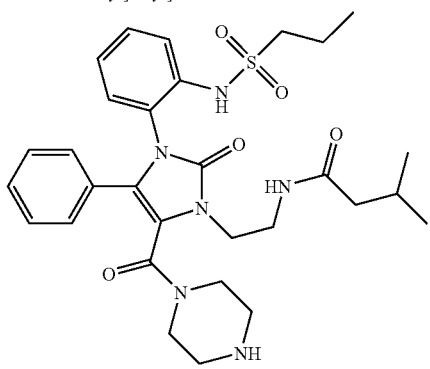

3-methyl-N-[2-[2-oxo-4-phenyl-5-(piperazine-1-
carbonyl)-3-[2-
(propylsulfonylamino)phenyl]imidazol-1-
yl]ethyl]butanamide

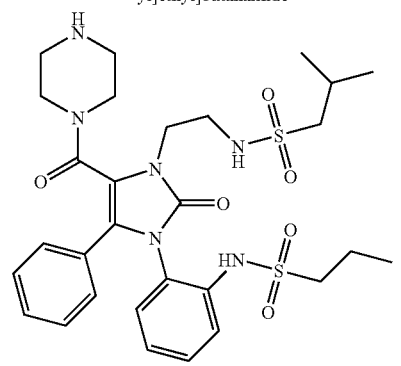

2-methyl-N-[2-[2-oxo-4-phenyl-5-(piperazine-1-
carbonyl)-3-[2-
(propylsulfonylamino)phenyl]imidazol-1-
yl]ethyl]propane-1-sulfonamide

366

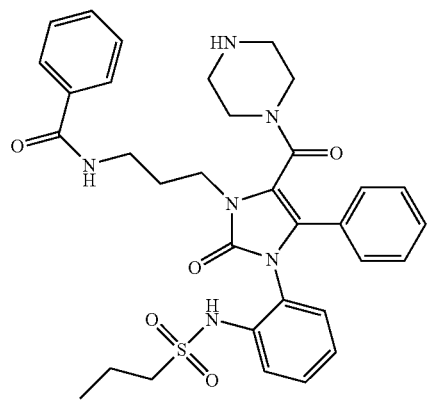

N-[3-[2-oxo-4-phenyl-5-(piperazine-1-carbonyl)-
3-[2-(propylsulfonylamino)phenyl]imidazol-1-
yl]propyl]benzamide

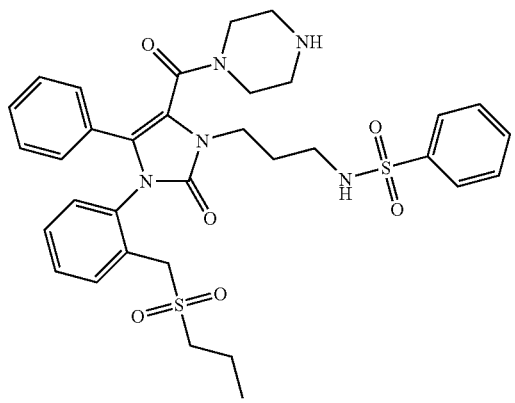

N-[3-[2-oxo-4-phenyl-5-(piperazine-1-carbonyl)-3-
[2-(propylsulfonylamino)phenyl]imidazol-1-
yl]propyl]benzenesulfonamide

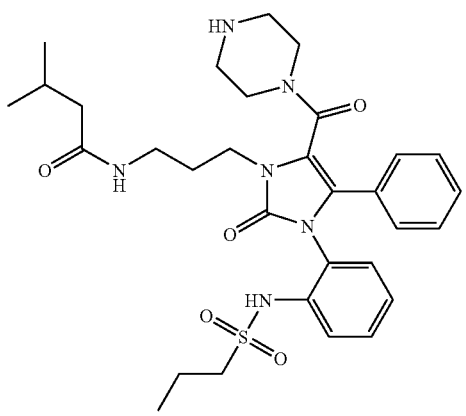

3-methyl-N-[3-[2-oxo-4-phenyl-5-(piperazine-1-
carbonyl)-3-[2-
(propylsulfonylamino)phenyl]imidazol-1-
yl]propyl]butanamide

367

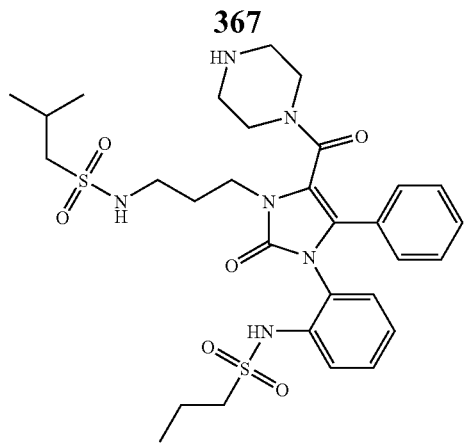

2-methyl-N-[3-[2-oxo-4-phenyl-5-(piperazine-1-carbonyl)-3-[2-(propylsulfonylamino)phenyl]imidazol-1-yl]propyl]propane-1-sulfonamide

368

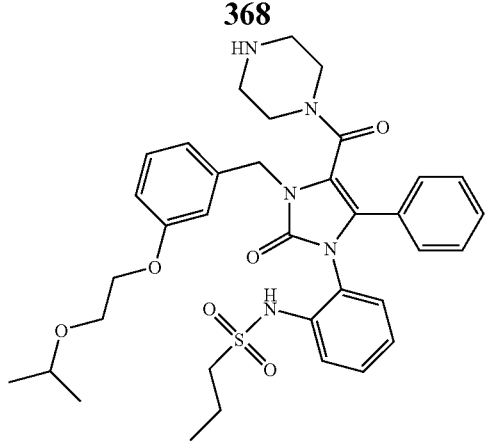

N-[2-[2-oxo-5-phenyl-4-(piperazine-1-carbonyl)-3-[[3-(2-propan-2-yloxyethoxy)phenyl]methyl]imidazol-1-yl]phenyl]propane-1-sulfonamide

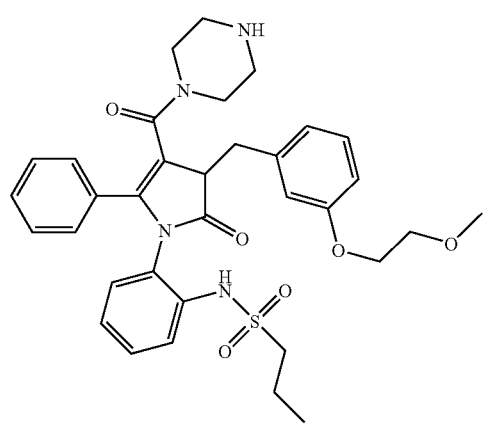

N-[2-[3-[[3-(2-methoxyethoxy)phenyl]methyl]-2-oxo-5-phenyl-4-(piperazine-1-carbonyl)imidazol-1-yl]phenyl]propane-1-sulfonamide

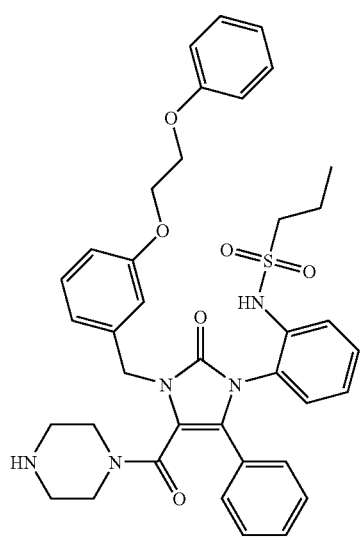

N-[2-[2-oxo-3-[[3-(2-phenoxyethoxy)phenyl]methyl]-5-phenyl-4-(piperazine-1-carbonyl)imidazol-1-yl]phenyl]propane-1-sulfonamide

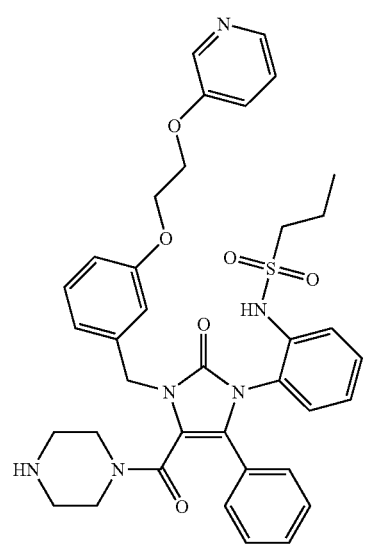

N-[2-[2-oxo-5-phenyl-4-(piperazine-1-carbonyl)-3-[[3-(2-pyridin-3-yloxyethoxy)phenyl]methyl]imidazol-1-yl]phenyl]propane-1-sulfonamide

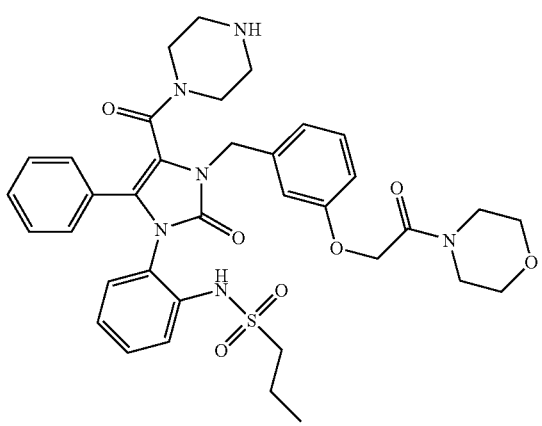

N-[2-[3-[[3-(2-morpholin-4-yl-2-oxo-ethoxy)phenyl]methyl]-2-oxo-5-phenyl-4-(piperazine-1-carbonyl)imidazol-1-yl]phenyl]propane-1-sulfonamide

369

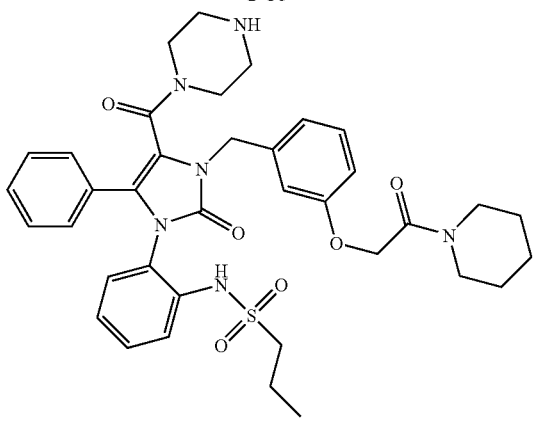

N-[2-[2-oxo-3-[[3-[2-oxo-2-(1-piperidyl)ethoxy]phenyl]methyl]-5-phenyl-4-(piperazine-1-carbonyl)imidazol-1-yl]phenyl]propane-1-sulfonamide

370

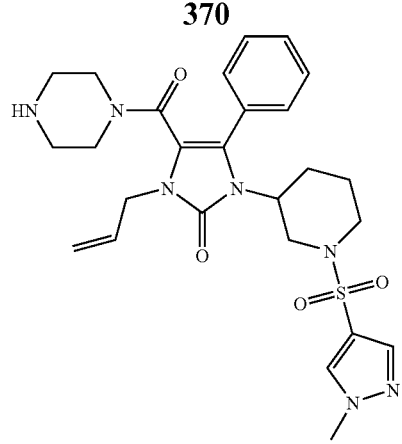

1-[1-(1-methylpyrazol-4-yl)sulfonyl-3-piperidyl]-5-phenyl-4-(piperazine-1-carbonyl)-3-prop-2-enyl-imidazol-2-one

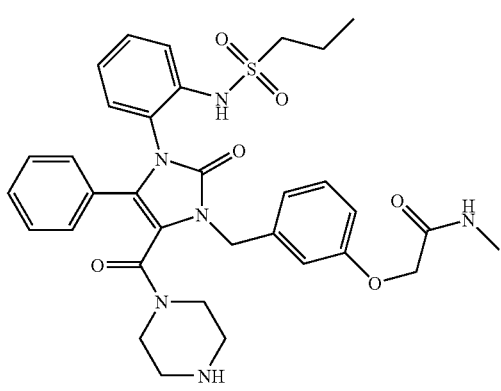

N-methyl-2-[3-[[2-oxo-4-phenyl-5-(piperazine-1-carbonyl)-3-[2-(propylsulfonylamino)phenyl]imidazol-1-yl]methyl]phenoxy]acetamide

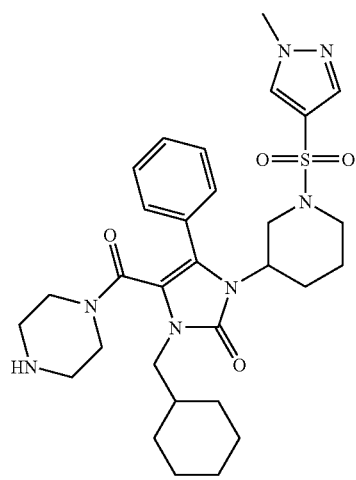

1-(cyclohexylmethyl)-3-[1-(1-methylpyrazol-4-yl)sulfonyl-3-piperidyl]-4-phenyl-5-(piperazine-1-carbonyl)imidazol-2-one

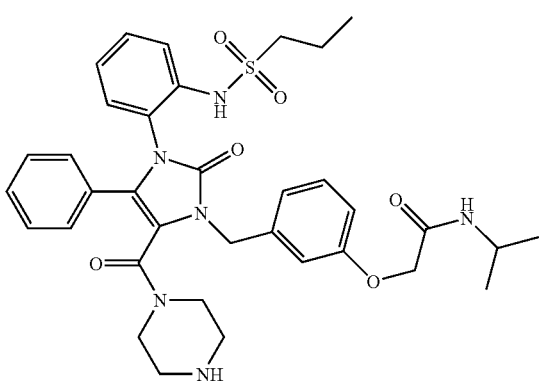

2-[3-[[2-oxo-4-phenyl-5-(piperazine-1-carbonyl)-3-[2-(propylsulfonylamino)phenyl]imidazol-1-yl]methyl]phenoxy]-N-propan-2-yl-acetamide

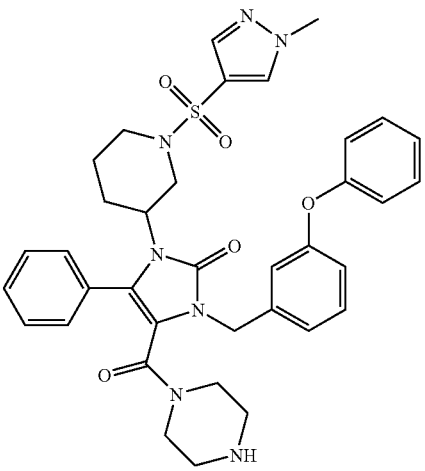

1-[1-(1-methylpyrazol-4-yl)sulfonyl-3-piperidyl]-3-[(3-phenoxyphenyl)methyl]-5-phenyl-4-(piperazine-1-carbonyl)imidazol-2-one

371

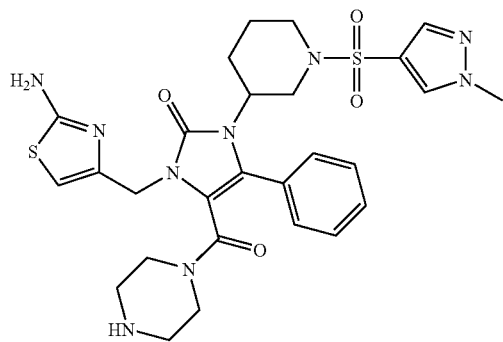

1-[(2-amino1,3-thiazol-4-yl)methyl]-3-[1-(1-methylpyrazol-4-yl)sulfonyl-3-piperidyl]-4-phenyl-5-(piperazine-1-carbonyl)imidazol-2-one

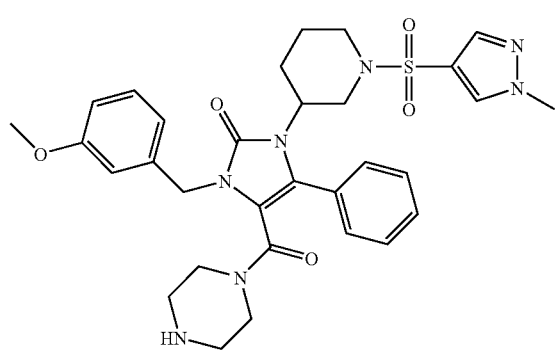

1-[(3-methoxyphenyl)methyl]-3-[1-(1-methylpyrazol-4-yl)sulfonyl-3-piperidyl]-4-phenyl-5-(piperazine-1-carbonyl)imidazol-2-one

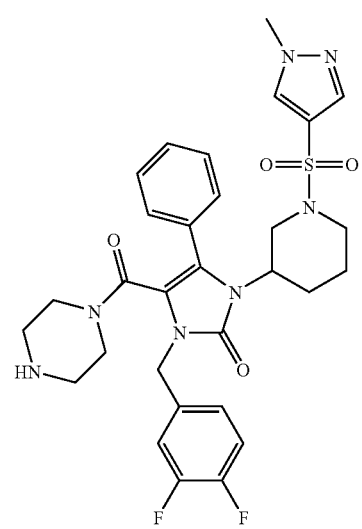

1-[(3,4-difluorophenyl)methyl]-3-[1-(1-methylpyrazol-4-yl)sulfonyl-3-piperidyl]-4-phenyl-5-(piperazine-1-carbonyl)imidazol-2-one

372

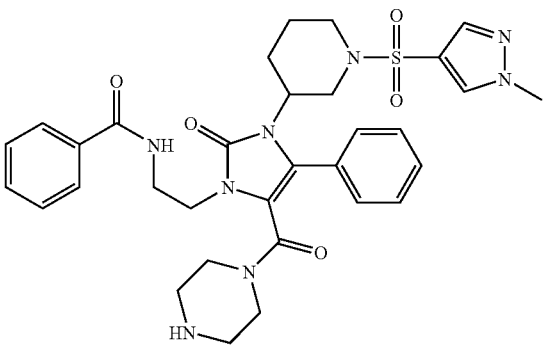

N-[2-[3-[1-(1-methylpyrazol-4-yl)sulfonyl-3-piperidyl]-2-oxo-4-phenyl-5-(piperazine-1-carbonyl)imidazol-1-yl]ethyl]benzamide

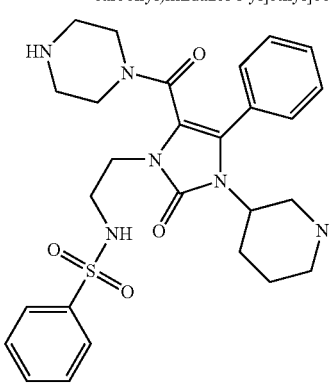

N-[2-[3-[1-(1-methylpyrazol-4-yl)sulfonyl-3-piperidyl]-2-oxo-4-phenyl-5-(piperazine-1-carbonyl)imidazol-1-yl]ethyl]benzenesulfonamide

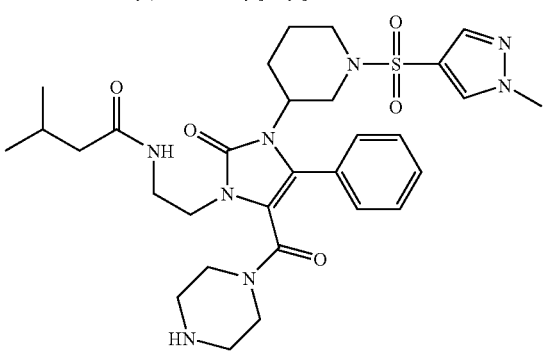

3-methyl-N-[2-[3-[1-(1-methylpyrazol-4-yl)sulfonyl-3-piperidyl]-2-oxo-4-phenyl-5-(piperazine-1-carbonyl)imidazol-1-yl]ethyl]butanamide

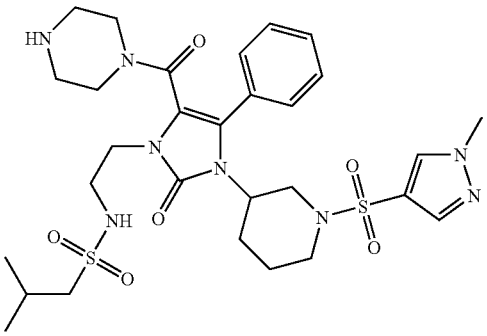

2-methyl-N-[2-[3-[1-(1-methylpyrazol-4-yl)sulfonyl-3-piperidyl]-2-oxo-4-phenyl-5-(piperazine-1-carbonyl)imidazol-1-yl]ethyl]propane-1-sulfonamide

373

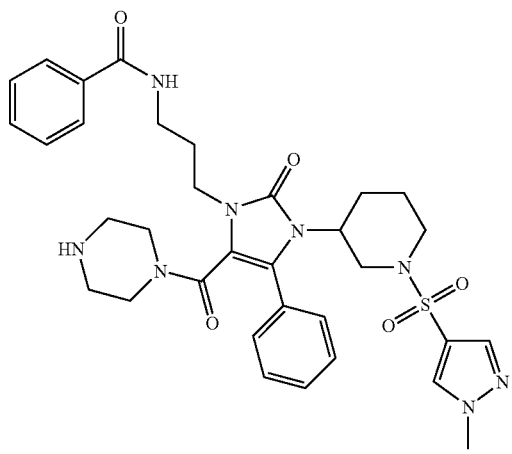

N-[3-[3-[1-(1-methylpyrazol-4-yl)sulfonyl-3-
piperidyl]-2-oxo-4-phenyl-5-(piperazine-1-
carbonyl)imidazol-1-yl]propyl]benzamide

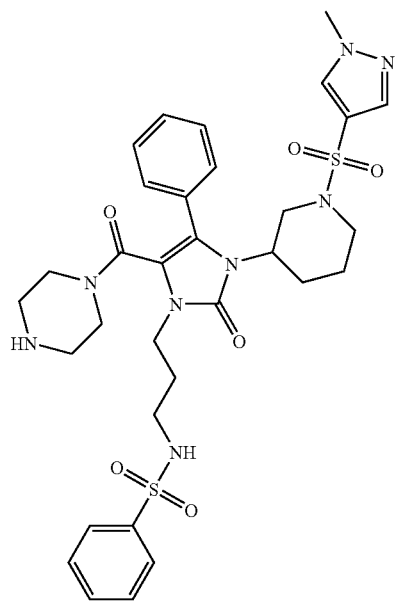

N-[3-[3-[1-(1-methylpyrazol-4-yl)sulfonyl-3-
piperidyl]-2-oxo-4-phenyl-5-(piperazine-1-
carbonyl)imidazol-1-yl]propyl]benzenesulfonamide

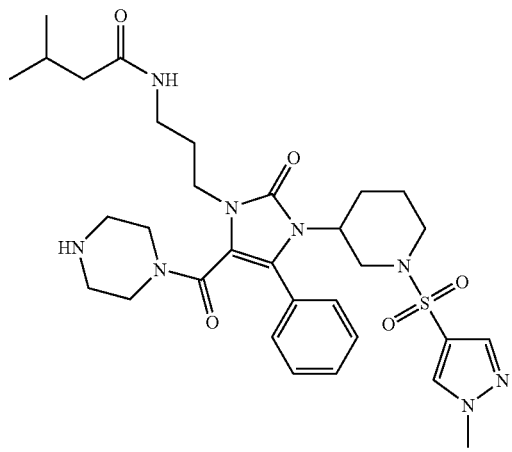

3-methyl-N-[3-[3-[1-(1-methylpyrazol-4-
yl)sulfonyl-3-piperidyl]-2-oxo-4-phenyl-5-
(piperazine-1-carbonyl)imidazol-1-
yl]propyl]butanamide

374

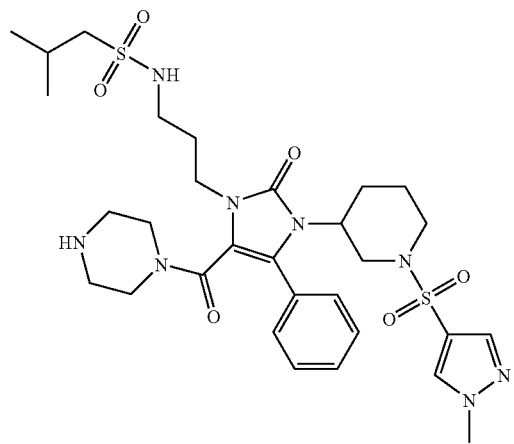

2-methyl-N-[3-[3-[1-(1-methylpyrazol-4-
yl)sulfonyl-3-piperidyl]-2-oxo-4-phenyl-5-
(piperazine-1-carbonyl)imidazol-1-
yl]propyl]propane-1-sulfonamide

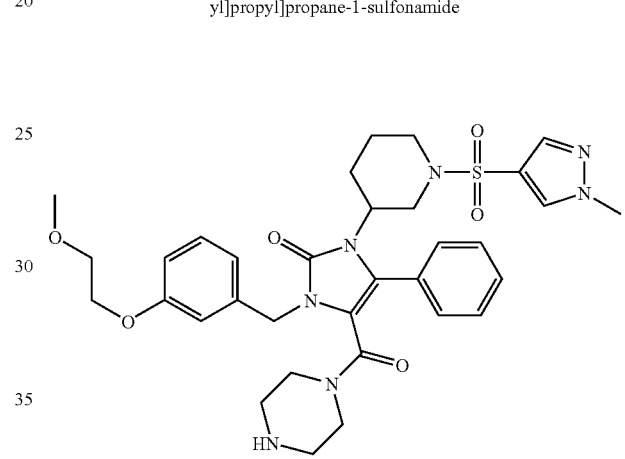

1-[[3-(2-methoxyethoxy)phenyl]methyl]-3-[1-(1-
methylpyrazol-4-yl)sulfonyl-3-piperidyl]-4-
phenyl-5-(piperazine-1-carbonyl)imidazol-2-one

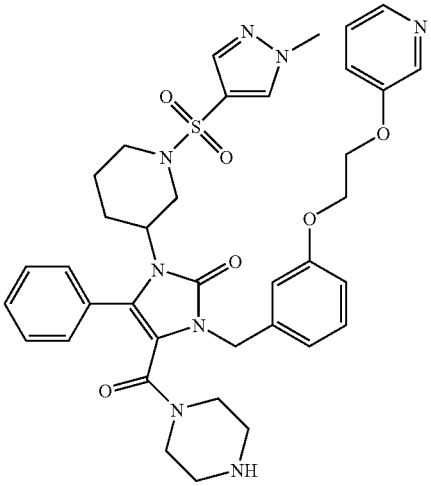

1-[1-(1-methylpyrazol-4-yl)sulfonyl-3-piperidyl]-5-
phenyl-4-(piperazine-1-carbonyl)-3-[[3-(2-pyridin-
3-yloxyethoxy)phenyl]methyl]imidazol-2-one

375

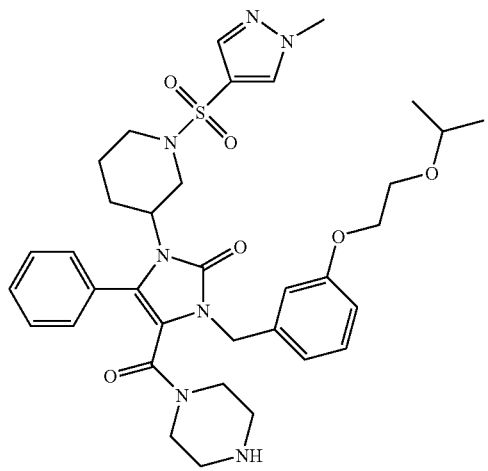

1-[1-(1-methylpyrazol-4-yl)sulfonyl-3-piperidyl]-
5-phenyl-4-(piperazine-1-carbonyl)-3-[[3-(2-
propan-2-yloxyethoxy)phenyl]methyl]imidazol-
2-one

376

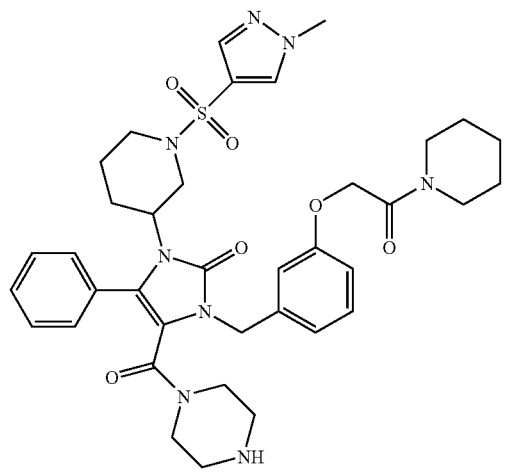

1-[1-(1-methylpyrazol-4-yl)sulfonyl-3-piperidyl]-3-
[[3-[2-oxo-2-(1-piperidyl)ethoxy]phenyl]methyl]-5-
phenyl-4-(piperazine-1-carbonyl)imidazol-2-one

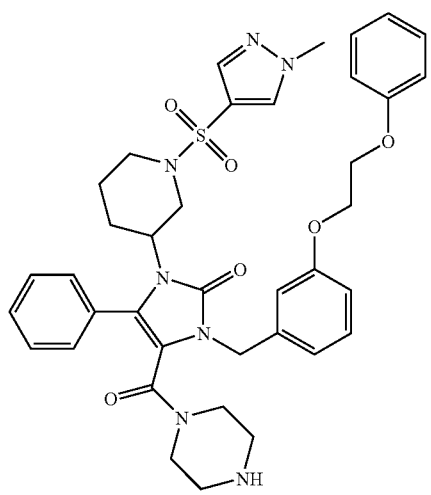

1-[1-(1-methylpyrazol-4-yl)sulfonyl-3-piperidyl]-3-
[[3-(2-phenoxyethoxy)phenyl]methyl]-5-phenyl-4-
(piperazine-1-carbonyl)imidazol-2-one

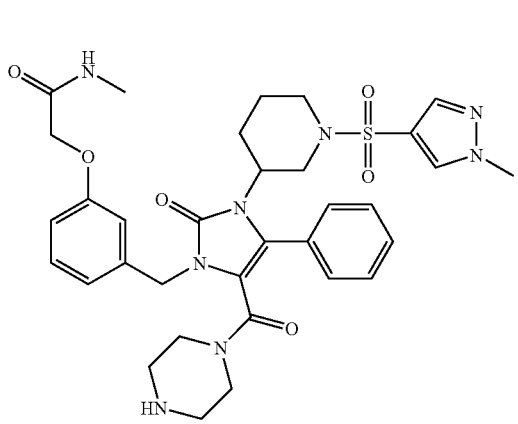

N-methyl-2-[3-[[3-[1-(1-methylpyrazol-4-
yl)sulfonyl-3-piperidyl]-2-oxo-4-phenyl-5-
(piperazine-1-carbonyl)imidazol-1-
yl]methyl]phenoxy]acetamide

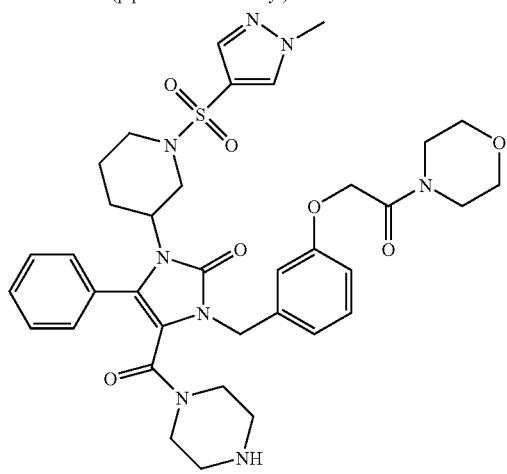

1-[1-(1-methylpyrazol-4-yl)sulfonyl-3-piperidyl]-
3-[[3-(2-morpholin-4-yl-2-oxo-
ethoxy)phenyl]methyl]-5-phenyl-4-(piperazine-1-
carbonyl)imidazol-2-one

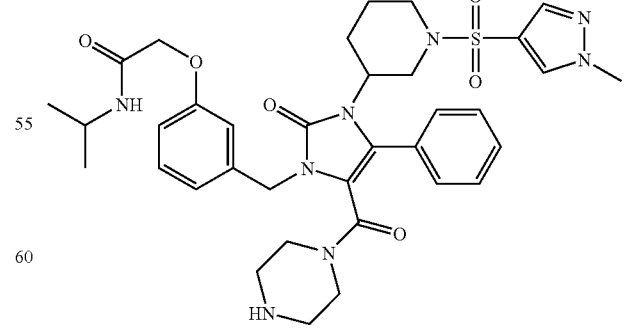

2-[3-[[3-[1-(1-methylpyrazol-4-yl)sulfonyl-3-
piperidyl]-2-oxo-4-phenyl-5-(piperazine-1-
carbonyl)imidazol-1-yl]methyl]phenoxy]-N-
propan-2-yl-acetamide

377

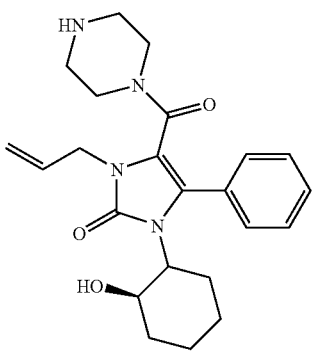

1-[(2R)-2-hydroxycyclohexyl]-5-phenyl-4-(piperazine-1-carbonyl)-3-prop-2-enyl-imidazol-2-one

378

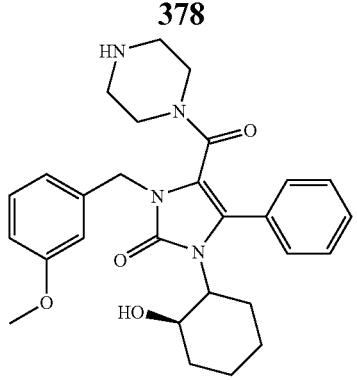

1-[(2R)-2-hydroxycyclohexyl]-3-[(3-methoxyphenyl)methyl]-5-phenyl-4-(piperazine-1-carbonyl)imidazol-2-one

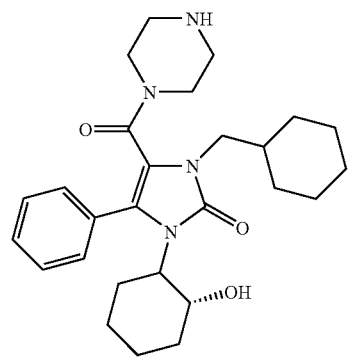

1-(cyclohexylmethyl)-3-[(2R)-2-hydroxycyclohexyl]-4-phenyl-5-(piperazine-1-carbonyl)imidazol-2-one

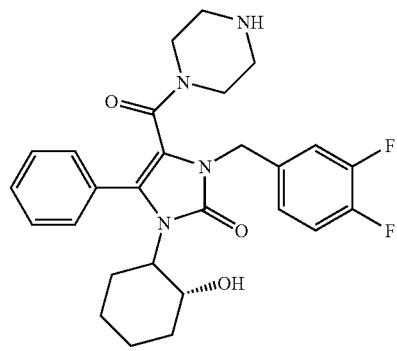

1-[(3,4-difluorophenyl)methyl]-3-[(2R)-2-hydroxycyclohexyl]-4-phenyl-5-(piperazine-1-carbonyl)imidazol-2-one

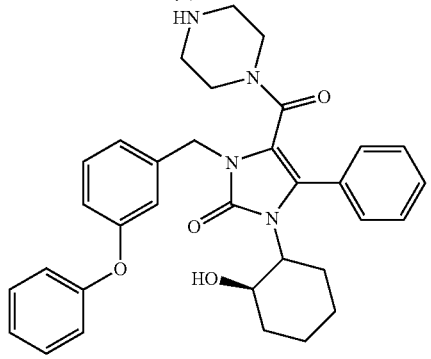

1-[(2R)-2-hydroxycyclohexyl]-3-[(3-phenoxyphenyl)methyl]-5-phenyl-4-(piperazine-1-carbonyl)imidazol-2-one

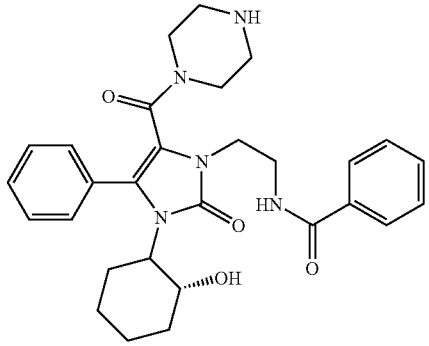

N-[2-[3-[(2R)-2-hydroxycyclohexyl]-2-oxo-4-phenyl-5-(piperazine-1-carbonyl)imidazol-1-yl]ethyl]benzamide

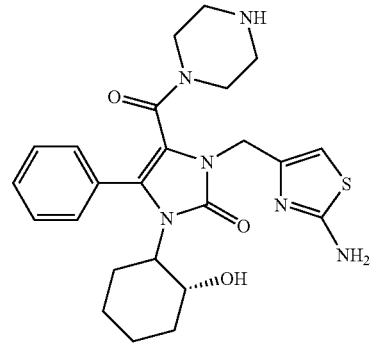

1-[(2-amino1,3-thiazol-4-yl)methyl]-3-[(2R)-2-hydroxycyclohexyl]-4-phenyl-5-(piperazine-1-carbonyl)imidazol-2-one

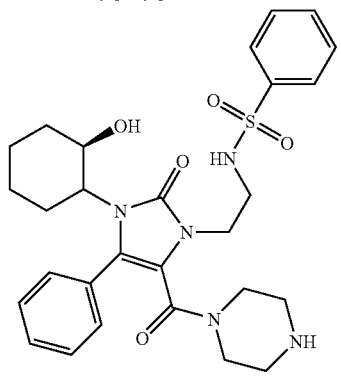

N-[2-[3-[(2R)-2-hydroxycyclohexyl]-2-oxo-4-phenyl-5-(piperazine-1-carbonyl)imidazol-1-yl]ethyl]benzenesulfonamide

379

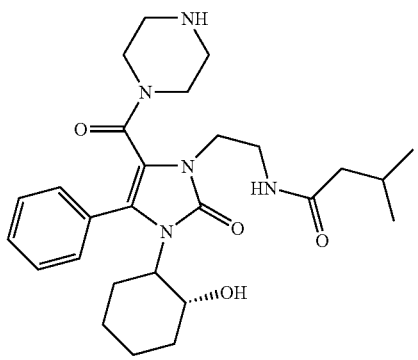

N-[2-[3-[(2R)-2-hydroxycyclohexyl]-2-oxo-4-phenyl-5-(piperazine-1-carbonyl)imidazol-1-yl]ethyl]-3-methyl-butanamide

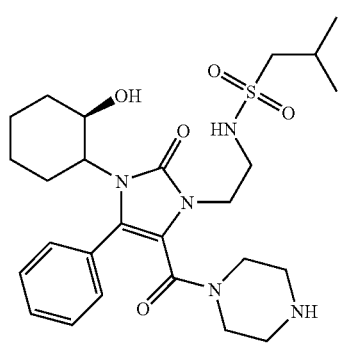

N-[2-[3-[(2R)-2-hydroxycyclohexyl]-2-oxo-4-phenyl-5-(piperazine-1-carbonyl)imidazol-1-yl]ethyl]-2-methyl-propane-1-sulfonamide

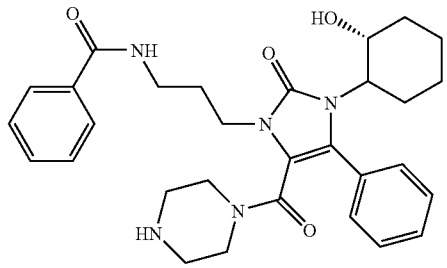

N-[3-[3-[(2R)-2-hydroxycyclohexyl]-2-oxo-4-phenyl-5-(piperazine-1-carbonyl)imidazol-1-yl]propyl]benzamide

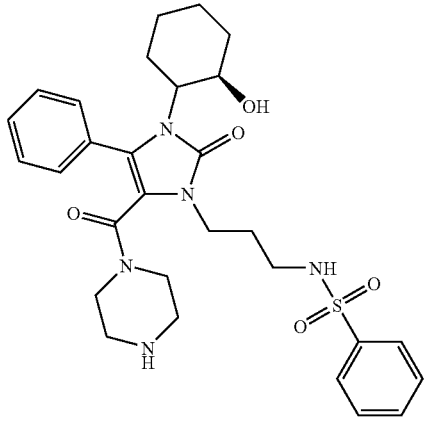

N-[3-[3-[(2R)-2-hydroxycyclohexyl]-2-oxo-4-phenyl-5-(piperazine-1-carbonyl)imidazol-1-yl]propyl]benzenesulfonamide

380

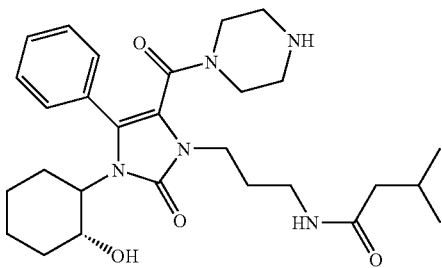

N-[3-[3-[(2R)-2-hydroxycyclohexyl]-2-oxo-4-phenyl-5-(piperazine-1-carbonyl)imidazol-1-yl]propyl]-3-methyl-butanamide

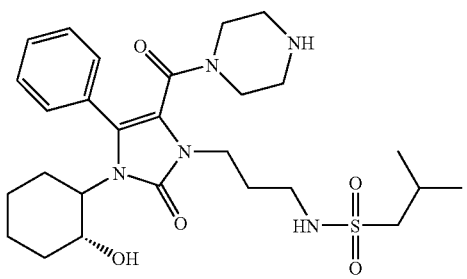

N-[3-[3-[(2R)-2-hydroxycyclohexyl]-2-oxo-4-phenyl-5-(piperazine-1-carbonyl)imidazol-1-yl]propyl]-2-methyl-propane-1-sulfonamide

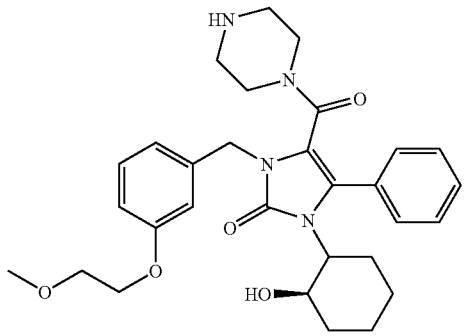

1-[(2R)-2-hydroxycyclohexyl]-3-[[3-(2-methoxyethoxy)phenyl]methyl]-5-phenyl-4-(piperazine-1-carbonyl)imidazol-2-one

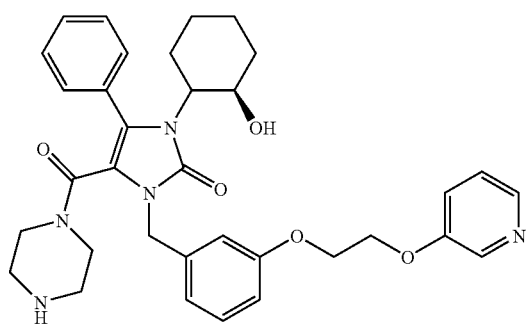

1-[(2R)-2-hydroxycyclohexyl]-5-phenyl-4-(piperazine-1-carbonyl)-3-[[3-(2-pyridin-3-yloxyethoxy)phenyl]methyl]imidazol-2-one

381

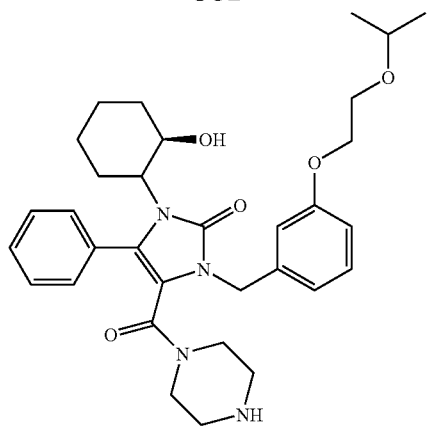

1-[(2R)-2-hydroxycyclohexyl]-5-phenyl-4-
(piperazine-1-carbonyl)-3-[[3-(2-propan-2-
yloxyethoxy)phenyl]methyl]imidazol-2-one

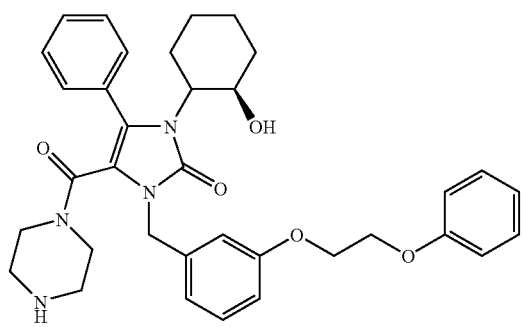

1-[(2R)-2-hydroxycyclohexyl]-3-[[3-(2-
phenoxyethoxy)phenyl]methyl]-5-phenyl-4-
(piperazine-1-carbonyl)imidazol-2-one

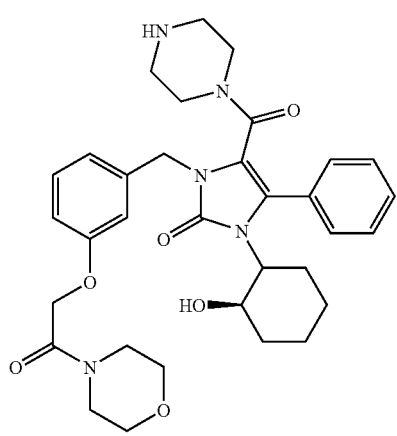

1-[(2R)-2-hydroxycyclohexyl]-3-[[3-(2-
morpholin-4-yl-2-oxo-ethoxy)phenyl]methyl]-5-
phenyl-4-(piperazine-1-carbonyl)imidazol-2-on

382

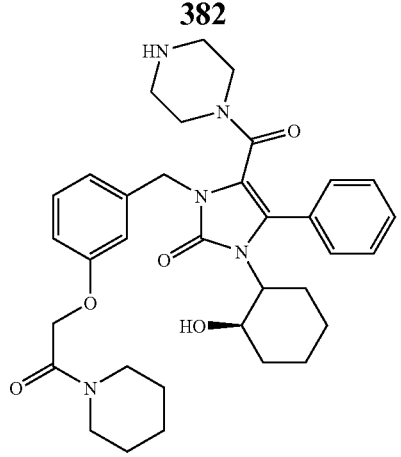

1-[(2R)-2-hydroxycyclohexyl]-3-[[3-[2-oxo-2-(1-
piperidyl)ethoxy]phenyl]methyl]-5-phenyl-4-
(piperazine-1-carbonyl)imidazol-2-one

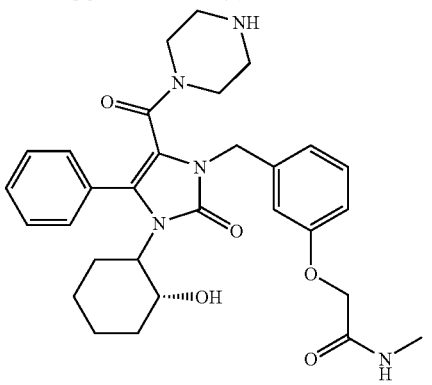

2-[3-[[3-[(2R)-2-hydroxycyclohexyl]-2-oxo-4-
phenyl-5-(piperazine-1-carbonyl)imidazol-1-
yl]methyl]phenoxy]-N-methyl-acetamide

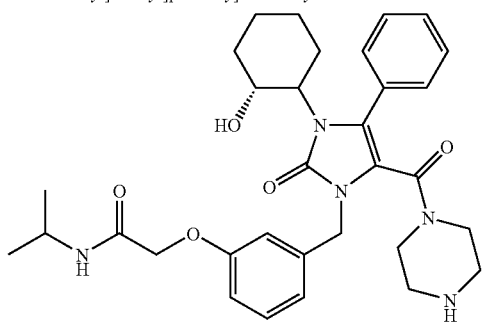

2-[3-[[3-[(2R)-2-hydroxycyclohexyl]-2-oxo-4-
phenyl-5-(piperazine-1-carbonyl)imidazol-1-
yl]methyl]phenoxy]-N-propan-2-yl-acetamide

BIOLOGICAL EXAMPLES

Example A

Expression of Preprorenin and Purification of Prorenin

The sequence of human wild-type renin is known in the art; see, Imai, T. et al., *Proc. Natl. Acad. Sci. USA* 1983, 80, 7105-7409. It is noted that the fragment of the renin protein useful for the assay comprises amino acid residues 67-406 of human renin (active Renin). To prepare active Renin, a fragment longer than active renin (a preprorenin) (e.g., comprising residues 1-406), may be expressed and from which a prorenin (e.g., comprising residues 23-406) may be recovered. The prorenin may later be cleaved to obtain active Renin.

Expression of human preprorenin (residues 1-406) can be conducted using a FreeStyle 293 Expression System (Invitrogen Corp.), wherein the plasmid DNA for human prorenin expression (pcDNA3.1(+)/hREN) is used to conduct transient expression in FreeStyle 293-F cells. After transfection of the plasmid DNA, the cells are subjected to shaking at 37° C., 8% $CO_2$ and 125 rpm for 3 days.

The prorenin protein is then accumulated and purified by salting out. Powdered ammonium sulfate is added to the culture medium and dissolved to make a 40% saturation of the salt. The resulting precipitate can be collected by centrifugation and discarded. Ammonium sulfate is added to the remaining solution and dissolved to make a 80% saturation of salt. The resulting precipitate can be collected by, for example, centrifugation. The prorenin protein is recovered by dissolving the precipitate in buffer.

The concentrated liquid is subjected to gel filtration chromatography using, for example, HiLoad 16/60 Superdex 200 pg (Amersham Biosciences, Inc.) equilibrated with 20 mM Tris-hydrochloric acid (pH 8.0) containing 0.15 M sodium chloride, at a flow rate of 1.4 mL/min, to obtain 3.6 mg of purified prorenin (residues 24-406).

Example B

Purification of Active Renin

To 3.6 mg of prorenin (residues 24-406, as prepared in Example A) dissolved in 5.2 mL of 0.1 M Tris-hydrochloric acid (pH 8.0), is added 12 μg of trypsin (Roche Diagnostics Corp.), and the mixture is allowed to react at 28° C. for 55 minutes to carry out activation of Renin. After the reaction, 0.4 mL of immobilized trypsin inhibitor (Pierce Biotechnology, Inc.) is added to remove the trypsin used in the activation, by adsorption. The reaction liquid containing the active renin is concentrated using Vivaspin 20 (molecular weight of the fraction 10,000; Vivascience, Inc.), and diluted with 20 mM Tris-hydrochloric acid (pH 8.0). The diluted liquid is fed to a TSKgel DEAE-5 PW column (7.5 mm I.D.×75 mm, Tosoh Corp.) equilibrated with 20 mM Tris-hydrochloric acid (pH 8.0) at a flow rate of 1 mL/min to adsorb the active renin (residues 67-406). The column is washed with the buffer solution used for the equilibration, and then elution is carried out by means of a linear concentration gradient of sodium chloride from 0 M to 0.3 M, to obtain 1.5 mg of purified active renin (residues 67-406).

Example C

Establishment of Renin Expressing Vector

A plasmid DNA to express human renin in HEK293 cells can be prepared as follows. PCR is carried out using human renal cDNA (Clontech Laboratories, Inc., Marathon Ready cDNA) as the template and using two synthetic DNAs (5'-AAGCTTATGGATGGATGGAGA-3' (SEQ ID NO: 1) and 5'-GGATCCTCAGCGGGCCAAGGC-3' (SEQ ID NO: 2)), and the obtained fragment is cloned using TOPO TA Cloning Kit (Invitrogen Corp.). The obtained fragment is subcloned into pcDNA3.1(+) that has been cleaved by HindIII and BamHI, to obtain a plasmid DNA for human preprorenin expression (pcDNA3.1(+)/hREN).

Example D

Assaying the In Vitro Enzymatic Activity of Renin Inhibitors

Solutions of test compounds in varying concentrations (≦2 mM final concentration) are prepared in dimethyl sulfoxide (DMSO) and then diluted into assay buffer comprising 50 mM Hepes, 1 mM EDTA, 1 mM DTT, 0.1 mg/mL BSA, 0.01% Brij35, pH 7.4. Alternatively, the assay can be performed with a high BSA concentration, wherein the buffer contains an additional 2% BSA.

Recombinant human renin (3 nM final concentration) is added to the dilutions and pre-incubated with the compounds for 10 minutes at 37° C. As described in Examples A-C above, human renin can be obtained by expressing preprorenin (residue 1-406) in mammalian cells, treating the prorenin (residues 24-406) contained in the culture supernatant with trypsin, and isolate the active form (residues 67-406). After pre-incubation, the reaction is initiated with 1 μM of substrate QXL520-γ-Abu-Ile-His-Pro-Phe-His-Leu-Val-Ile-His-Thr-Lys (HiLyteFluo488)-Arg-OH (Anaspec, San Jose, Calif.). The final DMSO in the assay is 5%. The total volume of the reaction mixture is 20 μL, which can be placed on Greiner 384-well small volume plates.

Renin activity may be determined via fluorescence (excitation λ=485 nm; emission λ=538 nm), e.g., on a Molecular Devices SPECTROmax GEMINI XPS. The fluorescence intensity is determined upon the addition of substrate and determined again after incubation at 37° C. for one hour. The fluorescence intensity of a blank (no inhibition) using vehicle alone is also determined. Renin activity is linearly proportional to the change in fluorescence observed (final–initial).

The percent inhibition of renin at a given compound concentration is defined as:

$$100\% \times [1-(F_{compound}/F_{blank})]$$

where $F_{compound}$ is the observed fluorescence at a given concentration of test compound and $F_{blank}$ is the observed fluorescence in the presence of vehicle alone.

The $pIC_{50}$ value (negative log of the molar concentration of the compound that produces 50% inhibition) of a test compound is calculated by non-linear least squares curve fitting of the equation:

$$\text{Percent Inhibition} = 100\%/(1+(10^{-pIC50}/10^{\log[I]}))$$

to percent inhibition versus compound concentration. The 50% inhibitory concentration ($IC_{50}$) of a test compound is calculated by raising 10 to the negative $pIC_{50}$ ($10^{-pIC50}$).

$IC_{50}$ values for selected compounds of the present invention are given in Table 1.

TABLE 1

$IC_{50}$ of Exemplified Compounds Against Renin

| EXAMPLE | $IC_{50}$ (nM) |
| --- | --- |
| 13 | >1,000 |
| 14 | <100 |
| 17C | 500-1,000 |
| 17D | >1,000 |
| 17E | 100-500 |
| 17F | 100-500 |
| 17H | 100-500 |
| 17J | 100-500 |
| 18 | >1,000 |
| 19 | >1,000 |
| 20 | >1,000 |

TABLE 1-continued

IC$_{50}$ of Exemplified Compounds Against Renin

| EXAMPLE | IC$_{50}$ (nM) |
|---|---|
| 21 | >1,000 |
| 22 | 500-1,000 |
| 23 | >1,000 |
| 24 | >1,000 |
| 25 | >1,000 |
| 26 | >1,000 |
| 27 | 100-500 |
| 28 | >1,000 |
| 29 | 500-1,000 |
| 32 | >1,000 |
| 33 | >1,000 |
| 34 | >1,000 |
| 35 | 500-1,000 |
| 36 | >1,000 |
| 37 | >1,000 |
| 38 | >1,000 |
| 39 | >1,000 |
| 40 | >1,000 |
| 41 | >1,000 |
| 42 | >1,000 |
| 43 | >1,000 |
| 44 | >1,000 |
| 45 | 100-500 |
| 46 | >1,000 |
| 47 | >1,000 |
| 48 | >1,000 |
| 49 | >1,000 |
| 50 | 500-1,000 |
| 51 | 100-500 |
| 52 | 100-500 |
| 53 | >1,000 |
| 54 | >1,000 |
| 55 | 100-500 |
| 56 | 100-500 |
| 57 | >1,000 |
| 58 | >1,000 |
| 59 | >1,000 |
| 60 | >1,000 |
| 61 | >1,000 |
| 62 | >1,000 |
| 63 | >1,000 |
| 64 | <100 |
| 65 | <100 |
| 66 | <100 |
| 67 | 100-500 |
| 68 | >1,000 |
| 69 | 100-500 |
| 70 | <100 |
| 71 | 100-500 |
| 72 | 100-500 |
| 73 | 100-500 |
| 74 | <100 |
| 75 | <100 |
| 76 | <100 |
| 77 | <100 |
| 78 | >1,000 |
| 79 | 500-1,000 |
| 80 | >1,000 |
| 81 | >1,000 |
| 82 | >1,000 |
| 83 | 100-500 |
| 84 | 100-500 |
| 85 | >1,000 |
| 86 | 100-500 |
| 87 | 100-500 |
| 88 | <100 |
| 89 | >1,000 |
| 90 | 500-1,000 |
| 91 | 100-500 |
| 92 | >1,000 |
| 93 | >1,000 |
| 94 | >1,000 |
| 95 | >1,000 |
| 96 | 500-1,000 |
| 97 | >1,000 |
| 98 | 500-1,000 |
| 99 | >1,000 |
| 100 | 500-1,000 |
| 101 | >1,000 |
| 102 | 100-500 |
| 103 | 100-500 |
| 104 | 500-1,000 |
| 105 | >1,000 |
| 106 | 100-500 |
| 107 | 500-1,000 |
| 108 | <100 |
| 109 | <100 |
| 110 | <100 |
| 111 | <100 |
| 112 | <100 |
| 113 | <100 |
| 114 | <100 |
| 115 | 500-1,000 |
| 116 | <100 |
| 117 | <100 |
| 118 | <100 |
| 119 | <100 |
| 120 | 100-500 |
| 121 | 100-500 |
| 122 | <100 |
| 123 | 100-500 |
| 124 | <100 |
| 125 | <100 |
| 126 | <100 |
| 127 | 100-500 |
| 128 | <100 |
| 129 | <100 |
| 130 | <100 |
| 131 | <100 |
| 132 | <100 |
| 133 | >1,000 |
| 134 | 500-1,000 |
| 135 | <100 |
| 136 | <100 |
| 137 | <100 |
| 138 | 100-500 |
| 139 | <100 |
| 140 | <100 |
| 141 | >1,000 |
| 142 | 100-500 |
| 143 | 100-500 |
| 144 | 500-1,000 |
| 145 | >1,000 |
| 146 | 100-500 |
| 147 | >1,000 |
| 148 | >1,000 |
| 149 | 100-500 |
| 150 | >1,000 |
| 151 | 100-500 |
| 152 | 500-1,000 |
| 153 | >1,000 |
| 154 | >1,000 |
| 155 | >1,000 |
| 156 | >1,000 |
| 157 | >1,000 |
| 158 | >1,000 |
| 159 | >1,000 |
| 160 | >1,000 |
| 161 | 100-500 |

TABLE 1-continued

IC$_{50}$ of Exemplified Compounds Against Renin

| EXAMPLE | IC$_{50}$ (nM) |
|---|---|
| 162 | 100-500 |
| 163 | >1,000 |
| 164 | 500-1,000 |
| 165 | >1,000 |
| 166 | 500-1,000 |
| 167 | >1,000 |
| 168 | 100-500 |
| 169 | >1,000 |
| 170 | >1,000 |
| 171 | >1,000 |
| 172 | >1,000 |
| 173 | >1,000 |
| 174 | >1,000 |
| 175 | 100-500 |
| 176 | >1,000 |
| 177 | 500-1,000 |
| 178 | >1,000 |
| 179 | 500-1,000 |
| 180 | 100-500 |
| 181 | >1,000 |
| 182 | 100-500 |
| 183 | >1,000 |
| 184 | >1,000 |
| 185 | >1,000 |
| 186 | 100-500 |
| 187 | >1,000 |
| 188 | 100-500 |
| 189 | >1,000 |
| 190 | 500-1,000 |
| 191 | 100-500 |
| 192 | >1,000 |
| 193 | >1,000 |
| 194 | <100 |
| 195 | 500-1,000 |
| 196 | >1,000 |
| 197 | >1,000 |
| 198 | 100-500 |
| 199 | 500-1,000 |
| 200 | 500-1,000 |
| 202 | 500-1,000 |
| 203 | 500-1,000 |
| 204 | 500-1,000 |
| 205 | >1,000 |
| 206 | 500-1,000 |
| 207 | >1,000 |
| 208 | 500-1,000 |
| 209 | >1,000 |
| 210 | >1,000 |
| 211 | 100-500 |
| 212 | 500-1,000 |
| 213 | 100-500 |
| 214 | 500-1,000 |
| 215 | 100-500 |
| 216 | >1,000 |
| 217 | <100 |
| 218 | 100-500 |
| 219 | 100-500 |
| 220 | <100 |
| 221 | 100-500 |
| 222 | 100-500 |
| 223 | 500-1,000 |
| 224 | 100-500 |
| 225 | 100-500 |
| 226 | 100-500 |
| 227 | >1,000 |
| 228 | 500-1,000 |
| 229 | 500-1,000 |
| 230 | >1,000 |
| 231 | >1,000 |
| 232 | 500-1,000 |
| 233 | 500-1,000 |
| 234 | 500-1,000 |
| 235 | 500-1,000 |
| 236 | >1,000 |
| 237 | >1,000 |
| 238 | >1,000 |
| 239 | >1,000 |
| 240 | >1,000 |
| 241 | >1,000 |
| 242 | >1,000 |
| 243 | >1,000 |
| 244 | >1,000 |
| 245 | >1,000 |
| 246 | >1,000 |
| 247 | >1,000 |
| 248 | >1,000 |
| 249 | >1,000 |
| 250 | >1,000 |
| 251 | >1,000 |
| 252 | >1,000 |
| 253 | >1,000 |
| 254 | >1,000 |
| 255 | >1,000 |

It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

What is claimed is:

1. A compound of the formula

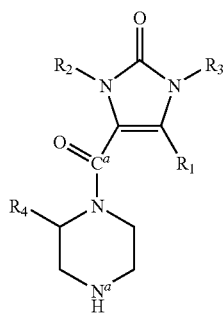

or a pharmaceutically acceptable salt thereof, wherein
- $C^a$ denotes a carbon atom;
- $N^a$ denotes a nitrogen atom;
- $R_1$ is selected from

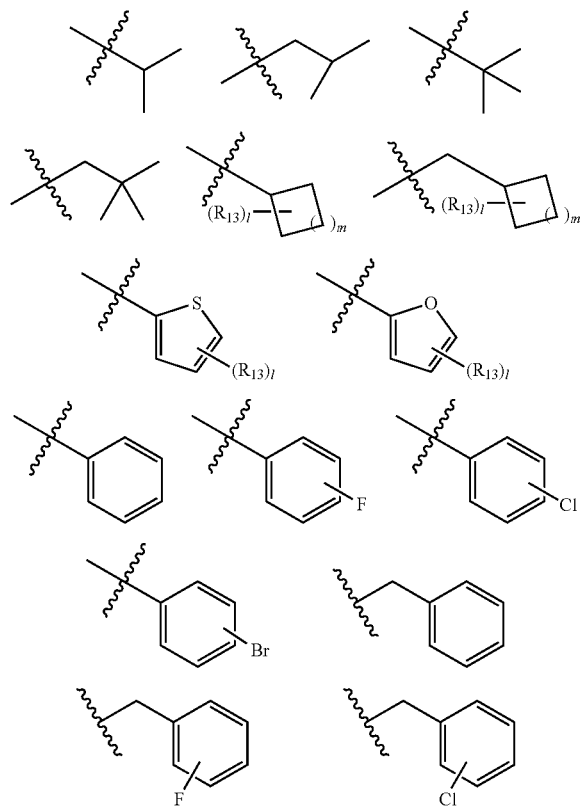

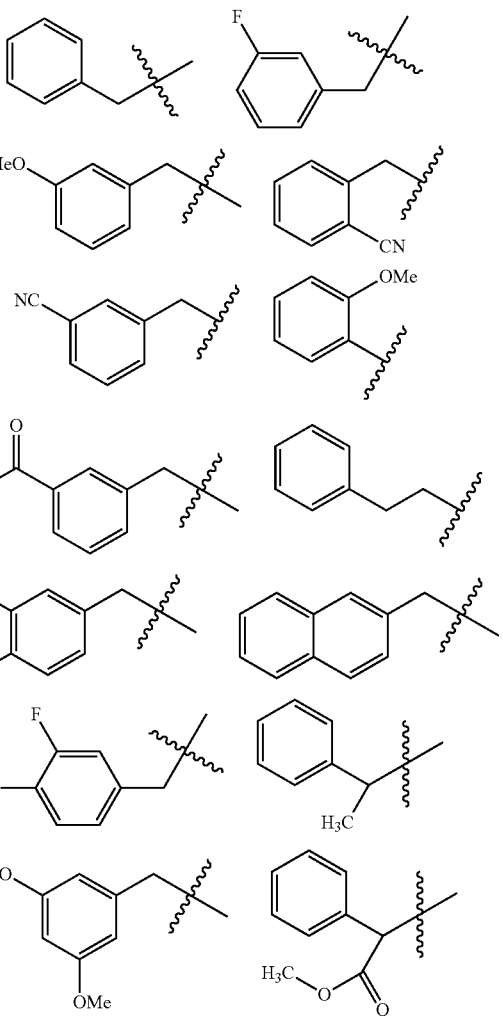

wherein
m is 0, 1, 2, 3 or 4;
l is 0, 1, 2 or 3; and
each $R_{13}$ is selected from alkyl, halo, and alkoxy;
$R_2$ is selected from methyl, isobutyl, —$CH_2C(O)NH_2$, —$CH_2CH_2OCH_3$, —$CH_2CH_2$=$CH_2$, 391
-continued
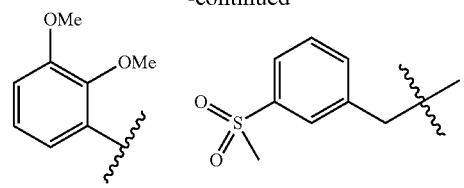
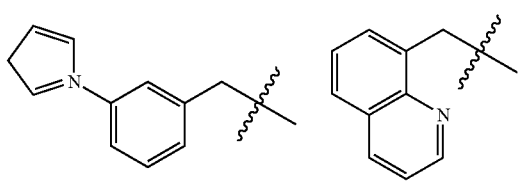
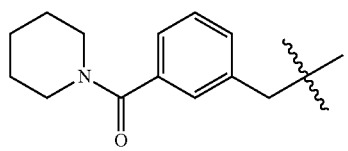
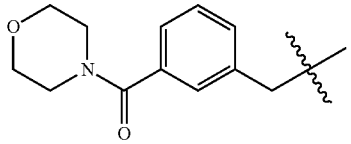
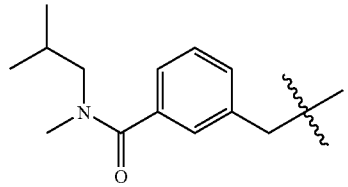
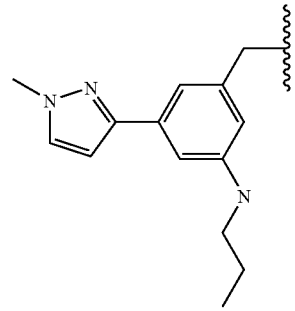
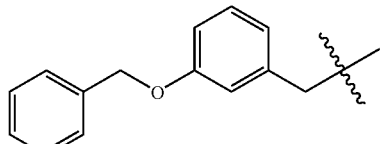
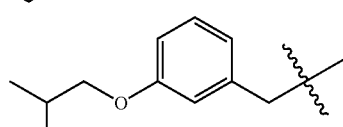
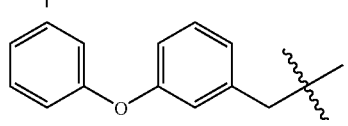
392
-continued
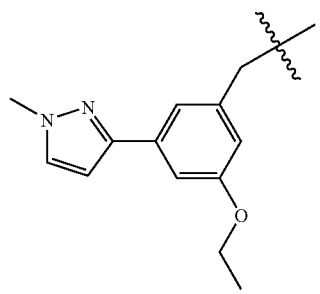
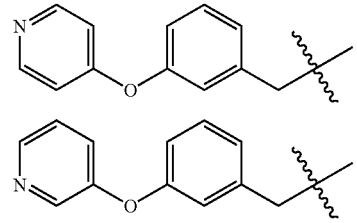
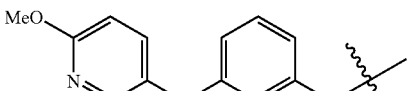
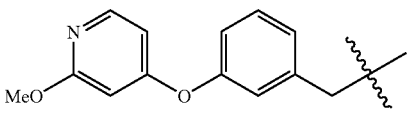
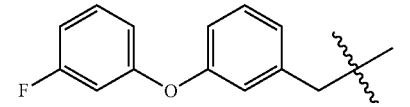
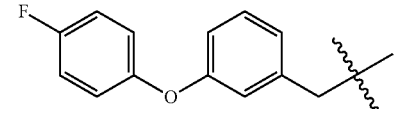
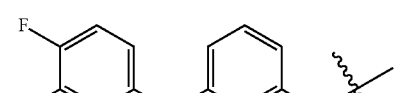
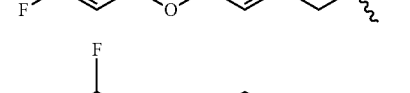
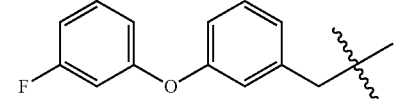
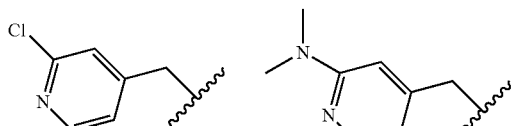
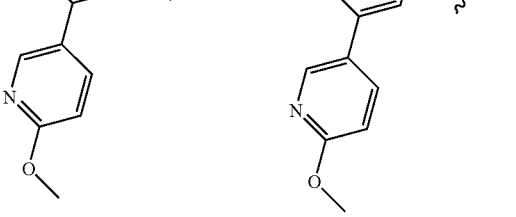

393
-continued
394
-continued
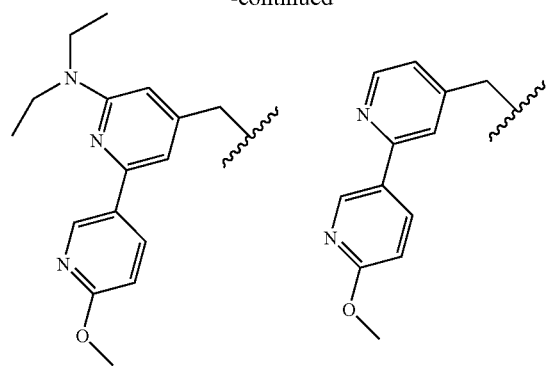
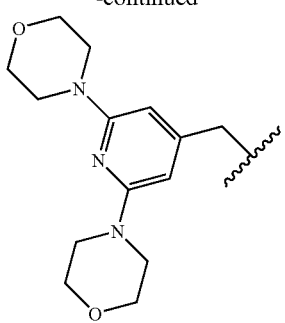
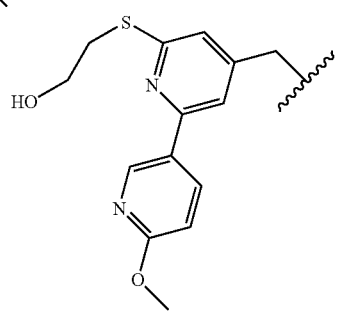
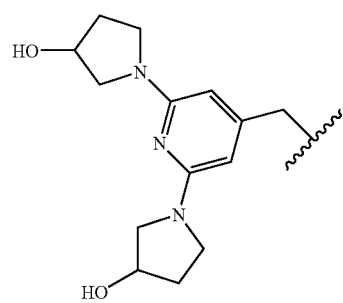
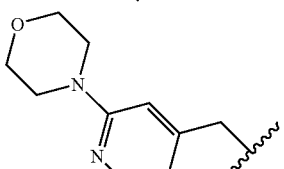
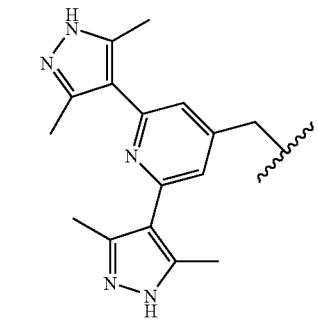
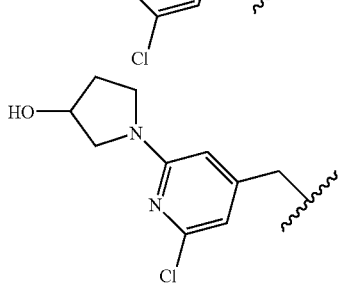
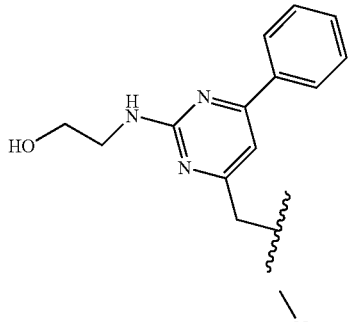
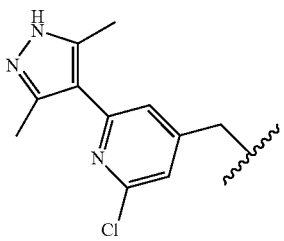
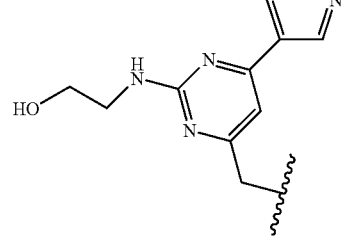
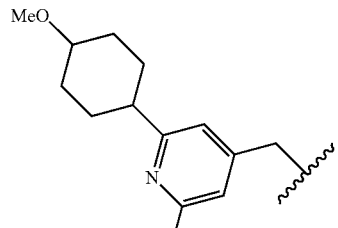

395
-continued
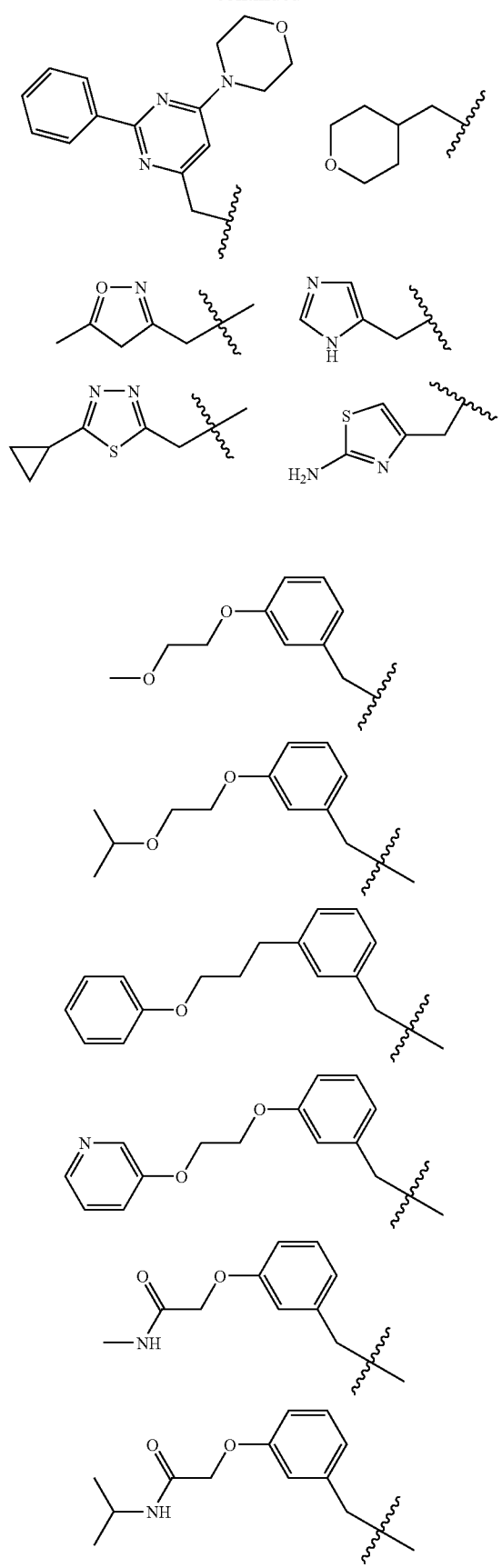
396
-continued
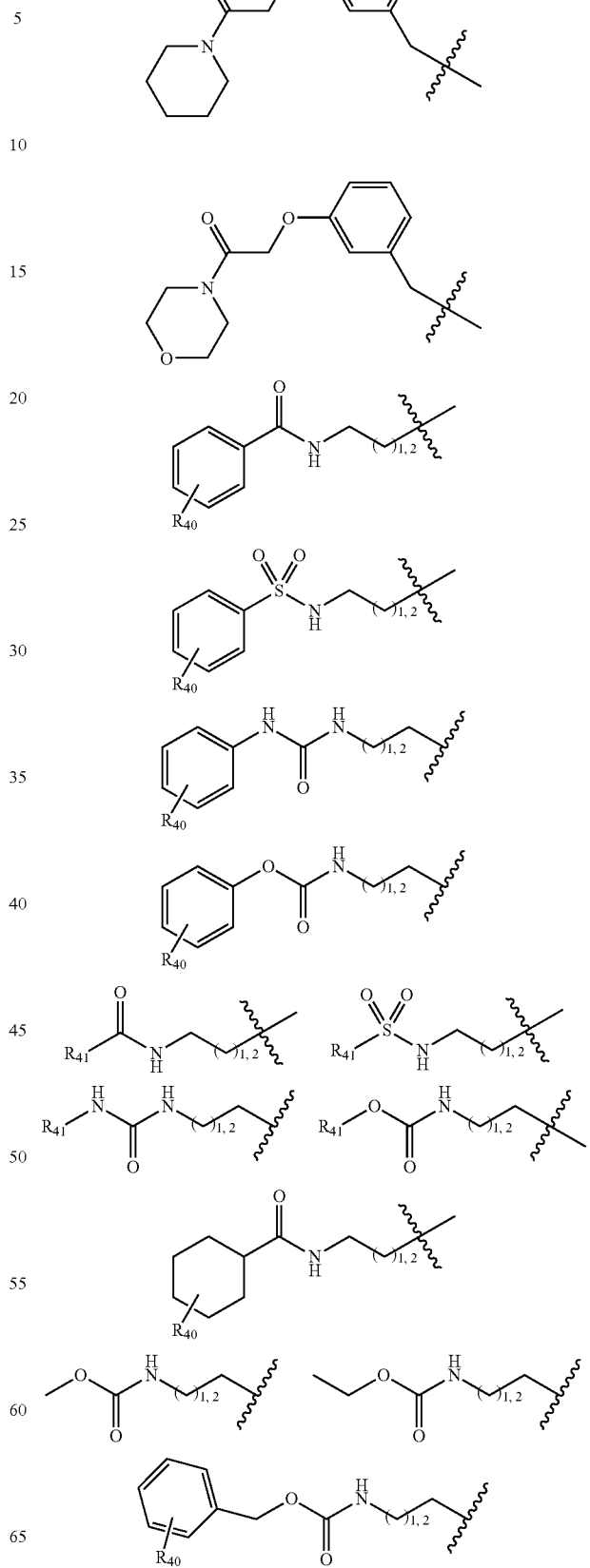

397
-continued
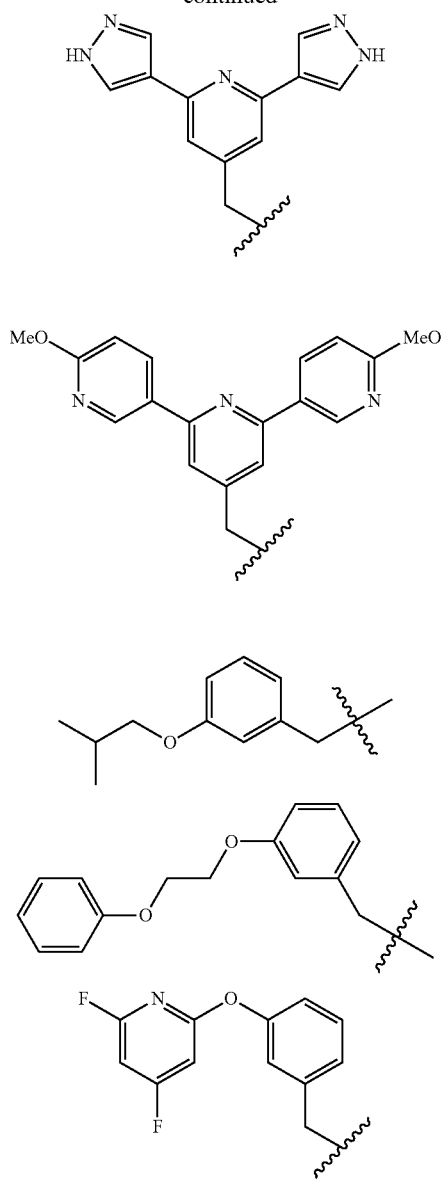
wherein
R$_{40}$ is selected from H, fluoro, chloro, methyl, and methoxy; and
R$_{41}$ is selected from isopropyl and isobutyl;
R$_3$ is selected from
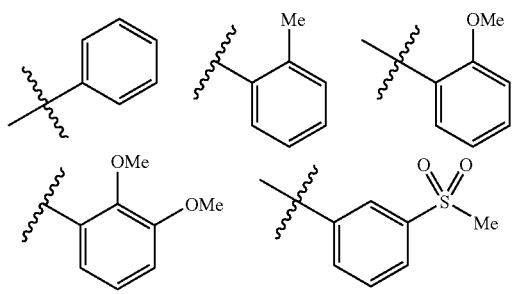
398
-continued
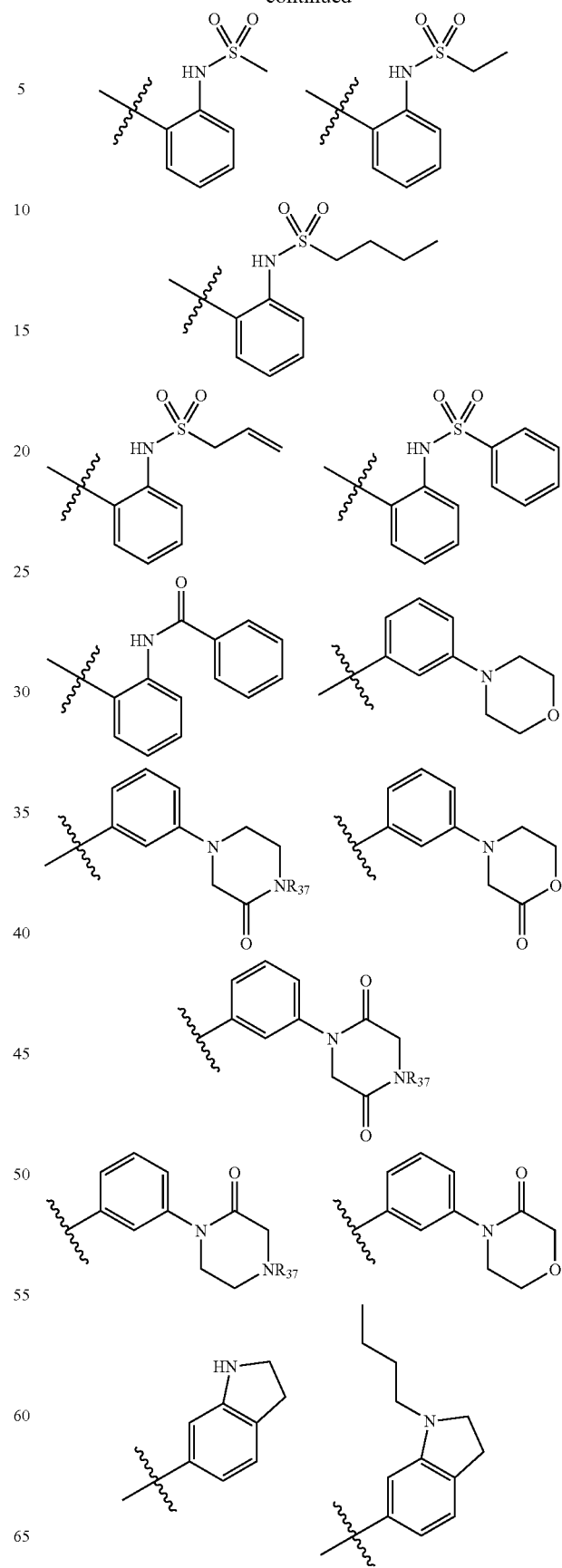

399
-continued
400
-continued
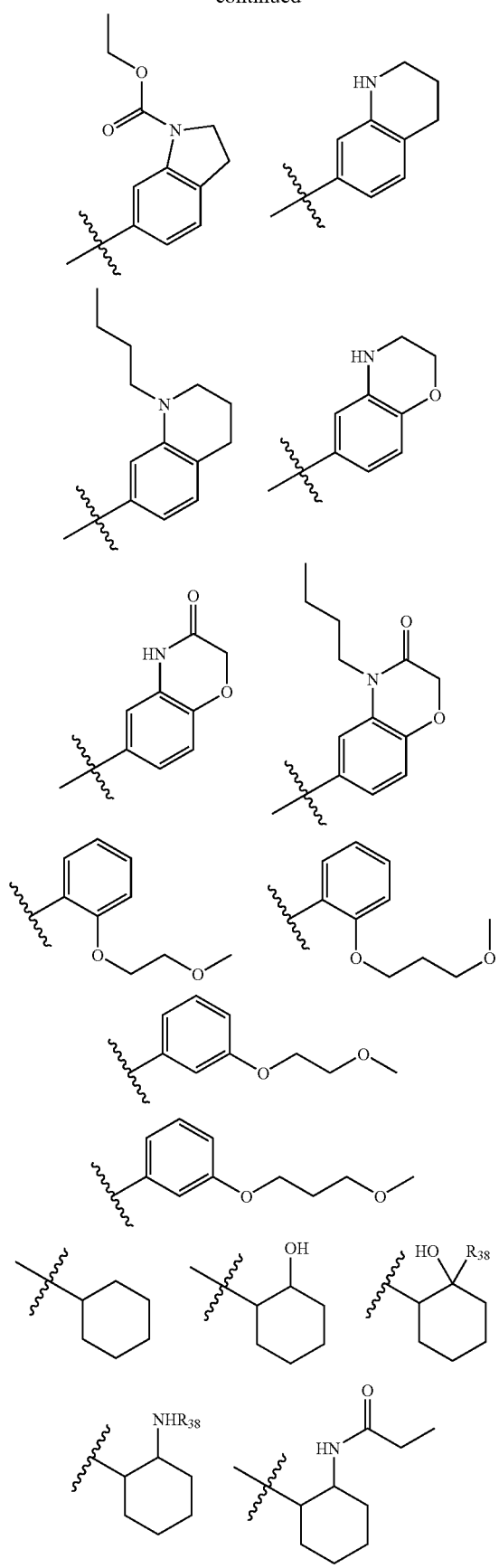
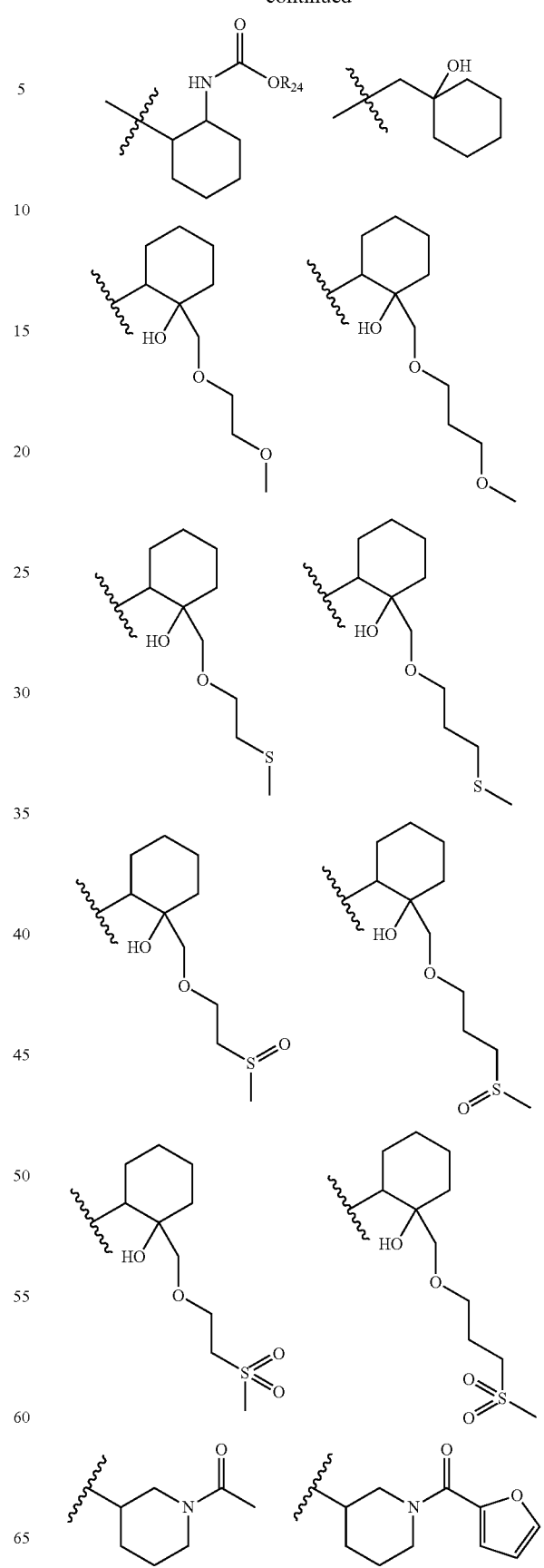

401

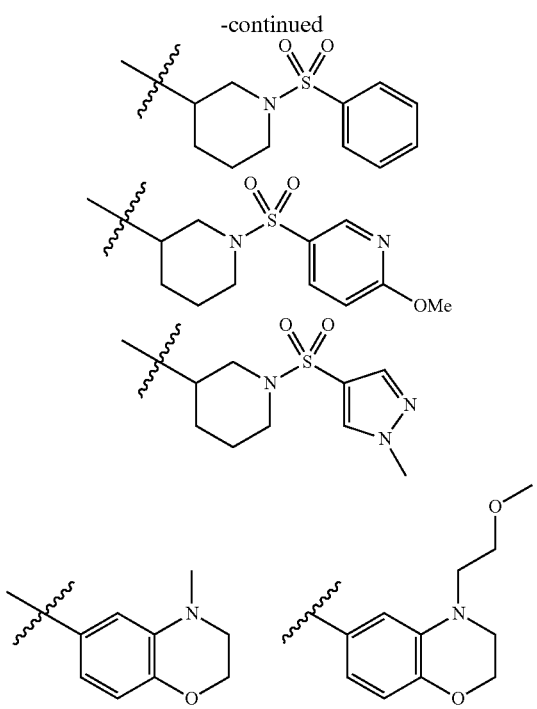

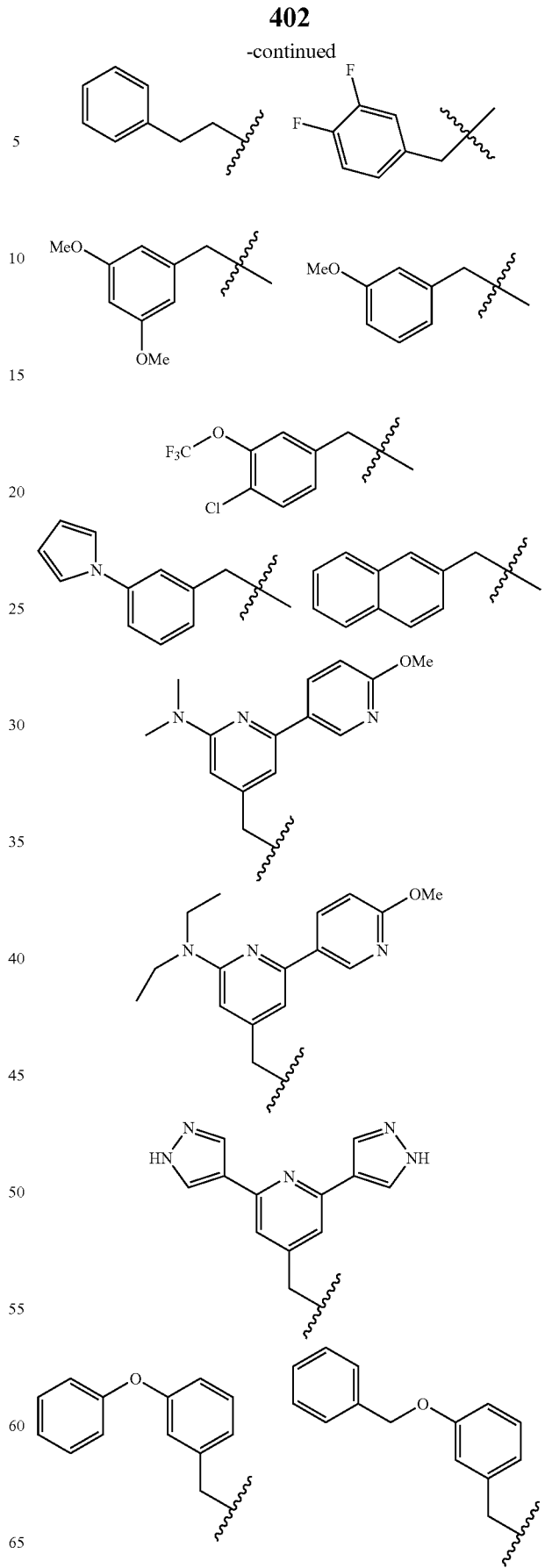

wherein
R$_{24}$ is selected from hydrogen, alkyl, aryl, and heteroaryl;
R$_{37}$ is selected from hydrogen, (C$_{1-8}$)alkyl, (C$_{1-4}$)alkoxy (C$_{1-8}$)alkyl; and
R$_{38}$ is selected from (C$_{1-8}$)alkyl, (C$_{1-4}$)alkoxy(C$_{1-8}$)alkyl, and —(C$_{1-8}$)alkyl-NHC(O)(C$_{1-4}$)alkyl;
R$_4$ is selected from hydrogen, (C$_{1-6}$)alkyl, —CH$_2$N(R$_{28}$)C(O)R$_{29}$, —(CH$_2$)$_n$OR$_{28}$,

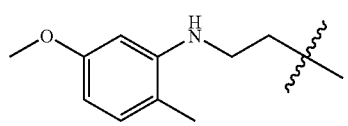

wherein
n is 1, 2, or 3;
R$_{28}$ is hydrogen; and
R$_{29}$ is phenyl.

2. The compound according to claim 1, wherein R$_1$ is a fluoro or chloro substituted phenyl or benzyl.

3. The compound according to claim 1, wherein R$_1$ is selected from the group consisting of isopropyl, cyclopropyl, and cyclopropylmethyl.

4. The compound according to claim 1, wherein R$_2$ is selected from methyl, —CH$_2$CH$_2$=CH$_2$,

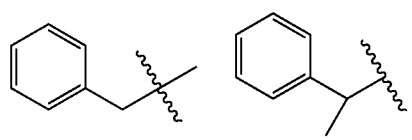

-continued
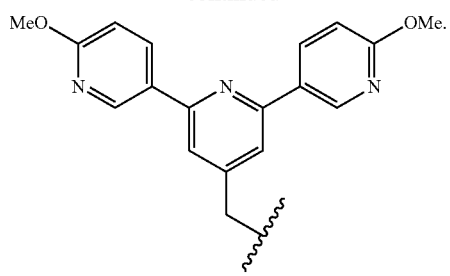
5. The compound according to claim 1, wherein $R_2$ is selected from isobutyl, —CH$_2$C(O)NH$_2$, —CH$_2$CH=CH$_2$,
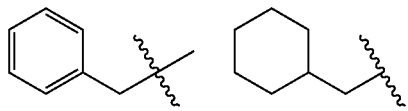
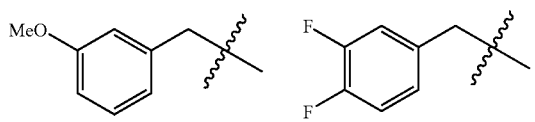
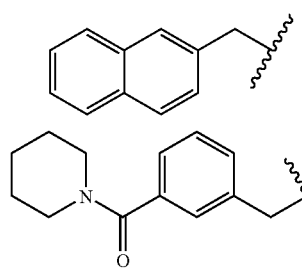
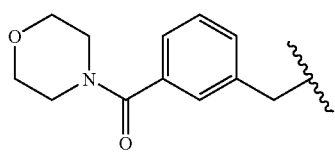
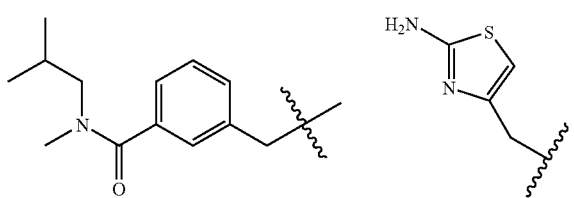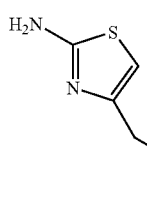
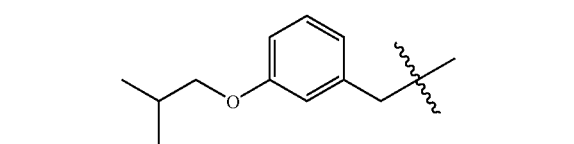
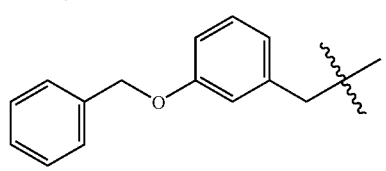
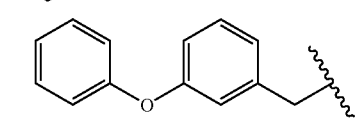
-continued
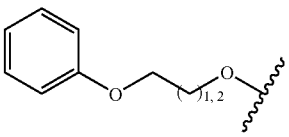
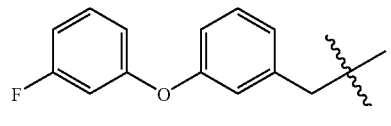
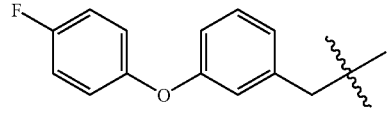
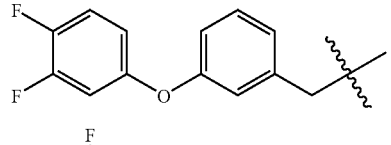
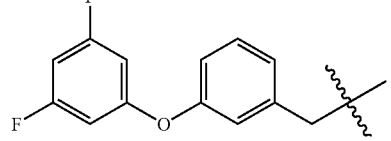
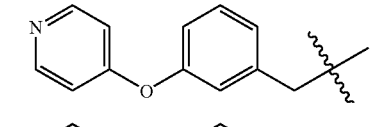
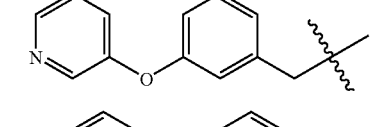
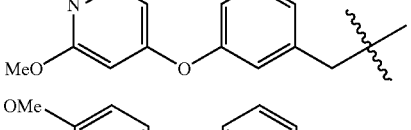
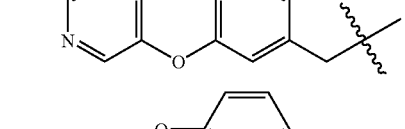
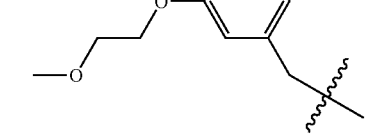
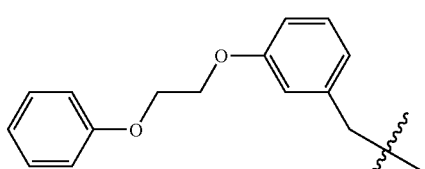
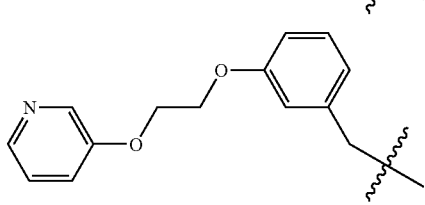

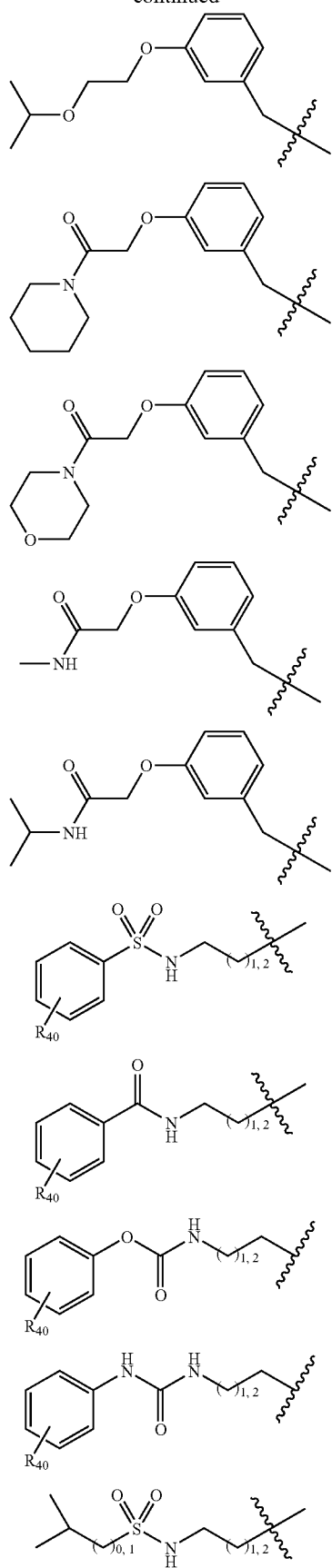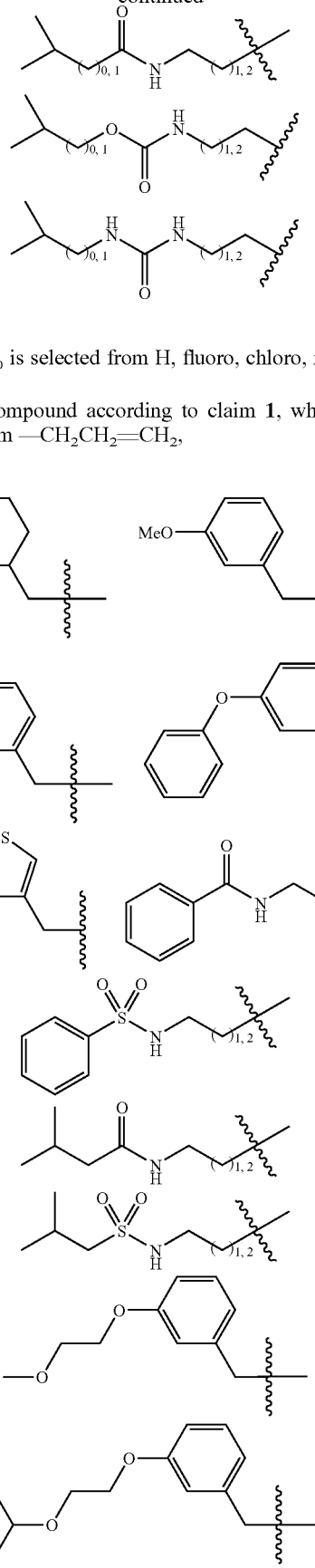
wherein $R_{40}$ is selected from H, fluoro, chloro, methyl, and methoxy.
6. The compound according to claim 1, wherein $R_2$ is selected from $-CH_2CH=CH_2$,

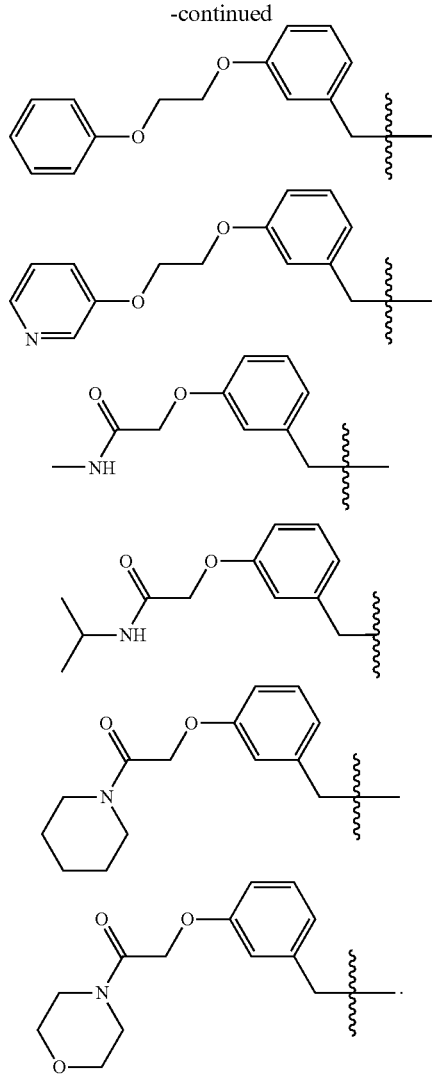
7. The compound according to claim 1, wherein $R_2$ is selected from methyl, —$CH_2C(O)NH_2$, —$CH_2CH$=$CH_2$,
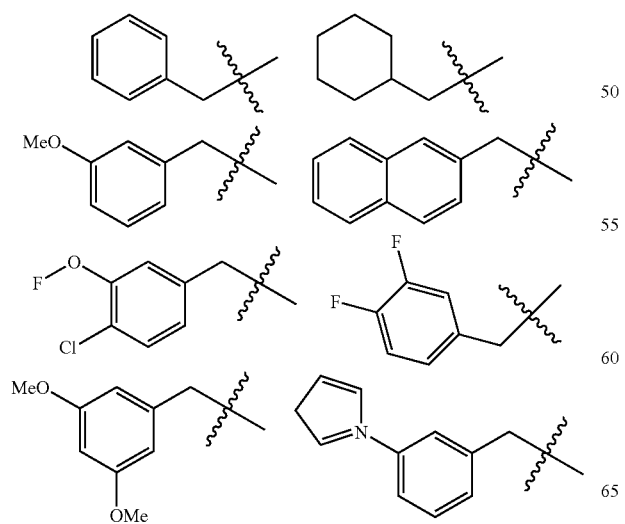
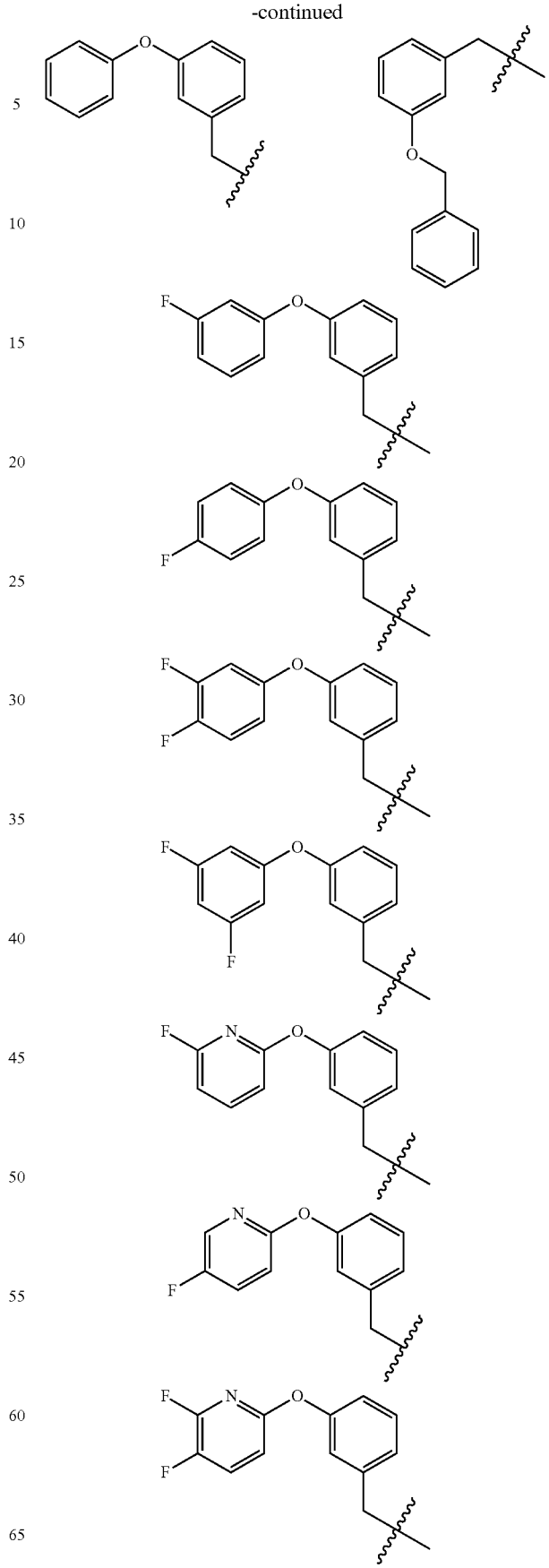

409
-continued
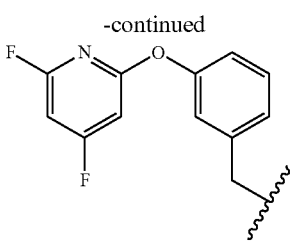
8. The compound according to claim 1, wherein $R_3$ is selected from:
410
-continued
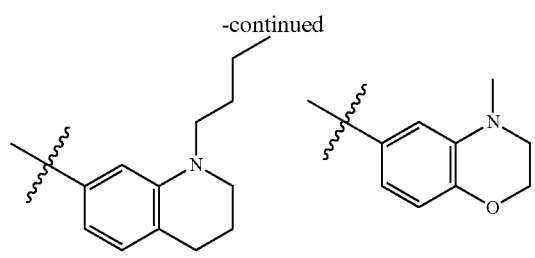
9. The compound according to claim 1, wherein $R_3$ is selected from:
10. The compound according to claim 1, wherein
$R_1$ is phenyl;
$R_3$ is selected from
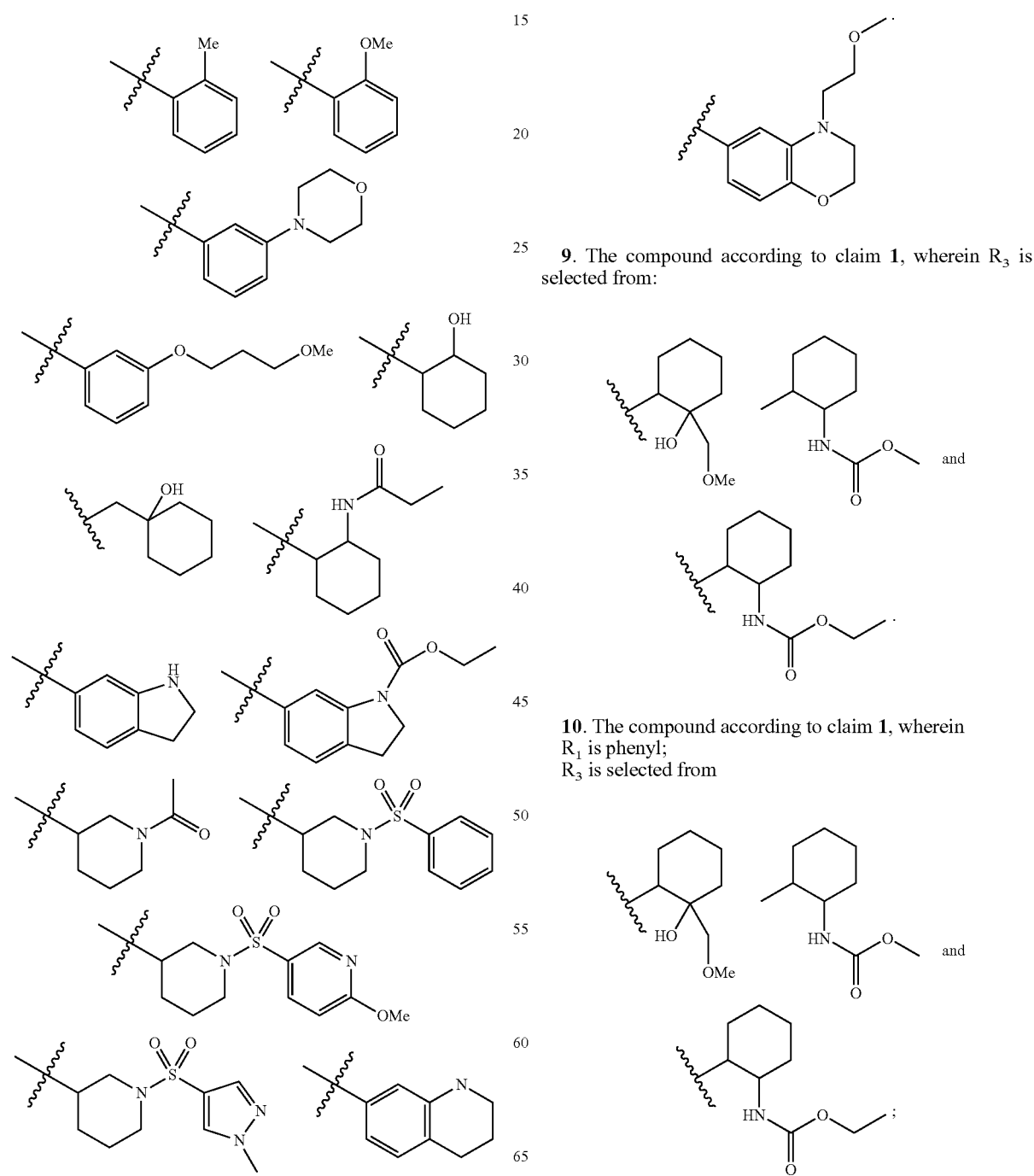

and
R4 is selected from

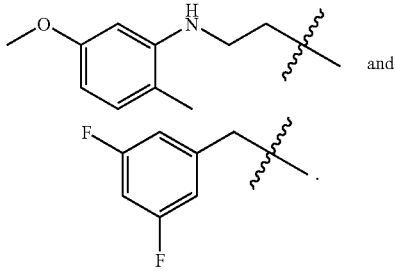

and

11. A compound selected from:
(S)-1-((2-Chloro-6-(3-hydroxypyrrolidin-1-yl)pyridin-4-yl)methyl)-3-cyclohexyl-4-phenyl-5-(piperazine-1-carbonyl)-1H-imidazol-2(3H)-one;
(R)-1-((2-Chloro-6-(3-hydroxypyrrolidin-1-yl)pyridin-4-yl)methyl)-3-cyclohexyl-4-phenyl-5-(piperazine-1-carbonyl)-1H-imidazol-2(3H)-one;
1-((2,6-bis((R)-3-Hydroxypyrrolidin-1-yl)pyridin-4-yl)methyl)-3-cyclohexyl-4-phenyl-5-(piperazine-1-carbonyl)-1H-imidazol-2(3H)-one;
1-((2,6-bis((S)-3-Hydroxypyrrolidin-1-yl)pyridin-4-yl)methyl)-3-cyclohexyl-4-phenyl-5-(piperazine-1-carbonyl)-1H-imidazol-2(3H)-one;
1-Cyclohexyl-3-((2,6-di(2methoxyl-pyridine-4-yl)pyridin-4-yl)methyl)-5-phenyl-4-(piperazine-1-carbonyl)-1H-imidazol-2(3H)-one;
1-Cyclohexyl-3-((6'-methoxy-2,3'-bipyridin-4-yl)methyl)-5-phenyl-4-(piperazine-1-carbonyl)-1H-imidazol-2(3H)-one;
1-((6-Chloro-6'-methoxy-2,3'-bipyridin-4-yl)methyl)-3-cyclohexyl-4-phenyl-5-(piperazine-1-carbonyl)-1H-imidazol-2(3H)-one;
1-Cyclohexyl-3-((6-(dimethylamino)-6'-methoxy-2,3'-bipyridin-4-yl)methyl)-5-phenyl-4-(piperazine-1-carbonyl)-1H-imidazol-2(3H)-one;
1-Cyclohexyl-3-((6-(diethylamino)-6'-methoxy-2,3'-bipyridin-4-yl)methyl)-5-phenyl-4-(piperazine-1-carbonyl)-1H-imidazol-2(3H)-one;
1,5-Diphenyl-4-(piperazine-1-carbonyl)-1H-imidazol-2(3H)-one;
5-Phenyl-4-(piperazine-1-carbonyl)-1-(pyridin-2-yl)-1H-imidazol-2(3H)-one;
4-(2-(Hydroxymethyl)piperazine-1-carbonyl)-1,5-diphenyl-1H-imidazol-2(3H)-one;
5-(3-Fluorophenyl)-1-phenyl-4-(piperazine-1-carbonyl)-1H-imidazol-2(3H)-one;
1-(3-Morpholinophenyl)-5-phenyl-4-(piperazine-1-carbonyl)-1H-imidazol-2(3H)-one;
5-Isopropyl-1-phenyl-4-(piperazine-1-carbonyl)-1H-imidazol-2(3H)-one;
5-Cyclopropyl-1-phenyl-4-(piperazine-1-carbonyl)-1H-imidazol-2(3H)-one;
5-(Cyclopropylmethyl)-1-phenyl-4-(piperazine-1-carbonyl)-1H-imidazol-2(3H)-one;
5-(2-Chlorophenyl)-1-phenyl-4-(piperazine-1-carbonyl)-1H-imidazol-2(3H)-one;
5-(3-Chlorophenyl)-1-phenyl-4-(piperazine-1-carbonyl)-1H-imidazol-2(3H)-one;
5-(4-Chlorophenyl)-1-phenyl-4-(piperazine-1-carbonyl)-1H-imidazol-2(3H)-one;
1-Cyclohexyl-5-phenyl-4-(piperazine-1-carbonyl)-1H-imidazol-2(3H)-one;
Benzyl 3-(2-oxo-5-phenyl-4-(piperazine-1-carbonyl)-2,3-dihydro-1H-imidazol-1-yl)piperidine-1-carboxylate;
1-((1R,2R)-2-(Benzyloxy)cyclohexyl)-5-phenyl-4-(piperazine-1-carbonyl)-1H-imidazol-2(3H)-one;
1-(2-(2-Methoxyethoxy)phenyl)-5-phenyl-4-(piperazine-1-carbonyl)-1H-imidazol-2(3H)-one;
1-(2-(3-Methoxypropoxy)phenyl)-5-phenyl-4-(piperazine-1-carbonyl)-1H-imidazol-2(3H)-one;
1-(3-(2-Methoxyethoxy)phenyl)-5-phenyl-4-(piperazine-1-carbonyl)-1H-imidazol-2(3H)-one;
1-(3-(3-Methoxypropoxy)phenyl)-5-phenyl-4-(piperazine-1-carbonyl)-1H-imidazol-2(3H)-one;
1-(6-(3-Methoxypropoxy)pyridin-2-yl)-5-phenyl-4-(piperazine-1-carbonyl)-1H-imidazol-2(3H)-one;
(R)-1-Cyclohexyl-4-(3-methylpiperazine-1-carbonyl)-5-phenyl-1H-imidazol-2(3H)-one;
1-Cyclohexyl-4-(3-methylpiperazine-1-carbonyl)-5-phenyl-1H-imidazol-2(3H)-one;
(S)-1-Cyclohexyl-4-(3-methylpiperazine-1-carbonyl)-5-phenyl-1H-imidazol-2(3H)-one;
1-Cyclohexyl-4-(3,5-dimethylpiperazine-1-carbonyl)-5-phenyl-1H-imidazol-2(3H)-one;
1-Cyclohexyl-4-(2,5-dimethylpiperazine-1-carbonyl)-5-phenyl-1H-imidazol-2(3H)-one;
5-(3-Chlorophenyl)-1-(3-(3-methoxypropoxy)phenyl)-4-(piperazine-1-carbonyl)-1H-imidazol-2(3H)-one;
5-(3-Chlorophenyl)-1-(3-(2-methoxyethoxy)phenyl)-4-(piperazine-1-carbonyl)-1H-imidazol-2(3H)-one;
1-(1H-Benzo[d]imidazol-2-yl)-5-phenyl-4-(piperazine-1-carbonyl)-1H-imidazol-2(3H)-one;
1-Benzyl-3,4-diphenyl-5-(piperazine-1-carbonyl)-1H-imidazol-2(3H)-one;
1-Benzyl-4-phenyl-5-(piperazine-1-carbonyl)-3-(pyridin-2-yl)-1H-imidazol-2(3H)-one;
1-((5-Methylisoxazol-3-yl)methyl)-3,4-diphenyl-5-(piperazine-1-carbonyl)-1H-imidazol-2(3H)-one;
1-((5-Cyclopropyl-1,3,4-thiadiazol-2-yl)methyl)-3,4-diphenyl-5-(piperazine-1-carbonyl)-1H-imidazol-2(3H)-one;
1-((1H-Imidazol-4-yl)methyl)-3,4-diphenyl-5-(piperazine-1-carbonyl)-1H-imidazol-2(3H)-one;
1-((2-Aminothiazol-4-yl)methyl)-3,4-diphenyl-5-(piperazine-1-carbonyl)-1H-imidazol-2(3H)-one;
1-(3-Fluorobenzyl)-3,4-diphenyl-5-(piperazine-1-carbonyl)-1H-imidazol-2(3H)-one;
1-(3,4-Difluorobenzyl)-3,4-diphenyl-5-(piperazine-1-carbonyl)-1H-imidazol-2(3H)-one;
1,5-Diphenyl-4-(piperazine-1-carbonyl)-3-((tetrahydro-2H-pyran-4-yl)methyl)-1H-imidazol-2(3H)-one;
1-Methyl-3,4-diphenyl-5-(piperazine-1-carbonyl)-1H-imidazol-2(3H)-one;
(R)-4-(2-Benzylpiperazine-1-carbonyl)-3-methyl-1-(3-morpholinophenyl)-5-phenyl-1H-imidazol-2(3H)-one;
1-Benzyl-3-(3-morpholinophenyl)-4-phenyl-5-(piperazine-1-carbonyl)-1H-imidazol-2(3H)-one;
1-(3-(Morpholine-4-carbonyl)benzyl)-3-(3-morpholinophenyl)-4-phenyl-5-(piperazine-1-carbonyl)-1H-imidazol-2(3H)-one;
1-(3-Morpholinophenyl)-5-phenyl-4-(piperazine-1-carbonyl)-3-(3-(piperidine-1-carbonyl)benzyl)-1H-imidazol-2(3H)-one;
2-(3-((3-(3-Morpholinophenyl)-2-oxo-4-phenyl-5-(piperazine-1-carbonyl)-2,3-dihydro-1H-imidazol-1-yl)methyl)phenoxy)acetic acid;

1-Cyclohexyl-3-methyl-5-phenyl-4-(piperazine-1-carbonyl)-1H-imidazol-2(3H)-one;
1-Allyl-3-cyclohexyl-4-phenyl-5-(piperazine-1-carbonyl)-1H-imidazol-2(3H)-one;
2-(3-Cyclohexyl-2-oxo-4-phenyl-5-(piperazine-1-carbonyl)-2,3-dihydro-1H-imidazol-1-yl)acetamide;
(R)-1-Allyl-5-(2-benzylpiperazine-1-carbonyl)-3-cyclohexyl-4-phenyl-1H-imidazol-2(3H)-one;
(R)-4-(2-Benzylpiperazine-1-carbonyl)-1-cyclohexyl-3-methyl-5-phenyl-1H-imidazol-2(3H)-one;
(R)-4-(2-Benzylpiperazine-1-carbonyl)-1-cyclohexyl-3-(2-methoxyethyl)-5-phenyl-1H-imidazol-2(3H)-one;
(R)-2-(5-(2-Benzylpiperazine-1-carbonyl)-3-cyclohexyl-2-oxo-4-phenyl-2,3-dihydro-1H-imidazol-1-yl)acetamide;
Methyl 2-(3-cyclohexyl-2-oxo-4-phenyl-5-(piperazine-1-carbonyl)-2,3-dihydro-1H-imidazol-1-yl)-2-phenylacetate;
1-Cyclohexyl-5-phenyl-3-(1-phenylethyl)-4-(piperazine-1-carbonyl)-1H-imidazol-2(3H)-one;
(R)-4-(2-Benzylpiperazine-1-carbonyl)-1-cyclohexyl-3-methyl-5-phenyl-1H-imidazol-2(3H)-one;
1-Cyclohexyl-3-phenethyl-5-phenyl-4-(piperazine-1-carbonyl)-1H-imidazol-2(3H)-one;
1-(3-(1H-Pyrrol-1-yl)benzyl)-3-cyclohexyl-4-phenyl-5-(piperazine-1-carbonyl)-1H-imidazol-2(3H)-one;
(R)-2-(5-(2-Benzylpiperazine-1-carbonyl)-2-oxo-3,4-diphenyl-2,3-dihydro-1H-imidazol-1-yl)acetamide;
1-(3-Morpholinophenyl)-3-(3-phenoxybenzyl)-5-phenyl-4-(piperazine-1-carbonyl)-1H-imidazol-2(3H)-one;
1-(3-(3-Methoxypropoxy)phenyl)-3-(3-phenoxybenzyl)-5-phenyl-4-(piperazine-1-carbonyl)-1H-imidazol-2(3H)-one;
1-(3-(Benzyloxy)benzyl)-3-(3-morpholinophenyl)-4-phenyl-5-(piperazine-1-carbonyl)-1H-imidazol-2(3H)-one;
1-(3-(1H-Pyrrol-1-yl)benzyl)-3-(3-morpholinophenyl)-4-phenyl-5-(piperazine-1-carbonyl)-1H-imidazol-2(3H)-one;
N-Isobutyl-N-methyl-3-((3-(3-morpholinophenyl)-2-oxo-4-phenyl-5-(piperazine-1-carbonyl)-2,3-dihydro-1H-imidazol-1-yl)methyl)benzamide;
3-((2-oxo-3,4-Diphenyl-5-(piperazine-1-carbonyl)-2,3-dihydro-1H-imidazol-1-yl)methyl)benzonitrile;
Methyl 3-((2-oxo-3,4-Diphenyl-5-(piperazine-1-carbonyl)-2,3-dihydro-1H-imidazol-1-yl)methyl)benzoate;
1-Benzyl-4-phenyl-5-(piperazine-1-carbonyl)-3-(tetrahydro-2H-pyran-4-yl)-1H-imidazol-2(3H)-one;
1,5-Diphenyl-4-(piperazine-1-carbonyl)-3-(quinolin-8-ylmethyl)-1H-imidazol-2(3H) one;
1-(3-Methoxybenzyl)-3,4-diphenyl-5-(piperazine-1-carbonyl)-1H-imidazol-2(3H)-one;
1-(Naphthalen-2-ylmethyl)-3,4-diphenyl-5-(piperazine-1-carbonyl)-1H-imidazol-2(3H)-one;
2-((2-oxo-3,4-Diphenyl-5-(piperazine-1-carbonyl)-2,3-dihydro-1H-imidazol-1-yl)methyl)benzonitrile;
1-(3,5-Dimethoxybenzyl)-3,4-diphenyl-5-(piperazine-1-carbonyl)-1H-imidazol-2(3H)-one;
1-(4-Chloro-3-(trifluoromethoxy)benzyl)-3,4-diphenyl-5-(piperazine-1-carbonyl)-1H imidazol-2(3H)-one;
1-(3-(1H-Pyrrol-1-yl)benzyl)-3,4-diphenyl-5-(piperazine-1-carbonyl)-1H-imidazol-2(3H)-one;
1-((2-Chloro-6-morpholinopyridin-4-yl)methyl)-3-cyclohexyl-4-phenyl-5-(piperazine-1-carbonyl)-1H-imidazol-2(3H)-one;
1-Cyclohexyl-3-((2,6-di(1H-pyrazol-4-yl)pyridin-4-yl)methyl)-5-phenyl-4-(piperazine-1-carbonyl)-1H-imidazol-2(3H)-one;
1-(1-Acetylpiperidin-3-yl)-3-(3-methoxybenzyl)-5-phenyl-4-(piperazine-1 carbonyl)-1H-imidazol-2(3H)-one;
1-(1-Acetylpiperidin-3-yl)-3-benzyl-5-phenyl-4-(piperazine-1-carbonyl)-1H-imidazol-2(3H)-one;
1-(1-Acetylpiperidin-3-yl)-5-phenyl-4-(piperazine-1-carbonyl)-1H-imidazol-2(3H)-one;
1-(1-Benzoylpiperidin-3-yl)-3-benzyl-5-phenyl-4-(piperazine-1-carbonyl)-1H-imidazol-2(3H)-one;
1-Benzyl-4-phenyl-3-(1-(phenylsulfonyl)piperidin-3-yl)-5-(piperazine-1-carbonyl)-1H-imidazol-2(3H)-one;
1-Benzyl-3-(1-(furan-2-carbonyl)piperidin-3-yl)-4-phenyl-5-(piperazine-1-carbonyl)-1H-imidazol-2(3H)-one;
5-Phenyl-1-(1-(phenylsulfonyl)piperidin-3-yl)-4-(piperazine-1-carbonyl)-1H-imidazol-2(3H)-one;
1-(1-Acetylpiperidin-3-yl)-3-(3-phenoxybenzyl)-5-phenyl-4-(piperazine-1-carbonyl)-1H-imidazol-2(3H)-one;
1-Benzyl-4-phenyl-3-(1-(phenylsulfonyl)piperidin-3-yl)-5-(piperazine-1-carbonyl)-1H-imidazol-2(3H)-one;
1-Benzyl-4-phenyl-5-(piperazine-1-carbonyl)-3-(1-(pyridin-2-ylsulfonyl)piperidin-3-yl)-1H-imidazol-2(3H)-one;
1-(3-Phenoxybenzyl)-4-phenyl-3-(1-(phenylsulfonyl)piperidin-3-yl)-5-(piperazine-1-carbonyl)-1H-imidazol-2(3H)-one;
1-(3-Phenoxybenzyl)-4-phenyl-5-(piperazine-1-carbonyl)-3-(1-(pyridin-2-ylsulfonyl)piperidin-3-yl)-1H-imidazol-2(3H)-one;
1-(1-Acetylpiperidin-3-yl)-4-((R)-2-benzylpiperazine-1-carbonyl)-5-phenyl-1H-imidazol-2(3H)-one;
1-Benzyl-3-((1R,2R)-2-hydroxycyclohexyl)-4-phenyl-5-(piperazine-1-carbonyl)-1H-imidazol-2(3H)-one;
1-((1R,2R)-2-Hydroxycyclohexyl)-3-(3-phenoxybenzyl)-5-phenyl-4-(piperazine-1-carbonyl)-1H-imidazol-2(3H)-one;
N—(((S)-1-(1-((1R,2R)-2-Hydroxycyclohexyl)-2-oxo-5-phenyl-2,3-dihydro-1H-imidazole-4-carbonyl)piperazin-2-yl)methyl)benzamide;
(S)—N-((1-(1-Cyclohexyl-2-oxo-5-phenyl-2,3-dihydro-1H-imidazole-4-carbonyl)piperazin-2-yl)methyl)benzamide;
(R)-4-(2-Benzylpiperazine-1-carbonyl)-1,5-diphenyl-1H-imidazol-2(3H)-one;
(R)-4-(2-Benzylpiperazine-1-carbonyl)-1-(3-morpholinophenyl)-5-phenyl-1H-imidazol-2(3H)-one;
(R)-4-(2-Benzylpiperazine-1-carbonyl)-1-cyclohexyl-5-phenyl-1H-imidazol-2(3H)-one;
(R)-4-(2-Benzylpiperazine-1-carbonyl)-1-(2,3-dimethoxyphenyl)-5-phenyl-1H-imidazol-2(3H)-one;
(R)-4-(2-Benzylpiperazine-1-carbonyl)-1-(2-methoxyphenyl)-5-phenyl-1H-imidazol-2(3H)-one;
(R)-4-(2-Benzylpiperazine-1-carbonyl)-1-(3-(methylsulfonyl)phenyl)-5-phenyl-1H-imidazol-2(3H)-one;
1-(1-Acetylpiperidin-3-yl)-4-((R)-2-benzylpiperazine-1-carbonyl)-5-phenyl-1H-imidazol-2(3H)-one;
(R)-4-(2-Benzylpiperazine-1-carbonyl)-5-phenyl-1-o-tolyl-1H-imidazol-2(3H)-one;
(R)-4-(2-Benzylpiperazine-1-carbonyl)-1-(2-nitrophenyl)-5-phenyl-1H-imidazol-2(3H)-one;
(R)—N-(2-(4-(2-Benzylpiperazine-1-carbonyl)-2-oxo-5-phenyl-2,3-dihydro-1H-imidazol-1-yl)phenyl)methanesulfonamide;

(R)—N-(2-(4-(2-Benzylpiperazine-1-carbonyl)-2-oxo-5-phenyl-2,3-dihydro-1H-imidazol-1-yl)phenyl)propane-1-sulfonamide;
(R)—N-(2-(4-(2-Benzylpiperazine-1-carbonyl)-2-oxo-5-phenyl-2,3-dihydro-1H-imidazol-1-yl)phenyl)cyclopropanecarboxamide;
(R)—N-(2-(4-(2-Benzylpiperazine-1-carbonyl)-2-oxo-5-phenyl-2,3-dihydro-1H-imidazol-1-yl)phenyl)butyramide;
(R)—N-(2-(4-(2-Benzylpiperazine-1-carbonyl)-2-oxo-5-phenyl-2,3-dihydro-1H-imidazol-1-yl)phenyl)acetamide;
(R)—N-(2-(4-(2-Benzylpiperazine-1-carbonyl)-2-oxo-5-phenyl-2,3-dihydro-1H-imidazol-1-yl)phenyl)cyclopropanesulfonamide;
(R)—N-(2-(4-(2-Benzylpiperazine-1-carbonyl)-2-oxo-5-phenyl-2,3-dihydro-1H-imidazol-1-yl)phenyl)benzamide;
(R)—N-(2-(4-(2-Benzylpiperazine-1-carbonyl)-2-oxo-5-phenyl-2,3-dihydro-1H-imidazol-1-yl)phenyl)Benzenesulfonamide;
4-((R)-2-Benzylpiperazine-1-carbonyl)-1-((1S,2S)-2-hydroxycyclohexyl)-5-phenyl-1H-imidazol-2(3H)-one;
(R)—N-(2-(4-(2-Benzylpiperazine-1-carbonyl)-2-oxo-5-phenyl-2,3-dihydro-1H-imidazol-1-yl)phenyl)ethanesulfonamide;
(R)—N-(2-(4-(2-Benzylpiperazine-1-carbonyl)-2-oxo-5-phenyl-2,3-dihydro-1H-imidazol-1-yl)phenyl)butane-1-sulfonamide;
(R)—N-(2-(4-(2-Benzylpiperazine-1-carbonyl)-2-oxo-5-phenyl-2,3-dihydro-1H-imidazol-1-yl)phenyl)prop-2-ene-1-sulfonamide;
(R)-4-(2-Benzylpiperazine-1-carbonyl)-1-((1-hydroxycyclohexyl)methyl)-5-phenyl-1H-imidazol-2(3H)-one;
(R)-4-(2-Benzylpiperazine-1-carbonyl)-5-phenyl-1-(1,2,3,4-tetrahydroquinolin-7-yl)-1H-imidazol-2(3H)-one;
(R)-4-(2-Benzylpiperazine-1-carbonyl)-5-phenyl-1-(1,2,3,4-tetrahydroquinolin-7-yl)-1H-imidazol-2(3H)-one;
(R)-4-(2-Benzylpiperazine-1-carbonyl)-1-(1-butyl-1,2,3,4-tetrahydroquinolin-7-yl)-5-cyclopropyl-1H-imidazol-2(3H)-one;
(R)-4-(2-Benzylpiperazine-1-carbonyl)-5-cyclopropyl-1-(1,2,3,4-tetrahydroquinolin-7-yl)-1H-imidazol-2(3H)-one;
(R)-4-(2-Benzylpiperazine-1-carbonyl)-1-(4-methyl-3,4-dihydro-2H-benzo[b][1,4]oxazin-6-yl)-5-phenyl-1H-imidazol-2(3H)-one;
(R)-4-(2-Benzylpiperazine-1-carbonyl)-1-(indolin-6-yl)-5-phenyl-1H-imidazol-2(3H)-one;
(R)-4-(2-Benzylpiperazine-1-carbonyl)-1-(4-(2-methoxyethyl)-3,4-dihydro-2H-benzo[b][1,4]oxazin-6-yl)-5-phenyl-1H-imidazol-2(3H)-one;
4-((R)-2-Benzylpiperazine-1-carbonyl)-1-(3-methoxy-2,3-dihydro-1H-inden-5-yl)-5-phenyl-1H-imidazol-2(3H)-one;
(R)-4-(2-(2-Phenoxyethyl)piperazine-1-carbonyl)-5-phenyl-1-(1,2,3,4-tetrahydroquinolin-7-yl)-1H-imidazol-2(3H)-one;
1-Allyl-4-phenyl-5-(piperazine-1-carbonyl)-3-o-tolyl-1H-imidazol-2(3H)-one;
1-(3-Phenoxybenzyl)-4-phenyl-5-(piperazine-1-carbonyl)-3-o-tolyl-1H-imidazol-2(3H)-one;
1-(3-Methoxybenzyl)-4-phenyl-5-(piperazine-1-carbonyl)-3-o-tolyl-1H-imidazol-2(3H)-one;
1-(3,4-Difluorobenzyl)-4-phenyl-5-(piperazine-1-carbonyl)-3-o-tolyl-1H-imidazol-2(3H)-one;
1-Allyl-3-(2-methoxyphenyl)-4-phenyl-5-(piperazine-1-carbonyl)-1H-imidazol-2(3H)-one;
1-(2-Methoxyphenyl)-3-(3-phenoxybenzyl)-5-phenyl-4-(piperazine-1-carbonyl)-1H-imidazol-2(3H)-one;
1-(3-Methoxybenzyl)-3-(2-methoxyphenyl)-4-phenyl-5-(piperazine-1-carbonyl)-1H-imidazol-2(3H)-one;
1-(3,4-Difluorobenzyl)-3-(2-methoxyphenyl)-4-phenyl-5-(piperazine-1-carbonyl)-1H-imidazol-2(3H)-one;
1-(3-(2-Phenoxyethoxy)benzyl)-4-phenyl-5-(piperazine-1-carbonyl)-3-o-tolyl-1H-imidazol-2(3H)-one;
1-Allyl-3-(3-morpholinophenyl)-4-phenyl-5-(piperazine-1-carbonyl)-1H-imidazol-2(3H)-one;
1-(3-Methoxybenzyl)-3-(3-morpholinophenyl)-4-phenyl-5-(piperazine-1-carbonyl)-1H-imidazol-2(3H)-one;
1-((1S,2R)-2-Hydroxycyclohexyl)-3-(3-phenoxybenzyl)-5-phenyl-4-(piperazine-1-carbonyl)-1H-imidazol-2(3H)-one;
1-((1S,2R)-2-Hydroxycyclohexyl)-3-(3-methoxybenzyl)-5-phenyl-4-(piperazine-1-carbonyl)-1H-imidazol-2(3H)-one;
1-(3,4-Difluorobenzyl)-3-((1S,2R)-2-hydroxycyclohexyl)-4-phenyl-5-(piperazine-1-carbonyl)-1H-imidazol-2(3H)-one;
N-(2-(2-oxo-4-Phenyl-5-(piperazine-1-carbonyl)-3-o-tolyl-2,3-dihydro-1H-imidazol-1-yl)ethyl)benzenesulfonamide;
N-(3-(2-oxo-4-Phenyl-5-(piperazine-1-carbonyl)-3-o-tolyl-2,3-dihydro-1H-imidazol-1-yl)propyl)benzamide;
1-(Cyclohexylmethyl)-3-((1S,2R)-2-hydroxycyclohexyl)-4-phenyl-5-(piperazine-1-carbonyl)-1H-imidazol-2(3H)-one;
N-(2-(3-(2-Methoxyphenyl)-2-oxo-4-phenyl-5-(piperazine-1-carbonyl)-2,3-dihydro-1H-imidazol-1-yl)ethyl)benzenesulfonamide;
N-(3-(3-(2-Methoxyphenyl)-2-oxo-4-phenyl-5-(piperazine-1-carbonyl)-2,3-dihydro-1H-imidazol-1-yl)propyl)benzamide;
1-(Cyclohexylmethyl)-3-(2-methoxyphenyl)-4-phenyl-5-(piperazine-1-carbonyl)-1H-imidazol-2(3H)-one;
N-(3-(3-(2-Methoxyphenyl)-2-oxo-4-phenyl-5-(piperazine-1-carbonyl)-2,3-dihydro-1H-imidazol-1-yl)propyl)benzenesulfonamide;
N-(3-(2-oxo-4-Phenyl-5-(piperazine-1-carbonyl)-3-o-tolyl-2,3-dihydro-1H-imidazol-1-yl)propyl)benzenesulfonamide;
1-(Cyclohexylmethyl)-4-phenyl-5-(piperazine-1-carbonyl)-3-o-tolyl-1H-imidazol-2(3H)-one;
1-(3,4-Difluorobenzyl)-3-(3-(3-methoxypropoxy)phenyl)-4-phenyl-5-(piperazine-1-carbonyl)-1H-imidazol-2(3H)-one;
3-Methyl-N-(3-(2-oxo-4-phenyl-5-(piperazine-1-carbonyl)-3-o-tolyl-2,3-dihydro-1H-imidazol-1-yl)propyl)butanamide;
N-(2-(2-oxo-4-Phenyl-5-(piperazine-1-carbonyl)-3-o-tolyl-2,3-dihydro-1H-imidazol-1-yl)ethyl)benzamide;
N-(3-(3-(2-Methoxyphenyl)-2-oxo-4-phenyl-5-(piperazine-1-carbonyl)-2,3-dihydro-1H-imidazol-1-yl)propyl)-3-methylbutanamide;
N-(2-(3-(2-Methoxyphenyl)-2-oxo-4-phenyl-5-(piperazine-1-carbonyl)-2,3-dihydro-1H-imidazol-1-yl)ethyl)benzamide;
N-(2-(3-(2-Methoxyphenyl)-2-oxo-4-phenyl-5-(piperazine-1-carbonyl)-2,3-dihydro-1H-imidazol-1-yl)ethyl)-3-methylbutanamide;

N-(3-(3-((2S)-2-Hydroxycyclohexyl)-2-oxo-4-phenyl-5-(piperazine-1-carbonyl)-2,3-dihydro-1H-imidazol-1-yl)propyl)benzamide;

N-(3-(3-((2S)-2-Hydroxycyclohexyl)-2-oxo-4-phenyl-5-(piperazine-1-carbonyl)-2,3-dihydro-1H-imidazol-1-yl)propyl)benzenesulfonamide;

N-(3-(3-((2S)-2-Hydroxycyclohexyl)-2-oxo-4-phenyl-5-(piperazine-1-carbonyl)-2,3-dihydro-1H-imidazol-1-yl)propyl)-3-methylbutanamide;

N-(2-(3-((2S)-2-Hydroxycyclohexyl)-2-oxo-4-phenyl-5-(piperazine-1-carbonyl)-2,3-dihydro-1H-imidazol-1-yl)ethyl)-3-methylbutanamide;

N-(3-(3-(3-Morpholinophenyl)-2-oxo-4-phenyl-5-(piperazine-1-carbonyl)imidazolidin-1-yl)propyl)benzamide;

N-(3-(3-(3-Morpholinophenyl)-2-oxo-4-phenyl-5-(piperazine-1-carbonyl)-2,3-dihydro-1H-imidazol-1-yl)propyl)benzenesulfonamide;

3-Methyl-N-(3-(3-(3-morpholinophenyl)-2-oxo-4-phenyl-5-(piperazine-1-carbonyl)-2,3-dihydro-1H-imidazol-1-yl)propyl)butanamide;

N-(2-(3-(3-Morpholinophenyl)-2-oxo-4-phenyl-5-(piperazine-1-carbonyl)-2,3-dihydro-1H-imidazol-1-yl)ethyl)benzamide;

3-Methyl-N-(2-(3-(3-morpholinophenyl)-2-oxo-4-phenyl-5-(piperazine-1-carbonyl)-2,3-dihydro-1H-imidazol-1-yl)ethyl)butanamide;

N-(3-(3-(3-(3-Methoxypropoxy)phenyl)-2-oxo-4-phenyl-5-(piperazine-1-carbonyl)-2,3-dihydro-1H-imidazol-1-yl)propyl)benzamide;

N-(3-(3-(3-(3-Methoxypropoxy)phenyl)-2-oxo-4-phenyl-5-(piperazine-1-carbonyl)-2,3-dihydro-1H-imidazol-1-yl)propyl)benzenesulfonamide;

N-(3-(3-(3-(3-Methoxypropoxy)phenyl)-2-oxo-4-phenyl-5-(piperazine-1-carbonyl)-2,3-dihydro-1H-imidazol-1-yl)propyl)-3-methylbutanamide;

N-(2-(3-(3-(3-Methoxypropoxy)phenyl)-2-oxo-4-phenyl-5-(piperazine-1-carbonyl)-2,3-dihydro-1H-imidazol-1-yl)ethyl)benzamide;

N-(2-(3-(3-(3-Methoxypropoxy)phenyl)-2-oxo-4-phenyl-5-(piperazine-1-carbonyl)-2,3-dihydro-1H-imidazol-1-yl)ethyl)benzenesulfonamide;

N-(2-(3-(3-(3-Methoxypropoxy)phenyl)-2-oxo-4-phenyl-5-(piperazine-1-carbonyl)-2,3-dihydro-1H-imidazol-1-yl)ethyl)-3-methylbutanamide;

N-(2-(3-(3-Morpholinophenyl)-2-oxo-4-phenyl-5-(piperazine-1-carbonyl)-2,3-dihydro-1H-imidazol-1-yl)ethyl)benzenesulfonamide;

1-(3-(2-Methoxyethoxy)benzyl)-4-phenyl-5-(piperazine-1-carbonyl)-3-o-tolyl-1H-imidazol-2(3H)-one;

1-(3-(2-Methoxyethoxy)benzyl)-3-(2-methoxyphenyl)-4-phenyl-5-(piperazine-1-carbonyl)-1H-imidazol-2(3H)-one;

1-(2-Methoxyphenyl)-3-(3-(2-phenoxyethoxy)benzyl)-5-phenyl-4-(piperazine-1-carbonyl)-1H-imidazol-2(3H)-one;

1-(Cyclohexylmethyl)-3-(3-morpholinophenyl)-4-phenyl-5-(piperazine-1-carbonyl)-1H-imidazol-2(3H)-one;

1-(3,4-Difluorobenzyl)-3-(3-morpholinophenyl)-4-phenyl-5-(piperazine-1-carbonyl)-1H-imidazol-2(3H)-one;

1-(3-Morpholinophenyl)-3-(3-(2-phenoxyethoxy)benzyl)-5-phenyl-4-(piperazine-1-carbonyl)-1H-imidazol-2(3H)-one;

1-(3-(2-Methoxyethoxy)benzyl)-3-(3-(3-methoxypropoxy)phenyl)-4-phenyl-5-(piperazine-1-carbonyl)-1H-imidazol-2(3H)-one;

2-Fluoro-N-(3-(3-(3-morpholinophenyl)-2-oxo-4-phenyl-5-(piperazine-1-carbonyl)-2,3-dihydro-1H-imidazol-1-yl)propyl)benzenesulfonamide;

2-Chloro-N-(3-(3-(3-morpholinophenyl)-2-oxo-4-phenyl-5-(piperazine-1-carbonyl)-2,3-dihydro-1H-imidazol-1-yl)propyl)benzenesulfonamide;

3-Chloro-N-(3-(3-(3-morpholinophenyl)-2-oxo-4-phenyl-5-(piperazine-1-carbonyl)-2,3-dihydro-1H-imidazol-1-yl)propyl)benzenesulfonamide;

N-(3-(3-(3-Morpholinophenyl)-2-oxo-4-phenyl-5-(piperazine-1-carbonyl)-2,3-dihydro-1H-imidazol-1-yl)propyl)propane-2-sulfonamide;

2-Methyl-N-(3-(3-(3-morpholinophenyl)-2-oxo-4-phenyl-5-(piperazine-1-carbonyl)-2,3-dihydro-1H-imidazol-1-yl)propyl)benzenesulfonamide;

3-Methoxy-N-(3-(3-(3-morpholinophenyl)-2-oxo-4-phenyl-5-(piperazine-1-carbonyl)-2,3-dihydro-1H-imidazol-1-yl)propyl)benzenesulfonamide;

4-Methoxy-N-(3-(3-(3-morpholinophenyl)-2-oxo-4-phenyl-5-(piperazine-1-carbonyl)-2,3-dihydro-1H-imidazol-1-yl)propyl)benzenesulfonamide;

1-(3-(3-(3-Morpholinophenyl)-2-oxo-4-phenyl-5-(piperazine-1-carbonyl)-2,3-dihydro-1H-imidazol-1-yl)propyl)-3-phenylurea;

1-Isopropyl-3-(3-(3-(3-morpholinophenyl)-2-oxo-4-phenyl-5-(piperazine-1-carbonyl)-2,3-dihydro-1H-imidazol-1-yl)propyl)urea;

4-Chloro-N-(3-(3-(3-morpholinophenyl)-2-oxo-4-phenyl-5-(piperazine-1-carbonyl)-2,3-dihydro-1H-imidazol-1-yl)propyl)benzenesulfonamide;

2-Fluoro-N-(2-(2-oxo-4-phenyl-5-(piperazine-1-carbonyl)-3-o-tolyl-2,3-dihydro-1H-imidazol-1-yl)ethyl)benzenesulfonamide;

2-Chloro-N-(2-(2-oxo-4-phenyl-5-(piperazine-1-carbonyl)-3-o-tolyl-2,3-dihydro-1H-imidazol-1-yl)ethyl)benzenesulfonamide;

3-Chloro-N-(2-(2-oxo-4-phenyl-5-(piperazine-1-carbonyl)-3-o-tolyl-2,3-dihydro-1H-imidazol-1-yl)ethyl)benzenesulfonamide;

4-Chloro-N-(2-(2-oxo-4-phenyl-5-(piperazine-1-carbonyl)-3-o-tolyl-2,3-dihydro-1H-imidazol-1-yl)ethyl)benzenesulfonamide;

N-(2-(2-oxo-4-phenyl-5-(piperazine-1-carbonyl)-3-o-tolyl-2,3-dihydro-1H-imidazol-1-yl)ethyl)propane-2-sulfonamide;

2-Methyl-N-(2-(2-oxo-4-phenyl-5-(piperazine-1-carbonyl)-3-o-tolyl-2,3-dihydro-1H-imidazol-1-yl)ethyl)benzenesulfonamide;

3-Methoxy-N-(2-(2-oxo-4-phenyl-5-(piperazine-1-carbonyl)-3-o-tolyl-2,3-dihydro-1H-imidazol-1-yl)ethyl)benzenesulfonamide;

4-Methoxy-N-(2-(2-oxo-4-phenyl-5-(piperazine-1-carbonyl)-3-o-tolyl-2,3-dihydro-1H-imidazol-1-yl)ethyl)benzenesulfonamide;

1-(2-(2-Oxo-4-phenyl-5-(piperazine-1-carbonyl)-3-o-tolyl-2,3-dihydro-1H-imidazol-1-yl)ethyl)-3-phenylurea;

1-(2-Chlorophenyl)-3-(2-(2-oxo-4-phenyl-5-(piperazine-1-carbonyl)-3-o-tolyl-2,3-dihydro-1H-imidazol-1-yl)ethyl)urea;

1-(4-Chlorophenyl)-3-(2-(2-oxo-4-phenyl-5-(piperazine-1-carbonyl)-3-o-tolyl-2,3-dihydro-1H-imidazol-1-yl)ethyl)urea;

1-(2-Methoxyphenyl)-3-(2-(2-oxo-4-phenyl-5-(piperazine-1-carbonyl)-3-o-tolyl-2,3-dihydro-1H-imidazol-1-yl)ethyl)urea;
1-(3-Methoxyphenyl)-3-(2-(2-oxo-4-phenyl-5-(piperazine-1-carbonyl)-3-o-tolyl-2,3-dihydro-1H-imidazol-1-yl)ethyl)urea;
1-Isopropyl-3-(2-(2-oxo-4-phenyl-5-(piperazine-1-carbonyl)-3-o-tolyl-2,3-dihydro-1H-imidazol-1-yl)ethyl)urea;
2-Chloro-N-(3-(2-oxo-4-phenyl-5-(piperazine-1-carbonyl)-3-o-tolyl-2,3-dihydro-1H-imidazol-1-yl)propyl)benzenesulfonamide;
3-Chloro-N-(3-(2-oxo-4-phenyl-5-(piperazine-1-carbonyl)-3-o-tolyl-2,3-dihydro-1H-imidazol-1-yl)propyl)benzenesulfonamide;
4-Chloro-N-(3-(2-oxo-4-phenyl-5-(piperazine-1-carbonyl)-3-o-tolyl-2,3-dihydro-1H-imidazol-1-yl)propyl)benzenesulfonamide;
2-Methyl-N-(3-(2-oxo-4-phenyl-5-(piperazine-1-carbonyl)-3-o-tolyl-2,3-dihydro-1H-imidazol-1-yl)propyl)benzenesulfonamide;
3-Methoxy-N-(3-(2-oxo-4-phenyl-5-(piperazine-1-carbonyl)-3-o-tolyl-2,3-dihydro-1H-imidazol-1-yl)propyl)benzenesulfonamide;
4-Methoxy-N-(3-(2-oxo-4-phenyl-5-(piperazine-1-carbonyl)-3-o-tolyl-2,3-dihydro-1H-imidazol-1-yl)propyl)benzenesulfonamide;
1-(3-(2-Oxo-4-phenyl-5-(piperazine-1-carbonyl)-3-o-tolyl-2,3-dihydro-1H-imidazol-1-yl)propyl)-3-phenylurea;
1-(2-Chlorophenyl)-3-(3-(2-oxo-4-phenyl-5-(piperazine-1-carbonyl)-3-o-tolyl-2,3-dihydro-1H-imidazol-1-yl)propyl)urea;
1-(2-Methoxyphenyl)-3-(3-(2-oxo-4-phenyl-5-(piperazine-1-carbonyl)-3-o-tolyl-2,3-dihydro-1H-imidazol-1-yl)propyl)urea;
1-(3-Methoxyphenyl)-3-(3-(2-oxo-4-phenyl-5-(piperazine-1-carbonyl)-3-o-tolyl-2,3-dihydro-1H-imidazol-1-yl)propyl)urea;
1-Isopropyl-3-(3-(2-oxo-4-phenyl-5-(piperazine-1-carbonyl)-3-o-tolyl-2,3-dihydro-1H-imidazol-1-yl)propyl)urea;
1-(4-Methoxyphenyl)-3-(2-(2-oxo-4-phenyl-5-(piperazine-1-carbonyl)-3-o-tolyl-2,3-dihydro-1H-imidazol-1-yl)ethyl)urea;
2-Fluoro-N-(3-(2-oxo-4-phenyl-5-(piperazine-1-carbonyl)-3-o-tolyl-2,3-dihydro-1H-imidazol-1-yl)propyl)benzenesulfonamide;
2-Fluoro-N-(2-(2-oxo-4-phenyl-5-(piperazine-1-carbonyl)-3-o-tolyl-2,3-dihydro-1H-imidazol-1-yl)ethyl)benzamide;
2-Chloro-N-(2-(2-oxo-4-phenyl-5-(piperazine-1-carbonyl)-3-o-tolyl-2,3-dihydro-1H-imidazol-1-yl)ethyl)benzamide;
2-Chloro-N-(2-(2-oxo-4-phenyl-5-(piperazine-1-carbonyl)-3-o-tolyl-2,3-dihydro-1H-imidazol-1-yl)ethyl)benzamide;
3-Chloro-N-(2-(2-oxo-4-phenyl-5-(piperazine-1-carbonyl)-3-o-tolyl-2,3-dihydro-1H-imidazol-1-yl)ethyl)benzamide;
4-Chloro-N-(2-(2-oxo-4-phenyl-5-(piperazine-1-carbonyl)-3-o-tolyl-2,3-dihydro-1H-imidazol-1-yl)ethyl)benzamide;
2-Methoxy-N-(2-(2-oxo-4-phenyl-5-(piperazine-1-carbonyl)-3-o-tolyl-2,3-dihydro-1H-imidazol-1-yl)ethyl)benzamide;
4-Methoxy-N-(2-(2-oxo-4-phenyl-5-(piperazine-1-carbonyl)-3-o-tolyl-2,3-dihydro-1H-imidazol-1-yl)ethyl)benzamide;
N-(2-(2-Oxo-4-phenyl-5-(piperazine-1-carbonyl)-3-o-tolyl-2,3-dihydro-1H-imidazol-1-yl)ethyl)isobutyramide;
N-(2-(2-Oxo-4-phenyl-5-(piperazine-1-carbonyl)-3-o-tolyl-2,3-dihydro-1H-imidazol-1-yl)ethyl)cyclohexanecarboxamide
3-Methyl-N-(2-(2-oxo-4-phenyl-5-(piperazine-1-carbonyl)-3-o-tolyl-2,3-dihydro-1H-imidazol-1-yl)ethyl)butanamide;
N-(3-(2-Oxo-4-phenyl-5-(piperazine-1-carbonyl)-3-o-tolyl-2,3-dihydro-1H-imidazol-1-yl)propyl)propane-2-sulfonamide;
2-Fluoro-N-(3-(2-oxo-4-phenyl-5-(piperazine-1-carbonyl)-3-o-tolyl-2,3-dihydro-1H-imidazol-1-yl)propyl)benzamide;
2-Chloro-N-(3-(2-oxo-4-phenyl-5-(piperazine-1-carbonyl)-3-o-tolyl-2,3-dihydro-1H-imidazol-1-yl)propyl)benzamide;
3-Chloro-N-(3-(2-oxo-4-phenyl-5-(piperazine-1-carbonyl)-3-o-tolyl-2,3-dihydro-1H-imidazol-1-yl)propyl)benzamide;
4-Chloro-N-(3-(2-oxo-4-phenyl-5-(piperazine-1-carbonyl)-3-o-tolyl-2,3-dihydro-1H-imidazol-1-yl)propyl)benzamide;
2-Methoxy-N-(3-(2-oxo-4-phenyl-5-(piperazine-1-carbonyl)-3-o-tolyl-2,3-dihydro-1H-imidazol-1-yl)propyl)benzamide;
4-Methoxy-N-(3-(2-oxo-4-phenyl-5-(piperazine-1-carbonyl)-3-o-tolyl-2,3-dihydro-1H-imidazol-1-yl)propyl)benzamide;
N-(3-(2-Oxo-4-phenyl-5-(piperazine-1-carbonyl)-3-o-tolyl-2,3-dihydro-1H-imidazol-1-yl)propyl)isobutyramide;
N-(3-(2-Oxo-4-phenyl-5-(piperazine-1-carbonyl)-3-o-tolyl-2,3-dihydro-1H-imidazol-1-yl)propyl)cyclohexanecarboxamide;
Phenyl 2-(2-oxo-4-phenyl-5-(piperazine-1-carbonyl)-3-o-tolyl-2,3-dihydro-1H-imidazol-1-yl)ethylcarbamate;
Methyl 2-(2-oxo-4-phenyl-5-(piperazine-1-carbonyl)-3-o-tolyl-2,3-dihydro-1H-imidazol-1-yl)ethylcarbamate;
Ethyl 2-(2-oxo-4-phenyl-5-(piperazine-1-carbonyl)-3-o-tolyl-2,3-dihydro-1H-imidazol-1-yl)ethylcarbamate;
Benzyl 2-(2-oxo-4-phenyl-5-(piperazine-1-carbonyl)-3-o-tolyl-2,3-dihydro-1H-imidazol-1-yl)ethylcarbamate;
Phenyl 3-(2-oxo-4-phenyl-5-(piperazine-1-carbonyl)-3-o-tolyl-2,3-dihydro-1H-imidazol-1-yl)propylcarbamate;
Methyl 3-(2-oxo-4-phenyl-5-(piperazine-1-carbonyl)-3-o-tolyl-2,3-dihydro-1H-imidazol-1-yl)propylcarbamate;
Ethyl 3-(2-oxo-4-phenyl-5-(piperazine-1-carbonyl)-3-o-tolyl-2,3-dihydro-1H-imidazol-1-yl)propylcarbamate;
Benzyl 3-(2-oxo-4-phenyl-5-(piperazine-1-carbonyl)-3-o-tolyl-2,3-dihydro-1H-imidazol-1-yl)propylcarbamate;
1-(2-Methylphenyl)-5-phenyl-4-(piperazine-1-carbonyl)-3-prop-2-enyl-imidazol-2-one;
1-(Cyclohexylmethyl)-3-(2-methylphenyl)-4-phenyl-5-(piperazine-1-carbonyl)imidazol-2-one;
1-(2-Methylphenyl)-3-[(3-phenoxyphenyl)methyl]-5-phenyl-4-(piperazine-1-carbonyl)imidazol-2-one;
1-[(2-Amino1,3-thiazol-4-yl)methyl]-3-(2-methylphenyl)-4-phenyl-5-(piperazine-1-carbonyl)imidazol-2-one;
1-[(3-Methoxyphenyl)methyl]-3-(2-methylphenyl)-4-phenyl-5-(piperazine-1-carbonyl)imidazol-2-one;

1-[(3,4-Difluorophenyl)methyl]-3-(2-methylphenyl)-4-phenyl-5-(piperazine-1-carbonyl)imidazol-2-one;
N-[2-[3-(2-Methylphenyl)-2-oxo-4-phenyl-5-(piperazine-1-carbonyl)imidazol-1-yl]ethyl]benzamide;
N-[2-[3-(2-Methylphenyl)-2-oxo-4-phenyl-5-(piperazine-1-carbonyl)imidazol-1-yl]ethyl]benzenesulfonamide;
3-Methyl-N-[2-[3-(2-methylphenyl)-2-oxo-4-phenyl-5-(piperazine-1-carbonyl)imidazol-1-yl]ethyl]butanamide;
2-Methyl-N-[2-[3-(2-methylphenyl)-2-oxo-4-phenyl-5-(piperazine-1-carbonyl)imidazol-1-yl]ethyl]propane-1-sulfonamide;
N-[3-[3-(2-Methylphenyl)-2-oxo-4-phenyl-5-(piperazine-1-carbonyl)imidazol-1-yl]propyl]benzamide;
N-[3-[3-(2-Methylphenyl)-2-oxo-4-phenyl-5-(piperazine-1-carbonyl)imidazol-1-yl]propyl]benzenesulfonamide;
3-Methyl-N-[3-[3-(2-methylphenyl)-2-oxo-4-phenyl-5-(piperazine-1-carbonyl)imidazol-1-yl]propyl]butanamide;
2-Methyl-N-[3-[3-(2-methylphenyl)-2-oxo-4-phenyl-5-(piperazine-1-carbonyl)imidazol-1-yl]propyl]propane-1-sulfonamide;
1-[[3-(2-Methoxyethoxy)phenyl]methyl]-3-(2-methylphenyl)-4-phenyl-5-(piperazine-1-carbonyl)imidazol-2-one;
1-(2-Methylphenyl)-5-phenyl-4-(piperazine-1-carbonyl)-3-[[3-(2-pyridin-3-yloxyethoxy)phenyl]methyl]imidazol-2-one;
1-(2-Methylphenyl)-5-phenyl-4-(piperazine-1-carbonyl)-3-[[3-(2-propan-2-yloxyethoxy)phenyl]methyl]imidazol-2-one;
1-(2-Methylphenyl)-3-[[3-(2-phenoxyethoxy)phenyl]methyl]-5-phenyl-4-(piperazine-1-carbonyl)imidazol-2-one;
1-(2-Methylphenyl)-3-[[3-(2-morpholin-4-yl-2-oxoethoxy)phenyl]methyl]-5-phenyl-4-(piperazine-1-carbonyl)imidazol-2-one;
1-(2-Methylphenyl)-3-[[3-[2-oxo-2-(1-piperidyl)ethoxy]phenyl]methyl]-5-phenyl-4-(piperazine-1-carbonyl)imidazol-2-one;
N-Methyl-2-[3-[[3-(2-methylphenyl)-2-oxo-4-phenyl-5-(piperazine-1-carbonyl)imidazol-1-yl]methyl]phenoxy]acetamide;
2-[3-[[3-(2-Methylphenyl)-2-oxo-4-phenyl-5-(piperazine-1-carbonyl)imidazol-1-yl]methyl]phenoxy]-N-propan-2-yl-acetamide;
1-(2-Methoxyphenyl)-5-phenyl-4-(piperazine-1-carbonyl)-3-prop-2-enyl-imidazol-2-one;
1-(Cyclohexylmethyl)-3-(2-methoxyphenyl)-4-phenyl-5-(piperazine-1-carbonyl)imidazol-2-one;
1-(2-Methoxyphenyl)-3-[(3-phenoxyphenyl)methyl]-5-phenyl-4-(piperazine-1-carbonyl)imidazol-2-one;
1-[(2-Amino1,3-thiazol-4-yl)methyl]-3-(2-methoxyphenyl)-4-phenyl-5-(piperazine-1-carbonyl)imidazol-2-one;
1-(2-Methoxyphenyl)-3-[(3-methoxyphenyl)methyl]-5-phenyl-4-(piperazine-1-carbonyl)imidazol-2-one;
1-[(3,4-Difluorophenyl)methyl]-3-(2-methoxyphenyl)-4-phenyl-5-(piperazine-1-carbonyl)imidazol-2-one;
N-[2-[3-(2-Methoxyphenyl)-2-oxo-4-phenyl-5-(piperazine-1-carbonyl)imidazol-1-yl]ethyl]benzamide;
N-[2-[3-(2-Methoxyphenyl)-2-oxo-4-phenyl-5-(piperazine-1-carbonyl)imidazol-1-yl]ethyl]benzenesulfonamide;
N-[2-[3-(2-Methoxyphenyl)-2-oxo-4-phenyl-5-(piperazine-1-carbonyl)imidazol-1-yl]ethyl]-3-methyl-butanamide;
N-[2-[3-(2-Methoxyphenyl)-2-oxo-4-phenyl-5-(piperazine-1-carbonyl)imidazol-1-yl]ethyl]-2-methyl-propane-1-sulfonamide;
N-[3-[3-(2-Methoxyphenyl)-2-oxo-4-phenyl-5-(piperazine-1-carbonyl)imidazol-1-yl]propyl]benzamide;
N-[3-[3-(2-Methoxyphenyl)-2-oxo-4-phenyl-5-(piperazine-1-carbonyl)imidazol-1-yl]propyl]benzenesulfonamide;
N-[3-[3-(2-Methoxyphenyl)-2-oxo-4-phenyl-5-(piperazine-1-carbonyl)imidazol-1-yl]propyl]-3-methyl-butanamide;
N-[3-[3-(2-Methoxyphenyl)-2-oxo-4-phenyl-5-(piperazine-1-carbonyl)imidazol-1-yl]propyl]-2-methyl-propane-1-sulfonamide;
1-[[3-(2-Methoxyethoxy)phenyl]methyl]-3-(2-methoxyphenyl)-4-phenyl-5-(piperazine-1-carbonyl)imidazol-2-one;
1-(2-Methoxyphenyl)-5-phenyl-4-(piperazine-1-carbonyl)-3-[[3-(2-pyridin-3-yloxyethoxy)phenyl]methyl]imidazol-2-one;
1-(2-Methoxyphenyl)-5-phenyl-4-(piperazine-1-carbonyl)-3-[[3-(2-propan-2-yloxyethoxy)phenyl]methyl]imidazol-2-one;
1-(2-Methoxyphenyl)-3-[[3-(2-phenoxyethoxy)phenyl]methyl]-5-phenyl-4-(piperazine-1-carbonyl)imidazol-2-one;
1-(2-Methoxyphenyl)-3-[[3-(2-morpholin-4-yl-2-oxoethoxy)phenyl]methyl]-5-phenyl-4-(piperazine-1-carbonyl)imidazol-2-one;
1-(2-Methoxyphenyl)-3-[[3-[2-oxo-2-(1-piperidyl)ethoxy]phenyl]methyl]-5-phenyl-4-(piperazine-1-carbonyl)imidazol-2-one;
2-[3-[[3-(2-Methoxyphenyl)-2-oxo-4-phenyl-5-(piperazine-1-carbonyl)imidazol-1-yl]methyl]phenoxy]-N-methyl-acetamide;
2-[3-[[3-(2-Methoxyphenyl)-2-oxo-4-phenyl-5-(piperazine-1-carbonyl)imidazol-1-yl]methyl]phenoxy]-N-propan-2-yl-acetamide;
1-(3-Morpholin-4-ylphenyl)-5-phenyl-4-(piperazine-1-carbonyl)-3-prop-2-enyl-imidazol-2-one;
1-(Cyclohexylmethyl)-3-(3-morpholin-4-ylphenyl)-4-phenyl-5-(piperazine-1-carbonyl)imidazol-2-one;
1-(3-Morpholin-4-ylphenyl)-3-[(3-phenoxyphenyl)methyl]-5-phenyl-4-(piperazine-1-carbonyl)imidazol-2-one;
1-[(2-Amino1,3-thiazol-4-yl)methyl]-3-(3-morpholin-4-ylphenyl)-4-phenyl-5-(piperazine-1-carbonyl)imidazol-2-one;
1-[(3-Methoxyphenyl)methyl]-3-(3-morpholin-4-ylphenyl)-4-phenyl-5-(piperazine-1-carbonyl)imidazol-2-one;
1-[(3,4-Difluorophenyl)methyl]-3-(3-morpholin-4-ylphenyl)-4-phenyl-5-(piperazine-1-carbonyl)imidazol-2-one;
N-[2-[3-(3-Morpholin-4-ylphenyl)-2-oxo-4-phenyl-5-(piperazine-1-carbonyl)imidazol-1-yl]ethyl]benzamide;
N-[2-[3-(3-Morpholin-4-ylphenyl)-2-oxo-4-phenyl-5-(piperazine-1-carbonyl)imidazol-1-yl]ethyl]benzenesulfonamide;
3-Methyl-N-[2-[3-(3-morpholin-4-ylphenyl)-2-oxo-4-phenyl-5-(piperazine-1-carbonyl)imidazol-1-yl]ethyl]butanamide;

2-Methyl-N-[2-[3-(3-morpholin-4-ylphenyl)-2-oxo-4-phenyl-5-(piperazine-1-carbonyl)imidazol-1-yl]ethyl]propane-1-sulfonamide;

N-[3-[3-(3-Morpholin-4-ylphenyl)-2-oxo-4-phenyl-5-(piperazine-1-carbonyl)imidazol-1-yl]propyl]benzamide;

N-[3-[3-(3-Morpholin-4-ylphenyl)-2-oxo-4-phenyl-5-(piperazine-1-carbonyl)imidazol-1-yl]propyl]benzenesulfonamide;

3-Methyl-N-[3-[3-(3-morpholin-4-ylphenyl)-2-oxo-4-phenyl-5-(piperazine-1-carbonyl)imidazol-1-yl]propyl]butanamide;

2-Methyl-N-[3-[3-(3-morpholin-4-ylphenyl)-2-oxo-4-phenyl-5-(piperazine-1-carbonyl)imidazol-1-yl]propyl]propane-1-sulfonamide;

1-[[3-(2-Methoxyethoxy)phenyl]methyl]-3-(3-morpholin-4-ylphenyl)-4-phenyl-5-(piperazine-1-carbonyl)imidazol-2-one;

1-(3-Morpholin-4-ylphenyl)-5-phenyl-4-(piperazine-1-carbonyl)-3-[[3-(2-pyridin-3-yloxyethoxy)phenyl]methyl]imidazol-2-one;

1-(3-Morpholin-4-ylphenyl)-5-phenyl-4-(piperazine-1-carbonyl)-3-[[3-(2-propan-2-yloxyethoxy)phenyl]methyl]imidazol-2-one 1-(3-Morpholin-4-ylphenyl)-3-[[3-(2-phenoxyethoxy)phenyl]methyl]-5-phenyl-4-(piperazine-1-carbonyl)imidazol-2-one;

1-[[3-(2-Morpholin-4-yl-2-oxo-ethoxy)phenyl]methyl]-3-(3-morpholin-4-ylphenyl)-4-phenyl-5-(piperazine-1-carbonyl)imidazol-2-one;

1-(3-Morpholin-4-ylphenyl)-3-[[3-[2-oxo-2-(1-piperidyl)ethoxy]phenyl]methyl]-5-phenyl-4-(piperazine-1-carbonyl)imidazol-2-one;

N-Methyl-2-[3-[[3-(3-morpholin-4-ylphenyl)-2-oxo-4-phenyl-5-(piperazine-1-carbonyl)imidazol-1-yl]methyl]phenoxy]acetamide;

2-[3-[[3-(3-Morpholin-4-ylphenyl)-2-oxo-4-phenyl-5-(piperazine-1-carbonyl)imidazol-1-yl]methyl]phenoxy]-N-propan-2-yl-acetamide;

1-[3-(3-Methoxypropoxy)phenyl]-5-phenyl-4-(piperazine-1-carbonyl)-3-prop-2-enyl-imidazol-2-one;

1-(Cyclohexylmethyl)-3-[3-(3-methoxypropoxy)phenyl]-4-phenyl-5-(piperazine-1-carbonyl)imidazol-2-one;

1-[3-(3-Methoxypropoxy)phenyl]-3-[(3-phenoxyphenyl)methyl]-5-phenyl-4-(piperazine-1-carbonyl)imidazol-2-one;

1-[(2-Amino1,3-thiazol-4-yl)methyl]-3-[3-(3-methoxypropoxy)phenyl]-4-phenyl-5-(piperazine-1-carbonyl)imidazol-2-one;

1-[(3-Methoxyphenyl)methyl]-3-[3-(3-methoxypropoxy)phenyl]-4-phenyl-5-(piperazine-1-carbonyl)imidazol-2-one;

1-[(3,4-Difluorophenyl)methyl]-3-[3-(3-methoxypropoxy)phenyl]-4-phenyl-5-(piperazine-1-carbonyl)imidazol-2-one;

N-[2-[3-[3-(3-Methoxypropoxy)phenyl]-2-oxo-4-phenyl-5-(piperazine-1-carbonyl)imidazol-1-yl]ethyl]benzamide;

N-[2-[3-[3-(3-Methoxypropoxy)phenyl]-2-oxo-4-phenyl-5-(piperazine-1-carbonyl)imidazol-1-yl]ethyl]benzenesulfonamide;

N-[2-[3-[3-(3-Methoxypropoxy)phenyl]-2-oxo-4-phenyl-5-(piperazine-1-carbonyl)imidazol-1-yl]ethyl]-3-methyl-butanamide;

N-[2-[3-[3-(3-Methoxypropoxy)phenyl]-2-oxo-4-phenyl-5-(piperazine-1-carbonyl)imidazol-1-yl]ethyl]-2-methyl-propane-1-sulfonamide;

N-[3-[3-[3-(3-Methoxypropoxy)phenyl]-2-oxo-4-phenyl-5-(piperazine-1-carbonyl)imidazol-1-yl]propyl]benzamide;

N-[3-[3-[3-(3-Methoxypropoxy)phenyl]-2-oxo-4-phenyl-5-(piperazine-1-carbonyl)imidazol-1-yl]propyl]benzenesulfonamide;

N-[3-[3-[3-(3-Methoxypropoxy)phenyl]-2-oxo-4-phenyl-5-(piperazine-1-carbonyl)imidazol-1-yl]propyl]-3-methyl-butanamide;

N-[3-[3-[3-(3-Methoxypropoxy)phenyl]-2-oxo-4-phenyl-5-(piperazine-1-carbonyl)imidazol-1-yl]propyl]-2-methyl-propane-1-sulfonamide;

1-[[3-(2-Methoxyethoxy)phenyl]methyl]-3-[3-(3-methoxypropoxy)phenyl]-4-phenyl-5-(piperazine-1-carbonyl)imidazol-2-one;

1-[3-(3-Methoxypropoxy)phenyl]-5-phenyl-4-(piperazine-1-carbonyl)-3-[[3-(2-pyridin-3-yloxyethoxy)phenyl]methyl]imidazol-2-one;

1-[3-(3-Methoxypropoxy)phenyl]-5-phenyl-4-(piperazine-1-carbonyl)-3-[[3-(2-propan-2-yloxyethoxy)phenyl]methyl]imidazol-2-one;

1-[3-(3-Methoxypropoxy)phenyl]-3-[[3-(2-phenoxyethoxy)phenyl]methyl]-5-phenyl-4-(piperazine-1-carbonyl)imidazol-2-one;

1-[3-(3-Methoxypropoxy)phenyl]-3-[[3-(2-morpholin-4-yl-2-oxo-ethoxy)phenyl]methyl]-5-phenyl-4-(piperazine-1-carbonyl)imidazol-2-one;

1-[3-(3-Methoxypropoxy)phenyl]-3-[[3-[2-oxo-2-(1-piperidyl)ethoxy]phenyl]methyl]-5-phenyl-4-(piperazine-1-carbonyl)imidazol-2-one;

2-[3-[[3-[3-(3-Methoxypropoxy)phenyl]-2-oxo-4-phenyl-5-(piperazine-1-carbonyl)imidazol-1-yl]methyl]phenoxy]-N-methyl-acetamide;

2-[3-[[3-[3-(3-Methoxypropoxy)phenyl]-2-oxo-4-phenyl-5-(piperazine-1-carbonyl)imidazol-1-yl]methyl]phenoxy]-N-propan-2-yl-acetamide;

N-[(1S)-2-[2-oxo-5-Phenyl-4-(piperazine-1-carbonyl)-3-prop-2-enyl-imidazol-1-yl]cyclohexyl]propanamide;

N-[(1S)-2-[3-(Cyclohexylmethyl)-2-oxo-5-phenyl-4-(piperazine-1-carbonyl)imidazol-1-yl]cyclohexyl]propanamide;

N-[(1S)-2-[2-oxo-3-[(3-Phenoxyphenyl)methyl]-5-phenyl-4-(piperazine-1-carbonyl)imidazol-1-yl]cyclohexyl]propanamide;

N-[(1S)-2-[3-[(2-Amino 1,3-thiazol-4-yl)methyl]-2-oxo-5-phenyl-4-(piperazine-1-carbonyl)imidazol-1-yl]cyclohexyl]propanamide;

N-[(1S)-2-[3-[(3-Methoxyphenyl)methyl]-2-oxo-5-phenyl-4-(piperazine-1-carbonyl)imidazol-1-yl]cyclohexyl]propanamide;

N-[(1S)-2-[3-[(3,4-Difluorophenyl)methyl]-2-oxo-5-phenyl-4-(piperazine-1-carbonyl)imidazol-1-yl]cyclohexyl]propanamide;

N-[2-[2-oxo-4-Phenyl-5-(piperazine-1-carbonyl)-3-[(2S)-2-(propanoylamino)cyclohexyl]imidazol-1-yl]ethyl]benzamide;

N-[(1S)-2-[3-[2-(Benzenesulfonamido)ethyl]-2-oxo-5-phenyl-4-(piperazine-1-carbonyl)imidazol-1-yl]cyclohexyl]propanamide;

3-Methyl-N-[2-[2-oxo-4-phenyl-5-(piperazine-1-carbonyl)-3-[(2S)-2-(propanoylamino)cyclohexyl]imidazol-1-yl]ethyl]butanamide;

N-[(1S)-2-[3-[2-(2-Methylpropylsulfonylamino)ethyl]-2-oxo-5-phenyl-4-(piperazine-1-carbonyl)imidazol-1-yl]cyclohexyl]propanamide;

N-[3-[2-oxo-4-Phenyl-5-(piperazine-1-carbonyl)-3-[(2S)-2-(propanoylamino)cyclohexyl]imidazol-1-yl]propyl]benzamide;
N-[(1S)-2-[3-[3-(Benzenesulfonamido)propyl]-2-oxo-5-phenyl-4-(piperazine-1-carbonyl)imidazol-1-yl]cyclohexyl]propanamide;
3-Methyl-N-[3-[2-oxo-4-phenyl-5-(piperazine-1-carbonyl)-3-[(2S)-2-(propanoylamino)cyclohexyl]imidazol-1-yl]propyl]butanamide;
N-[(1S)-2-[3-[3-(2-Methylpropylsulfonylamino)propyl]-2-oxo-5-phenyl-4-(piperazine-1-carbonyl)imidazol-1-yl]cyclohexyl]propanamide;
N-[(1S)-2-[3-[[3-(2-Methoxyethoxy)phenyl]methyl]-2-oxo-5-phenyl-4-(piperazine-1-carbonyl)imidazol-1-yl]cyclohexyl]propanamide;
N-[(1S)-2-[2-oxo-5-Phenyl-4-(piperazine-1-carbonyl)-3-[[3-(2-pyridin-3-yloxyethoxy)phenyl]methyl]imidazol-1-yl]cyclohexyl]propanamide;
N-[(1S)-2-[2-oxo-5-Phenyl-4-(piperazine-1-carbonyl)-3-[[3-(2-propan-2-yloxyethoxy)phenyl]methyl]imidazol-1-yl]cyclohexyl]propanamide;
N-[(1S)-2-[2-oxo-3-[[3-(2-Phenoxyethoxy)phenyl]methyl]-5-phenyl-4-(piperazine-1-carbonyl)imidazol-1-yl]cyclohexyl]propanamide;
N-[(1S)-2-[3-[[3-(2-Morpholin-4-yl-2-oxo-ethoxy)phenyl]methyl]-2-oxo-5-phenyl-4-(piperazine-1-carbonyl)imidazol-1-yl]cyclohexyl]propanamide;
N-[(1S)-2-[2-oxo-3-[[3-[2-oxo-2-(1-Piperidyl)ethoxy]phenyl]methyl]-5-phenyl-4-(piperazine-1-carbonyl)imidazol-1-yl]cyclohexyl]propanamide;
N-[(1S)-2-[3-[[3-(Methylcarbamoylmethoxy)phenyl]methyl]-2-oxo-5-phenyl-4-(piperazine-1-carbonyl)imidazol-1-yl]cyclohexyl]propanamide;
N-[(1S)-2-[2-oxo-5-Phenyl-4-(piperazine-1-carbonyl)-3-[[3-(propan-2-ylcarbamoylmethoxy)phenyl]methyl]imidazol-1-yl]cyclohexyl]propanamide;
1-(1-Acetyl-3-piperidyl)-5-phenyl-4-(piperazine-1-carbonyl)-3-prop-2-enyl-imidazol-2-one;
1-(1-Acetyl-3-piperidyl)-3-(cyclohexylmethyl)-5-phenyl-4-(piperazine-1-carbonyl)imidazol-2-one;
1-(1-Acetyl-3-piperidyl)-3-[(3-phenoxyphenyl)methyl]-5-phenyl-4-(piperazine-1-carbonyl)imidazol-2-one;
1-(1-Acetyl-3-piperidyl)-3-[(2-amino1,3-thiazol-4-yl)methyl]-5-phenyl-4-(piperazine-1-carbonyl)imidazol-2-one;
1-(1-Acetyl-3-piperidyl)-3-[(3-methoxyphenyl)methyl]-5-phenyl-4-(piperazine-1-carbonyl)imidazol-2-one;
1-(1-Acetyl-3-piperidyl)-3-[(3,4-difluorophenyl)methyl]-5-phenyl-4-(piperazine-1-carbonyl)imidazol-2-one;
N-[2-[3-(1-Acetyl-3-piperidyl)-2-oxo-4-phenyl-5-(piperazine-1-carbonyl)imidazol-1-yl]ethyl]benzamide;
N-[2-[3-(1-Acetyl-3-piperidyl)-2-oxo-4-phenyl-5-(piperazine-1-carbonyl)imidazol-1-yl]ethyl]benzenesulfonamide;
N-[2-[3-(1-Acetyl-3-piperidyl)-2-oxo-4-phenyl-5-(piperazine-1-carbonyl)imidazol-1-yl]ethyl]-3-methyl-butanamide;
N-[2-[3-(1-Acetyl-3-piperidyl)-2-oxo-4-phenyl-5-(piperazine-1-carbonyl)imidazol-1-yl]ethyl]-2-methyl-propane-1-sulfonamide;
N-[3-[3-(1-Acetyl-3-piperidyl)-2-oxo-4-phenyl-5-(piperazine-1-carbonyl)imidazol-1-yl]propyl]benzamide;
N-[3-[3-(1-Acetyl-3-piperidyl)-2-oxo-4-phenyl-5-(piperazine-1-carbonyl)imidazol-1-yl]propyl]benzenesulfonamide;
N-[3-[3-(1-Acetyl-3-piperidyl)-2-oxo-4-phenyl-5-(piperazine-1-carbonyl)imidazol-1-yl]propyl]-3-methyl-butanamide;
N-[3-[3-(1-Acetyl-3-piperidyl)-2-oxo-4-phenyl-5-(piperazine-1-carbonyl)imidazol-1-yl]propyl]-2-methyl-propane-1-sulfonamide;
1-(1-Acetyl-3-piperidyl)-3-[[3-(2-methoxyethoxy)phenyl]methyl]-5-phenyl-4-(piperazine-1-carbonyl)imidazol-2-one;
1-(1-Acetyl-3-piperidyl)-5-phenyl-4-(piperazine-1-carbonyl)-3-[[3-(2-pyridin-3-yloxyethoxy)phenyl]methyl]imidazol-2-one;
1-(1-Acetyl-3-piperidyl)-5-phenyl-4-(piperazine-1-carbonyl)-3-[[3-(2-propan-2-yloxyethoxy)phenyl]methyl]imidazol-2-one;
1-(1-Acetyl-3-piperidyl)-3-[[3-(2-phenoxyethoxy)phenyl]methyl]-5-phenyl-4-(piperazine-1-carbonyl)imidazol-2-one;
1-(1-Acetyl-3-piperidyl)-3-[[3-(2-morpholin-4-yl-2-oxo-ethoxy)phenyl]methyl]-5-phenyl-4-(piperazine-1-carbonyl)imidazol-2-one;
1-(1-Acetyl-3-piperidyl)-3-[[3-[2-oxo-2-(1-piperidyl)ethoxy]phenyl]methyl]-5-phenyl-4-(piperazine-1-carbonyl)imidazol-2-one;
2-[3-[[3-(1-Acetyl-3-piperidyl)-2-oxo-4-phenyl-5-(piperazine-1-carbonyl)imidazol-1-yl]methyl]phenoxy]-N-methyl-acetamide;
2-[3-[[3-(1-Acetyl-3-piperidyl)-2-oxo-4-phenyl-5-(piperazine-1-carbonyl)imidazol-1-yl]methyl]phenoxy]-N-propan-2-yl-acetamide;
1-[1-(Benzenesulfonyl)-3-piperidyl]-5-phenyl-4-(piperazine-1-carbonyl)-3-prop-2-enyl-imidazol-2-one;
1-[1-(Benzenesulfonyl)-3-piperidyl]-3-(cyclohexylmethyl)-5-phenyl-4-(piperazine-1-carbonyl)imidazol-2-one;
1-[1-(Benzenesulfonyl)-3-piperidyl]-3-[(3-phenoxyphenyl)methyl]-5-phenyl-4-(piperazine-1-carbonyl)imidazol-2-one;
1-[(2-Amino1,3-thiazol-4-yl)methyl]-3-[1-(benzenesulfonyl)-3-piperidyl]-4-phenyl-5-(piperazine-1-carbonyl)imidazol-2-one;
1-[1-(Benzenesulfonyl)-3-piperidyl]-3-[(3-methoxyphenyl)methyl]-5-phenyl-4-(piperazine-1-carbonyl)imidazol-2-one;
1-[1-(Benzenesulfonyl)-3-piperidyl]-3-[(3,4-difluorophenyl)methyl]-5-phenyl-4-(piperazine-1-carbonyl)imidazol-2-one;
N-[2-[3-[1-(Benzenesulfonyl)-3-piperidyl]-2-oxo-4-phenyl-5-(piperazine-1-carbonyl)imidazol-1-yl]ethyl]benzamide;
N-[2-[3-[1-(Benzenesulfonyl)-3-piperidyl]-2-oxo-4-phenyl-5-(piperazine-1-carbonyl)imidazol-1-yl]ethyl]benzenesulfonamide;
N-[2-[3-[1-(Benzenesulfonyl)-3-piperidyl]-2-oxo-4-phenyl-5-(piperazine-1-carbonyl)imidazol-1-yl]ethyl]-3-methyl-butanamide;
N-[2-[3-[1-(Benzenesulfonyl)-3-piperidyl]-2-oxo-4-phenyl-5-(piperazine-1-carbonyl)imidazol-1-yl]ethyl]-2-methyl-propane-1-sulfonamide;
N-[3-[3-[1-(Benzenesulfonyl)-3-piperidyl]-2-oxo-4-phenyl-5-(piperazine-1-carbonyl)imidazol-1-yl]propyl]benzamide;
N-[3-[3-[1-(Benzenesulfonyl)-3-piperidyl]-2-oxo-4-phenyl-5-(piperazine-1-carbonyl)imidazol-1-yl]propyl]benzenesulfonamide;

N-[3-[3-[1-(Benzenesulfonyl)-3-piperidyl]-2-oxo-4-phenyl-5-(piperazine-1-carbonyl)imidazol-1-yl]propyl]-3-methyl-butanamide;

N-[3-[3-[1-(Benzenesulfonyl)-3-piperidyl]-2-oxo-4-phenyl-5-(piperazine-1-carbonyl)imidazol-1-yl]propyl]-2-methyl-propane-1-sulfonamide;

1-[1-(Benzenesulfonyl)-3-piperidyl]-3-[[3-(2-methoxyethoxy)phenyl]methyl]-5-phenyl-4-(piperazine-1-carbonyl)imidazol-2-one;

1-[1-(Benzenesulfonyl)-3-piperidyl]-5-phenyl-4-(piperazine-1-carbonyl)-3-[[3-(2-pyridin-3-yloxyethoxy)phenyl]methyl]imidazol-2-one;

1-[1-(Benzenesulfonyl)-3-piperidyl]-5-phenyl-4-(piperazine-1-carbonyl)-3-[[3-(2-propan-2-yloxyethoxy)phenyl]methyl]imidazol-2-one;

1-[1-(Benzenesulfonyl)-3-piperidyl]-3-[[3-(2-phenoxyethoxy)phenyl]methyl]-5-phenyl-4-(piperazine-1-carbonyl)imidazol-2-one;

1-[1-(Benzenesulfonyl)-3-piperidyl]-3-[[3-(2-morpholin-4-yl-2-oxo-ethoxy)phenyl]methyl]-5-phenyl-4-(piperazine-1-carbonyl)imidazol-2-one;

1-[1-(Benzenesulfonyl)-3-piperidyl]-3-[[3-[2-oxo-2-(1-piperidyl)ethoxy]phenyl]methyl]-5-phenyl-4-(piperazine-1-carbonyl)imidazol-2-one;

2-[3-[[3-[1-(Benzenesulfonyl)-3-piperidyl]-2-oxo-4-phenyl-5-(piperazine-1-carbonyl)imidazol-1-yl]methyl]phenoxy]-N-methyl-acetamide;

2-[3-[[3-[1-(Benzenesulfonyl)-3-piperidyl]-2-oxo-4-phenyl-5-(piperazine-1-carbonyl)imidazol-1-yl]methyl]phenoxy]-N-propan-2-yl-acetamide;

N-[2-[2-oxo-5-Phenyl-4-(piperazine-1-carbonyl)-3-prop-2-enyl-imidazol-1-yl]phenyl]propane-1-sulfonamide;

N-[2-[3-(Cyclohexylmethyl)-2-oxo-5-phenyl-4-(piperazine-1-carbonyl)imidazol-1-yl]phenyl]propane-1-sulfonamide;

N-[2-[2-oxo-3-[(3-Phenoxyphenyl)methyl]-5-phenyl-4-(piperazine-1-carbonyl)imidazol-1-yl]phenyl]propane-1-sulfonamide;

N-[2-[3-[(2-Amino1,3-thiazol-4-yl)methyl]-2-oxo-5-phenyl-4-(piperazine-1-carbonyl)imidazol-1-yl]phenyl]propane-1-sulfonamide;

N-[2-[3-[(3-Methoxyphenyl)methyl]-2-oxo-5-phenyl-4-(piperazine-1-carbonyl)imidazol-1-yl]phenyl]propane-1-sulfonamide;

N-[2-[3-[(3,4-Difluorophenyl)methyl]-2-oxo-5-phenyl-4-(piperazine-1-carbonyl)imidazol-1-yl]phenyl]propane-1-sulfonamide;

N-[2-[2-oxo-4-Phenyl-5-(piperazine-1-carbonyl)-3-[2-(propylsulfonylamino)phenyl]imidazol-1-yl]ethyl]benzamide;

N-[2-[2-oxo-4-Phenyl-5-(piperazine-1-carbonyl)-3-[2-(propylsulfonylamino)phenyl]imidazol-1-yl]ethyl]benzenesulfonamide;

3-Methyl-N-[2-[2-oxo-4-phenyl-5-(piperazine-1-carbonyl)-3-[2-(propylsulfonylamino)phenyl]imidazol-1-yl]ethyl]butanamide;

2-Methyl-N-[2-[2-oxo-4-phenyl-5-(piperazine-1-carbonyl)-3-[2-(propylsulfonylamino)phenyl]imidazol-1-yl]ethyl]propane-1-sulfonamide;

N-[3-[2-oxo-4-Phenyl-5-(piperazine-1-carbonyl)-3-[2-(propylsulfonylamino)phenyl]imidazol-1-yl]propyl]benzamide;

N-[3-[2-oxo-4-Phenyl-5-(piperazine-1-carbonyl)-3-[2-(propylsulfonylamino)phenyl]imidazol-1-yl]propyl]benzenesulfonamide;

3-Methyl-N-[3-[2-oxo-4-phenyl-5-(piperazine-1-carbonyl)-3-[2-(propylsulfonylamino)phenyl]imidazol-1-yl]propyl]butanamide;

2-Methyl-N-[3-[2-oxo-4-phenyl-5-(piperazine-1-carbonyl)-3-[2-(propylsulfonylamino)phenyl]imidazol-1-yl]propyl]propane-1-sulfonamide;

N-[2-[3-[[3-(2-Methoxyethoxy)phenyl]methyl]-2-oxo-5-phenyl-4-(piperazine-1-carbonyl)imidazol-1-yl]phenyl]propane-1-sulfonamide;

N-[2-[2-oxo-5-Phenyl-4-(piperazine-1-carbonyl)-3-[[3-(2-pyridin-3-yloxyethoxy)phenyl]methyl]imidazol-1-yl]phenyl]propane-1-sulfonamide;

N-[2-[2-oxo-5-Phenyl-4-(piperazine-1-carbonyl)-3-[[3-(2-propan-2-yloxyethoxy)phenyl]methyl]imidazol-1-yl]phenyl]propane-1-sulfonamide;

N-[2-[2-oxo-3-[[3-(2-Phenoxyethoxy)phenyl]methyl]-5-phenyl-4-(piperazine-1-carbonyl)imidazol-1-yl]phenyl]propane-1-sulfonamide;

N-[2-[3-[[3-(2-Morpholin-4-yl-2-oxo-ethoxy)phenyl]methyl]-2-oxo-5-phenyl-4-(piperazine-1-carbonyl)imidazol-1-yl]phenyl]propane-1-sulfonamide;

N-[2-[2-oxo-3-[[3-[2-oxo-2-(1-Piperidyl)ethoxy]phenyl]methyl]-5-phenyl-4-(piperazine-1-carbonyl)imidazol-1-yl]phenyl]propane-1-sulfonamide;

N-Methyl-2-[3-[[2-oxo-4-phenyl-5-(piperazine-1-carbonyl)-3-[2-(propylsulfonylamino)phenyl]imidazol-1-yl]methyl]phenoxy]acetamide;

2-[3-[[2-oxo-4-Phenyl-5-(piperazine-1-carbonyl)-3-[2-(propylsulfonylamino)phenyl]imidazol-1-yl]methyl]phenoxy]-N-propan-2-yl-acetamide;

1-[1-(1-Methylpyrazol-4-yl)sulfonyl-3-piperidyl]-5-phenyl-4-(piperazine-1-carbonyl)-3-prop-2-enyl-imidazol-2-one;

1-(Cyclohexylmethyl)-3-[1-(1-methylpyrazol-4-yl)sulfonyl-3-piperidyl]-4-phenyl-5-(piperazine-1-carbonyl)imidazol-2-one;

1-[1-(1-Methylpyrazol-4-yl)sulfonyl-3-piperidyl]-3-[(3-phenoxyphenyl)methyl]-5-phenyl-4-(piperazine-1-carbonyl)imidazol-2-one;

1-[(2-Amino-1,3-thiazol-4-yl)methyl]-3-[1-(1-methylpyrazol-4-yl)sulfonyl-3-piperidyl]-4-phenyl-5-(piperazine-1-carbonyl)imidazol-2-one;

1-[(3-Methoxyphenyl)methyl]-3-[1-(1-methylpyrazol-4-yl)sulfonyl-3-piperidyl]-4-phenyl-5-(piperazine-1-carbonyl)imidazol-2-one;

1-[(3,4-Difluorophenyl)methyl]-3-[1-(1-methylpyrazol-4-yl)sulfonyl-3-piperidyl]-4-phenyl-5-(piperazine-1-carbonyl)imidazol-2-one;

N-[2-[3-[1-(1-Methylpyrazol-4-yl)sulfonyl-3-piperidyl]-2-oxo-4-phenyl-5-(piperazine-1-carbonyl)imidazol-1-yl]ethyl]benzamide;

N-[2-[3-[1-(1-Methylpyrazol-4-yl)sulfonyl-3-piperidyl]-2-oxo-4-phenyl-5-(piperazine-1-carbonyl)imidazol-1-yl]ethyl]benzenesulfonamide;

3-Methyl-N-[2-[3-[1-(1-methylpyrazol-4-yl)sulfonyl-3-piperidyl]-2-oxo-4-phenyl-5-(piperazine-1-carbonyl)imidazol-1-yl]ethyl]butanamide;

2-Methyl-N-[2-[3-[1-(1-methylpyrazol-4-yl)sulfonyl-3-piperidyl]-2-oxo-4-phenyl-5-(piperazine-1-carbonyl)imidazol-1-yl]ethyl]propane-1-sulfonamide;

N-[3-[3-[1-(1-Methylpyrazol-4-yl)sulfonyl-3-piperidyl]-2-oxo-4-phenyl-5-(piperazine-1-carbonyl)imidazol-1-yl]propyl]benzamide;

N-[3-[3-[1-(1-Methylpyrazol-4-yl)sulfonyl-3-piperidyl]-2-oxo-4-phenyl-5-(piperazine-1-carbonyl)imidazol-1-yl]propyl]benzenesulfonamide;

3-Methyl-N-[3-[3-[1-(1-methylpyrazol-4-yl)sulfonyl-3-piperidyl]-2-oxo-4-phenyl-5-(piperazine-1-carbonyl)imidazol-1-yl]propyl]butanamide;

2-Methyl-N-[3-[3-[1-(1-methylpyrazol-4-yl)sulfonyl-3-piperidyl]-2-oxo-4-phenyl-5-(piperazine-1-carbonyl)imidazol-1-yl]propyl]propane-1-sulfonamide;

1-[[3-(2-Methoxyethoxy)phenyl]methyl]-3-[1-(1-methylpyrazol-4-yl)sulfonyl-3-piperidyl]-4-phenyl-5-(piperazine-1-carbonyl)imidazol-2-one;

1-[1-(1-Methylpyrazol-4-yl)sulfonyl-3-piperidyl]-5-phenyl-4-(piperazine-1-carbonyl)-3-[[3-(2-pyridin-3-yloxyethoxy)phenyl]methyl]imidazol-2-one;

1-[1-(1-Methylpyrazol-4-yl)sulfonyl-3-piperidyl]-5-phenyl-4-(piperazine-1-carbonyl)-3-[[3-(2-propan-2-yloxyethoxy)phenyl]methyl]imidazol-2-one;

1-[1-(1-Methylpyrazol-4-yl)sulfonyl-3-piperidyl]-3-[[3-(2-phenoxyethoxy)phenyl]methyl]-5-phenyl-4-(piperazine-1-carbonyl)imidazol-2-one;

1-[1-(1-Methylpyrazol-4-yl)sulfonyl-3-piperidyl]-3-[[3-(2-morpholin-4-yl-2-oxo-ethoxy)phenyl]methyl]-5-phenyl-4-(piperazine-1-carbonyl)imidazol-2-one;

1-[1-(1-Methylpyrazol-4-yl)sulfonyl-3-piperidyl]-3-[[3-[2-oxo-2-(1-piperidyl)ethoxy]phenyl]methyl]-5-phenyl-4-(piperazine-1-carbonyl)imidazol-2-one;

N-Methyl-2-[3-[[3-[1-(1-methylpyrazol-4-yl)sulfonyl-3-piperidyl]-2-oxo-4-phenyl-5-(piperazine-1-carbonyl)imidazol-1-yl]methyl]phenoxy]acetamide;

2-[3-[[3-[1-(1-Methylpyrazol-4-yl)sulfonyl-3-piperidyl]-2-oxo-4-phenyl-5-(piperazine-1-carbonyl)imidazol-1-yl]methyl]phenoxy]-N-propan-2-yl-acetamide;

1-[(2R)-2-Hydroxycyclohexyl]-5-phenyl-4-(piperazine-1-carbonyl)-3-prop-2-enyl-imidazol-2-one;

1-(Cyclohexylmethyl)-3-[(2R)-2-hydroxycyclohexyl]-4-phenyl-5-(piperazine-1-carbonyl)imidazol-2-one;

1-[(2R)-2-Hydroxycyclohexyl]-3-[(3-phenoxyphenyl)methyl]-5-phenyl-4-(piperazine-1-carbonyl)imidazol-2-one;

1-[(2-Amino1,3-thiazol-4-yl)methyl]-3-[(2R)-2-hydroxycyclohexyl]-4-phenyl-5-(piperazine-1-carbonyl)imidazol-2-one;

1-[(2R)-2-Hydroxycyclohexyl]-3-[(3-methoxyphenyl)methyl]-5-phenyl-4-(piperazine-1-carbonyl)imidazol-2-one;

1-[(3,4-Difluorophenyl)methyl]-3-[(2R)-2-hydroxycyclohexyl]-4-phenyl-5-(piperazine-1-carbonyl)imidazol-2-one;

N-[2-[3-[(2R)-2-Hydroxycyclohexyl]-2-oxo-4-phenyl-5-(piperazine-1-carbonyl)imidazol-1-yl]ethyl]benzamide;

N-[2-[3-[(2R)-2-Hydroxycyclohexyl]-2-oxo-4-phenyl-5-(piperazine-1-carbonyl)imidazol-1-yl]ethyl]benzenesulfonamide;

N-[2-[3-[(2R)-2-Hydroxycyclohexyl]-2-oxo-4-phenyl-5-(piperazine-1-carbonyl)imidazol-1-yl]ethyl]-3-methyl-butanamide;

N-[2-[3-[(2R)-2-Hydroxycyclohexyl]-2-oxo-4-phenyl-5-(piperazine-1-carbonyl)imidazol-1-yl]ethyl]-2-methyl-propane-1-sulfonamide;

N-[3-[3-[(2R)-2-Hydroxycyclohexyl]-2-oxo-4-phenyl-5-(piperazine-1-carbonyl)imidazol-1-yl]propyl]benzamide;

N-[3-[3-[(2R)-2-Hydroxycyclohexyl]-2-oxo-4-phenyl-5-(piperazine-1-carbonyl)imidazol-1-yl]propyl]benzenesulfonamide;

N-[3-[3-[(2R)-2-Hydroxycyclohexyl]-2-oxo-4-phenyl-5-(piperazine-1-carbonyl)imidazol-1-yl]propyl]-3-methyl-butanamide;

N-[3-[3-[(2R)-2-Hydroxycyclohexyl]-2-oxo-4-phenyl-5-(piperazine-1-carbonyl)imidazol-1-yl]propyl]-2-methyl-propane-1-sulfonamide;

1-[(2R)-2-Hydroxycyclohexyl]-3-[[3-(2-methoxyethoxy)phenyl]methyl]-5-phenyl-4-(piperazine-1-carbonyl)imidazol-2-one;

1-[(2R)-2-Hydroxycyclohexyl]-5-phenyl-4-(piperazine-1-carbonyl)-3-[[3-(2-pyridin-3-yloxyethoxy)phenyl]methyl]imidazol-2-one;

1-[(2R)-2-Hydroxycyclohexyl]-5-phenyl-4-(piperazine-1-carbonyl)-3-[[3-(2-propan-2-yloxyethoxy)phenyl]methyl]imidazol-2-one;

1-[(2R)-2-Hydroxycyclohexyl]-3-[[3-(2-phenoxyethoxy)phenyl]methyl]-5-phenyl-4-(piperazine-1-carbonyl)imidazol-2-one;

1-[(2R)-2-Hydroxycyclohexyl]-3-[[3-(2-morpholin-4-yl-2-oxo-ethoxy)phenyl]methyl]-5-phenyl-4-(piperazine-1-carbonyl)imidazol-2-one;

1-[(2R)-2-Hydroxycyclohexyl]-3-[[3-[2-oxo-2-(1-piperidyl)ethoxy]phenyl]methyl]-5-phenyl-4-(piperazine-1-carbonyl)imidazol-2-one;

2-[3-[[3-[(2R)-2-Hydroxycyclohexyl]-2-oxo-4-phenyl-5-(piperazine-1-carbonyl)imidazol-1-yl]methyl]phenoxy]-N-methyl-acetamide;

2-[3-[[3-[(2R)-2-Hydroxycyclohexyl]-2-oxo-4-phenyl-5-(piperazine-1-carbonyl)imidazol-1-yl]methyl]phenoxy]-N-propan-2-yl-acetamide;

(R)-Ethyl 6-(4-(2-benzylpiperazine-1-carbonyl)-2-oxo-5-phenyl-2,3-dihydro-1H-imidazol-1-yl)indoline-1-carboxylate; and a pharmaceutically acceptable salt of any one of the aforementioned compounds.

12. A pharmaceutical composition comprising a compound as defined in claim 1 and a pharmaceutically acceptable excipient.

13. A method of treating a disease in a subject, the method comprising administering a compound as defined in claim 1 to the subject having the disease, wherein the disease is hypertension.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Synthetic Primers

<400> SEQUENCE: 1
aagcttatgg atggatggag a                                           21

<210> SEQ ID NO 2
<211> LENGTH: 21
<212> TYPE: DNA

```
<213> ORGANISM: Artificial Sequence
<220> FEATURE:
<223> OTHER INFORMATION: Synthetic Primers

<400> SEQUENCE: 2
ggatcctcag cgggccaagg c                                21
```